US007238356B2

(12) United States Patent
Bosman et al.

(10) Patent No.: US 7,238,356 B2
(45) Date of Patent: Jul. 3, 2007

(54) CORE-GLYCOSYLATED HCV ENVELOPE PROTEINS

(75) Inventors: Fons Bosman, Opwijk (BE); Erik Depla, Destelbergen (BE); Geert Deschamps, Aalter (BE); Erwin Sablon, Merchtem (BE); Manfred Suckow, Düsseldorf (DE); Isabelle Samson, Heule (BE); Gert Verheyden, Holsbeek (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 10/128,590

(22) Filed: Apr. 24, 2002

(65) Prior Publication Data

US 2003/0108561 A1 Jun. 12, 2003

Related U.S. Application Data

(60) Provisional application No. 60/305,604, filed on Jul. 17, 2001.

(30) Foreign Application Priority Data

Apr. 24, 2001 (EP) .................................. 01870088

(51) Int. Cl.
  A61K 39/29 (2006.01)
  A61K 48/00 (2006.01)
  C12P 21/04 (2006.01)
(52) U.S. Cl. ............................... 424/228.1; 424/185.1; 424/189.1; 424/193.1; 424/93.1; 435/69.1; 435/69.9; 435/69.7; 435/70.1
(58) Field of Classification Search ................ 424/185, 424/189.1, 192.1, 193.1, 228.1, 93.12, 185.1, 424/93.2, 192, 93.1; 435/69.1, 325, 239, 435/320.1, 255.1, 69.7, 70.1; 242/228.1, 242/93.1
See application file for complete search history.

(56) References Cited

U.S. PATENT DOCUMENTS

| | | | |
|---|---|---|---|
| 4,395,395 A | | 7/1983 | Tabor et al. |
| 5,135,854 A | | 8/1992 | MacKay et al. |
| 5,350,671 A | | 9/1994 | Houghton et al. |
| 5,683,864 A | | 11/1997 | Houghton et al. |
| 5,698,390 A | | 12/1997 | Houghton et al. |
| 5,712,087 A | | 1/1998 | Houghton et al. |
| 5,747,239 A | | 5/1998 | Wang et al. |
| 6,150,134 A | * | 11/2000 | Maertens et al. .......... 435/69.3 |
| 6,245,503 B1 | * | 6/2001 | Maertens et al. ............... 435/5 |
| 6,613,333 B1 | | 9/2003 | Leroux-Roels et al. |
| 6,855,318 B1 | | 2/2005 | Maertens et al. |
| 6,890,737 B1 | * | 5/2005 | Maertens et al. .......... 435/69.3 |
| 7,048,930 B2 | | 5/2006 | Bosman et al. |
| 2004/0151735 A1 | | 8/2004 | Maertens et al. |
| 2006/0078932 A1 | | 4/2006 | Maertens et al. |

FOREIGN PATENT DOCUMENTS

| | | |
|---|---|---|
| EP | 0 468 527 A2 | 1/1992 |
| WO | WO 93/00365 | 1/1993 |
| WO | WO 94/01132 | 1/1994 |
| WO | WO 95/12677 | 5/1995 |
| WO | 96/04385 | 2/1996 |
| WO | WO 99/24466 | 5/1999 |
| WO | 99/54735 | 10/1999 |
| WO | 99/67285 | 12/1999 |
| WO | WO 02/055548 | 7/2002 |
| WO | WO 03/051912 | 6/2003 |

OTHER PUBLICATIONS

Liang et al. Annual of internal Medicine 2000, vol. 132, No. 4, pp. 296-305.*
Frasca et al. J. Immunol. 1999, vol. 163, pp. 650-658.*
Faic et al. Science 2000, vol. 289, 2003a-2004.*
Sarobe et al. J. Virol. 2003. vol. 77, No. 20.*
Rosa et al. Proc. Natl. Acad. Sci. 1996, vol. 93, pp. 1759-1763.*
Ralston et al. J. Virol. 1993, vol. 67, No. 11, pp. 6753-6761.*
Lechmann et al. Hepatology 1996, vol. 24(4), pp. 790-795.*
Fournilier et al. J. Virol. 2001,vol. 75, No. 24, pp. 12088-12097.*
Dubuisson et al. J. B. C. 2000, vol. 275, No. 39, pp. 30605-30609.*
Meunier et al. J. Gene. Virol. 1999, vol. 80, pp. 887-896.*
Inudoh et al. Vaccine 1996, vol. 14, No. 17/18, pp. 1590-1596.*
Fournillier-Jacob et al. J. Gene. Virol. 1996, vol. 77, pp. 1055-1064.*
Kuroda et al., "Heptitis B Virus Envelope L Protein Particles", The Journal of Biological Chemistry, vol. 267, No. 3, Issue of Jan. 25, pp. 1953-1961, 1992.
Kuroda et al., "*Saccharomyces cerevisiae* can release hepatitis B virus surface antigen (HbsAg) particles into the medium by its secretory apparatus", Applied Microbiology Biotechnology (1993) 40:333-340.
Helenius, "How N-linked Oligosaccharides Affect Glycoprotein Folding in the Endoplasmic Reticulum", Molecular Biology of the Cell, vol. 5, 253-265, Mar. 1994.
Ghany et al, Hepatology, 2003, vol. 38, No. 5, pp. 1092-1094.
Choo et al, PNAS, Vaccination of Chimpanzees Against Infection by the Hepatitis C Virus, 1994, pp. 1294-1298.

(Continued)

*Primary Examiner*—Bruce R. Campell
*Assistant Examiner*—Bao Qun Li
(74) *Attorney, Agent, or Firm*—Nixon & Vanderhye P.C.

(57) ABSTRACT

The current invention relates to HCV envelope proteins or parts thereof which are the product of expression in eukaryotic cells. More particularly said HCV envelope proteins are characterized in that on average up to 80% of their N-glycosylation sites are core-glycosylated. Of these N-glycosylated sites more than 70% are glycosylated with an oligomannose having a structure defined by Man(8 to 10)-GlcNAc(2). Furthermore, the ratio of the oligomannose with structure Man(7)-GlcNAc(2) over the oligomannose with structure Man(8)-GlcNAc(2) is less than or equal to 0.45. Less than 10% of the oligomannoses is terminated with an α1,3 linked mannose. The HCV envelope proteins of the invention are particularly suited for diagnostic, prophylactic and therapeutic purposes. A suitable eukaryotic cell for production of the HCV envelope proteins of the invention is a *Hansenula* cell.

36 Claims, 70 Drawing Sheets

OTHER PUBLICATIONS

Figure 1:
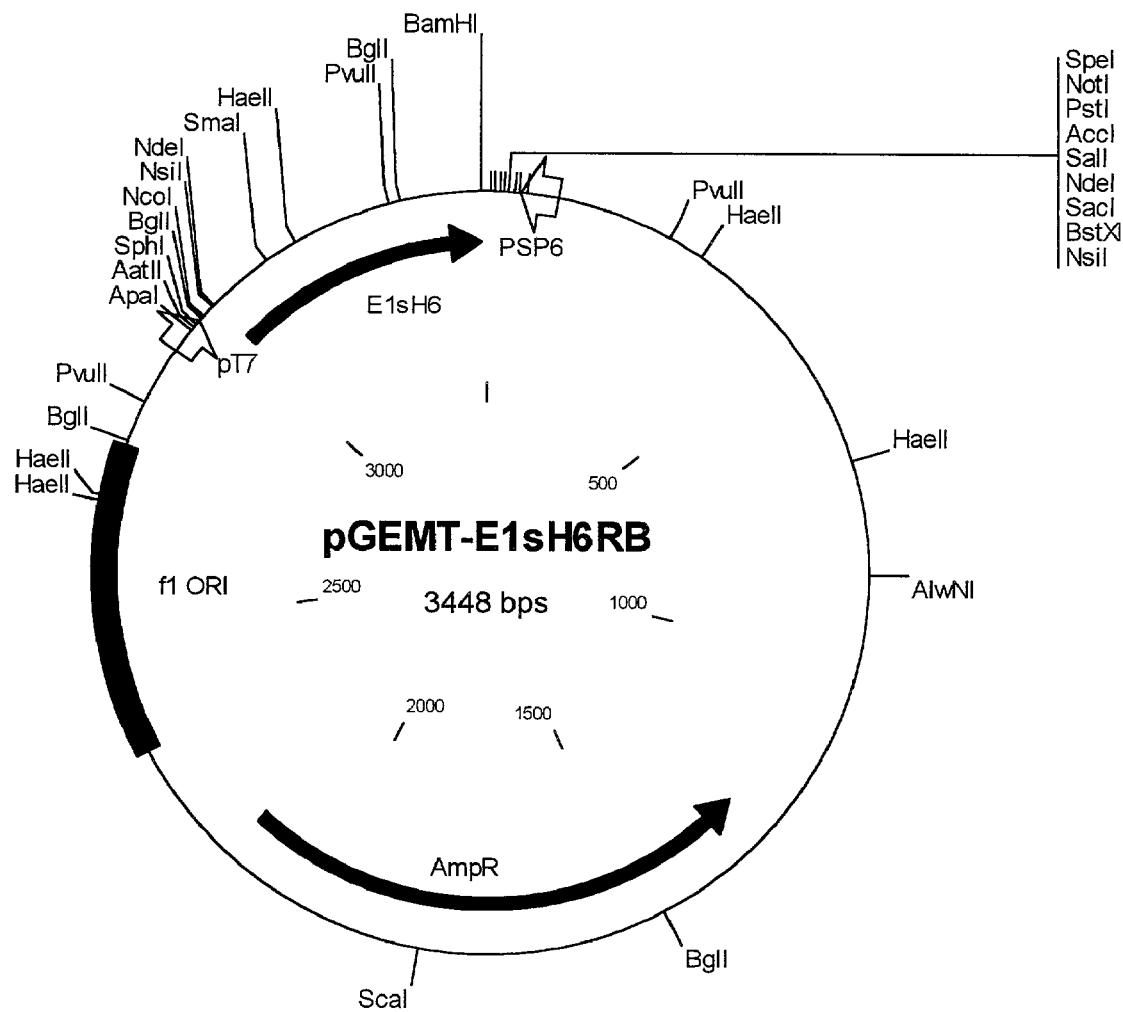

Houghton et al, Prospects for Prophylactic and Therapeutic Hepatitis C Virus Vaccines, 1995, pp. 237-243.
Houghton et al, Viral Hepatitis and Liver Disease, 1997, Apr. 21-25, 1996, pp. 656-659.
Leroux-Roels et al, Hepatology, 2003, 34, 449A.
Nevens et al, Hepatology, A Pilot Study of Therapeutic Vaccination With Envelope Protein E1 in 35 Patients With Chronic Hepatitis C, 2003, 38, pp. 1289-1296.
Pawlotsky, Hepatology, Hepatitis C. Development of New Drugs and Clinical Trials: Promises and Pitfalls, 2003, 39, pp. 554-567.
Forns et al, J. Hepatol, The Challenge of Developing a Vaccine Against Hepatitis C Virus, 2002, 37, pp. 684-695.
Major et al, J. Virology, Previously Infected and Recovered Chimpanzees Exhibit Rapid Responses . . . upon Rechallenge, 2002, 76, pp. 6586-6595.
Bassett et al, Hepatology, Protective Immune Response to Hepatitis C Virus . . . Infection, 2001, 33, pp. 1479-1487.
Weiner et al, J. Virology, Intrahepatic Genetic Inoculation of Hepatitis C Virus . . . Immunity, 2001, 75, pp. 7142-7148.
Mehta et al, Lancet, Protection Agaist Persistence of Hepatitis C, 2002, 359, pp. 1478-1483.
Herscovics, FASEB, Glycoprotein Biosynthesis in Yeast, 1993, 7, pp. 540-550.
Botarelli et al, Gastroenterology, T-Lymphocyte Response to Hepatitis C Virus in Different Clinical Courses of Infection, 1993, 104, pp. 580-587.
Pages 36-38 of WO2004/041853 (2004).
Pages 58-59 of WO02/055548 (2002).
Grogan et al. Annu Rev. Biochem 2002, 71; 593-634.
Bertozzi et al, Chemical Glycobiology,Science, vol. 291, Mar. 23, 2001, 2357-2364.
Innogenetics web site print out (URL: innogenetics.be) (2004).
Diminsky et al, Vaccine, 1997, vol. 15, No. 6/7, pp. 637-647.
Mustilli et al, Res. Microbiol. 1999, vol. 150, pp. 179-187.
Gellissen G, Janowicz ZA, Weydemann U, Melber K, Strasser AW, Hollenberg CP. High-level expression of foreign genes in Hansenula polymorpha. Biotechnol Adv. 1992;10(2):179-89.

* cited by examiner

FIGURE 7

A. MAN-9

B. MAN-8

C. MAN-7

D. MAN-6

E. MAN-5

```
  1                 6              11             16             21             26             31             36             41             46
  H T R V S G G A A A S D T R G L I V S L F S P G S A Q K I Q L V N T D G S W H I D R T A L N B
                                                                        *
                    51             56             61             66             71             76             81             86             91
  D D S L Q T G F F A A L F Y K H K F D S S G B P E R L A S B R S I D K F A Q G W G P L T Y T
*                                                     *
        96           101            106            111            116            121            126            131            136
  E P D S S D Q R P Y B W H Y A P R P B G I V P A S Q V B G P V Y B F T P S P V V V G T T D R
*
       141            146            151            156            161            166            171            176            181
  F G V P T Y N W G A D D S D V L I L D N T R P P R G N W F G B T W M D G T F T K T B G G P
                                    *
       186            191            196            201            206            211            216            221            226
  P B N I G G A G D N T L T B P T D B F R K H P E A T Y A R B G S G P W L T P R B M V H Y P Y
                  *
       231            236            241            246            251            256            261            266            271            276
  R L W H Y P B T V D F T I F K V R M Y V G G V E H R F E A A B D W T R G E R B D L E D R D R
                    *                                                            *
       281            286            291            296
  S E L S P L L L S T T E W Q V I E G R H H H H H H
```

FIGURE 68

CORE-GLYCOSYLATED HCV ENVELOPE PROTEINS

The present application claims benefit of U.S. Provisional Application No. 60/305,604, filed Jul. 17, 2001.

FIELD OF THE INVENTION

The present invention relates to the general field of recombinant protein expression, to diagnosis of HCV infection, to treatment or prevention of HCV infection and to the prognosing/monitoring of the clinical efficiency of treatment of an individual with chronic hepatitis, or the prognosing/monitoring of the natural disease.

More particularly, the present invention relates to the expression of hepatitis C virus envelope proteins in yeast, yeast strains for the expression of core-glycosylated viral envelope proteins, and the use in diagnosis, prophylaxis or therapy of HCV envelope proteins according to the present invention.

BACKGROUND OF THE INVENTION

Hepatitis C virus (HCV) infection is a major health problem in both developed and developing countries. It is estimated that about 1 to 5% of the world population is affected by the virus. HCV infection appears to be the most important cause of transfusion-associated hepatitis and frequently progresses to chronic liver damage. Moreover, evidence exists implicating HCV in induction of hepatocellular carcinoma. Consequently, the demand for reliable diagnostic methods and effective therapeutic agents is high. Also sensitive and specific screening methods of HCV-contaminated blood-products and improved methods to culture HCV are needed.

HCV is a positive stranded RNA virus of approximately 9,600 bases which encode a single polyprotein precursor of about 3000 amino acids. Proteolytic cleavage of the precursor coupled to co- and posttranslational modifications has been shown to result in at least three structural and six non-structural proteins. Based on sequence homology, the structural proteins have been functionally assigned as one single core protein and two envelope glycoproteins: E1 and E2. The E1 protein consists of 192 amino acids and contains 4 to 5 N-glycosylation sites, depending on the HCV genotype. The E2 protein consists of 363 to 370 amino acids and contains 9 to 11 N-glycosylation sites, depending on the HCV genotype (for reviews see: Major and Feinstone, 1997; Maertens and Stuyver, 1997). The E1 protein contains various variable domains (Maertens and Stuyver, 1997). The E2 protein contains three hypervariable domains, of which the major domain is located at the N-terminus of the protein (Maertens and Stuyver, 1997). The HCV glycoproteins localize predominantly in the ER where they are modified and assembled into oligomeric complexes.

In eukaryotes, sugar residues are commonly linked to four different amino acid residues. These amino acid residues are classified as O-linked (serine, threonine, and hydroxylysine) and N-linked (asparagine). The O-linked sugars are synthesized in the Golgi or rough Endoplasmic Reticulum (ER) from nucleotide sugars. The N-linked sugars are synthesized from a common precursor, and subsequently processed. It is believed that HCV envelope proteins are N-glycosylated. It is known in the art that addition of N-linked carbohydrate chains is important for stabilization of folding intermediates and thus for efficient folding, prevention of malfolding and degradation in the endoplasmic reticulum, oligomerization, biological activity, and transport of glycoproteins (see reviews by Rose et al., 1988; Doms et al., 1993; Helenius, 1994). The tripeptide sequences Asn-X-Ser and Asn-X-Thr (in which X can be any amino acid) on polypeptides are the consensus sites for binding N-linked oligosaccharides. After addition of the N-linked oligosaccharide to the polypeptide, the oligosaccharide is further processed into the complex type (containing N-acetylglucosamine, mannose, fucose, galactose and sialic acid) or the high-mannose type (containing N-acetylglucosamine and mannose). HCV envelope proteins are believed to be of the high-mannose type. N-linked oligosaccharide processing in yeast is very different from mammalian Golgi processing. In yeast the oligosaccharide chains are elongated in the Golgi through stepwise addition of mannose, leading to elaborate high mannose structures, referred to as hyperglycosylation. In contrast therewith, proteins expressed in prokaryotes are never glycosylated.

Patterns of high mannose-type glycosylation of proteins or peptides have been determined for a variety of eukaryotic cells. In mammalian cells, an average of 5 to 9 mannose units is linked to two N-acetylglucosamine moieties in a core-glycosylation-type oligosaccharide (the structure represented in short as Man(5-9)GlcNAc(2)). Core-glycosylation refers to a structure similar to the boxed structure in FIG. 3 of Herscovics and Orleans (1993).

The methylotrophic yeast *Pichia pastoris* was reported to attach an average of 8 to 14 mannose units, i.e. Man(8-14)GlcNAc(2) per glycosylation site (Tschopp in EP0256421) and approximately 85% of the N-linked oligosaccharides are in the size range Man(8-14)GlcNAc(2) (Grinna and Tschopp 1989). Other researchers have published slightly different oligosaccharide structures attached to heterologous proteins expressed in *P. pastoris:* Man(8-9)GlcNAc(2) (Montesino et al. 1998), Man(9-14)GlcNAc(2) or Man(9-15)GlcNAc(2) (Kalidas et al. 2001), and Man(8-18)GlcNAc(2) with a preponderence of Man(9-12)GlcNAc(2) and with the major overall oligosaccharide being Man(10)GlcNAc(2) (Miele et al. 1998). Trimble et al. (1991) reported an equal distribution of Man(8)GlcNAc(2) and Man(9)GlcNAc(2) in about 75% of the N-linked oligosaccharides with additionally 17% of the N-glycosylation sites being occupied by Man(10)GlcNAc(2) and the remaining 8% of the sites by Man(11)GlcNAc(2). Hyperglycosylation of a *P. pastoris*-expressed protein has been reported occasionally (Scorer et al. 1993).

*Aspergillus niger* is adding Man(5-10)GlcNAc(2) to N-glycosylation sites (Panchal and Wodzinski 1998).

The *Saccharomyces cerevisiae* glycosylation deficient mutant mnn9 differs from wild-type *S. cerevisiae* in that mnn9 cells produce glycosylated proteins with a modified oligosaccharide consisting of Man(9-13)GlcNAc(2) instead of hyperglycosylated proteins (Mackay et al. in U.S. Pat. No. 5,135,854 and Kniskern et al. in WO94/01132). Another *S. cerevisiae* mutant, och1mnn9, was reported to add Man(8)GlcNAc(2) to N-glycosylation sites in proteins (Yoshifumi et al. JP06277086).

Characteristic for *S. cerevisiae* (wild-type and mnn9 mutant) core oligosaccharides is the presence of terminal α1,3-linked mannose residues (Montesino et al. 1998). Oligosaccharides attached to N-glycosylation sites of proteins expressed in *P. pastoris* or *S. cerevisiae* och1mnn1 are devoid of such terminal α1,3-linked mannoses (Gellissen et al. 2000). Terminal α1,3-linked mannoses are considered to be allergenic (Jenkins et al. 1996). Therefor, proteins carrying on their oligosaccharides terminal α1,3-linked mannose residues are not suitable for diagnostic or therapeutic purposes.

The glycosylation pattern on proteins expressed in the methylotrophic yeast *Hansenula polymorpha* have, despite the use of this yeast for production of a considerable number of heterologous proteins (see Table 3 in Gellissen et al. 2000), not been studied in great detail. From the experiments of Janowicz et al. (1991) and Diminsky et al. (1997), it seems that *H. polymorpha* is not or only poorly glycosylating the large or small hepatitis B viral surface antigen (HBsAg). Most likely this is due to the fact that the HBsAg was expressed without signal peptide, thus preventing the produced HBsAg to enter the lumen of the endoplasmic reticulum (ER) and glycosylation. Limited addition of mono- or dihexoses to G-CSF (granulocyte colony stimulating factor) produced in *H. polymorpha* was reported (Fischer et al. in WO00/40727). At the other hand, hyperglycosylation was observed of a heterologous α-galactosidase expressed in *H. polymorpha* cells (Fellinger et al. 1991).

To date, vaccination against disease has been proven to be the most cost effective and efficient method for controlling diseases. Despite promising results, efforts to develop an efficacious HCV vaccine, however, have been plagued with difficulties. A condition sine qua non for vaccines is the induction of an immune response in patients. Consequently, HCV antigenic determinants should be identified, and administered to patients in a proper setting. Antigenic determinants can be divided in at least two forms, i.e. lineair and conformational epitopes. Conformational epitopes result from the folding of a molecule in a three-dimensional space, including co- and posttranslational modifications, such as glycosylation. In general, it is believed that conformational epitopes will realize the most efficacious vaccines, since they represent epitopes which resemble native-like HCV epitopes, and which may be better conserved than the actual linear amino acid sequence. Hence, the eventual degree of glycosylation of the HCV envelope proteins is of the utmost importance for generating native-like HCV antigenic determinants. However, there are seemingly insurmountable problems with culturing HCV, that result in only minute amounts of virions. In addition, there are vast problems with the expression and purification of recombinant proteins, that result in either low amounts of proteins, hyperglycosylated proteins, or proteins that are not glycosylated.

The HCV envelope proteins have been produced by recombinant techniques in *Escherichia coli*, insect cells, yeast cells and mammalian cells. However, expression in higher eukaryotes has been characterised by the difficulty of obtaining large amounts of antigens for eventual vaccine production. Expression in prokaryotes, such as *E. coli* results in HCV envelope proteins that are not glycosylated. Expression of HCV envelope proteins in yeast resulted in hyperglycosylation. As already demonstrated by Maertens et al. in WO 96/04385, the expression of HCV envelope protein E2 in *Saccharomyces cerevisiae* leads to proteins which are heavily glycosylated. This hyperglycosylation leads to shielding of protein epitopes. Although Mustilli et al. (1999) claims that expression of HCV E2 in *S. cerevisiae* results in core-glycosylation, the results of the intracellularly expressed material demonstrate that part of it is at least hyperglycosylated, while the correct processing of the remainder of this material has not been shown. Moreover, the hyperglycosylation observed by Mustilli et al. (1999) could only be prevented in the presence of tunicamycin, an inhibitor of glycosylation, and this does thus not reflect glycosylation occurring under normal, natural growth conditions. The need for HCV envelope proteins derived from an intracellular source is well accepted (Maertens et al. in WO 96/04385, Heile et al., 2000). This need is further exemplified by the poor reactivity of the secreted yeast derived E2 with sera of chimpanzee immunized with mammalian cell culture derived E2 proteins as evidenced in FIG. 5 of Mustilli et al (1999). This is further documented by Rosa et al (1996) who show that immunization with yeast derived HCV envelope proteins fails to protect from challenge.

Consequently, there is a need for efficient expression systems resulting in large and cost-effective amounts of proteins that at the same time have a native-like glycosylation pattern devoid of terminal α1,3-linked mannoses. In particular, such systems are needed for production of HCV envelope proteins.

SUMMARY OF THE INVENTION

A first aspect of the current invention relates to an isolated HCV envelope protein or a fragment thereof comprising at least one N-glycosylation site, said protein or fragment thereof characterized in that it is the product of expression in a eukaryotic cell and further characterized in that on average up to 80% of the N-glycosylation sites are core-glycosylated. In particular, more than 70% of said core-glycosylated sites are glycosylated with an oligomannose with a structure defined by Man(8 to 10)-GlcNAc(2). Furthermore, the ratio of the oligomannose with structure Man(7)-GlcNAc(2) over the oligomannose with structure Man(8)-GlcNAc(2) is less than or equal to 0.45. More specifically said oligomannoses contain less than 10% terminal α1,3 mannose. The eukaryotic cell expressing said isolated HCV envelope protein or part thereof can be a yeast cell such as a *Hansenula* cell.

A further aspect of the current invention relates to an isolated HCV envelope protein or part thereof according to the invention which is derived from a protein comprising an avian lysozyme leader peptide or a functional variant thereof joined to said HCV envelope protein or fragment thereof More specifically, said isolated HCV envelope protein or part thereof is derived from a protein characterized by the structure $$CL\text{-}[(A1)_a\text{-}(PS1)_b\text{-}(A2)_c]\text{-}HCVENV\text{-}[(A3)_d\text{-}(PS2)_e\text{-}(A4)_f]$$

wherein:

CL is an avian lysozyme leader peptide or a functional equivalent thereof,

A1, A2, A3 and A4 are adaptor peptides which can be different or the same,

PS1 and PS2 are processing sites which can be the different or the same,

HCVENV is a HCV envelope protein or a part thereof, a, b, c, d, e and f are 0 or 1, and wherein, optionally, A1 and/or A2 are part of PS1 and/or wherein A3 and/or A4 are part of PS2.

Another aspect of the invention covers an isolated HCV envelope protein or fragment thereof according to the invention which is comprised in a structure chosen from the group consisting of monomers, homodimers, heterodimers, homo-oligomers and hetero-oligomers. Alternatively, said isolated HCV envelope protein or fragment thereof according to the invention which is comprised in a virus-like particle. More specifically, any of the isolated HCV envelope protein or fragment thereof according to the invention may comprise cysteines of which the cysteine thiol-groups are chemically modified.

Specific aspects of the invention relate to isolated HCV envelope proteins or fragment thereof according to the invention which are antigenic or immunogenic and/or which comprise a T-cell stimulating epitope.

A further aspect relates to a composition comprising an isolated HCV envelope protein or fragment thereof according to the invention. Said composition may further comprise a pharmaceutically acceptable carrier and can be a medicament or a vaccine.

The invention also relates to a method for producing the isolated HCV envelope protein or fragment thereof according to the invention.

Another method of the invention is a method for the detection of the presence of anti-HCV antibodies in a sample suspected to comprise anti-HCV antibodies, said method comprising:

(i) contacting a HCV envelope protein or part thereof according to any of claims 1 to 15 with said sample under conditions allowing complexation of said HCV envelope protein or part thereof with said anti-HCV antibodies, (ii) detecting the complex formed in (i), and (iii) inferring from (ii) the presence of said anti-HCV antibodies in said sample.

More specifically, said method may comprise step (i) in which said contacting is occurring under competitive conditions. In particular, said methods may utilize a solid support to which said HCV envelope protein or part thereof is attached.

The invention further relates to a diagnostic kit for the detection of the presence of anti-HCV antibodies in a sample suspected to comprise anti-HCV antibodies, said kit comprising a HCV envelope protein or part thereof according to the invention. More specifically, said kit may comprise said HCV envelope protein or part thereof attached to a solid support.

The invention also relates to a medicament or a vaccine comprising a HCV envelope protein or part thereof according to the invention.

Also covered by the invention is a pharmaceutical composition for inducing a HCV-specific immune response in a mammal, said composition comprising an effective amount of a HCV envelope protein or part thereof according to the invention and, optionally, a pharmaceutically acceptable adjuvant. Said pharmaceutical composition may alternatively be capable of inducing HCV-specific antibodies in a mammal or of inducing a T-cell function in a mammal. Furthermore, said pharmaceutical composition may be a prophylactic composition or a therapeutic composition. In particular, said mammal is a human.

FIGURE LEGENDS

FIG. 1. Schematic map of the vector pGEMT-E1sH6RB which has the sequence as defined in SEQ ID NO:6.

Figure 2:
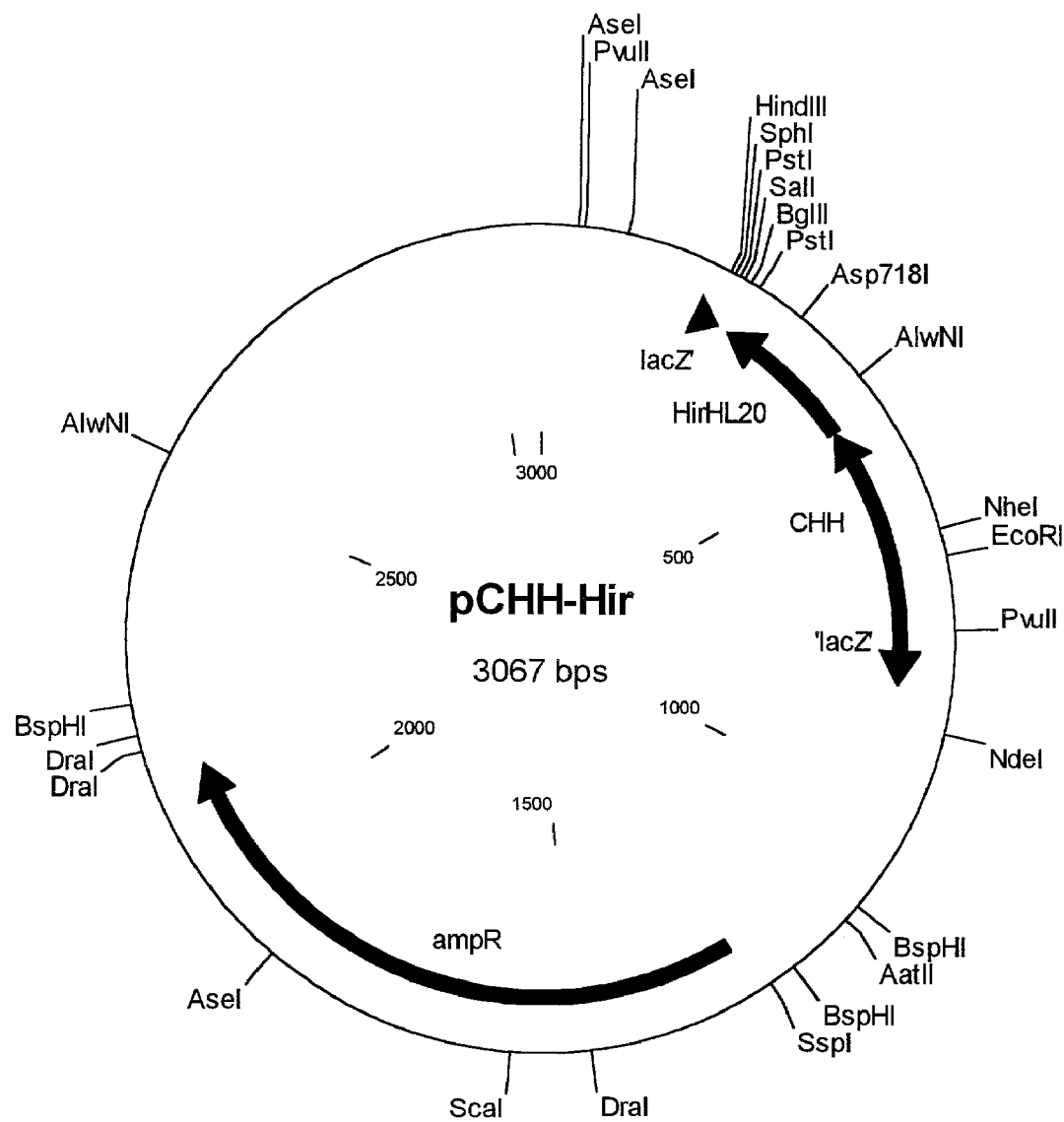

FIG. 2. Schematic map of the vector pCHH-Hir which has the sequence as defined in SEQ ID NO:9.

Figure 3:
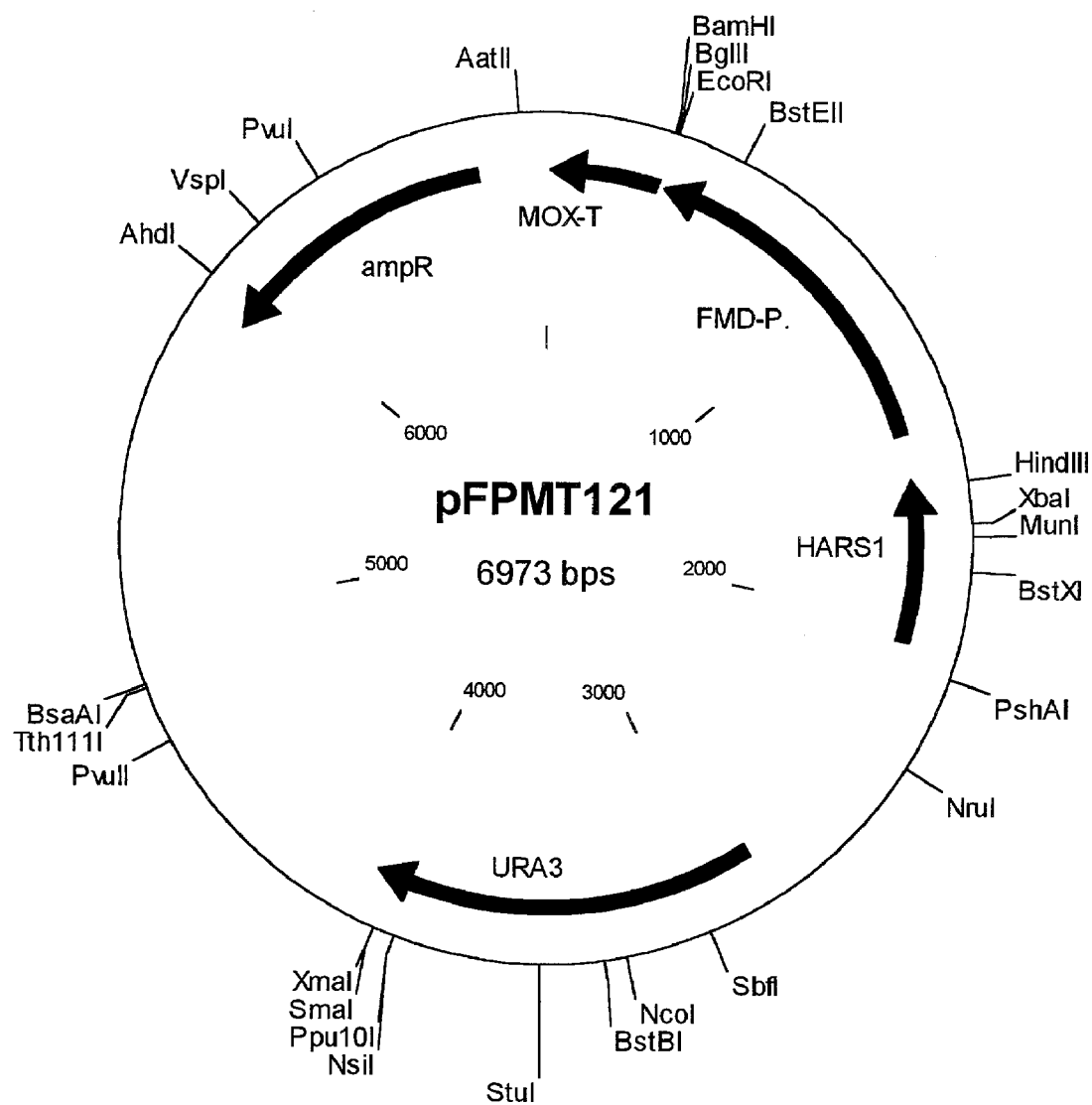

FIG. 3. Schematic map of the vector pFPMT121 which has the sequence as defined in SEQ ID NO:12.

Figure 4:
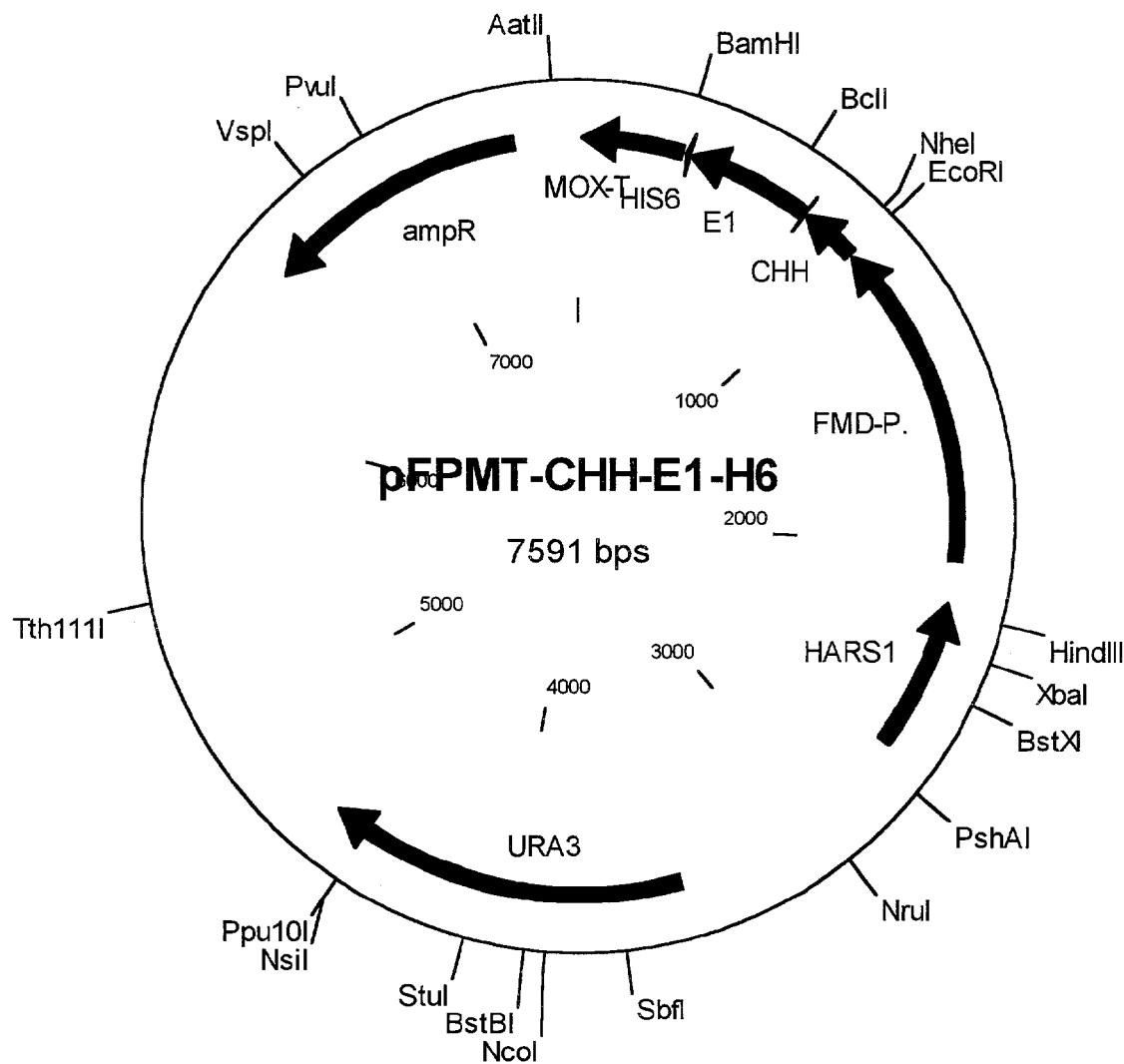

FIG. 4. Schematic map of the vector pFPMT-CHH-E1-H6 which has the sequence as defined in SEQ ID NO:13.

Figure 5:
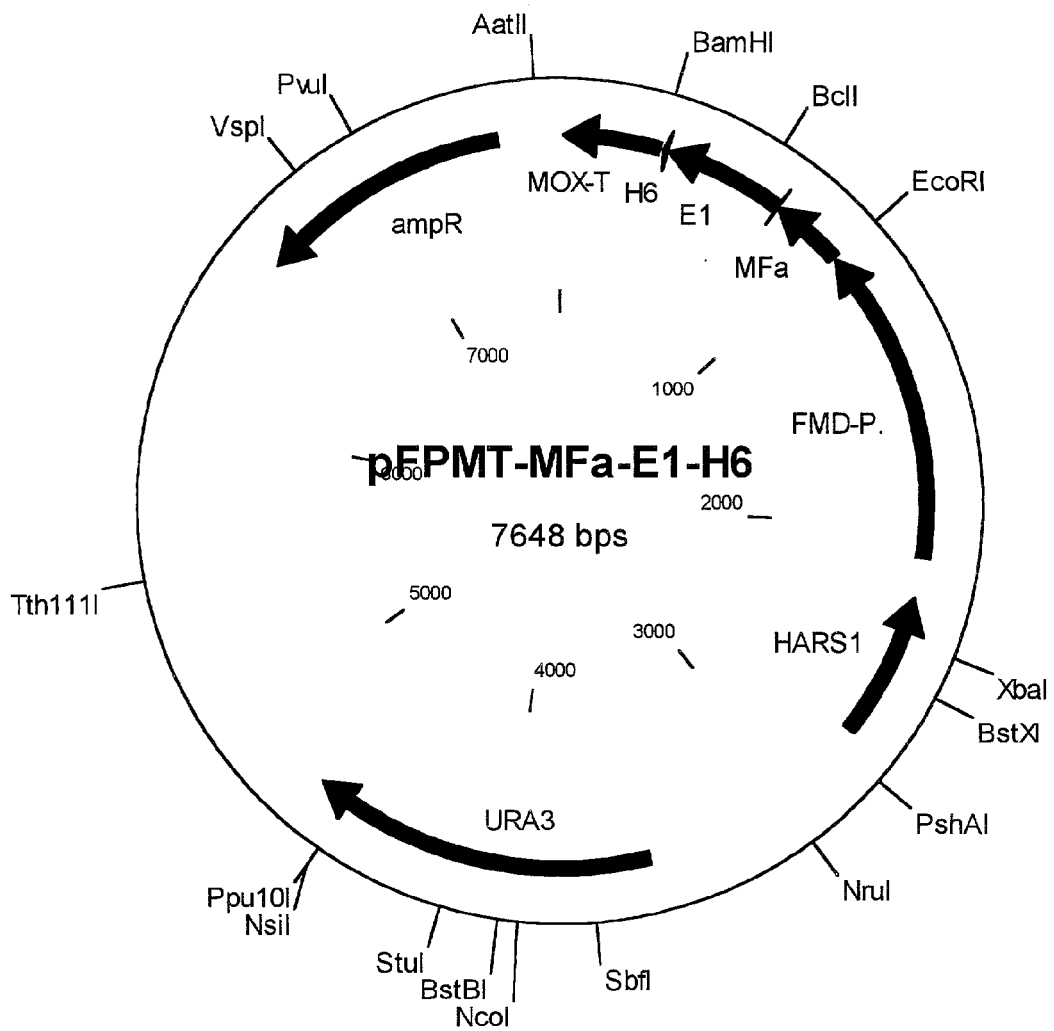

FIG. 5. Schematic map of the vector pFPMT-MFa-E1-H6 which has the sequence as defined in SEQ ID NO:16.

Figure 6:
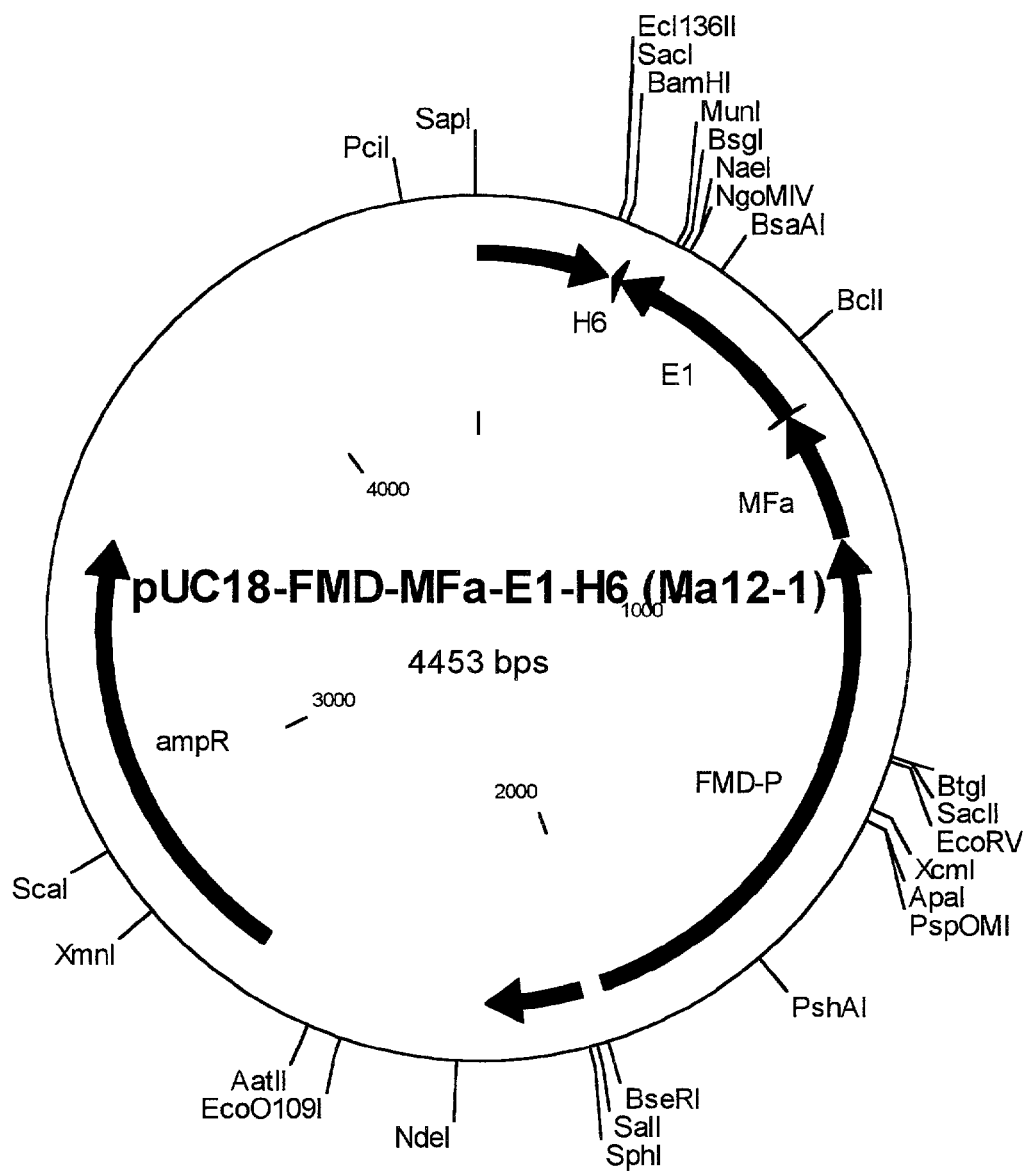

FIG. 6. Schematic map of the vector pUC18-FMD-MFa-E1-H6 which has the sequence as defined in SEQ ID NO:17.

Figure 7:
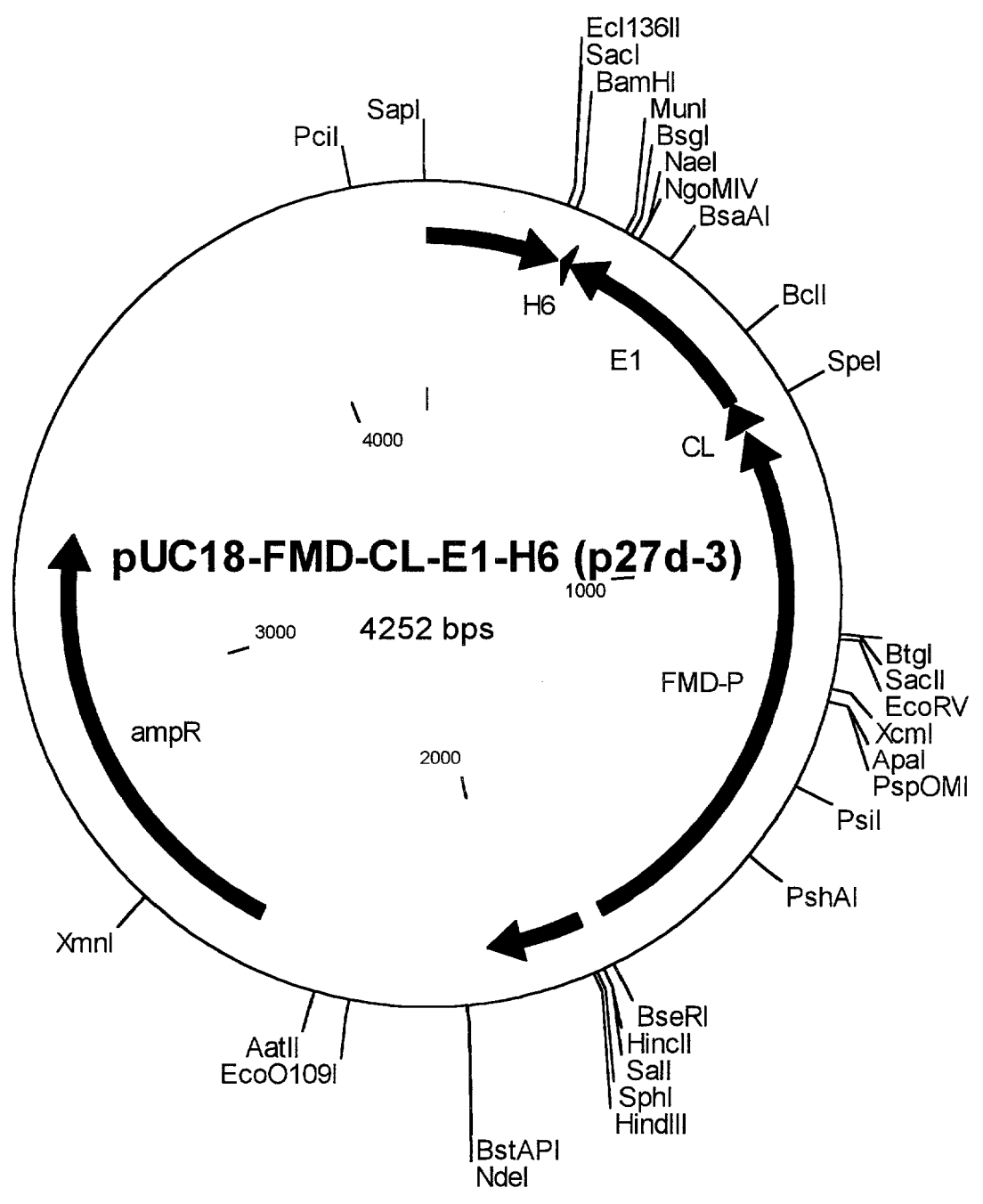

FIG. 7. Schematic map of the vector pUC18-FMD-CL-E1-H6 which has the sequence as defined in SEQ ID NO:20.

Figure 8:
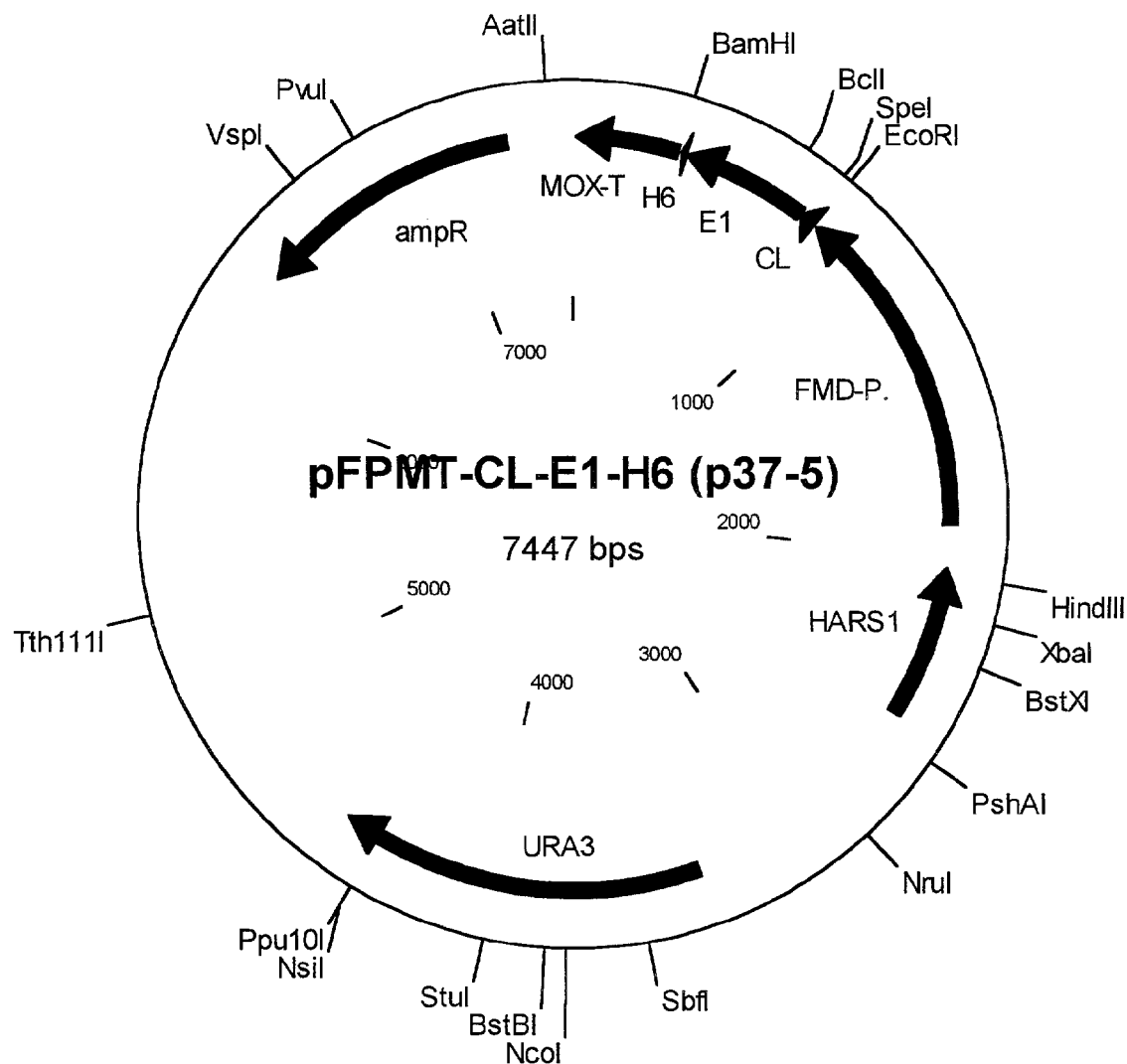

FIG. 8. Schematic map of the vector pFPMT-CL-E1-H6 which has the sequence as defined in SEQ ID NO:21.

Figure 9:
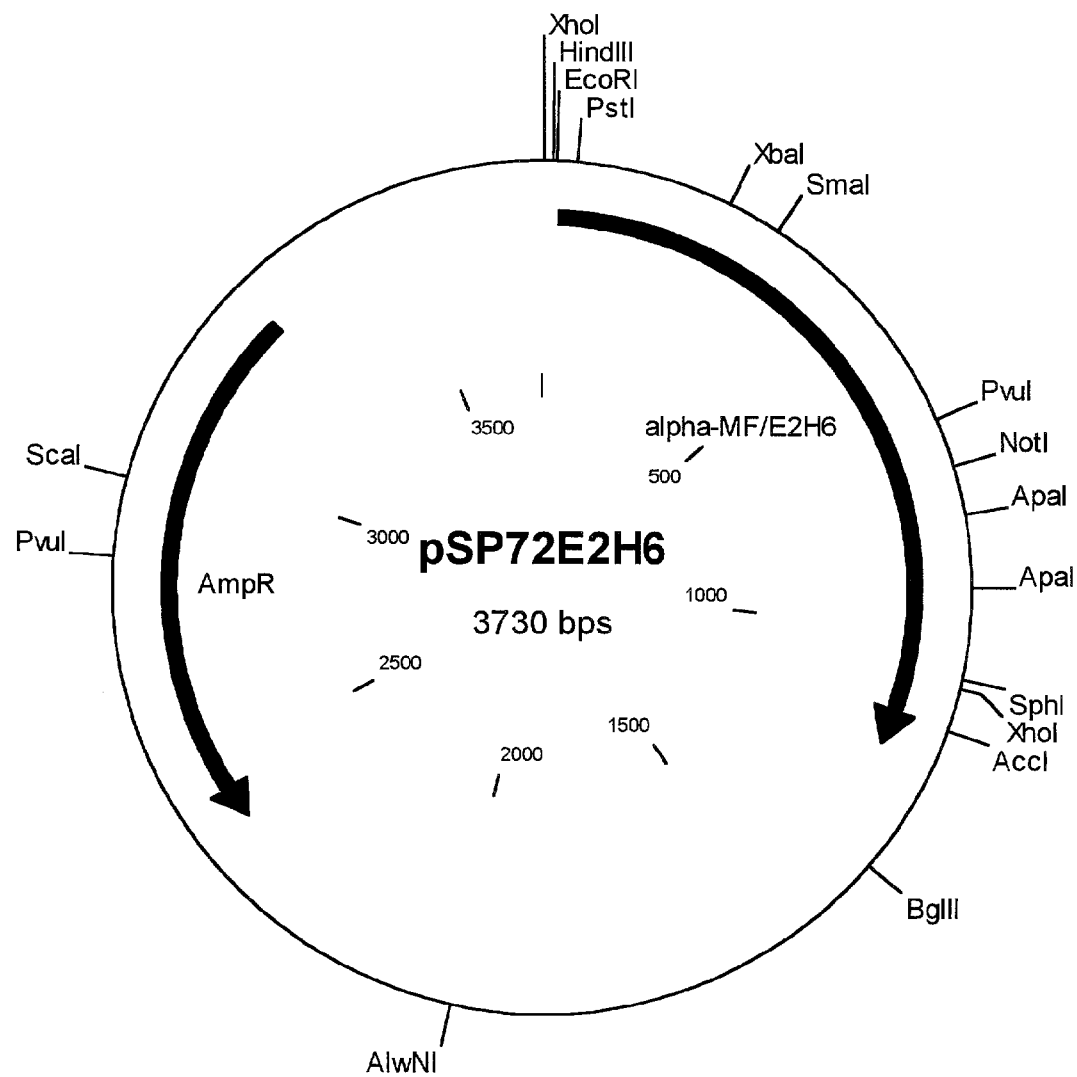

FIG. 9. Schematic map of the vector pSP72E2H6 which has the sequence as defined in SEQ ID NO:22.

FIG. 10. Schematic map of the vector pMPT121 which has the sequence as defined in SEQ ID NO:23.

FIG. 11. Schematic map of the vector pFPMT-MFa-E2-H6 which has the sequence as defined in SEQ ID NO:24.

FIG. 12. Schematic map of the vector pMPT-MFa-E2-H6 which has the sequence as defined in SEQ ID NO:25.

FIG. 13. Schematic map of the vector pMF30 which has the sequence as defined in SEQ ID NO:28.

FIG. 14. Schematic map of the vector pFPMT-CL-E2-H 6 which has the sequence as defined in SEQ ID NO:32.

FIG. 15. Schematic map of the vector pUC18-FMD-CL-E1 which has the sequence as defined in SEQ ID NO:35.

FIG. 16. Schematic map of the vector pFPMT-CL-E1 which has the sequence as defined in SEQ ID NO:36.

FIG. 17. Schematic map of the vector pUC18-FMD-CL-H6-E1-K-H6 which has the sequence as defined in SEQ ID NO:39.

FIG. 18. Schematic map of the vector pFPMT-CL-H6-K-E1 which has the sequence as defined in SEQ ID NO:40.

FIG. 19. Schematic map of the vector pYIG5 which has the sequence as defined in SEQ ID NO:41.

FIG. 20. Schematic map of the vector pYIG5E1H6 which has the sequence as defined in SEQ ID NO:42.

FIG. 21. Schematic map of the vector pSY1 which has the sequence as defined in SEQ ID NO:43.

FIG. 22. Schematic map of the vector pSY1aMFE1sH6a which has the sequence as defined in SEQ ID NO:44.

FIG. 23. Schematic map of the vector pBSK-E2sH6 which has the sequence as defined in SEQ ID NO:45.

FIG. 24. Schematic map of the vector pYIG5HCCL-22aH6 which has the sequence as defined in SEQ ID NO:46.

FIG. 25. Schematic map of the vector pYYIGSE2H6 which has the sequence as defined in SEQ ID NO:47.

FIG. 26. Schematic map of the vector pYIG7 which has the sequence as defined in SEQ ID NO:48.

FIG. 27. Schematic map of the vector pYIG7E1 which has the sequence as defined in SEQ ID NO:49.

FIG. 28. Schematic map of the vector pSY1YIG7E1s which has the sequence as defined in SEQ ID NO:50.

FIG. 29. Schematic map of the vector pPICZalphaA which has the sequence as defined in SEQ ID NO:51.

FIG. 30. Schematic map of the vector pPICZalphaD' which has the sequence as defined in SEQ ID NO:52.

FIG. 31. Schematic map of the vector pPICZalphaE' which has the sequence as defined in SEQ ID NO:53.

FIG. 32. Schematic map of the vector pPICZalphaD'E1sH6 which has the sequence as defined in SEQ ID NO:58.

FIG. 33. Schematic map of the vector pPICZalphaE'E1sH6 which has the sequence as defined in SEQ ID NO:59.

FIG. 34. Schematic map of the vector pPICZalphaD'E2sH6 which has the sequence as defined in SEQ ID NO:60.

FIG. 35. Schematic map of the vector pPICZalphaE'E2sH6 which has the sequence as defined in SEQ ID NO:61.

FIG. 36. Schematic map of the vector pUC18MFa which has the sequence as defined in SEQ ID NO:62.

FIG. 37. Elution profile of size exclusion chromatography of IMAC-purified E2-H6protein expressed from the MFα-E2-H6-expressing *Hansenula polymorpha* (see Example 15). The X-axis indicates the elution volume (in mL). The vertical lines through the elution profile indicate the fractions collected. "P1"=pooled fractions 4 to 9, "P2"=pooled fractions 30 to 35, and "P3"=pooled fractions 37 to 44. The Y-axis indicates absorbance given in mAU (milli absorbance units). The X-axis indicates the elution volume in mL.

Figure 37:
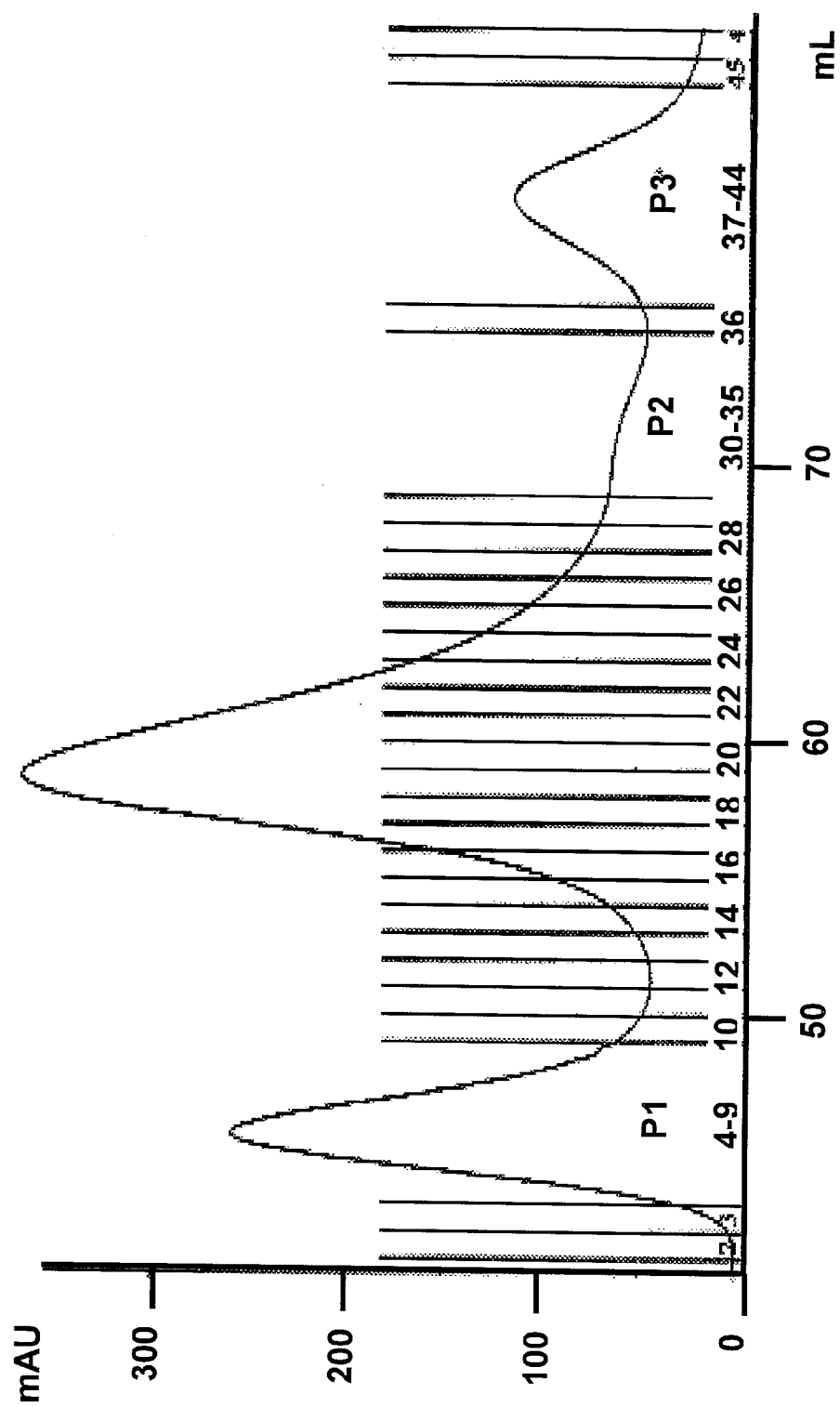
Figure 38:
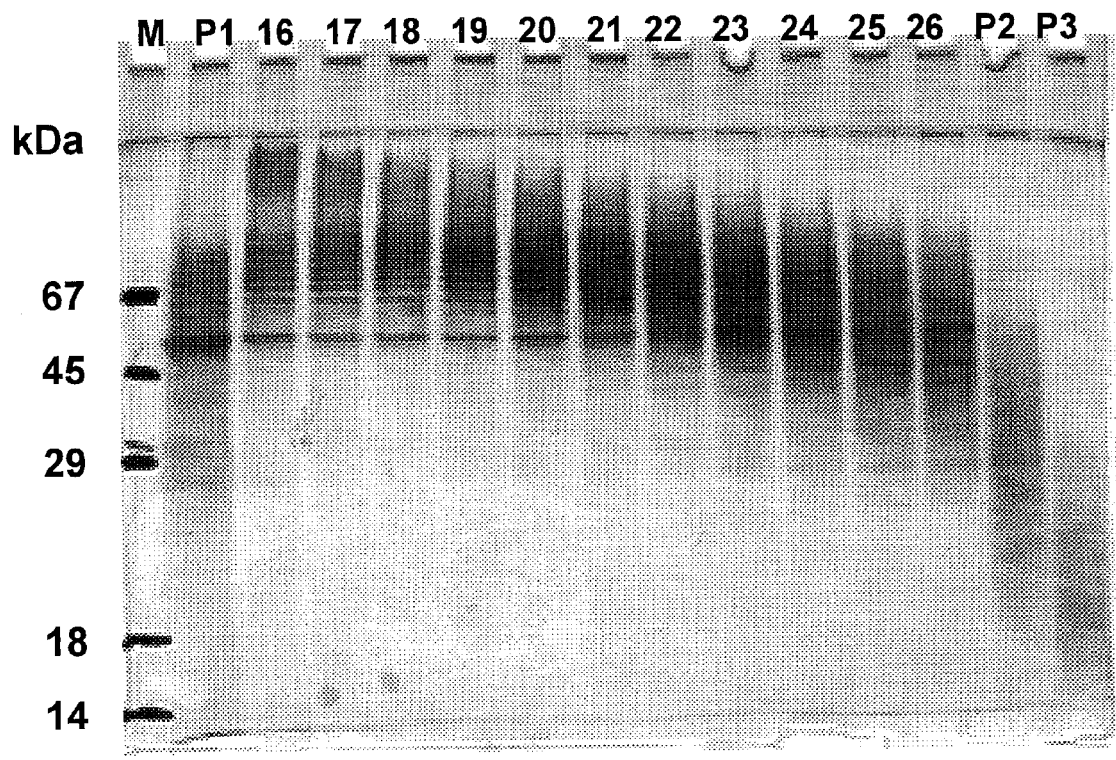

FIG. 38. The different pools and fractions collected after size exclusion chromatography (see FIG. 37) were analyzed by non-reducing SDS-PAGE followed by silver staining of the polyacrylamide gel. The analyzed pools ("P1", "P2", and "P3") and fractions (16 to 26) are indicated on top of the picture of the silver-stained gel. At the left (lane "M") are indicated the sizes of the molecular mass markers.

Figure 39:
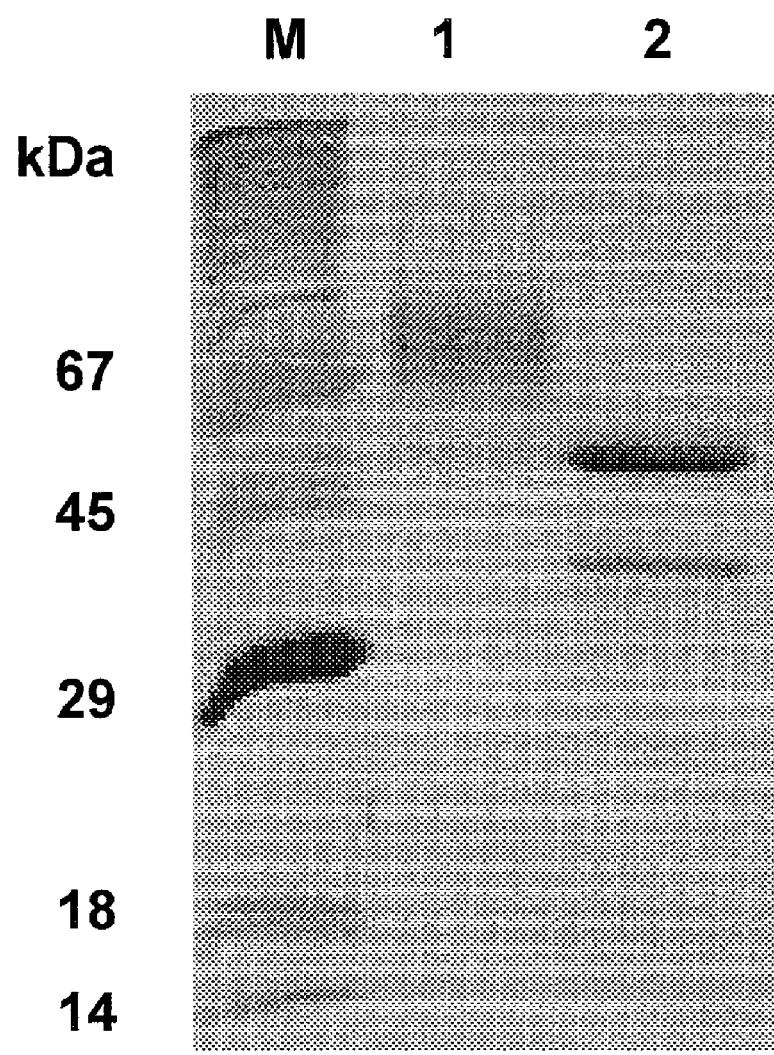

FIG. 39. Fractions 17 to 23 of the size exclusion chromatographic step as shown in FIG. 37 were pooled and alkylated. Thereafter, the protein material was subjected to Endo H treatment for deglycosylation. Untreated material and Endo H-treated material were separated on an SDS-PAGE gel and blotted to a PVDF membrane. The blot was stained with amido black.
Lane 1: Alkylated E2-H6 before Endo H-treatment
Lane 2: Alkylated E2-H6 after Endo H-treatment.

Figure 40:
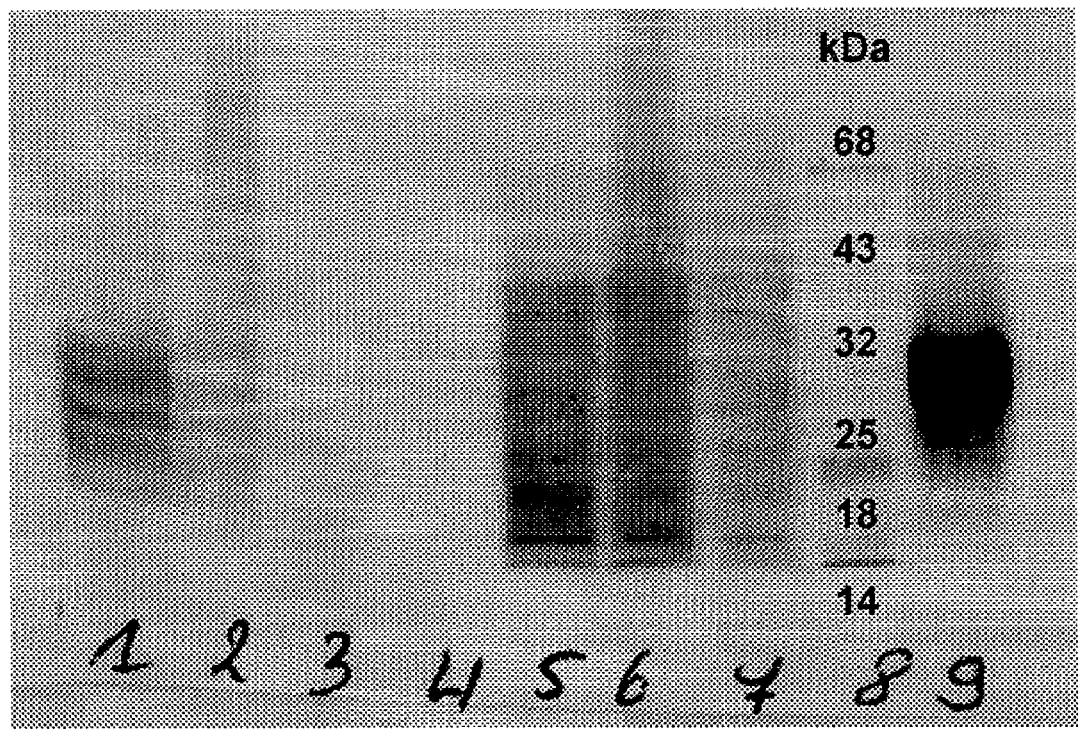

FIG. 40. Western-blot analysis of cell lysates of E1 expressed in *Saccharomyces cerevisiae*. The Western-blot was developed using the E1-specific monoclonal antibody IGH 201.
Lanes 1-4: expression product after 2, 3, 5 or 7 days expression, respectively, in a *Saccharomyces* clone transformed with pSY1YIG7E1s (SEQ ID NO:50, FIG. 28) comprising the nucleotide sequence encoding the chicken lysozyme leader peptide joined to E1-H6.
Lanes 5-7: expression product after 2, 3 or 5 days expression, respectively, in a *Saccharomyces* clone transformed with pSY1aMFE1sH6aYIG1 (SEQ ID NO:44, FIG. 22) comprising the nucleotide sequence encoding the α-mating factor leader peptide joined to E1-H6.
Lane 8: molecular weight markers with sizes as indicated.
Lane 9: purified E1s produced by HCV-recombinant vaccinia virus-infected mammalian cells.

Figure 41:
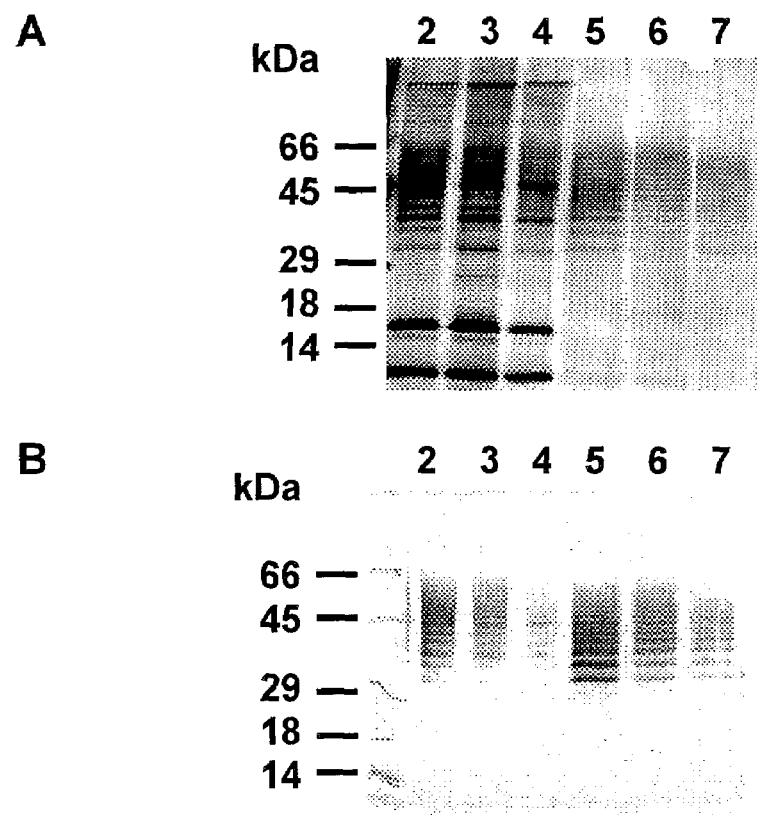

FIG. 41. Analysis of the immobilized metal ion affinity chromatography (IMAC)-purified E2-H6 protein expressed by and processed from CL-E2-H6 to E2-H6 by *H. polymorpha* (see Example 17). Proteins in different wash fractions (lanes 2 to 4) and elution fractions (lanes 5 to 7) were analyzed by reducing SDS-PAGE followed by silver staining of the gel (A, top picture) or by western blot using using a specific monoclonal antibody directed against E2 (B, bottom picture). The sizes of the molecular mass markers are indicated at the left.

Figure 42:
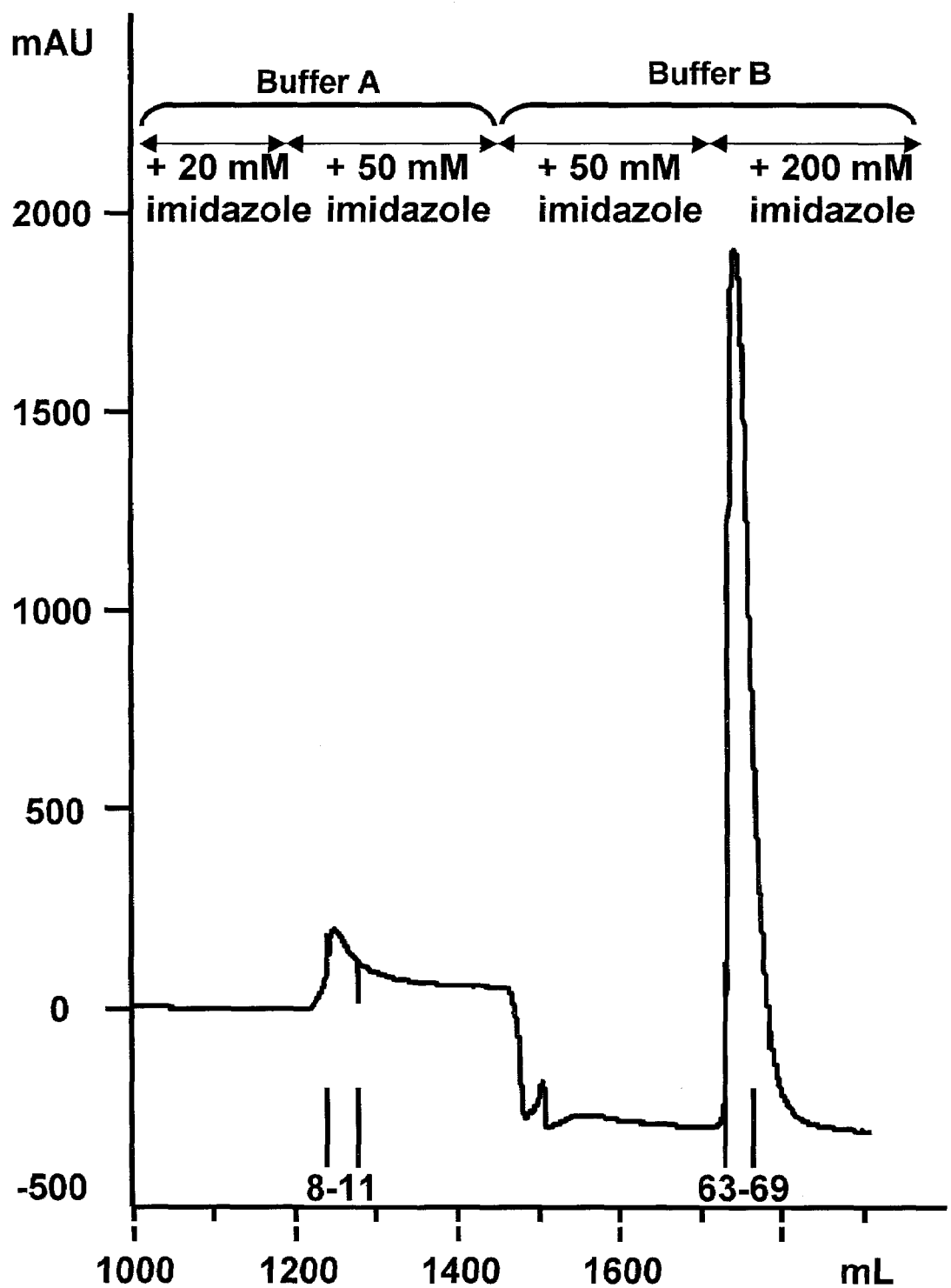

FIG. 42. Elution profile of the first IMAC chromatography step on a Ni-IDA column (Chelating Sepharose FF loaded with $Ni^{2+}$, Pharmacia) for the purification of the sulfonated H6-K-E1 protein produced by *H. polymorpha* (see Example 18). The column was equilibrated with buffer A (50 mM phosphate, 6 M GuHCl, 1% Empigen BB (v/v), pH 7.2) supplemented with 20 mM imidazole. After sample application, the column was washed sequentially with buffer A containing 20 mM and 50 mM imidazole, respectively (as indicated on chromatogram). A further washing and elution step of the His-tagged products was performed by the sequential application of buffer B (PBS, 1% empigen BB, pH 7.2) supplemented with 50 mM imidazole and 200 mM imidazole respectively (as indicated on chromatogram). Following fractions were pooled: the wash pool 1 (fractions 8 to 11, wash with 50 mM imidazole). The eluted material was collected as separate fractions 63 to 72 or an elution pool (fractions 63 to 69) was made. The Y-axis indicates absorbance given in mAU (milli absorbance units). The X-axis indicates the elution volume in mL.

Figure 43:
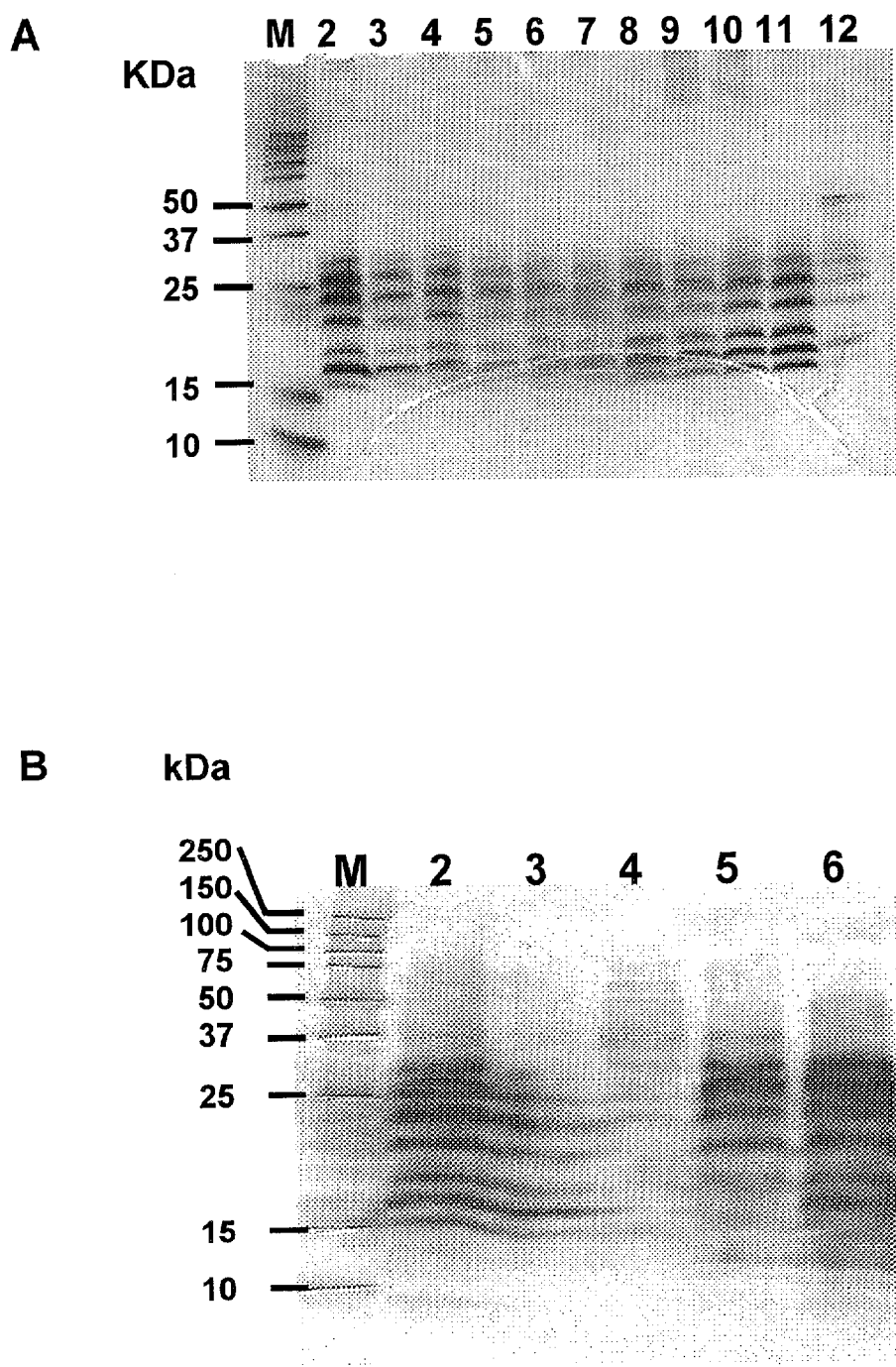

FIG. 43. Analysis of the IMAC-purified H6-K-E1 protein (see FIG. 42) expressed by and processed from CL-H6-K-E1 to H6-K-E1 by *H. polymorpha*. Proteins in the wash pool 1 (lane 12) and elution fractions 63 to 72 (lanes 2 to 11) were analyzed by reducing SDS-PAGE followed by silver staining of the gel (A, top picture). Proteins present in the sample before IMAC (lane 2), in the flow-through pool (lane 4), in wash pool 1 (lane 5) and in the elution pool (lane 6) were analyzed by western blot using a specific monoclonal antibody directed against E1 (B, bottom picture; no sample was loaded in lane 3). The sizes of the molecular mass markers (lanes M) are indicated at the left.

Figure 44:
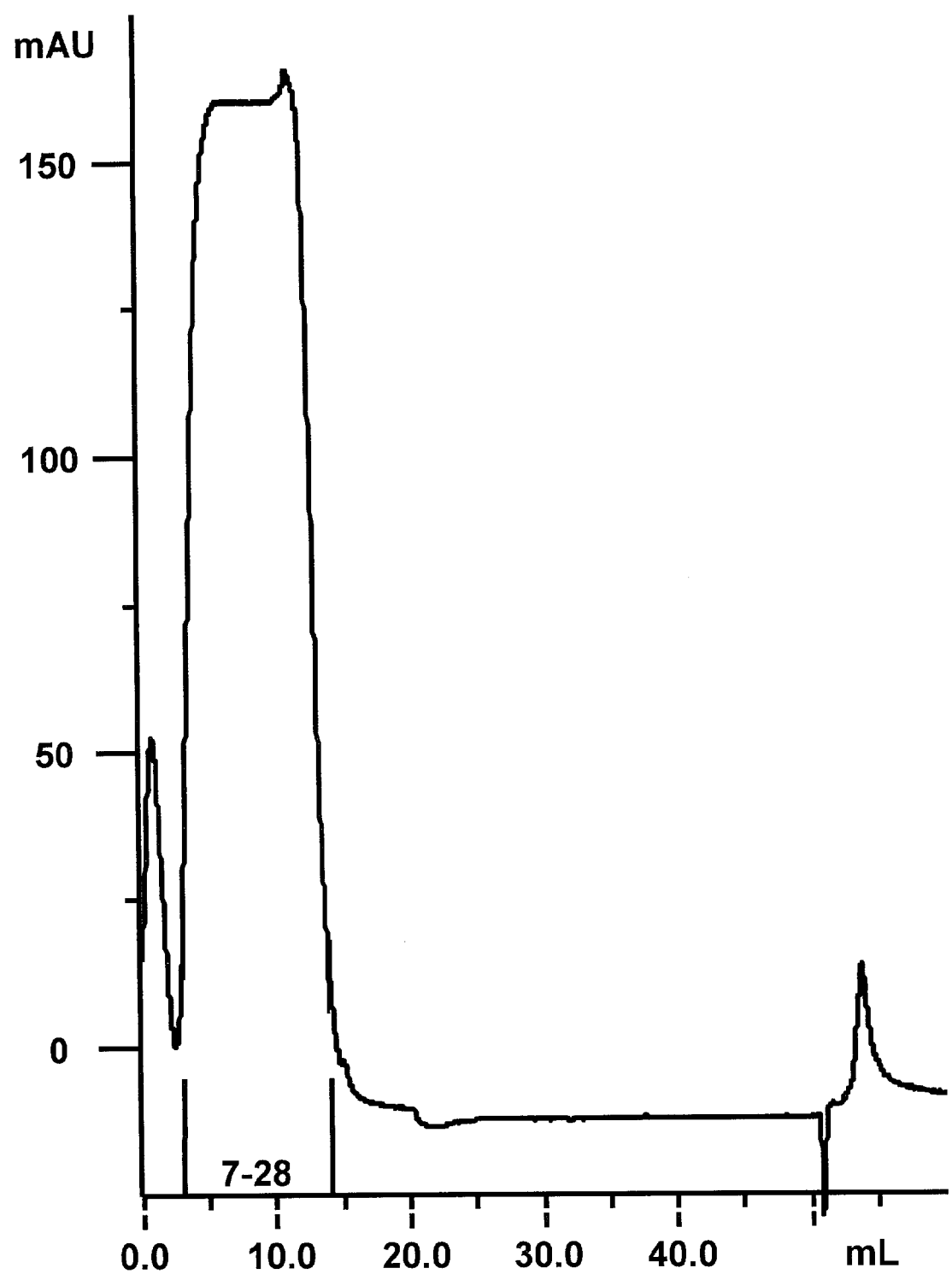

FIG. 44. Elution profile of the second IMAC chromatography step on a Ni-IDA column (Chelating Sepharose FF loaded with $Ni^{2+}$, Pharmacia) for the purification of E1 resulting from the in vitro processing of H6-K-E1 (purification: see FIG. 42) with Endo Lys-C. The flow through was collected in different fractions (1 to 40) that were screened for the presence of E1s-products. The fractions (7 to 28), containing intact E1 processed from H6-K-E1 were pooled. The Y-axis indicates absorbance given in mAU (milli absorbance units). The X-axis indicates the elution volume in mL.

Figure 45:
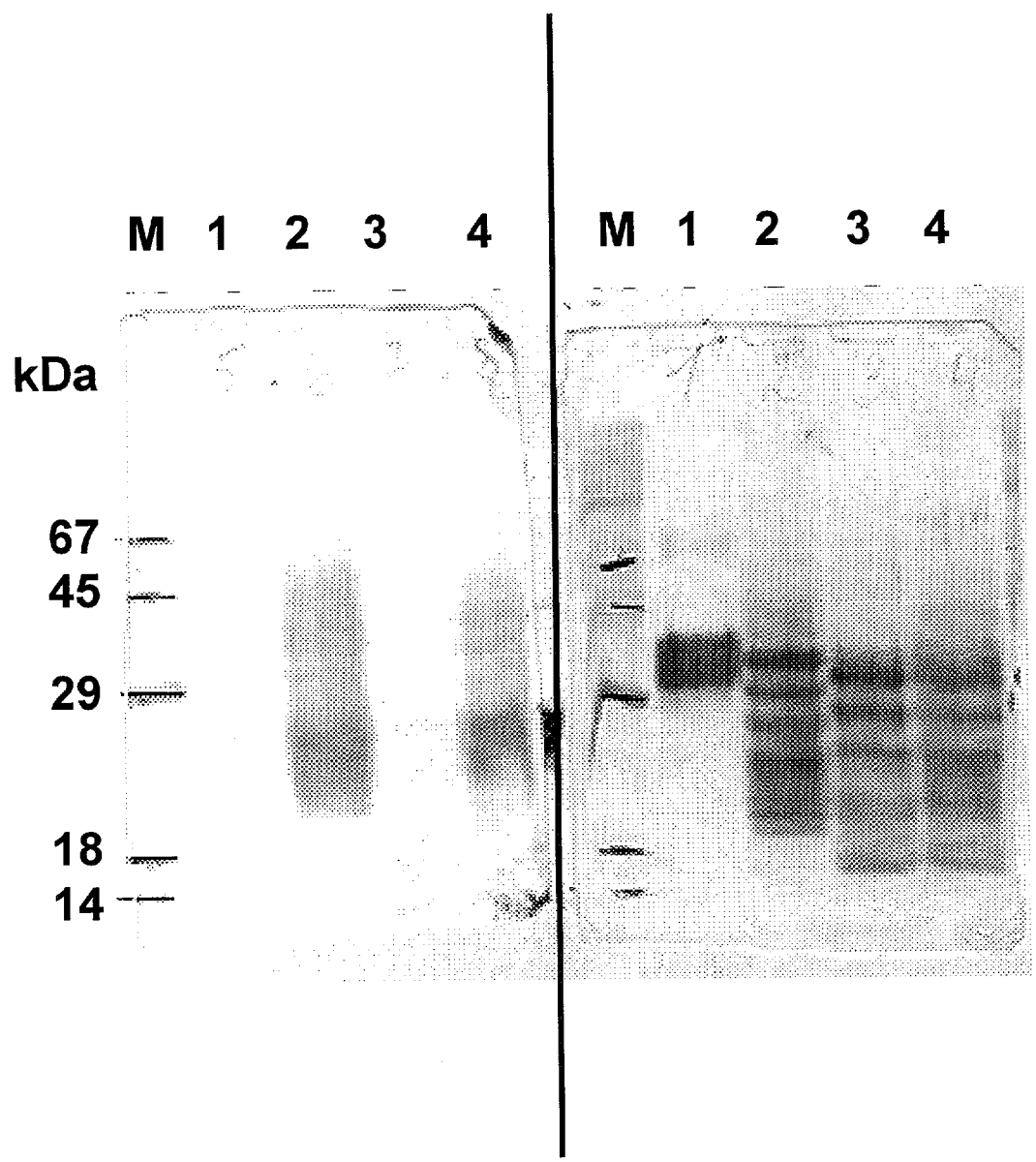

FIG. 45. Western-blot analysis indicating specific E1s proteins bands reacting with biotinylated heparin (see also Example 19). E1s preparations purified from HCV-recombinant vaccinia virus-infected mammalian cell culture or expressed by *H. polymorpha* were analyzed. The panel right from the vertical line shows a Western-blot developed with the biotinylated E1 specific monoclonal IGH 200. The panel left from the vertical line shows a Western-blot developed with biotinylated heparin. From these results it is concluded that mainly the lower-glycosylated E1 s has high affinity for heparin.
Lanes M: molecular weight marker (molecular weights indicated at the left).
Lanes 1: E1s from mammalian cells and alkylated during isolation.
Lanes 2: E1s-H6 expressed by *H. polymorpha* and sulphonated during isolation.
Lanes 3: E1s-H6 expressed by *H. polymorpha* and alkylated during isolation.
Lanes 4: same material as loaded in lane 2 but treated with dithiotreitol to convert the sulphonated Cys-thiol groups to Cys-thiol.

Figure 46:
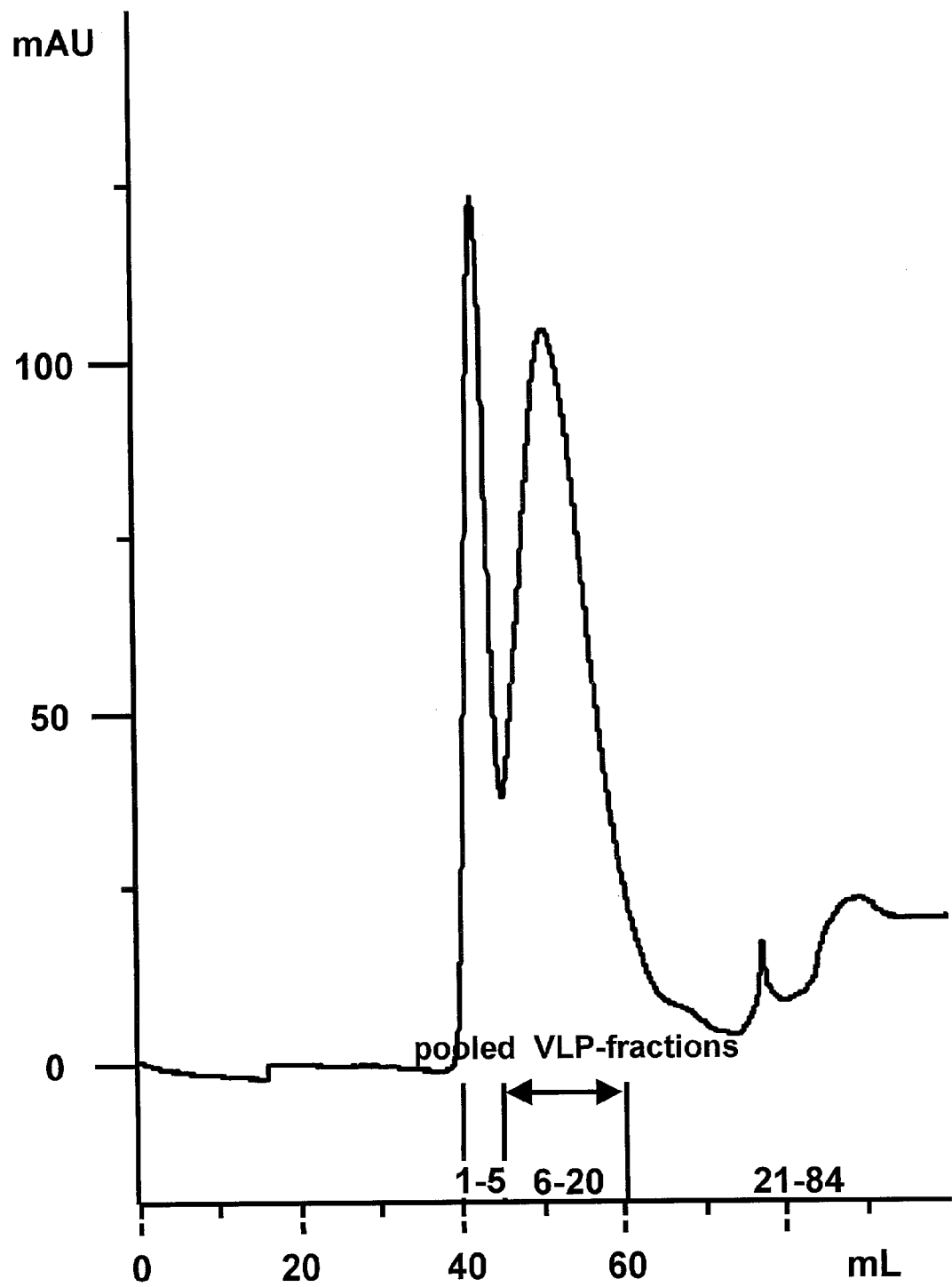

FIG. 46. Size exclusion chromatography (SEC) profile of the purified *H. polymorpha*-expressed E2-H6 in its sulphonated form, submitted to a ran in PBS, 3% betain to force virus-like particle formation by exchange of Empigen BB for betain. The pooled fractions containing the VLPs used for further study are indicated by "⇆". The Y-axis indicates absorbance given in mAU (milli absorbance units). The X-axis indicates the elution volume in mL. See also Example 20.

Figure 47:
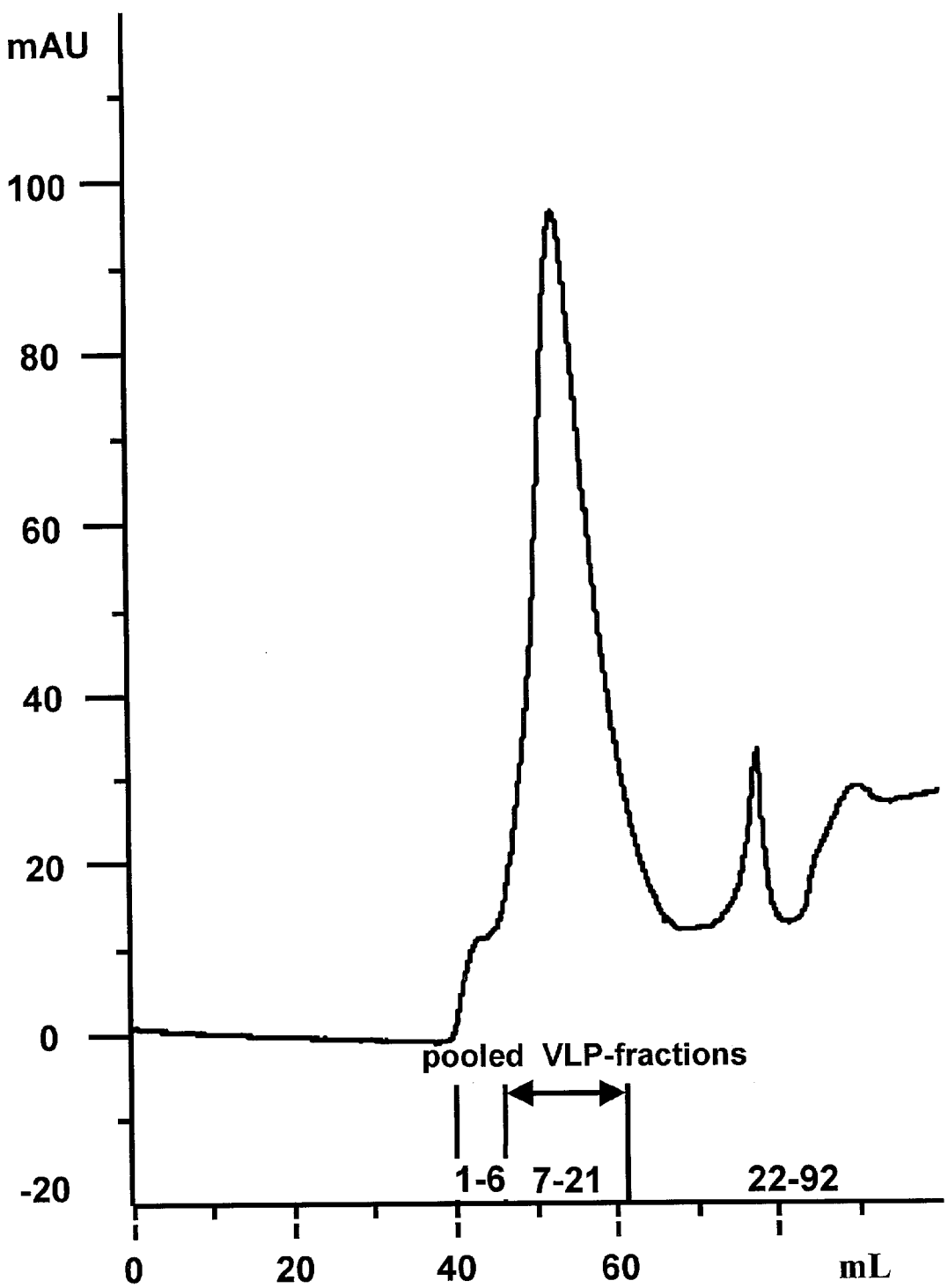

FIG. 47. Size exclusion chromatography (SEC) profile of the purified *H. polymorpha*-expressed E2-H6 in its alkylated form, submitted to a run in PBS, 3% betain to force virus-like particle formation by exchange of Empigen BB for betain. The pooled fractions containing the VLPs are indicated by "⇆". The Y-axis indicates absorbance given in mAU (milli absorbance units). The X-axis indicates the elution volume in mL. See also Example 20.

Figure 48:
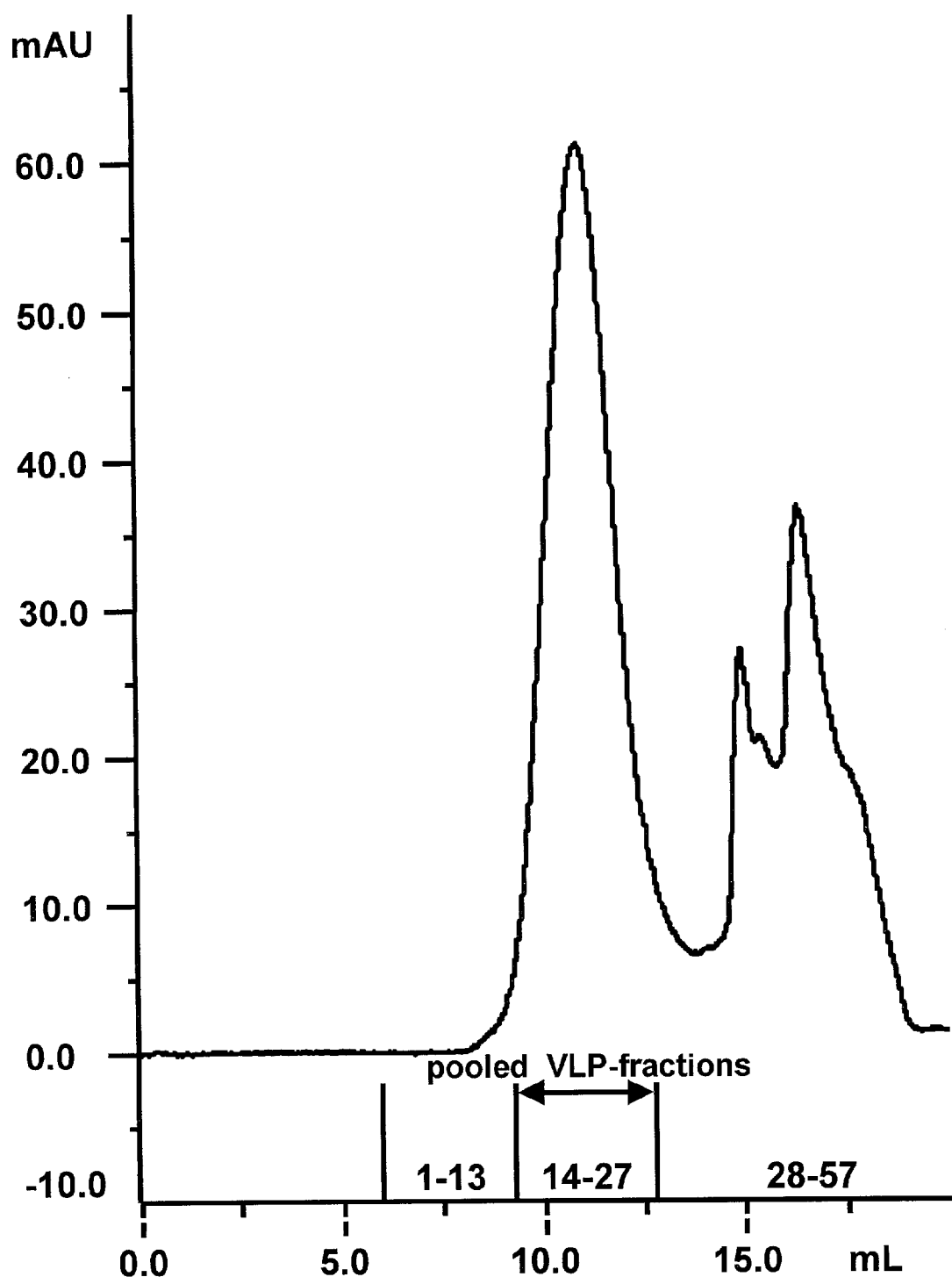

FIG. 48. Size exclusion chromatography (SEC) profile of the purified *H. polymorpha*-expressed E1 in its sulphonated form, submitted to a run in PBS, 3% betain to force virus-like particle formation by exchange of Empigen BB for betain. The pooled fractions containing the VLPs are indicated by "⇆". The Y-axis indicates absorbance given in mAU (milli absorbance units). The X-axis indicates the elution volume in mL. See also Example 20.

Figure 49:
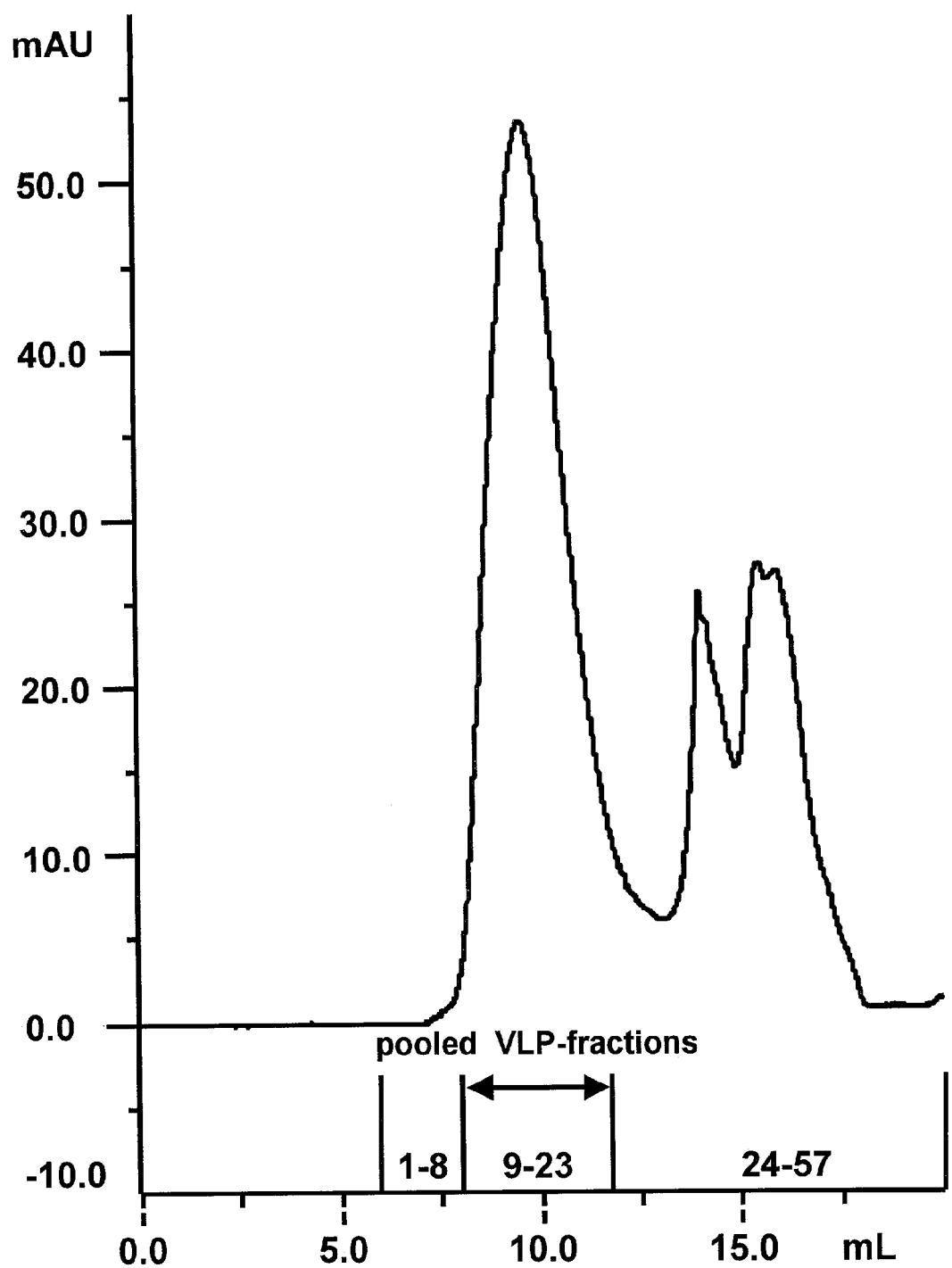

FIG. 49. Size exclusion chromatography (SEC) profile of the purified *H. polymorpha*-expressed E1 in its alkylated form, submitted to a run in PBS, 3% betain to force virus-like particle formation by exchange of Empigen BB for betain. The pooled fractions containing the VLPs are indicated by "⇆". The Y-axis indicates absorbance given in mAU (milli absorbance units). The X-axis indicates the elution volume in mL. See also Example 20.

Figure 50:
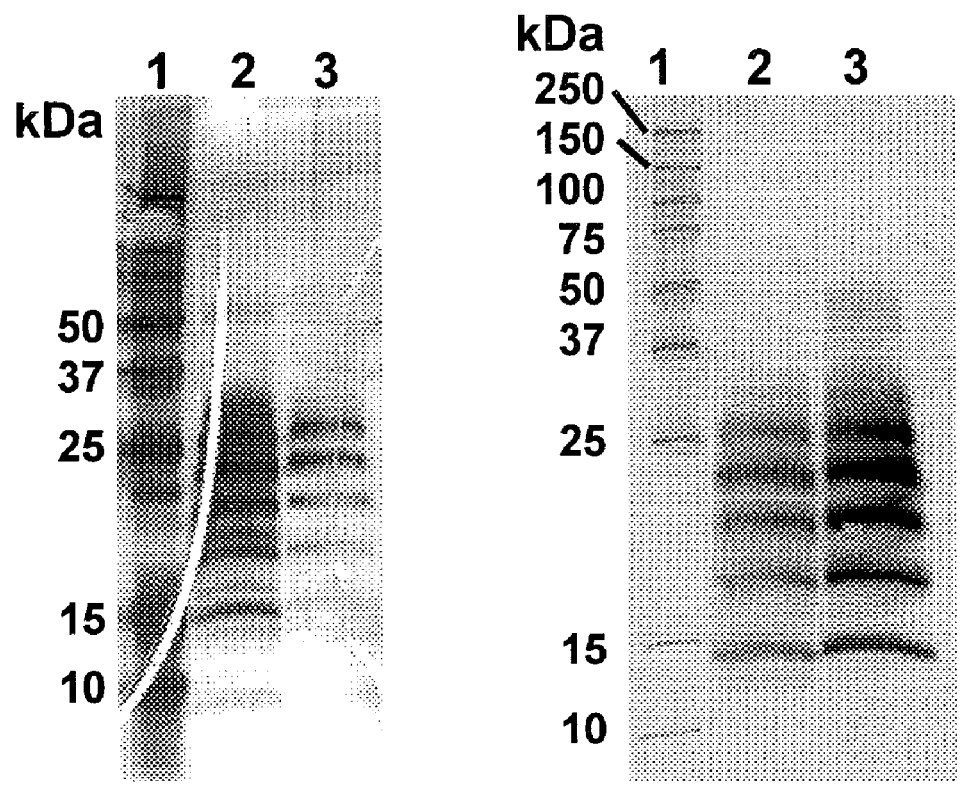

FIG. 50. SDS-PAGE (under reducing conditions) and western blot analysis of VLPs as isolated after size exclusion chromatography (SEC) as described in FIGS. 48 and 49. Left panel: silver-stained SDS-PAGE gel. Right panel: western blot using a specific monoclonal antibody directed against E1 (IGH201). Lanes 1: molecular weight markers (molecular weights indicated at the left); lanes 2: pool of VLPs containing sulphonated E1 (cfr. FIG. 48); lanes 3: pool of VLPs containing alkylated E1 (cfr. FIG. 49). See also Example 20.

Figure 51:
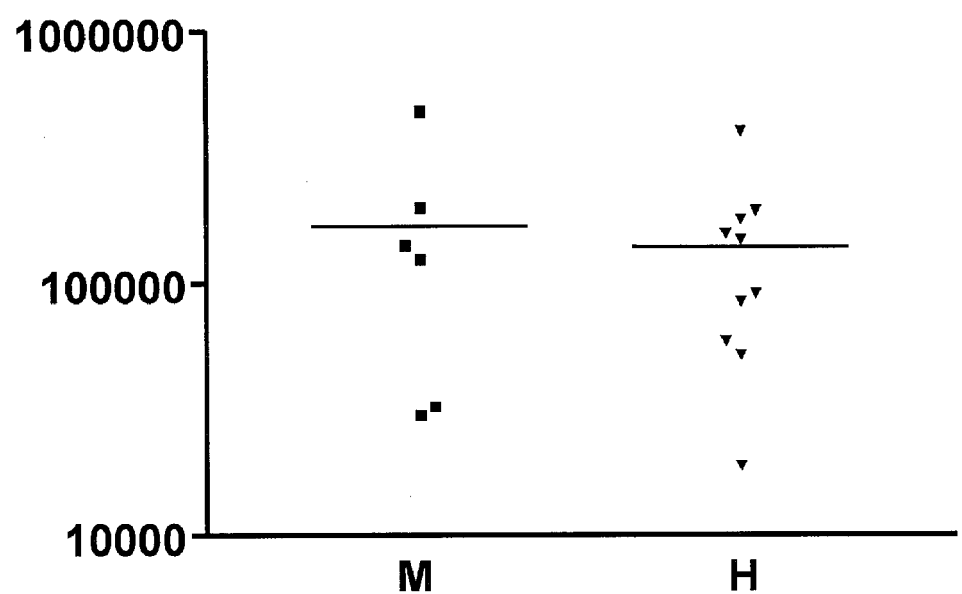
Figure 51:
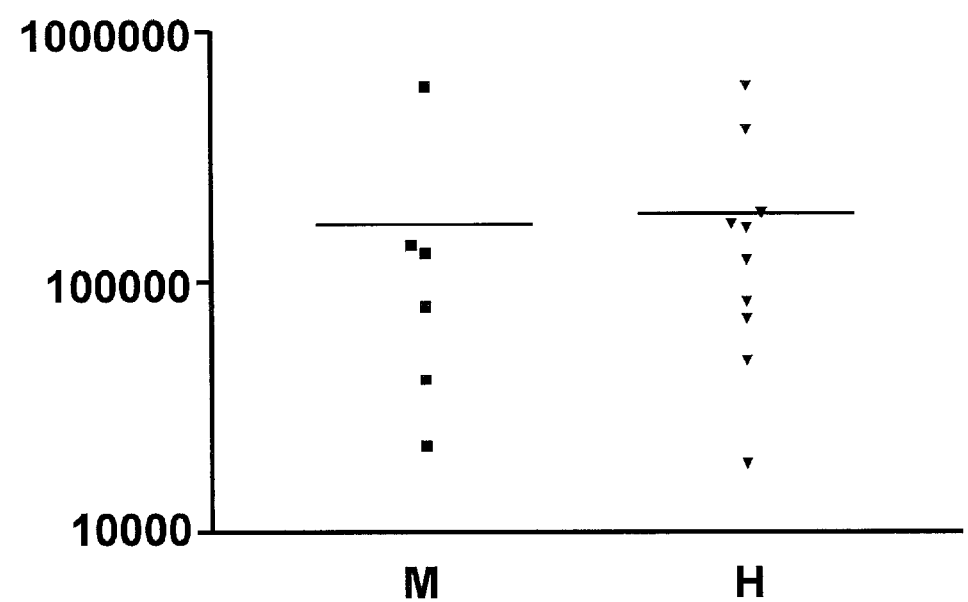

FIG. 51. E1 produced in mammalian cells ("M") or *Hansenula*-produced E1 ("H") were coated on a ELISA solid support to determine the end point titer of antibodies present in sera after vaccination of mice with E1 produced in mammalian cells (top panel), or after vaccination of mice with *Hansenula*-produced E1 (bottom panel). The horizontal bar represents the mean antibody titer. The end-point titers (fold-dilution) are indicated on the Y-axis. See also Example 22.

Figure 52:
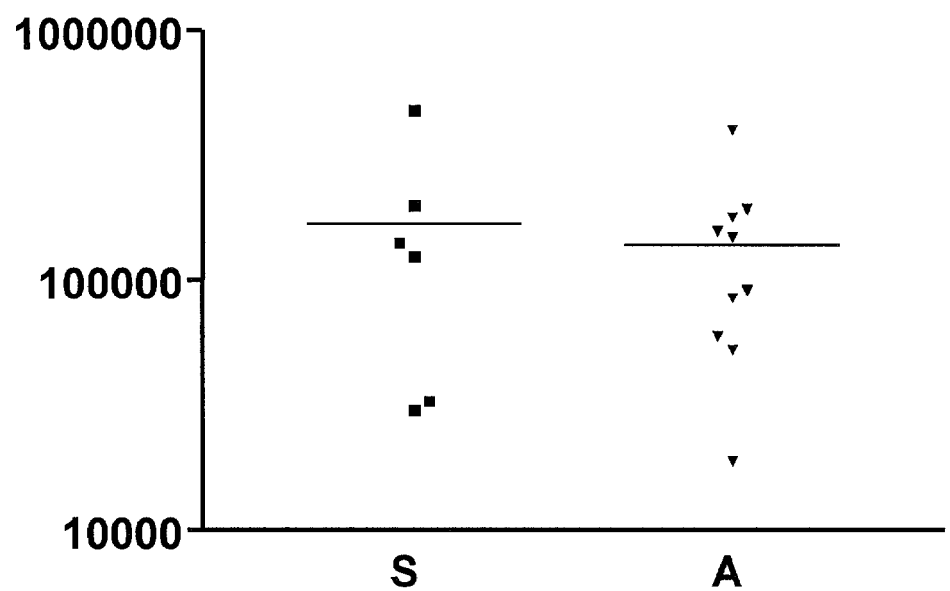
Figure 52:
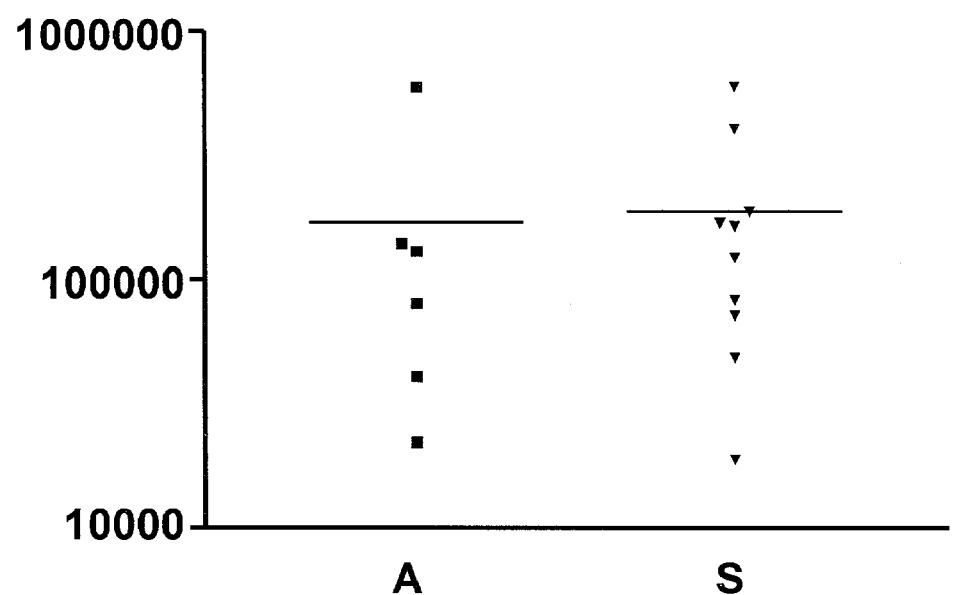

FIG. 52. *Hansenula*-produced E1 was alkylated ("A") or sulphonated ("S") and coated on a ELISA solid support to determine the end point titer of antibodies present in sera after vaccination of mice with *Hansenula*-produced E1 that was alkylated (top panel), or after vaccination of mice with *Hansenula*-produced E1 that was sulphonated (bottom panel). The horizontal bar represents the mean antibody titer. The end-point titers (fold-dilution) are indicated on the Y-axis. See also Example 23.

Figure 53:
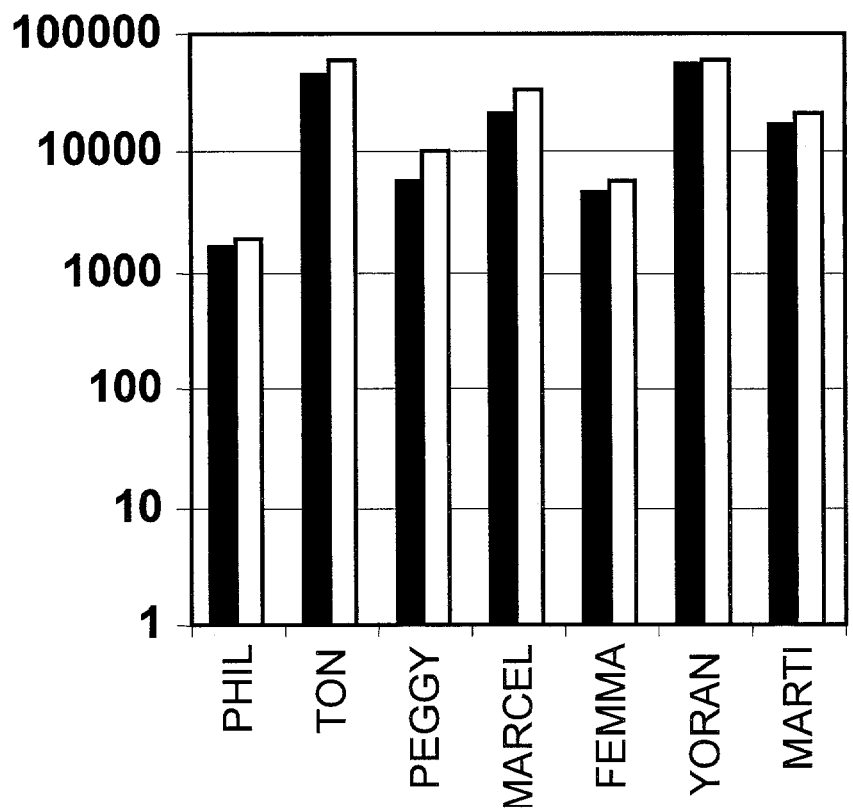
Figure 53:
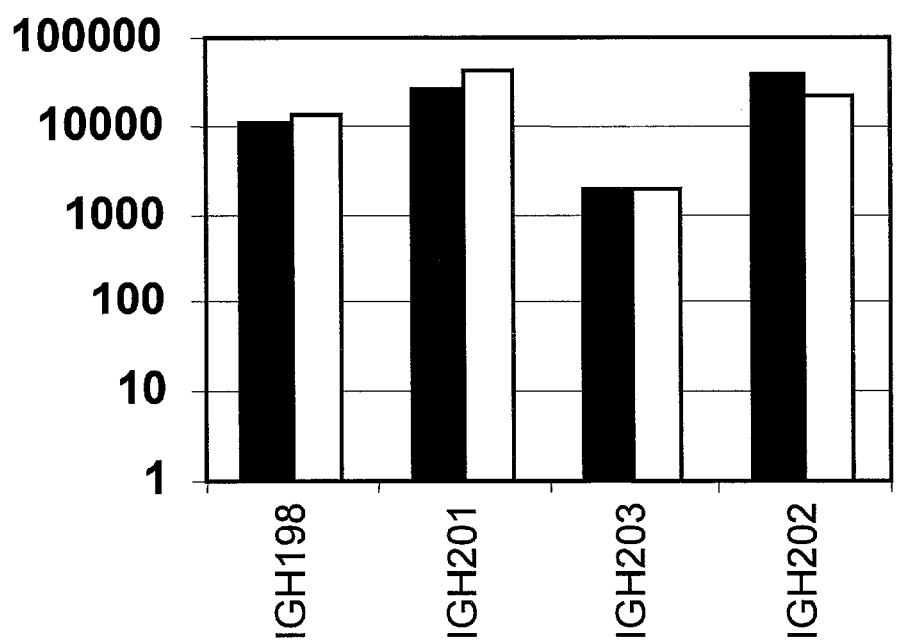

FIG. 53. HCV E1 produced by HCV-recombinant vaccinia virus-infected mammalian cells and HCV E1 produced by *H. polymorpha* were coated directly to ELISA plates. End point titers of antibodies were determined in sera of chimpanzees vaccinated with E1 produced by mammalian cells (top panel) and of murine monoclonal antibodies raised against E1 produced by mammalian cells (bottom panel). Chimpanzees Yoran and Marti were prophylactically vaccinated. Chimpanzees Ton, Phil, Marcel, Peggy and Femma were therapeutically vaccinated. Black filled bars: ELISA plate coated with E1 produced by mammalian cells. Open bars: ELISA plate coated with E1 produced by *Hansenula*. The end-point titers (fold-dilution) are indicated on the Y-axis. See also Example 24.

Figure 54:
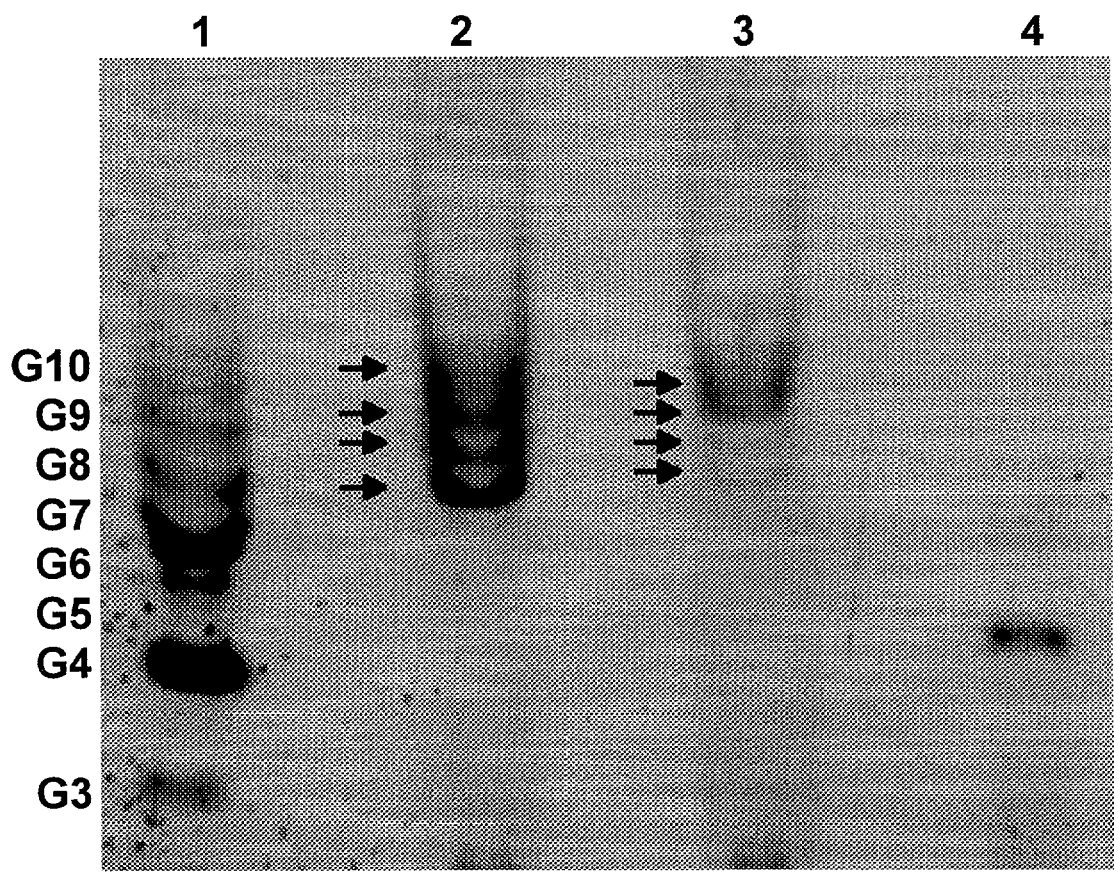

FIG. 54. Fluorophore-assisted carbohydrate gelelectrophoresis of oligosaccharides released from E1 produced by recombinant vaccinia virus-infected mammalian cells and from E1-H6 protein produced by *Hansenula*.
Lane 1: Glucose ladder standard with indication at the left of the number of monosaccharides (3 to 10, indicated by G3 to G10).
Lane 2: 25 µg N-linked oligosaccharides released from (alkylated) E1 produced by mammalian cells.
Lane 3: 25 µg N-linked oligosaccharides released from (alkylated) E1-H6 produced by *Hansenula*.
Lane 4: 100 pmoles maltotetraose.
See also Example 25.

Figure 55:
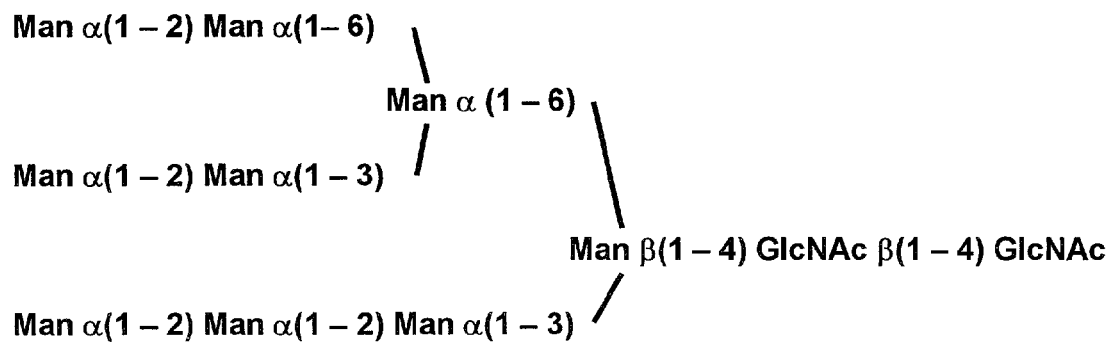
Figure 55:
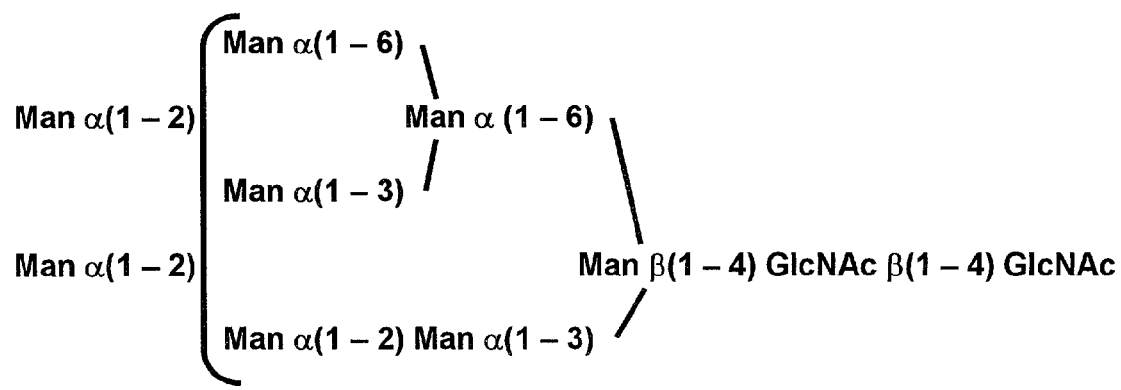
Figure 55:
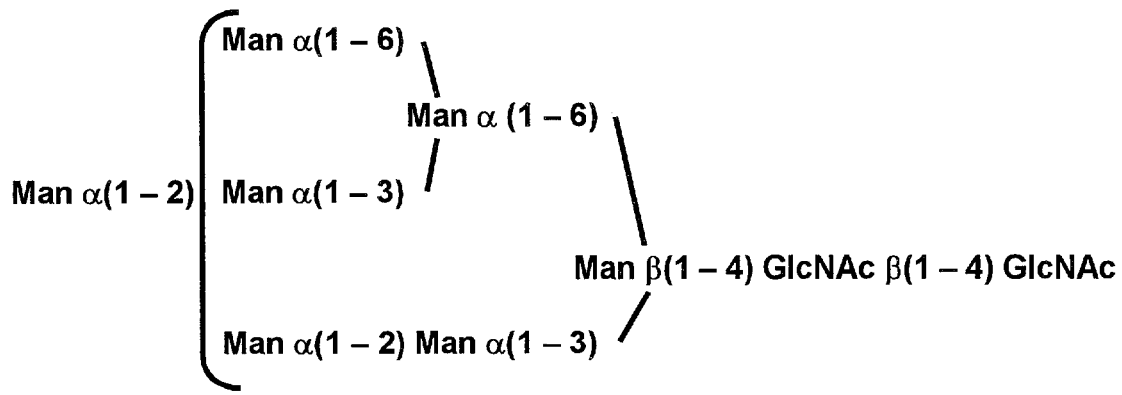
Figure 55:
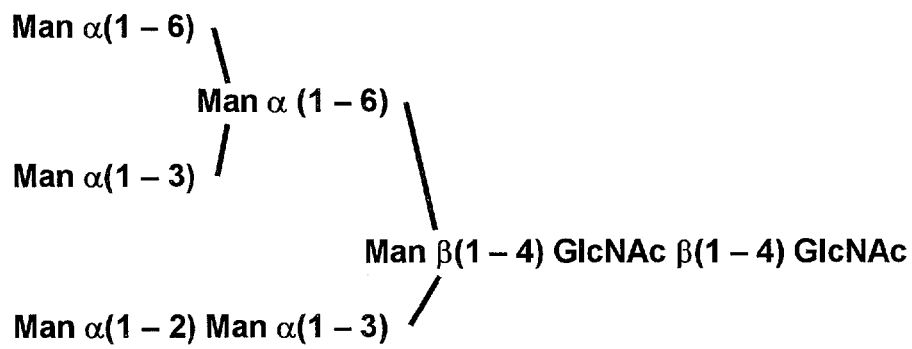
Figure 55:
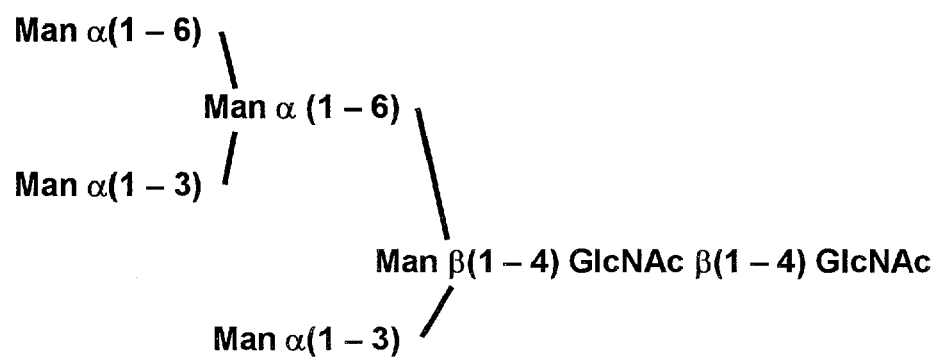

FIG. 55. This figure shows the simplified structures of the reference oligomannoses Man-9 (FIG. 55.A), Man-8 (FIG. 55.B), Man-7 (FIG. 55.C), Man-6 (FIG. 55.D) and Man-5 (FIG. 55.E). "Man"=mannose; "GlcNAc"=N-acetylglucosamine; "α"=α-linkage between 2 mannoses; "β"=β-linkage between 2 mannoses; "(1-3)", "(1-4)" and "(1-6)"=(1-3), (1-4) and (1-6) linkage between 2 mannoses, respectively. The brackets in FIGS. 55.B and 55.C indicate that the 2 and 1, respectively, mannose residue(s) to the left of the bracket are coupled in an α (1-2) bond to 2 and 1, respectively, of the 3 mannose residues right from the bracket. See also Example 26.

Figure 56:
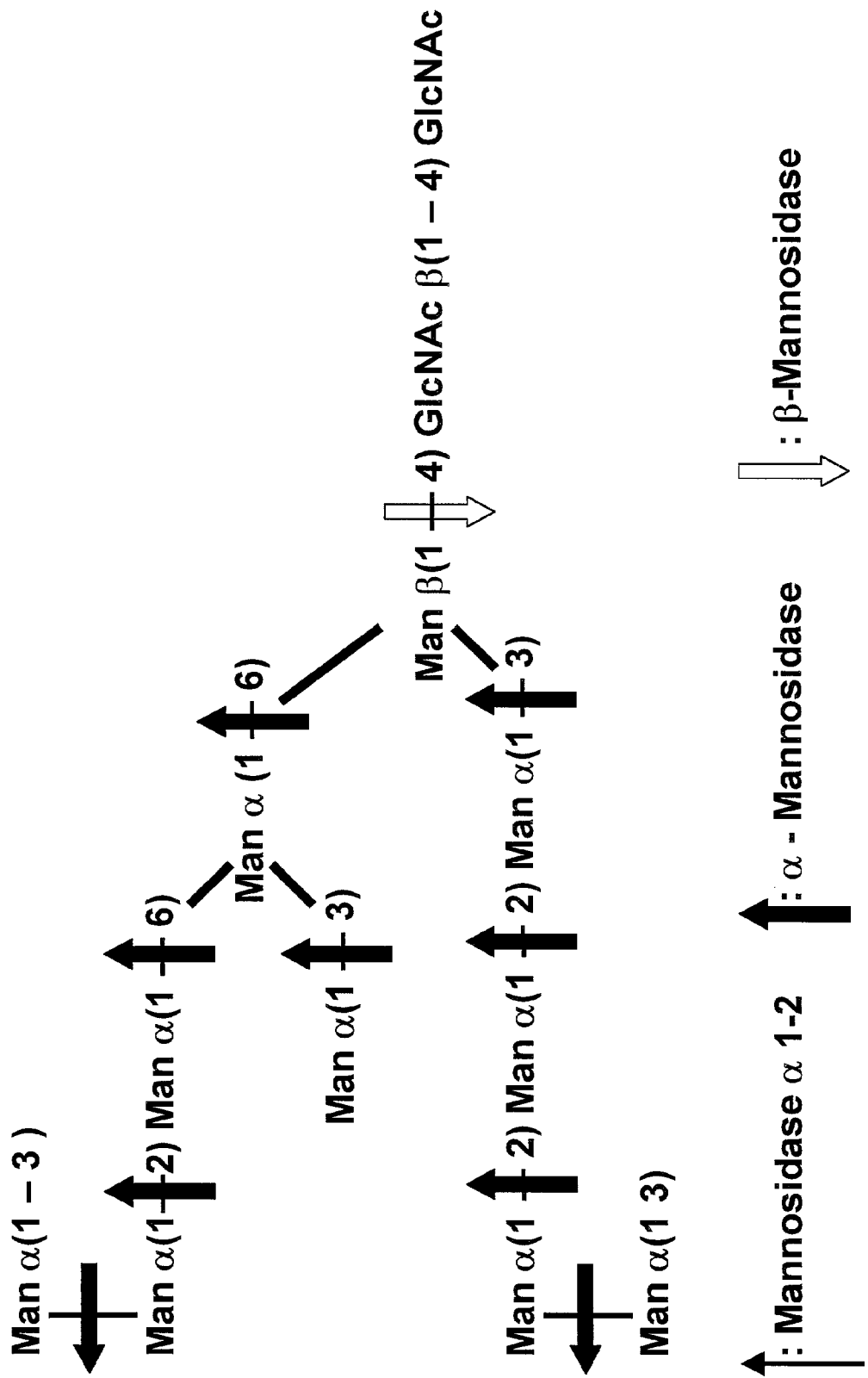

FIG. 56. This figure shows a higher oligomannose consisting of 10 mannose moieties coupled to chitobiose. Each terminal mannose residue is linked by an α 1-3 bond to a non-terminal mannose residue. The thin upward pointing arrow indicates the oligosaccharide bonds which are prone to cleavage by α 1-2 Mannosidase (none for this oligomannose), the thick upward or leftward pointing arrow indicates the oligosaccharide bonds which are prone to cleavage by a Mannosidase after removal of the α 1-2-linked mannoses (not applicable to this oligomannose) and the empty downward pointing arrow indicates the oligosaccharide bonds which are prone to cleavage by β Mannosidase after removal of the α-linked mannoses. See also Example 26.

Figure 57:
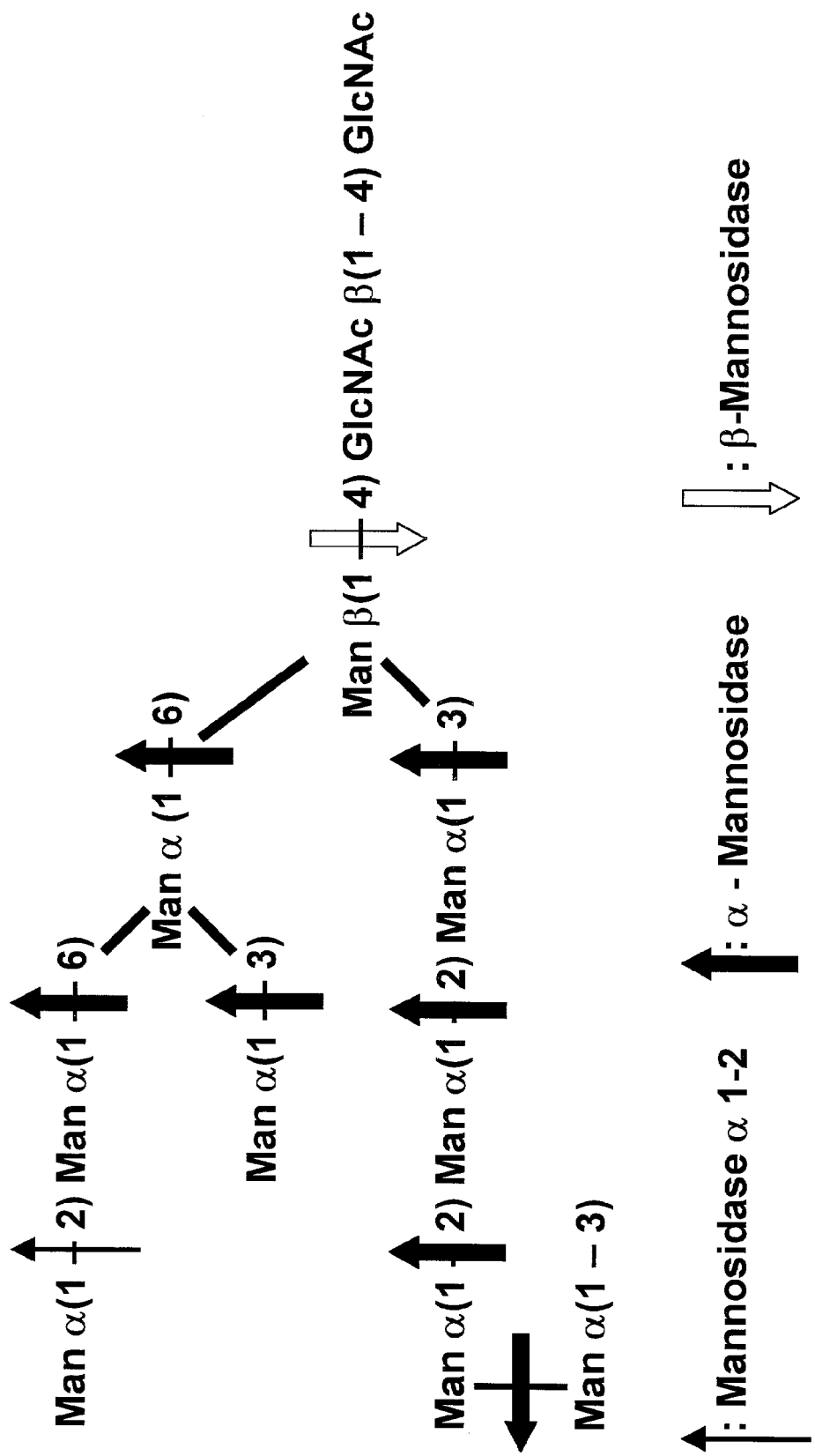

FIG. 57. This figure shows a higher oligomannose consisting of 9 mannose moieties coupled to chitobiose. In this oligomannose, one terminal mannose residue is linked by an α 1-2 bond to the non-terminal mannose residue. The thin upward pointing arrow indicates the oligosaccharide bonds which are prone to cleavage by α 1-2 Mannosidase, the thick upward or leftward pointing arrow indicates the oligosaccharide bonds which are prone to cleavage by α Mannosidase after removal of the α 1-2-linked mannoses and the empty downward pointing arrow indicates the oligosaccharide bonds which are prone to cleavage by β Mannosidase after removal of the α-linked mannoses. See also Example 26.

Figure 58:
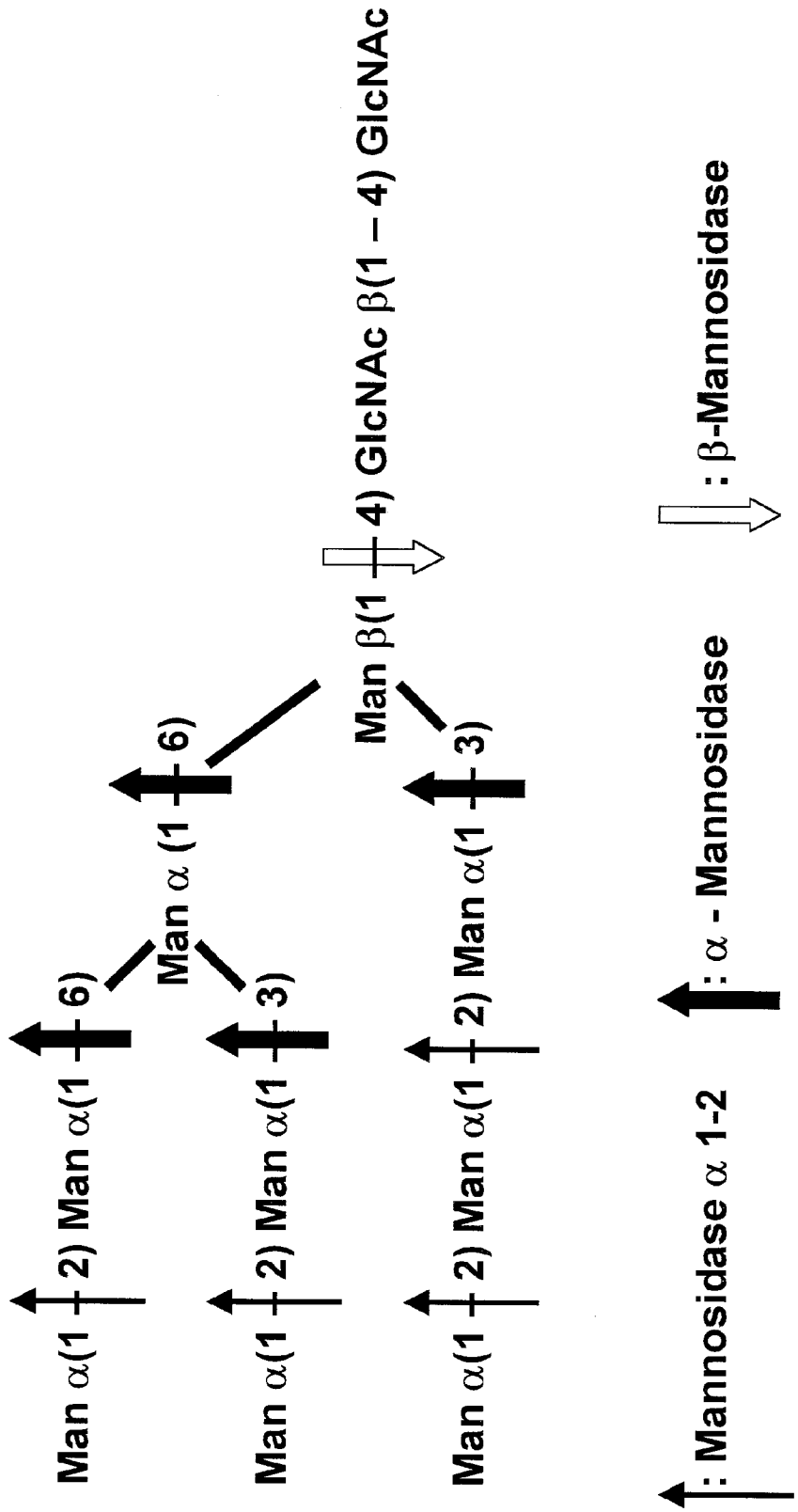

FIG. 58. This figure shows the reference higher oligomannose Man-9 consisting of 9 mannose moieties coupled to chitobiose. In this oligomannose, all terminal mannose residues are linked by an α 1-2 bond to a non-terminal mannose residue. The thin upward pointing arrow indicates the oligosaccharide bonds which are prone to cleavage by α 1-2 Mannosidase, the thick upward pointing arrow indicates the oligosaccharide bonds which are prone to cleavage by a Mannosidase after removal of the α 1-2-linked mannoses and the empty downward pointing arrow indicates the oligosaccharide bonds which are prone to cleavage by β Mannosidase after removal of the α-linked mannoses. See also Example 26.

Figure 59:
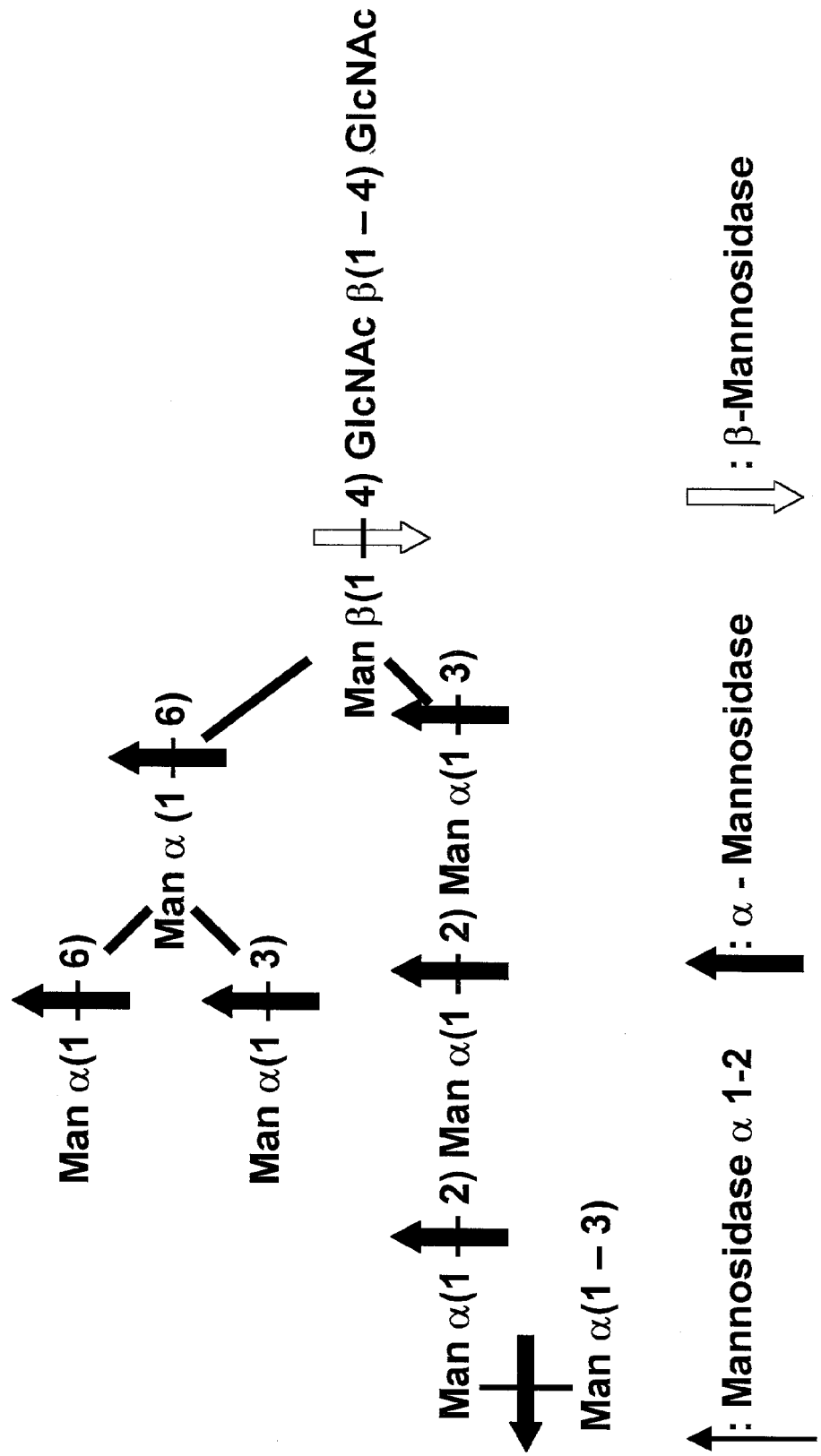

FIG. 59. This figure shows the higher oligomannose Man-8 consisting of 8 mannose moieties coupled to chitobiose. In this oligomannose, all terminal mannose residues are linked by an α 1-3 or an α 1-6 bond to a non-terminal mannose residue which renders this structure fully resistant to cleavage by α 1-2 Mannosidase. The thick upward pointing arrow indicates the oligosaccharide bonds which are prone to cleavage by α Mannosidase and the empty downward pointing arrow indicates the oligosaccharide bonds which are prone to cleavage by β Mannosidase after removal of the α-linked mannoses. See also Example 26.

Figure 60:
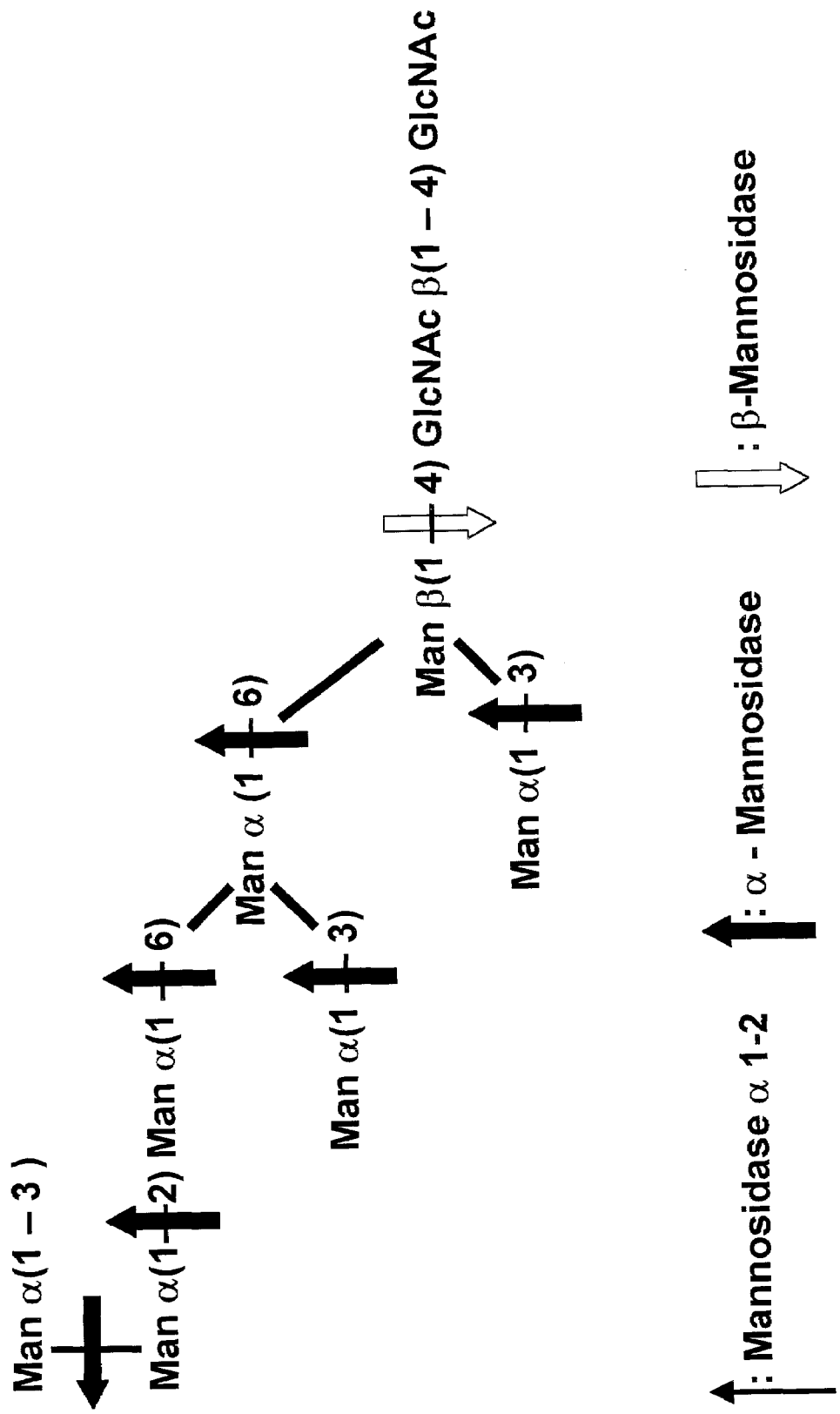

FIG. 60. This figure shows the higher oligomannose Man-7 consisting of 7 mannose moieties coupled to chitobiose. In this oligomannose, all terminal mannose residues are linked by an α 1-3 bond to a non-terminal mannose residue which renders this structure fully resistant to cleavage by α 1-2 Mannosidase. The thick upward pointing arrow indicates the oligosaccharide bonds which are prone to cleavage by α Mannosidase and the empty downward pointing arrow indicates the oligosaccharide bonds which are prone to cleavage by β Mannosidase after removal of the α-linked mannoses. See also Example 26.

Figure 61:
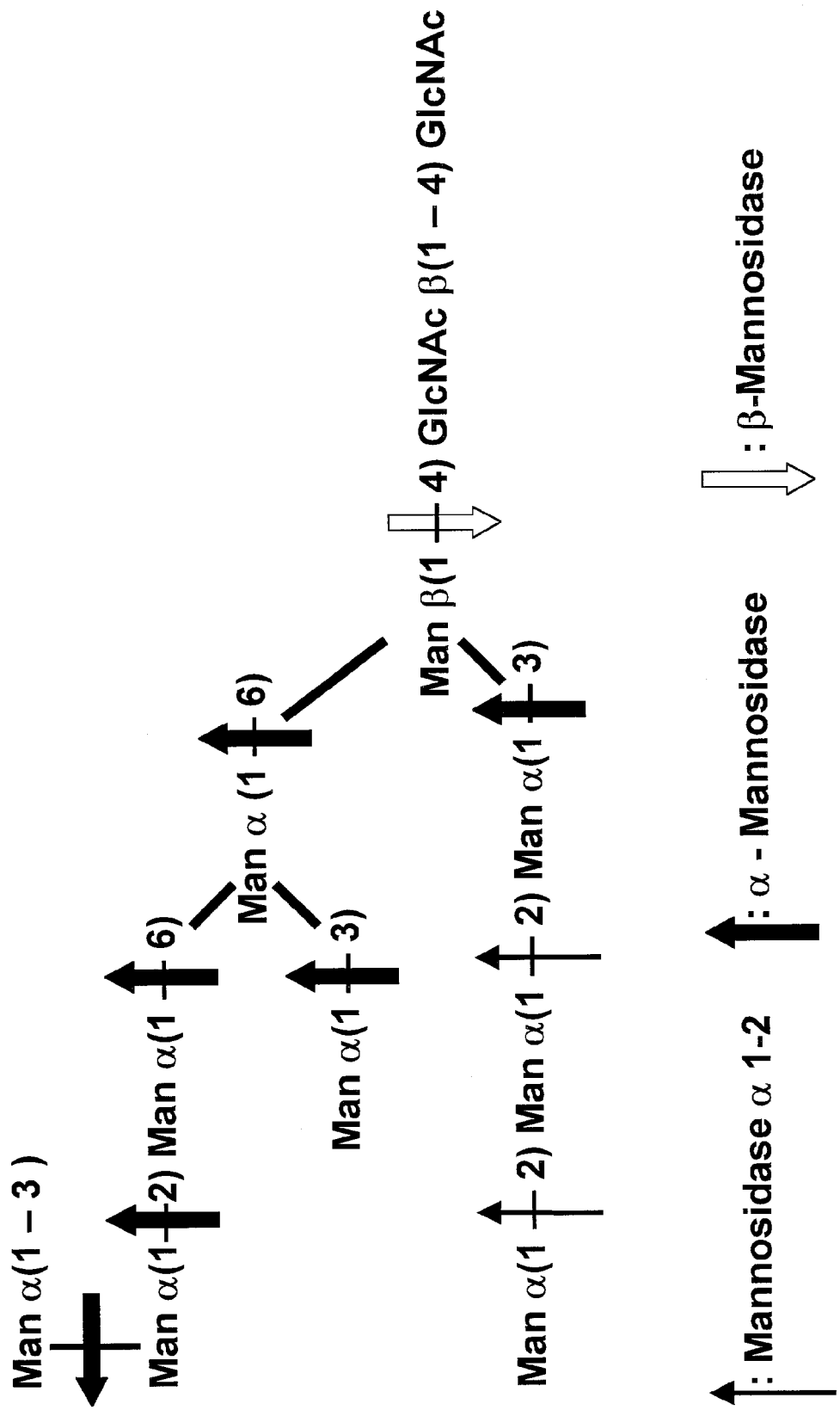

FIG. 61. This figure shows a higher oligomannose consisting of 9 mannose moieties coupled to chitobiose. In this oligomannose, one terminal mannose residue is linked by an α 1-2 bond to the non-terminal mannose residue. The thin upward pointing arrow indicates the oligosaccharide bonds which are prone to cleavage by α 1-2 Mannosidase, the thick upward or leftward pointing arrow indicates the oligosaccharide bonds which are prone to cleavage by α Mannosidase after removal of the α 1-2-linked mannoses and the empty downward pointing arrow indicates the oligosaccharide bonds which are prone to cleavage by β Mannosidase after removal of the C-linked mannoses. See also Example 26.

Figure 62:
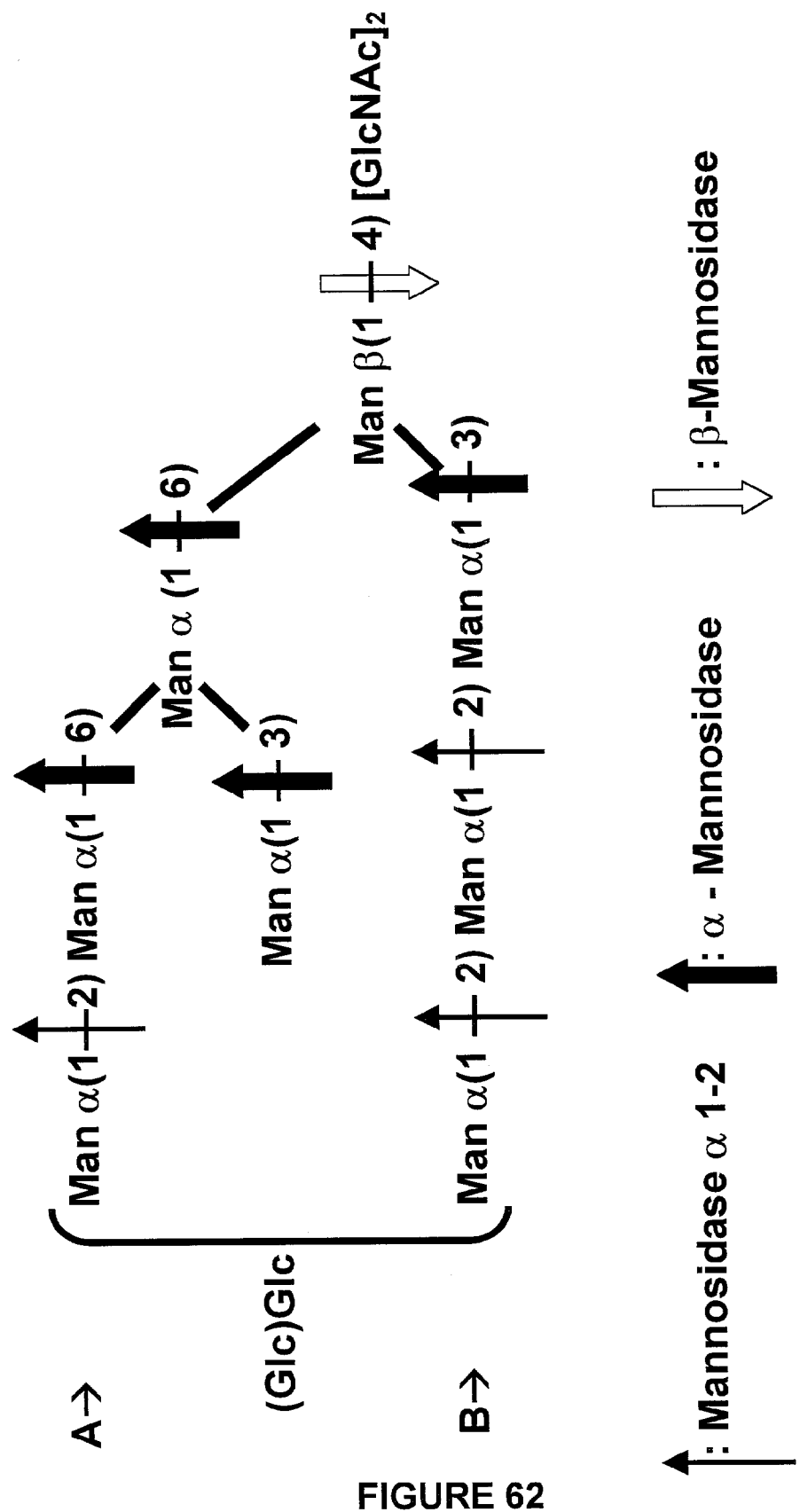

FIG. 62. This figure shows the putative glucose-containing oligosaccharide consisting of 1 or 2 glucose moieties and 8 mannose moieties coupled to chitobiose. In this oligosaccharide, either one of the terminal α 1-2-linked mannose residues of the A- or B-branch ("A→" and "B→" in the Figure) is carrying one or two glucose residues, as indicated by (Glc)Glc to the left of the of the bracket. The thin upward pointing arrow indicates the oligosaccharide bonds which are prone to cleavage by α 1-2 Mannosidase given that no glucose is attached to the terminal mannose residue. The thick upward or leftward pointing arrow indicates the oligosaccharide bonds which are prone to cleavage by α Mannosidase after removal of the α 1-2-linked mannoses and the empty downward pointing arrow indicates the oligosaccharide bonds which are prone to cleavage by β Mannosidase after removal of the α-linked mannoses. An overview of the possible reaction products is given in Table 10 of Example 26.

Figure 63:
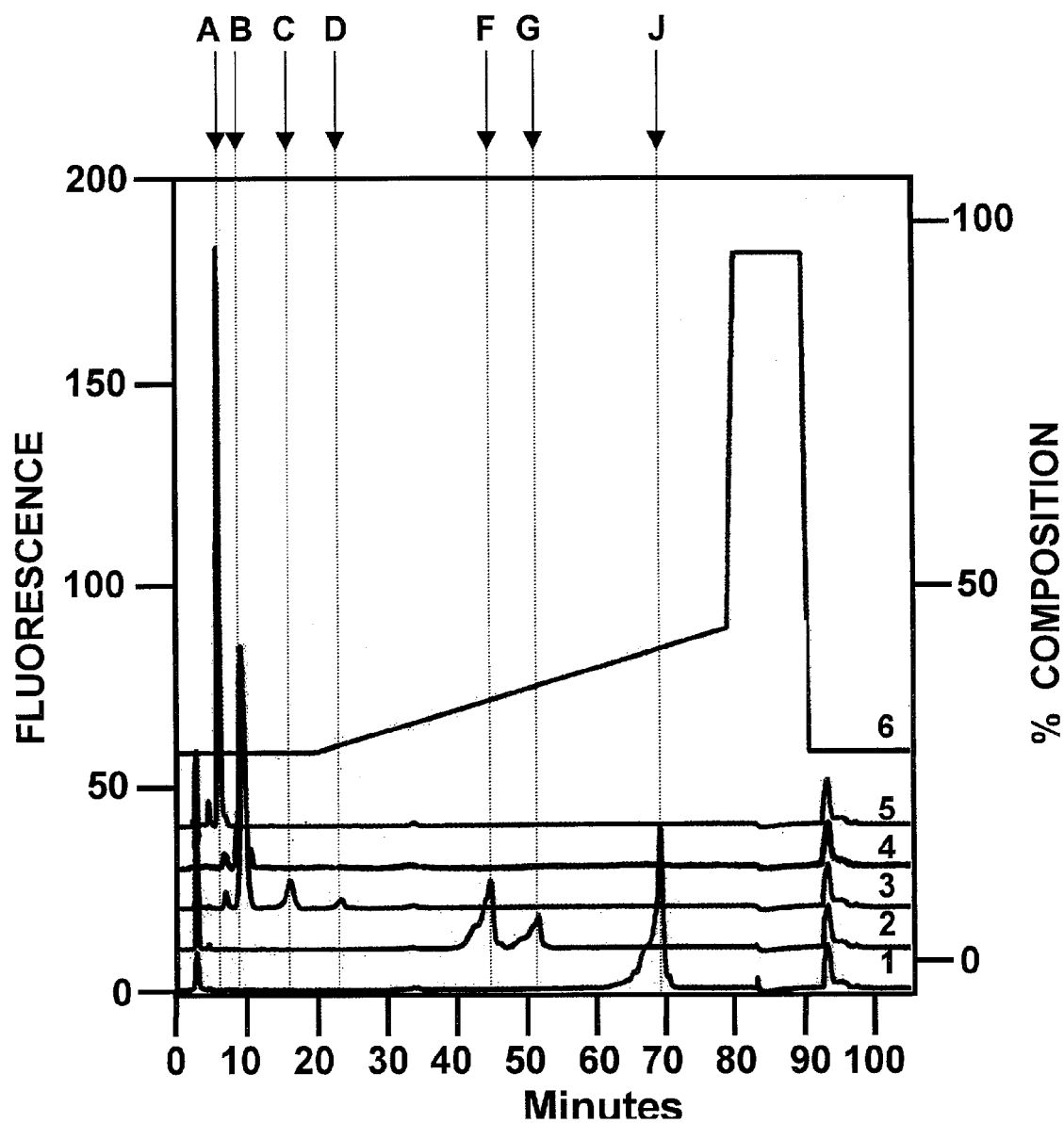

FIG. 63. The reaction products of Man-9 after overnight incubation with or without exoglycosidases were separated on a TSK gel-Amide-80 (0.46×25 cm, Tosoh Biosep) column coupled to a Waters Alliance HPLC station. Separation of the oligosaccharides was carried out at ambient temperature at 1.0 mL/min. Solvent A consisted of 0.1% acetic acid in acetonitrile and solvent B consisted of 0.2% acetic acid-0.2% triethylamine in water. Separation of 2-AB labeled oligosaccharides was carried out using 28% B isocratic for 5 column volumes followed by a linear increase to 45% B over fifteen column volumes. The composition of the elution solvent is indicate on the right Y-axis as % solvent B in solvent A (v/v). The elution time is indicated in minutes on the X-axis. The left Y-axis indicates fluorescence of eluting 2-aminobenzamide (2-AB)-labeled oligosaccharides. The excitation wavelength of 2-AB is 330 nm, the emission wavelength 420 nm.

Trace 1 ("1") of the chromatogram shows the elution of Man-9 incubated overnight without exoglycosidases. Trace 2 ("2") shows the elution of a mixture of Man-5 and Man-6 after overnight incubation of Man-9 with α 1-2 Mannosidase. Traces 3 and 4 ("3" and "4") show the elution of 4'-β-mannosyl chitobiose after 1 h and overnight incubation, respectively, of Man-9 with α-Mannosidase. Trace 5 ("5") shows the elution of chitobiose after overnight incubation of Man-9 with α and β-Mannosidase. Traces 1-5 are represented as overlays, as such their respective baselines are not all on the zero level. Trace 6 ("6") indicates the applied solvent gradient.

The peaks, when present, indicated by the letters A to K on top of the Figure represent: A, chitobiose; B, 4'-β-mannosyl-chitobiose; C, Man-2; D, Man-3; E, Man-4; F, Man-5; G, Man-6; H, Man-7; I, Man-8; J, Man-9; and K, Man-10. See also Example 26.

Figure 64:
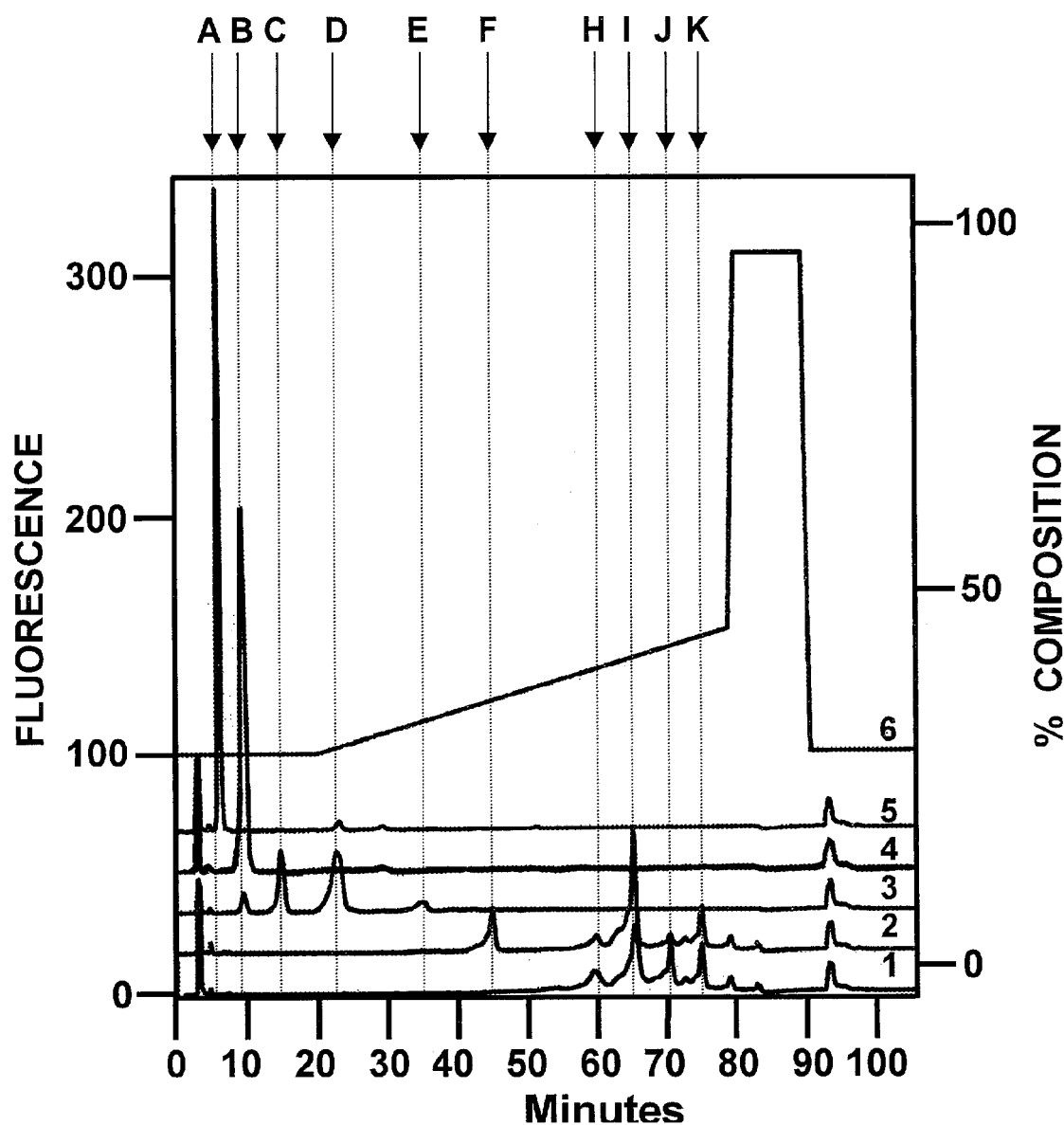

FIG. 64. The reaction products of the oligosaccharides derived from *Saccharomyces*-produced E1s after overnight incubation with or without exoglycosidases were separated on a TSK gel-Amide-80 (0.46×25 cm, Tosoh Biosep) column coupled to a Waters Alliance HPLC station. Separation of the oligosaccharides was carried out at ambient temperature at 1.0 mL/min. Solvent A consisted of 0.1% acetic acid in acetonitrile and solvent B consisted of 0.2% acetic acid-0.2% triethylamine in water. Separation of 2-AB labeled oligosaccharides was carried out using 28% B isocratic for 5 column volumes followed by a linear increase to 45% B over fifteen column volumes. The composition of the elution solvent is indicate on the right Y-axis as % solvent B in solvent A (v/v). The elution time is indicated in minutes on the X-axis. The left Y-axis indicates fluorescence of eluting 2-aminobenzamide (2-AB)-labeled oligosaccharides. The excitation wavelength of 2-AB is 330 nm, the emission wavelength 420 nm.

Trace 1 ("1") of the chromatogram shows the elution of oligosaccharides derived from *Saccharomyces*-produced E1s incubated overnight without exoglycosidases. Trace 2 ("2") shows the elution of oligosaccharides derived from *Saccharomyces*-produced E1s after overnight incubation of Man-9 with α 1-2 Mannosidase. Traces 3 and 4 ("3" and "4") show the elution of oligosaccharides derived from *Saccharomyces*-produced E1s after 1 h and overnight incubation, respectively, with α-Mannosidase. Trace 5 ("5") shows the elution of oligosaccharides derived from *Saccharomyces*-produced E1s after overnight incubation with α- and β-Mannosidase. Traces 1-5 are represented as overlays, as such their respective baselines are not all on the zero level. Trace 6 ("6") indicates the applied solvent gradient.

The peaks, when present, indicated by the letters A to K on top of the Figure represent: A, chitobiose; B, 4'-β-mannosyl-chitobiose; C, Man-2; D, Man-3; E, Man-4; F, Man-5; G, Man-6; H, Man-7; I, Man-8; J, Man-9; and K, Man-10. See also Example 26.

Figure 65:
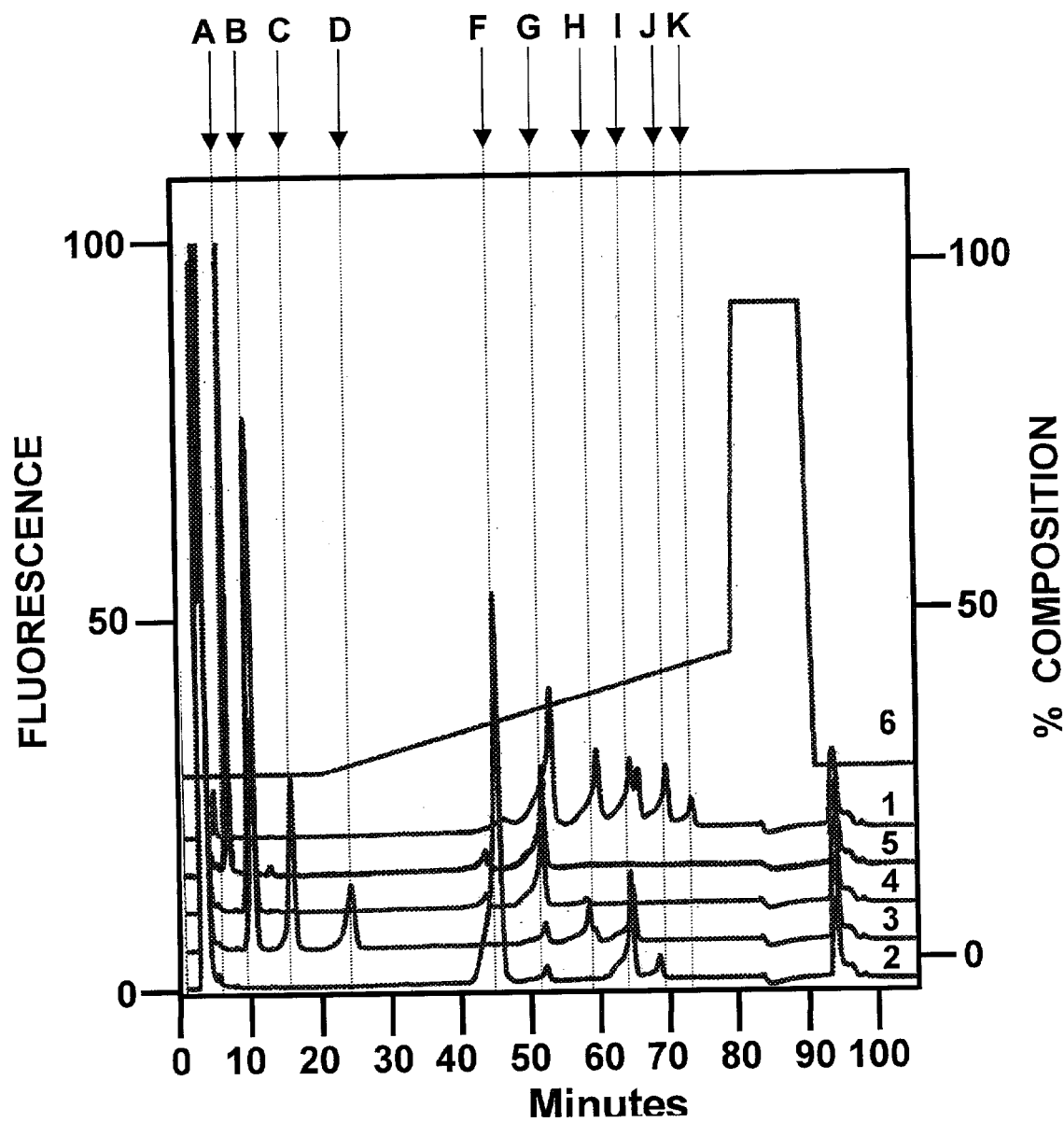

FIG. 65. The reaction products of the oligosaccharides derived from E1s produced in vaccinia-transfected mammalian cells after overnight incubation with or without exoglycosidases were separated on a TSK gel-Amide-80 (0.46×25 cm, Tosoh Biosep) column coupled to a Waters Alliance HPLC station. Separation of the oligosaccharides was carried out at ambient temperature at 1.0 mL/min. Solvent A consisted of 0.1% acetic acid in acetonitrile and solvent B consisted of 0.2% acetic acid-0.2% triethylamine in water. Separation of 2-AB labeled oligosaccharides was carried out using 28% B isocratic for 5 column volumes followed by a linear increase to 45% B over fifteen column volumes. The composition of the elution solvent is indicate on the right Y-axis as % solvent B in solvent A (v/v). The elution time is indicated in minutes on the X-axis. The left Y-axis indicates fluorescence of eluting 2-aminobenzamide (2-AB)-labeled oligosaccharides. The excitation wavelength of 2-AB is 330 nm, the emission wavelength 420 nm.

Trace 1 ("1") of the chromatogram shows the elution of oligosaccharides derived from E1s produced in vaccinia-transfected mammalian cells incubated overnight without exoglycosidases. Trace 2 ("2") shows the elution of oligosaccharides derived from E1s produced in vaccinia-transfected mammalian cells after overnight incubation of Man-9 with a 1-2 Mannosidase. Traces 3 and 4 ("3" and "4") show the elution of oligosaccharides derived from E1s produced in vaccinia-transfected mammalian cells after 1 h and overnight incubation, respectively, with α-Mannosidase. Trace 5 ("5") shows the elution of oligosaccharides derived from E1s produced in vaccinia-transfected mammalian cells after overnight incubation with α- and β-Mannnosidase. Traces 1-5 are represented as overlays, as such their respective baselines are not all on the zero level. Trace 6 ("6") indicates the applied solvent gradient.

The peaks, when present, indicated by the letters A to K on top of the Figure represent: A, chitobiose; B, 4'-β-mannosyl-chitobiose; C, Man-2; D, Man-3; E, Man-4; F, Man-5; G, Man-6; H, Man-7; I, Man-8; J, Man-9; and K, Man-10. See also Example 26.

Figure 66:
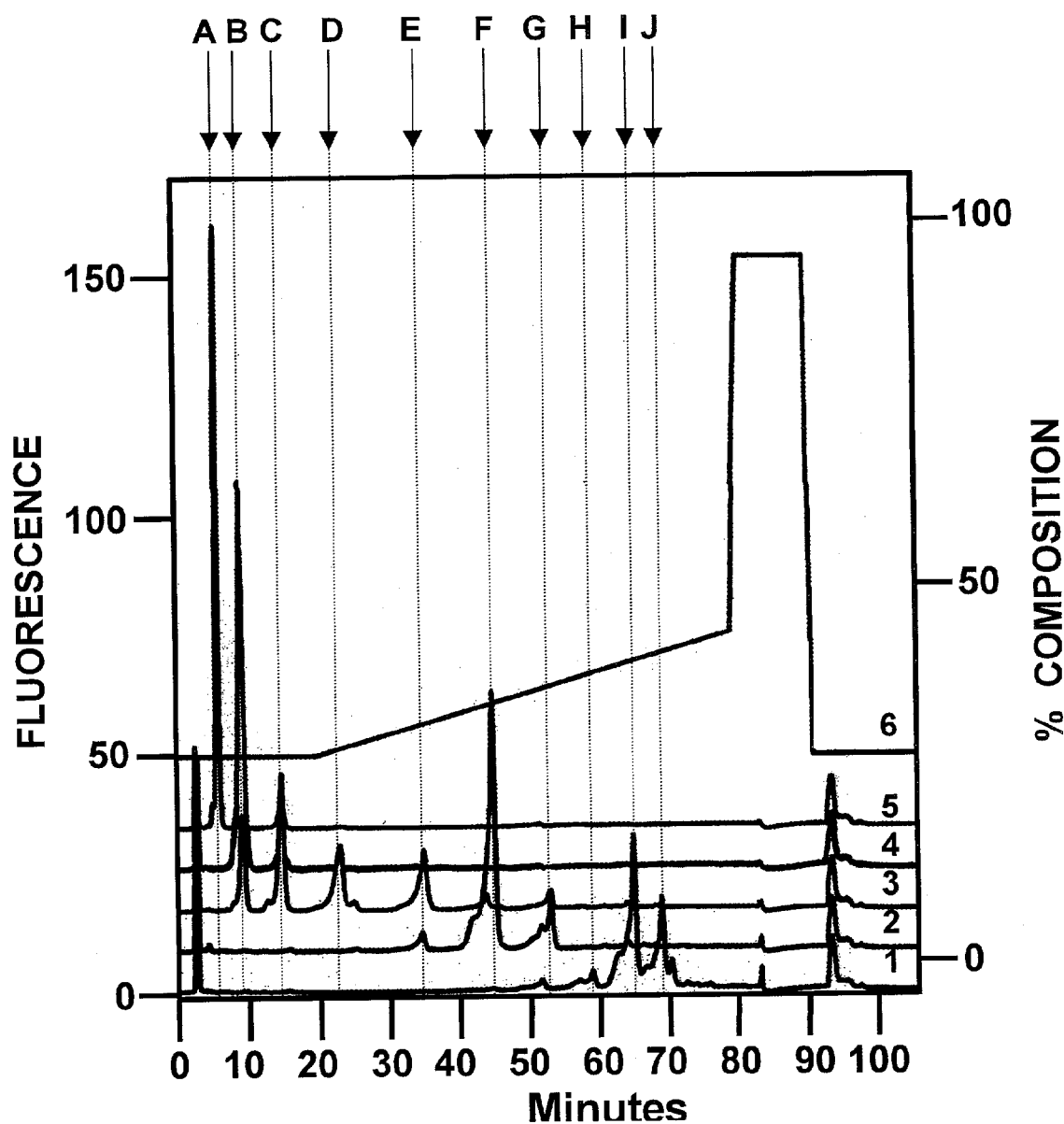

FIG. 66. The reaction products of the oligosaccharides derived from *Hansenula*-produced E1s after overnight incubation with or without exoglycosidases were separated on a TSK gel-Amide-80 (0.46×25 cm, Tosoh Biosep) column coupled to a Waters Alliance HPLC station. Separation of the oligosaccharides was carried out at ambient temperature at 1.0 mL/min. Solvent A consisted of 0.1% acetic acid in acetonitrile and solvent B consisted of 0.2% acetic acid-0.2% triethylamine in water. Separation of 2-AB labeled oligosaccharides was carried out using 28% B isocratic for 5 column volumes followed by a linear increase to 45% B over fifteen column volumes. The composition of the elution solvent is indicate on the right Y-axis as % solvent B in solvent A (v/v). The elution time is indicated in minutes on the X-axis. The left Y-axis indicates fluorescence of eluting 2-aminobenzamide (2-AB)-labeled oligosaccharides. The excitation wavelength of 2-AB is 330 nm, the emission wavelength 420 nm.

Trace 1 ("1") of the chromatogram shows the elution of oligosaccharides derived from *Hansenula*-produced E1s incubated overnight without exoglycosidases. Trace 2 ("2") shows the elution of oligosaccharides derived from *Hansenula*-produced E1s after overnight incubation of Man-9 with α 1-2 Mannosidase. Traces 3 and 4 ("3" and "4") show the elution of oligosaccharides derived from *Hansenula*-produced E1s after overnight incubation with α-Mannosidase. Trace 5 ("5") shows the elution of oligosaccharides derived from *Hansenula-produced E*1s after overnight incubation with α- and β-Mannosidase. Traces 1-5 are represented as overlays, as such their respective baselines are not all on the zero level. Trace 6 ("6") indicates the applied solvent gradient.

The peaks, when present, indicated by the letters A to K on top of the Figure represent: A, chitobiose; B, 4'-β-mannosyl-chitobiose; C, Man-2; D, Man-3; E, Man-4; F, Man-5; G, Man-6; H, Man-7; I, Man-7; J, Man-8; and K, Man-10. See also Example 26.

Figure 67:
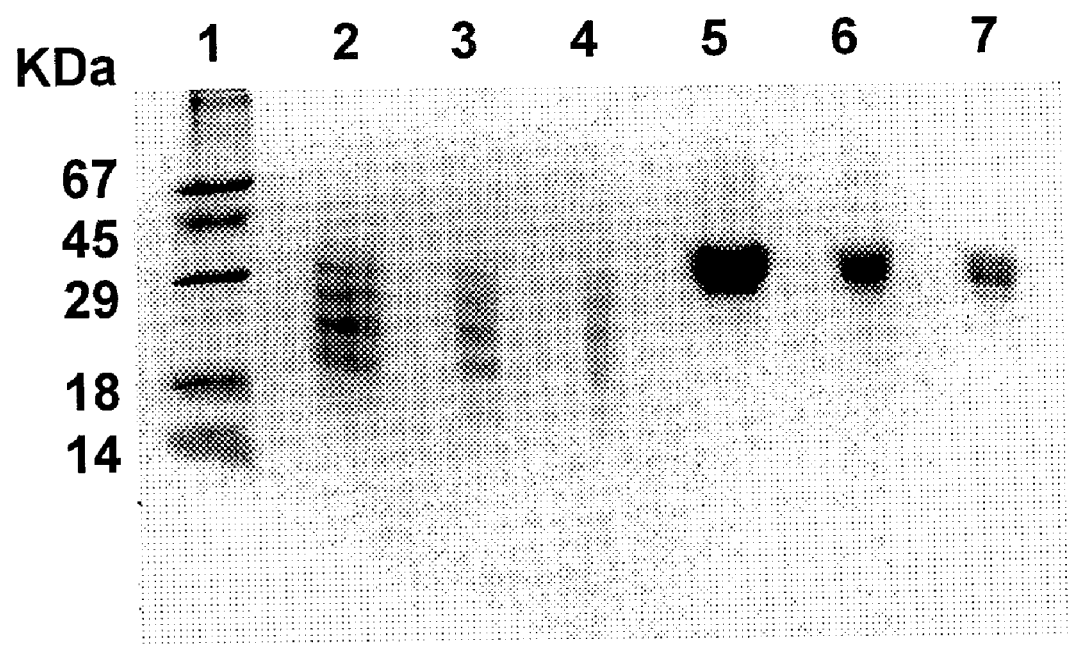

FIG. 67. SDS-PAGE analysis and Coomassie Brilliant Blue staining of E1 proteins produced by *Hansenula* and by a HCV-recombinant vaccinia virus-infected mammalian cells. Lane 1: molecular weight markers with molecular weights indicated at the left; Lane 2: alkylated E1s produced by *Hansenula polymorpha* (10 μg); Lane 3: alkylated E1s produced by *Hansenula polymorpha* (5 μg); Lane 4: alkylated E1s produced by *Hansenula polymorpha* (2.5 μg); Lane 5: alkylated E1s produced by HCV-recombinant vaccinia virus-infected vero cells (10 μg); Lane 6: alkylated E1s produced by HCV-recombinant vaccinia virus-infected vero cells (5 μg); Lane 7: alkylated E1s produced by HCV-recombinant vaccinia virus-infected vero cells (2.5 μg). See also Example 27.

FIG. 68. Sequence of HCV E2-H6 protein (SEQ ID NO:5) with indication of tryptic fragments (boxed sequences) of the deglycosylated protein. The glycosylated Asn-residues are converted into Asp-residues by the PNGase F enzyme and are indicated with a "*" under the sequence. The Asn-residues are prone to proteolytic cleavage by the Asp-N endoproteinase. The possible N-glycosylation sites in E2-H6 (SEQ ID NO:5) are $N_{417}$, $N_{423}$, $N_{430}$, $N_{448}$, $N_{478}$, $N_{532}$, $N_{540}$, $N_{556}$, $N_{576}$, $N_{623}$ and $N_{645}$ according to the numbering in the HCV polyprotein; these sites are numbered $N_{34}$, $N_{40}$, $N_{47}$, $N_{65}$, $N_{95}$, $N_{149}$, $N_{157}$, $N_{173}$, $N_{193}$, $N_{240}$ and $N_{262}$ in this figure. See also Example 28.

DETAILED DESCRIPTION OF THE INVENTION

In work leading to the present invention, it was observed that expression of glycosylated HCV envelope proteins in *Saccharomyces cerevisiae*, *Pichia pastoris* and *Hansenula polymorpha* was possible by expression of said HCV envelope proteins as proteins comprising a signal peptide sequence joined to said HCV envelope proteins. The glycosylation patterns of the HCV envelope proteins expressed in these three yeast species were, however, very different (see Examples 6, 10, 13 and 25). More specifically the *S. cerevisiae* (glycosylation deficient mutant)- and *H. polymorpha*-expressed HCV envelope proteins were glycosylated in a manner resembling core-glycosylation. The HCV envelope proteins expressed in *Pichia pastoris* were hyperglycosylated despite earlier reports that proteins expressed in this yeast are normally not hyperglycosylated (Gellissen et al. 2000, Sugrue et al. 1997).

Upon further analysis of the glycosylation patterns of HCV proteins produced in *S. cerevisiae* (glycosylation deficient strain), *H. polymorpha* and in HCV-recombinant vaccinia virus-infected mammalian cells, it was surprisingly found that the *Hansenula*-produced HCV envelope proteins displayed a glycosylation pattern which is very advantageous for diagnostic, prophylactic and therapeutic application of these HCV envelope proteins (see Examples 21-24 and 26-29). This unexpected finding is reflected in the different aspects and embodiments of the present invention as presented below.

A first aspect of the invention is related to an isolated HCV envelope protein or a fragment thereof comprising at least one N-glycosylation site, said protein or fragment thereof characterized in that it is the product of expression in a eukaryotic cell and further characterized in that on average up to 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80% of the N-glycosylated sites are core-glycosylated. More specific thereto, more than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% of the N-glycosylated sites are glycosylated with an oligomannose with a structure defined by Man(8 to 10)-GlcNAc(2). More specific to any of the above N-glycosylation characteristics, the ratio of sites core-glycosylated with an oligomannose with structure Man(7)-GlcNAc(2) over the sites core-glycosylated with an oligomannose with structure Man(8)-GlcNAc(2) is less than or equal to 0.15, 0.2, 0.25, 0.30, 0.35, 0.40, 0.44, 0.45, or 0.50. Further more specific to any of the above N-glycosylation characteristics, said oligomannoses contain less than 20%, 19%, 18%, 17%, 16%, 15%, 14%, 13%, 12%, 11%, 10%, 9%, 8%, 7%, 6%, or 5% terminal α 1,3 mannose.

With "N-glycosylated sites glycosylated with an oligomannose with a structure defined by Man(8 to 10)-GlcNAc (2)" is meant that said N-glycosylated sites are glycosylated with either one of Man(8)-GlcNAc(2), Man(9)-GlcNAc(2), or Man(10)-GlcNAc(2).

It will be clear that the same N-glycosylation site in two proteins may be occupied by a different oligomannose.

The term "protein" refers to a polymer of amino acids and does not refer to a specific length of the product; thus, peptides, oligopeptides, and polypeptides are included within the definition of protein. This term also does not refer to or exclude post-expression modifications of the protein, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

With "pre-pro-protein" or "pre-protein" is, when used herein, meant a protein comprising a pre-pro-sequence joined to a protein of interest or a protein comprising a pro-sequence joined to a protein of interest, respectively. As alternatives for "pre-sequence", the terms "signal sequence", "signal peptide", "leader peptide", or "leader sequence" are used; all refer to an amino acid sequence that targets a pre-protein to the rough endoplasmic reticulum (ER) which is a prerequisite for (N-)glycosylation. The "signal sequence", "signal peptide", "leader peptide", or "leader sequence" is cleaved off, i.e. "removed" from the protein comprising the signal sequence joined to a protein of interest, at the on the luminal side of this ER by host specific proteases referred to as signal peptidases. Likewise, a pre-pro-protein is converted to a pro-protein upon translocation to the lumen of the ER. Depending on the nature of the "pro" amino acid sequence, it can or can not be removed by the host cell expressing the pre-pro-protein. A well known pre-pro-amino acid sequence is the a mating factor pre-pro-sequence of the *S. cerevisiae* α mating factor.

With "HCV envelope protein" is meant a HCV E1 or HCV E2 envelope protein or a part thereof whereby said proteins may be derived from a HCV strain of any genotype. More specifically, HCVENV is chosen from the group of amino acid sequences consisting of SEQ ID NOs:85 to 98, amino acid sequences which are at least 90% identical to SEQ ID NOs:85 to 98, and fragments of any thereof. As "identical" amino acids are considered the groups of conserved amino acids as described above, i.e. the group consisting of Met, Ile, Leu and Val; the group consisting of Arg, Lys and His; the group consisting of Phe, Trp and Tyr; the group consisting of Asp and Glu; the group consisting of Asn and Gln; the group consisting of Cys, Ser and Thr; and the group consisting of Ala and Gly.

More specifically, the term "HCV envelope proteins" relates to a polypeptide or an analogue thereof (e.g. mimotopes) comprising an amino acid sequence (and/or amino acid analogues) defining at least one HCV epitope of either the E1 or the E2 region, in addition to a glycosylation site. These envelope proteins may be both monomeric, hetero-oligomeric or homo-oligomeric forms of recombinantly expressed envelope proteins. Typically, the sequences defining the epitope correspond to the amino acid sequences of either the E1 or the E2 region of HCV (either identically or via substitutions of analogues of the native amino acid residue that do not destroy the epitope).

It will be understood that the HCV epitope may co-locate with the glycosylation site.

In general, the epitope-defining sequence will be 3 or 4 amino acids in length, more typically, 5, 6, or 7 amino acids in length, more typically 8 or 9 amino acids in length, and even more typically 10 or more amino acids in length. With respect to conformational epitopes, the length of the epitope-defining sequence can be subject to wide variations, since it is believed that these epitopes are formed by the three-dimensional shape of the antigen (e.g. folding). Thus, the amino acids defining the epitope can be relatively few in number, but widely dispersed along the length of the molecule being brought into the correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer.

As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to genotypes 1a, 1b, 1c, 1d, 1e, 1f, 2a, 2b, 2c, 2d, 2e, 2f, 2g, 2h, 2i, 3a, 3b, 3c, 3d, 3e, 3f, 3g, 4a, 4b, 4c, 4d, 4e, 4f, 4g, 4h, 4i, 4j, 4k, 4l, 5a, 5b, 6a, 6b, 6c, 7a, 7b, 7c, 8a, 8b, 9a, 9b, 10a, 11 (and subtypes thereof), 12 (and subtypes thereof) or 13 (and subtypes thereof) or any other newly defined HCV (sub)type. It is to be understood that the amino acids constituting the epitope need not be part of a linear sequence, but may be interspersed by any number of amino acids, thus forming a conformational epitope.

The HCV antigens of the present invention comprise conformational epitopes from the E1 and/or E2 (envelope) domains of HCV. The E1 domain, which is believed to correspond to the viral envelope protein, is currently estimated to span amino acids 192-383 of the HCV polyprotein (Hijikata et al., 1991). Upon expression in a mammalian system (glycosylated), it is believed to have an approximate molecular weight of 35 kDa as determined via SDS-PAGE. The E2 protein, previously called NS1, is believed to span amino acids 384-809 or 384-746 (Grakoui et al., 1993) of the HCV polyprotein and also to be an envelope protein. Upon expression in a vaccinia system (glycosylated), it is believed to have an apparent gel molecular weight of about 72 kDa. It is understood that these protein endpoints are approximations (e.g. the carboxy terminal end of E2 could lie somewhere in the 730-820 amino acid region, e.g. ending at amino acid 730, 735, 740, 742, 744, 745, preferably 746, 747, 748, 750, 760, 770, 780, 790, 800, 809, 810, 820). The E2 protein may also be expressed together with E1, and/or core (aa 1-191), and/or P7 (aa 747-809), and/or NS2 (aa 810-1026), and/or NS3 (aa 1027-1657), and/or NS4A (aa 1658-1711) and/or NS4B (aa 1712-1972) and/or NS5A (aa 1973-2420), and/or NS5B (aa 2421-3011), and/or any part of any of these HCV proteins different from E2. Likewise, the E1 protein may also be expressed together with the E2, and/or core (aa 1-191), and/or P7 (aa 747-809), and/or NS2 (aa 810-1026), and/or NS3 (aa 1027-1657), and/or NS4A (aa 1658-1711) and/or NS4B (aa 1712-1972), and/or NS5A (aa 1973-2420), and/or NS5B (aa 2421-3011), and/or any part of any of these HCV proteins different from E1. Expression together with these other HCV proteins may be important for obtaining the correct protein folding.

The term "E1" as used herein also includes analogs and truncated forms that are immunologically cross-reactive with natural E1, and includes E1 proteins of genotypes 1, 2, 3, 4, 5, 6, 7, 8, 9, 10, 11, 12 or 13 or any other newly identified HCV type or subtype. The term 'E2' as used herein also includes analogs and truncated forms that are immunologically cross-reactive with natural E2, and includes E2 proteins of genotypes 1, 2, 3, 4, 5, 6, 7, 8, 9, 10, 11, 12 or 13 or any other newly identified HCV type or subtype. For example, insertions of multiple codons between codon 383 and 384, as well as deletions of amino acids 384-387 have been reported by Kato et al. (1992). It is thus also understood that the isolates used in the examples section of the present invention were not intended to limit the scope of the invention and that any HCV isolate from type 1, 2, 3, 4, 5, 6, 7, 8, 9, 10, 11, 12 or 13 or any other new genotype of HCV is a suitable source of E1 and/or E2 sequence for the practice of the present invention. Similarly, as described above, the HCV proteins that are co-expressed with the HCV envelope proteins of the present invention, can be derived from any HCV type, thus also from the same type as the HCV envelope proteins of the present invention.

"E1/E2" as used herein refers to an oligomeric form of envelope proteins containing at least one E1 component and at least one E2 component.

The term "specific oligomeric" E1 and/or E2 and/or E1/E2 envelope proteins refers to all possible oligomeric forms of recombinantly expressed E1 and/or E2 envelope proteins which are not aggregates. E1 and/or E2 specific oligomeric envelope proteins are also referred to as homo-oligomeric E1 or E2 envelope proteins (see below). The term 'single or specific oligomeric' E1 and/or E2 and/or E1/E2 envelope proteins refers to single monomeric E1 or E2 proteins (single in the strict sense of the word) as well as specific oligomeric E1 and/or E2 and/or E1/E2 recombinantly expressed proteins. These single or specific oligomeric envelope proteins according to the present invention can be further defined by the following formula $(E1)_x(E2)_y$ wherein x can be a number between 0 and 100, and y can be a number between 0 and 100, provided that x and y are not both 0. With x=1 and y=0 said envelope proteins include monomeric E1.

The term "homo-oligomer" as used herein refers to a complex of E1 or E2 containing more than one E1 or E2 monomer, e.g. E1/E1 dimers, E1/E1/E1 trimers or E1/E1/E1/E1 tetramers and E2/E2 dimers, E2/E2/E2 trimers or E2/E2/E2/E2 tetramers, E1 pentamers and hexamers, E2 pentamers and hexamers or any higher-order homo-oligomers of E1 or E2 are all 'homo-oligomers' within the scope of this definition. The oligomers may contain one, two, or several different monomers of E1 or E2 obtained from different types or subtypes of hepatitis C virus including for example those described by Maertens et al. in WO94/25601 and WO96/13590, both by the present applicants. Such mixed oligomers are still homo-oligomers within the scope of this invention, and may allow more universal diagnosis, prophylaxis or treatment of HCV.

The E1 and E2 antigens used in the present invention may be full-length viral proteins, substantially full-length versions thereof, or functional fragments thereof (e.g. fragments comprising at least one epitope and/or glycosylation site). Furthermore, the HCV antigens of the present invention can also include other sequences that do not block or prevent the formation of the conformational epitope of interest. The presence or absence of a conformational epitope can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to adsorb the polyclonal serum first with the denatured antigen and see if it retains antibodies to the antigen of interest.

The HCV proteins of the present invention may be glycosylated. Glycosylated proteins intend proteins that contain one or more carbohydrate groups, in particular sugar groups. In general, all eukaryotic cells are able to glycosylate proteins. After alignment of the different envelope protein sequences of HCV genotypes, it may be inferred that not all 6 glycosylation sites on the HCV E1 protein are required for proper folding and reactivity. It is further known that the glycosylation site at position 325 is not modified by N-glycosylation (Fournillier-Jacob et al. 1996, Meunier et al. 1999). Furthermore, HCV subtype 1b E1 protein contains 6 glycosylation sites, but some of these glycosylation sites are absent in certain other (sub)types. The fourth carbohydrate motif (on Asn250), present in types 1b, 6a, 7, 8, and 9, is absent in all other types know today. This sugar-addition motif may be mutated to yield a type 1b E1 protein with improved reactivity. Also, the type 2b sequences show an extra glycosylation site in the V5 region (on Asn299). The isolate S83, belonging to genotype 2c, even lacks the first carbohydrate motif in the V1 region (on Asn), while it is present on all other isolates (Stuyver et al., 1994). However, even among the completely conserved sugar-addition motifs, the presence of the carbohydrate may not be required for folding, but may have a role in evasion of immune surveillance. Thus, the identification of the role of glycosylation can be further tested by mutagenesis of the glycosylation motifs. Mutagenesis of a glycosylation motif (NXS or NXT sequences) can be achieved by either mutating the codons for N, S, or T, in such a way that these codons encode amino acids different from N in the case of N, and/or amino acids different from S or T in the case of S and in the case of T. Alternatively, the X position may be mutated into P, since it is known that NPS or NPT are not frequently modified with carbohydrates. After establishing which carbohydrate-addition motifs are required for folding and/or reactivity and which are not, combinations of such mutations may be made. Such experiments have been described extensively by Maertens et al. in Example 8 of WO96/04385, which is included herein specifically by reference.

The term glycosylation as used in the present invention refers to N-glycosylation unless otherwise specified.

In particular, the present invention relates to HCV envelope proteins, or parts thereof that are core-glycosylated. In this respect, the term "core-glycosylation" refers to a structure "similar" to the structure as depicted in the boxed structure in FIG. 3 of Herscovics and Orlean (1993). Thus, the carbohydrate structure referred to contains 10 to 11 monosaccharides. Notably, said disclosure is herein incorporated by reference. The term "similar" intends that not more than 4 additional monosaccharide has been added to the structure or that not more than about 3 monosaccharides have been removed from the structure. Consequently, the core-glycosylation carbohydrate structure referred to in the current invention consists minimally of 7 and maximally of 15 monosaccharides and can consist of 8, 9, 10, 11, 12, 13 or 14 monosaccharides. The monosaccharides connoted are preferentially glucose, mannose or N-acetyl glucosamine.

An alternative aspect of the current invention relates to an isolated HCV envelope protein or a fragment thereof comprising at least one N-glycosylation site, said protein or fragment thereof characterized in that it is the product of expression in a eukaryotic cell and further characterized in that more than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% of the N-glycosylated sites are glycosylated with an oligomannose with a structure defined by Man(8 to 10)-GlcNAc(2). More specific to the above N-glycosylation characteristic, the ratio of sites core-glycosylated with an oligomannose with structure Man(7)-GlcNAc(2) over the sites core-glycosylated with an oligomannose with structure Man(8)-GlcNAc(2) is less than or equal to 0.15, 0.2, 0.25, 0.30, 0.35, 0.40, 0.44, 0.45, or 0.50. Further more specific to any of the above N-glycosylation characteristics, said oligomannoses contain less than 20%, 19%, 18%, 17%, 16%, 15%, 14%, 13%, 12%, 11%, 10%, 9%, 8%, 7%, 6%, or 5% terminal α 1,3 mannose.

Another alternative aspect of the invention is related to an isolated HCV envelope protein or a fragment thereof comprising at least one N-glycosylation site, said protein or fragment thereof characterized in that it is the product of expression in a eukaryotic cell and further characterized in that N-glycosylated sites are occupied by oligomannoses wherein the ratio of the oligomannoses with structure Man(7)-GlcNAc(2) over the oligomannoses with structure Man(8)-GlcNAc(2) is less than or equal to 0.15, 0.2, 0.25, 0.30, 0.35, 0.40, 0.44, 0.45, or 0.50. Further more specific to the above N-glycosylation characteristics, said oligomannoses contain less than 20%, 19%, 18%, 17%, 16%, 15%, 14%, 13%, 12%, 11%, 10%, 9%, 8%, 7%, 6%, or 5% terminal α 1,3 mannose.

In another alternative aspect of the current invention is covered an isolated HCV envelope protein or a fragment thereof comprising at least one N-glycosylation site, said protein or fragment thereof characterized in that it is the product of expression in a non-mammalian eukaryotic cell and further characterized in that the number of N-glycosylated sites is at least 5%, 6%, 7%, 8%, 9%, 10%, 11%, 12%, 13%, 14%, or 15%, less than the number of N-glycosylated sites in the same protein or fragment thereof expressed from a vaccinia virus in a eukaryotic cell liable of being infected with said vaccinia virus. More particular to the above N-glycosylation characteristic, up to 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80% of said N-glycosylated sites are core-glycosylated. More specifically, more than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% of the N-glycosylated sites are glycosylated with an oligomannose with a structure defined by Man(8 to 10)-GlcNAc(2). More specific to any of the above N-glycosylation characteristics, the ratio of sites core-glycosylated with an oligomannose with structure Man(7)-GlcNAc(2) over the sites core-glycosylated with an oligomannose with structure Man(8)-GlcNAc(2) is less than or equal to 0.15, 0.2, 0.25, 0.30, 0.35, 0.40, 0.45, or 0.50. Further more specific to any of the above N-glycosylation characteristics, said oligomannoses contain less than 20%, 19%, 18%, 17%, 16%, 15%, 14%, 13%, 12%, 11%, 10%, 9%, 8%, 7%, 6%, or 5% terminal α 1,3 mannose.

In another aspect of the invention, the isolated HCV envelope protein or part thereof according to the invention is the product of expression in a yeast cell. More particularly, the isolated HCV envelope protein or part thereof according to the invention is the product of expression in a cell of strains of *Saccharomyces*, such as *Saccharomyces cerevisiae*, *Saccharomyces kluyveri*, or *Saccharomyces uvarum*, *Schizosaccharomyces*, such as *Schizosaccharomyces pombe*, *Kluyveromyces*, such as *Kluyveromyces lactis*, *Yarrowia*, such as *Yarrowia lipolytica*, *Hansenula*, such as *Hansenula polymorpha*, *Pichia*, such as *Pichia pastoris*, *Aspergillus species*, *Neurospora*, such as *Neurospora crassa*, or *Schwanniomyces*, such as *Schwanniomyces occidentalis*, or mutant cells derived from any thereof More specifically, the isolated HCV envelope protein or part thereof according to the invention is the product of expression in a *Hansenula* cell. Even more specifically, the isolated HCV envelope protein or part thereof according to the invention is the product of expression in a yeast, e.g. *Hansenula*, cell in the absence of glycosylation inhibitors such as tunicamycin.

In another aspect of the invention the isolated HCV envelope protein or part thereof according to the invention is derived from a protein comprising an avian lysozyme leader peptide or a functional variant thereof joined to said HCV envelope protein or fragment thereof More specifically, the isolated HCV envelope protein or part thereof according to the invention is derived from a protein characterized by the structure $$CL-[(A1)_a-(PS1)_b-(A2)_c]-HCVENV-[(A3)_d-(PS2)_e-(A4)_f]$$

wherein:
CL is an avian lysozyme leader peptide or a functional equivalent thereof,
A1, A2, A3 and A4 are adaptor peptides which can be different or the same,
PS1 and PS2 are processing sites which can be the different or the same,
HCVENV is a HCV envelope protein or a part thereof,
a, b, c, d, e and f are 0 or 1, and
wherein, optionally, A1 and/or A2 are part of PS1 and/or wherein A3 and/or A4 are part of PS2.

With "an avian leader peptide or a functional equivalent thereof joined to a HCV envelope protein or a part thereof" is meant that the C-terminal amino acid of said leader peptide is covalently linked via a peptide bond to the N-terminal amino acid of said HCV envelope protein or part thereof. Alternatively, the C-terminal amino acid of said leader peptide is separated from the N-terminal amino acid of said HCV envelope protein or part thereof by a peptide or protein. Said peptide or protein may have the structure—$[(A1)_a-(PS1)_b-(A2)_c]$ as defined above.

The derivation of the HCV envelope protein of interest from the protein comprising an avian lysozyme leader peptide or a functional equivalent thereof joined to an HCV envelope protein or a part thereof or of the protein characterized by the structure $CL-[(A1)_a-(PS1)_b-(A2)_c]-HCVENV-[(A3)_d-(PS2)_e-(A4)_f]$ can be performed in vivo by the proteolytic machinery of the cells in which the pre-protein protein is expressed. More specifically, the step consisting of removal of the avian leader peptide is preferably performed in vivo by the proteolytic machinery of the cells in which the pre-protein is expressed. Derivation may, however, also be performed solely in vitro after and/or during isolation and/or purification of the pre-protein and/or protein from the cells expressing the pre-protein and/or from the culture fluid in which the cells expressing the pre-protein are grown. Alternatively, said in vivo derivation is performed in combination with said in vitro derivation. Derivation of the HCV protein of interest from a recombinantly expressed pre-protein can further comprise the use of (an) proteolytic enzyme(s) in a polishing step wherein all or most of the contaminating proteins co-present with the protein of interest are degraded and wherein the protein of interest is resistant to the polishing proteolytic enzyme(s). Derivation and polishing are not mutually exclusive processes and may be obtained by using the same single proteolytic enzyme. As an example is given here the HCV E1s protein of HCV genotype 1b (SEQ ID NO:2) which is devoid of Lys-residues. By digesting of a protein extract containing said HCV E1 proteins with the Endoproteinase Lys-C (endo-lys C), the E1 proteins will not be degraded whereas contaminating proteins containing one or more Lys-residues are degraded. Such a process may significantly simplify or enhance isolation and/or purification of the HCV E1 proteins. Furthermore, by including in a pre-protein an additional Lys-residue, e.g. between a leader peptide and a HCV E1 protein, the additional advantageous possibility of correct in vitro separation of the leader peptide from the HCV E1 pre-protein is obtainable. Other HCV E1 proteins may comprise a Lys-residue at either one or more of the positions 4, 40, 42, 44, 61, 65 or 179 (wherein position 1 is the first, N-terminal natural amino acid of the E1 protein, i.e. position 192 in the HCV polyprotein). In order to enable the use of endo-lys C as described above, said Lys-residues may be mutated into another amino acid residue, preferably into an Arg-residue.

With a "correctly removed" leader peptide is meant that said leader peptide is removed from the protein comprising the signal sequence joined to a protein of interest with high efficiency, i.e. a large number of pre-(pro-)proteins is converted to (pro-)proteins, and with high fidelity, i.e. only the pre-amino acid sequence is removed and not any amino acids of the protein of interest joined to said pre-amino acid sequence. With "removal of a leader peptide with high efficiency" is meant that at least about 40%, but more preferentially about 50%, 55%, 60%, 65%, 70%, 75%, 80%, 85%, 90%, 95%, 96%, 97%, 98% or even 99% of the pre-proteins is converted to the protein from which the pre-sequence is removed. Alternatively, if a substantial part of the expressed pre-proteins is not converted to the protein from which the pre-sequence is removed, these pre-proteins may still be purified or be removed during purification.

With "functional equivalent of the avian lysozyme (CL) leader peptide" is meant a CL leader peptide wherein one or more amino acids have been substituted for another amino acid and whereby said substitution is a conservative amino acid substitution. With "conservative amino acid substitution" is meant a substitution of an amino acid belonging to a group of conserved amino acids with another amino acid belonging to the same group of conserved amino acids. As groups of conserved amino acids are considered: the group consisting of Met, Ile, Leu and Val; the group consisting of Arg, Lys and His; the group consisting of Phe, Trp and Tyr; the group consisting of Asp and Glu; the group consisting of Asn and Gln; the group consisting of Cys, Ser and Thr; and the group consisting of Ala and Gly. An exemplary conservative amino acid substitution in the CL leader peptide is the naturally variation at position 6, the amino acid at this position being either Val or Ile; another variation occurs at position 17, the amino acid at this position being, amongst others, Leu or Pro (see SEQ ID NO:1). The resulting CL leader peptides are thus to be considered as functional equivalents. Other functional equivalents of the CL leader peptides include those leader peptides reproducing the same technical aspects as the CL leader peptides as described throughout the current invention, including deletion variants and insertion variants.

With "A" or "adaptor peptide" is meant a peptide (e.g. 1 to 30 amino acids) or a protein which may serve as a linker between e.g. a leader peptide and a processing site (PS), a leader peptide and a protein of interest, a PS and a protein of interest, and/or a protein of interest and a PS; and/or may serve as a linker N- or C-terminal of e.g. a leader peptide, a PS or a protein of interest. The adaptor peptide "A" may have a certain three-dimensional structure, e.g. an α-helical or β-sheet structure or a combination thereof. Alternatively the three-dimensional structure of A is not well defined, e.g. a coiled-coil structure. The adaptor A may be part of e.g. a pre-sequence, a pro-sequence, a protein of interest sequence or a processing site. The adaptor A may serve as a tag enhancing or enabling detection and/or purification and/or processing of the protein of which A is a part. One examples of an A peptide is the his-tag peptide (HHHHHH; SEQ ID NO:63) Hn wherein n usually is six, but may be 7, 8, 9, 10, 11, or 12. Other examples of A-peptides include the peptides EEGEPK (Kjeldsen et al. in WO98/28429; SEQ ID NO:64) or EEAEPK (Kjeldsen et al. in WO97/22706; SEQ ID NO:65) which, when present at the N-terminal of the a protein of interest, were reported to increase fermentation yield but also to protect the N-terminus of the protein of interest against processing by dipeptidyl aminopeptidase and thus resulting in a homogenous N-terminus of the polypeptide. At the same time, in vitro maturation of the protein of interest, i.e. removal of said peptides EEGEPK (SEQ ID NO:64) and EEAEPK (SEQ ID NO:65) from the protein of interest can be achieved by using e.g. endo-lys C which cleaves C-terminal of the Lys-residue in said peptides. Said peptides thus serve the function of adaptor peptide (A) as well as processing site (PS), (see below). Adaptor peptides are given in SEQ ID NOs:63-65, 70-72 and 74-82. Another example of an adaptor peptide is the G4S immunosilent linker. Other examples of adaptor peptides or adaptor proteins are listed in Table 2 of Stevens (Stevens et al. 2000).

With "PS" or "processing site" is meant a specific protein processing or processable site. Said processing may occur enzymatically or chemically. Examples of processing sites prone to specific enzymatic processing include IEGR↓X (SEQ ID NO:66), IDGR↓X (SEQ ID NO:67), AEGR↓X (SEQ ID NO:68), all recognized by and cleaved between the Arg and Xaa (any amino acid) residues as indicated by the "↓" by the bovine factor Xa protease (Nagai, K. and Thogersen, H. C. 1984). Another example of a PS site is a dibasic site, e.g. Arg-Arg, Lys-Lys, Arg-Lys or Lys-Arg, which is cleavable by the yeast Kex2 protease (Julius, D. et al. 1984). The PS site may also be a monobasic Lys-site. Said monobasic Lys-PS-site may also be included at the C-terminus of an A peptide. Examples of A adaptor peptides comprising a C-terminal monobasic Lys-PS-site are given by SEQ ID NOs:64-65 and 74-76. Exoproteolytic removal of a His-tag (HHHHHH; SEQ ID NO:63) is possible by using the dipeptidyl aminopeptidase I (DAPase) alone or in combination with glutamine cyclotransferase (Qcyclase) and pyroglutamic aminopeptidase (pGAPase) (Pedersen, J. et al. 1999). Said exopeptidases comprising a recombinant His-tag (allowing removal of the peptidase from the reaction mixture by immobilize metal-affinity chromatography, IMAC) are commercially available, e.g. as the TAGZyme System of Unizyme Laboratories (Hørsholm, DK). With "processing" is thus generally meant any method or procedure whereby a protein is specifically cleaved or cleavable at at least one processing site when said processing site is present in said protein. A PS may be prone to endoproteolytic cleavage or may be prone to exproteolytic cleavage, in any case the cleavage is specific, i.e. does not extend to sites other than the sites recognized by the processing proteolytic enzyme. A number of PS sites are given in SEQ ID NOs:66-68 and 83-84.

The versatility of the $[(A1/3)_{a/d}\text{-}(PS1/2)_{b/e}\text{-}(A2/4)_{c/f}]$ structure as outlined above is demonstrated by means of some examples. In a first example, said structure is present at the C-terminal end of a protein of interest comprised in a pre-protein and wherein A3 is the "VIEGR" peptide (SEQ ID NO:69) which is overlapping with the factor Xa "IEGRX" PS site (SEQ ID NO:66) and wherein X=A4 is the histidine-tag (SEQ ID NO:63) (d, e and f thus are all 1 in this case). The HCV protein of interest can (optionally) be purified by IMAC. After processing with factor Xa, the (optionally purified) HCV protein of interest will carry at its C-terminus a processed PS site which is "IEGR" (SEQ ID NO:70). Variant processed factor Xa processing site, can be IDGR (SEQ ID NO:71) or AEGR (SEQ ID NO:72). In a further example, the $[(A1/3)_{a/d}\text{-}(PS1/2)_{b/e}\text{-}(A2/4)_{c/f}]$ structure is present at the N-terminus of the HCV protein of interest. Furthermore, A1 is the histidine-tag (SEQ ID NO:63), PS is the factor Xa recognition site (any of SEQ ID NOs:66-68) wherein X is the protein of interest, and wherein a=b=1 and c=0. Upon correct removal of a leader peptide, e.g. by the host cell, the resulting HCV protein of interest can be purified by IMAC (optional). After processing with factor Xa, the protein of interest will be devoid of the $[(A1)_a\text{-}(PS1)_b\text{-}(A2)_c]$ structure.

It will furthermore be clear that any of A1, A2, A3, A4, PS1 and PS2, when present, may be present in a repeat structure. Such a repeat structure, when present, is in this context still counted as 1, i.e. a, b, c, d, e, or f are 1 even if e.g. A1 is occurring as e.g. 2 repeats (A1-A1).

Yet another aspect of the current invention relates to any of the isolated HCV envelope protein or fragment thereof according to the invention in which the cysteine thiol-groups are chemically modified.

Yet another aspect of the current invention relates to any of the isolated HCV envelope protein or fragment thereof according to the invention which is antigenic.

Yet another aspect of the current invention relates to any of the isolated HCV envelope protein or fragment thereof according to the invention which is immunogenic.

Yet another aspect of the current invention relates to any of the isolated HCV envelope protein or fragment thereof according to the invention which comprises a T-cell stimulating epitope.

Another aspect of the current invention relates to any of the isolated HCV envelope protein or fragment thereof according to the invention which is comprised in a structure chosen from the group consisting of monomers, homodimers, heterodimers, homo-oligomers and hetero-oligomers.

Yet another aspect of the current invention relates to any of the isolated HCV envelope protein or fragment thereof according to the invention which is comprised in a virus-like particle.

In the HCV envelope proteins or parts thereof as described herein comprising at least one cysteine residue, but preferably 2 or more cysteine residues, the cysteine thiol-groups can be irreversibly protected by chemical or enzymatic means. In particular, "irreversible protection" or "irreversible blocking" by chemical means refers to alkylation, preferably alkylation of the HCV envelope proteins by means of alkylating agents, such as, for example, active halogens, ethylenimine or N-(iodoethyl)trifluoro-acetamide. In this respect, it is to be understood that alkylation of cysteine thiol-groups refers to the replacement of the thiol-hydrogen by $(CH_2)_nR$, in which n is 0, 1, 2, 3 or 4 and R=H, COOH, $NH_2$, $CONH_2$, phenyl, or any derivative thereof. Alkylation can be performed by any method known in the art, such as, for example, active halogens $X(CH_2)_nR$ in which X is a halogen such as I, Br, Cl or F. Examples of active halogens are methyliodide, iodoacetic acid, iodoacetamide, and 2-bromoethylamine. Other methods of alkylation include the use of NEM (N-ethylmaleimide) or Biotin-NEM, a mixture thereof, or ethylenimine or N-(iodoethyl)trifluoroacetamide both resulting in substitution of —H by $-CH_2-CH_2-NH_2$ (Hermanson, G. T. 1996). The term "alkylating agents" as used herein refers to compounds which are able to perform alkylation as described herein. Such alkylations finally result in a modified cysteine, which can mimic other aminoacids. Alkylation by an ethylenimine results in a structure resembling lysine, in such a way that new cleavage sites for trypsine are introduced (Hermanson, G. T. 1996). Similarly, the usage of methyliodide results in an amino acid resembling methionine, while the usage of iodoacetate and iodoacetamide results in amino acids resembling glutamic acid and glutamine, respectively. In analogy, these amino acids are preferably used in direct mutation of cysteine. Therefore, the present invention pertains to HCV envelope proteins as described herein, wherein at least one cysteine residue of the HCV envelope protein as described herein is mutated to a natural amino acid, preferentially to methionine, glutamic acid, glutamine or lysine. The term "mutated" refers to site-directed mutagenesis of nucleic acids encoding these amino acids, ie to the well known methods in the art, such as, for example, site-directed mutagenesis by means of PCR or via oligonucleotide-mediated mutagenesis as described in (Sambrook, J. et al. 1989). It should be understood that for the Examples section of the present invention, alkylation refers to the use of iodo-acetamide as an alkylating agent unless otherwise specified.

It is further understood that in the purification procedure, the cysteine thiol-groups of the HCV proteins or the parts thereof of the present invention can be reversibly protected. The purpose of reversible protection is to stabilize the HCV protein or part thereof Especially, after reversible protection the sulfur-containing functional group (eg thiols and disulfides) is retained in a non-reactive condition. The sulfur-containing functional group is thus unable to react with other compounds, e.g. have lost their tendency of forming or exchanging disulfide bonds, such as, for example $R_1-SH + R_2-SH \text{ ---X---> } R_1-S-S-R_2$;

$R_1-S-S-R_2 + R_3-SH \text{ ---X---> } R_1-S-S-R_3 + R_2-SH$;

$R_1-S-S-R_2 + R_3-S-S-R_4 \text{ ---X---> } R_1-S-S-R_3 + R_2-S-S-R_4$.

The described reactions between thiols and/or disulphide residues are not limited to intermolecular processes, but may also occur intramolecularly.

The term "reversible protection" or "reversible blocking" as used herein contemplates covalently binding of modification agents to the cysteine thiol-groups, as well as manipulating the environment of the HCV protein such, that the redox state of the cysteine thiol-groups remains unaffected throughout subsequent steps of the purification procedure (shielding). Reversible protection of the cysteine thiol-groups can be carried out chemically or enzymatically.

The term "reversible protection by enzymatical means" as used herein contemplates reversible protection mediated by enzymes, such as for example acyl-transferases, e.g. acyl-transferases that are involved in catalysing thio-esterification, such as palmitoyl acyltransferase (see below).

The term "reversible protection by chemical means" as used herein contemplates reversible protection:

1. by modification agents that reversibly modify cysteinyls such as for example by sulphonation and thio-esterification;

Sulphonation is a reaction where thiol or cysteines involved in disulfide bridges are modified to S-sulfonate: $RSH \rightarrow RS-SO_3^-$ (Darbe, A. 1986) or $RS-SR \rightarrow 2 RS-SO_3^-$ (sulfitolysis; (Kumar, N. et al. 1986)). Reagents for sulfonation are e.g. $Na_2SO_3$, or sodium tetrathionate. The latter reagents for sulfonation are used in a concentration of 10-200 mM, and more preferentially in a concentration of 50-200 mM. Optionally sulfonation can be performed in the presence of a catalysator such as, for example $Cu^{2+}$ (100 μM-1 mM) or cysteine (1-10 mM).

The reaction can be performed under protein denaturing as well as native conditions (Kumar, N. et al. 1985, Kumar, N. et al. 1986).

Thioester bond formation, or thio-esterification is characterised by:

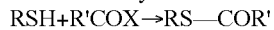

in which X is preferentially a halogenide in the compound R'CO—X.

2. by modification agents that reversibly modify the cysteinyls of the present invention such as, for example, by heavy metals, in particular $Zn^{2+}$, $Cd^{2+}$, mono-, dithio- and disulfide-compounds (e.g. aryl- and alkylmethanethiosulfonate, dithiopyridine, dithiomorpholine, dihydrolipoamide, Ellmann reagent, aldrothiol™ (Aldrich) (Rein, A. et al. 1996), dithiocarbamates), or thiolation agents (e.g. gluthathion, N-Acetyl cysteine, cysteineamine). Dithiocarbamate comprise a broad class of molecules possessing an $R_1R_2NC(S)SR_3$ functional group, which gives them the ability to react with sulphydryl groups. Thiol containing compounds are preferentially used in a concentration of 0.1-50 mM, more preferentially in a concentration of 1-50 mM, and even more preferentially in a concentration of 10-50 mM;

3. by the presence of modification agents that preserve the thiol status (stabilise), in particular antioxidantia, such as for example DTT, dihydroascorbate, vitamins and derivates, mannitol, amino acids, peptides and derivates (e.g. histidine, ergothioneine, carnosine, methionine), gallates, hydroxyanisole, hydoxytoluene, hydroquinon, hydroxymethylphenol and their derivates in concentration range of 10 μM-10 mM, more preferentially in a concentration of 1-10 mM;

4. by thiol stabilising conditions such as, for example, (i) cofactors as metal ions ($Zn^{2+}$, $Mg^{2+}$), ATP, (ii) pH control (e.g. for proteins in most cases pH~5 or pH is preferentially thiol $pK_a$-2; e.g. for peptides purified by Reversed Phase Chromatography at pH~2).

Combinations of reversible protection as described in (1), (2), (3) and (4) may result in similarly pure and refolded HCV proteins. In effect, combination compounds can be used, such as, for example Z103 (Zn carnosine), preferentially in a concentration of 1-10 mM. It should be clear that reversible protection also refers to, besides the modification groups or shielding described above, any cysteinyl protection method which may be reversed enzymatically or chemically, without disrupting the peptide backbone. In this respect, the present invention specifically refers to peptides prepared by classical chemical synthesis (see above), in which, for example, thioester bounds are cleaved by thioesterase, basic buffer conditions (Beekman, N. J. et al. 1997) or by hydroxylamine treatment (Vingerhoeds, M. H. et al. 1996).

Thiol containing HCV proteins can be purified, for example, on affinity chromatography resins which contain (1) a cleavable connector arm containing a disulfide bond (e.g. immobilised 5,5' dithiobis(2-nitrobenzoic acid) (Jayabaskaran, C. et al. 1987) and covalent chromatography on activated thio-Sepharose 4B (Pharmacia)) or (2) a aminohexanoyl-4-aminophenylarsine as immobilised ligand. The latter affinity matrix has been used for the purification of proteins, which are subject to redox regulation and dithiol proteins that are targets for oxidative stress (Kalef, E. et al. 1993).

Reversible protection may also be used to increase the solubilisation and extraction of peptides (Pomroy, N. C. and Deber, C. M. 1998).

The reversible protection and thiol stabilizing compounds may be presented under a monomeric, polymeric or liposomic form.

The removal of the reversibly protection state of the cysteine residues can chemically or enzymatically accomplished by e.g.:

a reductant, in particular DTT, DTE, 2-mercaptoethanol, dithionite, $SnCl_2$, sodium borohydride, hydroxylamine, TCEP, in particular in a concentration of 1-200 mM, more preferentially in a concentration of 50-200 mM;

removal of the thiol stabilising conditions or agents by e.g. pH increase;

enzymes, in particular thioesterases, glutaredoxine, thioredoxine, in particular in a concentration of 0.01-5 μM, even more particular in a concentration range of 0.1-5 μM;

combinations of the above described chemical and/or enzymatical conditions.

The removal of the reversibly protection state of the cysteine residues can be carried out in vitro or in vivo, e.g. in a cell or in an individual.

It will be appreciated that in the purification procedure, the cysteine residues may or may not be irreversibly blocked, or replaced by any reversible modification agent, as listed above.

A reductant according to the present invention is any agent which achieves reduction of the sulfur in cysteine residues, e.g. "S—S" disulfide bridges, desulphonation of the cysteine residue ($RS-SO_3^- \rightarrow RSH$). An antioxidant is any reagent which preserves the thiol status or minimises "S—S" formation and/or exchanges. Reduction of the "S—S" disulfide bridges is a chemical reaction whereby the disulfides are reduced to thiol (—SH). The disulfide bridge breaking agents and methods disclosed by Maertens et al. in WO 96/04385 are hereby incorporated by reference in the present description. "S—S" Reduction can be obtained by (1) enzymatic cascade pathways or by (2) reducing compounds. Enzymes like thioredoxin, glutaredoxin are known to be involved in the in vivo reduction of disulfides and have also been shown to be effective in reducing "S—S" bridges in vitro. Disulfide bonds are rapidly cleaved by reduced thioredoxin at pH 7.0, with an apparent second order rate that is around $10^4$ times larger than the corresponding rate constant for the reaction with DTT. The reduction kinetic can be dramatically increased by preincubation the protein solution with 1 mM DTT or dihydrolipoamide (Holmgren, A. 1979). Thiol compounds able to reduce protein disulfide bridges are for instance Dithiothreitol (DTT), Dithioerythritol (DTE), β-mercaptoethanol, thiocarbamates, bis(2-mercaptoethyl) sulfone and N,N'-bis(mercaptoacetyl)hydrazine, and sodium-dithionite. Reducing agents without thiol groups like ascorbate or stannous chloride ($SnCl_2$), which have been shown to be very useful in the reduction of disulfide bridges in monoclonal antibodies (Thakur, M. L. et al. 1991), may also be used for the reduction of HCV proteins. In addition, changes in pH values may influence the redox status of HCV proteins. Sodium borohydride treatment has been shown to be effective for the reduction of disulfide bridges in peptides (Gailit, J. 1993). Tris (2-carboxyethyl) phosphine (TCEP) is able to reduce disulfides at low pH (Burns, J. et al. 1991). Selenol catalyses the reduction of disulfide to thiols when DTT or sodium borohydride is used as reductant. Selenocysteamine, a commercially available diselenide, was used as precursor of the catalyst (Singh, R. and Kats, L. 1995).

The term "immunogenic" refers to the ability of a protein or a substance to produce an immune response. The immune response is the total response of a body to the introduction of an antigen, including antibody formation, cellular immunity, hypersensitivity, or immunological tolerance. Cellular immunity refers to a T-helper cell- and/or CTL-response.

The term "antigenic" refers to the ability of a protein or a substance to causes the formation of an antibody or to elicit a cellular response.

The expression "T-cell stimulating epitope" according to the present invention refers to an epitope capable of stimulating T-cells or CTL-cells, respectively. A T-helper cell stimulating epitope may be selected by monitoring the lymphoproliferative response towards polypeptides containing in their amino acid sequence a (putative) T-cell stimulating epitope. Said lymphoproliferative response may be measured by either a T-helper assay comprising in vitro stimulation of peripheral blood mononuclear cells (PMBCs) from patient sera with varying concentrations of peptides to be tested for T-cell stimulating activity and counting the amount of radiolabelled thymidine uptake. A CTL-stimulating epitope may be selected by means of a cytotoxic T-cell (CTL) assay measuring the lytic activity of cytotoxic cells using $^{51}Cr$ release. Proliferation is considered positive when the stimulation index (mean cpm of antigen-stimulated cultures/mean cpm of controle cultures) is more than 1, preferably more than 2, most preferably more than 3.

Another aspect of the invention refers to a composition comprising an isolated HCV envelope protein or fragment thereof according to the invention. Said composition may further comprise a pharmaceutically acceptable carrier and can be a medicament or a vaccine.

A further aspect of the invention covers a medicament or a vaccine comprising a HCV envelope protein or part thereof according to the invention.

Yet another aspect of the invention comprises a pharmaceutical composition for inducing a HCV-specific immune response in a mammal, said composition comprising an effective amount of a HCV envelope protein or part thereof according to the invention and, optionally, a pharmaceutically acceptable adjuvant. Said pharmaceutical composition comprising an effective amount of a HCV envelope protein or part thereof according to the invention may also be capable of inducing HCV-specific antibodies in a mammal, or capable of inducing a T-cell function in a mammal. Said pharmaceutical compostion comprising an effective amount of a HCV envelope protein or part thereof according to the invention may be prophylactic composition or a therapeutic composition. In a specific embodiment said mammal is a human.

A "mammal" is to be understood as any member of the higher vertebrate class Mammalia, including humans; characterized by live birth, body hair, and mammary glands in the female that secrete milk for feeding the young. Mammals thus also include non-human primates and trimera mice (Zauberman et al. 1999).

A "vaccine" or "medicament" is a composition capable of eliciting protection against a disease, whether partial or complete, whether against acute or chronic disease; in this case the vaccine or medicament is a prophylactic vaccine or medicament. A vaccine or medicament may also be useful for treatment of an already ill individual, in which case it is called a therapeutic vaccine or medicament. Likewise, a pharmaceutical composition can be used for either prophylactic and/or therapeutic purposes in which cases it is a prophylactic and/or therapeutic composition, respectively.

The HCV envelope proteins of the present invention can be used as such, in a biotinylated form (as explained in WO 93/18054) and/or complexed to Neutralite Avidin (Molecular Probes Inc., Eugene, Ore., USA), avidin or streptavidin. It should also be noted that "a vaccine" or "a medicament" may comprise, in addition to an active substance, a "pharmaceutically acceptable carrier" or "pharmaceutically acceptable adjuvant" which may be a suitable excipient, diluent, carrier and/or adjuvant which, by themselves, do not induce the production of antibodies harmful to the individual receiving the composition nor do they elicit protection. Suitable carriers are typically large slowly metabolized macromolecules such as proteins, polysaccharides, polylactic acids, polyglycolic acids, polymeric amino acids, amino acid copolymers and inactive virus particles. Such carriers are well known to those skilled in the art. Preferred adjuvants to enhance effectiveness of the composition include, but are not limited to: aluminium hydroxide, aluminium in combination with 3-0-deacylated monophosphoryl lipid A as described in WO 93/19780, aluminium phosphate as described in WO 93/24148, N-acetyl-muramyl-L-threonyl-D-isoglutamine as described in U.S. Pat. No. 4,606,918, N-acetyl-normuramyl-L-alanyl-D-isoglutamine, N-acetyl-muramyl-L-alanyl-D-isoglutamyl-L-alanine2-(1'2'dipalmitoyl-sn-glycero-3-hydroxyphosphoryloxy) ethylamine, RIBI (ImmunoChem Research Inc., Hamilton, Mont., USA) which contains monophosphoryl lipid A, detoxified endotoxin, trehalose-6,6-dimycolate, and cell wall skeleton (MPL+TDM+CWS) in a 2% squalene/Tween 80 emulsion. Any of the three components MPL, TDM or CWS may also be used alone or combined 2 by 2. The MPL may also be replaced by its synthetic analogue referred to as RC-529. Additionally, adjuvants such as Stimulon (Cambridge Bioscience, Worcester, Mass., USA), SAF-1 (Syntex) or bacterial DNA-based adjuvants such as ISS (Dynavax) or CpG (Coley Pharmaceuticals) may be used, as well as adjuvants such as combinations between QS21 and 3-de-O-acetylated monophosphoryl lipid A (WO94/00153), or MF-59 (Chiron), or poly[di(carboxylatophenoxy) phosphazene] based adjuvants (Virus Research Institute), or blockcopolymer based adjuvants such as Optivax (Vaxcel, Cythx) or inulin-based adjuvants, such as Algammulin and Gammalnulin (Anutech), Incomplete Freund's Adjuvant (IFA) or Gerbu preparations (Gerbu Biotechnik). It is to be understood that Complete Freund's Adjuvant (CFA) may be used for non-human applications and research purposes as well. "A vaccine composition" may further contain excipients and diluents, which are inherently non-toxic and non-therapeutic, such as water, saline, glycerol, ethanol, wetting or emulsifying agents, pH buffering substances, preservatives, and the like. Typically, a vaccine composition is prepared as an injectable, either as a liquid solution or suspension. Injection may be subcutaneous, intramuscular, intravenous, intraperitoneal, intrathecal, intradermal. Other types of administration comprise implantation, suppositories, oral ingestion, enteric application, inhalation, aerosolization or nasal spray or drops. Solid forms, suitable for solution on, or suspension in, liquid vehicles prior to injection may also be prepared. The preparation may also be emulsified or encapsulated in liposomes for enhancing adjuvant effect. The polypeptides may also be incorporated into Immune Stimulating Complexes together with saponins, for example Quil A (IS-COMS). Vaccine compositions comprise an effective amount of an active substance, as well as any other of the above-mentioned components. "Effective amount" of an active substance means that the administration of that amount to an individual, either in a single dose or as part of a series, is effective for prevention or treatment of a disease or for inducing a desired effect. This amount varies depending upon the health and physical condition of the individual to be treated, the taxonomic group of the individual to be treated (e.g. human, non-human primate, primate, etc.), the capacity of the individual's immune system to mount an effective immune response, the degree of protection desired, the formulation of the vaccine, the treating doctor's assessment, the strain of the infecting pathogen and other relevant factors. It is expected that the amount will fall in a relatively broad range that can be determined through routine trials. Usually, the amount will vary from 0.01 to 1000 µg/dose, more particularly from 0.1 to 100 µg/dose. Dosage treatment may be a single dose schedule or a multiple dose schedule. The vaccine may be administered in conjunction with other immunoregulatory agents.

Another aspect of the current invention relates to a method for producing the isolated HCV envelope protein or fragment thereof according to the invention.

Said method for producing an HCV envelope protein or part thereof is e.g. comprising transformation of a host cell with a recombinant nucleic acid or vector comprising an open reading frame encoding said HCV envelope protein or part thereof, and wherein said host cell is capable of expressing said HCV envelope protein or part thereof Said method may further comprise cultivation of said host cells in a suitable medium to obtain expression of said protein, isolation of the expressed protein from a culture of said host cells, or from said host cells. Said isolation may include one or more of (i) lysis of said host cells in the presence of a chaotropic agent, (ii) chemical modification of the cysteine thiol-groups in the isolated proteins wherein said chemical modification may be reversible or irreversible and (iii) heparin affinity chromatography.

Exemplary "chaotropic agents" are guanidinium chloride and urea. In general, a chaotropic agent is a chemical that can disrupt the hydrogen bonding structure of water. In concentrated solutions they can denature proteins because they reduce the hydrophobic effect.

With "recombinant nucleic acid" is intended a nucleic acid of natural or synthetic origin which has been subjected to at least one recombinant DNA technical manipulation such as restriction enzyme digestion, PCR, ligation, dephosphorylation, phosphorylation, mutagenesis, adaptation of codons for expression in a heterologous cell etc. In general, a recombinant nucleic acid is a fragment of a naturally occurring nucleic acid or comprises at least two nucleic acid fragments not naturally associated or is a fully synthetic nucleic acid.

The terms "polynucleotide", "polynucleic acid", "nucleic acid sequence", "nucleotide sequence", "nucleic acid molecule", "oligonucleotide", "probe" or "primer", when used herein refer to nucleotides, either ribonucleotides, deoxyribonucleotides, peptide nucleotides or locked nucleotides, or a combination thereof, in a polymeric form of any length or any shape (e.g. branched DNA). Said terms furthermore include double-stranded (ds) and single-stranded (ss) polynucleotides as well as triple-stranded polynucleotides. Said terms also include known nucleotide modifications such as methylation, cyclization and 'caps' and substitution of one or more of the naturally occurring nucleotides with an analog such as inosine or with non-amplifiable monomers such as HBEG (hexethylene glycol). Ribonucleotides are denoted as NTPs, deoxyribonucleotides as dNTPs and dideoxyribonucleotides as ddNTPs.

Nucleotides can generally be labeled radioactively, chemiluminescently, fluorescently, phosphorescently or with infrared dyes or with a surface-enhanced Raman label or plasmon resonant particle (PRP).

Said terms "polynucleotide", "polynucleic acid", "nucleic acid sequence", "nucleotide sequence", "nucleic acid molecule", "oligonucleotide", "probe" or "primer" also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. PNA probes can generally be shorter than DNA probes and are generally from 6 to 20 bases in length and more optimally from 12 to 18 bases in length (Nielsen, P. E. 2001). Said terms further encompass locked nucleic acids (LNAs) which are RNA derivatives in which the ribose ring is constrained by a methylene linkage between the 2'-oxygen and the 4'-carbon. LNAs display unprecedented binding affinity towards DNA or RNA target sequences. LNA nucleotides can be oligomerized and can be incorporated in chimeric or mix-meric LNA/DNA or LNA/RNA molecules. LNAs seem to be nontoxic for cultured cells (Orum, H. and Wengel, J. 2001, Wahlestedt, C. et al. 2000). In general, chimeras or mix-mers of any of DNA, RNA, PNA and LNA are considered as well as any of these wherein thymine is replaced by uracil.

It is clear from the above that the present invention also relates to the use of a core-glycosylated HCV envelope proteins according to the invention or a composition according to the invention for the manufacture of an HCV vaccine composition. In particular, the present invention relates to the use of a core-glycosylated HCV envelope protein according to the invention for inducing immunity against HCV in chronic HCV carriers. More in particular, the present invention relates to the use of a core-glycosylated HCV envelope protein as defined herein for inducing immunity against HCV in chronic HCV carriers prior to, simultaneously to or after any other therapy, such as, for example, the well-known interferon therapy either or not in combination with the administration of small drugs treating HCV, such as, for example, ribavirin. Such composition may also be employed before or after liver transplantation, or after presumed infection, such as, for example, needle-stick injury.

Another aspect of the invention relates to a method for the detection of the presence of anti-HCV antibodies in a sample suspected to comprise anti-HCV antibodies, said method comprising:
(i) contacting a HCV envelope protein or part thereof according to the invention with said sample under conditions allowing complexation of said HCV envelope protein or part thereof with said anti-HCV antibodies,
(ii) detecting the complex formed in (i), and
(iii) inferring from (ii) the presence of said anti-HCV antibodies in said sample.

In a specific embodiment, the contacting in step (i) of said method is occurring under competitive conditions. In another specific embodiment to said method, said HCV envelope protein or part thereof is attached to a solid support. In a further embodiment, said sample suspected to comprise anti-HCV antibodies is a biological sample.

A further aspect of the invention relates to a diagnostic kit for the detection of the presence of anti-HCV antibodies in a sample suspected to comprise anti-HCV antibodies, said kit comprising a HCV envelope protein or part thereof according to the invention. In a specific embodiment thereto, said HCV envelope protein or part thereof is attached to a solid support. In a further embodiment, said sample suspected to comprise anti-HCV antibodies is a biological sample.

The term "biological sample" as used herein, refers to a sample of tissue or fluid isolated from an individual, including but not limited to, for example, serum, plasma, lymph fluid, the external sections of the skin, respiratory-, intestinal- or genito-urinary tracts, oocytes, tears, saliva, milk, blood cells, tumors, organs, gastric secretions, mucus, spinal cord fluid, external secretions such as, for example, excrement, urine, sperm, and the like.

The HCV envelope proteins of the present invention, or the parts thereof, are particularly suited for incorporation into methods, such as immunoassay methods, for the detection of HCV, and/or genotyping of HCV, for prognosing/monitoring of HCV disease, or as a therapeutic agent.

The methods, such as immunoassay methods, according to the present invention utilize the HCV envelope proteins of the present invention that maintain linear (in case of peptides) and conformational epitopes, recognized by antibodies in the sera from individuals infected with HCV. The HCV E1 and E2 antigens of the present invention may be employed in virtually any assay format that employs a known antigen to detect antibodies. Of course, a format that denatures the HCV conformational epitope should be avoided or adapted. A common feature of all of these assays is that the antigen is contacted with the body component suspected of containing HCV antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of an immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA and RIA assays.

An immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ 1 or Immunlon™ 2 microtiter plates can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of antibodies, such as anti-HCV antibodies, in the antibody-antigen complexes is directly monitored. This may be accomplished by determining whether labeled anti-xenogeneic (e.g. anti-human) antibodies which recognize an epitope on said antibodies, such as said anti-HCV antibodies, will bind due to complex formation. In a competitive format, the amount of said antibodies, such as said anti-HCV antibodies, in a sample is deduced by monitoring the competitive effect on the binding of a known amount of (labeled) antibody (or other competing ligand) or antigen in the complex.

Antigen-antibody complexes can be detected by any of a number of known techniques, depending on the format. For example, unlabeled antibodies such as anti-HCV antibodies in the complex may be detected using a conjugate of anti-xenogeneic Ig complexed with a label (e.g. an enzyme label).

In an immunoprecipitation or agglutination assay format the reaction between an antigen and an antibody forms a protein cluster that precipitates from the solution or suspension and forms a visible layer or film of precipitate. If no antibody is present in the test specimen or sample, no such precipitate is formed.

The HCV envelope proteins, or specific parts thereof of the present invention comprised of conformational epitopes will typically be packaged in the form of a kit for use in these immunoassays. The kit will normally contain in separate containers the native HCV antigen, control antibody formulations (positive and/or negative), labeled antibody when the assay format requires the same and signal generating reagents (e.g. enzyme substrate) if the label does not generate a signal directly. The native HCV antigen may be already bound to a solid matrix or separate with reagents for binding it to the matrix. Instructions (e.g. written, tape, CD-ROM, etc.) for carrying out the assay usually will be included in the kit.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin. In order to block the effects of rheumatoid factor-like substances, the test sample is subjected to conditions sufficient to block the effect of rheumatoid factor-like substances. These conditions comprise contacting the test sample with a quantity of anti-human IgG to form a mixture, and incubating the mixture for a time and under conditions sufficient to form a reaction mixture product substantially free of rheumatoid factor-like substance.

In particular, the present invention relates to the use of an HCV envelope protein or part thereof according to the invention for the preparation of a diagnostic kit.

Since the a core-glycosylated HCV envelope proteins according to the present invention are highly immunogenic, and stimulate both the humoral and cellular immune response, the present invention further relates also to a kit for detecting HCV related T cell response, comprising the oligomeric particle or the purified single HCV envelope protein of the instant invention. HCV T cell response can for example be measured as described by Leroux-Roels et al. in WO95/12677.

A further aspect of the invention relates to a method of inducing a HCV-specific immune response in a mammal, said method comprising administering to said mammal an effective amount of a HCV envelope protein or part thereof according to the invention optionally comprising a pharmaceutically acceptable adjuvant. Said method comprising administering to said mammal an effective amount of a HCV envelope protein or part thereof according to the invention may also be used for inducing HCV-specific antibodies in a mammal or for inducing a specific T-cell function in a mammal. In said methods, said administering may be for prophylactic purposes, i.e. prophylactic administering or for therapeutic purposes, i.e. therapeutic administering.

Yet another aspect of the invention relates to a method of immunizing a mammal, said method comprising administering to said mammal an effective amount of a HCV envelope protein or part thereof according to the invention optionally comprising a pharmaceutically acceptable adjuvant.

The current invention also relates to a method of treating a mammal infected with HCV, said method comprising administering to said mammal an effective amount of a HCV envelope protein or part thereof according to the invention optionally comprising a pharmaceutically acceptable adjuvant.

Any of the above described aspects of the invention or the embodiments specific to said aspects is also applicable generally to proteins of interest which are the product of expression in a eukaryotic cells and which are further characterized by the same glycosylation properties as described above for the two different HCV envelope proteins.

More particularly, the invention thus relates to an isolated protein of interest or a fragment thereof comprising at least one N-glycosylation site, said protein or fragment thereof characterized in that it is the product of expression in a eukaryotic cell and further characterized in that on average up to 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80% of the N-glycosylated sites are core-glycosylated. More specific thereto, more than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% of the N-glycosylated sites are glycosylated with an oligomannose with a structure defined by Man(8 to 10)-GlcNAc(2). More specific to any of the above N-glycosylation characteristics, the ratio of sites core-glycosylated with an oligomannose with structure Man(7)-GlcNAc(2) over the sites core-glycosylated with an oligomannose with structure Man(8)-GlcNAc(2) is less than or equal to 0.15, 0.2, 0.25, 0.30, 0.35, 0.40, 0.45, or 0.50. Further more specific to any of the above N-glycosylation characteristics, said oligomannoses contain less than 20%, 19%, 18%, 17%, 16%, 15%, 14%, 13%, 12%, 11%, 10%, 9%, 8%, 7%, 6%, or 5% terminal α 1,3 mannose.

Another alternative aspect of the invention is related to an isolated protein of interest or a fragment thereof comprising at least one N-glycosylation site, said protein or fragment thereof characterized in that it is the product of expression in a eukaryotic cell and further characterized in that N-glycosylated sites are occupied by oligomannoses wherein the ratio of the oligomannoses with structure Man(7)-GlcNAc(2) over the oligomannoses with structure Man(8)-GlcNAc(2) is less than or equal to 0.15, 0.2, 0.25, 0.30, 0.35, 0.40, 0.44, 0.45, or 0.50. Further more specific to the above N-glycosylation characteristics, said oligomannoses contain less than 20%, 19%, 18%, 17%, 16%, 15%, 14%, 13%, 12%, 11%, 10%, 9%, 8%, 7%, 6%, or 5% terminal α 1,3 mannose.

In particular, said isolated protein of interest or fragment thereof is the product of expression in a yeast cell such as a *Hansenula* cell. Said isolated protein of interest or fragment thereof can e.g. be a viral envelope protein or a fragment thereof such as a HCV envelope protein or HBV (hepatitis B) envelope protein, or fragments thereto. Other examplary viral envelope proteins include the HIV (human immunodeficiency virus) envelope protein gp120 and viral envelope proteins of a virus belonging to the Flavirideae. In general, said isolated protein of interest or fragment thereof can be any protein needing the N-glycosylation characteristics of the current invention.

With "HCV-recombinant vaccinia virus" is meant a vaccinia virus comprising a nucleic acid sequence encoding a HCV protein or part thereof.

The terms "HCV virus-like particle formed of a HCV envelope protein" "oligomeric particles formed of HCV envelope proteins" are herein defined as structures of a specific nature and shape containing several basic units of the HCV E1 and/or E2 envelope proteins, which on their own are thought to consist of one or two E1 and/or E2 monomers, respectively. It should be clear that the particles of the present invention are defined to be devoid of infectious HCV RNA genomes. The particles of the present invention can be higher-order particles of spherical nature which can be empty, consisting of a shell of envelope proteins in which lipids, detergents, the HCV core protein, or adjuvant molecules can be incorporated. The latter particles can also be encapsulated by liposomes or apolipoproteins, such as, for example, apolipoprotein B or low density lipoproteins, or by any other means of targeting said particles to a specific organ or tissue. In this case, such empty spherical particles are often referred to as "virus-like particles" or VLPs. Alternatively, the higher-order particles can be solid spherical structures, in which the complete sphere consists of HCV E1 or E2 envelope protein oligomers, in which lipids, detergents, the HCV core protein, or adjuvant molecules can be additionally incorporated, or which in turn may be themselves encapsulated by liposomes or apolipoproteins, such as, for example, apolipoprotein B, low density lipoproteins, or by any other means of targeting said particles to a specific organ or tissue, e.g. asialoglycoproteins. The particles can also consist of smaller structures (compared to the empty or solid spherical structures indicated above) which are usually round (see further)-shaped and which usually do not contain more than a single layer of HCV envelope proteins. A typical example of such smaller particles are rosette-like structures which consist of a lower number of HCV envelope proteins, usually between 4 and 16. A specific example of the latter includes the smaller particles obtained with E1s in 0.2% CHAPS as exemplified herein which apparently contain 8-10 monomers of E1s. Such rosette-like structures are usually organized in a plane and are round-shaped, e.g. in the form of a wheel. Again lipids, detergents, the HCV core protein, or adjuvant molecules can be additionally incorporated, or the smaller particles may be encapsulated by liposomes or apolipoproteins, such as, for example, apolipoprotein B or low density lipoproteins, or by any other means of targeting said particles to a specific organ or tissue. Smaller particles may also form small spherical or globular structures consisting of a similar smaller number of HCV E1 or E2 envelope proteins in which lipids, detergents, the HCV core protein, or adjuvant molecules could be additionally incorporated, or which in turn may be encapsulated by liposomes or apolipoproteins, such as, for example, apolipoprotein B or low density lipoproteins, or by any other means of targeting said particles to a specific organ or tissue. The size (i.e. the diameter) of the above-defined particles, as measured by the well-known-in-the-art dynamic light scattering techniques (see further in examples section), is usually between 1 to 100 nm, more preferentially between 2 to 70 nm, even more preferentially between 2 and 40 nm, between 3 to 20 nm, between 5 to 16 nm, between 7 to 14 nm or between 8 to 12 nm.

In particular, the present invention relates to a method for purifying core glycosylated hepatitis C virus (HCV) envelope proteins, or any part thereof, suitable for use in an immunoassay or vaccine, which method comprising:
(i) growing *Hansenula* or *Saccharomyces* glycosylation minus strains transformed with an envelope gene encoding an HCV E1 and/or HCV E2 protein, or any part thereof, in a suitable culture medium;
(ii) causing expression of said HCV E1 and/or HCV E2 gene, or any part thereof, and
(iii) purifying said core-glycosylated HCV E1 and/or HCV E2 protein, or any part thereof, from said cell culture.

The invention further pertains to a method for purifying core-glycosylated hepatitis C virus (HCV) envelope proteins, or any part thereof, suitable for use in an immunoassay or vaccine, which method comprising:
(i) growing *Hansenula* or *Saccharomyces* glycosylation minus strains transformed with an envelope gene encoding an HCV E1 and/or HCV E2 protein, or any part thereof, in a suitable culture medium;
(ii) causing expression of said HCV E1 and/or HCV E2 gene, or any part thereof; and
(iii) purifying said intracellularly expressed core-glycosylated HCV E1 and/or HCV E2 protein, or any part thereof, upon lysing the transformed host cell.

The invention further pertains to a method for purifying core-glycosylated hepatitis C virus (HCV) envelope proteins, or any part thereof, suitable for use in an immunoassay or vaccine, which method comprising:
(i) growing *Hansenula* or *Saccharomyces* glycosylation minus strains transformed with an envelope gene encoding an HCV E1 and/or HCV E2 protein, or any part thereof, in a suitable culture medium, in which said HCV E1 and/or HCV E2 protein, or any part thereof, comprises at least two Cys-amino acids;
(ii) causing expression of said HCV E1 and/or HCV E2 gene, or any part thereof; and
(iii) purifying said core-glycosylated HCV E1 and/or HCV E2 protein, or any part thereof, in which said Cys-amino acids are reversibly protected by chemical and/or enzymatic means, from said culture.

The invention further pertains to a method for purifying core-glycosylated hepatitis C virus (HCV) envelope proteins, or any part thereof, suitable for use in an immunoassay or vaccine, which method comprising:
(i) growing *Hansenula* or *Saccharomyces* glycosylation minus strains transformed with an envelope gene encoding an HCV E1 and/or HCV E2 protein, or any part thereof, in a suitable culture medium, in which said HCV E1 and/or HCV E2 protein, or any part thereof, comprises at least two Cys-amino acids;
(ii) causing expression of said HCV E1 and/or HCV E2 gene, or any part thereof; and,
(iii) purifying said intra-cellulary expressed core-glycosylated HCV E1 and/or HCV E2 protein, or any part thereof, upon lysing the transformed host cell, in which said Cys-amino acids are reversibly protected by chemical and/or enzymatic means.

The present invention specifically relates to a method for purifying recombinant core-glycosylated HCV yeast proteins, or any part thereof, as described herein, in which said purification includes heparin affinity chromatography.

Hence, the present invention also relates to a method for purifying recombinant core-glycosylated HCV yeast proteins, or any part thereof, as described above, in which said chemical means is sulfonation.

Hence, the present invention also relates to a method for purifying recombinant core-glycosylated HCV yeast proteins, or any part thereof, as described above, in which said reversibly protection of Cys-amino acids is exchanged for an irreversible protection by chemical and/or enzymatic means.

Hence, the present invention also relates to a method for purifying recombinant core-glycosylated HCV yeast proteins, or any part thereof, as described above, in which said irreversible protection by chemical means is iodo-acetamide.

Hence, the present invention also relates to a method for purifying recombinant core-glycosylated HCV yeast proteins, or any part thereof, as described above, in which said irreversible protection by chemical means is NEM or Biotin-NEM or a mixture thereof The present invention also relates to a composition as defined above which also comprises HCV core, E1, E2, P7, NS2, NS3, NS4A, NS4B, NS5A and/or NS5B protein, or parts thereof. The core-glycosylated proteins E1, E2, and/or E1/E2 of the present invention may, for example, be combined with other HCV antigens, such as, for example, core, P7, NS3, NS4A, NS4B, NS5A and/or NS5B. The purification of these NS3 proteins will preferentially include a reversible modification of the cysteine residues, and even more preferentially sulfonation of cysteines. Methods to obtain such a reversible modification, including sulfonation have been described for NS3 proteins in Maertens et al. (PCT/EP99/02547). It should be stressed that the whole content, including all the definitions, of the latter document is incorporated by reference in the present application.

Also, the present invention relates to the use of a core-glycosylated envelope protein as described herein for inducing immunity against HCV, characterized in that said core-glycosylated envelope protein is used as part of a series of time and compounds. In this regard, it is to be understood that the term "a series of time and compounds" refers to administering with time intervals to an individual the compounds used for eliciting an immune response. The latter compounds may comprise any of the following components: a core-glycosylated envelope protein, HCV DNA vaccine composition, HCV polypeptides. In this respect, a series comprises administering, either:

(i) an HCV antigen, such as, for example, a core-glycosylated envelope protein, with time intervals, or (ii) an HCV antigen, such as, for example, a core-glycosylated envelope protein in combination with a HCV DNA vaccine composition, in which said core-glycosylated envelope protein oligomeric particles and said HCV DNA vaccine composition, can be administered simultaneously, or at different time intervals, including at alternating time intervals, or (iii) either (i) or (ii), possibly in combination with other HCV peptides, with time intervals.

In this regard, it should be clear that a HCV DNA vaccine composition comprises nucleic acids encoding HCV envelope peptide, including E1-, E2-, E1/E2-peptides, NS3 peptide, other HCV peptides, or parts of said peptides. Moreover, it is to be understood that said HCV peptides comprises HCV envelope peptides, including E1-, E2-, E1/E2-peptides, other HCV peptides, or parts thereof The term "other HCV peptides" refers to any HCV peptide or fragment thereof In item (ii) of the above scheme, the HCV DNA vaccine composition comprises preferentially nucleic acids encoding HCV envelope peptides. In item (ii) of the above scheme, the HCV DNA vaccine composition consists even more preferentially of nucleic acids encoding HCV envelope peptides, possibly in combination with a HCV-NS3 DNA vaccine composition. In this regard, it should be clear that an HCV DNA vaccine composition comprises a plasmid vector comprising a polynucleotide sequence encoding an HCV peptide as described above, operably linked to transcription regulatory elements. As used herein, a "plasmid vector" refers to a nucleic acid molecule capable of transporting another nucleic acid to which it has been linked. Preferred vectors are those capable of autonomous replication and/or expression of nucleic acids to which they have been linked. In general, but not limited to those, plasmid vectors are circular double stranded DNA loops which, in their vector form, are not bound to the chromosome. As used herein, a "polynucleotide sequence" refers to polynucleotides such as deoxyribonucleic acid (DNA), and, where appropriate, ribonucleic acid (RNA). The term should also be understood to include, as equivalents, analogs of either RNA or DNA made from nucleotide analogs, and single (sense or antisense) and double-stranded polynucleotides. As used herein, the term "transcription regulatory elements" refers to a nucleotide sequence which contains essential regulatory elements, such that upon introduction into a living vertebrate cell it is able to direct the cellular machinery to produce translation products encoded by the polynucleotide. The term "operably linked" refers to a juxtaposition wherein the components are configured so as to perform their usual function. Thus, transcription regulatory elements operably linked to a nucleotide sequence are capable of effecting the expression of said nucleotide sequence. Those skilled in the art can appreciate that different transcriptional promoters, terminators, carrier vectors or specific gene sequences may be used successfully.

Alternatively, the DNA vaccine may be delivered through a live vector such as adenovirus, canary pox virus, MVA, and the like.

The present invention is illustrated by the Examples as set forth below. These Examples are merely illustrative and are not construed to restrict or limit the invention in any way.

EXAMPLES

Example 1

Construction of pFPMT-MT-MTα-E1-H6 Shuttle Vector

Plasmids for *Hansenula polymorpha* transformation were constructed as follows. The pFPMT-MFα-E1-H6shuttle vector has been constructed in a multi-step procedure. Initially the nucleic acid sequence encoding the HCV E1s protein (SEQ ID NO:2) was cloned after a CHH leader sequence (CHH=*Carcinus maenas* hyperglycemic hormone) which was subsequently changed for a MFα leader sequence (MFα=*Saccharomyces cerevisiae* α-mating factor).

At first a pUC18 derivative has been constructed harboring the CHH-E1-H6 unit as a EcoRI/BamHI fragment by the seamless cloning method (Padgett, K. A. and Sorge, J. A. 1996). Thereto, the E1s-H6-encoding DNA fragment and the pCHH-Hir-derived acceptor plasmid were generated by PCR as described below.

Generation of E1s-H6-Encoding DNA Fragment

The E1-H6 DNA fragment (coding for HCV type 1b E1s protein consisting of the amino acids 192 to 326 of E1s elongated with 6 His-residues; SEQ ID NO:5) was isolated by PCR from the plasmid pGEMTE1sH6 (SEQ ID NO:6; FIG. 1). The following primers were used thereto:

CHHE1-F: 5'-agtta<u>ctcttc</u>a.aggtatgaggtgcgcaacgtgtccg-3' (SEQ ID NO:7);

The Eam1104I site is underlined, the dot marks the cleavage site. The bold printed bases are complementary to those of primer CHH-links. The non-marked bases anneal within the start region of E1 (192-326) in sense direction; and

CHHE1-R:

5'-agtta<u>ctcttc</u>a.cagggatcctccttaatggtgatggtggtggtgcc-3' (SEQ ID NO: 8);

The Eam1104I site is underlined, the dot marks the cleavage site. The bold printed bases are complementary to those of primer MF30-rechts. The bases forming the BamHI site usefull for later cloning procedures are printed in italics. The non-marked bases anneal in antisense direction within the end of the E1-H6 unit, including the stop codon and three additional bases between the stop codon and the BamHI site.

The reaction mixture was constituted as follows: total volume of 50 μL containing 20 ng of Eco311-linearized pGEMTE1sH6, each 0.2 μM of primers CHHE1-F and CHHE1-R, dNTP's (each at 0.2 μM), 1× buffer 2 (Expand Long Template PCR System; Boehringer; Cat No 1681 834), 2.5 U polymerase mix (Expand Long Template PCR System; Boehringer; Cat No 1681 834).

Program 1 was used, said program consisting of the following steps:

1. denaturation: 5 min 95° C.;
2. 10 cycles of 30 sec denaturation at 95° C., 30 sec annealing at 65° C., and 130 sec elongation at 68° C.
3. termination at 4° C.

Then 5 μL 10× buffer 2 (Expand Long Template PCR System; Boeringer; Cat No 1681 834), 40 μL H₂O, and 5 μL of [dATP, dGTP, and dTTP (2 mM each); 10 mM 5-methyl-dCTP] were added to the sample derived from program 1, and further amplification was performed following program 2 consisting of the following steps:
1. denaturation: 5 min at 95° C.
2. 5 cycles of 45 sec denaturation at 95° C., 30 sec annealing at 65° C., and 130 sec at 68° C.
3. termination at 4° C.

Generation of pCHH-Hir-Derived Acceptor Plasmid

The acceptor fragment was made by PCR from the pCHH-Hir plasmid (SEQ ID NO:9; FIG. 2) and consists of almost the complete pCHH-Hir plasmid, except that the Hir-coding sequence is not present in the PCR product. Following primers were used for this PCR:
1. CHH-links: 5'-agttactcttca.cctcttttccaacgggtgtgtag-3' (SEQ ID NO:10);
   The Eam1104I site is underlined, the dot marks the cleavage site. The bold printed bases are complementary to those of primer CHHE1-F. The non-marked bases anneal within the end of the CHH sequence in antisense direction; and
2. MF30-rechts: 5'-agtcactcttca.ctgcaggcatgcaagcttggcg-3' (SEQ ID NO:11);
   The Eam1104I site is underlined, the dot marks the cleavage site. The bold printed bases are complementary to those of primer CHHE1-R. The non-marked bases anneal within the pUC18 sequences behind the cloned CHH-Hirudin HL20 of pCHH-Hir, pointing away from the insert.

The reaction mixture was constituted as follows: total volume of 50 μL containing 20 ng of Asp718I-linearized pCHH-Hir, each 0.2 μM of primers CHH-links and MF30-rechts, dNTP's (each at 0.2 μM), 1× buffer 2 (Expand Long Template PCR System; Boeringer; Cat No 1681 834), 2.5 U polymerase mix (Expand Long Template PCR System; Boeringer; Cat No 1681 834).

Program 1 was as described above was used.

Then 5 μL 10× buffer 2 (Expand Long Template PCR System; Boeringer; Cat No 1681 834), 40 μL H₂O, and 5 μL of [dATP, dGTP, and dTTP (2 mM each); 10 mM 5-methyl-dCTP] were added to the sample derived from program 1, and further amplification was performed following program 2 as described above.

Generation of Vector pCHHE1

The E1s-H6-encoding DNA fragment and the pCHH-Hir-derived acceptor plasmid generated by PCR as described above were purified using the PCR product purification kit (Qiagen) according to the supplier's specifications. Subsequently the purified fragments were digested separately with Eam1104I. Subsequently, the E1s-H6 DNA fragment was ligated into the pCHH-Hir-derived acceptor plasmid using T4 ligase (Boehringer) following the specifications of the supplier.

E. coli XL-Gold cells were transformed with the ligation mixture and the plasmid DNA of several ampicillin-resistant colonies were analyzed by digestion with EcoRI and BamHI. A positive clone was selected and denominated as pCHHE1.

Generation of Vector pFPMT-CHH-E1H6

The EcoRI/BamHI fragment of pCHHE1 was ligated with the EcoRI/BamHI digested vector pFPMT121 (SEQ ID NO:12; FIG. 3). T4 ligase (Boehringer) was used according to the supplier's instructions. The ligation mixture was used to transform E. coli DH5αF' cells. Several transformants were analyzed on restriction pattern of the plasmid DNA and a positive clone was withheld which was denominated pFPMT-CHH-E1H6 (SEQ ID NO:13; FIG. 4).

Generation of pFPMT-MFα-E1-H6

Figure 36:
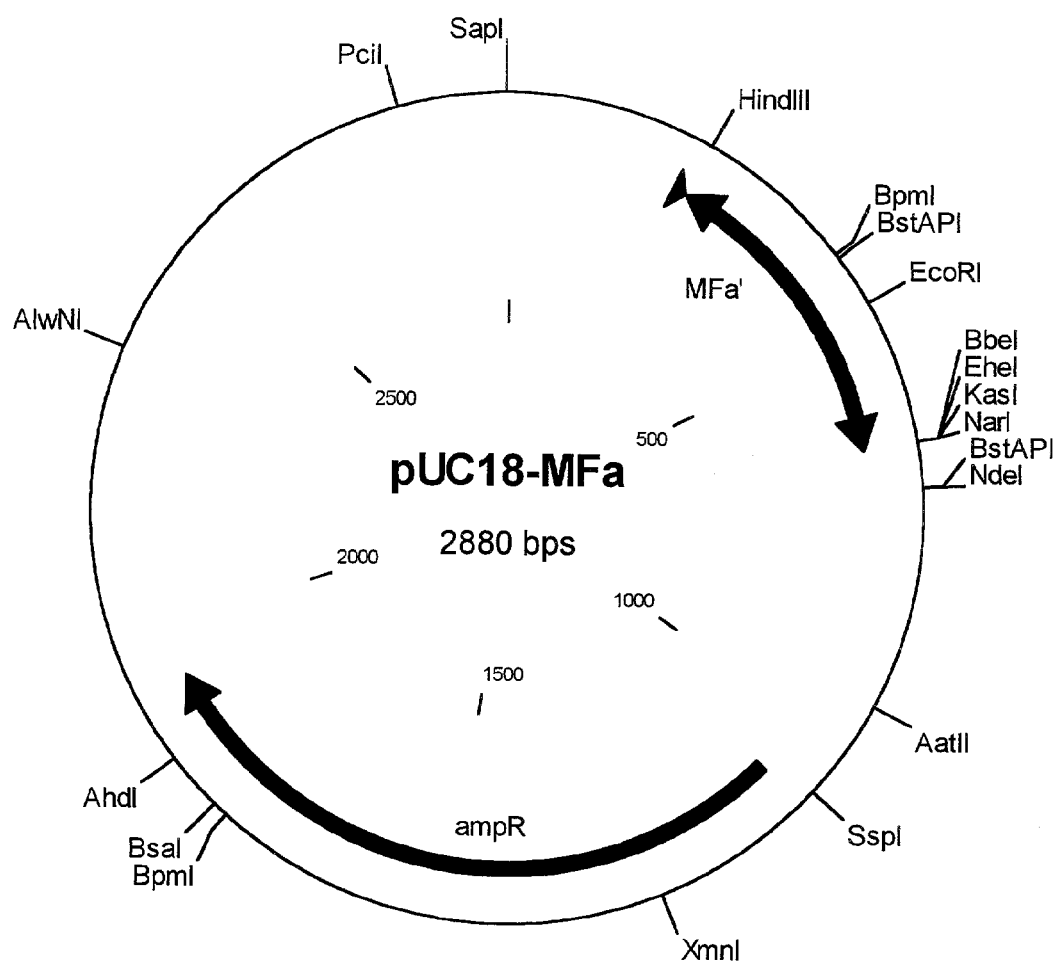

Finally the shuttle vector pFPMT-MFα-E1-H6 was generated by ligation of three fragments, said fragments being:
1. the 6.961 kb EcoRI/BamHI digested pFPMT121 (SEQ ID NO:12; FIG. 3),
2. the 0.245 EcoRI/HindIII fragment of pUC18-MFa (SEQ ID NO:62; FIG. 36), and
3. the 0.442 kb HindIII/BamHI fragment of a 0.454 kb PCR product derived from pFPMT-CHH-E1H6.

The 0.454 kb PCR product giving rise to fragment No. 3 was obtained by PCR using the following primers:
1. primer MFa-E1 f-Hi:
   5'-aggggtaagcttggataaaaggtatgaggtgcgcaacgtgtccgggatgt-3' (SEQ ID NO:14); and
2. primer E1 back-Bam:
   5'-agttacggatccttaatggtgatggtggtggtgccagttcat-3' (SEQ ID NO:15).

The reaction mixture was constituted as follows: Reaction mixture volume 50 μL, pFPMT-CHH-E1-H6 (EcoRI-linearized; 15 ng/μL), 0.5 μL; primer MFa-E1 f-Hi (50 μM), 0.25 μL; primer E1 back-Bam (50 μM), 0.25 μL; dNTP's (all at 2 mM), 5 μL; DMSO, 5 μL; H₂O, 33.5 μL; Expand Long Template PCR System (Boeringer Mannheim; Cat No 1681 834) Buffer 2 (10× concentrated), 5 μL; Expand Long Template PCR System Polymerase mixture (1 U/μL), 0.5 μL.

The PCR program consisting of the following steps was used:
1. denaturation: 5 min at 95° C.
2. 29 cycles of 45 sec denaturation at 95° C., 45 sec annealing at 55° C., and 40 sec elongation at 68° C.
3. termination at 4° C.

Based on the primers used, the resulting 0.454 kb PCR product contained the codons of E1 (192-326) followed by six histidine codons and a "taa" stop codon, upstream flanked by the 22 3'-terminal base pairs of the MFα prepro sequence (including the cloning relevant HindIII site plus a six base pairs overhang) and downstream flanked by a (cloning relevant) BamHI site and a six base pairs overhang.

For the ligation reaction, T4 DNA ligase (Boehringer Mannheim) has been used according to the supplier's conditions (sample volume 20 μL).

E. coli HB101 cells were transformed with the ligation mixture and positive clones withheld after restriction analysis of the plasmids isolated from several transformants. A positive plasmid was selected and denominated as pFPMT-MFα-E1-H6 (SEQ ID NO:16; FIG. 5).

Example 2

Construction of pFPMT-CL-E1-H6 Shuttle Vector

Plasmids for *Hansenula polymorpha* transformation were constructed as follows. The pFPMT-CL-E1-H6 shuttle vector was constructed in three steps starting from pFPMT-MFα-E1-H6 (SEQ ID NO:16, FIG. 5).

In a first step, the MFα-E1-H6 reading frame of pFPMT-MFα-E1-H6 was subcloned into the pUC18 vector. Therefore a 1.798 kb SalI/BamHI fragment of pFPMT-MFα-E1-H6 (containing the FMD promotor plus MFα-E1-H6) was ligated to the SalI/BamHI vector fragment of pUC18 with T4 ligase (Boehringer) according to the supplier's conditions. This resulted in plasmid that is depicted in FIG. 6 (SEQ ID NO:17), and further denominated as pMa12-1 (pUC18-FMD-MFα-E1-H6). The ligation mixture was used to transform *E. coli* DH5αF' cells. Several ampicillin-resistant colonies were picked and analyzed by restriction enzyme digestion of plasmid DNA isolated from the picked clones. A positive clone was further analyzed by determining the DNA sequence of the MFα-E1-H6 coding sequence. A correct clone was used for PCR directed mutagenesis to replace the MFα pre-pro-sequence with the codons of the avian lysozyme pre-sequence ("CL"; corresponding to amino acids 1 to 18 of avian lysozyme; SEQ ID NO:1). The principle of the applied PCR-directed mutagenesis method is based on the amplification of an entire plasmid with the desired alterations located at the 5'-ends of the primers. In downstream steps, the ends of the linear PCR product are modified prior to self-ligation resulting in the desired altered plasmid.

The following primers were used for the PCR reaction:

1. primer CL hin:      5'-<u>tgcttcctaccactagcagcactagga</u>tatgaggtgcgcaacgtgtccggg-3'    (SEQ ID NO:18);

2. primer CL her neu:  5'-<u>tagtactagtattagtaggcttcgcat</u>gaattcccgatgaaggcagagagcg-3'   (SEQ ID NO:19).

The underlined 5' regions of the primers contain the codons of about half of the avian lysozyme pre-sequence. Primer CL her neu includes a SpeI restriction site (italic). The non-underlined regions of the primers anneal with the codons for amino acid residues 192 to 199 of E1 (CL hin) or the with the "atg" start codon over the EcoRI site up to position −19 (counted from the EcoRI site) of FMD promoter. The primers are designed to amplify the complete pMa12-1 thereby replacing the codons of the MFα pre-pro-sequence with the codons of the avian lysozyme pre sequence.

The reaction mixture was constituted as follows: pUC18-FMD-Mfα-E1-H6 (pMa12-1; 1.3 ng/μL), 1 μL; primer CL hin (100 μM), 2 μL; primer CL her neu (100 μM), 2 μL; dNTP's (all at 2.5 mM), 8 μL; H₂O, 76 μL; Expand Long Template PCR System (Boeringer; Cat No 1681 834) Buffer 2 (10× concentrated), 10 μL; Expand Long Template PCR System Polymerase mixture (1 U/μL), 0.75 μL.

The PCR program consisting of the following steps was applied:
1. denaturation: 15 min at 95° C.
2. 35 cycles of 30 sec denaturation at 95° C., 1 min annealing at 60° C., and 1 min elongation at 72° C.
3. termination at 4° C.

The resulting PCR product was checked by agarose gel electrophoresis for its correct size (3.5 kb). Thereafter the 3'-A overhangs form the PCR product were removed by a T4 polymerase reaction resulting in blunt ends with 3'- and 5'-OH-groups. Therefore, the PCR product was treated with T4 polymerase (Boehringer; 1 U/μL): to the remaining 95 μL of PCR reaction mix were added 1 μL T4 polymerase and 4 μL dNTP's (all at 2.5 mM). The sample was incubated for 20 min at 37° C. Subsequently, the DNA was precipitated with ethanol and taken up in 16 μL H₂O.

Subsequently 5'-phosphates were added to the blunt-ended PCR product by a kinase reaction. Therefore, to the 16 μL blunt-ended PCR product were added 1 PL T4 polynucleotide kinase (Boehringer; 1 U/μL), 2 μL 10-fold concentrated T4 polynucleotide kinase reaction buffer (Boehringer), and 1 μL ATP (10 mM). The sample was incubated for 30 min at 37° C.

Subsequently the DNA was applied onto a 1% agarose gel and the correct product band was isolated by means of the gel extraction kit (Qiagen) according to the supplier's conditions. Fifty (50) ng of the purified product was then self-ligated by use of T4 ligase (Boehringer) according to the supplier's conditions. After 72 h incubation at 16° C., the DNA in the ligation mix was precipitated with ethanol and dissolved in 20 μL water.

*E. coli* DH5α-F' cells were subsequently transformed with 10 μL of the ligation sample. The plasmid DNA of several ampicillin-resistant clones was checked by means of restriction enzyme digestion. A positive clone was withheld and denominated p27d-3 (pUC18-FMD-CL-E1-H6, SEQ ID NO:20, FIG. 7). Subsequently the CL-E1-H6 reading frame was verified by DNA sequencing.

In a last step the pFPMT-CL-E1-H6 shuttle vector was constructed as described below. The 0.486 kb EcoRI/BamHI fragment of p27d-3 (harboring CL-E1 (192-326)-H6) was ligated with EcoRI/BamHI-digested pFPMT121 (SEQ ID NO:12, FIG. 3). For the reaction, T4 ligase (Boehringer) has been used according to the supplier's recommendations. The DNA in the ligation sample was precipitated with ethanol and dissolved in 10 μL H₂O. *E. coli* DH5α-F' cells were transformed with 10 μL of the ligation sample, and the plasmid DNA of several ampicillin-resistant colonies were analyzed by digestion with EcoRI and BamHI. Plasmid Dan clone p37-5 (pFPMT-CL-E1-H6; SEQ ID NO:21, FIG. 8) showed the desired fragment sizes of 0.486 kb and 6.961 kb. The correct sequence of CL-E1-H6 of p37-5 was verified by sequencing.

Example 3

Construction of pFPMT-MFα-E2-H6 and pMPT-MFα-E2-H6 Shuttle Vectors

Figure 10:
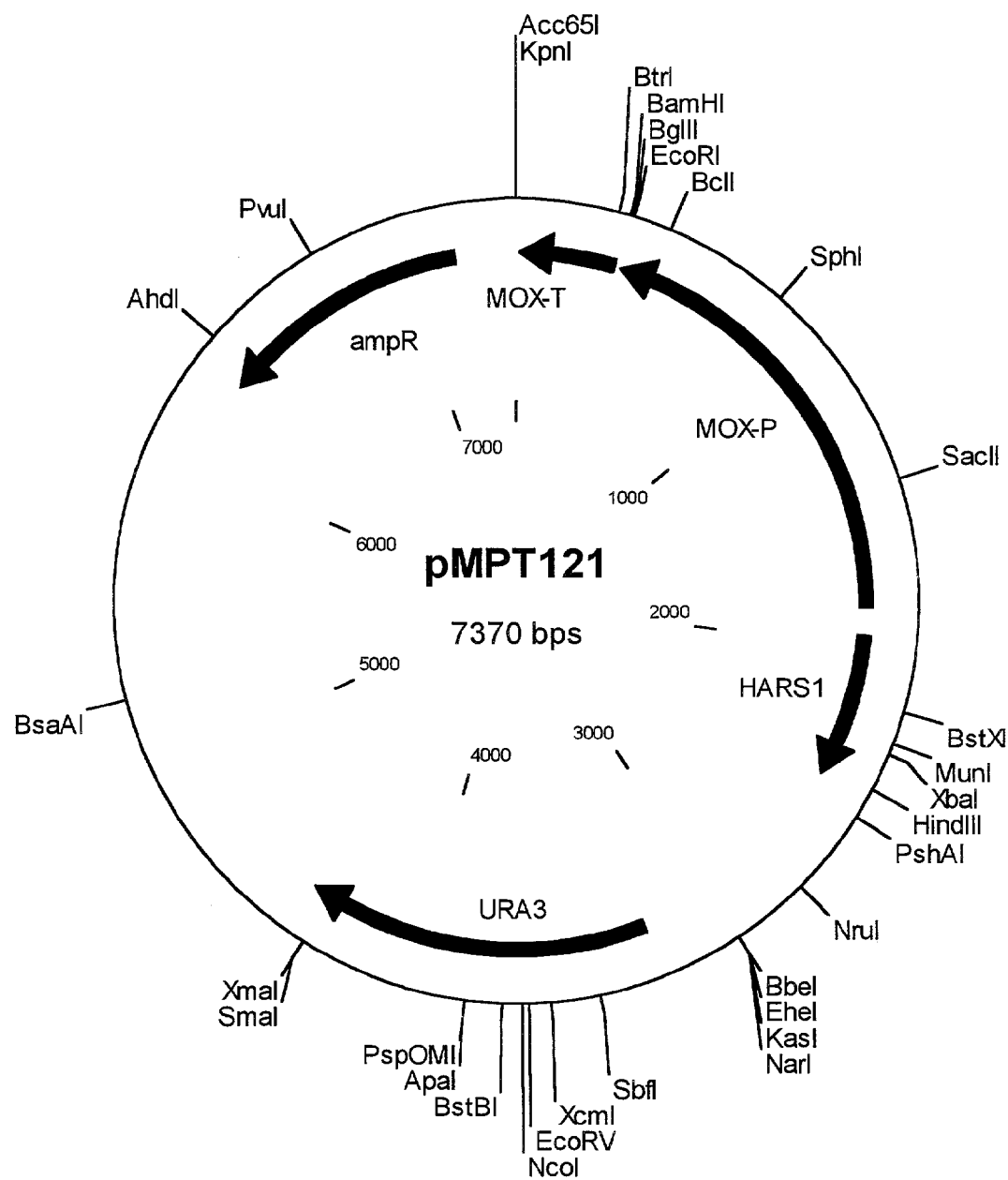
Figure 11:
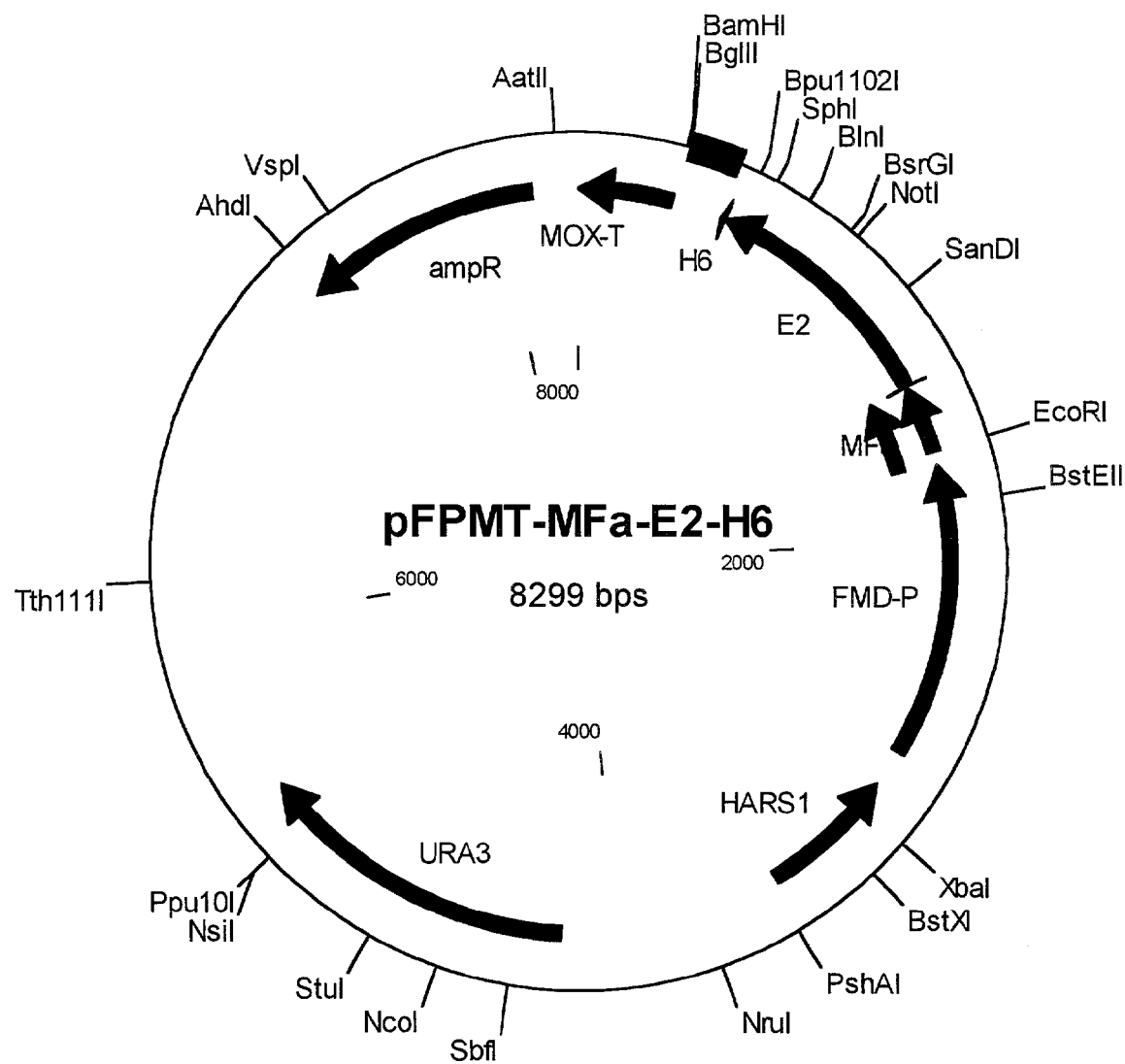
Figure 12:
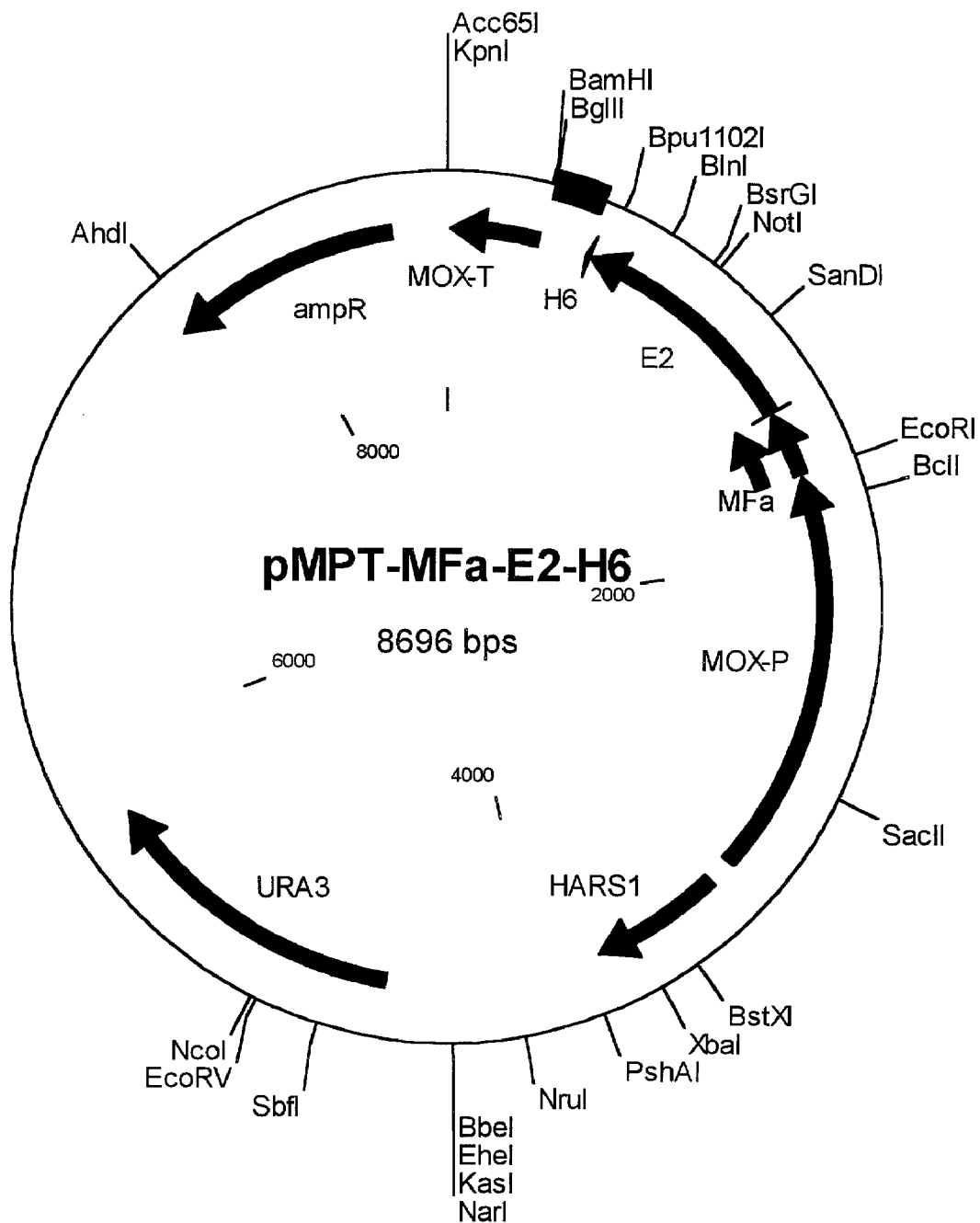

Plasmids for *Hansenula polymorpha* transformation were constructed as follows. The DNA sequence encoding the MFα-E2s (amino acids 384-673 of HCV E2)-VIEGR-His6 (SEQ ID NO:5) was isolated as a 1.331 kb EcoRI/BglII fragment from plasmid pSP72 E2H6 (SEQ ID NO:22, FIG. 9). This fragment was ligated with either the EcoRI/BglII-digested vectors pFPMT121 (SEQ ID NO:12, FIG. C+2) or pMPT 121 (SEQ ID NO:23, FIG. 10) using T4 DNA ligase (Boeringer Mannheim) according to the supplier's recommendations. After transformation of *E. coli* and checking of plasmid DNA isolated from different transformants by restriction enzyme digestion, positive clones were withheld and the resulting shuttle vectors are denominated pFPMT-MFα-E2-H6 (SEQ ID NO:22, FIG. 11) and pMPT-MFα-E2-H6 (SEQ ID NO:23, FIG. 12), respectively.

Example 4

Construction of pFPMT-CL-E2-H6 Shuttle Vector

The shuttle vector pFPMT-CL-E2-H6 was assembled in a three-step procedure. An intermediate construct was prepared in which the E2 coding sequence was cloned behind the signal sequence of α-amylase of *Schwanniomyces acci-*

*dentalis*. This was done by the seamless cloning method (Padgett, K. A. and Sorge, J. A. 1996).

Generation of E2s-H6 Encoding DNA Fragment

At first the DNA sequence encoding E2-H6 (amino acids 384 to 673 of HCV E2 extended with the linker peptide "VIEGR" and with 6 His residues, SEQ ID NO:5) was amplified from the pSP72E2H6 plasmid (SEQ ID NO:24, FIG. 11) by PCR. The used primers were denoted MF30E2/F and MF30E2/R and have the following sequences:

primer MF30E2/F: 5'-agtca ctcttca.aggcatacccgcgtgtcaggaggg-3' (SEQ ID NO:26; the Eam1104I site is underlined, the dot marks the enzyme's cleavage site; the last codon of the *S. occidentalis* signal sequence is printed in bold; the non-marked bases anneal with the codons of E2 (amino acids 384-390 of HCV E2);

primer MF30E2/R:
5'-agtcactcttca.caggggatccttagtgatggtggtgatg-3' (SEQ ID NO:27; the Eam1104I site is underlined, the dot marks the enzyme's cleavage site; the bold printed bases are complementary to the bold printed bases of primer MF30-Rechts (see below); a BamHI site to be introduced into the construct is printed in italic; the non-marked sequence anneals with the stop codon and the six terminal His codons of E2 (384-673)-VIEGR-H6 (SEQ ID NO:5).

The reaction mixture was constituted as follows: total volume of 50 µL containing 20 ng of the 1.33 kb EcoRI/ BglII fragment of pSP72E2H6, each 0.2 µM of primers MF30E2/F and MF30E2/R, dNTP's (each 0.2 µM), 1× buffer 2 (Expand Long Template PCR System; Boeringer; Cat No 1681 834), 2.5 U polymerase mix (Expand Long Template PCR System; Boeringer; Cat No 1681 834).

The PCR program 3 consisting of the following steps was used:
1. denaturation: 5 min at 95° C.
2. 10 cycles of 30 sec denaturation at 95° C., 30 sec annealing at 65° C., and 1 min elongatio at 68° C.
3. termination at 4° C.

Then 10 µL 10× buffer 2 (Expand Long Template PCR System; Boeringer; Cat No 1681 834), 40 µL H$_2$O, and 5 µL of [dATP, dGTP, and dTTP (2 mM each); 10 mM 5-methyl-dCTP] have been added to the sample derived from PCR program 3, and it has been continued with PCR program 4 consisting of the following steps:
1. denaturation: 5 min at 95° C.
2. 5 cycles of 45 sec denaturation at 95° C., 30 sec annealing at 65° C., and 1 min elongation at 68° C.
3. termination at 4° C.

Generation of pMF30-Derived Acceptor Plasmid

Figure 13:
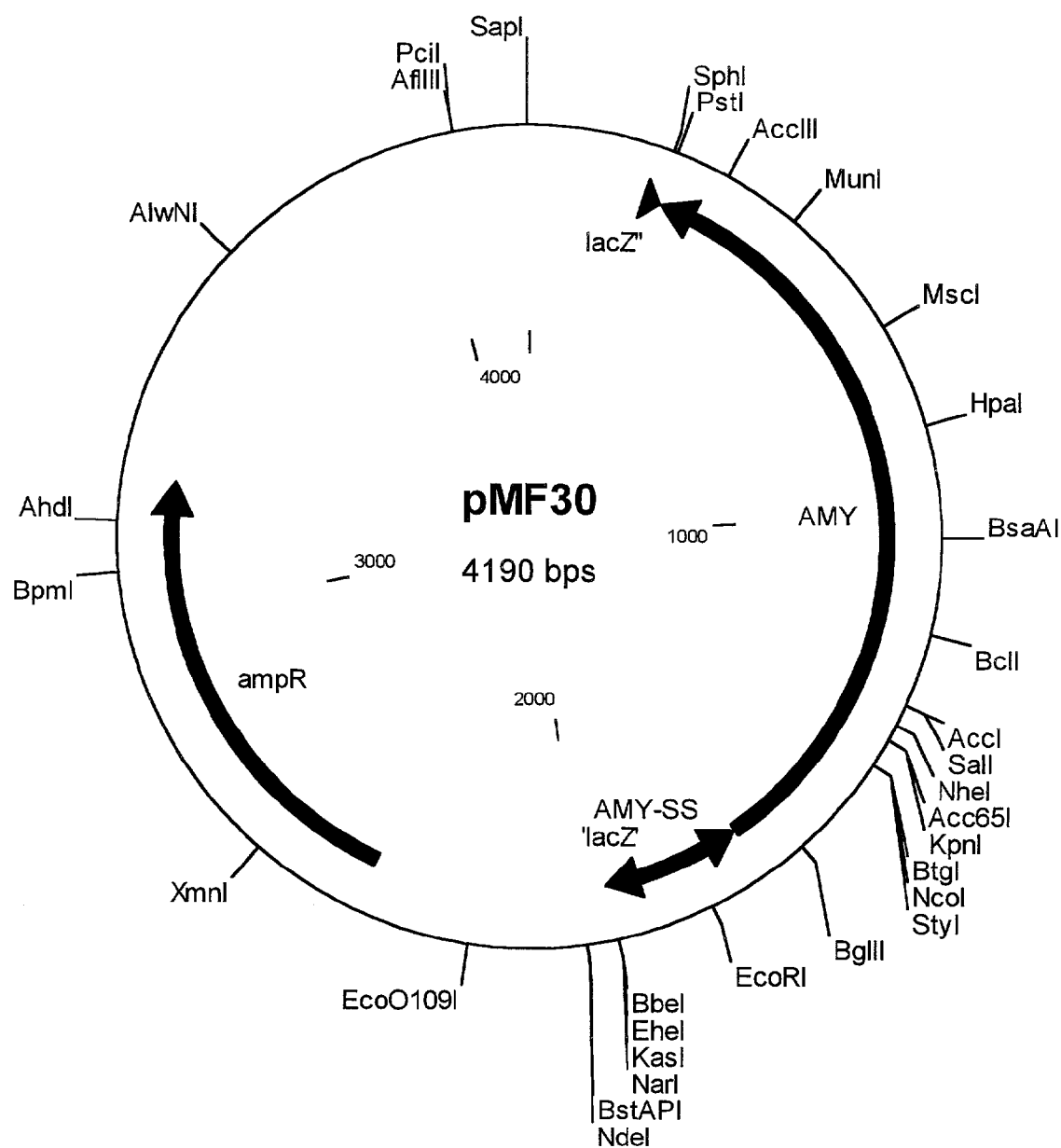

The second fragment originated from the plasmid pMF30 (SEQ ID NO:28, FIG. 13), the amplicon was almost the complete pMF30 plasmid excluding the codons of the mature α-amylase of *S. occidentalis*, modifications relevant for cloning were introduced by primer design. The following set of primers was used:

primer MF30-Links:
5'-agtcactcttca.cctcttgtcaaaaataatcggttgag-3' (SEQ ID NO:29; the Eam1104I site is underlined, the dot marks the enzyme's cleavage site; the bold printed "cct" is complementary to the bold printed "agg" of primer MF30E2/F (see above); the non-marked and the bold printed bases anneal with the 26 terminal bases of the codons of the α-Amylase of *S. occidentalis* in pMF30);

primer MF30-Rechts: 5'-agtca ctcttca.ctgcaggcatgcaagcttggcg-3' (SEQ ID NO:11; the Eam1104I site is underlined, the dot marks the enzyme's cleavage site; the bold printed "ctg" is complementary to the bold printed "cag" of primer MF30E2/R (see above); the non-marked bases anneal with pUC18sequences downstream of the stop codon of the α-Amylase of *S. occidentalis* in pMF30).

The reaction mixture was constituted as follows: total volume of 50 µL containing 20 ng of the BglII-linearized pMF30, each 0.2 µM of primers MF30-Links and MF30-Rechts, dNTP's (each 0.2 µM), 1× buffer 1 (Expand Long Template PCR System; Boeringer; Cat No 1681 834), 2.5 U polymerase mix (Expand Long Template PCR System; Boeringer; Cat No 1681 834). The same PCR programs (programs 3 and 4) as described above were used, except for the elongation times which were extended from 1 minute to 4 minutes in both programs.

Generation of Vector pAMY-E2

The E2s-H6 encoding DNA fragment and pMF30-derived acceptor plasmid obtained by PCR were controlled on their respective size by gel electrophoresis on a 1% agarose gel. The PCR products were purified with a PCR product purification kit (Qiagen) according to the supplier's instructions. Subsequently the purified fragments were digested separately with Eam1100I. Ligation of the E2s-H6 fragment with the pMF30-derived acceptor plasmid was performed by using T4 ligase (Boehringer) according to the supplier's recommendations. The ligation mixture was used to transform *E. coli* DH5αF' cells and the plasmid DNA of several clones was analyzed by EcoRI/BamHI digestion. A positive clone was selected, its plasmid further denominated as pAMY-E2, and utilized for further modifications as described below.

Generation of Vector pUC18-CL-E2-H6

The pAMY-E2 was subjected to PCR-directed mutagenesis in order to replace the codons of the α-amylase signal sequence with the codons of the avian lysozyme pre sequence. This is further denominated as "CL", corresponding to the first 18 amino acids of avian lysozyme ORF (SEQ ID NO:1). For this mutagenesis following primers were used:

```
primer CL2 hin:
5'-tgcttcctaccactagcagcactaggacatacccgcgtgtcaggagggcag-3'; (SEQ ID NO:30)
and primer CL2 her:
5'-tagtactagtattagtaggcttcgcatggaattcactggccgtcgtttta-    (SEQ ID NO:31)
caacgtc-3'.
```

The underlined 5'-regions of the primers contain the DNA sequence of about half of the avian lysozyme pre sequence. Primer CL2 her includes SpeI (italic) and EcoRI (italic, double underlined) restriction sites. The non-underlined regions of the primers anneal with the codons of amino acid residues 384 to 392 of E2 (CL2 hin) or the with the "atg" start codon over the EcoRI site up to position –19 (counted from the EcoRI site) of FMD promoter. The primers are designed to amplify the complete pAMY-E2 vector thereby replacing the codons of the α-amylase signal sequence with the codons of the avian lysozyme pre-sequence. The PCR reaction was performed according to the following program:
1. denaturation: 15 min at 95° C.
2. 35 cycles of 30 sec denaturation at 95° C., 1 min annealing at 60° C., and 1 min elongation at 72° C.
3. termination at 4° C.

The following reaction mixture was used: pAMY-E2 (1 ng/µL), 1 µL; primer CL2 hin (100 µM), 2 µL; primer CL2 her (100 µM), 2 µL; dNTP's (2.5 mM each), 8 µL; H₂O, 76 µL; Expand Long Template PCR System (Boeringer; Cat No 1681 834) Buffer 2 (10×concentrated), 10 µL; Expand Long Template PCR System Polymerase mixture (1 U/µL), 0.75 µL.

The resulting PCR product was checked by gel electrophoresis on a 1% agarose gel. Prior to ligation the PCR fragment was modified as follows. The 3'-A overhangs were removed by T4 polymerase resulting in blunt ends with 3'- and 5'-OH-groups. Thereto 1 µL T4 polymerase (Boehringer, 1 U/µL) was added to the residual 95 µL PCR reaction mixture along with 4 µL dNTP's (2.5 mM each). The sample was incubated for 20 min at 37° C. Subsequently the DNA was precipitated with ethanol and dissolved in 16 µL deionized water. This was followed by a kinase treatment to add 5'-phosphates to the blunt-ended PCR product. To the 16 µL dissolved blunt-ended PCR product were added 1 µL T4 polynucleotide kinase (Boehringer, 1 U/µL), 2 µL 10-fold concentrated T4 polynucleotide kinase reaction buffer (Boehringer) and 1 µL ATP (10 mM). The sample was incubated for 30 min at 37° C.

The kinase treated sample was subsequently separated on a 1% agarose gel. The product band was isolated. The DNA was extracted from the agarose slice by means of the Gel Extraction kit (Qiagen) according to the supplier's recommendations. Fifty (50) ng of the purified product was then self-ligated by use of T4 ligase (Boehringer) according to the supplier's conditions. After 16 h incubation at 16° C., the DNA in the ligation mix was precipitated with ethanol and dissolved in 20 µL H₂O (ligation sample).

E. coli DH5αF' cells were transformed with 10 µL of the ligation sample. Several ampicillin-resistant clones were further characterized via restriction analysis of the isolated plasmid DNA. A positive clone was denominated as pUC18-CL-E2-H6 and was used for further modifications as described below.

Generation of Shuttle Vector pFPMT-CL-E2-H6

Figure 14:
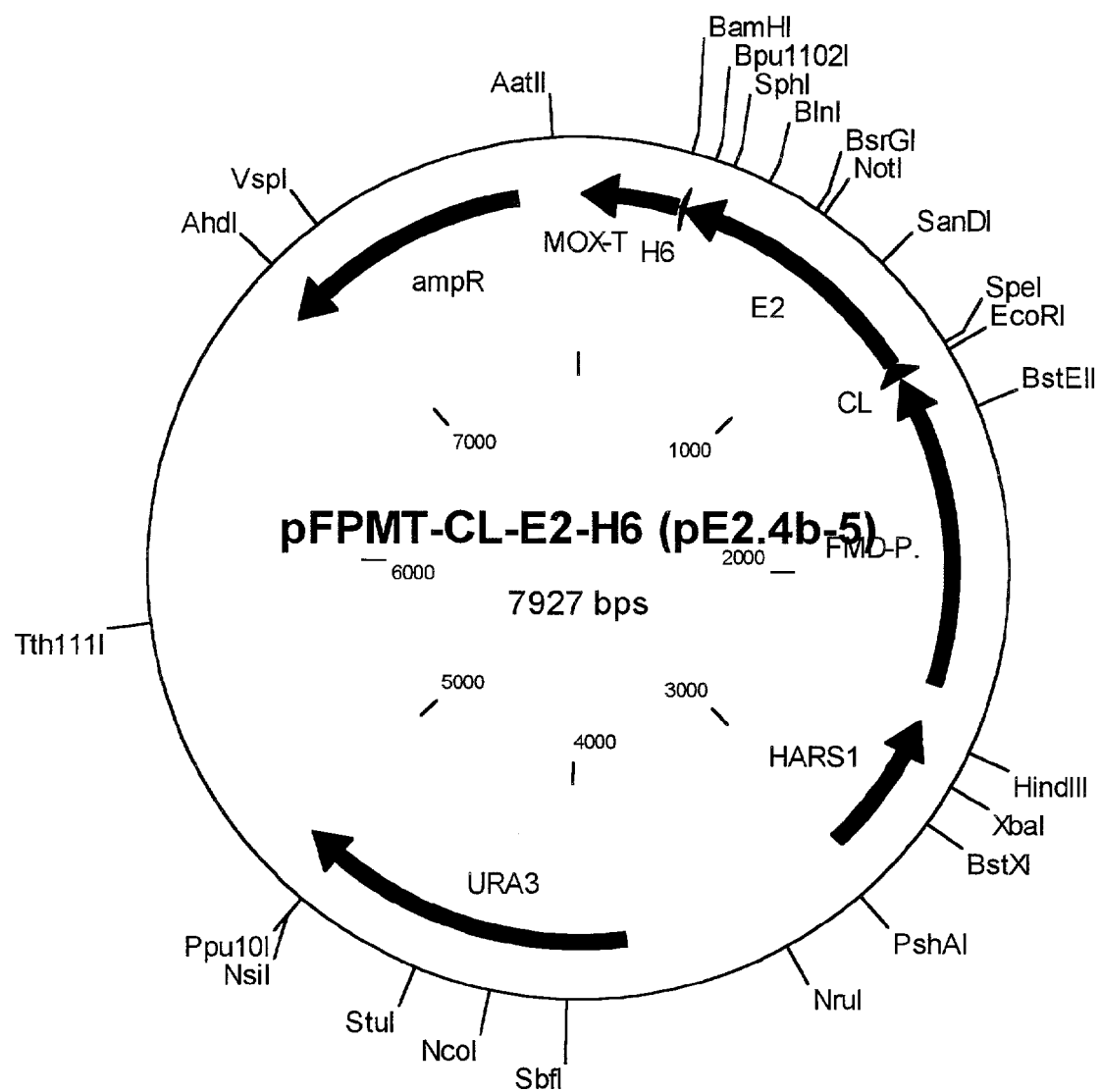
Figure 15:
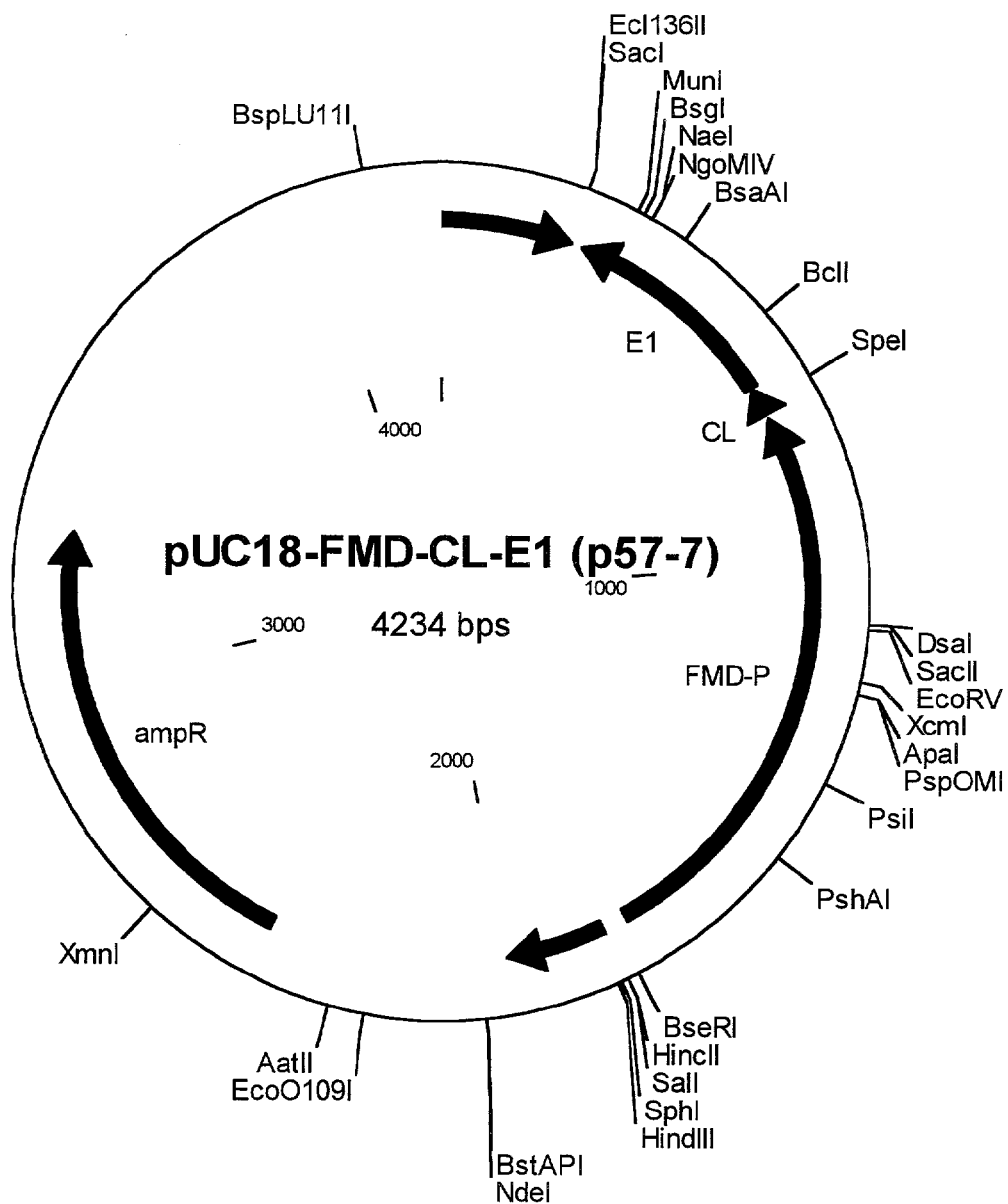

A 0.966 kb EcoRI/BamHI fragment was isolated from pUC18-CL-E2-H6 (harboring CL-E2(384-673)-VIEGR-H6) and was ligated into the EcoRI/BamHI-digested pFPMT121 (SEQ ID NO:12, FIG. 3). For the reaction, T4 ligase (Boehringer) was used according to the supplier's conditions. The ligation sample was precipitated with ethanol and dissolved in 10 µL water. This was used to transform E. coli DH5αF' cells, a positive clone was withheld after restriction analysis and the respective plasmid is denominated pFPMT-CL-E2-H6 (SEQ ID NO:32, FIG. 14).

Example 5

Construction of pFPMT-CL-K-H6-E1 Shuttle Vector

The construction of the shuttle vector was comprised of two steps.

In a first step the pUC18-FMD-CL-H6-K-E1-H6 construct was constructed by site-directed mutagenesis. The pUC18-FMD-CL-E1-H6 was used as template (SEQ ID NO:20; FIG. 7). The following primers were used:

```
Primer H6K hin neu:                       (SEQ ID NO:37)
5'-catcacaaatatgaggtgcgcaacgtgtccgggatgtac-3'.

Primer H6KRK her neu:                     (SEQ ID NO:38)
5'-gtgatggtggtgtcctagtgctgctagtggtaggaagcatag-3'.
```

(The bases providing additional codons are underlined.)

The PCR reaction mixture was constituted as follows: pUC18-FMD-CL-E1-H6 (2 ng/µL), 1 µL; primer H6K hin neu (100 µL), 2 µL; primer H6KRK her neu (100 µM), 2 µL; dNTP's (2.5 mM each), 8 µL; H₂O, 76 µL; Expand Long Template PCR System (Boeringer; Cat No 1681 834) Buffer 2 (10× concentrated), 10 µL; Expand Long Template PCR System Polymerase mixture (1 U/µL), 0.75 µL.

The PCR program used consisted of the following steps:
denaturation step: 15 min at 95° C.
35 cycles of 30 sec denaturation at 95° C., 1 min annealing at 60° C., and 5 min elongation at 72° C.
termination at 4° C.

An aliquot of the PCR sample was analyzed on a 1% agarose gel to check its size, which was correct (~4.2 kb).

Thereafter the 3'-A overhangs from the PCR product were removed by a T4 polymerase reaction resulting in blunt ends with 3'- and 5'-OH groups. Therefore, to the remaining 95 µL of the PCR reaction were added 1 µL T4 polymerase (Boehringer; 1 U/µL) and 4 µL dNTP's (2.5 mM each). The sample was incubated for 20 min at 37° C. Subsequently, the DNA in the sample was precipitated with ethanol and dissolved in 16 µL H₂O.

Subsequently 5'-phosphates were added to the blunt-ended PCR product by a kinase reaction. Therefore, to the 16 µL dissolved blunt-ended PCR product were added 1 µL T4 polynucleotide kinase (Boehringer; 1 U/µL), 2 µL 10-fold concentrated T4 polynucleotide kinase reaction buffer (Boehringer), and 1 µL ATP (10 mM). The sample was incubated for 30 min at 37° C.

Figure 17:
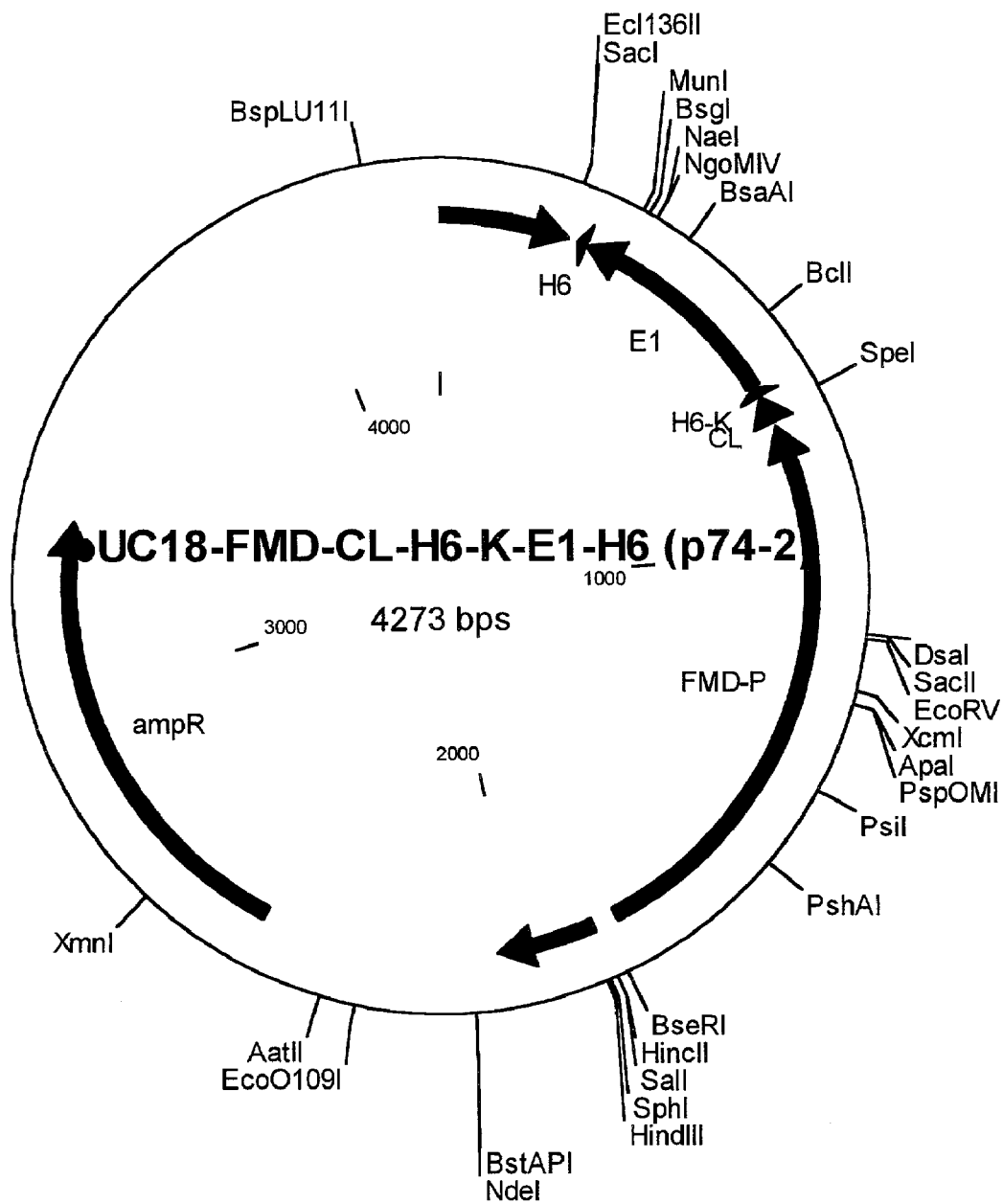

Subsequently the sample was applied onto a 1% agarose gel and the correct product band was isolated, by means of the gel extraction kit (Qiagen) according to the supplier's conditions. Fifty (50) ng of the purified product has then been self-ligated by use of T4 ligase (Boehringer) according to the supplier's recommendations. After 72 h incubation at 16° C. the DNA in the ligation sample was precipitated with ethanol and dissolved in 10 µL water. E. coli DH5αF' cells were transformed with 5 µL of the ligation sample. The plasmid DNA of several ampicillin-resitant colonies was analyzed by restriction enzyme digestion, a positive clone was withheld and the corresponding plasmid denominated: pUC18-FMD-CL-H6-E1-K-H6 (SEQ ID NO:39, FIG. 17).

Figure 16:
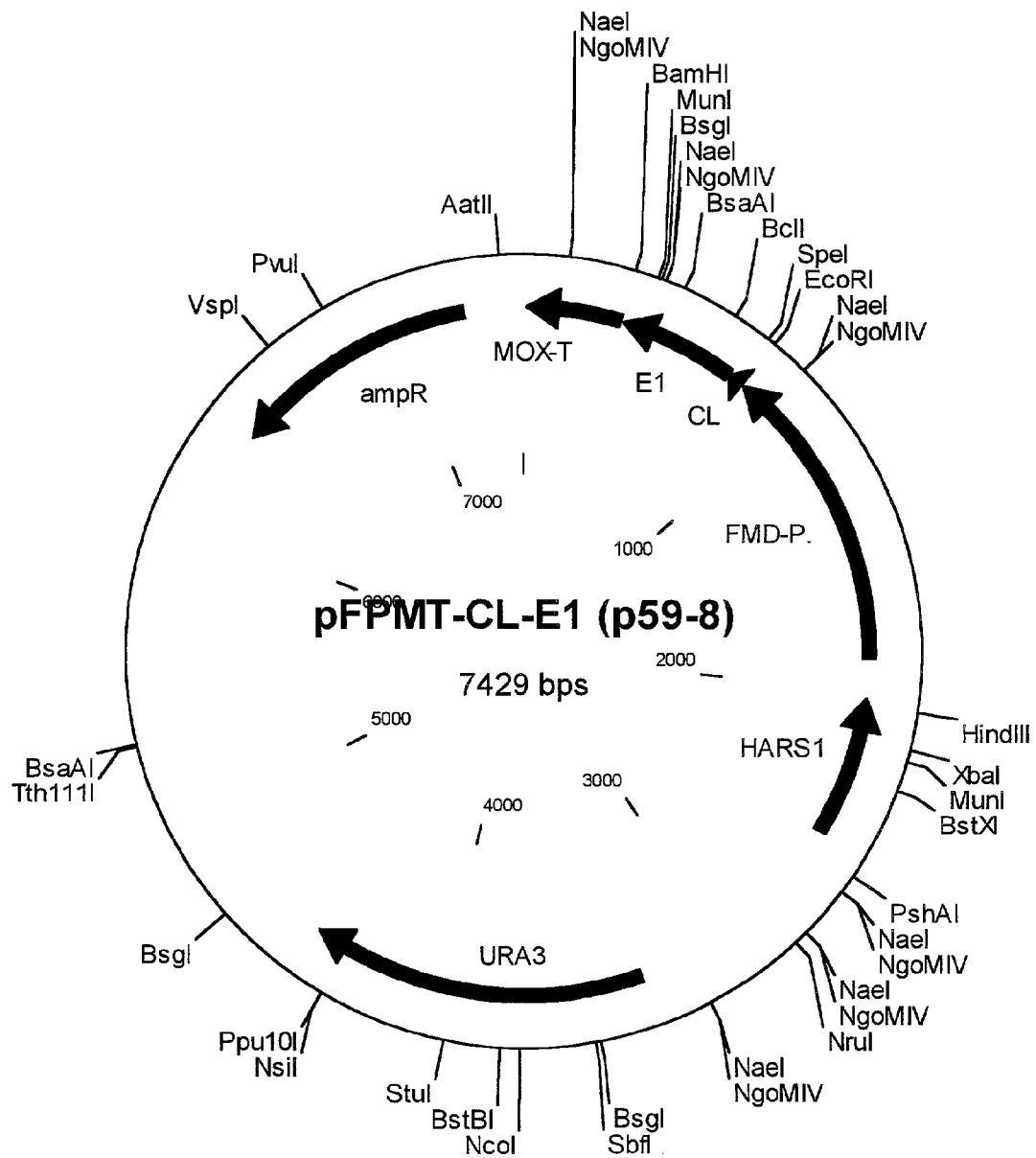
Figure 18:
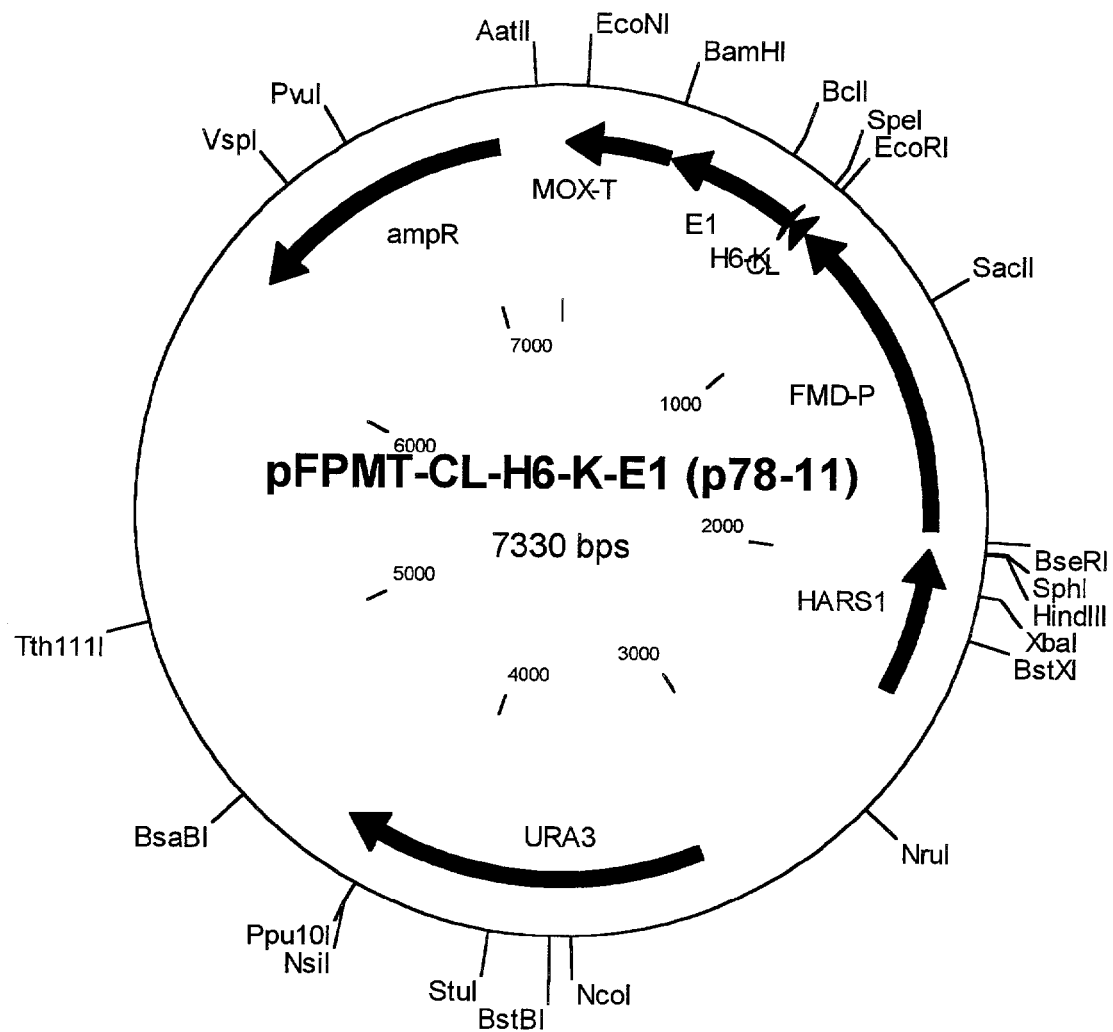

In a second step the transfer vector was constructed by a two-fragment ligation. In the following construction fragments with BclI cohesive ends were involved. Since BclI can cleave its site only on unmethylated DNA, an E. coli dam⁻ strain was transformed with the involved plasmids pUC18-FMD-CL-H6-K-E1-H6 (SEQ ID NO:39, FIG. 17) and pFPMT-CL-E1 (SEQ ID NO:36, FIG. 16). From each transformation, an ampicillin-resistant colony was picked, grown in a liquid culture and the unmethylated plasmid DNAs were prepared for the further use. The 1.273 kb BclI/HindIII fragment of the unmethylated plasmid pUC18-FMD-CL-H6-K-E1-H6 (harbouring the FMD promoter, the codons of the CL-H6-K unit, and the start of E1) and the 6.057 kb BclI/HindIII fragment of plasmid pFPMT-CL-E1 (harbouring the missing part of the E1 reading frame starting from the BclI site, without C-terminal His tag, as well as the pFPMT121-located elements except for the FMD promoter) were prepared and ligated together for 72 h at 16° C. by use of T4 ligase (Boehringer) in a total volume of 20 µL according to the supplier's specifications. Subsequently, the ligation mixture was placed on a piece of nitrocellulose membrane floating on sterile deionized water in order to desalt the ligation mixture (incubation for 30 min at room temperature). E. coli TOP10 cells were transformed by electroporation with 5 µL of the desalted sample. The plasmid DNA of several resulting ampicillin-resistant colonies was analyzed by restriction enzyme digestion. A positive clone was withheld and denominated pFPMT-CL-H6-K-E1 (SEQ ID NO:40, FIG. 18).

Example 6

Transformation of *Hansenula polymorpha* and Selection of Transformants

*H. polymorpha* strain RB11 was been transformed (PEG-mediated DNA uptake protocol essentially as described by (Klebe, R. J. et al. 1983) with the modification of (Roggenkamp, R. et al. 1986) with the different parental shuttle vectors as described in Examples 1 to 5. For each transformation, 72 uracil-prototrophic colonies were selected and used for strain generation by the following procedure. For each colony, a 2 mL liquid culture was inoculated and grown in test tubes for 48 h (37° C.; 160 rpm; angle 45°) in selective medium (YNB/glucose, Difco). This step is defined as the first passaging step. A 150 µL aliquot of the cultures of the first passaging step were used to inoculate 2 mL fresh YNB/glucose medium. Again, the cultures have been incubated as described above (second passaging step). Together, eight of such passaging steps were carried out. Aliquots of the cultures after the third and the eighth passaging steps were used to inoculate 2 mL of non-selective YPD medium (Difco). After 48 h of incubation at 37° C. (160 rpm; angle 45°; the so-called first stabilization step), 150 µL aliquots of these YPD cultures have been used to inoculate fresh 2 mL YPD cultures which were incubated as described above (second stabilization step). Aliquots of the cultures of the second stabilization step were then streaked on plates containing selective YNB/agar. These plates were incubated for four days until macroscopic colonies became visible. A well-defined single colony of each separation was defined as strain and used for further expression analysis.

Expression analysis was performed on small-scale shake flask cultures. A colony was picked from the above mentioned YNB/agar plate and inoculated in 2 mL YPD and incubated for 48 h as mentioned above. This 2 mL-aliquot was used as seed culture for 20 mL shake flask culture. YPGlycerol (1%) was used as medium and the shake flask was incubated on a rotary shaker (200 rpm, 37° C.). After 48 h of growth 1% MeOH was added to the culture for induction of the expression cassette. At different time intervals cell pellets of 1 mL aliquots were collected and stored at −20° C. until further analysis. Specific protein expression was analyzed by SDS-PAGE/Western blotting. Therefore cell pellets were solubilized in sample-buffer (TrisHCl-SDS) and incubated for >15 minutes at 95° C. Proteins were separated on a 15% polyacryl-amide gel and blotted (wet-blot; bicarbonate buffer) onto nitrocellulose membranes. Blots were developed using a specific murine anti-E1 (IGH 201) or murine anti-E2 (IGH 216, described by Maertens et al. in WO96/04385) as first antibody, Rabbit-Anti-Mouse-AP was used as second antibody. Staining was performed with NBT-BCIP. Positive strains were withheld for further investigation.

Five of these positive clones were used in a shake flask expression experiment. A colony of the respective strain was picked from YNB plate and used to inoculate 2 mL YPD. These cultures were incubated as described above. This cell suspension was used to inoculate a second seed culture of 100 mL YPD medium in a 500 mL shake flask. This shake flask was incubated on a rotary shaker for 48 h at 37° C. and 200 rpm. A 25 mL aliquot of this seed culture was used to inoculate 250 mL YPGlycerol (1%) medium and was incubated in a baffled 2-l shake flask under the above described conditions. 48 h after inoculation 1% MeOH (promotor induction) was added and the shake flasks were further incubated under the above described conditions. 24 h post induction, the experiment was stopped and cell pellets collected by centrifugation. The expression level of the five different clones was analyzed by SDS-PAGE/Western blotting (conditions as above). A titration series of each clone was loaded onto the gel and the most productive strain was selected for further fermentation and purification trials.

Surprisingly, *H. polymorpha*, a yeast strain closely related to *Pichia pastoris* (Gellissen, G. 2000), is able to express HCV proteins essentially without hyperglycosylation and thus with sugar moieties comparable in size to the HCV envelope proteins expressed by HCV-recombinant vaccinia virus-infected mammalian cells.

The *Hansenula polymorpha* strain RB11 was deposited on Apr. 19, 2002 under the conditions of the Budapest Treaty at the Mycothèque de l'UCL (MUCL), Université Catholique de Louvain, Laboratoire de mycologie, Place Croix du Sud 3 bte 6, B-1348 Louvain-la-Neuve, Belgium and has the MUCL accession number MUCL43805.

Example 7

Construction of pSY1aMFE1sH6a Vector

Figure 19:
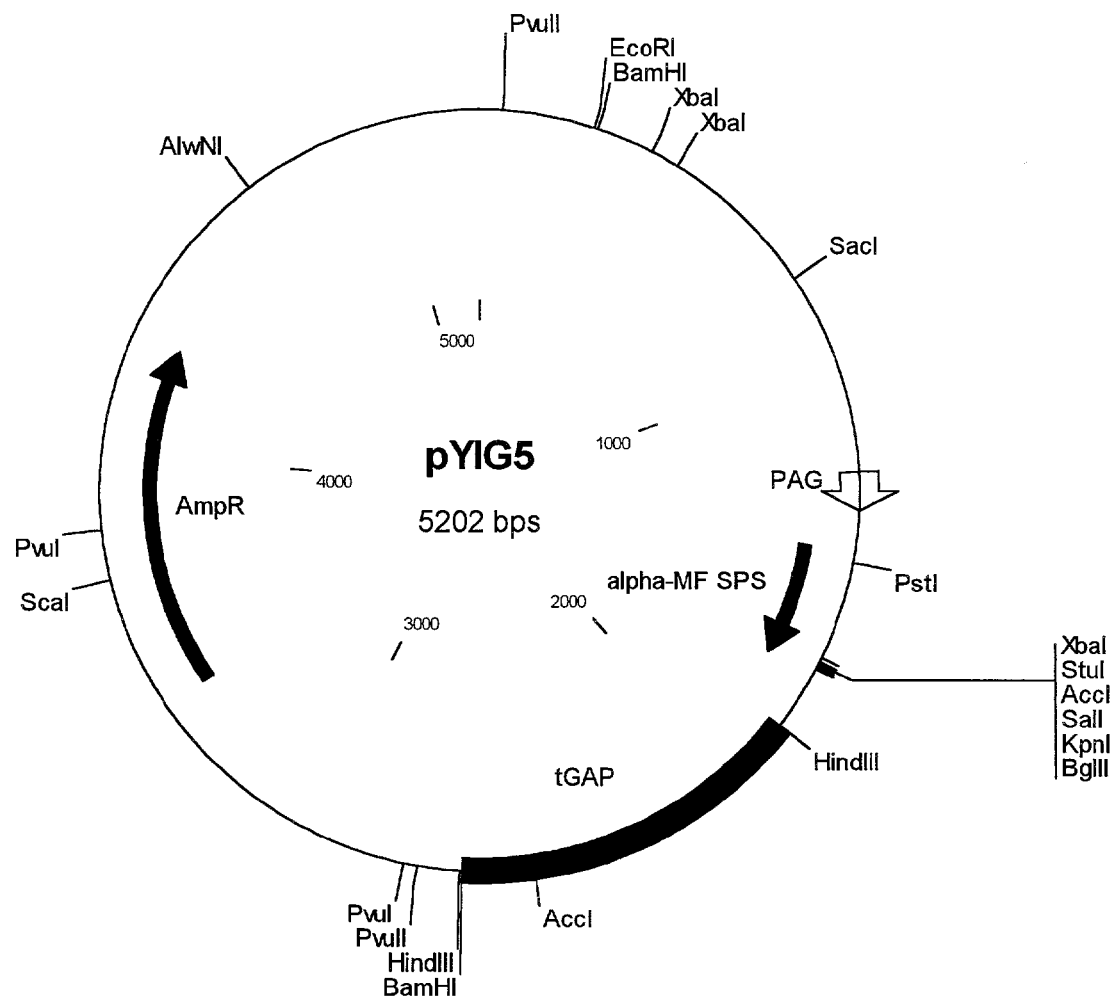
Figure 20:
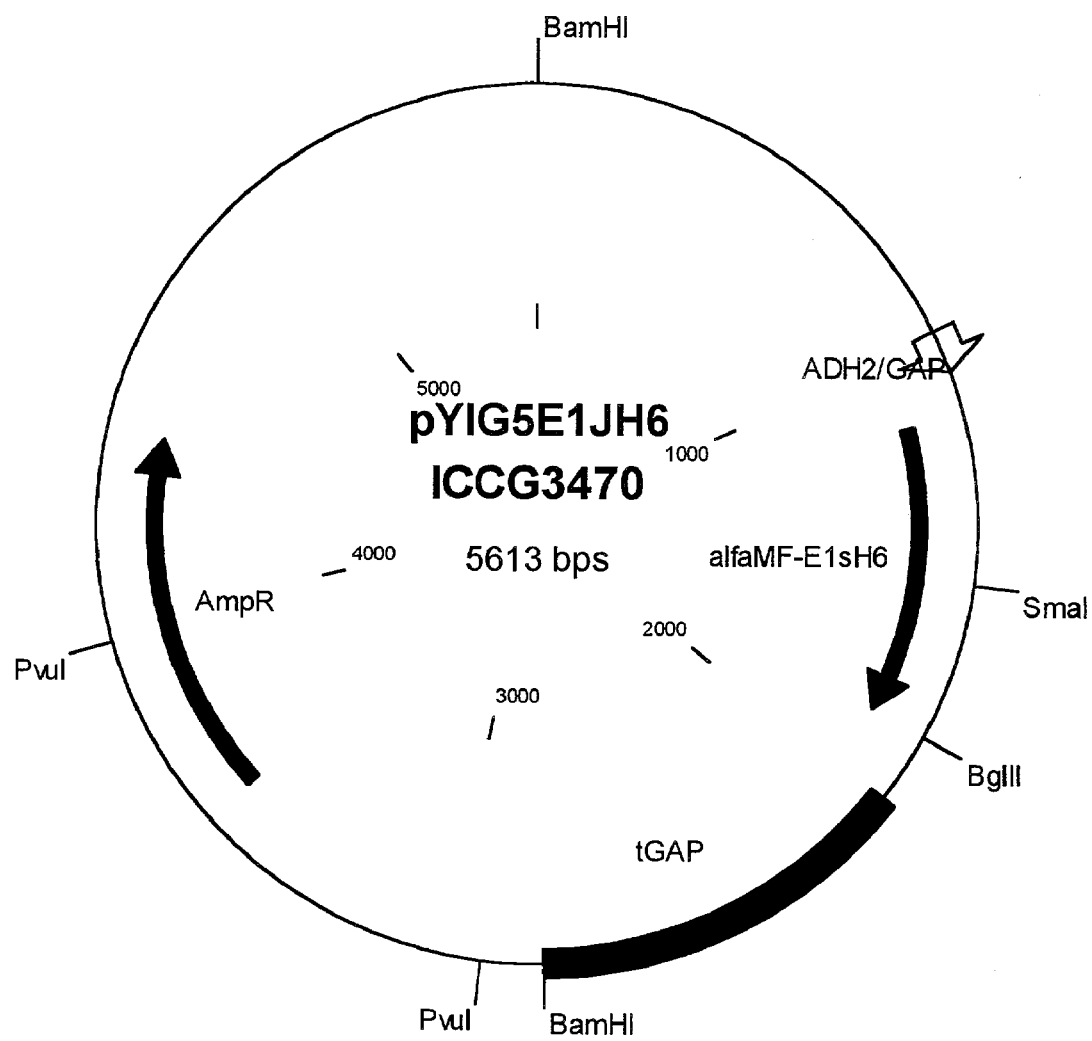

The *S. cerevisiae* expression plasmid was constructed as follows. An E1-coding sequence was isolated as a NsiI/Eco52I fragment from pGEMT-E1sH6 (SEQ ID NO:6, FIG. 1) which was made blunt-ended (using T4 DNA polymerase) and cloned in the pYIG5 vector (SEQ ID NO:41, FIG. 19) using T4 DNA ligase (Boehringer) according to the supplier's specifications. The cloning was such that the E1s-H6 encoding fragment was joined directly and in frame to the αMF-coding sequence. The ligation mixture was transformed in *E. coli* DH5αF' cells. Subsequently, the plasmid DNA of several ampicilin resistant clones was analyzed by restriction digestion and a positive clone was withheld and denominated as pYIG5E1H6 (ICCG3470; SEQ ID NO:42, FIG. 20).

The expression cassette (containing the αMF-sequence and the E1s-coding region with a His-tag) was transferred as a BamHI fragment (2790 bp) of pYIG5E1H6 into the BamHI-digested *E. coli/S. cerevisiae* pSY1 shuttle vector (SEQ ID NO:21, FIG. 43). The ligation was performed with T4 DNA ligase (Boehringer) according to supplier's conditions. The ligation mix was transformed to *E. coli* DH5αF' cells, and the plasmid DNA of several ampicilin resistant colonies was analyzed by restriction enzyme digestion. A positive clone was withheld and denominated pSY1aMFE1sH6 (ICCG3479; SEQ ID NO:44, FIG. 22).

Example 8

Construction of pSYY1GSE2H6 Vector

The *S. cerevisiae* expression plasmid pSYY1GSE2H6 was constructed as follows. An E2 coding sequence was isolated as a SalI/KpnI fragment from pBSK-E2sH6 (SEQ ID NO:45, FIG. 23) which was made blunt-ended (using T4 DNA polymerase) and subsequently cloned in the pYIG5 vector (SEQ ID NO:41, FIG. 19) using T4 DNA ligase (Boehringer) according to the supplier's specifications. The cloning was such that the E2-H6 encoding fragment was joined directly and in frame to the αMF-coding sequence. The ligation mixture was then transformed to *E. coli* DH5αF' cells, the plasmid DNA of several ampicilin resistant clones was analyzed by restriction digestion and a positive clone withheld and denominated as pYIG5HCCL-22aH6 (ICCG2424; SEQ ID NO:46, FIG. 24).

Figure 21:
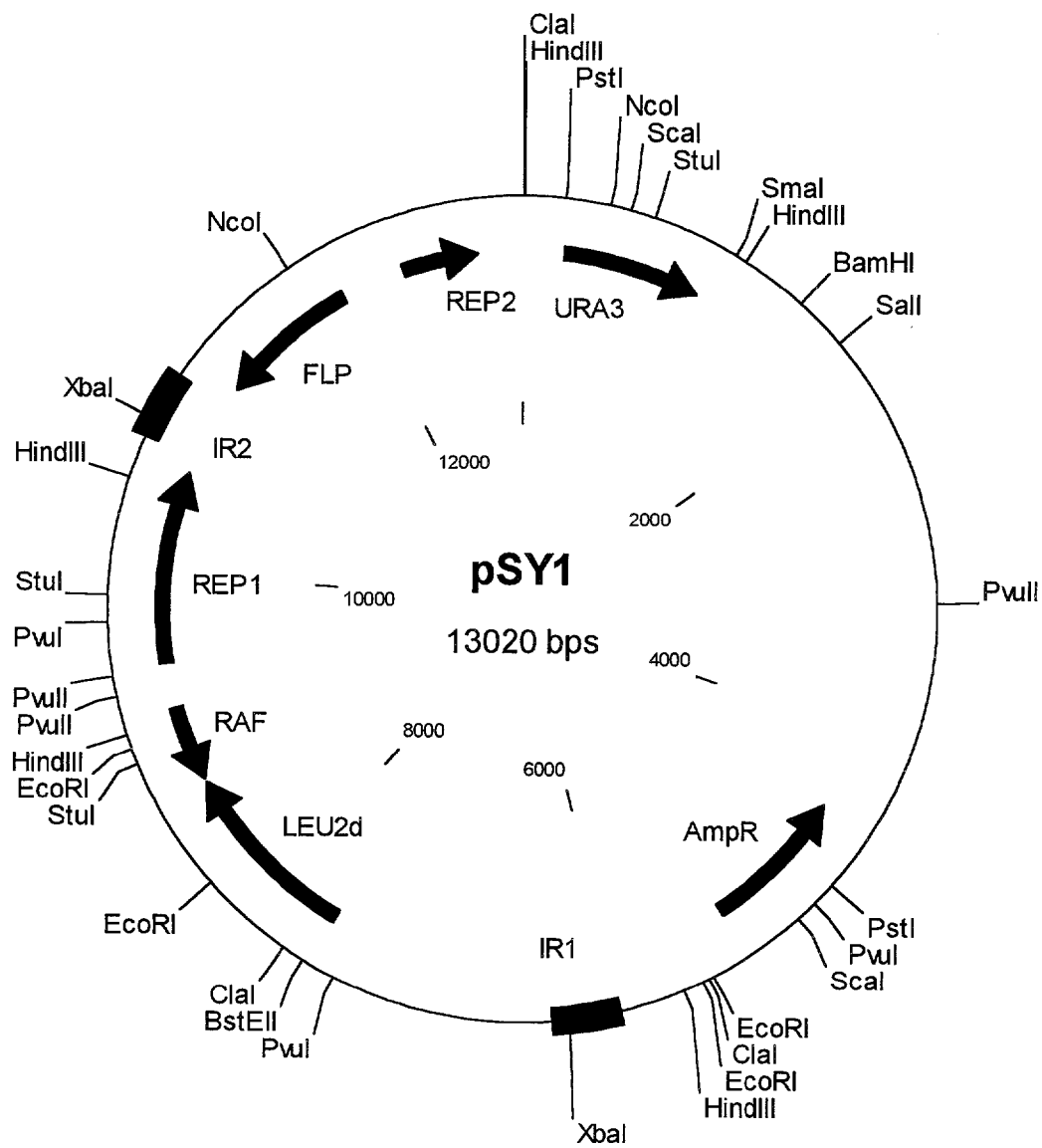
Figure 25:
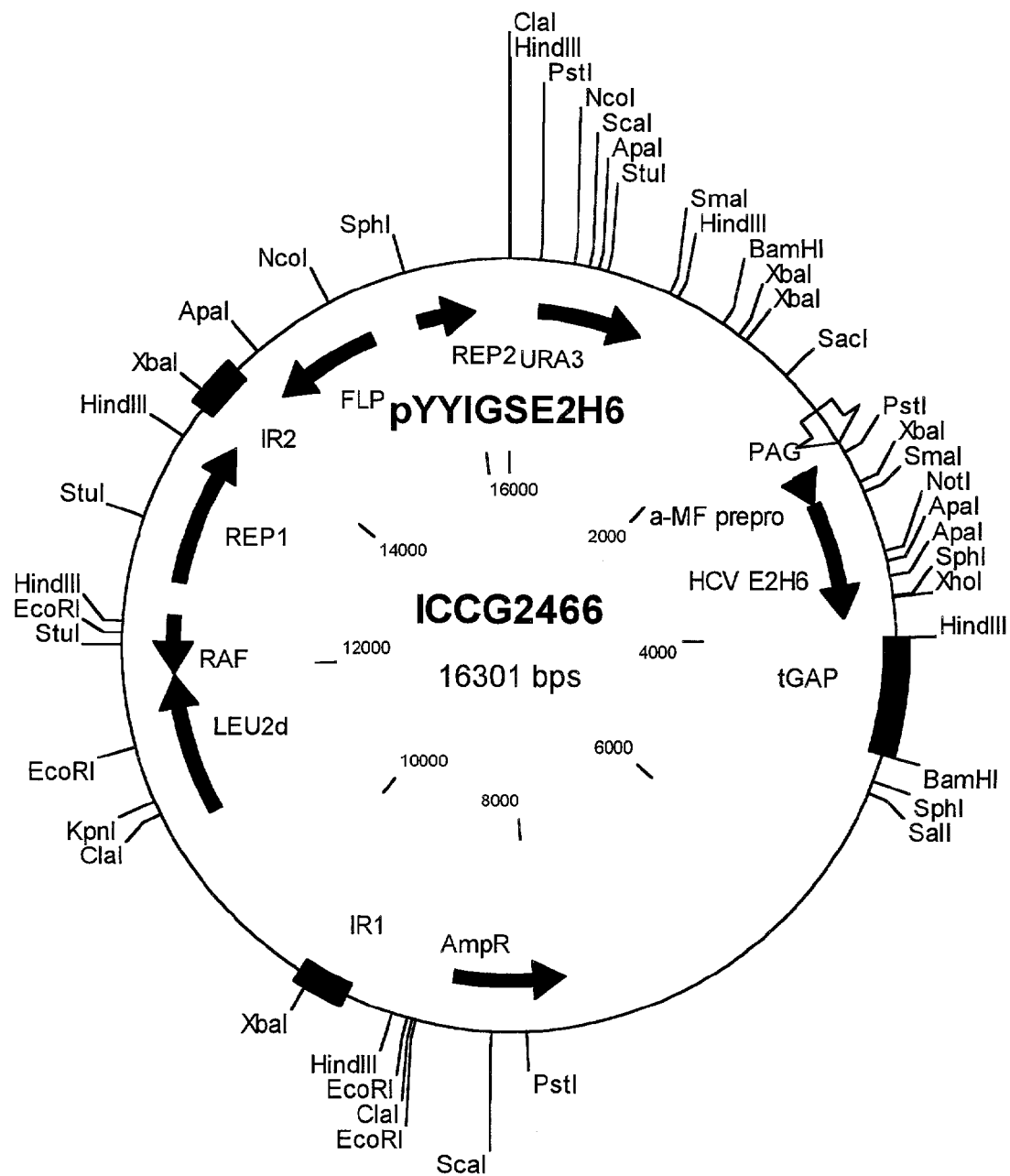

The expression cassette (containing the αMF-sequence and the E2 (384-673) coding region with a His-tag) was transferred as a BamHI fragment (3281 bp) of pYIG5HCCL-22aH6 into the BamHI opened *E. coli/S. cerevisiae* pSY1 shuttle vector (SEQ ID NO:43, FIG. 21). The ligation was performed with T4 DNA ligase (Boehringer) according to supplier's conditions. The ligation mix was transformed to *E. coli* DH5αF' cells and the plasmid DNA of several ampicilin resistant colonies was analyzed by restriction enzyme digestion. A restriction positive clone was withheld and denominated pSYYIGSE2H6 (ICCG2466; SEQ ID NO:47, FIG. 25).

Example 9

Construction of pSY1YIG7E1s Vector

Figure 26:
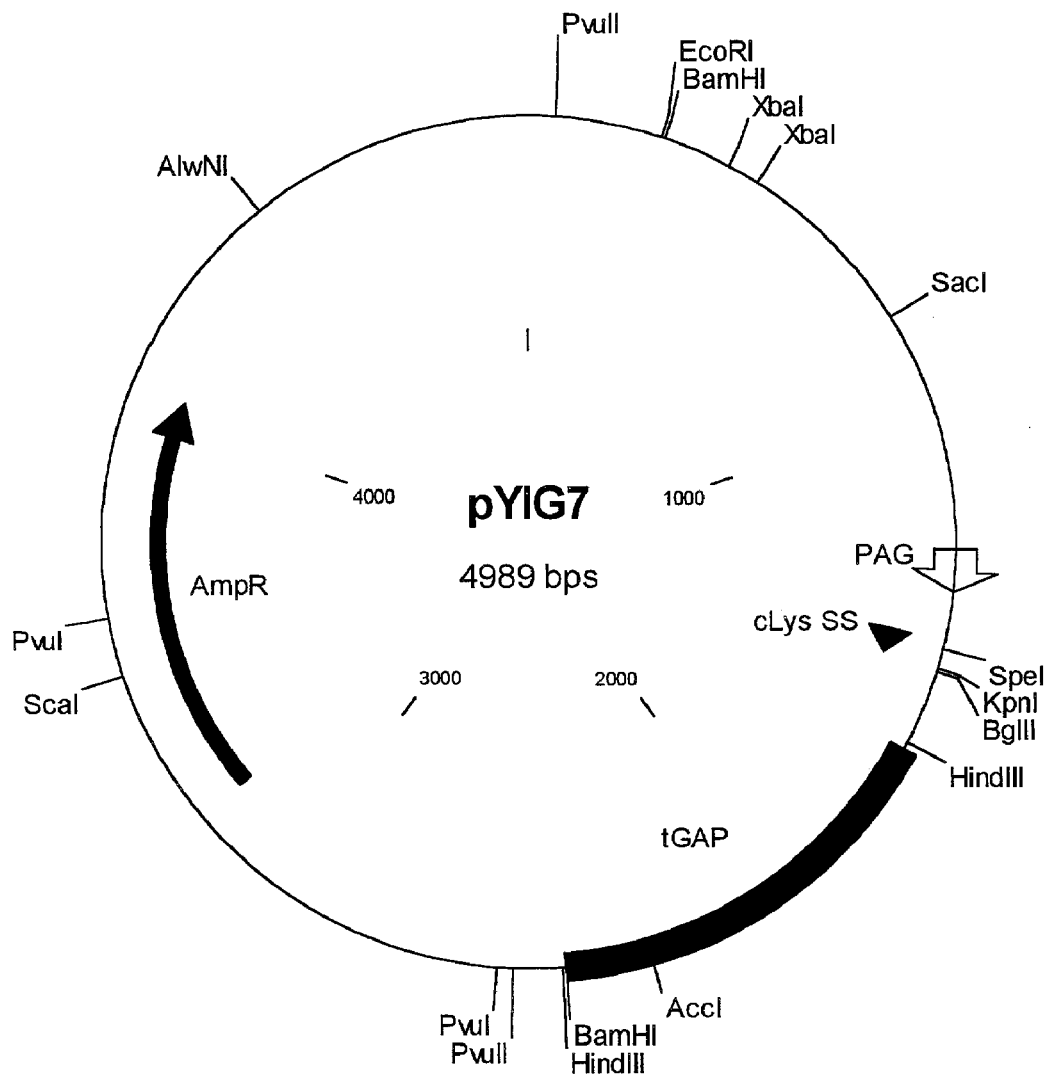
Figure 27:
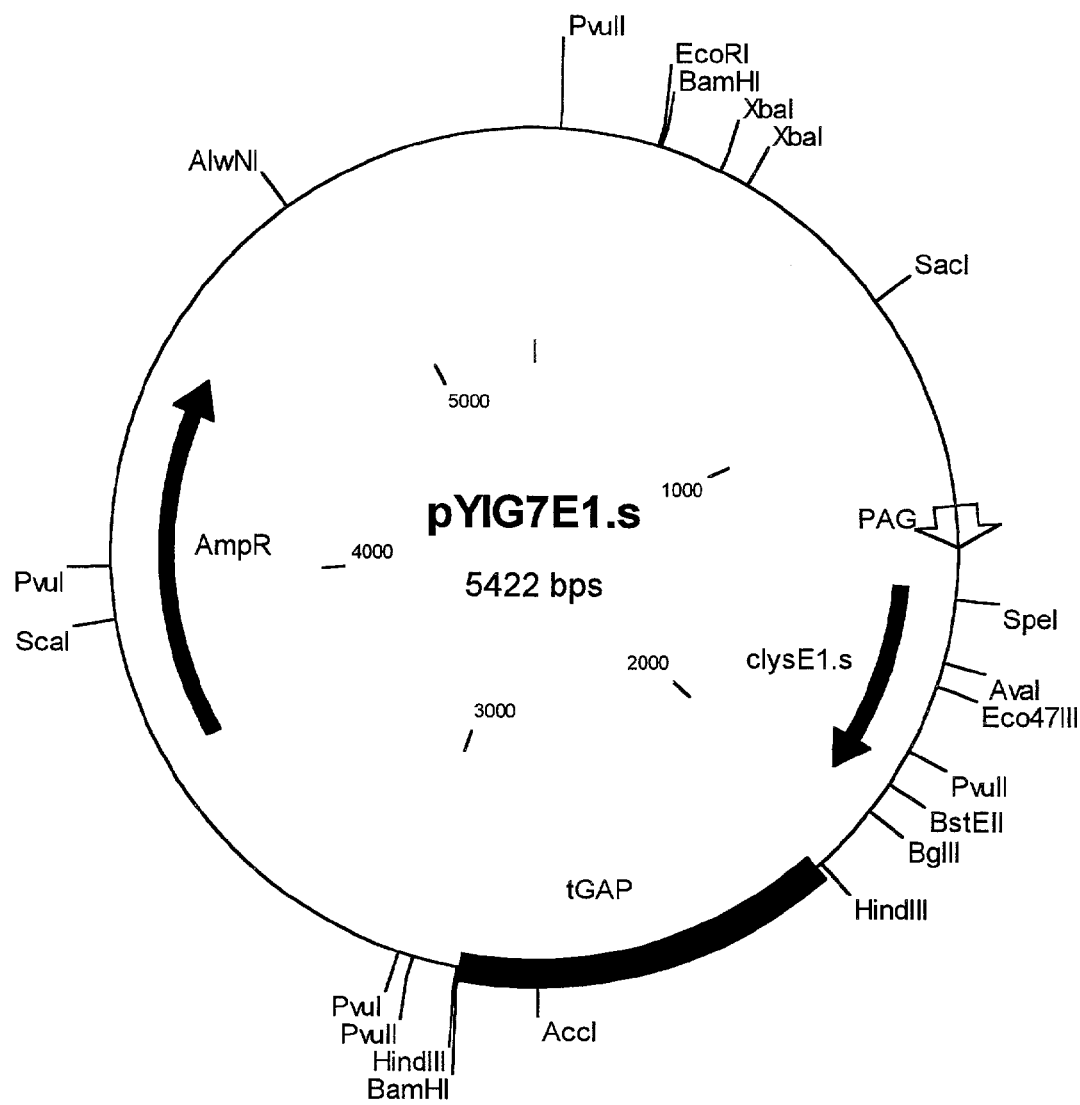

The *S. cerevisiae* expression plasmid pSY1Y1G7E1s was constructed as follows. An E1 coding sequence was isolated as a NsI1/Eco52I fragment from pGEMT-E1s (SEQ ID NO:6, FIG. 1) which was made blunt-ended and cloned into the pYIG7 vector (SEQ ID NO:48, FIG. 26) using T4 DNA ligase (Boehringer) according to the supplier's specifications. The cloning was such that the E1-encoding fragment was joined directly and in frame to the αMF-coding sequence. The ligation mixture was transformed to *E. coli* DH5αF' cells, the plasmid DNA of several ampicilin resistant clones analyzed by restriction digestion and a positive clone withheld and denominated as pYIG7E1 (SEQ ID NO:49, FIG. 27).

The expression cassette (containing the CL leader sequence and the E1 (192-326) coding region) was transferred as a BamHI fragment (2790 bp) of pYIG7E1 into the BamHI-digested *E. coli/S. cerevisiae* pSY1 shuttle vector (SEQ ID NO:43, FIG. 21). The ligation was performed with T4 DNA ligase (Boehringer) according to supplier's conditions. The ligation mix was transformed to *E. coli* DH5αF' cells and the plasmid DNA of several ampicilin resistant colonies was analyzed by restriction enzyme digestion. A positive clone was withheld and denominated pSY1Y1G7E1s (SEQ ID NO:50, FIG. 28).

Example 10

Transformation of *Saccharomyces cerevisiae* and Selection of Transformants

In order to overcome hyper-glycosylation problems, often reported for proteins over-expressed in *Saccharomyces cerevisiae*, a mutant screening was set-up. This screening was based on the method of Ballou (Ballou, L. et al. 1991), whereby spontaneous recessive orthovanadate-resistant mutants were selected. Initial strain selection was performed based on the glycosylation pattern of invertase, as observed after native gel electrophoresis. A strain, reduced in glycosylation capabilities, was withheld for further recombinant protein expression experiments and denominated strain IYCC155. The nature of mutation has not been further studied.

Said glycosylation-deficient strain IYCC155 was transformed with the plasmids as described in Examples 7 to 9 essentially by to the lithium acetate method as described by Elble (Elble, R. 1992). Several Ura complemented strains were picked from a selective YNB+2% agar plate (Difco) and used to inoculate 2 ml YNB+2% glucose. These cultures were incubated for 72 h, 37° C., 200 rpm on orbital shaker, and the culture supernatant and intracellular fractions were analysed for expression of E1 by western blot developed with a E1 specific murine monoclonal antibody (IGH 201). A high producing clone was withheld for further experiments.

The expression of proteins in the *S. cerivisiae* glycosylation deficient mutant used here is hampered by the suboptimal growth characteristics of such strains which leads to a lower biomass yield and thus a lower yield of the desired proteins compared to wild-type *S. cerivisiae* strains. The yield of the desired proteins was still substantially higher than in mammalian cells.

Example 11

Construction of pPICZalphaD'E1sH6 and pPICZalphaE'E1sH6 Vectors

Figure 29:
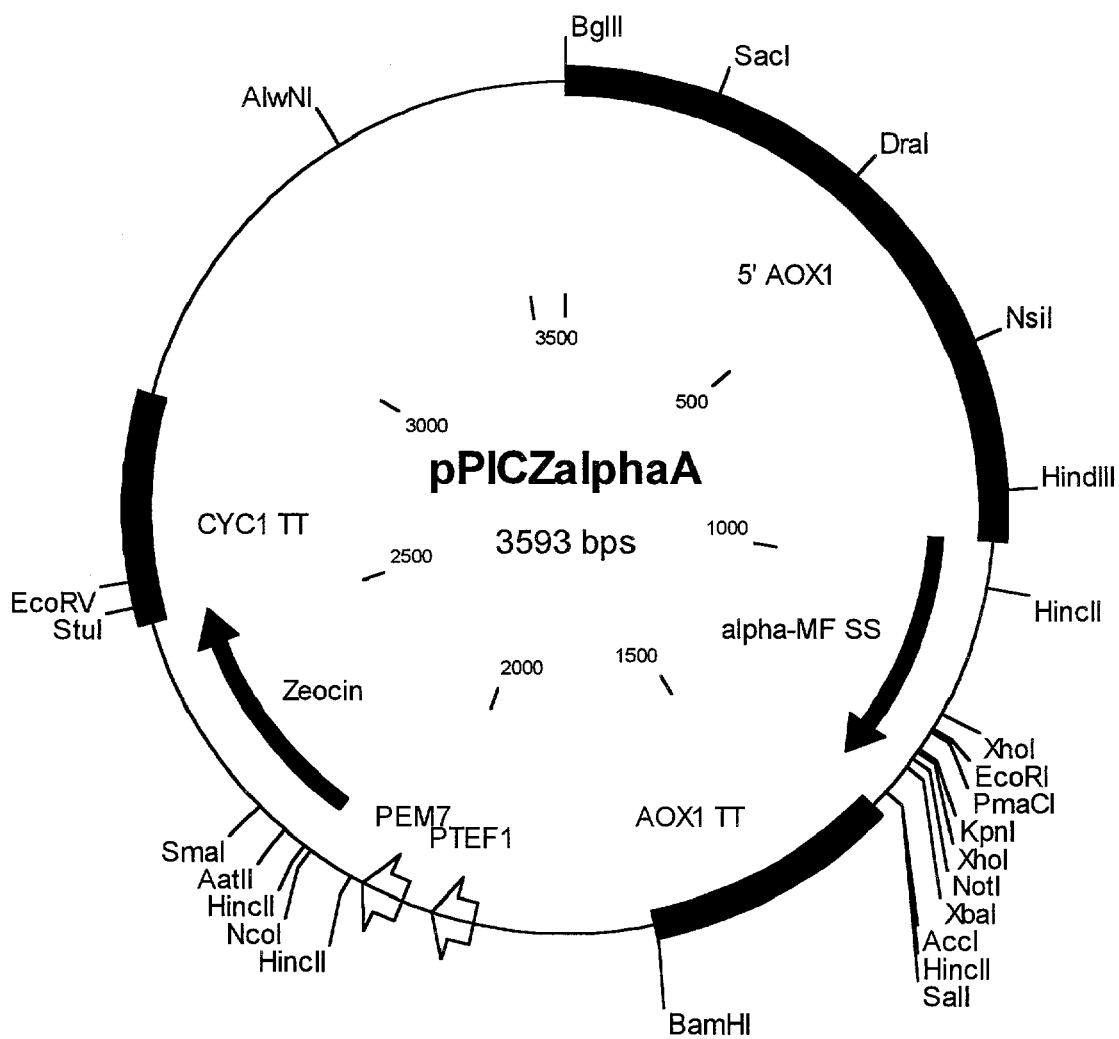
Figure 30:
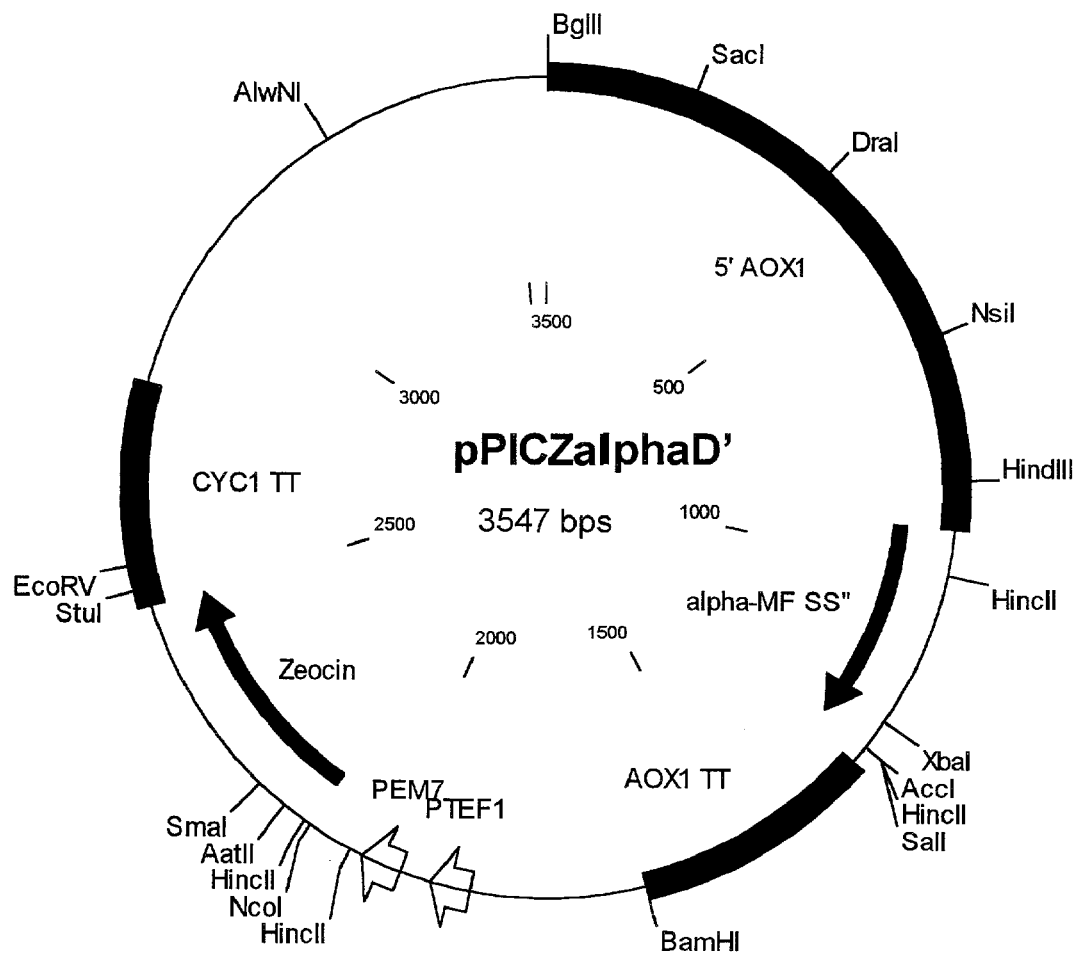
Figure 31:
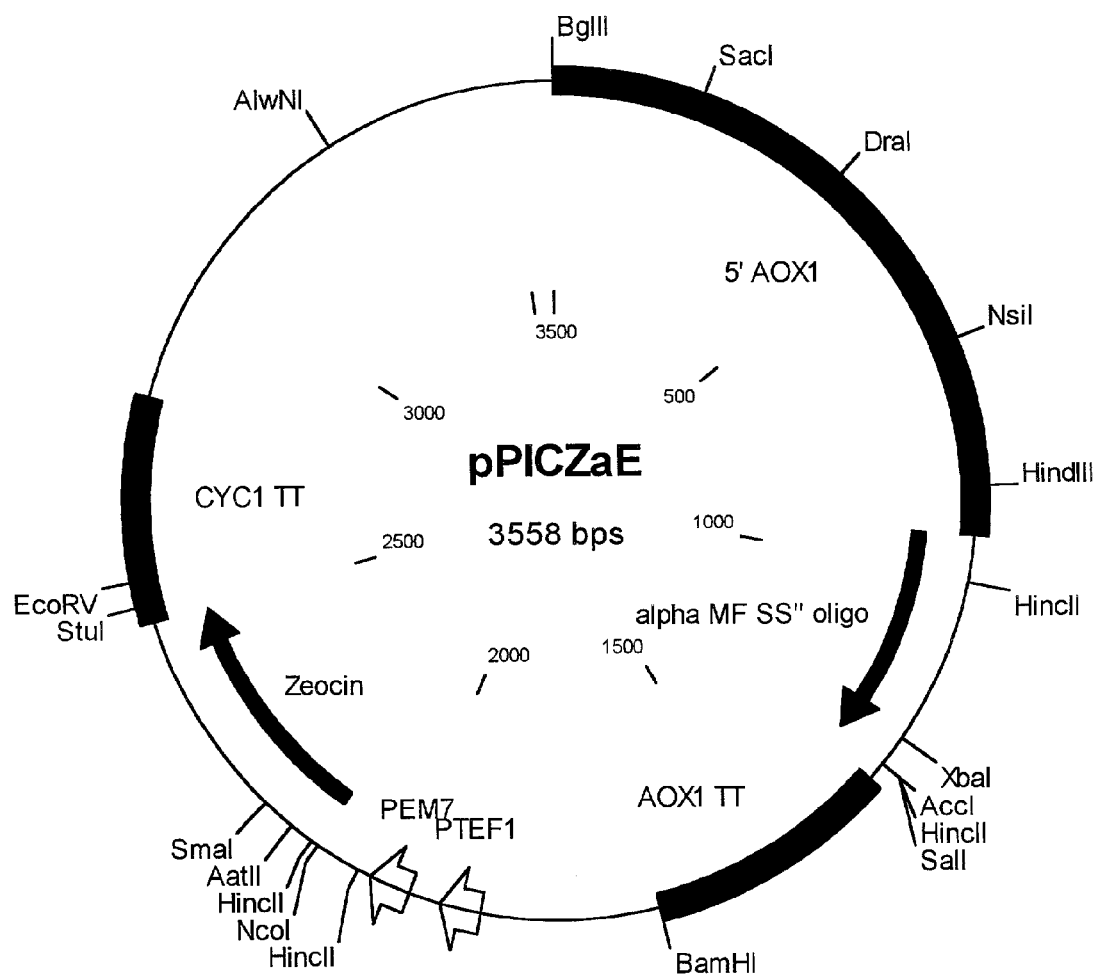

The shuttle vector pPICZalphaE'E1sH6 was constructed starting from the pPICZalphaA vector (Invitrogen; SEQ ID NO:51, FIG. 29). In a first step said vector was adapted in order to enable cloning of the E1 coding sequence directly behind the cleavage site of the KEX2 or STE13 processing proteases, respectively. Therefore pPICZalphaA was digested with XhoI and NotI. The digest was separated on a 1% agarose gel and the 3519 kb fragment (major part of vector) was isolated and purified by means of a gel extraction kit (Qiagen). This fragment was then ligated using T4 polymerase (Boehringer) according to the supplier's conditions in presence of specific oligonucleotides yielding pPICZalphaD' (SEQ ID NO:52, FIG. 30) or pPICZalphaE' (SEQ ID NO:53, FIG. 31).

The following oligonucleotides were used:
for constructing pPICZalphaD':

```
                                          (SEQ ID NO:54)
8822: 5'-TCGAGAAAAGGGGCCCGAATTCGCATGC-3'; and (SEQ ID NO:55)
8823: 5'-GGCCGCATGCGAATTCGGGCCCCTTTTC-3'
``` which yield, after annealing, the linker oligonucleotide:

```
TCGAGAAAAGGGGCCCGAATTCGCATGC    (SEQ ID NO:54)
    CTTTTCCCCGGGCTTAAGCGTACGCCGG (SEQ ID NO:55)
``` for constructing pPICZalphaE'

```
8649:  5'-TCGAGAAAAGAGAGGCTGAAGCCTGCAGCATATGC-3'      (SEQ ID NO:56)

8650:  5'-GGCCGCATATGCTGCAGGCTTCAGCCTCTCTTTTC-3'     (SEQ ID NO:57)
``` which yield, after annealing, the linker oligonucleotide:

```
TCGAGAAAAGAGAGGCTGAAGCCTGCAGCATATGC              (SEQ ID
                                                  NO:56)

CTTTTCTCTCCGACTTCGGACGTCGTATACGCCGG          (SEQ ID
                                                  NO:57)
```

These shuttle vectors pPICZalphaD' and pPICZalphaE' have newly introduced cloning sites directly behind the cleavage site of the respective processing proteases, KEX2 and STE13. The E1-H6 coding sequence was isolated as a NsI1/Eco52I fragment from pGEMT-E1sH6 (SEQ ID NO:6, FIG. 1). The fragment was purified using a gel extraction kit (Qiagen) after separation of the digest on a 1% agarose gel. The resulting fragment was made blunt-ended (using T4 DNA polymerase) and ligated into either pPICZalphaD' or pPICZalphaE' directly behind the respective processing protease cleavage site.

Figure 32:
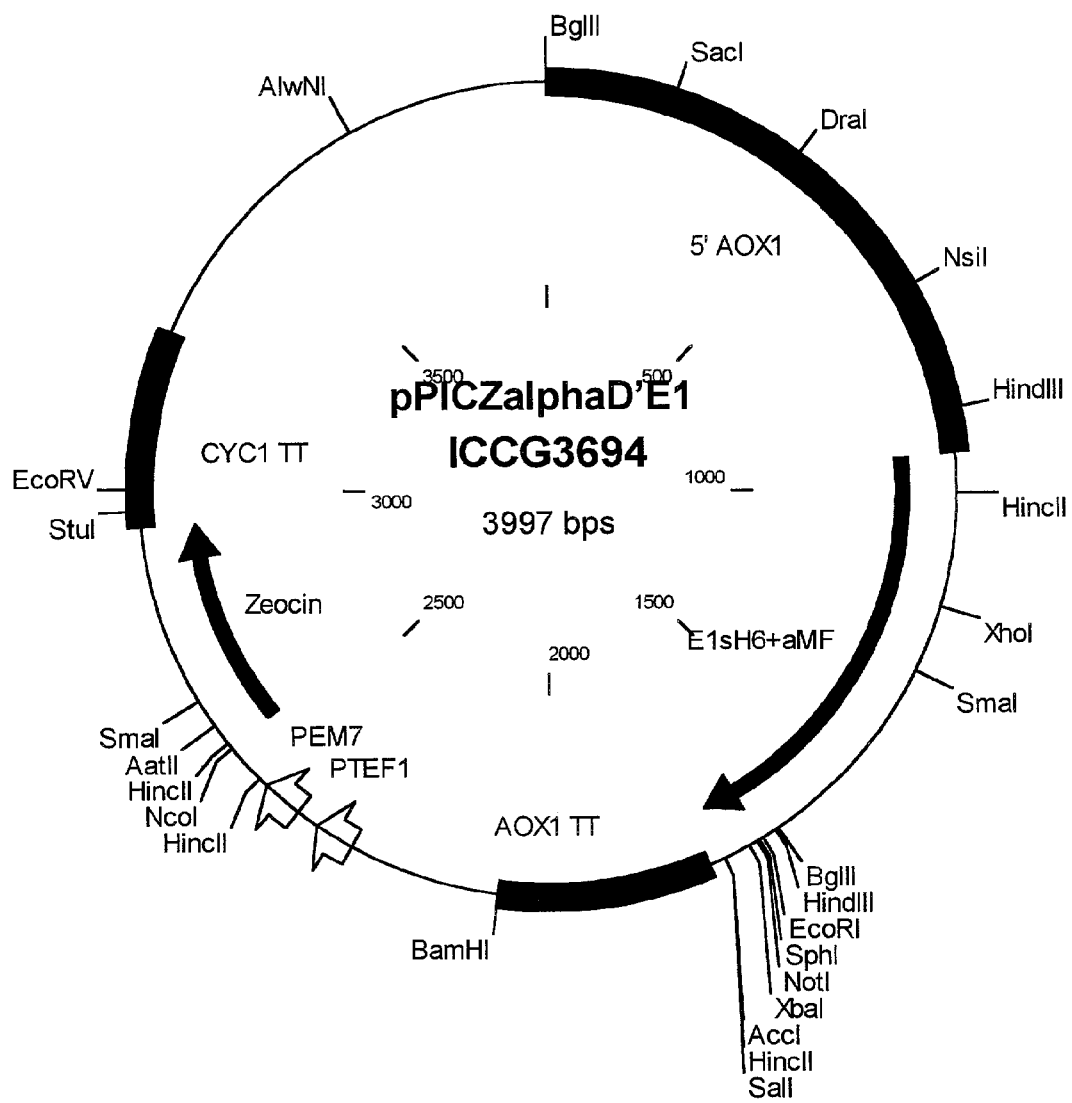
Figure 33:
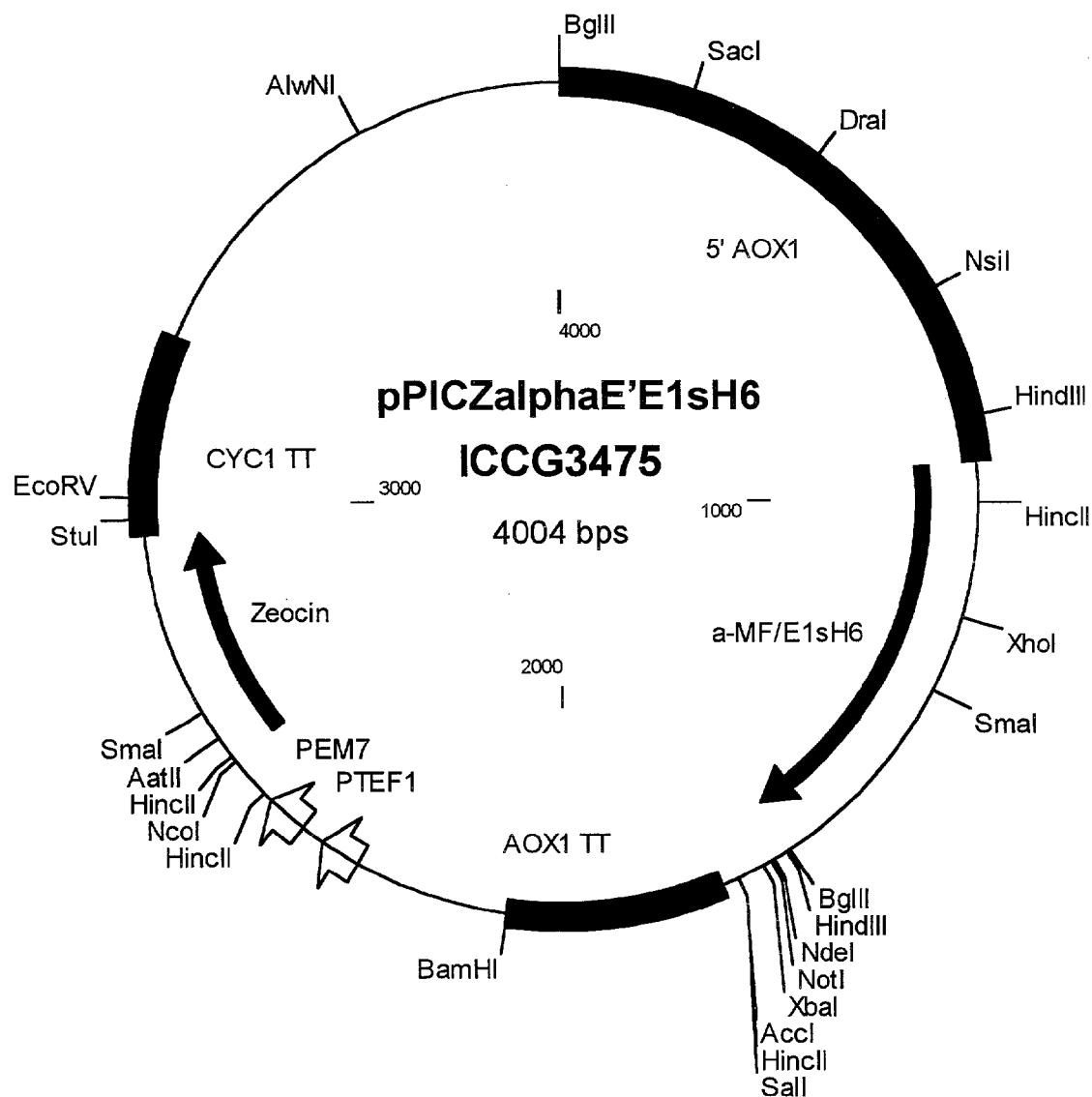

The ligation mixtures were transformed to E. coli TOP10F' cells and plasmid DNA of several zeocin resistant colonies analyzed by restriction enzyme digestion. Positive clones were withheld and denominated pPICZalphaD'E1sH6 (ICCG3694; SEQ ID NO:58, FIG. 32) and pPICZalphaE'E1sH6 (ICCG3475; SEQ ID NO:59, FIG. 33), respectively.

Example 12

Construction of pPICZalphaD'E2sH6 and pPICZalphaE'E2sH6 Vectors

The shuttle vectors pPICZalphaD' and pPICZalphaE' were constructed as described in Example 11.

Figure 23:
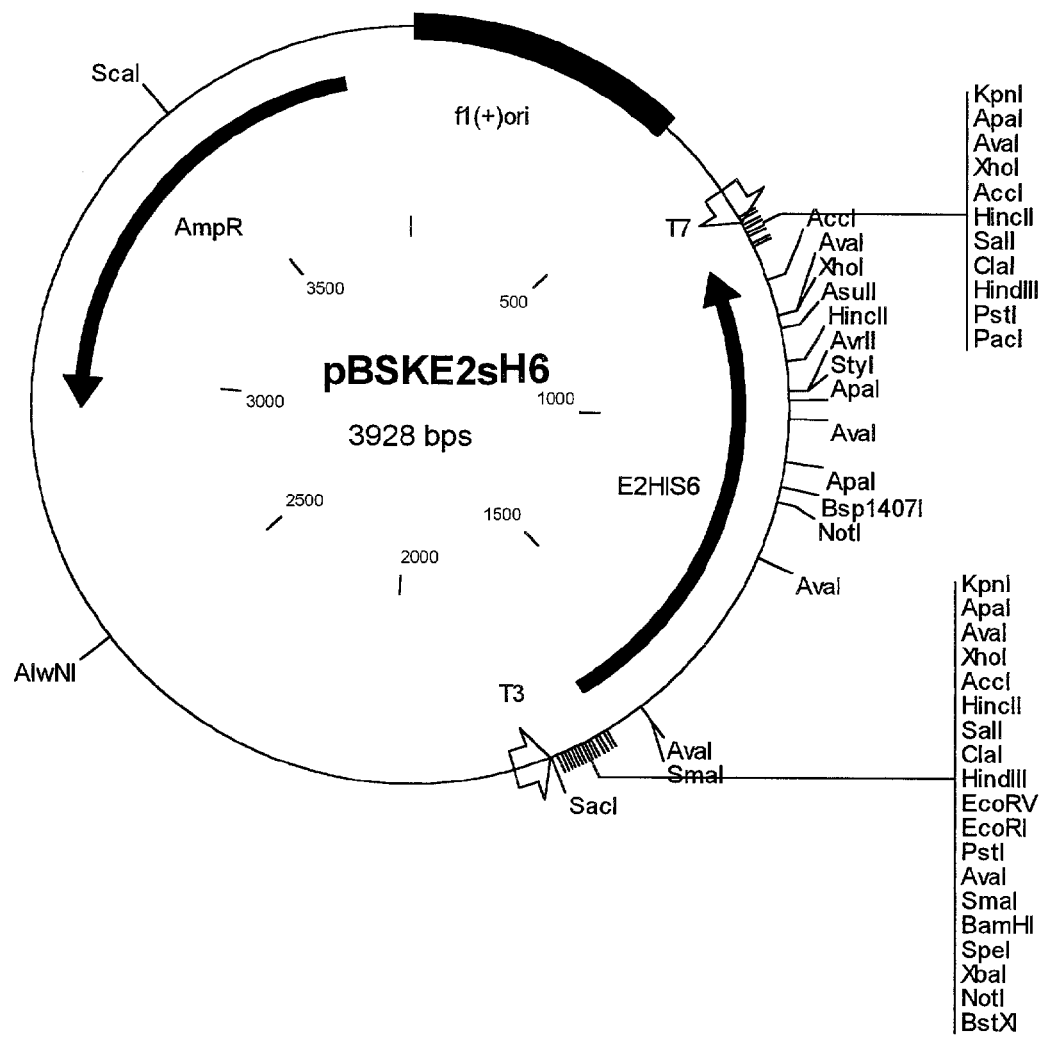
Figure 24:
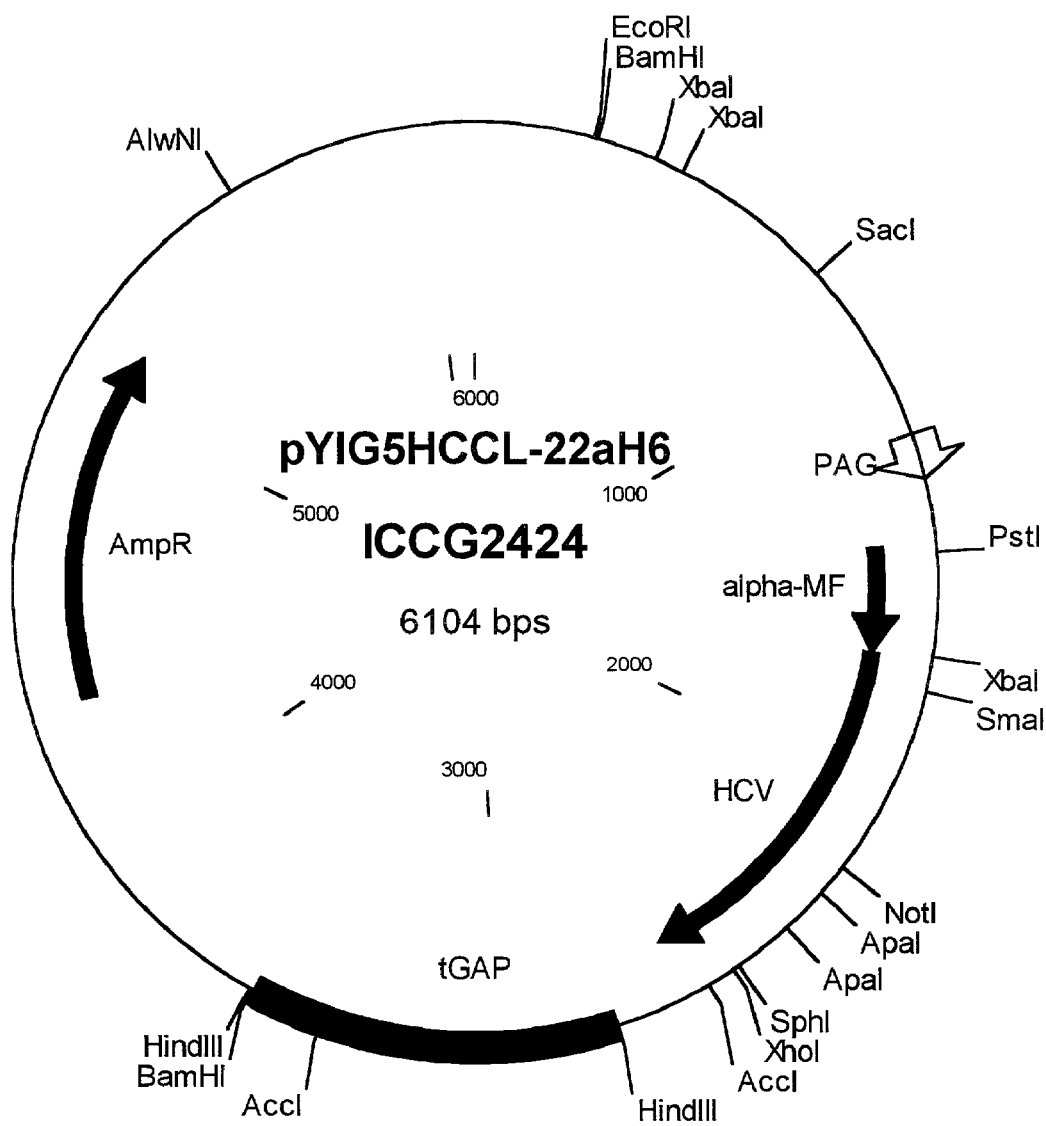

The E2-H6 coding sequence was isolated as a SalI/KpnI fragment from pBSK-E2sH6 (SEQ ID NO:45, FIG. 23). The fragment was purified with a gel extraction kit (Qiagen) after separation of the digest on a 1% agarose gel. The resulting fragment was made blunt-ended (using T4 DNA polymerase) and ligated into either pPICZalphaD' or pPICZalphaE' directly behind the respective processing protease cleavage site.

Figure 34:
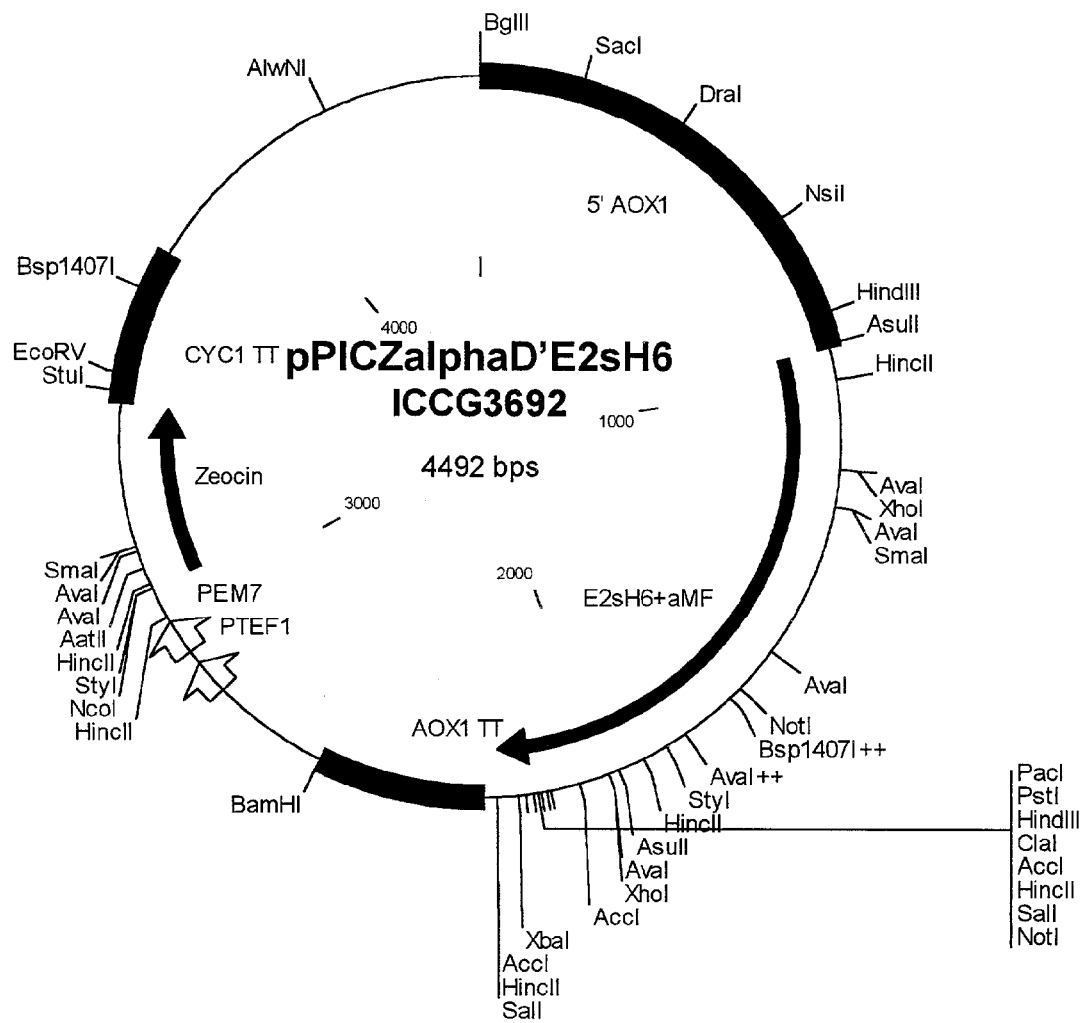
Figure 35:
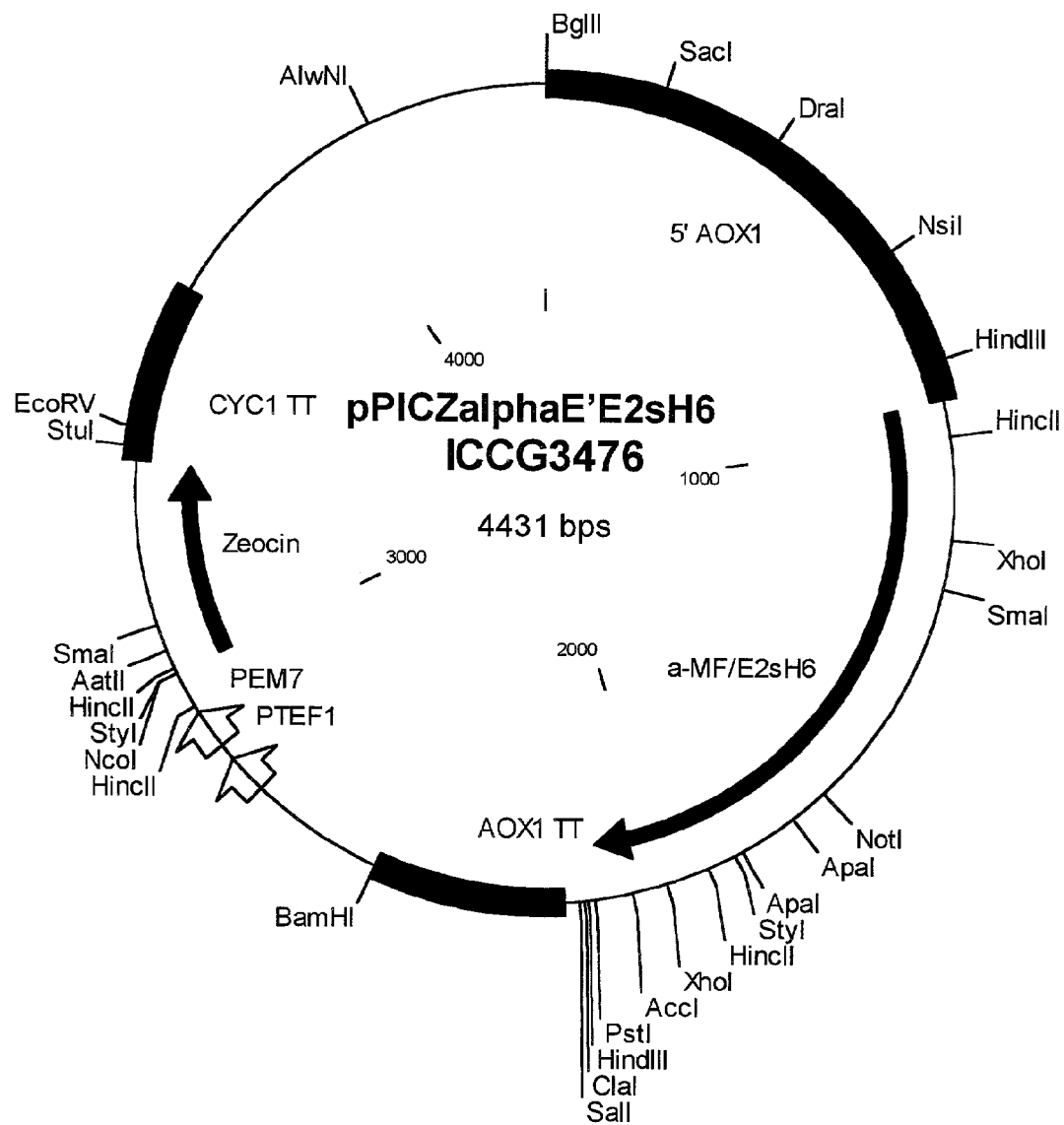

The ligation mixture was transformed to E. coli TOP10F' cells and the plasmid DNA of several zeocin resistant colonies was analyzed by restriction enzyme digestion. Positive clone were withheld and denominated pPICZalphaD'E2sH6 (ICCG3692; SEQ ID NO:60, FIG. 34) and pPICZalphaE'E2sH6 (ICGG3476; SEQ ID NO:61, FIG. 35), respectively.

Example 13

Transformation of Pichia pastoris and Selection of Transformants

The P. pastoris shuttle plasmids as described in Examples 11 and 12 were transformed to P. pastoris cells according to the supplier's conditions (Invitrogen). An E1- and an E2-producing strain were withheld for further characterization.

The HCV envelope proteins were expressed in P. pastoris, a yeast strain well known for the fact that hyperglycosylation is normally absent (Gellissen, G. 2000) and previously used to express dengue virus E protein as GST fusion (Sugrue, R. J. et al. 1997). Remarkably, the resulting P. pastoris-expressed HCV envelope proteins displayed a comparable glycosylation as is observed in wild-type Saccharomyces strains. More specifically, the HCV envelope proteins produced by P. pastoris are hyperglycosylated (based on the molecular weight of the expression products detected in western-blots of proteins isolated from transformed P. pastoris cells).

Example 14

Culture Conditions of Saccharomyces cerevisiae, Hansenula polymorpha and Pichia Pastoris Saccharomyces cerevisiae Cell Banking Of the selected recombinant clone a master cell bank and working cell bank were prepared. Cryo-vials were prepared from a mid-exponentially grown shake flask culture (incubation conditions as for fermentation seed cultures, see below). Glycerol was added (50% final conc.) as a cryoprotectant.

Fermentation

Seed cultures were started from a cryo-preserved working cell bank vial and grown in 500 mL medium (YNB supplemented with 2% sucrose, Difco) in a 2 L Erlenmeyer shake flasks at 37° C., 200 rpm for 48 h.

Fermentations were typically performed in Biostat C fermentors with a working volume of 15 L (B. Braun Int., Melsungen, Germany). The fermentation medium contained 1% Yeast Extract, 2% Peptone and 2% sucrose as carbon source. Poly-ethylene glycol was used as anti-foam agent.

Temperature, pH and dissolved oxygen were typically controlled during the fermentation, applicable set-points are summarised in Table 1. Dissolved oxygen was cascade controlled by agitation/aeration. pH was controlled by addition of NaOH (0.5 M) or $H_3PO_4$ solution (8.5%).

TABLE 1

| Typical parameter settings for S. cerevisiae fermentations | |
|---|---|
| Parameter | set-point |
| Temperature | 33–37° C. |
| pH | 4.2–5.0 |
| DO (growth phase) | 10–40% air saturation |
| DO (induction) | 0–5% |
| aeration | 0.5–1.8 vvm* |
| agitation | 150–900 rpm |

*volume replacement per minute

The fermentation was started by the addition of 10% seed-culture. During the growth phase the sucrose concentration was monitored off-line by HPLC analysis (Polysphere Column OAKC Merck).

During the growth phase the dissolved oxygen was controlled by cascade control (agitation/aeration). After complete metabolisation of sucrose the heterologous protein production was driven by the endogenous produced ethanol supplemented with stepwise addition of EtOH in order to maintain the concentration at approximately 0.5% (off-line BPLC analysis, polyspher OAKC column) During this induction phase the dissolved oxygen was controlled below 5% air-saturation, by manual adjustment of airflow rate and agitator speed.

Typically the fermentation was harvested 48 to 72 h post induction by concentration via tangential flow filtration followed by centrifugation of the concentrated cell suspension to obtain cell pellets. If not analyzed immediately, cell pellets were stored at −70° C.

*Hansenula polymorpha*

Cell Banking

Of the selected recombinant clone a master cell bank and working cell bank were prepared.

Cryo-vials were prepared from a mid-exponentially grown shake flask culture (incubation conditions as for fermentation seed cultures, see below). Glycerol was added (50% final conc.) as a cryoprotectant.

Fermentation

Seed cultures were started from a cryo-preserved (−70° C.) working cell bank vial and grown in 500 mL medium (YPD, Difco) in a 2 L Erlenmeyer shake flasks at 37° C., 200 rpm for 48 h. Fermentations were typically performed in Biostat C fermentors with a working volume of 15 L (B. Braun Int., Melsungen, Germany). The fermentation medium contained 1% Yeast Extract, 2% Peptone and 1% glycerol as carbon source. Poly-ethylene glycol was used as anti-foam agent.

Temperature, pH, air-in and dissolved oxygen were typically controlled during the fermentation, applicable set-points are summarised in Table 2. Dissolved oxygen was controlled by agitation. pH was controlled by addition of NaOH (0.5 M) or $H_3PO_4$ solution (8.5%).

TABLE 2

Typical parameter settings for *H. polymorpha* fermentations

| Parameter | set-point |
|---|---|
| Temperature | 30–40° C. |
| pH | 4.2–5.0 |
| DO | 10–40% air saturation |
| aeration | 0.5–1.8 vvm* |
| agitation | 150–900 rpm |

*volume replacement per minute

The fermentation was started by the addition of 10% seed-culture. During the growth phase the glycerol concentration was monitored off-line (Polysphere Column OAKC Merck) and 24 h after complete glycerol consumption 1% methanol was added in order to induce the heterologous protein expression. The fermentation was harvested 24 h post induction by concentration via tangential flow filtration followed by centrifugation of the concentrated cell suspension to obtain cell pellets. If not analyzed immediately, cell pellets were stored at −70° C.

*Pichia pastoris*

Small scale protein production experiments with recombinant *Pichia pastoris* were set up in shake flask cultures. Seed cultures were grown overnight in YPD medium (Difco). Initial medium pH was corrected to 4.5. Shake flasks were incubated on a rotary shaker at 200-250 rpm, 37° C.

The small scale production was typically performed at 500 mL scale in 2 L shake flasks and were started with a 10% inoculation in expression medium, containing 1% Yeast extract, 2% Peptone (both Difco), and 2% glycerol as carbon source. Incubation conditions were as for the seed culture. Induction was started by addition of 1% MeOH approximately 72 h after inoculation. The cells were collected 24 h post induction by centrifugation. If not analyzed immediately, cell pellets were stored at −70° C.

Example 15

Leader Peptide Removal from MFα-E1-H6 and MFα-E2-H6 Proteins Expressed in Selected Yeast Cells The expression products in *Hansenula polymorpha* and a *Saccharomyces cerevisiae* glycosylation minus strain of the HCV E1 and E2 protein constructs with the α-mating factor (αMF) leader sequence of *S. cerevisiae* were further analyzed. Since both genotype 1b HCV E1s (aa 192-326) and HCV E2s (aa 383-673 extended by the VIEGR (SEQ ID NO:69)-sequence) were expressed as C-terminal his-tagged (H6, HHHHHH, SEQ ID NO:63; said HCV proteins are furtheron in this Example denoted as αMF-E1-H6, and αMF-E2-H6) proteins, a rapid and efficient purification of the expressed products after guanidinium chloride (GuHCl)-solubilization of the yeast cells was performed on Ni-IDA (Ni-iminodiacetic acid). In brief, cell pellets were resuspended in 50 mM phosphate, 6M GuHCl, pH 7.4 (9 vol/g cells). Proteins were sulfonated overnight at room temperature (RT) in the presence of 320 mM (4% w/v) sodium sulfite and 65 mM (2% w/v) sodium tetrathionate. The lysate was cleared after a freeze-thaw cycle by centrifugation (10.000 g, 30 min, 4° C.) and Empigen (Albright & Wilson, UK) and imidazole were added to the supernatant to final concentrations of 1% (w/v) and 20 mM, respectively. The sample was filtrated (0.22 μM) and loaded on a Ni-IDA Sepharose FF column, which was equilibrated with 50 mM phosphate, 6M GuHCl, 1% Empigen (buffer A) supplemented with 20 mM imidazole. The column was washed sequentially with buffer A containing 20 mM and 50 mM imidazole, respectively, till absorbance at 280 nm reached baseline level. The his-tagged products were eluted by applying buffer D, 50 mM phosphate, 6M GuHCl, 0.2% (for E1) or 1% (for E2) Empigen, 200 mM imidazole. The eluted materials were analyzed by SDS-PAGE and western-blot using a specific monoclonal antibodies directed against E1 (IGH201), or E2 (IGH212).

The E1-products were immediately analyzed by Edman degradation.

Since at this stage, SDS-PAGE revealed already a very complex picture of protein bands for HCV E2, a further fractionation by size exclusion chromatography was performed. The Ni-IDA eluate was concentrated by ultrafiltration (MWCO 10 kDa, centriplus, Amicon, Millipore) and loaded on Superdex G200 (10/30 or 16/60; Pharmacia) in PBS, 1% Empigen or PBS, 3% Empigen. Elution fractions, containing E2 products, with a Mr between ~80 kDa and ~45 kDa, i.e. fractions 17-23 of the elution profile in FIG. 37 based on the migration on SDS-PAGE (FIG. 38), were pooled and alkylated (incubation with 10 mM DTT 3 h at RT followed by incubation with 30 mM iodo-acetamide for 3 hours at RT). Samples for amino-terminal sequencing were treated with Endo H (Roche Biochemicals) or left untreated. The glycosylated and deglycosylated E2 products were blotted on PVDF-membranes for amino-terminal sequencing. An amido-black stained blot of glycosylated and deglycosylated E2 is shown in FIG. 39.

The sequencing of both E1 and E2 purified products lead to the disappointing observation that removal of the signal sequence from the HCV envelope proteins is occurring only partially (see Table 3). In addition, the majority of the side products (degradation products and products still containing the leader sequence or part thereof) are glycosylated. This glycosylation resides even in part on the non-cleaved fragment of the signal sequence which contains also an N-glycosylation site. These sites can be mutated in order to result in less glycosylated side products. However, even more problematic is the finding that some alternatively cleaved products have only 1 to 4 amino acids difference compared to the desired intact envelope protein. Consequently, purification of the correctly processed product is virtually impossible due to the lack of sufficiently discriminating biochemical characteristics between the different expression products. Several of the degradation products may be a result of a Kex-2 like cleavage (e.g. the cleavage observed after aa 196 of E1 which is a cleavage after an arginine), which is also required for the cleavage of the α-mating factor leader and which can thus not be blocked without disturbing this essential process.

Figure 22:
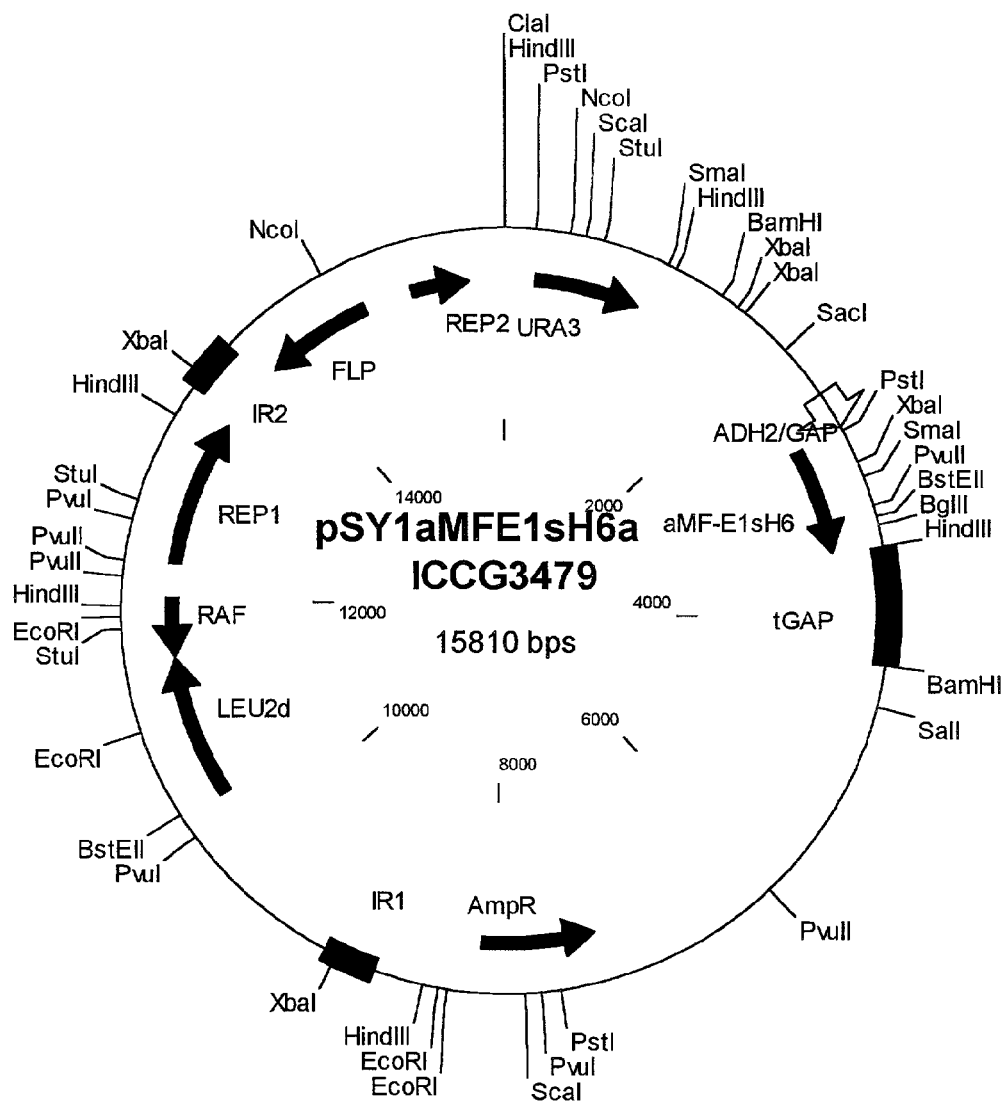
Figure 28:
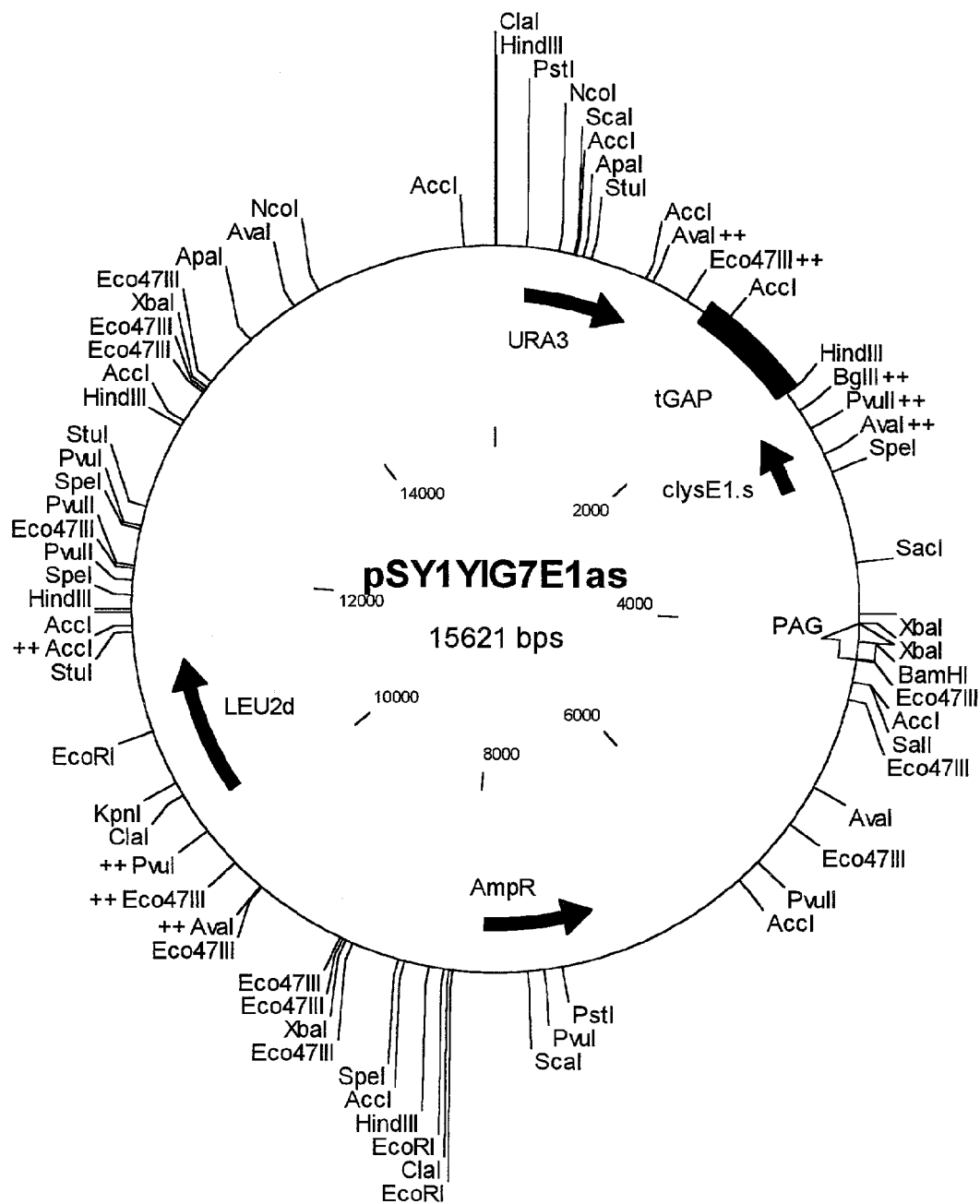

A high E1 producing clone derived from transformation of S. cerevisiae IYCC155 with pSY1YIG7E1s (SEQ ID NO:50; FIG. 28) was compared with a high producing clone derived from transformation of S. cerevisiae IYCC155 with pSY1aMFE1sH6aYIG1E1s (SEQ ID NO:44; FIG. 22). The intracellular expression of the E1 protein was evaluated after 2 up to 7 days after induction, and this by means of Western-blot using the E1 specific monoclonal antibody (IGH 201). As can be judged from FIG. 40, maximal expression was observed after 2 days for both strains but the expression patterns for both strains are completely different. Expression with the α-mating factor leader results in a very complex pattern of bands, which is a consequence from the fact that the processing of the leader is not efficient. This leads to several expression products with a different amino-terminus and of which some are modified by 1 to 5 N-glycosylations. However, for the E1 expressed with the CL leader a limited number of distinct bands is visible which reflects the high level of correct CL leader removal and the fact that only this correctly processed material may be modified by N-glycosylation (1 to 5 chains), as observed for Hansenula-derived E1 expressed with the same CL leader (see Example 16).

The hybridoma cell line producing the monoclonal antibody directed against E1 (IGH201) was deposited on Mar. 12, 1998 under the conditions of the Budapest Treaty at the European Collection of Cell Cultures, Centre for Applied Microbiology & Research, Salisbury, Wiltshire SP40JG, UK, and has the accession number ECACC 98031216). The monoclonal antibody directed against E2 (IGH212) has been described as antibody 12D11 F2 in Example 7.4 by Maertens et al. in WO96/04385.

TABLE 3

Identification of N-termini of αMF-E1-H6 and αMF-E2-H6 proteins expressed in S. cerevisiae or H. polymorpha. Based on the N-terminal sequencing the amount of N-termini of the mature E1-H6 and E2-H6 proteins could be estimated ("mature" indicating correct removal of the αMF signal sequence). The total amount of protein products was calculated as pmol of protein based on the intensity of the peaks recovered by Edman degradation. Subsequently, for each specific protein (i.e. for each 'detected N-terminus') the mol % versus the total was estimated.

| Yeast | αMF-E1-H6 | αMF-E2-VIEGR-H6 |
|---|---|---|
| S. cerevisiae | Experiment 1:<br>16% of proteins still containing αMF sequences<br>18% of proteins cleaved | / |

TABLE 3-continued

Identification of N-termini of αMF-E1-H6 and αMF-E2-H6 proteins expressed in S. cerevisiae or H. polymorpha. Based on the N-terminal sequencing the amount of N-termini of the mature E1-H6 and E2-H6 proteins could be estimated ("mature" indicating correct removal of the αMF signal sequence). The total amount of protein products was calculated as pmol of protein based on the intensity of the peaks recovered by Edman degradation. Subsequently, for each specific protein (i.e. for each 'detected N-terminus') the mol % versus the total was estimated.

| Yeast | αMF-E1-H6 | αMF-E2-VIEGR-H6 |
|---|---|---|
|  | between aa 195 and 196 of E1<br>66% of proteins with correctly removed αMF<br>Experiment 2<br>18% of proteins still containing αMF sequences<br>33% of proteins cleaved between aa 195 and 196 of E1<br>8% of other proteins other E1 cleavage products<br>44% of proteins with correctly removed αMF | / |
| H. polymorpha | 64% of proteins still containing αMF sequences<br>6% of proteins cleaved between aa 192 and 193 of E1<br>30% of proteins with correctly removed αMF | 75% of proteins still containing αMF sequences<br>25% of proteins with correctly removed αMF |

Example 16

Expression of an E1 Construct in Yeast Suitable for Large Scale Production and Purification Several other leader sequences were used to replace the S. cerevisiae αMF leader peptide including CHH (leader sequence of Carcinus maenas hyperglycemic hormone), Amyl (leader sequence of amylase from S. occidentalis), Gam1 (leader sequence of glucoamylase from S. occidentalis), Phy5 (leader sequence from fungal phytase), pho1 (leader sequence from acid phosphatase from Pichia pastoris) and CL (leader of avian lysozyme C, 1,4-beta-N-acetylmuramidase C) and linked to E1-H6 (i.e. E1 with C-terminal his-tag). All constructs were expressed in Hansenula polymorpha and each of the resulting cell lysates was subjected to western blot analysis. This allowed already to conclude that the extent of removal of the leader or signal sequence or peptide was extremely low, except for the construct wherein CL is used as leader peptide. This was confirmed for the CHH-E1-H6 construct by Edman-degradation of Ni-IDA purified material: no correctly cleaved product could be detected although several different sequences were recovered (see Table 4).

TABLE 4

Identification of N-termini of CHH-E1-H6 proteins expressed in H. polymorpha, based on N-terminal amino acid sequencing of different protein bands after separation by SDS-PAGE and blotting to a PVDF membrane.

| Molecular size | Identified N-termini |
|---|---|
| 45 kD | starts at amino acid 27 of CHH leader = only pre-sequence cleaved, pro-sequence still attached |
| 26 kD | partially starts at amino acid 1 of CHH leader = no removal of pre-pro-sequence |

TABLE 4-continued

Identification of N-termini of CHH-E1-H6 proteins
expressed in *H. polymorpha*, based on N-terminal amino
acid sequencing of different protein bands after separation
by SDS-PAGE and blotting to a PVDF membrane.

| Molecular size | Identified N-termini |
|---|---|
| 24 kD | partially starts at amino acid 9 of CHH leader = product of alternative translation starting at second AUG codon<br>partially starts at amino acid 1 of CHH leader = no removal of pre-pro-sequence<br>partially starts at amino acid 9 of CHH leader = product of alternative translation starting at second AUG codon |

As mentioned already, the western-blots of the cell lysates revealed a pattern of E1 specific protein bands, indicative for a higher degree of correct removal of the CL leader peptide. This is surprising since this leader is not derived from a yeast. Amino acid sequencing by Edman degradation of GuHCl solubilized and Ni-IDA purified material indeed confirmed that 84% of the E1 proteins is correctly cleaved and the material is essentially free of degradation products. Still 16% of non-processed material is present but since this material is non-glycosylated it can be easily removed from the mixture allowing specific enrichment of correctly cleaved and glycosylated E1. Such a method for enrichment may be an affinity chromatography on lectins, other alternatives are also given in Example 19. Alternatively, the higher hydrophobic character of the non-glycosylated material may be used to select and optimize other enrichment procedures. The correct removal of the CL leader peptide from the CL-E1-H6 protein was further confirmed by mass spectrometry which also confirmed that up to 4 out of the 5 N-glycosylation sites of genotype 1b E1s can be occupied, whereby the sequence NNSS (amino acids 233 to 236; SEQ ID NO:73) are considered to be a single N-glycosylation site.

Example 17

Purification and Biochemical Characterization of the HCV E2 Protein Expressed in *Hansenula polymorpha* from the CL-E2-H6 Encoding Construct The efficiency of removal of the CL leader peptide from CL-E2-VIEGR-H6 (furtheron in this Example denoted as "CL-E2-H6") protein expressed in *Hansenula polymorpha* was analyzed. Since the HCV E2s (aa 383-673) was expressed as a his-tagged protein, a rapid and efficient purification of the expressed protein after GuHCl-solubilization of collected cells was performed on Ni-IDA. In brief, cell pellets were resuspended in 30 mM phosphate, 6 M GuHCl, pH 7.2 (9 mL buffer/g cells). The protein was sulfonated overnight at room temperature in the presence of 320 mM (4% w/v) sodium sulfite and 65 mM (2% w/v) sodium tetrathionate. The lysate was cleared after a freeze-thaw cycle by centrifugation (10.000 g, 30 min, 4° C.). Empigen BB (Albright & Wilson) and imidazole were added to a final concentration of 1% (w/v) and 20 mM, respectively. All further chromatographic steps were executed on an Ä kta FPLC workstation (Pharmacia). The sample was filtrated through a 0.22 µm pore size membrane (cellulose acetate) and loaded on a Ni-IDA column (Chelating Sepharose FF loaded with Ni$^{2+}$, Pharmacia), which was equilibrated with 50 mM phosphate, 6 M GuHCl, 1% Empigen BB, pH 7.2 (buffer A) supplemented with 20 mM imidazole. The column was washed sequentially with buffer A containing 20 mM and 50 mM imidazole, respectively, till the absorbance at 280 nm reached the baseline level. The his-tagged products were eluted by applying buffer D, 50 mM phosphate, 6 M GuHCl, 0.2% Empigen BB (pH 7.2), 200 mM imidazole. The purified materials were analysed by SDS-PAGE and western-blot using a specific monoclonal antibody directed against E2 (IGH212) (FIG. 41). The IMAC-purified E2-H6 protein was also subjected to N-terminal sequencing by Edman degradation. Thereto proteins were treated with N-glycosidase F (Roche) (0.2 U/µg E2, 1 h incubation at 37° C. in PBS/3% empigen BB) or left untreated. The glycosylated and deglycosylated E2-H6 proteins were subjected to SDS-PAGE and blotted on a PVDF-membrane for amino acid sequencing (analysis was performed on a PROCISE™ 492 protein sequencer, Applied Biosystems). Since at this stage, SDS-PAGE revealed some degradation products, a further fractionation by size exclusion chromatography was performed. Hereto, the Ni-IDA eluate was concentrated by ultrafiltration (MWCO 10 kDa, centriplus, Amicon, Millipore) and loaded on a Superdex G200 (Pharmacia) in PBS, 1% Empigen BB. Elution fractions, containing mainly intact E2s related products with a Mr between ~30 kDa and ~70 kDa based on the migration on SDS-PAGE, were pooled and eventually alkylated (incubation with 5 mM DTT for 30 minutes at 37° C., followed by incubation with 20 mM iodoacetamide for 30 minutes at 37° C.). The possible presence of degradation products after IMAC purification can thus be overcome by a further fractionation of the intact product by means of size exclusion chromatography. An unexpectedly good result was obtained. Based on the N-terminal sequencing the amount of E2 product from which the CL leader peptide is removed could be estimated. The total amount of protein products is calculated as pmol of protein based on the intensity of the peaks recovered by Edman degradation. Subsequently, for each specific protein (i.e. for each 'detected N-terminus') the mol % versus the total is estimated. In the current experiment, only the correct N-terminus of E2-H6 was detected and other variants of E2-H6 lacking amino acid of the E2 protein or containing N-terminal amino acids not comprised in the E2 protein were absent. In conclusion, the E2-H6 protein expressed by *H. polymorpha* as CL-E2-H6 protein was isolated without any further in vitro processing as a >95% correctly cleaved protein. This is in sharp contrast with the fidelity of leader peptide removal by *H. polymorpha* of the αMF-E2-H6 protein to the E2-H6 protein, which was estimated to occur in 25% of the isolated proteins (see Table 3).

Example 18

Purification and Biochemical Characterization of the HCV E1 Protein Expressed in *Hansenula polymorpha* from the CL-H6-K-E1 Encoding Construct and In Vitro Processing of H6-Containing Proteins The efficiency of removal of the CL leader peptide from the CL-H6-K-E1 protein expressed in *H. polymorpha* was analyzed, as well as the efficiency of subsequent in vitro processing in order to remove the H6 (his-tag)-adaptor peptide and the Endo Lys-C processing site. Since the HCV E1s (aa 192-326) was expressed as a N-terminal His-K-tagged protein CL-H6-K-E1, a rapid and efficient purification could be performed as described in Example 17. The elution profile of the IMAC-chromatographic purification of H6-K-E1 (and possibly residual CL-H6-K-E1) proteins is shown in FIG. 42. After SDS-PAGE and silver staining of the gel and western-blot analysis using a specific monoclonal antibody directed against E1 (IGH201) (FIG. 43), the elution fractions (63-69) containing the recombinant E1s products were pooled ('IMAC pool') and subjected to an overnight Endoproteinase Lys-C (Roche) treatment (enzyme/substrate ratio of 1/50 (w/w), 37° C.) in order to remove the H6-K-fusion tail. Removal of non-processed fusion product was performed by a negative IMAC chromatography step on a Ni-IDA column whereby Endo-Lys-C-processed proteins are collected in the flow-through fraction. Hereto the Endoproteinase Lys-C digested protein sample was applied on a Ni-IDA column after a 10-fold dilution with 10 mM $NaH_2PO_4.3H_2O$, 1% (v/v) Empigen B, pH 7.2 (buffer B) followed by washing with buffer B till the absorbance at 280 nm reached the baseline level. The flow through was collected in different fractions (1-40) that were screened for the presence of E1s-products (FIG. 44). The fractions (7-28), containing intact E1 from which the N-terminal H6-K (and possibly residual CL-H6-K) tail is removed (with a Mr between ~15 kDa and ~30 kDa based on the migration on SDS-PAGE followed by silver staining or western blot analysis using a specific monoclonal antibody directed against E1 (IGH201), were pooled and eventually alkylated (incubation with 5 mM DTT for 30 minutes at 37° C., followed by incubation with 20 mM iodoacetamide for 30 minutes at 37° C.).

This material was subjected to N-terminal sequencing (Edman degradation). Hereto, protein samples were treated with N-glycosidase F (Roche) (0.2 U/µg E1, 1 h incubation at 37° C. in PBS/3% empigen BB) or left untreated. The glycosylated and deglycosylated E1 proteins were then separated by SDS-PAGE and blotted on a PVDF-membrane for further analysis by Edman degradation (analysis was performed on a PROCISE™ 492 protein sequencer, Applied Biosystems). Based on the N-terminal sequencing the amount of correctly processed E1 product could be estimated (processing includes correct cleavage of the H6-K-sequence). The total amount of protein products is calculated as pmol of protein based on the intensity of the peaks recovered by Edman degradation. Subsequently, for each specific protein (i.e. for each 'detected N-terminus') the mol % versus the total is estimated. In the current experiment, only the correct N-terminus of E1 was detected and not the N-termini of other processing variants of H6-K-E1. Based thereon, in vitro processing by Endo Lys-C of the H6-K-E1E1 (and possibly residual CL-H6-K-E1) protein to the E1 protein was estimated to occur with a fidelity of more than 95%.

Example 19

Specific Removal of Low-Glycosylated Forms of HCV E1 by Heparin

In order to find specific purification steps for HCV envelope proteins from yeast cells binding with heparin was evaluated. Heparin is known to bind to several viruses and consequently binding to the HCV envelope has already been suggested (Garson, J. A. et al. 1999). In order to analyze this potential binding, heparin was biotinylated and interaction with HCV E1 analyzed in microtiterplates coated with either sulfonated HCV E1 from *H. polymorpha*, alkylated HCV E1 from *H. polymorpha* (both produced as described in Example 16) and alkylated HCV E1 from a culture of mammalian cells transfected with a vaccinia expression vector. Surprisingly, a strong binding could only be observed with sulfonated HCV E1 from *H. polymorpha*, while binding with HCV E1 from mammalian cell culture was completely absent. By means of western-blot we could show that this binding was specific for the lower molecular weight bands of the HCV E1 protein mixture (FIG. 45), corresponding to low-glycosylated mature HCV E1s. FIG. 45 also reveals that sulfonation is not essential for heparin binding since upon removal of this sulfonation binding is still observed for the low molecular weight E1 (lane 4). Alternatively, alkylation is reducing this binding substantially, however, this may be caused by the specific alkylation agent (iodo-acetamide) used in this example. This finding further demonstrated the industrial applicability of the CL-HCV-envelope expression cassettes for yeast since we specifically can enrich HCV E1 preparations towards a preparation with HCV E1 proteins with a higher degree of glycosylation (i.e. more glycosylation sites occupied).

Example 20

Formation and Analysis of Virus-Like Particles (VLPs)

Conversion of the HCV E1 and E2 envelope proteins expressed in *H. polymorpha* (Examples 16 to 18) to VLPs was done essentially as described by Depla et al. in WO99/67285 and by Bosman et al. in WO01/30815. Briefly, after cultivation of the transformed *H. polymorpha* cells during which the HCV envelope proteins were expressed, cells were harvested, lysed in GuHCl and sulphonated as described in Example 17. His-tagged proteins were subsequently purified by IMAC and concentrated by ultrafiltration as described in Example 17.

VLP-Formation of HCV Envelope Proteins with Sulphonated Cys-Thiol Groups

The concentrated HCV envelope proteins sulphonated during the isolation procedure were not subjected to a reducing treatment and loaded on a size-exclusion chromatograpy column (Superdex G200, Pharmacia) equilibrated with PBS, 1% (v/v) Empigen. The eluted fractions were analyzed by SDS-PAGE and western blotting. The fractions with a relative Mr ~29-~15 kD (based on SDS-PAGE migration) were pooled, concentrated and loaded on Superdex G200, equilibrated with PBS, 3% (w/v) betain, to enforce virus like particle formation (VLP). The fractions were pooled, concentrated and desalted to PBS, 0.5% (w/v) betain.

VLP-Formation of HCV Envelope Proteins with Irreversibly Modified Cys-Thiol Groups The concentrated HCV envelope proteins sulphonated during the isolation procedure were subjected to a reducing treatment (incubation in the presence of 5 mM DTT in PBS) to convert the sulphonated Cys-thiol groups to free Cys-thiol groups. Irreversible Cys-thiol modification was performed by (i) incubation for 30 min in the presence of 20 mM iodoacetamide, or by (ii) incubation for 30 min in the presence of 5 mM N-ethylmaleimide (NEM) and 15 mM biotin-N-ethylmaleimide. The proteins were subsequently loaded on a size-exclusion chromatograpy column (Superdex G200, Pharmacia) equilibrated with PBS, 1% (v/v) Empigen in case of iodoacetamide-blocking, or with PBS, 0.2% CHAPS in case of blocking with NEM and biotin-NEM. The eluted fractions were analyzed by SDS-PAGE and Western blotting. The fractions with a relative Mr ~29-~15 kD (based on SDS-PAGE migration) were pooled, concentrated and, to force virus-like particle formation, loaded on a Superdex G200 column equilibrated with PBS, 3% (w/v) betain. The fractions were pooled, concentrated and desalted to PBS, 0.5% (w/v) betain in case of iodoacetamide-blocking, or with PBS, 0.05% CHAPS in case of blocking with NEM and biotin-NEM.

VLP-Formation of HCV Envelope Proteins with Reversibly Modified Cys-Thiol Groups The concentrated HCV envelope proteins sulphonated during the isolation procedure were subjected to a reducing treatment (incubation in the presence of 5 mM DTT in PBS) to convert the sulphonated Cys-thiol groups to free Cys-thiol groups. Reversible Cys-thiol modification was performed by incubation for 30 min in the presence of dithiodipyridine (DTDP), dithiocarbamate (DTC) or cysteine. The proteins were subsequently loaded on a size-exclusion chromatograpy column (Superdex G200, Pharmacia) equilibrated with PBS, 1% (v/v) Empigen. The eluted fractions were analyzed by SDS-PAGE and Western blotting. The fractions with a relative Mr ~29-~15 kD (based on SDS-PAGE migration) were pooled, concentrated and loaded on Superdex G200, equilibrated with PBS, 3% (w/v) betain, to enforce virus like particle formation (VLP). The fractions were pooled, concentrated and desalted to PBS, 0.5% (w/v) betain.

The elution profiles of size-exclusion chromatography in PBS, 3% (w/v) betain to obtain VLPs of *H. polymorpha*-expressed E2-H6 are shown in FIG. 46 (sulphonated) and FIG. 47 (alkylated with iodoacetamide).

The elution profiles of size-exclusion chromatography in PBS, 3% (w/v) betain to obtain VLPs of *H. polymorpha*-expressed E1 are shown in FIG. 48 (sulphonated) and FIG. 49 (alkylated with iodoacetamide). The resulting VLPs were analyzed by SDS-PAGE and western blotting as shown in FIG. 50.

Size-Analysis of VLPs Formed by *H. polymorpha*-Expressed HCV Envelope Proteins

The VLP particle size was determined by Dynamic Light Scattering. For the light-scattering experiments, a particle-size analyzer (Model Zetasizer 1000 HS, Malvern Instruments Ltd., Malvern, Worcester UK) was used which was controlled by photon correlation spectroscopy (PCS) software. Photon correlation spectroscopy or dynamic light scattering (DLS) is an optical method that measures brownian motion and relates this to the size of particles. Light from a continuous, visible laser beam is directed through an ensemble of macromolecules or particles in suspension and moving under brownian motion. Some of the laser light is scattered by the particles and this scattered light is measured by a photomultiplier. Fluctuations in the intensity of scattered light are converted into electrical pulses which are fed into a correlator. This generates the autocorrelation function which is passed to a computer where the appropriate data analysis is performed. The laser used was a 10 mW monochromatic coherent He—Ne laser with a fixed wavelength of 633 nm. For each sample, three to six consecutive measurements were taken.

The results of these experiments are summarized in Table 5.

TABLE 5

Results of dynamic light scattering analysis on the indicated VLP-compositions of HCV envelope proteins expressed by *H. polymorpha*. The VLP particle sizes are given as mean diameter of the particles.

| Cys-thiol modification | E1-H6 | E2-VIEGR-H6 | E1 |
|---|---|---|---|
| sulphonation | 25–45 nm | 20 nm | 20–26 nm |
| alkylation (iodoacetamide) | 23–56 nm | 20–56 nm | 21–25 nm |

The observation that sulphonated HCV E1 derived from *H. polymorpha* still forms particles with a size in the same range as alkylated HCV E1 from *Hansenula* is surprising. Such an effect was not expected since the high (up to 8 Cys-thiol groups can be modified on HCV E1) net increase of negative charges as a consequence of sulphonation should induce an ionic repulsion between the subunits. The other reversible cysteine modifying agents tested also allowed particle formation, the HCV E1 produced in this way, however, proved to be less stable than the sulphonated material, resulting in disulfide-based aggregation of the HCV E1. In order to use these other reversible blockers, further optimization of the conditions is required.

Example 21

Antigenic Equivalence of *Hansenula*-Produced HCV E1-H6 and HCV E1 Produced by Vaccinia-Infected Mammalian Cells The reactivity of *Hansenula*-produced HCV E1-H6 with sera from HCV chronic carriers was compared to the reactivity of HCV E1 produced by HCV-recombinant vaccinia virus-infected mammalian cells as described by Depla et al. in WO 99/67285. Both HCV-E1 preparations tested consisted of VLP's wherein the HCV E1 proteins were alkylated with NEM and biotin-NEM. The reactivities of both HCV E1 VLP-preparations with sera from HCV chronic carriers was determined by ELISA. The results are summarized in Table 6. As can be derived from Table 6, no differences in reactivity were noted between HCV E1 expressed in HCV-recombinant vaccinia virus-infected mammalian cells and HCV E1 expressed in *H. polymorpha*.

TABLE 6

Antigenicity of E1 produced in a mammalian cell culture or produced in *H. polymorpha* were evaluated on a panel of sera from human HCV chronic carriers. For this purpose biotinylated E1 was bound to streptavidin coated ELISA plates. Thereafter human sera were added at a 1/20 dilution and bound immunoglobulins from the sera bound to E1 were detected with a rabbit-anti-human IgG-Fc specific secondary antibody labeled with peroxidase. Results are expressed as OD-values. The average values are the averages of the OD-values of all serum samples tested.

| Serum | *Hansenula* | mammalian |
|---|---|---|
| 17766 | 1.218 | 1.159 |
| 17767 | 1.513 | 1.363 |
| 17777 | 0.806 | 0.626 |
| 17784 | 1.592 | 1.527 |
| 17785 | 1.508 | 1.439 |
| 17794 | 1.724 | 1.597 |
| 17798 | 1.132 | 0.989 |
| 17801 | 1.636 | 1.504 |
| 17805 | 1.053 | 0.944 |
| 17810 | 1.134 | 0.999 |

TABLE 6-continued

Antigenicity of E1 produced in a mammalian cell culture or
produced in *H. polymorpha* were evaluated on a panel
of sera from human HCV chronic carriers. For this purpose
biotinylated E1 was bound to streptavidin coated ELISA plates.
Thereafter human sera were added at a 1/20 dilution and bound
immunoglobulins from the sera bound to E1 were detected with
a rabbit-anti-human IgG-Fc specific secondary antibody labeled
with peroxidase. Results are expressed as OD-values. The
average values are the averages of the OD-values of all
serum samples tested.

| Serum | *Hansenula* | mammalian |
|---|---|---|
| 17819 | 1.404 | 1.24 |
| 17820 | 1.308 | 1.4 |
| 17826 | 1.163 | 1.009 |
| 17827 | 1.668 | 1.652 |
| 17849 | 1.595 | 1.317 |
| 55333 | 1.217 | 1.168 |
| 55337 | 1.591 | 1.416 |
| 55348 | 1.392 | 1.261 |
| 55340 | 1.202 | 0.959 |
| 55342 | 1.599 | 1.477 |
| 55345 | 1.266 | 1.428 |
| 55349 | 1.329 | 1.137 |
| 55350 | 1.486 | 1.422 |
| 55352 | 0.722 | 1.329 |
| 55353 | 1.065 | 1.157 |
| 55354 | 1.118 | 1.092 |
| 55355 | 0.754 | 0.677 |
| 55362 | 1.43 | 1.349 |
| 55365 | 1.612 | 1.608 |
| 55368 | 0.972 | 0.959 |
| 55369 | 1.506 | 1.377 |
| average | 1.313 | 1.245 |

Example 22

Immunogenic Equivalence of *Hansenula*-Produced
HDV E1-H6 and HCV E1 Produced by
Vaccinia-Infected Mammalian Cells The immunogenecity of *Hansenula*-produced HCV E1-H6 was compared to the immunogenecity of HCV E1 produced by HCV-recombinant vaccinia virus-infected mammalian cells as described by Depla et al. in WO99/67285. Both HCV-E1 preparations tested consisted of VLP's wherein the HCV E1 proteins were alkylated with iodoacetamide. Both VLP preparations were formulated with alum and injected in Balb/c mice (3 intramuscular/subcutaneous injections with a three week interval between each and each consisting of 5 µg E1 in 125 µl containing 0.13% Alhydrogel, Superfos, Denmark). Mice were bled ten days after the third immunization.

Results of this experiment are shown in FIG. 51. For the top part of FIG. 51, antibodies raised following immunization with VLPs of E1 produced in mammalian cells were determined. Antibody titers were determined by ELISA (see Example 21) wherein either E1 produced in mammalian cells ("M") or *Hansenula*-produced E1 ("H") were coated directly on the ELISA solid support whereafter the ELISA plates were blocked with casein. For the bottom part of FIG. 51, antibodies raised following immunization with VLPs of *Hansenula*-produced E1 were determined. Antibody titers were determined by ELISA (see Example 21) wherein either E1 produced in mammalian cells ("M") or *Hansenula*-produced E1 ("H") were coated directly on the ELISA solid support whereafter the ELISA plates were blocked with casein.

The antibody titers determined were end point titers. The end point titer is determined as the dilution of serum resulting in an OD (as determined by ELISA) equal to two times the mean of the background of the assay.

FIG. 51 shows that no significant differences were observed between the immunogenic properties of both E1-compositions and that the determined antibody titers are independent of the antigen used in the ELISA to perform the end point titration.

The yeast-derived HCV E1 induced upon vaccination a protective response similar to the protective response obtained upon vaccination with alkylated HCV E1 derived from mammalian cell culture. The latter response was able to prevent chronic evolution of HCV after an acute infection.

Example 23

Antigenic and Immunogenic Profile of
*Hansenula*-Produced HCV E1-H16 which is
Sulphonated The reactivity of *Hansenula*-produced HCV E1-H6 with sera from HCV chronic carriers was compared to the reactivity of HCV E1 produced by HCV-recombinant vaccinia virus-infected mammalian cells as described by Depla et al. in WO99/67285. Both HCV-E1 preparations tested consisted of VLP's wherein the *Hansenula*-produced HCV E1 proteins were sulphonated and the HCV E1 produced by mammalian cells was alkylated. The results are given in Table 7. Although the overall (average) reactivity was identical, some major differences were noted for individual sera. This implies that the sulphonated material presents at least some of its epitopes in a way different from alkylated HCV E1.

The immunogenecity of *Hansenula*-produced HCV E1-H6 which was sulphonated was compared to the immunogenecity of *Hansenula*-produced HCV E1-H6 which was alkylated. Both HCV-E1 preparations tested consisted of VLP's. Both VLP preparations were formulated with alum and injected in Balb/c mice (3 intramuscular/subcutaneous injections with a three week interval between each and each consisting of 5 µg E1 in 125 µl containing 0.13% Alhydrogel, Superfos, Denmark). Mice were bled ten days after the third immunization.

Antibody titers were determined similarly as described in Example 22. Surprisingly, immunization with sulphonated material resulted in higher antibody titers, regardless of the antigen used in ELISA to assess these titers (FIG. 51; top panel: titration of antibodies raised against alkylated E1; bottom panel: titration of antibodies raised against sulphonated E1; "A": alkylated E1 coated on ELISA plate; "S": sulphonated E1 coated on ELISA plate). However, in this experiment individual titers are different dependent on the antigen used for analysis which confirms the observation noted with sera from HCV patients. Consequently, HCV E1 wherein the cysteine thiol-groups are modified in a reversible way may be more immunogenic and thus have an increased potency as a vaccine protecting against HCV (chronic infection). In addition thereto, induction of a response to neo-epitopes induced by irreversible blocking is less likely to occur.

TABLE 7

Antigenicity of alkylated E1 (produced in mammalian cell
culture) or sulphonated E1-H6 (produced in *H. polymorpha*)
was evaluated on a panel of sera from human HCV chronic
carriers ("patient sera") and a panel of control sera
("blood donor sera"). To this purpose E1 was bound to
ELISA plates, after which the plates were further saturated
with casein. Human sera were added at a 1/20 dilution and bound
immunoglobulins were detected with a rabbit-anti-human IgG-Fc
specific secondary antibody labeled with peroxidase. Results
are expressed as OD-values. The average values are the averages
of the OD-values of all serum samples tested.

| patient sera | | | blood donor sera | | |
| --- | --- | --- | --- | --- | --- |
| sernr | Hansenula | Mammalian | sernr | Hansenula | mammalian |
| 17766 | 0.646 | 0.333 | F500 | 0.055 | 0.054 |
| 17777 | 0.46 | 0.447 | F504 | 0.05 | 0.05 |
| 17785 | 0.74 | 0.417 | F508 | 0.05 | 0.054 |
| 17794 | 1.446 | 1.487 | F510 | 0.05 | 0.058 |
| 17801 | 0.71 | 0.902 | F511 | 0.05 | 0.051 |
| 17819 | 0.312 | 0.539 | F512 | 0.051 | 0.057 |
| 17827 | 1.596 | 1.576 | F513 | 0.051 | 0.052 |
| 17849 | 0.586 | 0.964 | F527 | 0.057 | 0.054 |
| 55333 | 0.69 | 0.534 | average | 0.052 | 0.054 |
| 55338 | 0.461 | 0.233 | | | |
| 55340 | 0.106 | 0.084 | | | |
| 55345 | 1.474 | 1.258 | | | |
| 55352 | 1.008 | 0.668 | | | |
| 55355 | 0.453 | 0.444 | | | |
| 55362 | 0.362 | 0.717 | | | |
| 55369 | 0.24 | 0.452 | | | |
| average | 0.706 | 0.691 | | | |

Example 24

Identical Antigenic Reactivity of
*Hansenula*-Produced HCV E1-H6 and HCV E1
Produced by Vaccinia-Infected Mammalian Cells
with Sera from Vaccinated Chimpanzees The reactivities of the E1 produced by HCV-recombinant vaccinia virus-infected mammalian cells and the E1-H6 produced by *Hansenula* (both alkylated) with sera from vaccinated chimpanzees and with monoclonal antibodies were compared. Thereto, said E1 proteins were coated directly to ELISA plates followed by saturation of the plates with casein. The end point titers of antibodies binding the E1 proteins coated to the ELISA plates was determined for chimpanzee sera and for specific murine monoclonal antibodies, all obtained from animals immunized with E1 produced by mammalian cells. End point titer determination was done as described in Example 22. The murine monoclonal antibodies used were IGH201 (see Example 15), IGH198 (IGH198=23C12 in Maertens et al. in WO96/04385), IGH203 (IGH203=15G6 in Maertens et al. in WO96/04385) and IGH202 (IGH202=3F3 in Maertens et al. in WO99/50301).

As can be derived from FIG. 53, the reactivities of 7 different chimpanzee are identical when tested with E1 protein produced by either *Hansenula* or mammalian cells. The reactivities of the monoclonal antibodies against HCV E1 are also almost equal. Two of the chimpanzees (Yoran and Marti) were involved in a prophylactic vaccine study and were able to clear an acute infection upon challenge while a control animal did not clear the infection. The five other chimpanzees (Ton, Phil, Marcel, Peggy, Femma) were involved in therapeutic vaccination studies and showed a reduction in liver damage, as measured by ALT in serum and/or histological activity index on liver biopsy, upon the HCV E1 immunizations.

The results obtained in this experiment are clearly different from the findings of Mustilli and coworkers (Mustilli, A. C. et al. 1999) who expressed the HCV E2 protein both in *Saccharomyces cerevisiae* and *Kluyveromyces lactis*. The purified yeast-produced E2 was, however, different from the HCV E2 produced by mammalian (CHO) cells in that a lower reactivity was observed with sera from chimpanzees immunized with HCV E2 produced by mammalian cells while reactivity with monoclonal antibodies was higher for the yeast-produced HCV E2.

Example 26

Glycoprofiling of HCV E1 by Fluorophore-Assisted Carbohydrate Electrophoresis (FACE)

The glycosylation profiles were compared of *Hansenula*-produced HCV E1 a and HCV E1 produced by HCV-recombinant vaccinia virus-infected mammalian cells as described by Depla et al. in WO99/67285. This was done by means of fluorophore-assisted carbohydrate electrophoresis (FACE). Thereto, oligosaccharides were released from E1s produced by mammalian cells or *Hansenula* by peptide-N-glycosidase (PNGase F) and labelled with ANTS (the E1 proteins were alkylated with iodoacetamide prior to PNGase F digestion). ANTS-labeled oligosaccharides were separated by PAGE on a 21% polyacrylamide gel at a current of 15 a mA at 4° C. for 2-3 h. From FIG. 54, it was concluded that the oligosaccharides on E1 produced by mammalian cells and E1-H6 produced by *Hansenula* migrate like oligomaltose with a degree of polymerization between 7 and 11 monosaccharides. This indicates that the *Hansenula* expression system surprisingly leads to an E1 protein which is not hyperglycosylated and which has sugar chains with a length similar to the sugar chains added to E1 proteins produced in mammalian cells.

Example 26

Sequencing of N-Linked Oligosaccharade Derived from *Saccharomyces*- and *Hansenula*-Produced E1s and from E1s Produced by HCV-Recombinant Vaccinia Virus-Infected Mammalian Cells E1s (225 μg) purified from a *Saccharomyces* or *Hansenula* culture (see Examples 15-16) or from a culture of RK13 cells infected with a HCV-recombinant vaccinia virus (see Maertens et al. in WO96/04385) and present in PBS, 0.5% betaine was diluted with deglycosilation incubation buffer (50 mM $Na_2HPO_4$, 0.75% Nonidet P-40) to a final concentration of 140 μg/mL. The pH of the solution was adjusted to pH 5.5 with concentrated $H_3PO_4$. To this solution was added 2 U PNGase F (Peptide-$N^4$-(acetyl-beta-glucosaminyl)-asparagine amidase of *Flaobacterium meningosepticum*; EC 3.5.1.52; obtained from Roche) and the sample was incubated overnight at 37° C. After overnight incubation, the pH of the solution was adjusted to pH 5.5 with concentrated $H_3PO_4$. Proteins and oligosaccharides were subsequently precipitated by adding 4 volumes of acetone (at −20° C.), and the mixtures were incubated at −20° C. for 15 min. Samples were centrifuged at 4° C. at 13000 rpm during 5 min. The acetone supernatant was discarded and the pellet was incubated at −20° C. for 1 hour after adding 150 μL ice-cold 60% methanol. The methanol supernatant containing the released oligosaccharides was collected and dried by rotary evaporation (SpeedVac).

The dried E1s glycans as well as reference oligosaccharides (all from Glyko, Bicester, UK; see FIG. 55) Man-9 (11 monosaccharide units), Man-8 (10 monosaccharide units), Man-7 (9 monosaccharide units), Man-6 (8 monosaccharide units) and Man-5 (7 monosaccharide units) were dissolved in 5 μL 2-aminobenzamide (2-AB) labeling reagent (±0.35 M 2-AB+±1 M NaCNBH$_3$ in 30% HOAc/70% DMSO) to obtain a final glycan concentration between 5 and 100 μM. The glycan solution was then incubated for 2 hours at 65° C. After 30 minutes, the sample was mixed by vortexing. After conjugation, the excess of 2-AB was removed as follows. The sample was diluted with 16-μL purified water (MilliQ) and applied to a Sephadex G-10 column (diameter of 1 cm, height of 1.2 cm, Amersham Biosciences; coupled to a VacElut system, Varian) after the column was pulled dry.

The labeled oligosaccharides were eluted by applying 2×100-μL purified water (MilliQ) to the column. The eluates of the reference carbohydrates (Man-9, Man-8, Man-7 and Man-6) were dried and stored at −70° C. until HPLC analysis. The eluates of the E1s samples as well as the Man-9 reference glycan were distributed over 4 numbered PCR tubes and dried. The reactions as outlined in Table 8 were performed, all reactions were allowed to proceed overnight at 37° C., except for the reaction in tube 3 which was terminated after 1 h. The final concentration of the exoglycosidase enzymes (all obtained from Glyko, Bicester, UK) used were: for α 1-2 Mannosidase (*Aspergillus saitoi*): 2 mU/mL; for α-Mannosidase (Jack Bean): 50 U/mL; and for β-Mannosidase (Helixpomatia): 4 U/mL.

TABLE 8

Overview of reaction mixes for sequencing of oligosaccharides.

| | Tube 1 | Tube 2 | Tube 3 | Tube 4 | Tube 5 |
|---|---|---|---|---|---|
| Els (pmol) | 400 | 400 | 400 | 400 | 400 |
| α 1-2 Mannosidase (μL) | — | 4 | — | — | — |
| α Mannosidase (μL) | — | — | 5 | 5 | 5 |
| β Mannosidase (μL) | — | — | — | — | 4 |
| Incubation buffer 4x (μL) | 5 | 5 | 5 | 5 | 5 |
| MilliQ H$_2$O (μL) | 15 | 11 | 10 | 10 | 6 |

FIG. 56 shows a higher oligomannose consisting of 10 mannose moieties coupled to chitobiose. Each terminal mannose residue is linked by an α 1-3 bond to a non-terminal mannose residue. The oligomannose of FIG. 56 is fully resistant to cleavage by the exoglycosidase α 1-2 Mannosidase. Long-term (overnight) incubation of the oligomannose of FIG. 56 with the exoglycosidase α-Mannosidase will result in cleavage of all α-linkages (α 1-2, α 1-3, α 1-6), but not of the β-linkages. The resulting oligosaccharide will thus be 4'-β-mannosyl chitobiose. This 4'-β-mannosyl chitobiose moiety can be converted to mannose and chitobiose through the action of the exoglycosidase β-Mannosidase. According to the specifications of the supplier (Glyko), α-Mannosidase converts the reference oligosaccharide Man-6 (see FIG. 55.D) to 4'-β-mannosyl chitobiose completely and the further conversion thereof to mannose and chitobiose by β-Mannosidase is also reported to be complete.

FIG. 57 shows a higher oligomannose consisting of 9 mannose moieties coupled to chitobiose. In this oligomannose, one terminal mannose residue is linked by an α 1-2 bond to the non-terminal mannose residue. Upon action of the exoglycosidase α 1-2 Mannosidase, said α 1-2-linked mannose will be removed. Upon subsequent action of α-Mannosidase and β-Mannosidase, the reaction products as described for the oligomannose of FIG. 56 will be obtained. According to the specifications of the supplier (Glyko), α 1-2 Mannosidase is capable of converting the reference oligosaccharides Man-9 and Man-6 to Man-5 (see FIG. 55) with an efficiency of >90%.

FIG. 58 shows the reference higher oligomannose Man-9 consisting of 9 mannose moieties coupled to chitobiose. In this oligomannose, all terminal mannose residue is linked by an α 1-2 bond to a non-terminal mannose residue. Upon action of the exoglycosidase α 1-2 Mannosidase, Man-9 will thus be converted to Man-5, according to the specification of the supplier by >90%. Subsequent digestion with α-Mannosidase will convert Man-5 to 4'-β-mannosyl chitobiose.

The contents of the different reaction tubes as indicated in Table 8 were dried in a centrifugal vacuum evaporator or in a lyophilizer and stored at −70° C. until HPLC analysis. Before applying to the column, each sample (E1s and reference) was dissolved in 25 μL water and loaded on a TSK gel-Amide-80 (0.46×25 cm, Tosoh Biosep) column coupled to a Waters Alliance BPLC station.

Separation of the oligosaccharides was carried out at ambient temperature at 1.0 mL/min. Solvent A consisted of 0.1% acetic acid in acetonitrile and solvent B consisted of 0.2% acetic acid-0.2% triethylamine in water. Separation of 2-AB labeled oligosaccharides was carried out using 28% B isocratic for 5 column volumes followed by a linear increase to 45% B over fifteen column volumes.

The reference oligosaccharide Man-6 is eluting at 53±1 min, Man-7 is eluting at 59±1 min, Man-8 at 67±2 min, and Man-9 at 70±1 min; 4'-β-mannosyl chitobiose is eluting at 10±1 min and chitobiose at 6±1 min (not shown). This is exemplified for the reaction products of Man-9 after overnight incubation without exoglycosidases (trace 1 of the chromatogram in FIG. 63; Man-9 only), after overnight incubation with α 1-2 Mannosidase (trace 2 of the chromatogram in FIG. 63; mixture of Man-5 and Man-6), after 1 hr or overnight incubation with α-Mannosidase (traces 3 and 4, respectively, of the chromatogram in FIG. 63; 4'-β-mannosyl chitobiose only), and after overnight incubation with α- and β-Mannosidase (trace 5 of the chromatogram in FIG. 63; chitobiose only). Trace 6 of the chromatogram in FIG. 63 is indicating the applied solvent gradient.

The products of the reaction of the oligosaccharides of *Saccharomyces*-produced E1s (obtained after PNGaseF treatment) without exoglycosidases were mainly four carbohydrates present eluting at 59±1 min (15%), 67±1 min (45%), 70±1 min (25%) and 75±1 min (15%). The overall content of Man(8)-GlcNAc(2) and Man(9)GlcNAc(2) in *Saccharomyces*-produced E1s was 65%. In the reaction with α 1-2 Mannosidase, only the carbohydrates with retention time 70±1 min has disappeared. The intensity of the carbohydrate with retention time 75±1 min remained the same and the intensity of carbohydrate with retention time 67±1 min was increased. This means that not all terminal mannose units have the α(1-2) configuration. After overnight incubation with α Mannosidase all carbohydrate chains were reduced to the 4'-β-mannosyl chitobiose moiety. This means that the carbohydrate is high mannose and all mannose residues except one have the α configuration. Reduction of this 4'-β-mannosyl chitobiose moiety to chitobiose was apparent after overnight incubation with β-mannosidase. The resulting chromatograms are depicted in FIG. 64 which were obtained under the same conditions as described for the chromatograms of FIG. 63. The results are summarized in Table 9.

The same experiments were repeated with E1s produced by vaccinia-infected cells and surprisingly showed a completely different picture. In the reaction without enzymes, a complex mixture of carbohydrates was present (see FIG. 65 and Table 9). The overall content of monosaccharide(8)-GlcNAc(2) and monosaccharide(9)-GlcNAc(2) was 37%. After reaction with α 1-2 Mannosidase, the carbohydrates with retention times 70±1 and 59±1 min have disappeared. After overnight incubation with with α Mannosidase, a substantial amount of monosaccharide(6)-GlcNAc(2) remained in addition to the 4'-β-mannosyl chitobiose product. This is an indication that one of the oligosaccharide branches is resistant to α Mannosidase degradation. This can be explained by the presence of 1 or 2 glucose-residues linked to a Manα(1-2)-terminated branch of the N-linked oligosaccharide. A putative structure of such a glucose-containing oligosaccharide is depicted in FIG. 62. The possible reaction products of glucose-containing oligosaccharides is given in Table 10). As no Man-7-equivalent oligosaccharide (i.e. oligosaccharide consisting of 9 monosaccharides) is remaining after the α 1-2 Mannosidase reaction, these glucose residues are most likely linked to the B-branch of the oligosaccharide structure given in FIG. 62. It can, however, not be excluded that both the A- and B-branches of the oligosaccharide in FIG. 62 are partially terminated by glucose.

Reduction of the 4-β-mannosyl chitobiose moiety to chitobiose was apparent after overnight incubation with β Mannosidase. The resulting chromatograms are depicted in FIG. 65 which were obtained under the same conditions as described for the chromatograms of FIGS. 63-64.

The obtained results are summarized in Table 9.

The same experiments were repeated *Hansenula*-produced E1s and surprisingly showed a completely different picture. In the reaction without enzymes, mainly two carbohydrates with retention time 67±2 min and 70±1 min were present corresponding to respectively Man-8 and Man-9. The overall content of Man(8)-GlcNAc(2) and Man(9) GlcNAc(2) in *Hansenula*-produced E1s was ~90%. After reaction with α 1-2 Mannosidase, carbohydrates were reduced to mainly Man-5 with retention time 45±1 min and a Man-6 with retention time 53±1 min. After overnight incubation with with α Mannosidase all carbohydrate chains were reduced to the 4'-β-mannosyl chitobiose moiety. This means that the carbohydrate is high mannose and all mannose residues except one have the a configuration. Reduction of this 4'-β-mannosyl chitobiose moiety to chitobiose was apparent after overnight incubation with β Mannosidase. The resulting chromatograms are depicted in FIG. 66 which were obtained under the same conditions as described for the chromatograms of FIGS. 63-65.

The obtained results are summarized in Table 9.

Table 9. Oligomannoses resulting from digestion of oligomannoses derived from *Saccharomyces* ("Sc")-, and *Hansenula* ("Hp")-produced E1s as well as from E1s produced by HCV-recombinant vaccinia-infected mammalian cells ("Vac"). Indicated are the different oligomannoses with their chromatographic retention times ("Rt", in minutes) and the percentage of a given oligomannose relative to the total oligomannose content (top rows) as well as the most likely structure for each observed oligomannose indicated with reference to any of FIGS. 55-62. Oligomannoses with terminal α 1-3 mannoses have been marked with a "°". Oligomannoses with terminal glucoses have been marked with a "*", for some reference is made to "from 62*", meaning that the structure can be derived from the structure given in FIG. 62. "1" is the 'reaction' without exoglycosidases, "2" is the reaction with α 1-2 Mannosidase. The oligomannose with retention time 45±1 min is supposedly an oligomannose comprising 5 mannose residues linked to chitobiose. The oligomannose with retention time 75±1 min is supposedly an oligomannose comprising 10 mannose residues linked to chitobiose.

|  | (Man-5) Rt: 45 ± 1 | Man-6 Rt: 53 ± 1 | Man-7 Rt: 59 ± 1 | Man-8 Rt: 67 ± 1 | Man-9 Rt: 70 ± 1 | (Man-10) Rt: 75 ± 1 |
|---|---|---|---|---|---|---|
| Sc 1 structure | / | 1% 55.D | 14% 55.C | 42% 59° | 23% 57° 61° | 18% 56° |
| Sc 2 structure | 17% 55.E | / | 8% 60° | 50% 59° | 6% 57° 61° | 16% 56° |
| Vac 1 structure | 3% 55.E | 32% from 62* & Table 10 | 20% 55.C | 23% from 62* & Table 10 | 14% 62* & Table 10 | 5% 62* & Table 10 |
| Vac 1 structure | 74% 55.E | 2% from 62* & Table 10 | / | 20% from 62* & Table 10 | 4% 62* & Table 10 | / |
| Hp 1 structure | / | 2% 55.D | 7% 55.C | 54% 55.B | 36% 58 | / |
| Hp 2 structure | 80% 55.E | 20% 55.D | / | / | / | / |

TABLE 10

Products of glucose-containing N-linked oligosaccharides after reaction with α 1–2 Mannosidase or α 1–2 Mannosidase and α Mannosidase.

|  | Man-equivalent | α 1–2 Mannosidase product (1) | α Mannosidase product (after (1)) |
|---|---|---|---|
| Branch A + 2 Glc | Man-10 | Man-8 | Man-6 |
| Branch A + 1 Glc | Man-9 | Man-7 | Man-6 |
| Branch A no Glc | Man-8 | Man-5 | 4'-β-mannosyl chitobiose |
| Branch B + 2 Glc | Man-10 | Man-9 | Man-6 |
| Branch B + 1 Glc | Man-9 | Man-8 | Man-6 |
| Branch B no Glc | Man-8 | Man-5 | 4'-β-mannosyl chitobiose |

Example 27

Occupation of N-Glycosylation Sites in Recombinant HCV E1

Dependent on the amount of occupied N-glycosylation sites, E1s shows a different migration behavior on SDS-PAGE analysis. Based on this property, the average amount of occupied N-glycosylation sites in the E1 product could be estimated. Hereto, samples of the purified E1-product were subjected to SDS-PAGE and Coomassie Brilliant Blue staining (FIG. 67) and further analyzed by means of the ImageMaster 1D Prime Software packet (Pharmacia). In brief, the gel was scanned and for each specific protein band and the % of occurrence (its intensity in relation to the total intensity of the different bands whereby the total of all bands is 100%) was estimated (Table 11). It should be noted that each specific protein band is representing E1s-molecules with the same number of occupied N-glycosylation sites.

The obtained results indicated that the main part (>90%) of the *Hansenula*-produced E1-product has 1 or more N-glycosylation sites less occupied than the E1s obtained from the vaccinia expression system (as described by Maertens et al. in WO96/04385). Assuming that in the vaccinia derived E1 product all the N-glycosylation sites are occupied (in which the sequence "NNSS" (SEQ ID NO:73) on position 233-236 of E1 is considered as one glycosylation site), it is quite safe to conclude that the average number of occupied N-glycosylation sites in the *Hansenula*-expressed E1 protein does not exceed 80% of the total available N-glycosylation sites.

TABLE 11

Estimation of the average number of occupied N-glycosylation sites in the E1 proteins obtained from the *Hansenula polymorpha* and vaccinia/vero expression systems by means of SDS-PAGE and Coomassie Brilliant Blue staining intensity analysis. The protein bands are indicated by their molecular weight. See FIG. 67.

| Alkylated E1s | % occurrence (relative intensity) | |
|---|---|---|
| | Experiment 1 | Experiment 2 |
| *Hansenula polymorpha* | | |
| MW 29 | 9 | 8 |
| MW 25 | 25 | 27 |
| MW 21 | 38 | 42 |
| MW 18 | 27 | 22 |
| MW 14–15 | not quantified | not quantified |
| Vaccinia/Vero | | |
| MW 29 | 100 | 100 |

Example 28

Occupation of N-Glycosylation Sites in Recombinant HCV E2

Two-hundred (200) µg of the E2-H6 protein produced by *Hansenula* was deglycosylated with PNGaseF. The deglycosylated E2s-H6 was loaded on a mini-gel (10 µg/lane). The protein bands were digested with trypsine and endo Asp-N. The masses of the resulting peptides were determined by Maldi-MS (dried droplet and thin layer method). This method can be used to determine the degree of N-glycosylation: during the deglycosylation with the enzyme PNG-ase F the complete sugar chain is cleaved off, and at the same time the asparagine (N) is hydrolyzed to aspartic acid (D). The mass difference between these two amino acids is 1 Da which can be determined by mass spectrometry. Additionally, the hydrolysis of N to D creates new cleavage sites for the Asp-N enzyme.

Possible glycosylation sites in E2s are $N_{417}$, $N_{423}$, $N_{430}$, $N_{448}$, $N_{478}$, $N_{532}$, $N_{540}$, $N_{556}$, $N_{576}$, $N_{623}$ and $N_{645}$ (see FIG. 68). Maldi-MS analysis showed for each of these glycosylation sites that N-glycosylation was not complete, because after deglycosylation with PNGase F, peptides were found with either N or D at the glycosylation site (mass difference 1 Da). The ratio of the number of D-residues over the number of N-residues gives an indication of the average occupation, over all E2 proteins expressed by *Hansenula* and present in the analyzed sample, of a single N-glycosylation site by a sugar chain. These results are summarized in Tables 12 to 14.

From these results it was calculated that on average each glycosylation site was glycosylated for approximately 54%.

TABLE 12

Percent glycosylation determined from tryptic peptides containing one N-glycosylation site.

| N-glycosylation site | Glycosylated | Not glycosylated |
|---|---|---|
| N430 | 60% | 40% |
| N448 | 50% | 50% |
| N556 | 80% | 20% |
| N576 | 90% | 10% |
| N623 | 20% | 80% |
| N645 | 10% | 90% |

TABLE 13

Percent glycosylation determined from tryptic peptides containing two N-glycosylation sites.

| N-glycosylation sites | Both sites glycosylated | 1 out of 2 sites glycosylated | No site glycosylated | Calculated for individual N |
|---|---|---|---|---|
| N417 and N423 | 70% | 25% | 5% | 85% |
| N532 and N540 | 0% | 80% | 20% | 40% |

TABLE 14

Percent glycosylation determined for N478 in Asp-N digest.

| N-glycosylation site | Glycosylated | Not glycosylated |
|---|---|---|
| N478 | 35% | 65% |

Example 29

Reactivity of Blood Donor Sera with HCV E1 Produced by *Saccharomyces* or *Hansenula*

E1s-H6 produced by *Saccharomyces* (expressed with the α-MF leader) and E1s-H6 produced by *Hansenula* (expressed with the CL leader) were both purified as described in Examples 15 and 16 and were finally subjected to alkylation and VLP formation as described in Example 20. Both proteins were directly adsorbed on a microtiterplate at 0.5 µg/ml (1 h, 37° C.) and after blocking of the plate (PBS-0.1% casein, 1 h, 37° C.) sera from HCV-screened and negative blood donors were incubated at a dilution of 1/20 (PBS-0.5% casein, 10% (w/v) sucrose, 0.2% (v/v) Triton X-705, 1 h, 37° C.). Finally binding was detected using a secondary rabbit anti-human IgG-$F_c$ specific antiserum coupled to peroxidase (Dako, Denmark) at a dilution of 1/50000 (PBS-0.1% casein, 1 h, RT) followed by color development. Between all steps plates were washed 3 times with PBS-0.05% (w/v) Tween-20. For comparison the sera were also analyzed in an identical way on mammalian cell derived E1s, produced and purified as described by Depla et al. in WO99/67285.

The cut-off for this ELISA was set at 2 times the mean of the background (i.e. the reactivity of all sera in an identical set-up but with streptavidin adsorbed to the wells).

From Table 15 it can be judged that many (75%) sera show reactivity above the cut-off towards the *Saccharomyces*-produced E1 while only a few sera (6%) show some reactivity above cut-off with the *Hansenula*-produced E1. This difference in reactivity was attributed to the presence of terminal at α 1-3 mannoses linked to α 1-2 mannoses on the *Saccharomyces*-produced E1 as evidenced in Example 26. Young and coworkers (1998) already previously indicated that this type of mannoses is also responsible for reactivity of human sera with *Saccharomyces* derived mannan. In order to further confirm that the reactivity on *Saccharomyces*-derived E1 can be attributed to this type of mannose residues, the ELISA on *Saccharomyces*-produced E1 was repeated with dilutions of blood donor sera preincubated (1 h at 37° C.) with 1 or 5 mg/mL mannan (Sigma) added to the dilution buffer. As can be judged from Table 16, preincubation with mannan reduced the reactivity of this E1 with blood donor sera in a concentration dependent way to background levels for all but one (F556) sera analyzed. (mean OD is reduced from 0.24 without competition by mannan to 0.06, using 5 mg mannan/mL).

TABLE 15

Reactivity of E1 produced in *Hansenula*, *Saccharomyces* and mammalian cells. The reactivities above the cut-off value are indicated in black shaded cells.

| serum nr | Hansenula E1 | Saccharomyces E1 | Mammalian E1 | blank |
|---|---|---|---|---|
| F552 | [shaded] | [shaded] | 0.056 | 0.05 |
| F553 | 0.062 | [shaded] | 0.056 | 0.052 |
| F555 | 0.06 | 0.079 | 0.054 | 0.051 |
| F556 | 0.073 | [shaded] | 0.054 | 0.051 |
| F557 | 0.059 | [shaded] | 0.053 | 0.05 |
| F558 | 0.066 | [shaded] | 0.06 | 0.058 |
| F559 | 0.084 | [shaded] | 0.056 | 0.053 |
| F560 | 0.062 | [shaded] | 0.052 | 0.052 |
| F562 | 0.056 | [shaded] | 0.053 | 0.053 |
| F563 | 0.064 | [shaded] | 0.059 | 0.056 |
| F570 | 0.056 | [shaded] | 0.054 | 0.055 |
| F571 | 0.06 | [shaded] | 0.054 | 0.055 |
| F572 | 0.061 | [shaded] | 0.055 | 0.056 |
| F575 | 0.079 | 0.104 | 0.062 | 0.056 |
| F576 | 0.061 | [shaded] | 0.058 | 0.057 |
| F577 | 0.063 | [shaded] | 0.055 | 0.058 |
| F578 | 0.089 | [shaded] | 0.057 | 0.061 |
| F581 | 0.064 | 0.098 | 0.061 | 0.057 |
| F594 | 0.055 | [shaded] | 0.056 | 0.057 |
| F595 | 0.059 | [shaded] | 0.057 | 0.058 |
| F598 | 0.076 | [shaded] | 0.056 | 0.059 |
| F450 | [shaded] | 0.078 | 0.099 | 0.059 |
| F453 | 0.059 | [shaded] | 0.057 | 0.06 |
| F456 | 0.058 | [shaded] | 0.056 | 0.06 |
| F458 | 0.055 | 0.088 | 0.054 | 0.054 |
| F459 | 0.054 | 0.069 | 0.056 | 0.054 |
| F463 | 0.055 | 0.083 | 0.054 | 0.056 |
| F466 | 0.086 | [shaded] | 0.071 | 0.094 |
| F467 | 0.066 | [shaded] | 0.055 | 0.055 |
| F469 | 0.059 | 0.074 | 0.057 | 0.057 |
| F470 | 0.074 | | 0.056 | 0.056 |
| F473 | 0.094 | | 0.054 | 0.057 |
| F479 | 0.06 | 0.075 | 0.06 | 0.051 |
| F480 | 0.053 | | 0.056 | 0.053 |
| F481 | 0.059 | | 0.071 | 0.052 |
| F488 | 0.063 | | 0.059 | 0.053 |
| average | 0.072 | 0.242 | 0.058 | |
| # of sera above cut-off | 2/36 | 27/36 | 0/36 | |
| % of sera above cut-off | 6 | 75 | | |

| | | | | |
|---|---|---|---|---|
| | | 0.222 | | |
| | | 0.807 | | |
| | | | | |
| | | 0.305 | | |
| | | 0.395 | | |
| | | 0.467 | | |
| | | | | cut-off 0.113 |

TABLE 16

Reactivity of E1 produced in Saccharomyces cells as in Table 15 but in the presence of 5 mg mannan/mL. The reactivities above the cut-off value are indicated in black shaded cells.

| | Mannan concentration | | |
|---|---|---|---|
| Serum nr | 0 mg/mL | 1 mg/mL | 5 mg/mL |
| F552 | 0.207 | 0.128 | 0.103 |
| F553 | 0.487 | 0.098 | 0.050 |
| F555 | 0.066 | 0.044 | 0.041 |
| F556 | 0.769 | 0.540 | 0.372 |
| F557 | 0.158 | 0.094 | 0.088 |
| F558 | 0.250 | 0.076 | 0.046 |
| F559 | 0.300 | 0.077 | 0.066 |
| F560 | 0.356 | 0.088 | 0.044 |
| F562 | 0.122 | 0.106 | 0.089 |
| F563 | 0.164 | 0.091 | 0.049 |
| F570 | 0.110 | 0.043 | 0.040 |
| F571 | 0.212 | 0.057 | 0.042 |
| F572 | 0.464 | 0.087 | 0.043 |
| F575 | 0.095 | 0.081 | 0.062 |
| F576 | 0.138 | 0.042 | 0.043 |
| F577 | 0.216 | 0.042 | 0.041 |
| F578 | 0.125 | 0.100 | 0.093 |
| F581 | 0.083 | 0.064 | 0.042 |
| F594 | 0.102 | 0.044 | 0.041 |
| F595 | 0.520 | 0.088 | 0.044 |
| F598 | 0.340 | 0.054 | 0.042 |
| F450 | 0.053 | 0.060 | 0.053 |
| F453 | 0.116 | 0.049 | 0.044 |
| F456 | 0.112 | 0.050 | 0.043 |
| F458 | 0.086 | 0.051 | 0.042 |
| F459 | 0.054 | 0.044 | 0.042 |
| F463 | 0.078 | 0.043 | 0.041 |
| F466 | 0.172 | 0.111 | 0.085 |
| F467 | 0.420 | 0.117 | 0.049 |
| F469 | 0.053 | 0.043 | 0.041 |
| F470 | 0.220 | 0.070 | 0.061 |
| F473 | 0.924 | 0.183 | 0.063 |
| F479 | 0.059 | 0.049 | 0.043 |
| F480 | 0.281 | 0.155 | 0.054 |
| F481 | 0.355 | 0.042 | 0.046 |
| F488 | 0.474 | 0.090 | 0.046 |
| average | 0.243 | 0.089 | 0.062 |

REFERENCE LIST

Agaphonov, M. O., Beburov, M. Y., Ter Avanesyan, M. D., and Smirnov, V. N. (1995) A disruption-replacement approach for the targeted integration of foreign genes in *Hansenula polymorpha*. Yeast 11: 1241-1247.

Agaphonov, M. O., Trushkina, P. M., Sohn, J. H., Choi, E. S., Rhee, S. K., and Ter Avanesyan, M. D. (1999) Vectors for rapid selection of integrants with different plasmid copy numbers in the yeast *Hansenula polymorpha* DL1. Yeast 15:541-551.

Alber, T. and Kawasaki, G. (1982) Nucleotide sequence of the triose phosphate isomerase gene of *Saccharomyces cerevisiae*. J. Mol Appl. Genet 1:419-434.

Ammerer, G. (1983) Expression of genes in yeast using the ADCI promoter. Methods Enzymol. 101:192-201.

Ballou, L., Hitzeman, R. A., Lewis, M. S., and Ballou, C. E. (1991) Vanadate-resistant yeast mutants are defective in protein glycosylation. Proc. Natl. Acad. Sci. U.S.A 88:3209-3212.

Beekman, N. J., Schaaper, W. M., Tesser, G. I., Dalsgaard, K., Kamstrup, S., Langeveld, J. P., Boshuizen, R. S., and Meloen, R. E. (1997) Synthetic peptide vaccines: palmitoylation of peptide antigens by a thioester bond increases immunogenicity. J. Pept. Res. 50:357-364.

Burns, J., Butler, J., and Whitesides, G. (1991) Selective reduction of disulfides by Tris(2-carboxyethyl)phosphine. J. Org. Chem. 56:2648-2650.

Cox, H., Mead, D., Sudbery, P., Eland, R. M., Mannazzu, L, and Evans, L. (2000) Constitutive expression of recombinant proteins in the methylotrophic yeast *Hansenula polymorpha* using the PMA1 promoter. Yeast 16:1191-1203.

Cregg, J. M. (1999) Expression in the methylotophic yeast *Pichia pastoris*. In Gene expression systems: using nature for the art of expression, J. M. Fernandez and J. P. Hoeffer, eds (San Diego: Academic Press), pp. 157-191.

Darbre, A. (1986) *Practical protein chemistry: a handbook*. Whiley & Sons Ltd.

Diminsky, D., Schirmbeck, R., Reimann, J., and Barenholz, Y. (1997) Comparison between hepatitis B surface antigen (HBsAg) particles derived from mammalian cells (CHO) and yeast cells (*Hansenula polymorpha*): composition, structure and immunogenicity. Vaccine 15:637-647.

Doms, R. W., Lamb, R. A., Rose, J. K., and Helenius, A. (1993) Folding and assembly of viral membrane proteins. Virology 193:545-562.

Elble, R. (1992) A simple and efficient procedure for transformation of yeasts. Biotechniques 13:18-20.

Fellinger, A. J., Verbakel, J. M., Veale, R. A., Sudbery, P. E., Bom, I. J., Overbeeke, N., and Verrips, C. T. (1991) Expression of the alpha-galactosidase from *Cyamopsis tetragonoloba* (guar) by *Hansenula polymorpha*. Yeast 7:463-473.

Fournillier, J. A., Cahour, A., Escriou, N., Girad, M., and Wychowski, C. (1996) Processing of the E1 glycoprotein of hepatitis C virus expressed in mammalian cells. J. Gen Virol. 77 (Pt 5):1055-1064.

Gailit, J. (1993) Restoring free sulfhydryl groups in synthetic peptides. Anal. Biochem. 214:334-335.

Garson, J. A., Lubach, D., Passas, J., Whitby, K., and Grant, P. R. (1999) Suramin blocks hepatitis C binding to human hepatoma cells in vitro. J. Med. Virol. 57:238-242.

Gatzke, R., Weydemann, U., Janowicz, Z. A., and Hollenberg, C. P. (1995) Stable multicopy integration of vector sequences in *Hansenula polymorpha*. Appl. Microbiol. Biotechnol. 43:844-849.

Gellissen, G. (2000) Heterologous protein production in methylotrophic yeasts. Appl. Microbiol. Biotechnol. 54:741-750.

Grakoui, A., Wychowski, C., Lin, C., Feinstone, S. M., and Rice, C. M. (1993) Expression and identification of hepatitis C virus polyprotein cleavage products. J. Virol. 67:1385-1395.

Grinna, L. S. and Tschopp, J. F. (1989) Size distribution and general structural features of N-linked oligosaccharides from the methylotrophic yeast, *Pichia pastoris*. Yeast 5:107-115.

Heile, J. M., Fong, Y. L., Rosa, D., Berger, K., Saletti, G., Campagnoli, S., Bensi, G., Capo, S., Coates, S., Crawford, K., Dong, C., Wininger, M., Baker, G., Cousens, L., Chien, D., Ng, P., Archangel, P., Grandi, G., Houghton, M., and Abrignani, S. (2000) Evaluation of hepatitis C virus glycoprotein E2 for vaccine design: an endoplasmic reticulum-retained recombinant protein is superior to secreted recombinant protein and DNA-based vaccine candidates. J. Virol. 74:6885-6892.

Helenius, A. (1994) How N-linked oligosaccharides affect glycoprotein folding in the endoplasmic reticulum. Mol Biol. Cell 5:253-265.

Hermanson, G. T. (1996) Bioconjugate techniques. San Diego: Academic Press.

Herscovics, A. and Orlean, P. (1993) Glycoprotein biosynthesis in yeast. FASEB J. 7:540-550.

Hijikata, M., Kato, N., Ootsuyama, Y., Nakagawa, M., and Shimotohno, K. (1991) Gene mapping of the putative structural region of the hepatitis C virus genome by in vitro processing analysis. Proc. Natl. Acad. Sci. U.S.A 88:5547-5551.

Hitzeman, R. A., Clarke, L., and Carbon, J. (1980) Isolation and characterization of the yeast 3-phosphoglycerokinase gene (PGK) by an immunological screening technique. J. Biol. Chem. 255:12073-12080.

Hollenberg, C. P. and Gellissen, G. (1997) Production of recombinant proteins by methylotrophic yeasts. Curr. Opin. Biotechnol. 8:554-560.

Holmgren, A. (1979) Thioredoxin catalyzes the reduction of insulin disulfides by dithiothreitol and dihydrolipoamide. J. Biol. Chem. 254:9627-9632.

Janowicz, Z. A., Melber, K., Merckelbach, A., Jacobs, E., Harford, N., Comberbach, M., and Eollenberg, C. P. (1991) Simultaneous expression of the S and L surface antigens of hepatitis B, and formation of mixed particles in the methylotrophic yeast, Hansenula polymorpha. Yeast 7:431-443.

Jayabaskaran, C., Davison, P. F., and Paulus, H. (1987) Facile preparation and some applications of an affinity matrix with a cleavable connector arm containing a disulfide bond. Prep. Biochem. 17:121-141.

Jenkins, N., Parekh, R. B., and James, D. C. (1996) Getting the glycosylation right: implications for the biotechnology industry. Nat. Biotechnol. 14:975-981.

Julius, D., Brake, A., Blair, L., Kunisawa, R., and Thorner, J. (1984) Isolation of the putative structural gene for the lysine-arginine-cleaving endopeptidase required for processing of yeast prepro-alpha-factor. Cell 37:1075-1089.

Kalef, E., Walfish, P. G., and Gitler, C. (1993) Arsenical-based affinity chromatography of vicinal dithiol-containing proteins: purification of L1210 leukemia cytoplasmic proteins and the recombinant rat c-erb A beta 1 T3 receptor. Anal Biochem. 212:325-334.

Kalidas, C., Joshi, L., and Batt, C. (2001) Characterization of glycosylated variants of beta-lactoglobulin expressed in Pichia pastoris. Protein Eng 14:201-207.

Kato, N., Ootsuyama, Y., Tanaka, T., Nakagawa, M., Nakazawa, T., Muraiso, K., Ohkoshi, S., Hijikata, M., and Shimotohno, K. (1992) Marked sequence diversity in the putative envelope proteins of hepatitis C viruses. Virus Res. 22:107-123.

Kawasaki, G. and Fraenkel, D. G. (1982) Cloning of yeast glycolysis genes by complementation. Biochem. Biophys. Res. Commun. 108:1107-1122.

Klebe, R. J., Harriss, J. V., Sharp, Z. D., and Douglas, M. G. (1983) A general method for polyethylene-glycol-induced genetic transformation of bacteria and yeast. Gene 25:333-341.

Kumar, N., Kella, D., and Kinsella, J. E. (1985) A method for the controlled cleavage of disulfide bonds in proteins in the absence of denaturants. J. Biochem. Biophys. Methods 11:251-263.

Kumar, N., Kella, D., and Kinsella, J. E. (1986) Anomalous effects of denaturants on sulfitolysis of protein disulfide bonds. Int. J. Peptide Prot. Res. 28:586-592.

Maertens, G. and Stuyver, L. (1997) Genotypes and genetic variation of hepatitis C virus. In The molecular medicine of viral hepatitis, T. J. Harrison and A. J. Zuckerman, eds John Wiley & Sons), pp. 183-233.

Major, M. E. and Feinstone, S. M. (1997) The molecular virology of hepatitis C. Hepatology 25:1527-1538.

Miele, R. G., Nilsen, S. L., Brito, T., Bretthauer, R. K., and Castellino, F. J. (1997) Glycosylation properties of the Pichia pastoris-expressed recombinant kringle 2 domain of tissue-type plasminogen activator. Biotechnol. Appl. Biochem. 25 (Pt 2): 151-157.

Meunier, J. C., Fournillier, A., Choukhi, A., Cahour, A., Cocquerel, L., Dubuisson, J., and Wychowski, C. (1999) Analysis of the glycosylation sites of hepatitis C virus (HCV) glycoprotein E1 and the influence of E1 glycans on the formation of the HCV glycoprotein complex. J. Gen Virol. 80 (Pt 4):887-896.

Montesino, R., Garcia, R., Quintero, O., and Cremata, J. A. (1998) Variation in N-linked oligosaccharide structures on heterologous proteins secreted by the methylotrophic yeast Pichia pastoris. Protein Expr. Purif 14:197-207.

Mustilli, A. C., Izzo, E., Houghton, M., and Galeotti, C. L. (1999) Comparison of secretion of a hepatitis C virus glycoprotein in Saccharomyces cerevisiae and Kluyveromyces lactis. Res. Microbiol. 150:179-187.

Nagai, K. and Thogersen, H. C. (1984) Generation of beta-globin by sequence-specific proteolysis of a hybrid protein produced in Escherichia coli. Nature 309:810-812.

Nielsen, P. E. (2001) Targeting double stranded DNA with peptide nucleic acid (PNA). Curr Med Chem 8:545-550.

Okabayashi, K., Nakagawa, Y., Hayasuke, N., Ohi, H., Miura, M., Ishida, Y., Shimizu, M., Murakami, K., Iirabayashi, K., Minamino, H., and (1991) Secretory expression of the human serum albumin gene in the yeast, Saccharomyces cerevisiae. J. Biochem. (Tokyo) 110:103-110.

Orum, H. and Wengel, J. (2001) Locked nucleic acids: a promising molecular family for gene-function analysis and antisense drug development. Curr Opin. Mol. Ther. 3:239-243.

Padgett, K. A. and Sorge, J. A. (1996) Creating seamless junctions independent of restriction sites in PCR cloning. Gene 168:31-35.

Panchal, T. and Wodzinski, R. J. (1998) Comparison of glycosylation patterns of phytase from Aspergillus niger (A. ficuum) NRRL 3135 and recombinant phytase. Prep. Biochem. Biotechnol. 28:201-217.

Pedersen, J., Lauritzen, C., Madsen, M. T., and Weis, D. S. (1999) Removal of N-terminal polyhistidine tags from recombinant proteins using engineered aminopeptidases. Protein Expr. Purif 15:389-400.

Pomroy, N. C. and Deber, C. M. (1998) Solubilization of hydrophobic peptides by reversible cysteine PEGylation. Biochem. Biophys. Res. Commun. 245:618-621.

Raymond, C. K. (1999) Recombinant protein expression in Pichia methanolica. In Gene expression systems: using nature for the art of expression, J. M. Fernandez and J. P. Hoeffler, eds (San Diego: Academic Press), pp. 193-209.

Rein, A., Ott, D. E., Mirro, J., Arthur, L. O., Rice, W., and Henderson, L. E. (1996) Inactivation of murine leukemia virus by compounds that react with the zinc finger in the viral nucleocapsid protein. J. Virol. 70:4966-4972.

Roggenkamp, R., Hansen, H., Eckart, M., Janowicz, Z., and Hollenberg, C. P. (1986) Transformation of the methylotrophic yeast Hansenula polymorpha by autonomous replication and integration vectors. Mol Gen Genet 202: 302-308.

Rosa, D., Campagnoli, S., Moretto, C., Guenzi, E., Cousens, L., Chin, M., Dong, C., Weiner, A. J., Lau, J. Y., Choo, Q. L., Chien, D., Pileri, P., Houghton, M., and Abrignani, S.

(1996) A quantitative test to estimate neutralizing antibodies to the hepatitis C virus: cytofluorimetric assessment of envelope glycoprotein 2 binding to target cells. Proc. Natl. Acad. Sci. U.S.A 93:1759-1763.

Rose, J. K. and Doms, R. W. (1988) Regulation of protein export from the endoplasmic reticulum. Annu. Rev. Cell Biol. 4:257-288.

Russell, D. W., Smith, M., Williamson, V. M., and Young, E. T. (1983) Nucleotide sequence of the yeast alcohol dehydrogenase II gene. J. Biol. Chem. 258:2674-2682.

Russell, P. R. (1983) Evolutionary divergence of the mRNA transcription initiation mechanism in yeast. Nature 301: 167-169.

Russell, P. R. (1985) Transcription of the triose-phosphate-isomerase gene of Schizosaccharomyces pombe initiates from a start point different from that in Saccharomyces cerevisiae. Gene 40:125-130.

Russell, P. R. and Hall, B. D. (1983) The primary structure of the alcohol dehydrogenase gene from the fission yeast Schizosaccharomyces pombe. J. Biol. Chem. 258:143-149.

Sambrook, J., Fritsch, E. F., and Maniatis, T. (1989) Molecular Cloning: A Laboratory Manual. Cold Spring Harbor Laboratory Press.

Scorer, C. A., Clare, J. J., McCombie, W. R., Romanos, M. A., and Sreekrishna, K. (1994) Rapid selection using G418 of high copy number transformants of Pichia pastoris for high-level foreign gene expression. Biotechnology (N.Y.) 12:181-184.

Singh, R. and Kats, L. (1995) Catalysis of reduction of disulfide by selenol. Anal. Biochem. 232:86-91.

Sohn, J. H., Choi, E. S., Kang, H. A., Rhee, J. S., and Rhee, S. K. (1999) A family of telomere-associated autonomously replicating sequences and their functions in targeted recombination in Hansenula polymorpha DL-1. J. Bacteriol. 181:1005-1013.

Stuyver, L., van Arnhem, W., Wyseur, A., Hernandez, F., Delaporte, E., and Maertens, G. (1994) Classification of hepatitis C viruses based on phylogenetic analysis of the envelope 1 and nonstructural 5B regions and identification of five additional subtypes. Proc. Natl. Acad. Sci. U.S.A 91:10134-10138.

Sugrue, R. J., Cui, T., Xu, Q., Fu, J., and Chan, Y. C. (1997) The production of recombinant dengue virus E protein using Escherichia coli and Pichia pastoris. J. Virol. Methods 69:159-169.

Thakur, M. L., DeFulvio, J., Richard, M. D., and Park, C. H. (1991) Technetium-99m labeled monoclonal antibodies: evaluation of reducing agents. Int. J. Rad. Appl. Instrum. B 18:227-233.

Trimble, R. B., Atkinson, P. H., Tschopp, J. F., Townsend, R. R., and Maley, F. (1991) Structure of oligosaccharides on Saccharomyces SUC2 invertase secreted by the methylotrophic yeast Pichia pastoris. J. Biol. Chem. 266: 22807-22817.

Vingerhoeds, M. H., Haisma, H. J., Belliot, S. O., Smit, R. I., Crommelin, D. J., and Storm, G. (1996) Immunoliposomes as enzyme-carriers (immuno-enzymosomes) for antibody-directed enzyme prodrug therapy (ADEPT): optimization of prodrug activating capacity. Pharm. Res. 13:604-610.

Wahlestedt, C., Salmi, P., Good, L., Kela, J., Johnsson, T., Hokfelt, T., Broberger, C., Porreca, F., Lai, J., Ren, K, Ossipov, M., Koshkin, A., Jakobsen, N., SkouvJ., Oerum, H., Jacobsen, M. H., and Wengel, J. (2000) Potent and nontoxic antisense oligonucleotides containing locked nucleic acids. Proc Natl Acad Sci USA 97:5633-5638.

Weydemann, U., Keup, P., Piontek, M., Strasser, A. W., Schweden, J., Gellissen, G., and Janowicz, Z. A. (1995) High-level secretion of hirudin by Hansenula polymorpha-authentic processing of three different preprohirudins. Appl. Microbiol. Biotechnol. 44:377-385.

Young, M., Davies, M. J., Bailey, D., Gradwell, M. J., Smestad-Paulsen, B., Wold, J. K., Barnes, R. M. R., Hounsell, E. (1998) Characterization of oligosaccharides from an antigenic mannan of Saccharomyces cerevisiae. Glycoconjugate Journal 15:815-822.

Zauberman, A., Nussbaum, O., Ilan, E., Eren, R., Ben-Moshe, O., Arazi, Y., Berre, S., Lubin, I., Shouval, D., Galun, E., Reisner, Y., and Dagan, S. (1999) The trimera mouse system: a mouse model for hepatitis C infection and evaluation of therapeutic agents. 6th International Symposium on hepatitis C and related viruses. Bethesda Jun. 6-9, 1999.

The invention claimed is:

1. A composition comprising glycosylated HCV envelope proteins or glycosylated immunogenic fragments thereof, wherein said glycosylated HCV envelope proteins or glycosylated immunogenic fragments thereof are a yeast cell expression product, said glycosylated HCV envelope proteins or glycosylated immunogenic fragments thereof comprising N-glycosylated sites, said N-glycosylated sites being, on average, up to 80% core-glycosylated, said core-glycosylations containing less than 10% terminal α1,3 mannoses.

2. The composition according to claim 1 wherein more than 70% of said core-glycosylated sites are glycosylated with an oligomannose containing 8 to 10 mannoses.

3. A composition comprising glycosylated HCV E1 envelope proteins and/or glycosylated HCV E2 envelope proteins or glycosylated immunogenic fragments thereof, wherein said glycosylated HCV E1 envelope proteins and/or glycosylated HCV E2 envelope proteins or glycosylated immunogenic fragments thereof are a *Hansenula* cell expression product, said glycosylated HCV E1 envelope proteins and/or glycosylated HCV E2 envelope proteins or glycosylated immunogenic fragments thereof comprising N-glycosylated sites, said N-glycosylated sites being, on average, up to 80% core-glycosylated, said core-glycosylations containing less than 10% terminal ccl α1,3 mannoses.

4. The composition according to claim 3 wherein more than 70% of said core-glycosylated sites are glycosylated with an oligomannose containing 8 to 10 mannoses.

5. The composition according to any of claims 1, 2, 3 or 4 wherein the ratio of sites core-glycosylated with an oligomannose with a structure defined by Man(7)-GlcNAc(2) over the sites core-glycosylated with an oligomannose with a structure defined by Man(8)-GlcNAc(2) is less than or equal to 0.45.

6. The composition according to claim 1 wherein said yeast cell is a *Hansenula* cell.

7. The composition according to any of claims 1, 2, 3 or 4, wherein said glycosylated HCV envelope proteins or glycosylated immunogenic fragments thereof are expressed in said yeast cell as proteins comprising avian lysozyme leader peptides or functional variants thereof joined to said HCV envelope proteins or immunogenic fragments thereof.

8. The composition according to claim 7 wherein each of the proteins or the immunogenic fragments thereof comprise the structure CL-[(A1)$_a$-(PS1)$_b$-(A2)$_c$]-HCVENV-[(A3)$_d$-(PS2)$_e$-(A4)$_f$]

Wherein:
CL is an avian lysozyme leader peptide or a functional equivalent thereof, A1, A2, A3 and A4 are adaptor peptides which can be different or the same, PS1 and PS2 are processing sites which can be the different or the same, HCVENV is a HCV envelope protein or an immunogenic fragment thereof, A, b, c, d, e and f are 0 or 1, and wherein, optionally, A1 and/or A2 are part of PS1 and/or wherein A3 and/or A4 are part of PS2.

9. The composition according to claim 8 wherein said avian lysozyme leader peptide CL has an amino acid sequence defined by SEQ ID NO:1.

10. The composition according to claim 8 wherein A has an amino acid sequence chosen from SEQ ID NOs:63-65, 70-72 and 74-82, wherein PS has an amino acid sequence chosen from SEQ ID NOs:66-68 and 83-84 or wherein PS is a dibasic site such as Lys-Lys, Arg-Arg, Lys-Arg and Arg-Lys or a monobasic site such as Lys, and wherein HCVENV is chosen from SEQ ID NOS:2 and 85-98 and immunogenic fragments thereof.

11. The composition according to any of claims 1, 2, 3 or 4, wherein the structure of said glycosylated HCV envelope proteins or glycosylated immunogenic fragments is selected from the group consisting of monomers, homodimers, heterodimers, homo-oligomers and hetero-oligomers.

12. The composition according to any of claims 1, 2, 3 or 4, wherein the glycosylated HCV envelope proteins or glycosylated immunogenic fragments are contained in a virus-like particle.

13. The composition according to any of claims 1, 2, 3 or 4, wherein the glycosylated HCV envelope proteins or glycosylated immunogenic fragments contain chemically modified cysteine thiol-groups.

14. The composition according to any of claims 1, 2, 3 or 4, which is immunogenic.

15. The composition according to any of claims 1, 2, 3 or 4, which comprises a T-cell epitope.

16. The composition according to claim 1, 2, 3 or 4, further comprising a pharmaceutically acceptable carrier, said composition is a medicament.

17. A medicament comprising the composition according to any of claims 1, 2, 3 or 4.

18. A pharmaceutical composition for inducing a HCV-specific immune response in a mammal, said composition comprising an effective amount of a composition according to any of claims 1, 2, 3 or 4, and, optionally, a pharmaceutically acceptable adjuvant.

19. A pharmaceutical composition for inducing HCV-specific antibodies in a mammal, said composition comprising an effective amount of a composition according to any of claims 1, 2, 3 or 4, and, optionally, a pharmaceutically acceptable adjuvant.

20. A pharmaceutical composition for inducing a T-cell function in a mammal, said composition comprising an effective amount of a composition according to any of claims 1, 2, 3 or 4, and, optionally, a pharmaceutically acceptable adjuvant.

21. The pharmaceutical composition according to claim 18 which is a therapeutic composition.

22. The pharmaceutical composition according to claim 18 wherein said mammal is a human.

23. The composition according to claim 5 wherein said oligomannoses contain less than 10% terminal $\alpha 1,3$ mannose.

24. A composition comprising glycosylated HCV E1 envelope proteins and/or glycosylated HCV E2 envelope proteins or glycosylated immunogenic fragments thereof, said glycosylated HCV E1 envelope proteins and/or glycosylated HCV E2 envelope proteins or glycosylated immunogenic fragments thereof comprising N-glycosylated sites, said N-glycosylated sites being, on average, up to 80% core-glycosylated, said core-glycosylations containing less than 10% terminal $\alpha 1,3$ mannoses.

25. The composition according to claim 24 wherein more than 70% of said core-glycosylated sites are glycosylated with an oligomannose containing 8 to 10 mannoses.

26. A diagnostic kit for the detection of the presence of anti-HCV antibodies in a sample suspected to comprise anti-HCV antibodies, said kit comprising a composition according to any of claims 1, 2, 3 or 4.

27. The diagnostic kit according to claim 26 wherein said HCV envelope proteins or immunogenic fragments thereof are attached to a solid support.

28. A method for producing the composition according to any of claims 1, 2, 3 or 4, comprising expressing said glycosylated envelope proteins or glycosylated immunogenic fragments thereof in said yeast.

29. A method for the detection of the presence of anti-HCV antibodies in a sample suspected to comprise anti-HCV antibodies, said method comprising:

(i) contacting a composition according to any of claims 1, 2, 3 or 4, with said sample under conditions allowing complexation of said HCV envelope proteins or immunogenic fragments thereof with said anti-HCV antibodies, (ii) detecting the complex formed in (i), and (iii) inferring from (ii) the presence of said anti-HCV antibodies in said sample.

30. The method according to claim 29 wherein said contacting in step (i) is performed under competitive conditions.

31. The method according to claim 29 wherein said HCV envelope proteins or immunogenic fragments thereof are attached to solid support.

32. A method of inducing a HCV-specific immune response in a mammal, said method comprising administering to said mammal an effective amount of a composition according to any of claims 1, 2, 3 or 4, optionally comprising a pharmaceutically acceptable adjuvant.

33. A method of inducing HCV-specific antibodies in a mammal, said method comprising administering to said mammal an effective amount of a composition according to any of claims 1, 2, 3 or 4, optionally comprising a pharmaceutically acceptable adjuvant.

34. A method of inducing a specific T-cell function in a mammal, said method comprising administering to said mammal an effective amount of a composition according to any of claims 1, 2, 3 or 4, optionally comprising a pharmaceutically acceptable adjuvant.

35. The method according to claim 32 wherein said administering is a therapeutic administering.

36. A method of treating a mammal infected with HCV, said method comprising administering to said mammal an effective amount of a composition according to any of claims 1, 2, 3 or 4, optionally comprising a pharmaceutically acceptable adjuvant.

* * * * *

SEQUENCE LISTING

```
<160> NUMBER OF SEQ ID NOS: 98

<210> SEQ ID NO 1
<211> LENGTH: 18
<212> TYPE: PRT
<213> ORGANISM: avian lysozyme signal peptide
<220> FEATURE:
<221> NAME/KEY: MISC_FEATURE
<222> LOCATION: (2)..(2)
<223> OTHER INFORMATION: Xaa is Arg, Lys or Val
<220> FEATURE:
<221> NAME/KEY: MISC_FEATURE
<222> LOCATION: (3)..(3)
<223> OTHER INFORMATION: Xaa is Ser, Ala, Val, Arg or Met
<220> FEATURE:
<221> NAME/KEY: MISC_FEATURE
<222> LOCATION: (4)..(4)
<223> OTHER INFORMATION: Xaa is Leu or Phe
<220> FEATURE:
<221> NAME/KEY: MISC_FEATURE
<222> LOCATION: (5)..(5)
<223> OTHER INFORMATION: Xaa is Leu or Ala
```

```
<220> FEATURE:
<221> NAME/KEY: MISC_FEATURE
<222> LOCATION: (6)..(6)
<223> OTHER INFORMATION: Xaa is Ile, Thr, Phe or Val
<220> FEATURE:
<221> NAME/KEY: MISC_FEATURE
<222> LOCATION: (7)..(7)
<223> OTHER INFORMATION: Xaa is Leu, Phe or Ala
<220> FEATURE:
<221> NAME/KEY: MISC_FEATURE
<222> LOCATION: (8)..(8)
<223> OTHER INFORMATION: Xaa is Val, Ile, Ala, Leu or Cys
<220> FEATURE:
<221> NAME/KEY: MISC_FEATURE
<222> LOCATION: (9)..(9)
<223> OTHER INFORMATION: Xaa is Leu, Phe, Ala or Ile
<220> FEATURE:
<221> NAME/KEY: MISC_FEATURE
<222> LOCATION: (10)..(10)
<223> OTHER INFORMATION: Xaa is Cys, Phe, Ser or Leu
<220> FEATURE:
<221> NAME/KEY: MISC_FEATURE
<222> LOCATION: (11)..(11)
<223> OTHER INFORMATION: Xaa is Phe, Leu, Ser or Pro
<220> FEATURE:
<221> NAME/KEY: MISC_FEATURE
<222> LOCATION: (12)..(12)
<223> OTHER INFORMATION: Xaa is Leu, Ala or Met
<220> FEATURE:
<221> NAME/KEY: MISC_FEATURE
<222> LOCATION: (13)..(13)
<223> OTHER INFORMATION: Xaa is Pro, Ala or Ile
<220> FEATURE:
<221> NAME/KEY: MISC_FEATURE
<222> LOCATION: (14)..(14)
<223> OTHER INFORMATION: Xaa is Leu or Ala
<220> FEATURE:
<221> NAME/KEY: MISC_FEATURE
<222> LOCATION: (15)..(15)
<223> OTHER INFORMATION: Xaa is Ala, Val, Ser or Met
<220> FEATURE:
<221> NAME/KEY: MISC_FEATURE
<222> LOCATION: (16)..(16)
<223> OTHER INFORMATION: Xaa is Ala, Lys or Ser
<220> FEATURE:
<221> NAME/KEY: MISC_FEATURE
<222> LOCATION: (17)..(17)
<223> OTHER INFORMATION: Xaa is Leu, Pro, Gln or Ile

<400> SEQUENCE: 1

Met Xaa Xaa Xaa Xaa Xaa Xaa Xaa Xaa Xaa Xaa Xaa Xaa Xaa Xaa Xaa
1               5                   10                  15

Xaa Gly

<210> SEQ ID NO 2
<211> LENGTH: 135
<212> TYPE: PRT
<213> ORGANISM: hepatitis C virus

<400> SEQUENCE: 2

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
                20                  25                  30

Pro Gly Cys Val Pro Cys Val Arg Glu Asn Asn Ser Ser Arg Cys Trp
            35                  40                  45

Val Ala Leu Thr Pro Thr Leu Ala Ala Arg Asn Ala Ser Val Pro Thr
        50                  55                  60

Thr Thr Ile Arg Arg His Val Asp Leu Leu Val Gly Ala Ala Ala Phe
65                  70                  75                  80
```

```
Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Asn Trp
    130             135

<210> SEQ ID NO 3
<211> LENGTH: 290
<212> TYPE: PRT
<213> ORGANISM: hepatitis C virus

<400> SEQUENCE: 3

His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Gly Thr Thr Asp Arg Phe Gly Val Pro Thr Tyr
    130                 135                 140

Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205

Ala Thr Tyr Ala Arg Cys Gly Ser Gly Pro Trp Leu Thr Pro Arg Cys
    210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Glu
        275                 280                 285

Trp Gln
    290

<210> SEQ ID NO 4
```

```
<211> LENGTH: 141
<212> TYPE: PRT
<213> ORGANISM: hepatitis C virus

<400> SEQUENCE: 4

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Asn Trp His His His His His
    130                 135                 140

<210> SEQ ID NO 5
<211> LENGTH: 301
<212> TYPE: PRT
<213> ORGANISM: hepatitis C virus

<400> SEQUENCE: 5

His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Gly Thr Thr Asp Arg Phe Gly Val Pro Thr Tyr
    130                 135                 140

Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205
```

```
Ala Thr Tyr Ala Arg Cys Gly Ser Gly Pro Trp Leu Thr Pro Arg Cys
    210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Val Glu His Arg
                245                 250                 255

Phe Glu Ala Ala Cys Asn Trp Thr Arg Gly Glu Arg Cys Asp Leu Glu
                260                 265                 270

Asp Arg Asp Arg Ser Glu Leu Ser Pro Leu Leu Leu Ser Thr Thr Glu
            275                 280                 285

Trp Gln Val Ile Glu Gly Arg His His His His His
    290                 295                 300

<210> SEQ ID NO 6
<211> LENGTH: 3448
<212> TYPE: DNA
<213> ORGANISM: vector pGEMTE1sH6

<400> SEQUENCE: 6
aatcactagt gcggccgcct gcaggtcgac catatgggag agctcccaac gcgttggatg      60
catagcttga gtattctata gtgtcaccta aatagcttgg cgtaatcatg gtcatagctg     120
tttcctgtgt gaaattgtta tccgctcaca attccacaca acatacgagc cggaagcata     180
aagtgtaaag cctggggtgc ctaatgagtg agctaactca cattaattgc gttgcgctca     240
ctgcccgctt tccagtcggg aaacctgtcg tgccagctgc attaatgaat cggccaacgc     300
gcggggagag gcggtttgcg tattgggcgc tcttccgctt cctcgctcac tgactcgctg     360
cgctcggtcg ttcggctgcg gcgagcggta tcagctcact caaaggcggt aatacggtta     420
tccacagaat caggggataa cgcaggaaag aacatgtgag caaaaggcca gcaaaaggcc     480
aggaaccgta aaaaggccgc gttgctggcg tttttcgata ggctccgccc ccctgacgag     540
catcacaaaa atcgacgctc aagtcagagg tggcgaaacc cgacaggact ataaagatac     600
caggcgtttc cccctggaag ctccctcgtg cgctctcctg ttccgaccct gccgcttacc     660
ggatacctgt ccgcctttct cccttcggga agcgtggcgc tttctcatag ctcacgctgt     720
aggtatctca gttcggtgta ggtcgttcgc tccaagctgg gctgtgtgca cgaaccccc     780 gttcagcccg accgctgcgc cttatccggt aactatcgtc ttgagtccaa cccggtaaga     840
cacgacttat cgccactggc agcagccact ggtaacagga ttagcagagc gaggtatgta     900
ggcggtgcta cagagttctt gaagtggtgg cctaactacg gctacactag aaggacagta     960
tttggtatct gcgctctgct gaagccagtt accttcggaa aaagagttgg tagctcttga    1020
tccggcaaac aaaccaccgc tggtagcggt ggttttttg tttgcaagca gcagattacg    1080
cgcagaaaaa aaggatctca agaagatcct ttgatctttt ctacgggtc tgacgctcag    1140 tggaacgaaa actcacgtta agggattttg gtcatgagat tatcaaaaag gatcttcacc    1200
tagatccttt taaattaaaa atgaagtttt aaatcaatct aaagtatata tgagtaaact    1260
tggtctgaca gttaccaatg cttaatcagt gaggcaccta tctcagcgat ctgtctattt    1320
cgttcatcca tagttgcctg actccccgtc gtgtagataa ctacgatacg ggagggctta    1380
ccatctggcc ccagtgctgc aatgataccg cgagacccac gctcaccggc tccagattta    1440
tcagcaataa accagccagc cggaagggcc gagcgcagaa gtggtcctgc aactttatcc    1500
gcctccatcc agtctattaa ttgttgccgg gaagctagag taagtagttc gccagttaat    1560
```

-continued

```
agtttgcgca acgttgttgg cattgctaca ggcatcgtgg tgtcacgctc gtcgtttggt    1620
atggcttcat tcagctccgg ttcccaacga tcaaggcgag ttacatgatc ccccatgttg    1680
tgcaaaaaag cggttagctc cttcggtcct ccgatcgttg tcagaagtaa gttggccgca    1740
gtgttatcac tcatggttat ggcagcactg cataattctc ttactgtcat gccatccgta    1800
agatgctttt ctgtgactgg tgagtactca accaagtcat tctgagaata ccgcgcccgg    1860
cgaccgagtt gctcttgccc ggcgtcaata cgggataata gtgtatgaca tagcagaact    1920
ttaaaagtgc tcatcattgg aaaacgttct tcggggcgaa aactctcaag gatcttaccg    1980
ctgttgagat ccagttcgat gtaacccact cgtgcaccca actgatcttc agcatctttt    2040
actttcacca gcgtttctgg gtgagcaaaa acaggaaggc aaaatgccgc aaaaaaggga    2100
ataagggcga cacggaaatg ttgaatactc atactcttcc tttttcaata ttattgaagc    2160
atttatcagg gttattgtct catgagcgga tacatatttg aatgtattta gaaaaataaa    2220
caaatagggg ttccgcgcac atttccccga aaagtgccac ctgtatgcgg tgtgaaatac    2280
cgcacagatg cgtaaggaga aaataccgca tcaggcgaaa ttgtaaacgt taatattttg    2340
ttaaaattcg cgttaaatat ttgttaaatc agctcatttt ttaaccaata ggccgaaatc    2400
ggcaaaatcc cttataaatc aaaagaatag accgagatag ggttgagtgt tgttccagtt    2460
tggaacaaga gtccactatt aaagaacgtg gactccaacg tcaaagggcg aaaaaccgtc    2520
tatcagggcg atggcccact acgtgaacca tcacccaaat caagtttttt gcggtcgagg    2580
tgccgtaaag ctctaaatcg gaaccctaaa gggagccccc gatttagagc ttgacgggga    2640
aagccggcga acgtggcgag aaaggaaggg aagaaagcga aaggagcggg cgctagggcg    2700
ctggcaagtg tagcggtcac gctgcgcgta accaccacac ccgccgcgct taatgcgccg    2760
ctacagggcg cgtccattcg ccattcaggc tgcgcaactg ttgggaaggg cgatcggtgc    2820
gggcctcttc gctattacgc cagctggcga aggggggatg tgctgcaagg cgattaagtt    2880
gggtaacgcc agggttttcc cagtcacgac gttgtaaaac gacggccagt gaattgtaat    2940
acgactcact ataggcgaa ttgggcccga cgtcgcatgc tcccggccgc catgccgcg     3000 ggattccaat gcatatgagg tgcgcaacgt gtccgggatg taccatgtca cgaacgactg    3060
ctccaactca agcattgtgt atgaggcagc ggacatgatc atgcacaccc ccgggtgcgt    3120
gccctgcgtt cgggagaaca actcttcccg ctgctgggta gcgctcaccc ccacgctcgc    3180
agctaggaac gccagcgtcc ccactacgac aatacgacgc cacgtcgatt tgctcgttgg    3240
ggcggctgct ttctgttccg ctatgtacgt ggggggatctc tgcggatctg tcttcctcgt    3300
ctcccagctg ttcaccatct cgcctcgccg gcatgagacg gtgcaggact gcaattgctc    3360
aatctatccc ggccacataa caggtcaccg tatggcttgg gatatgatga tgaactggca    3420
ccaccaccat caccattaag gatccaag                                       3448
```

<210> SEQ ID NO 7
<211> LENGTH: 37
<212> TYPE: DNA
<213> ORGANISM: synthetic probe or primer

<400> SEQUENCE: 7

```
agttactctt caaggtatga ggtgcgcaac gtgtccg                               37
```

<210> SEQ ID NO 8
<211> LENGTH: 47
<212> TYPE: DNA
<213> ORGANISM: synthetic probe or primer

<400> SEQUENCE: 8

```
agttactctt cacagggatc ctccttaatg gtgatggtgg tggtgcc          47
```

<210> SEQ ID NO 9
<211> LENGTH: 3067
<212> TYPE: DNA
<213> ORGANISM: vector pCHH-Hir

<400> SEQUENCE: 9

```
gcgcccaata cgcaaaccgc ctctccccgc gcgttggccg attcattaat gcagctggca    60
cgacaggttt cccgactgga aagcgggcag tgagcgcaac gcaattaatg tgagttagct   120
cactcattag gcaccccagg ctttacactt tatgcttccg gctcgtatgt tgtgtggaat   180
tgtgagcgga taacaatttc acacaggaaa cagctatgac catgattacg ccaagcttgc   240
atgcctgcag tcgaccccta gatctctatt actgcaggta ttcttccggg atttcttcga   300
agtcgccgtc gttgtgagac tgcggacgcg gggtaccttc gccagtaacg cactggttac   360
gttcgccttt agagcccagg atgcatttgt tgccctggcc gcaaacgtta gagccttcgc   420
acaggcacag gttctgaccg gattcagtgc agtcagtgta acaaccctc ttttccaacg   480
ggtgtgtagt tccattctcc accgctaggg ctgcgctggg ctccattggc gaggttttca   540
aggccgctag gatgcgatcc atgcgtccgt agccttgcgt ggagcgtgcg tgtgcgtgcg   600
ggagtgcgca taggtaggct acggtgatga ttgctagcat ggcgggaata gttttgctat   660
acatgaattc actggccgtc gttttacaac gtcgtgactg ggaaaaccct ggcgttaccc   720
aacttaatcg ccttgcagca catccccctt tcgccagctg gcgtaatagc gaagaggccc   780
gcaccgatcg ccccttccaa cagttgcgca gcctgaatgg cgaatggcgc ctgatgcggt   840
attttctcct tacgcatctg tgcggtattt cacaccgcat atggtgcact ctcagtacaa   900
tctgctctga tgccgcatag ttaagccagc cccgacaccc gccaacaccc gctgacgcgc   960
cctgacgggc ttgtctgctc ccggcatccg cttacagaca agctgtgacc gtctccggga  1020
gctgcatgtg tcagaggttt tcaccgtcat caccgaaacg cgcgagacga agggcctcg  1080
tgatacgcct atttttatag gttaatgtca tgataataat ggtttcttag acgtcaggtg  1140
gcacttttcg gggaaatgtg cgcggaaccc ctatttgttt attttctaa atacattcaa  1200
atatgtatcc gctcatgaga caataaccct gataaatgct tcaataatat tgaaaagga  1260
agagtatgag tattcaacat ttccgtgtcg cccttattcc cttttttgcg cattttgcc  1320
ttcctgtttt tgctcaccca gaaacgctgg tgaaagtaaa agatgctgaa gatcagttgg  1380
gtgcacgagt gggttacatc gaactggatc tcaacagcgg taagatcctt gagagttttc  1440
gccccgaaga acgttttcca atgatgagca cttttaaagt tctgctatgt ggcgcggtat  1500
tatcccgtat tgacgccggg caagagcaac tcggtcgccg catacactat tctcagaatg  1560
acttggttga gtactcacca gtcacagaaa agcatcttac ggatggcatg acagtaagag  1620
aattatgcag tgctgccata accatgagtg ataacactgc ggccaactta cttctgacaa  1680
cgatcggagg accgaaggag ctaaccgctt ttttgcacaa catgggggat catgtaactc  1740
gccttgatcg ttgggaaccg gagctgaatg aagccatacc aaacgacgag cgtgacacca  1800
cgatgcctgt agcaatggca acaacgttgc gcaaactatt aactggcgaa ctacttactc  1860
tagcttcccg gcaacaatta atagactgga tggaggcgga taagttgca ggaccacttc  1920
tgcgctcggc ccttccggct ggctggttta ttgctgataa atctggagcc ggtgagcgtg  1980
```

```
ggtctcgcgg tatcattgca gcactggggc cagatggtaa gccctcccgt atcgtagtta    2040
tctacacgac ggggagtcag gcaactatgg atgaacgaaa tagacagatc gctgagatag    2100
gtgcctcact gattaagcat tggtaactgt cagaccaagt ttactcatat atactttaga    2160
ttgatttaaa acttcatttt taatttaaaa ggatctaggt gaagatcctt tttgataatc    2220
tcatgaccaa aatcccttaa cgtgagtttt cgttccactg agcgtcagac cccgtagaaa    2280
agatcaaagg atcttcttga tccttttttt tctgcgcgt aatctgctgc ttgcaaacaa    2340
aaaaaccacc gctaccagcg gtggtttgtt tgccggatca agagctacca actctttttc    2400
cgaaggtaac tggcttcagc agagcgcaga taccaaatac tgtccttcta gtgtagccgt    2460
agttaggcca ccacttcaag aactctgtag caccgcctac atacctcgct ctgctaatcc    2520
tgttaccagt ggctgctgcc agtggcgata agtcgtgtct taccgggttg gactcaagac    2580
gatagttacc ggataaggcg cagcggtcgg gctgaacggg gggttcgtgc acacagccca    2640
gcttggagcg aacgacctac accgaactga gatacctaca gcgtgagcta tgagaaagcg    2700
ccacgcttcc cgaagggaga aaggcggaca ggtatccggt aagcggcagg gtcggaacag    2760
gagagcgcac gagggagctt ccaggggaa acgcctggta tctttatagt cctgtcgggt    2820
ttcgccacct ctgacttgag cgtcgatttt tgtgatgctc gtcagggggg cggagcctat    2880
ggaaaaacgc cagcaacgcg gccttttac ggttcctggc cttttgctgg ccttttgctc    2940
acatgttctt tcctgcgtta tcccctgatt ctgtggataa ccgtattacc gcctttgagt    3000
gagctgatac cgctcgccgc agccgaacga ccgagcgcag cgagtcagtg agcgaggaag    3060
cggaaga                                                              3067

<210> SEQ ID NO 10
<211> LENGTH: 35
<212> TYPE: DNA
<213> ORGANISM: synthetic probe or primer

<400> SEQUENCE: 10
agttactctt cacctctttt ccaacgggtg tgtag                                35

<210> SEQ ID NO 11
<211> LENGTH: 34
<212> TYPE: DNA
<213> ORGANISM: synthetic probe or primer

<400> SEQUENCE: 11
agtcactctt cactgcaggc atgcaagctt ggcg                                 34

<210> SEQ ID NO 12
<211> LENGTH: 6973
<212> TYPE: DNA
<213> ORGANISM: vector pFPMT121

<400> SEQUENCE: 12
ggtaccctgc tcaatctccg gaatggtgat ctgatcgttc ctgaaaacct cgacattggc      60
tccctcctga cacaggtact cgtacaggtt ccaggtaaac gagtcgtagt tgtcgatcat    120
gacaacgttc ttagaagcgg ccggcatttt gaaggtgact aatagcctaa gaaatatt     180 aatttaattt tcattaaatt ttcctatact cgctatttca gcttttcatc tcatcacttc    240
ataaacgata taaaccagaa aaagaactat tttcaaacac gcttctcaaa agcggtatgt    300
ccttccacgt ctccttagaa tctggcaagt ccgcgagggg gatccagatc tgaattcccg    360
atgaagcaga gagcgcagga ggcggtattt atagtgccat tcccctctct gagagacccg    420
```

-continued

```
gatggtagtc gagtgtatcg gagacagctt gatgtagact ccgtgcctgc cggctcctct    480
tattggcgga caccagtgag acaccccgga acttgctgtt tttctgcaaa atccggggtg    540
accagtggga gcctatttgc acacacgagc gggacacccc actctggtga agagtgccaa    600
agtcattctt tttcccgttg cggggcagcc gattgcatgt tttaggaaaa tattaccttt    660
gctacaccct gtcagattta ccctccacac atatatattc cgtcacctcc agggactatt    720
attcgtcgtt gcgccgccag cggaagatat ccagaagctg ttttccgaga gactcggttg    780
gcgcctggta tatttgatgg atgtcgcgct gcctcacgtc ccggtaccca ggaacgcggt    840
gggatctcgg gcccatcgaa gactgtgctc cagactgctc gcccagcagg tgtttcttga    900
tcgccgcctc taaattgtcc gcgcatcgcc ggtaacattt ttccagctcg gagtttgcgt    960
ttagatacag tttctgcgat gccaaaggag cctgcagatt ataacctcgg atgctgtcat   1020
tcagcgcttt taatttgacc tccagatagt tgctgtattt ctgttcccat ggctgctgc    1080
gcagcttcgt ataactcgag ttattgttgc gctctgcctc ggcgtactgg ctcatgatct   1140
ggatcttgtc cgtgtcgctt ttcttcgagt gtttctcgca aacgatgtgc acggcctgca   1200
gtgtccaatc ggagtcgagc tggcgccgaa actggcggat ctgagcctcc acactgccct   1260
gtttctctat ccacggcgga accgcctcct gccgtttcag aatgttgttc aagtggtact   1320
ctgtgcggtc aatgaaggcg ttattgccgg tgaaatcttt gggaagcggt tttcctcggg   1380
gaagattacg aaattccccg cgtcgttgcg cttcctggat ctcgaggaga tcgttctccg   1440
cgtcgaggag atcgttctcc gcgtcgacac cattccttgc ggcggcggtg ctcaacggcc   1500
tcaacctact actgggctgc ttcctaatgc aggagtcgca taaggagag cgtcgacaaa   1560
cccgcgtttg agaacttgct caagcttctg gtaaacgttg tagtactctg aaacaaggcc   1620
ctagcactct gatctgtttc tcttgggtag cggtgagtgg tttattggag ttcactggtt   1680
tcagcacatc tgtcatctag acaatattgt tactaaattt ttttgaacta caattgttcg   1740
taattcatct attattatac atcctcgtca gcaatttctg gcagacggag tttactaacg   1800
tcttgagtat gaggccgaga atccagctct gtggccatac tcagtcttga cagcctgctg   1860
atgtggctgc gttcaacgca ataagcgtgt cctccgactc cgagttgtgc tcgttatcgt   1920
cgttctcatc ctcggaaaaa tcacacgaaa gaacatactc accagtaggc tttctggtcc   1980
ctggggcacg gctgtttctg acgtattccg gcgttgataa tagctcgaaa gtgaacgccg   2040
agtcgcggga gtcgaccgat gcccttgaga gccttcaacc cagtcagctc cttccggtgg   2100
gcgcggggca tgactatcgt cgccgcactt atgactgtct tctttatcat gcaactcgta   2160
ggacaggtgc cggcagcgct ctgggtcatt ttcggcgagg accgctttcg ctggagcgcg   2220
acgatgatcg gcctgtcgct tgcggtattc ggaatcttgc acgccctcgc tcaagccttc   2280
gtcactggtc ccgccaccaa acgtttcggc gagaagcagg ccattatcgc cggcatggcg   2340
gccgacgcgc tgggctacgt cttgctggcg ttcgcgacgc gaggctggat ggccttcccc   2400
attatgattc ttctcgcttc cggcggcatc gggatgcccg cgttgcaggc catgctgtcc   2460
aggcaggtag atgacgacca tcagggacag cttcaaggat cgctcgcggc tcttaccagc   2520
ctaacttcga tcactggacc gctgatcgtc acggcgattt atgccgcctc ggcgagcaca   2580
tggaacgggt tggcatggat tgtaggcgcc gccctatacc ttgtctgcct ccccgcgttg   2640
cgtcgcggtg catggagccg ggccacctcg acctgaatgg aagccggcgg cacctcgcta   2700
acggattcac cactccaaga attggagcca atcaattctt gcggagaact gtgaatgcgc   2760
```

```
aaaccaaccc ttggcagaac atatccatcg cgtccgccat ctccagcagc cgcacgcggc   2820
gcatcggggg ggggggggg ggggggggc aaacaattca tcatttttt tttattcttt     2880 tttttgattt cggtttcttt gaaatttttt tgattcggta atctccgaac agaaggaaga   2940
acgaaggaag gagcacagac ttagattggt atatatacgc atatgtagtg ttgaagaaac   3000
atgaaattgc ccagtattct aacccaact gcacagaaca aaaacctgca ggaaacgaag    3060
ataaatcatg tcgaaagcta catataagga acgtgctgct actcatccta gtcctgttgc   3120
tgccaagcta tttaatatca tgcacgaaaa gcaaacaaac ttgtgtgctt cattggatgt   3180
tcgtaccacc aaggaattac tggagttagt tgaagcatta ggtcccaaaa tttgtttact   3240
aaaaacacat gtggatatct tgactgattt ttccatggag ggcacagtta agccgctaaa   3300
ggcattatcc gccaagtaca attttttact cttcgaagac agaaaatttg ctgacattgg   3360
taatacagtc aaattgcagt actctgcggg tgtatacaga atagcagaat gggcagacat   3420
tacgaatgca cacggtgtgg tgggcccagg tattgttagc ggtttgaagc aggcggcaga   3480
agaagtaaca aaggaaccta gaggcctttt gatgttagca gaattgtcat gcaagggctc   3540
cctatctact ggagaatata ctaagggtac tgttgacatt gcgaagagcg acaaagattt   3600
tgttatcggc tttattgctc aaagagacat gggtggaaga gatgaaggtt acgattggtt   3660
gattatgaca cccggtgtgg gtttagatga caagggagac gcattgggtc aacagtatag   3720
aaccgtggat gatgtggtct ctacaggatc tgacattatt attgttggaa gaggactatt   3780
tgcaaaggga agggatgcta aggtagaggg tgaacgttac agaaaagcag ctgggaagc    3840 atatttgaga agatgcggcc agcaaaacta aaaaactgta ttataagtaa atgcatgtat   3900
actaaactca caaattagag cttcaattta attatatcag ttattacccg ggaatctcgg   3960
tcgtaatgat ttttataatg acgaaaaaa aaaaattgga agaaaagcc cccccccc     4020 cccccccccc cccccccccc ccgcagcgtt gggtcctggc cacgggtgcg catgatcgtg   4080
ctcctgtcgt tgaggacccg gctaggctgg cggggttgcc ttactggtta gcagaatgaa   4140
tcaccgatac gcgagcgaac gtgaagcgac tgctgctgca aaacgtctgc gacctgagca   4200
acaacatgaa tggtcttcgg tttccgtgtt tcgtaaagtc tggaaacgcg gaagtcagcg   4260
ccctgcacca ttatgttccg gatctgcatc gcaggatgct gctggctacc ctgtggaaca   4320
cctacatctg tattaacgaa gcgctggcat tgaccctgag tgattttct ctggtcccgc    4380 cgcatccata ccgccagttg tttaccctca caacgttcca gtaaccgggc atgttcatca   4440
tcagtaaccc gtatcgtgag catcctctct cgtttcatcg gtatcattac ccccatgaac   4500
agaaattccc ccttacacgg aggcatcaag tgaccaaaca ggaaaaaacc gcccttaaca   4560
tggcccgctt tatcagaagc cagacattaa cgcttctgga gaaactcaac gagctggacg   4620
cggatgaaca ggcagacatc tgtgaatcgc ttcacgacca cgctgatgag ctttaccgca   4680
gctgcctcgc gcgtttcggt gatgacggtg aaaacctctg acacatgcag ctcccggaga   4740
cggtcacagc ttgtctgtaa gcggatgccg ggagcagaca gcccgtcag ggcgcgtcag     4800 cgggtgttgg cgggtgtcgg ggcgcagcca tgacccagtc acgtagcgat agcggagtgt   4860
atactggctt aactatgcgg catcagagca gattgtactg agagtgcacc atatgcggtg   4920
tgaaataccg cacagatgcg taaggagaaa ataccgcatc aggcgctctt ccgcttcctc   4980
gctcactgac tcgctgcgct cggtcgttcg gctgcggcga gcggtatcag ctcactcaaa   5040
ggcggtaata cggttatcca cagaatcagg ggataacgca ggaaagaaca tgtgagcaaa   5100
aggccagcaa aaggccagga accgtaaaaa ggccgcgttg ctggcgtttt tccataggct   5160
```

-continued

| | |
|---|---|
| ccgccccct gacgagcatc acaaaaatcg acgctcaagt cagaggtggc gaaacccgac | 5220 |
| aggactataa agataccagg cgtttccccc tggaagctcc ctcgtgcgct ctcctgttcc | 5280 |
| gaccctgccg cttaccggat acctgtccgc ctttctccct tcgggaagcg tggcgctttc | 5340 |
| tcatagctca cgctgtaggt atctcagttc ggtgtaggtc gttcgctcca agctgggctg | 5400 |
| tgtgcacgaa ccccccgttc agcccgaccg ctgcgcctta tccggtaact atcgtcttga | 5460 |
| gtccaacccg gtaagacacg acttatcgcc actggcagca gccactggta acaggattag | 5520 |
| cagagcgagg tatgtaggcg gtgctacaga gttcttgaag tggtggccta actacggcta | 5580 |
| cactagaagg acagtatttg gtatctgcgc tctgctgaag ccagttacct tcggaaaaag | 5640 |
| agttggtagc tcttgatccg gcaaacaaac caccgctggt agcggtggtt ttttgtttg | 5700 |
| caagcagcag attacgcgca gaaaaaaagg atctcaagaa gatcctttga tcttttctac | 5760 |
| ggggtctgac gctcagtgga acgaaaactc acgttaaggg attttggtca tgagattatc | 5820 |
| aaaaaggatc ttcacctaga tccttttaaa ttaaaaatga agttttaaat caatctaaag | 5880 |
| tatatatgag taaacttggt ctgacagtta ccaatgctta atcagtgagg cacctatctc | 5940 |
| agcgatctgt ctatttcgtt catccatagt tgcctgactc cccgtcgtgt agataactac | 6000 |
| gatacgggag ggcttaccat ctggccccag tgctgcaatg ataccgcgag acccacgctc | 6060 |
| accggctcca gatttatcag caataaacca gccagccgga agggccgagc gcagaagtgg | 6120 |
| tcctgcaact ttatccgcct ccatccagtc tattaattgt tgccgggaag ctagagtaag | 6180 |
| tagttcgcca gttaatagtt tgcgcaacgt tgttgccatt gctgcaggca tcgtggtgtc | 6240 |
| acgctcgtcg tttggtatgg cttcattcag ctccggttcc caacgatcaa ggcgagttac | 6300 |
| atgatccccc atgttgtgca aaaaagcggt tagctccttc ggtcctccga tcgttgtcag | 6360 |
| aagtaagttg gccgcagtgt tatcactcat ggttatggca gcactgcata attctcttac | 6420 |
| tgtcatgcca tccgtaagat gcttttctgt gactggtgag tactcaacca agtcattctg | 6480 |
| agaatagtgt atgcggcgac cgagttgctc ttgcccggcg tcaacacggg ataataccgc | 6540 |
| gccacatagc agaactttaa aagtgctcat cattggaaaa cgttcttcgg ggcgaaaact | 6600 |
| ctcaaggatc ttaccgctgt tgagatccag ttcgatgtaa cccactcgtg cacccaactg | 6660 |
| atcttcagca tcttttactt tcaccagcgt ttctgggtga gcaaaaacag gaaggcaaaa | 6720 |
| tgccgcaaaa aagggaataa gggcgacacg gaaatgttga atactcatac tcttcctttt | 6780 |
| tcaatattat tgaagcattt atcagggtta ttgtctcatg agcggataca tatttgaatg | 6840 |
| tatttagaaa aataaacaaa tagggggttcc gcgcacattt ccccgaaaag tgccacctga | 6900 |
| cgtctaagaa accattatta tcatgacatt aacctataaa aataggcgta tcacgaggcc | 6960 |
| ctttcgtctt caa | 6973 |

<210> SEQ ID NO 13
<211> LENGTH: 7591
<212> TYPE: DNA
<213> ORGANISM: vector pFPMT-CHH-E1H6

<400> SEQUENCE: 13

| | |
|---|---|
| ggtaccctgc tcaatctccg gaatggtgat ctgatcgttc ctgaaaacct cgacattggc | 60 |
| tccctcctga cacaggtact cgtacaggtt ccaggtaaac gagtcgtagt tgtcgatcat | 120 |
| gacaacgttc ttagaagcgg ccggcatttt gaaggtgact aatagcctaa gaaaatattt | 180 |
| aatttaattt tcattaaatt ttcctatact cgctatttca gcttttcatc tcatcacttc | 240 |

```
ataaacgata taaaccagaa aaagaactat tttcaaacac gcttctcaaa agcggtatgt    300
ccttccacgt ctccttagaa tctggcaagt ccgcgagggg gatccttaat ggtgatggtg    360
gtggtgccag ttcatcatca tatcccaagc catacggtga cctgttatgt ggccgggata    420
gattgagcaa ttgcagtcct gcaccgtctc atgccggcga ggcgagatgg tgaacagctg    480
ggagacgagg aagacagatc cgcagagatc ccccacgtac atagcggaac agaaagcagc    540
cgccccaacc agcaaatcga cgtggcgtcg tattgtcgta gtggggacgc tggcgttcct    600
agctgcgagc gtgggggtga gcgctaccca gcagcgggaa gagttgttct cccgaacgca    660
gggcacgcac ccggggggtgt gcatgatcat gtccgctgcc tcatacacaa tgcttgagtt    720
ggagcagtcg ttcgtgacat ggtacatccc ggacacgttg cgcacctcat acctcttttc    780
caacgggtgt gtagttccat tctccaccgc tagggctgcg ctgggctcca ttggcgaggt    840
tttcaaggcc gctaggatgc gatccatgcg tccgtagcct tgcgtggagc gtgcgtgtgc    900
gtgcgggagt gcgcataggt aggctacggt gatgattgct agcatggcgg gaatagtttt    960
gctatacatg aattcccgat gaagcagaga gcgcaggagg cggtatttat agtgccattc   1020
ccctctctga gagacccgga tggtagtcga gtgtatcgga gacagcttga tgtagactcc   1080
gtgcctgccg gctcctctta ttggcggaca ccagtgagac accccggaac ttgctgtttt   1140
tctgcaaaat ccggggtgac cagtgggagc ctatttgcac acacgagcgg gacacccac    1200
tctggtgaag agtgccaaag tcattctttt tcccgttgcg gggcagccga ttgcatgttt   1260
taggaaaata ttacctttgc tacaccctgt cagatttacc ctccacacat atatattccg   1320
tcacctccag ggactattat tcgtcgttgc gccgccagcg gaagatatcc agaagctgtt   1380
ttccgagaga ctcggttggc gcctggtata tttgatggat gtcgcgctgc ctcacgtccc   1440
ggtacccagg aacgcggtgg gatctcgggc ccatcgaaga ctgtgctcca gactgctcgc   1500
ccagcaggtg tttcttgatc gccgcctcta aattgtccgc gcatcgccgg taacattttt   1560
ccagctcgga gtttgcgttt agatacagtt tctgcgatgc caaggagcc tgcagattat    1620
aacctcggat gctgtcattc agcgctttta atttgacctc cagatagttg ctgtatttct   1680
gttcccattg gctgctgcgc agcttcgtat aactcgagtt attgttgcgc tctgcctcgg   1740
cgtactggct catgatctgg atcttgtccg tgtcgctttt cttcgagtgt ttctcgcaaa   1800
cgatgtgcac ggcctgcagt gtccaatcgg agtcgagctg gcgccgaaac tggcggatct   1860
gagcctccac actgccctgt ttctctatcc acggcggaac cgcctcctgc cgtttcagaa   1920
tgttgttcaa gtggtactct gtgcggtcaa tgaaggcgtt attgccggtg aaatctttgg   1980
gaagcggttt tcctcgggga agattacgaa attccccgcg tcgttgcgct tcctggatct   2040
cgaggagatc gttctccgcg tcgaggagat cgttctccgc gtcgacacca ttccttgcgg   2100
cggcggtgct caacggcctc aacctactac tgggctgctt cctaatgcag gagtcgcata   2160
agggagagcg tcgacaaacc cgcgtttgag aacttgctca gcttctggt aaacgttgta    2220
gtactctgaa acaaggccct agcactctga tctgtttctc ttgggtagcg gtgagtggtt   2280
tattggagtt cactggtttc agcacatctg tcatctagac aatattgtta ctaaattttt   2340
ttgaactaca attgttcgta attcatctat tattatacat cctcgtcagc aatttctggc   2400
agacggagtt tactaacgtc ttgagtatga ggccgagaat ccagctctgt ggccatactc   2460
agtcttgaca gcctgctgat gtggctgcgt tcaacgcaat aagcgtgtcc tccgactccg   2520
agttgtgctc gttatcgtcg ttctcatcct cggaaaaatc acacgaaaga acatactcac   2580
cagtaggctt tctggtccct ggggcacggc tgtttctgac gtattccggc gttgataata   2640
```

```
gctcgaaagt gaacgccgag tcgcgggagt cgaccgatgc ccttgagagc cttcaaccca    2700
gtcagctcct tccggtgggc gcggggcatg actatcgtcg ccgcacttat gactgtcttc    2760
tttatcatgc aactcgtagg acaggtgccg gcagcgctct gggtcatttt cggcgaggac    2820
cgctttcgct ggagcgcgac gatgatcggc ctgtcgcttg cggtattcgg aatcttgcac    2880
gccctcgctc aagccttcgt cactggtccc gccaccaaac gtttcggcga agcaggcc     2940 attatcgccg gcatggcggc cgacgcgctg gctacgtct tgctggcgtt cgcgacgcga    3000
ggctggatgg ccttccccat tatgattctt ctcgcttccg gcggcatcgg gatgcccgcg    3060
ttgcaggcca tgctgtccag gcaggtagat gacgaccatc agggacagct tcaaggatcg    3120
ctcgcggctc ttaccagcct aacttcgatc actggaccgc tgatcgtcac ggcgatttat    3180
gccgcctcgg cgagcacatg gaacgggttg gcatggattg taggcgccgc cctataccct    3240
gtctgcctcc ccgcgttgcg tcgcggtgca tggagccggg ccacctcgac ctgaatggaa    3300
gccggcggca cctcgctaac ggattcacca ctccaagaat tggagccaat caattcttgc    3360
ggagaactgt gaatgcgcaa accaacccct tggcagaacat atccatcgcg tccgccatct    3420
ccagcagccg cacgcggcgc atcggggggg gggggggggg gggggggcaa acaattcatc    3480 atttttttt tattcttttt tttgatttcg gtttctttga aatttttttg attcggtaat    3540
ctccgaacag aaggaagaac gaaggaagga gcacagactt agattggtat atatacgcat    3600
atgtagtgtt gaagaaacat gaaattgccc agtattctta acccaactgc acagaacaaa    3660
aacctgcagg aaacgaagat aaatcatgtc gaaagctaca tataaggaac gtgctgctac    3720
tcatcctagt cctgttgctg ccaagctatt taatatcatg cacgaaaagc aaacaaactt    3780
gtgtgcttca ttggatgttc gtaccaccaa ggaattactg gagttagttg aagcattagg    3840
tcccaaaatt tgtttactaa aaacacatgt ggatatcttg actgattttt ccatggaggg    3900
cacagttaag ccgctaaagg cattatccgc caagtacaat tttttactct tcgaagacag    3960
aaaatttgct gacattggta atacagtcaa attgcagtac tctgcgggtg tatacagaat    4020
agcagaatgg gcagacatta cgaatgcaca cggtgtggtg ggcccaggta ttgttagcgg    4080
tttgaagcag gcggcagaag aagtaacaaa ggaacctaga ggccttttga tgttagcaga    4140
attgtcatgc aagggctccc tatctactgg agaatatact aagggtactg ttgacattgc    4200
gaagagcgac aaagatttg ttatcggctt tattgctcaa agagacatgg gtggaagaga    4260
tgaaggttac gattggttga ttatgacacc cggtgtgggt ttagatgaca agggagacgc    4320
attgggtcaa cagtatagaa ccgtggatga tgtggtctct acaggatctg acattattat    4380
tgttggaaga ggactatttg caaagggaag ggatgctaag gtagagggtg aacgttacag    4440
aaaagcaggc tgggaagcat atttgagaag atgcggccag caaaactaaa aaactgtatt    4500
ataagtaaat gcatgtatac taaactcaca aattagagct tcaattaat tatatcagtt    4560 attaccggg aatctcggtc gtaatgatt ttataatgac gaaaaaaaa aaattggaaa    4620 gaaaagcccc cccccccc cccccccc ccccccccc gcagcgttgg gtcctggcca    4680
cgggtgcgca tgatcgtgct cctgtcgttg aggacccggc taggctggcg gggttgcctt    4740
actggttagc agaatgaatc accgatacgc gagcgaacgt gaagcgactg ctgctgcaaa    4800
acgtctgcga cctgagcaac aacatgaatg gtcttcggtt tccgtgtttc gtaaagtctg    4860
gaaacgcgga agtcagcgcc ctgcaccatt atgttccgga tctgcatcgc aggatgctgc    4920
tggctaccct gtggaacacc tacatctgta ttaacgaagc gctggcattg accctgagtg    4980
```

```
atttttctct ggtcccgccg catccatacc gccagttgtt taccctcaca acgttccagt      5040
aaccgggcat gttcatcatc agtaacccgt atcgtgagca tcctctctcg tttcatcggt      5100
atcattaccc ccatgaacag aaattccccc ttacacggag gcatcaagtg accaaacagg      5160
aaaaaaccgc ccttaacatg gcccgcttta tcagaagcca gacattaacg cttctggaga      5220
aactcaacga gctggacgcg gatgaacagg cagacatctg tgaatcgctt cacgaccacg      5280
ctgatgagct ttaccgcagc tgcctcgcgc gtttcggtga tgacggtgaa aacctctgac      5340
acatgcagct cccggagacg gtcacagctt gtctgtaagc ggatgccggg agcagacaag      5400
cccgtcaggg cgcgtcagcg ggtgttggcg ggtgtcgggg cgcagccatg acccagtcac      5460
gtagcgatag cggagtgtat actggcttaa ctatgcggca tcagagcaga ttgtactgag      5520
agtgcaccat atgcggtgtg aaataccgca cagatgcgta aggagaaaat accgcatcag      5580
gcgctcttcc gcttcctcgc tcactgactc gctgcgctcg tcgttcggc tgcggcgagc       5640 ggtatcagct cactcaaagg cggtaatacg gttatccaca gaatcagggg ataacgcagg      5700
aaagaacatg tgagcaaaag gccagcaaaa ggccaggaac cgtaaaaagg ccgcgttgct      5760
ggcgtttttc cataggctcc gcccccctga cgagcatcac aaaaatcgac gctcaagtca      5820
gaggtggcga aacccgacag gactataaag ataccaggcg tttccccctg gaagctccct      5880
cgtgcgctct cctgttccga ccctgccgct taccggatac ctgtccgcct ttctcccttc      5940
gggaagcgtg gcgctttctc atagctcacg ctgtaggtat ctcagttcgg tgtaggtcgt      6000
tcgctccaag ctgggctgtg tgcacgaacc ccccgttcag cccgaccgct gcgccttatc      6060
cggtaactat cgtcttgagt ccaacccggt aagacacgac ttatcgccac tggcagcagc      6120
cactggtaac aggattagca gagcgaggta tgtaggcggt gctacagagt tcttgaagtg      6180
gtggcctaac tacggctaca ctagaaggac agtatttggt atctgcgctc tgctgaagcc      6240
agttaccttc ggaaaaagag ttggtagctc ttgatccggc aaacaaacca ccgctggtag      6300
cggtggtttt tttgtttgca agcagcagat tacgcgcaga aaaaaggat ctcaagaaga       6360 tcctttgatc ttttctacgg ggtctgacgc tcagtggaac gaaaactcac gttaagggat      6420
tttggtcatg agattatcaa aaaggatctt cacctagatc cttttaaatt aaaaatgaag      6480
ttttaaatca atctaaagta tatatgagta aacttggtct gacagttacc aatgcttaat      6540
cagtgaggca cctatctcag cgatctgtct atttcgttca tccatagttg cctgactccc      6600
cgtcgtgtag ataactacga tacgggaggg cttaccatct ggccccagtg ctgcaatgat      6660
accgcgagac ccacgctcac cggctccaga tttatcagca ataaaccagc cagccggaag      6720
ggccgagcgc agaagtggtc ctgcaacttt atccgcctcc atccagtcta ttaattgttg      6780
ccgggaagct agagtaagta gttcgccagt taatagtttg cgcaacgttg ttgccattgc      6840
tgcaggcatc gtggtgtcac gctcgtcgtt tggtatggct tcattcagct ccggttccca      6900
acgatcaagg cgagttacat gatcccccat gttgtgcaaa aaagcggtta gctccttcgg      6960
tcctccgatc gttgtcagaa gtaagttggc cgcagtgtta tcactcatgg ttatggcagc      7020
actgcataat tctcttactg tcatgccatc cgtaagatgc ttttctgtga ctggtgagta      7080
ctcaaccaag tcattctgag aatagtgtat gcggcgaccg agttgctctt gcccggcgtc      7140
aacacgggat aataccgcgc cacatagcag aactttaaaa gtgctcatca ttggaaaacg      7200
ttcttcgggg cgaaaactct caaggatctt accgctgttg agatccagtt cgatgtaacc      7260
cactcgtgca cccaactgat cttcagcatc ttttactttc accagcgttt ctgggtgagc      7320
aaaaacagga aggcaaaatg ccgcaaaaaa gggaataagg gcgacacgga aatgttgaat      7380
```

```
actcatactc ttccttttc aatattattg aagcatttat cagggttatt gtctcatgag      7440
cggatacata tttgaatgta tttagaaaaa taaacaaata ggggttccgc gcacatttcc      7500
ccgaaaagtg ccacctgacg tctaagaaac cattattatc atgacattaa cctataaaaa      7560
taggcgtatc acgaggccct ttcgtcttca a                                    7591

<210> SEQ ID NO 14
<211> LENGTH: 50
<212> TYPE: DNA
<213> ORGANISM: synthetic probe or primer

<400> SEQUENCE: 14
aggggtaagc ttggataaaa ggtatgaggt gcgcaacgtg tccgggatgt                  50

<210> SEQ ID NO 15
<211> LENGTH: 42
<212> TYPE: DNA
<213> ORGANISM: synthetic probe or primer

<400> SEQUENCE: 15
agttacggat ccttaatggt gatggtggtg gtgccagttc at                          42

<210> SEQ ID NO 16
<211> LENGTH: 7648
<212> TYPE: DNA
<213> ORGANISM: vector pFPMT-Mfalfa-E1-H6

<400> SEQUENCE: 16
ggtaccctgc tcaatctccg gaatggtgat ctgatcgttc ctgaaaacct cgacattggc       60
tccctcctga cacaggtact cgtacaggtt ccaggtaaac gagtcgtagt tgtcgatcat      120
gacaacgttc ttagaagcgg ccggcatttt gaaggtgact aatagcctaa gaaatatttt     180
aatttaattt tcattaaatt ttcctatact cgctatttca gcttttcatc tcatcacttc      240
ataaacgata taaaccagaa aaagaactat tttcaaacac gcttctcaaa gcggtatgt       300 ccttccacgt ctccttagaa tctggcaagt ccgcgagggg gatccttaat ggtgatggtg      360
gtggtgccag ttcatcatca tatcccaagc catacggtga cctgttatgt ggccgggata      420
gattgagcaa ttgcagtcct gcaccgtctc atgccggcga ggcagatgg tgaacagctg       480 ggagacgagg aagacagatc cgcagagatc ccccacgtac atagcggaac agaaagcagc      540
cgccccaacg agcaaatcga cgtggcgtcg tattgtcgta gtggggacgc tggcgttcct      600
agctgcgagc gtgggggtga gcgctaccca gcagcgggaa gagttgttct cccgaacgca      660
gggcacgcac ccggggtgt gcatgatcat gtccgctgcc tcatacacaa tgcttgagtt       720
ggagcagtcg ttcgtgacat ggtacatccc ggacacgttg cgcacctcat acctttatc      780 caagcttacc ccttcttctt tagcagcaat gctggcaata gtagtattta taaacaataa     840
cccgttattt gtgctgttgg aaaatggcaa aacagcaaca tcgaaatccc cttctaaatc     900
tgagtaaccg atgacagctt cagccggaat tgtgccgtt tcatcttctg ttgtagtgtt      960
gactggagca gctaatgcgg aggatgctgc gaataaaact gcagtaaaaa ttgaaggaaa    1020
tctcatgaat tcccgatgaa gcagagagcg caggaggcgg tatttatagt gccattcccc    1080
tctctgagag acccggatgg tagtcgagtg tatcggagac agcttgatgt agactccgtg    1140
cctgccggct cctcttattg gcggacacca gtgagacacc ccggaacttg ctgttttct     1200 gcaaaatccg gggtgaccag tgggagccta tttgcacaca cgagcgggac accccactct    1260
```

-continued

```
ggtgaagagt gccaaagtca ttcttttttcc cgttgcgggg cagccgattg catgttttag    1320
gaaaatatta cctttgctac accctgtcag atttaccctc cacacatata tattccgtca    1380
cctccaggga ctattattcg tcgttgcgcc gccagcggaa gatatccaga agctgttttc    1440
cgagagactc ggttggcgcc tggtatattt gatggatgtc gcgctgcctc acgtcccggt    1500
acccaggaac gcggtgggat ctcgggccca tcgaagactg tgctccagac tgctcgccca    1560
gcaggtgttt cttgatcgcc gcctctaaat tgtccgcgca tcgccggtaa cattttccca    1620
gctcggagtt tgcgtttaga tacagttct gcgatgccaa aggagcctgc agattataac    1680
ctcggatgct gtcattcagc gcttttaatt tgacctccag atagttgctg tatttctgtt    1740
cccattggct gctgcgcagc ttcgtataac tcgagttatt gttgcgctct gcctcggcgt    1800
actggctcat gatctggatc ttgtccgtgt cgcttttctt cgagtgtttc tcgcaaacga    1860
tgtgcacggc ctgcagtgtc caatcggagt cgagctggcg ccgaaactgg cggatctgag    1920
cctccacact gccctgtttc tctatccacg gcggaaccgc tcctgccgt ttcagaatgt    1980 tgttcaagtg gtactctgtg cggtcaatga aggcgttatt gccggtgaaa tctttgggaa    2040
gcggttttcc tcggggaaga ttacgaaatt ccccgcgtcg ttgcgcttcc tggatctcga    2100
ggagatcgtt ctccgcgtcg aggagatcgt tctccgcgtc gacaccattc cttgcggcgg    2160
cggtgctcaa cggcctcaac ctactactgg gctgcttcct aatgcaggag tcgcataagg    2220
gagagcgtcg acaaacccgc gtttgagaac ttgctcaagc ttctggtaaa cgttgtagta    2280
ctctgaaaca aggccctagc actctgatct gtttctcttg ggtagcggtg agtggtttat    2340
tggagttcac tggtttcagc acatctgtca tctagacaat attgttacta aatttttttg    2400
aactacaatt gttcgtaatt catctattat tatacatcct cgtcagcaat ttctggcaga    2460
cggagtttac taacgtcttg agtatgaggc cgagaatcca gctctgtggc catactcagt    2520
cttgacagcc tgctgatgtg gctgcgttca acgcaataag cgtgtcctcc gactccgagt    2580
tgtgctcgtt atcgtcgttc tcatcctcgg aaaaatcaca cgaaagaaca tactcaccag    2640 taggcttttct ggtccctggg gcacggctgt tctgacgta ttccggcgtt gataatagct    2700
cgaaagtgaa cgccgagtcg cgggagtcga ccgatgccct tgagagcctt caacccagtc    2760
agctccttcc ggtgggcgcg gggcatgact atcgtcgccg cacttatgac tgtcttcttt    2820
atcatgcaac tcgtaggaca ggtgccggca gcgctctggg tcattttcgg cgaggaccgc    2880
tttcgctgga gcgcgacgat gatcggcctg tcgcttgcgg tattcggaat cttgcacgcc    2940
ctcgctcaag ccttcgtcac tggtcccgcc accaaacgtt tcggcgagaa gcaggccatt    3000
atcgccggca tggcggccga cgcgctgggc tacgtcttgc tggcgttcgc gacgcgaggc    3060
tggatggcct tccccattat gattcttctc gcttccggcg gcatcgggat gcccgcgttg    3120
caggccatgc tgtccaggca ggtagatgac gaccatcagg gacagcttca aggatcgctc    3180
gcggctctta ccagcctaac ttcgatcact ggaccgctga tcgtcacggc gatttatgcc    3240
gcctcggcga gcacatggaa cgggttggca tggattgtag gcgccgccct ataccttgtc    3300
tgcctccccg cgttgcgtcg cggtgcatgg agccgggcca cctcgacctg aatggaagcc    3360
ggcggcacct cgctaacgga ttcaccactc caagaattgg agccaatcaa ttcttgcgga    3420
gaactgtgaa tgcgcaaacc aaccttggc agaacatatc catcgcgtcc gccatctcca    3480
gcagccgcac gcggcgcatc gggggggggg gggggggggg gggcaaaca attcatcatt    3540 tttttttttat tcttttttttt gatttcggtt tcttgaaat ttttttgatt cggtaatctc    3600
cgaacagaag gaagaacgaa ggaaggagca cagacttaga ttggtatata tacgcatatg    3660
```

-continued

```
tagtgttgaa gaaacatgaa attgcccagt attcttaacc caactgcaca gaacaaaaac    3720
ctgcaggaaa cgaagataaa tcatgtcgaa agctacatat aaggaacgtg ctgctactca    3780
tcctagtcct gttgctgcca agctatttaa tatcatgcac gaaaagcaaa caaacttgtg    3840
tgcttcattg gatgttcgta ccaccaagga attactggag ttagttgaag cattaggtcc    3900
caaaatttgt ttactaaaaa cacatgtgga tatcttgact gattttttcca tggagggcac    3960 agttaagccg ctaaaggcat tatccgccaa gtacaatttt ttactcttcg aagacagaaa    4020
atttgctgac attggtaata cagtcaaatt gcagtactct gcgggtgtat acagaatagc    4080
agaatgggca gacattacga atgcacacgg tgtggtgggc ccaggtattg ttagcggttt    4140
gaagcaggcg gcagaagaag taacaaagga acctagaggc cttttgatgt tagcagaatt    4200
gtcatgcaag ggctccctat ctactggaga atatactaag ggtactgttg acattgcgaa    4260
gagcgacaaa gattttgtta tcggctttat tgctcaaaga gacatgggtg aagagatga    4320 aggttacgat tggttgatta tgacacccgg tgtgggttta gatgacaagg gagacgcatt    4380
gggtcaacag tatagaaccg tggatgatgt ggtctctaca ggatctgaca ttattattgt    4440
tggaagagga ctatttgcaa agggaaggga tgctaaggta gagggtgaac gttacagaaa    4500
agcaggctgg gaagcatatt tgagaagatg cggccagcaa aactaaaaaa ctgtattata    4560
agtaaatgca tgtatactaa actcacaaat tagagcttca atttaattat atcagttatt    4620
acccgggaat ctcggtcgta atgatttta taatgacgaa aaaaaaaaaa ttggaaagaa    4680 aagcccccc cccccccccc cccccccccc ccccccgca gcgttgggtc ctggccacgg    4740
gtgcgcatga tcgtgctcct gtcgttgagg acccggctag gctggcgggg ttgccttact    4800
ggttagcaga atgaatcacc gatacgcgag cgaacgtgaa gcgactgctg ctgcaaaacg    4860
tctgcgacct gagcaacaac atgaatggtc ttcggtttcc gtgtttcgta aagtctggaa    4920
acgcggaagt cagcgccctg caccattatg ttccggatct gcatcgcagg atgctgctgg    4980
ctaccctgtg gaacacctac atctgtatta cgaagcgct ggcattgacc ctgagtgatt    5040
tttctctggt cccgccgcat ccataccgcc agttgtttac cctcacaacg ttccagtaac    5100
cgggcatgtt catcatcagt aacccgtatc gtgagcatcc tctctcgttt catcggtatc    5160 attacccccca tgaacagaaa ttccccctta cacggaggca tcaagtgacc aaacaggaaa    5220
aaaccgccct taacatggcc cgctttatca gaagccagac attaacgctt ctggagaaac    5280
tcaacgagct ggacgcggat gaacaggcag acatctgtga atcgcttcac gaccacgctg    5340
atgagcttta ccgcagctgc ctcgcgcgtt tcggtgatga cggtgaaaac ctctgacaca    5400
tgcagctccc ggagacggtc acagcttgtc tgtaagcgga tgccgggagc agacaagccc    5460
gtcagggcgc gtcagcgggt gttggcgggt gtcggggcgc agccatgacc cagtcacgta    5520
gcgatagcgg agtgtatact ggcttaacta tgcggcatca gagcagattg tactgagagt    5580
gcaccatatg cggtgtgaaa taccgcacag atgcgtaagg agaaaatacc gcatcaggcg    5640
ctcttccgct tcctcgctca ctgactcgct gcgctcggtc gttcggctgc ggcgagcggt    5700
atcagctcac tcaaaggcgg taatacggtt atccacagaa tcagggata acgcaggaaa    5760 gaacatgtga gcaaaaggcc agcaaaaggc caggaaccgt aaaaaggccg cgttgctggc    5820 gttttccat aggctccgcc cccctgacga gcatcacaaa aatcgacgct caagtcagag    5880
gtggcgaaac ccgacaggac tataaagata ccaggcgttt ccccctggaa gctccctcgt    5940
gcgctctcct gttccgaccc tgccgcttac cggatacctg tccgcctttc tcccttcggg    6000
```

-continued

```
aagcgtggcg ctttctcata gctcacgctg taggtatctc agttcggtgt aggtcgttcg   6060
ctccaagctg ggctgtgtgc acgaaccccc cgttcagccc gaccgctgcg ccttatccgg   6120
taactatcgt cttgagtcca acccggtaag acacgactta tcgccactgg cagcagccac   6180
tggtaacagg attagcagag cgaggtatgt aggcggtgct acagagttct tgaagtggtg   6240
gcctaactac ggctacacta gaaggacagt atttggtatc tgcgctctgc tgaagccagt   6300
taccttcgga aaaagagttg gtagctcttg atccggcaaa caaaccaccg ctggtagcgg   6360
tggttttttt gtttgcaagc agcagattac gcgcagaaaa aaaggatctc aagaagatcc   6420
tttgatcttt tctacggggt ctgacgctca gtggaacgaa aactcacgtt aagggatttt   6480
ggtcatgaga ttatcaaaaa ggatcttcac ctagatcctt ttaaattaaa aatgaagttt   6540
taaatcaatc taaagtatat atgagtaaac ttggtctgac agttaccaat gcttaatcag   6600
tgaggcacct atctcagcga tctgtctatt tcgttcatcc atagttgcct gactccccgt   6660
cgtgtagata actacgatac gggagggctt accatctggc cccagtgctg caatgatacc   6720
gcgagaccca cgctcaccgg ctccagattt atcagcaata aaccagccag ccggaagggc   6780
cgagcgcaga agtggtcctg caactttatc cgcctccatc cagtctatta attgttgccg   6840
ggaagctaga gtaagtagtt cgccagttaa tagtttgcgc aacgttgttg ccattgctgc   6900
aggcatcgtg gtgtcacgct cgtcgtttgg tatggcttca ttcagctccg gttcccaacg   6960
atcaaggcga gttacatgat cccccatgtt gtgcaaaaaa gcggttagct ccttcggtcc   7020
tccgatcgtt gtcagaagta agttggccgc agtgttatca ctcatggtta tggcagcact   7080
gcataattct cttactgtca tgccatccgt aagatgcttt tctgtgactg gtgagtactc   7140
aaccaagtca ttctgagaat agtgtatgcg gcgaccgagt tgctcttgcc cggcgtcaac   7200
acgggataat accgcgccac atagcagaac tttaaaagtg ctcatcattg gaaaacgttc   7260
ttcggggcga aaactctcaa ggatcttacc gctgttgaga tccagttcga tgtaacccac   7320
tcgtgcaccc aactgatctt cagcatcttt tactttcacc agcgtttctg ggtgagcaaa   7380
aacaggaagg caaaatgccg caaaaaaggg aataagggcg acacggaaat gttgaatact   7440
catactcttc ctttttcaat attattgaag catttatcag ggttattgtc tcatgagcgg   7500
atacatattt gaatgtattt agaaaaataa acaaataggg gttccgcgca catttccccg   7560
aaaagtgcca cctgacgtct aagaaaccat tattatcatg acattaacct ataaaaatag   7620
gcgtatcacg aggccctttc gtcttcaa                                      7648
```

<210> SEQ ID NO 17
<211> LENGTH: 4453
<212> TYPE: DNA
<213> ORGANISM: vector pUC18-FMD-MFalfa-E1-H6
<220> FEATURE:
<221> NAME/KEY: misc_feature
<222> LOCATION: (1207)..(1208)
<223> OTHER INFORMATION: N is any nucleotide
<220> FEATURE:
<221> NAME/KEY: misc_feature
<222> LOCATION: (1386)..(1387)
<223> OTHER INFORMATION: N is any nucleotide

<400> SEQUENCE: 17

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg aattcgagct    240
```

-continued

```
cggtacccgg ggatccttaa tggtgatggt ggtggtgcca gttcatcatc atatcccaag      300
ccatacggtg acctgttatg tggccgggat agattgagca attgcagtcc tgcaccgtct      360
catgccggcg aggcgagatg gtgaacagct gggagacgag gaagacagat ccgcagagat      420
cccccacgta catagcggaa cagaaagcag ccgccccaac gagcaaatcg acgtggcgtc      480
gtattgtcgt agtggggacg ctggcgttcc tagctgcgag cgtggggtg agcgctaccc       540
agcagcggga agagttgttc tcccgaacgc agggcacgca cccggggtg tgcatgatca       600
tgtccgctgc ctcatacaca atgcttgagt tggagcagtc gttcgtgaca tggtacatcc      660
cggacacgtt gcgcacctca tacctttat ccaagcttac cccttcttct ttagcagcaa       720
tgctggcaat agtagtattt ataaacaata acccgttatt tgtgctgttg gaaaatggca      780
aaacagcaac atcgaaatcc ccttctaaat ctgagtaacc gatgacagct tcagccggaa      840
tttgtgccgt ttcatcttct gttgtagtgt tgactggagc agctaatgcg gaggatgctg      900
cgaataaaac tgcagtaaaa attgaaggaa atctcatgaa ttcccgatga aggcagagag      960
cgcaaggagg cggtatttat agtgccattc ccctctctga gagacccgga tggtagtcga      1020
gtgttatcgg agacagcttg atgtagactc cgtgcctgcc ggtcctctta ttggcggaca     1080
ccagtgagac accccggaac ttgctgtttt tctgcaaaat ccggggtgac cagtgggagc     1140
ctatttgcac acacgagcgg gacaccccac tctggtgaag agtgccaaag tcattctttt     1200
tcccgtnncg gggcagccga ttgcatgttt taggaaaata ttacctttgc tacaccctgt     1260
cagatttacc ctccacacat atatattccg tcacctccag ggactattct tggctcgttg     1320
cgccgccgcg gaagatatcc agaagctgtg ttttccgaga gactcggttg gcgcctggta     1380
tatttnnagg atgtcgcgct gcctcacgtc ccggtaccca ggaacgcggt gggatctcgg     1440
gcccatcgaa gactgtgctc cagactgctc gcccagcagg tgtttcttga ttgccgcctc     1500
taaatagtcc gcgcatcgcc ggtaacattt ttccagctcg gagtttgcgt ttagatacat     1560
ttctgcgatg ccaaggagc ctgcagatta taacctcgga tgctgtcatt cagcgctttt      1620
aatttgacct ccagatagtt gctgtatttc tgttccattg gctgctggac gttcgtataa     1680
ctcgagttat tgttgcgctc tgcctcggcg tactggctca tgactgactg cggtcgcttc     1740
tcgagtgttc tcgcaacagg acgcctgcag gtcatcgagt cgagctggcg ccgaaactgg     1800
cggatctgac ctccacactg ccctgtatct ctatccaccg ggaaccgcct cctgccgttc     1860
cagaatgttg ttcaagtggt agctctgtgc ggtcaatgaa ggcgttattg ccggtgaaat     1920
cttttgggaag cggtttatcc tcggggaaga ttacgaaatt cccgcgcgtc gttgcgcttc    1980
ctggatctcg aggaagatcg ttctccgcgt cgaggagatc gttctccgcg tcgacctgca     2040
ggcatgcaag cttggcactg ccgtcgtttt acaacgtcg tgactgggaa accctggcg       2100
ttacccaact taatcgcctt gcagcacatc cccctttcgc cagctggcgt aatagcgaag     2160
aggcccgcac cgatcgccct tcccaacagt tgcgcagcct gaatggcgaa tggcgcctga     2220
tgcggtattt tctccttacg catctgtgcg gtatttcaca ccgcatatgg tgcactctca     2280
gtacaatctg ctctgatgcc gcatagttaa gccagccccg acacccgcca cacccgctg     2340
acgcgccctg acgggcttgt ctgctcccgg catccgctta cagacaagct gtgaccgtct     2400
ccgggagctg catgtgtcag aggttttcac cgtcatcacc gaaacgcgcg agacgaaagg    2460
gcctcgtgat acgcctattt ttataggtta atgtcatgat aataatggtt tcttagacgt     2520
caggtggcac ttttcgggga aatgtgcgcg gaacccctat ttgtttattt ttctaaatac    2580
```

-continued

```
attcaaatat gtatccgctc atgagacaat aaccctgata aatgcttcaa taatattgaa    2640
aaaggaagag tatgagtatt caacatttcc gtgtcgccct tattccctt tttgcggcat    2700 tttgccttcc tgttttgct cacccagaaa cgctggtgaa agtaaaagat gctgaagatc    2760
agttgggtgc acgagtgggt tacatcgaac tggatctcaa cagcggtaag atccttgaga    2820
gttttcgccc cgaagaacgt tttccaatga tgagcacttt taaagttctg ctatgtggcg    2880
cggtattatc ccgtattgac gccgggcaag agcaactcgg tcgccgcata cactattctc    2940
agaatgactt ggttgagtac tcaccagtca cagaaaagca tcttacggat ggcatgacag    3000
taagagaatt atgcagtgct gccataacca tgagtgataa cactgcggcc aacttacttc    3060
tgacaacgat cggaggaccg aaggagctaa ccgcttttt gcacaacatg ggggatcatg    3120
taactcgcct tgatcgttgg gaaccggagc tgaatgaagc cataccaaac gacgagcgtg    3180
acaccacgat gcctgtagca atggcaacaa cgttgcgcaa actattaact ggcgaactac    3240
ttactctagc ttcccggcaa caattaatag actggatgga ggcggataaa gttgcaggac    3300
cacttctgcg ctcggccctt ccggctggct ggtttattgc tgataaatct ggagccggtg    3360
agcgtgggtc tcgcggtatc attgcagcac tggggccaga tggtaagccc tcccgtatcg    3420
tagttatcta cacgacgggg agtcaggcaa ctatggatga acgaaataga cagatcgctg    3480
agataggtgc tcactgatt aagcattggt aactgtcaga ccaagtttac tcatatatac    3540
tttagattga tttaaaactt catttttaat ttaaaaggat ctaggtgaag atcctttttg    3600
ataatctcat gaccaaaatc ccttaacgtg agttttcgtt ccactgagcg tcagaccccg    3660
tagaaaagat caaaggatct cttgagatc cttttttct gcgcgtaatc tgctgcttgc    3720
aaacaaaaaa accaccgcta ccagcggtgg tttgtttgcc ggatcaagag ctaccaactc    3780
tttttccgaa ggtaactggc ttcagcagag cgcagatacc aaatactgtc cttctagtgt    3840
agccgtagtt aggccaccac ttcaagaact ctgtagcacc gcctacatac ctcgctctgc    3900
taatcctgtt accagtggct gctgccagtg gcgataagtc gtgtcttacc gggttggact    3960
caagacgata gttaccggat aaggcgcagc ggtcgggctg aacggggggt tcgtgcacac    4020
agcccagctt ggagcgaacg acctacaccg aactgagata cctacagcgt gagctatgag    4080
aaagcgccac gcttcccgaa gggagaaagg cggacaggta tccggtaagc ggcagggtcg    4140
gaacaggaga gcgcacgagg gagcttccag ggggaaacgc ctggtatctt tatagtcctg    4200
tcgggtttcg ccacctctga cttgagcgtc gatttttgtg atgctcgtca ggggggcgga    4260
gcctatggaa aaacgccagc aacgcggcct ttttacggtt cctggccttt tgctggcctt    4320
ttgctcacat gttctttcct gcgttatccc ctgattctgt ggataaccgt attaccgcct    4380
ttgagtgagc tgataccgct cgccgcagcc gaacgaccga gcgcagcgag tcagtgagcg    4440
aggaagcgga aga                                                       4453
```

<210> SEQ ID NO 18
<211> LENGTH: 51
<212> TYPE: DNA
<213> ORGANISM: synthetic probe or primer

<400> SEQUENCE: 18

```
tgcttcctac cactagcagc actaggatat gaggtgcgca acgtgtccgg g              51
```

<210> SEQ ID NO 19
<211> LENGTH: 52
<212> TYPE: DNA
<213> ORGANISM: synthetic probe or primer -continued

<400> SEQUENCE: 19
tagtactagt attagtaggc ttcgcatgaa ttcccgatga aggcagagag cg 52

<210> SEQ ID NO 20
<211> LENGTH: 4252
<212> TYPE: DNA
<213> ORGANISM: vector pUC18-FMD-CL-E1-H6
<220> FEATURE:
<221> NAME/KEY: misc_feature
<222> LOCATION: (1006)..(1007)
<223> OTHER INFORMATION: N is any nucleotide
<220> FEATURE:
<221> NAME/KEY: misc_feature
<222> LOCATION: (1185)..(1186)
<223> OTHER INFORMATION: N is any nucleotide

<400> SEQUENCE: 20
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240
cggtacccgg ggatccttaa tggtgatggt ggtggtgcca gttcatcatc atatcccaag 300
ccatacggtg acctgttatg tggccgggat agattgagca attgcagtcc tgcaccgtct 360
catgccggcg aggcgagatg gtgaacagct gggagacgag gaagacagat ccgcagagat 420
cccccacgta catagcggaa cagaaagcag ccgccccaac gagcaaatcg acgtggcgtc 480
gtattgtcgt agtggggacg ctggcgttcc tagctgcgag cgtgggggtg agcgctaccc 540
agcagcggga agagttgttc tcccgaacgc agggcacgca cccgggggtg tgcatgatca 600
tgtccgctgc ctcatacaca atgcttgagt tggagcagtc gttcgtgaca tggtacatcc 660
cggacacgtt gcgcacctca tatcctagtg ctgctagtgg taggaagcat agtactagta 720
ttagtaggct tcgcatgaat tcccgatgaa ggcagagagc gcaaggaggc ggtatttata 780
gtgccattcc cctctctgag agacccggat ggtagtcgag tgttatcgga gacagcttga 840
tgtagactcc gtgcctgccg gtcctcttat tggcggacac cagtgagaca ccccggaact 900
tgctgttttt ctgcaaaatc cggggtgacc agtgggagcc tatttgcaca cacgagcggg 960
acaccccact ctggtgaaga gtgccaaagt cattcttttt cccgtnncgg ggcagccgat 1020
tgcatgtttt aggaaaatat tacctttgct acaccctgtc agatttaccc tccacacata 1080
tatattccgt cacctccagg gactattctt ggctcgttgc gccgccgcgg aagatatcca 1140
gaagctgtgt tttccgagag actcggttgg cgcctggtat atttnnagga tgtcgcgctg 1200
cctcacgtcc cggtacccag gaacgcggtg ggatctcggg cccatcgaag actgtgctcc 1260
agactgctcg cccagcaggt gtttcttgat tgccgcctct aaatagtccg cgcatcgccg 1320
gtaacatttt tccagctcgg agtttgcgtt tagatacatt tctgcgatgc caaaggagcc 1380
tgcagattat aacctcggat gctgtcattc agcgctttta atttgacctc cagatagttg 1440
ctgtatttct gttccattgg ctgctggacg ttcgtataac tcgagttatt gttgcgctct 1500
gcctcggcgt actggctcat gactgactgc ggtcgcttct cgagtgttct cgcaacagga 1560
cgcctgcagg tcatcgagtc gagctggcgc cgaaactggc ggatctgacc tccacactgc 1620
cctgtatctc tatccaccgg gaaccgcctc ctgccgttcc agaatgttgt tcaagtggta 1680
gctctgtgcg gtcaatgaag gcgttattgc cggtgaaatc tttgggaagc ggtttatcct 1740

-continued

```
cggggaagat tacgaaattc ccgcgcgtcg ttgcgcttcc tggatctcga ggaagatcgt    1800
tctccgcgtc gaggagatcg ttctccgcgt cgacctgcag gcatgcaagc ttggcactgg    1860
ccgtcgtttt acaacgtcgt gactgggaaa accctggcgt tacccaactt aatcgccttg    1920
cagcacatcc cccttcgcc agctggcgta atagcgaaga ggcccgcacc gatcgccctt    1980
cccaacagtt gcgcagcctg aatggcgaat ggcgcctgat gcggtatttt ctccttacgc    2040
atctgtgcgg tatttcacac cgcatatggt gcactctcag tacaatctgc tctgatgccg    2100
catagttaag ccagccccga cacccgccaa cacccgctga cgcgccctga cgggcttgtc    2160
tgctcccggc atccgcttac agacaagctg tgaccgtctc cggagctgc atgtgtcaga    2220
ggttttcacc gtcatcaccg aaacgcgcga cgaaaggg cctcgtgata cgcctatttt    2280
tataggttaa tgtcatgata ataatggttt cttagacgtc aggtggcact tttcggggaa    2340
atgtgcgcgg aacccctatt tgtttatttt tctaaataca ttcaaatatg tatccgctca    2400
tgagacaata accctgataa atgcttcaat aatattgaaa aaggaagagt atgagtattc    2460
aacatttccg tgtcgccctt attcccttt ttgcggcatt ttgccttcct gttttgctc    2520
acccagaaac gctggtgaaa gtaaaagatg ctgaagatca gttgggtgca cgagtgggtt    2580
acatcgaact ggatctcaac agcggtaaga tccttgagag ttttcgcccc gaagaacgtt    2640
ttccaatgat gagcactttt aaagttctgc tatgtggcgc ggtattatcc cgtattgacg    2700
ccgggcaaga gcaactcggt cgccgcatac actattctca gaatgacttg gttgagtact    2760
caccagtcac agaaaagcat cttacggatg gcatgacagt aagagaatta tgcagtgctg    2820
ccataaccat gagtgataac actgcggcca acttacttct gacaacgatc ggaggaccga    2880
aggagctaac cgcttttttg cacaacatgg ggatcatgt aactcgcctt gatcgttggg    2940
aaccggagct gaatgaagcc ataccaaacg acgagcgtga ccaccgatg cctgtagcaa    3000
tggcaacaac gttgcgcaaa ctattaactg gcgaactact tactctagct tcccggcaac    3060
aattaataga ctggatggag gcggataaag ttgcaggacc acttctgcgc tcggcccttc    3120
cggctggctg gtttattgct gataaatctg gagccggtga gcgtgggtct cgcggtatca    3180
ttgcagcact ggggccagat ggtaagccct cccgtatcgt agttatctac acgacgggga    3240
gtcaggcaac tatggatgaa cgaaatagac agatcgctga gataggtgcc tcactgatta    3300
agcattggta actgtcagac caagtttact catatatact ttagattgat ttaaaacttc    3360
atttttaatt taaaaggatc taggtgaaga tcctttttga taatctcatg accaaaatcc    3420
cttaacgtga gttttcgttc cactgagcgt cagaccccgt agaaaagatc aaaggatctt    3480
cttgagatcc tttttttctg cgcgtaatct gctgcttgca acaaaaaaa ccaccgctac    3540
cagcggtggt ttgtttgccg gatcaagagc taccaactct ttttccgaag gtaactggct    3600
tcagcagagc gcagatacca atactgtcc ttctagtgta gccgtagtta ggccaccact    3660
tcaagaactc tgtagcaccg cctacatacc tcgctctgct aatcctgtta ccagtggctg    3720
ctgccagtgg cgataagtcg tgtcttaccg ggttggactc aagacgatag ttaccggata    3780
aggcgcagcg gtcgggctga acggggggtt cgtgcacaca gcccagcttg gagcgaacga    3840
cctacaccga actgagatac ctacagcgtg agctatgaga aagcgccacg cttcccgaag    3900
ggagaaaggc ggacaggtat ccggtaagcg gcagggtcgg aacaggagag cgcacgaggg    3960
agcttccagg gggaaacgcc tggtatcttt atagtcctgt cgggtttcgc cacctctgac    4020
ttgagcgtcg atttttgtga tgctcgtcag ggggcggag cctatggaaa aacgccagca    4080
acgcggcctt tttacggttc ctggcctttt gctggccttt tgctcacatg ttctttcctg    4140
```

```
cgttatcccc tgattctgtg gataaccgta ttaccgcctt tgagtgagct gataccgctc    4200
gccgcagccg aacgaccgag cgcagcgagt cagtgagcga ggaagcggaa ga            4252

<210> SEQ ID NO 21
<211> LENGTH: 7447
<212> TYPE: DNA
<213> ORGANISM: vector pFPMT-CL-E1-H6

<400> SEQUENCE: 21
ggtaccctgc tcaatctccg gaatggtgat ctgatcgttc ctgaaaacct cgacattggc      60
tccctcctga cacaggtact cgtacaggtt ccaggtaaac gagtcgtagt tgtcgatcat     120
gacaacgttc ttagaagcgg ccggcatttt gaaggtgact aatagcctaa gaaaatattt     180
aatttaattt tcattaaatt ttcctatact cgctatttca gcttttcatc tcatcacttc     240
ataaacgata taaccagaa aaagaactat tttcaaacac gcttctcaaa agcggtatgt      300
ccttccacgt ctccttagaa tctggcaagt ccgcgagggg gatccttaat ggtgatggtg     360
gtggtgccag ttcatcatca tatcccaagc catacggtga cctgttatgt ggccgggata     420
gattgagcaa ttgcagtcct gcaccgtctc atgccggcga ggcgagatgg tgaacagctg     480
ggagacgagg aagacagatc cgcagagatc ccccacgtac atagcggaac agaaagcagc     540
cgccccaacg agcaaatcga cgtggcgtcg tattgtcgta gtggggacgc tggcgttcct     600
agctgcgagc gtggggggtga gcgctaccca gcagcgggaa gagttgttct cccgaacgca    660
gggcacgcac ccgggggtgt gcatgatcat gtccgctgcc tcatacacaa tgcttgagtt     720
ggagcagtcg ttcgtgacat ggtacatccc ggacacgttg cgcacctcat atcctagtgc     780
tgctagtggt aggaagcata gtactagtat tagtaggctt cgcatgaatt cccgatgaag     840
cagagagcgc aggaggcggt atttatagtg ccattcccct ctctgagaga cccggatggt     900
agtcgagtgt atcggagaca gcttgatgta gactccgtgc ctgccggctc tcttattgg      960 cggacaccag tgagacaccc cggaacttgc tgttttttctg caaaatccgg ggtgaccagt   1020
gggagcctat ttgcacacac gagcgggaca ccccactctg gtgaagagtg ccaaagtcat    1080 tcttttttccc gttgcggggc agccgattgc atgttttagg aaaatattac ctttgctaca   1140
ccctgtcaga tttaccctcc acacatatat attccgtcac ctccagggac tattattcgt    1200
cgttgcgccg ccagcggaag atatccagaa gctgttttcc gagagactcg gttggcgcct    1260
ggtatatttg atggatgtcg cgctgcctca cgtcccggta cccaggaacg cggtgggatc     1320
tcgggcccat cgaagactgt gctccagact gctcgcccag caggtgtttc ttgatcgccg    1380
cctctaaatt gtccgcgcat cgccggtaac atttttccag ctcggagttt gcgtttagat    1440
acagtttctg cgatgccaaa ggagcctgca gattataacc tcggatgctg tcattcagcg    1500
cttttaattt gacctccaga tagttgctgt atttctgttc ccattggctg ctgcgcagct    1560
tcgtataact cgagttattg ttgcgctctg cctcggcgta ctggctcatg atctggatct    1620
tgtccgtgtc gctttttcttc gagtgttttct cgcaaacgat gtgcacggcc tgcagtgtcc    1680
aatcggagtc gagctggcgc cgaaactggc ggatctgagc ctccacactg ccctgtttct    1740
ctatccacgg cggaaccgcc tcctgccgtt tcagaatgtt gttcaagtgg tactctgtgc    1800
ggtcaatgaa ggcgttattg ccggtgaaat ctttgggaag cggttttcct cggggaagat    1860
tacgaaattc cccgcgtcgt tgcgcttcct ggatctcgag gagatcgttc ccgcgtcga     1920 ggagatcgtt ctccgcgtcg acaccattcc ttgcggcggc ggtgctcaac ggcctcaacc    1980
```

```
tactactggg ctgcttccta atgcaggagt cgcataaggg agagcgtcga caaacccgcg    2040
tttgagaact tgctcaagct tctggtaaac gttgtagtac tctgaaacaa ggccctagca    2100
ctctgatctg tttctcttgg gtagcggtga gtggtttatt ggagttcact ggtttcagca    2160
catctgtcat ctagacaata ttgttactaa attttttga actacaattg ttcgtaattc    2220
atctattatt atacatcctc gtcagcaatt tctggcagac ggagtttact aacgtcttga    2280
gtatgaggcc gagaatccag ctctgtggcc atactcagtc ttgacagcct gctgatgtgg    2340
ctgcgttcaa cgcaataagc gtgtcctccg actccgagtt gtgctcgtta tcgtcgttct    2400
catcctcgga aaaatcacac gaaagaacat actcaccagt aggctttctg gtccctgggg    2460
cacggctgtt tctgacgtat tccggcgttg ataatagctc gaaagtgaac gccgagtcgc    2520
gggagtcgac cgatgccctt gagagccttc aacccagtca gctccttccg gtgggcgcgg    2580
ggcatgacta tcgtcgccgc acttatgact gtcttcttta tcatgcaact cgtaggacag    2640
gtgccggcag cgctctgggt cattttcggc gaggaccgct ttcgctggag cgcgacgatg    2700
atcggcctgt cgcttgcggt attcggaatc ttgcacgccc tcgctcaagc cttcgtcact    2760
ggtcccgcca ccaaacgttt cggcgagaag caggccatta tcgccggcat ggcggccgac    2820
gcgctgggct acgtcttgct ggcgttcgcg acgcgaggct ggatggcctt ccccattatg    2880
attcttctcg cttccggcgg catcgggatg cccgcgttgc aggccatgct gtccaggcag    2940
gtagatgacg accatcaggg acagcttcaa ggatcgctcg cggctcttac cagcctaact    3000
tcgatcactg gaccgctgat cgtcacggcg atttatgccg cctcggcgag cacatggaac    3060
gggttggcat ggattgtagg cgccgcccta taccttgtct gcctccccgc gttgcgtcgc    3120
ggtgcatgga gccgggccac ctcgacctga atggaagccg gcggcacctc gctaacggat    3180
tcaccactcc aagaattgga gccaatcaat tcttgcggag aactgtgaat gcgcaaacca    3240
acccttggca gaacatatcc atcgcgtccg ccatctccag cagccgcacg cggcgcatcg    3300
gggggggggg gggggggggg gggcaaacaa ttcatcattt tttttttatt cttttttttg    3360
atttcggttt ctttgaaatt tttttgattc ggtaatctcc gaacagaagg aagaacgaag    3420
gaaggagcac agacttagat tggtatatat acgcatatgt agtgttgaag aaacatgaaa    3480
ttgcccagta ttcttaaccc aactgcacag aacaaaaacc tgcaggaaac gaagataaat    3540
catgtcgaaa gctacatata aggaacgtgc tgctactcat cctagtcctg ttgctgccaa    3600
gctatttaat atcatgcacg aaaagcaaac aaacttgtgt gcttcattgg atgttcgtac    3660
caccaaggaa ttactggagt tagttgaagc attaggtccc aaaatttgtt tactaaaaac    3720
acatgtggat atcttgactg attttttccat ggagggcaca gttaagccgc taaaggcatt    3780
atccgccaag tacaattttt tactcttcga agacagaaaa tttgctgaca ttggtaatac    3840
agtcaaattg cagtactctg cgggtgtata cagaatagca gaatgggcag acattacgaa    3900
tgcacacggt gtggtgggcc caggtattgt tagcggtttg aagcaggcgg cagaagaagt    3960
aacaaaggaa cctagaggcc ttttgatgtt agcagaattg tcatgcaagg gctccctatc    4020
tactggagaa tatactaagg gtactgttga cattgcgaag agcgacaaag atttttgttat    4080 cggctttatt gctcaaagag acatgggtgg aagagatgaa ggttacgatt ggttgattat    4140
gacacccggt gtgggtttag atgacaaggg agacgcattg gtcaacagt atagaaccgt    4200 ggatgatgtg gtctctacag gatctgacat tattattgtt ggaagaggac tatttgcaaa    4260
gggaagggat gctaaggtag agggtgaacg ttacagaaaa gcaggctggg aagcatattt    4320
gagaagatgc ggccagcaaa actaaaaaac tgtattataa gtaaatgcat gtatactaaa    4380
```

```
ctcacaaatt agagcttcaa tttaattata tcagttatta cccgggaatc tcggtcgtaa    4440
tgatttttat aatgacgaaa aaaaaaaaat tggaaagaaa agccccccccc ccccccccc    4500 cccccccccc ccccccgcag cgttgggtcc tggccacggg tgcgcatgat cgtgctcctg    4560
tcgttgagga cccggctagg ctggcgggt tgccttactg gttagcagaa tgaatcaccg     4620
atacgcgagc gaacgtgaag cgactgctgc tgcaaaacgt ctgcgacctg agcaacaaca    4680
tgaatggtct tcggtttccg tgtttcgtaa agtctggaaa cgcggaagtc agcgccctgc    4740
accattatgt tccggatctg catcgcagga tgctgctggc tacccgtgg aacacctaca     4800 tctgtattaa cgaagcgctg gcattgaccc tgagtgattt ttctctggtc ccgccgcatc    4860
cataccgcca gttgtttacc ctcacaacgt tccagtaacc gggcatgttc atcatcagta    4920
acccgtatcg tgagcatcct ctctcgtttc atcggtatca ttaccccat gaacagaaat     4980 tcccccttac acggaggcat caagtgacca acaggaaaa accgcccctt aacatggccc     5040
gctttatcag aagccagaca ttaacgcttc tggagaaact caacgagctg acgcggatg     5100 aacaggcaga catctgtgaa tcgcttcacg accacgctga tgagctttac cgcagctgcc    5160
tcgcgcgttt cggtgatgac ggtgaaaacc tctgacacat gcagctcccg gagacggtca    5220
cagcttgtct gtaagcggat gccgggagca gacaagcccg tcagggcgcg tcagcgggtg    5280
ttggcgggtg tcgggcgca gccatgaccc agtcacgtag cgatagcgga gtgtatactg      5340
gcttaactat gcggcatcag agcagattgt actgagagtg caccatatgc ggtgtgaaat    5400
accgcacaga tgcgtaagga gaaaataccg catcaggcgc tcttccgctt cctcgctcac    5460
tgactcgctg cgctcggtcg ttcggctgcg gcgagcggta tcagctcact caaaggcggt    5520
aatacggtta tccacagaat cagggggataa cgcaggaaag aacatgtgag caaaaggcca    5580
gcaaaaggcc aggaaccgta aaaaggccgc gttgctggcg ttttttccata ggctccgccc     5640 ccctgacgag catcacaaaa atcgacgctc aagtcagagg tggcgaaacc cgacaggact    5700
ataaagatac caggcgtttc ccctggaag ctccctcgtg cgctctcctg ttccgaccct      5760
gccgcttacc ggatacctgt ccgcctttct cccttcggga agcgtggcgc tttctcatag    5820
ctcacgctgt aggtatctca gttcggtgta ggtcgttcgc tccaagctgg gctgtgtgca    5880 cgaaccccc gttcagcccg accgctgcgc cttatccggt aactatcgtc ttgagtccaa      5940
cccggtaaga cacgacttat cgccactggc agcagccact ggtaacagga ttagcagagc    6000
gaggtatgta ggcggtgcta cagagttctt gaagtggtgg cctaactacg gctacactag    6060
aaggacagta tttggtatct gcgctctgct gaagccagtt accttcggaa aaagagttgg    6120
tagctcttga tccggcaaac aaaccaccgc tggtagcggt ggtttttttg tttgcaagca    6180
gcagattacg cgcagaaaaa aaggatctca agaagatcct ttgatctttt ctacggggtc    6240
tgacgctcag tggaacgaaa actcacgtta agggattttg gtcatgagat tatcaaaaag    6300
gatcttcacc tagatccttt taaattaaaa atgaagtttt aaatcaatct aaagtatata    6360
tgagtaaact tggtctgaca gttaccaatg cttaatcagt gaggcaccta tctcagcgat    6420
ctgtctattt cgttcatcca tagttgcctg actccccgtc gtgtagataa ctacgatacg    6480
ggagggctta ccatctggcc ccagtgctgc aatgataccg cgagacccac gctcaccggc    6540
tccagattta tcagcaataa accagccagc cggaagggcc gagcgcagaa gtggtcctgc    6600
aactttatcc gcctccatcc agtctattaa ttgttgccgg gaagctagag taagtagttc    6660
gccagttaat agtttgcgca acgttgttgc cattgctgca ggcatcgtgg tgtcacgctc    6720
```

-continued

```
gtcgtttggt atggcttcat tcagctccgg ttcccaacga tcaaggcgag ttacatgatc      6780
ccccatgttg tgcaaaaaag cggttagctc cttcggtcct ccgatcgttg tcagaagtaa      6840
gttggccgca gtgttatcac tcatggttat ggcagcactg cataattctc ttactgtcat      6900
gccatccgta agatgctttt ctgtgactgg tgagtactca accaagtcat tctgagaata      6960
gtgtatgcgg cgaccgagtt gctcttgccc ggcgtcaaca cgggataata ccgcgccaca      7020
tagcagaact ttaaaagtgc tcatcattgg aaaacgttct cgggggcgaa aactctcaag      7080
gatcttaccg ctgttgagat ccagttcgat gtaacccact cgtgcaccca actgatcttc      7140
agcatctttt actttcacca gcgtttctgg gtgagcaaaa acaggaaggc aaaatgccgc      7200
aaaaaaggga ataagggcga cacggaaatg ttgaatactc atactcttcc ttttcaata      7260 ttattgaagc atttatcagg gttattgtct catgagcgga tacatatttg aatgtattta      7320
gaaaaataaa caaatagggg ttccgcgcac atttccccga aaagtgccac ctgacgtcta      7380
agaaaccatt attatcatga cattaaccta taaaaatagg cgtatcacga ggccctttcg      7440
tcttcaa                                                                7447
```

<210> SEQ ID NO 22
<211> LENGTH: 3730
<212> TYPE: DNA
<213> ORGANISM: vector pSP72E2H6

<400> SEQUENCE: 22

```
gaactcgagc agctgaagct tgaattcatg agatttcctt caattttttac tgcagtttta       60 ttcgcagcat cctccgcatt agctgctcca gtcaacacta acagaagaa tgaaacggca      120 caaattccgg ctgaagctgt catcggttac tcagatttag aagggatttt cgatgttgct      180
gttttgccat tttccaacag cacaaataac gggttattgt ttataaatac tactattgcc      240
agcattgctg ctaaagaaga agggtatctc tagataaaaa ggcatacccg cgtgtcagga      300
ggggcagcag cctccgatac caggggcctt gtgtccctct ttagccccgg gtcggctcag      360
aaaatccagc tcgtaaacac caacggcagt tggcacatca acaggactgc cctgaactgc      420
aacgactccc tccaaacagg gttctttgcc gcactattct acaaacacaa attcaactcg      480
tctggatgcc cagagcgctt ggccagctgt cgctccatcg acaagttcgc tcaggggtgg      540
ggtcccctca cttacactga gcctaacagc tcggaccaga ggccctactg ctggcactac      600
gcgcctcgac cgtgtggtat tgtacccgcg tctcaggtgt gcggtccagt gtattgcttc      660
accccgagcc ctgttgtggt ggggacgacc gatcggtttg gtgtcccac gtataactgg      720 ggggcgaacg actcgatgt gctgattctc aacaacacgc ggccgccgcg aggcaactgg      780
ttcggctgta catggatgaa tggcactggg ttaccaaga cgtgtggggg ccccccgtgc      840
aacatcgggg gggccggcaa caacaccttg acctgcccca ctgactgttt tcggaagcac      900
cccgaggcca cttacgccag atgcggttct gggccctggc tgacacctag gtgtatggtt      960
cattacccat ataggctctg gcactacccc tgcactgtca acttcaccat cttcaaggtt     1020
aggatgtacg tgggggcgt ggagcacagg ttcgaagccg catgcaattg gactcgagga     1080
gagcgttgtg acttggagga cagggataga tcagagctta gctcgctgct gctgtctaca     1140
acagagtggc aggtgatcga gggcagacac catcaccacc atcactaata gttaattaac     1200
gatctcgact tggttgaaca cgttgccaag gcttaagtga atttactttta aagtcttgca     1260 tttaaataaa ttttctttttt atagctttat gacttagttt caatttatat actatttaa     1320 tgacattttc gattcattga ttgaaagcta tcagatctgc cggtctccct atagtgagtc     1380
```

-continued

```
gtattaattt cgataagcca ggttaacctg cattaatgaa tcggccaacg cgcggggaga    1440
ggcggtttgc gtattgggcg ctcttccgct tcctcgctca ctgactcgct gcgctcggtc    1500
gttcggctgc ggcgagcggt atcagctcac tcaaaggcgg taatacggtt atccacagaa    1560 tcagggata acgcaggaaa gaacatgtga gcaaaaggcc agcaaaaggc caggaaccgt     1620
aaaaaggccg cgttgctggc gttttttccat aggctccgcc ccctgacga gcatcacaaa    1680 aatcgacgct caagtcagag gtggcgaaac ccgacaggac tataaagata ccaggcgttt    1740 cccctggaa gctccctcgt gcgctctcct gttccgaccc tgccgcttac cggatacctg     1800 tccgccttc tcccttcggg aagcgtggcg ctttctcaat gctcacgctg taggtatctc     1860
agttcggtgt aggtcgttcg ctccaagctg ggctgtgtgc acgaaccccc cgttcagccc    1920
gaccgctgcg ccttatccgg taactatcgt cttgagtcca acccgtaag acacgactta     1980 tcgccactgg cagcagccac tggtaacagg attagcagag cgaggtatgt aggcggtgct    2040
acagagttct tgaagtggtg gcctaactac ggctacacta aaggacagt atttggtatc     2100 tgcgctctgc tgaagccagt taccttcgga aaaagagttg gtagctcttg atccggcaaa    2160
caaaccaccg ctggtagcgg tggtttttttt gtttgcaagc agcagattac gcgcagaaaa   2220
aaaggatctc aagaagatcc tttgatcttt tctacggggt ctgacgctca gtggaacgaa    2280
aactcacgtt aagggatttt ggtcatgaga ttatcaaaaa ggatcttcac ctagatcctt    2340
ttaaattaaa aatgaagttt taaatcaatc taaagtatat atgagtaaac ttggtctgac    2400
agttaccaat gcttaatcag tgaggcacct atctcagcga tctgtctatt tcgttcatcc    2460
atagttgcct gactccccgt cgtgtagata actacgatac gggagggctt accatctggc    2520
cccagtgctg caatgatacc gcgagaccca cgctcaccgg ctccagattt atcagcaata    2580
aaccagccag ccggaagggc cgagcgcaga agtggtcctg caactttatc cgcctccatc    2640
cagtctatta attgttgccg ggaagctaga gtaagtagtt cgccagttaa tagtttgcgc    2700
aacgttgttg ccattgctac aggcatcgtg gtgtcacgct cgtcgtttgg tatggcttca    2760
ttcagctccg gttcccaacg atcaaggcga gttacatgat cccccatgtt gtgcaaaaaa    2820
gcggttagct ccttcggtcc tccgatcgtt gtcagaagta agttggccgc agtgttatca    2880
ctcatggtta tggcagcact gcataattct cttactgtca tgccatccgt aagatgcttt    2940
tctgtgactg gtgagtactc aaccaagtca ttctgagaat agtgtatgcg gcgaccgagt    3000
tgctcttgcc cggcgtcaat acgggataat accgcgccac atagcagaac tttaaaagtg    3060
ctcatcattg gaaaacgttc ttcggggcga aaactctcaa ggatcttacc gctgttgaga    3120
tccagttcga tgtaacccac tcgtgcaccc aactgatctt cagcatcttt tactttcacc    3180
agcgtttctg ggtgagcaaa acaggaagg caaaatgccg caaaaaaggg aataagggcg    3240
acacggaaat gttgaatact catactcttc cttttttcaat attattgaag catttatcag    3300
ggttattgtc tcatgagcgg atacatattt gaatgtattt agaaaaataa acaaataggg    3360
gttccgcgca catttccccg aaaagtgcca cctgacgtct aagaaccat tattatcatg     3420 acattaaccct ataaaaatag gcgtatcacg aggccctttc gtctcgcgcg tttcggtgat    3480
gacggtgaaa acctctgaca catgcagctc ccggagacgg tcacagcttg tctgtaagcg    3540
gatgccggga gcagacaagc ccgtcaggc gcgtcagcgg gtgttggcgg gtgtcggggc    3600
tggcttaact atgcggcatc agagcagatt gtactgagag tgcaccatat ggacatattg    3660
tcgttagaac gcggctacaa ttaatacata accttatgta tcatacacat acgatttagg    3720
```

<210> SEQ ID NO 23
<211> LENGTH: 7370
<212> TYPE: DNA
<213> ORGANISM: vector pMPT121
<220> FEATURE:
<221> NAME/KEY: misc_feature
<222> LOCATION: (778)..(778)
<223> OTHER INFORMATION: N is any nucleotide

<400> SEQUENCE: 23

```
ggtaccctgc tcaatctccg gaatggtgat ctgatcgttc ctgaaaacct cgacattggc      60
tccctcctga cacaggtact cgtacaggtt ccaggtaaac gagtcgtagt tgtcgatcat     120
gacaacgttc ttagaagcgg ccggcatttt gaaggtgact aatagcctaa gaaatatttt     180
aatttaattt tcattaaatt ttcctatact cgctatttca gcttttcatc tcatcacttc     240
ataaacgata taaccagaaa aagaactat  tttcaaacac gcttctcaaa agcggtatgt     300
ccttccacgt ctccttagaa tctggcaagt ccgcgagggg gatccagatc tgaattcgtt     360
tttgtacttt agattgatgt caccaccgtg cactggcagc agtatttata gatggaccgt     420
gtggggacgg ttgggtacac ttagcggcag cgctgacccc atctgtgatc aagtagggca     480
aaaactgggg atgtcggagt cgctgcacgg tagcataaga atttactttc tggccggttc     540
acccgcattt gcactgtgga gaaacagcct gtccgacacc ccaccagttg ccacatcggc     600
cctctgctgc tctggtgatt ttctggtagc aggcacagac agcagtgggt agcgccgtcc     660
ggttaggcaa ggtcacgttg taggctaccc cagcaaacag agcctcacat gacaccatcc     720
agctgcgtcc tcgaagcgaa aagttcggtt gcggctgcag aaccccctca gttgccanat     780
tcacaagttt tacgcgacgg ctaaagcgag tgggttttaa aaacttgcgg tgcaaggatg     840
catgcggcaa caattaattg gtgcatccag cacagcaagc ccagtctcga gatgtccagt     900
cgctacagag tggagtacgc actcaaggaa caccgtcgag atggcctcat agaatggatc     960
aagggcctgc tggccacgcc gttcgtcctg tacgcggtga agagcaacgg catctctgca    1020
gtggacgacc tcatggtaaa ctctgaggca aaacgccgct acgcggaaat cttccacgac    1080
ctcgaactcc tcatcgacga caacattgaa atgaccaaag ccggcacccc cgaattgtct    1140
cggctcgtgc agctggttcc gagcgttggc agcttcttca cgagactgcc tctggaaaag    1200
gccttctaca tcgaggacga gcgccgcgcc atcagcaaac gccggcttgt ggcccctcg     1260
ttcaacgacg tccggctcat tctcaacacg gcccagctgt tggagatgtc gcggttcttc    1320
cattccaaaa ccatccgaga tcgcaagctg cagctcatta cattcgatgg tgacatcaca    1380
ctgtacgacg acggcaaaaa tttcgatgcc gagtcgccca cctgccccca cctcatcaaa    1440
ctaatggcca aggacctcta tgtgggtatc gtcaccgcgg ccggctacag cgacggaaca    1500
agtactacga gcgcctcaag ggcctcatcg acgccgtcca gacgtccccg ctgctcacag    1560
gccaccagaa agagaacctg ttcattatgg gcggcgaggc aaactacctc ttccggtaca    1620
gtaacgagga gcagagatta cgcttctact ccaaagacag atggctgctc gagaacatgc    1680
tgaattggtc cgaggaggac attcatctga cactggactt tgcgcaggac gttctaaacg    1740
acctcgttca caactgggc tcgccagcca ccgtggtccg caaggagcgt cgcgtcggcc     1800
tggttccatt accgggccac aagctgatcc gcgagcagct cgaggagatc gttctccgcg    1860
tcgacaccat tccttgcggc ggcggtgctc aacggcctca acctactact gggctgcttc    1920
ctaatgcagg agtcgcataa gggagagcgt cgactcccgc gactcggcgt tcactttcga    1980
```

```
gctattatca acgccggaat acgtcagaaa cagccgtgcc ccagggacca gaaagcctac    2040
tggtgagtat gttctttcgt gtgattttc cgaggatgag aacgacgata acgagcacaa     2100
ctcggagtcg gaggacacgc ttattgcgtt gaacgcagcc acatcagcag ctgtcaaga    2160 ctgagtatgg ccacagagct ggattctcgg cctcatactc aagacgttag taaactccgt   2220
ctgccagaaa ttgctgacga ggatgtataa taatagatga attacgaaca attgtagttc    2280 aaaaaattt agtaacaata ttgtctagat gacagatgtg ctgaaaccag tgaactccaa    2340
taaaccactc accgctaccc aagagaaaca gatcagagtg ctagggcctt gtttcagagt   2400
actacaacgt ttaccagaag cttgagcaag ttctcaaacg cgggtttgtc gaccgatgcc   2460
cttgagagcc ttcaacccag tcagctcctt ccggtgggcg cggggcatga ctatcgtcgc   2520
cgcacttatg actgtcttct ttatcatgca actcgtagga caggtgccgg cagcgctctg   2580
ggtcattttc ggcgaggacc gctttcgctg gagcgcgacg atgatcggcc tgtcgcttgc   2640
ggtattcgga atcttgcacg ccctcgctca agccttcgtc actggtcccg ccaccaaacg    2700
tttcggcgag aagcaggcca ttatcgccgg catggcggcc gacgcgctgg gctacgtctt    2760
gctggcgttc gcgacgcgag gctggatggc cttccccatt atgattcttc tcgcttccgg   2820
cggcatcggg atgcccgcgt tgcaggccat gctgtccagg caggtagatg acgaccatca    2880
gggacagctt caaggatcgc tcgcggctct taccagccta acttcgatca ctggaccgct    2940
gatcgtcacg gcgatttatg ccgcctcggc gagcacatgg aacgggttgg catggattgt   3000
aggcgccgcc ctataccttg tctgcctccc cgcgttgcgt cgcggtgcat ggagccgggc    3060
cacctcgacc tgaatggaag ccggcggcac ctcgctaacg gattcaccac tccaagaatt    3120
ggagccaatc aattcttgcg gagaactgtg aatgcgcaaa ccaacccttg cagaacata    3180 tccatcgcgt ccgccatctc cagcagccgc acgcggcgca tcggggggggg ggggggggg    3240 gggggcaaa caattcatca tttttttttt attcttttt ttgatttcgg tttctttgaa      3300 attttttga ttcggtaatc tccgaacaga aggaagaacg aaggaaggag cacagactta    3360
gattggtata tatacgcata tgtagtgttg aagaaacatg aaattgccca gtattcttaa    3420
cccaactgca cagaacaaaa acctgcagga acgaagata aatcatgtcg aaagctacat    3480
ataaggaacg tgctgctact catcctagtc ctgttgctgc caagctattt aatatcatgc    3540
acgaaaagca aacaaacttg tgtgcttcat tggatgttcg taccaccaag gaattactgg    3600
agttagttga agcattaggt cccaaaattt gtttactaaa aacacatgtg gatatcttga    3660 ctgattttc catggagggc acagttaagc cgctaaaggc attatccgcc aagtacaatt    3720
ttttactctt cgaagacaga aaatttgctg acattggtaa tacagtcaaa ttgcagtact    3780
ctgcgggtgt atacagaata gcagaatggg cagacattac gaatgcacac ggtgtggtgg   3840
gcccaggtat tgttagcggt ttgaagcagg cggcagaaga gtaacaaag gaacctagag    3900 gccttttgat gttagcagaa ttgtcatgca agggctccct atctactgga gaatatacta    3960
agggtactgt tgacattgcg aagagcgaca agattttgt tatcggcttt attgctcaaa    4020
gagacatggg tggaagagat gaaggttacg attggttgat tatgacaccc ggtgtgggtt   4080
tagatgacaa gggagacgca ttgggtcaac agtatagaac cgtggatgat gtggtctcta    4140
caggatctga cattattatt gttggaagag gactatttgc aaagggaagg gatgctaagg    4200
tagagggtga acgttacaga aaagcaggct gggaagcata tttgagaaga tgcggccagc    4260
aaaactaaaa aactgtatta taagtaaatg catgtatact aaactcacaa attagagctt    4320
```

```
caatttaatt atatcagtta ttacccggga atctcggtcg taatgatttt tataatgacg    4380
aaaaaaaaaa aattggaaag aaaagccccc cccccccccc cccccccccg               4440
cagcgttggg tcctggccac gggtgcgcat gatcgtgctc ctgtcgttga ggacccggct    4500
aggctggcgg ggttgcctta ctggttagca gaatgaatca ccgatacgcg agcgaacgtg    4560
aagcgactgc tgctgcaaaa cgtctgcgac ctgagcaaca acatgaatgg tcttcggttt    4620
ccgtgtttcg taaagtctgg aaacgcggaa gtcagcgccc tgcaccatta tgttccggat    4680
ctgcatcgca ggatgctgct ggctaccctg tggaacacct acatctgtat taacgaagcg    4740
ctggcattga ccctgagtga tttttctctg gtcccgccgc atccataccg ccagttgttt    4800
accctcacaa cgttccagta accgggcatg ttcatcatca gtaacccgta tcgtgagcat    4860
cctctctcgt ttcatcggta tcattacccc catgaacaga aattcccccct tacacggagg   4920
catcaagtga ccaaacagga aaaaccgcc cttaacatgg cccgctttat cagaagccag     4980
acattaacgc ttctggagaa actcaacgag ctggacgcgg atgaacaggc agacatctgt    5040
gaatcgcttc acgaccacgc tgatgagctt taccgcagct gcctcgcgcg tttcggtgat    5100
gacggtgaaa acctctgaca catgcagctc ccggagacgg tcacagcttg tctgtaagcg    5160
gatgccggga gcagacaagc ccgtcagggc gcgtcagcgg gtgttggcgg gtgtcggggc    5220
gcagccatga cccagtcacg tagcgatagc ggagtgtata ctggcttaac tatgcggcat    5280
cagagcagat tgtactgaga gtgcaccata tgcggtgtga ataccgcac agatgcgtaa     5340
ggagaaaata ccgcatcagg cgctcttccg cttcctcgct cactgactcg ctgcgctcgg    5400
tcgttcggct gcggcgagcg gtatcagctc actcaaaggc ggtaatacgg ttatccacag    5460
aatcagggga taacgcagga agaacatgt gagcaaaagg ccagcaaaag gccaggaacc     5520
gtaaaaaggc cgcgttgctg gcgttttttcc ataggctccg cccccctgac gagcatcaca   5580
aaaatcgacg ctcaagtcag aggtggcgaa acccgacagg actataaaga taccaggcgt    5640
ttcccccctgg aagctccctc gtgcgctctc ctgttccgac cctgccgctt accggatacc   5700
tgtccgcctt tctcccttcg ggaagcgtgg cgctttctca tagctcacgc tgtaggtatc    5760
tcagttcggt gtaggtcgtt cgctccaagc tgggctgtgt gcacgaaccc cccgttcagc    5820
ccgaccgctg cgccttatcc ggtaactatc gtcttgagtc caacccggta agacacgact    5880
tatcgccact ggcagcagcc actggtaaca ggattagcag agcgaggtat gtaggcggtg    5940
ctacagagtt cttgaagtgg tggcctaact acggctacac tagaaggaca gtatttggta    6000
tctgcgctct gctgaagcca gttaccttcg gaaaaagagt tggtagctct tgatccggca    6060
aacaaaccac cgctggtagc ggtggttttt ttgtttgcaa gcagcagatt acgcgcagaa    6120
aaaaaggatc tcaagaagat cctttgatct tttctacggg gtctgacgct cagtggaacg    6180
aaaactcacg ttaagggatt ttggtcatga gattatcaaa aaggatcttc acctagatcc    6240
ttttaaatta aaaatgaagt tttaaatcaa tctaaagtat atatgagtaa acttggtctg    6300
acagttacca atgcttaatc agtgaggcac ctatctcagc gatctgtcta tttcgttcat    6360
ccatagttgc ctgactcccc gtcgtgtaga taactacgat acgggagggc ttaccatctg    6420
gccccagtgc tgcaatgata ccgcgagacc cacgctcacc ggctccagat ttatcagcaa    6480
taaaccagcc agccggaagg gccgagcgca gaagtggtcc tgcaacttta tccgcctcca    6540
tccagtctat taattgttgc cgggaagcta gagtaagtag ttcgccagtt aatagtttgc    6600
gcaacgttgt tgccattgct gcaggcatcg tggtgtcacg ctcgtcgttt ggtatggctt    6660
cattcagctc cggttcccaa cgatcaaggc gagttacatg atcccccatg ttgtgcaaaa    6720
```

```
aagcggttag ctccttcggt cctccgatcg ttgtcagaag taagttggcc gcagtgttat    6780
cactcatggt tatggcagca ctgcataatt ctcttactgt catgccatcc gtaagatgct    6840
tttctgtgac tggtgagtac tcaaccaagt cattctgaga atagtgtatg cggcgaccga    6900
gttgctcttg cccggcgtca acacgggata ataccgcgcc acatagcaga actttaaaag    6960
tgctcatcat tggaaaacgt tcttcggggc gaaaactctc aaggatctta ccgctgttga    7020
gatccagttc gatgtaaccc actcgtgcac ccaactgatc ttcagcatct tttactttca    7080
ccagcgtttc tgggtgagca aaaacaggaa ggcaaaatgc cgcaaaaaag gaataagggg    7140
cgacacggaa atgttgaata ctcatactct tcctttttca atattattga agcatttatc    7200
agggttattg tctcatgagc ggatacatat ttgaatgtat ttagaaaaat aaacaaatag    7260
gggttccgcg cacatttccc cgaaaagtgc cacctgacgt ctaagaaacc attattatca    7320
tgacattaac ctataaaaat aggcgtatca cgaggccctt tcgtcttcaa               7370

<210> SEQ ID NO 24
<211> LENGTH: 8298
<212> TYPE: DNA
<213> ORGANISM: vector pFMPT-MFalfa-E2-H6

<400> SEQUENCE: 24
ggtaccctgc tcaatctccg gaatggtgat ctgatcgttc ctgaaaacct cgacattggc      60
tccctcctga cacaggtact cgtacaggtt ccaggtaaac gagtcgtagt tgtcgatcat     120
gacaacgttc ttagaagcgg ccggcatttt gaaggtgact aatagcctaa gaaatatttt     180
aatttaattt tcattaaatt ttcctatact cgctatttca gcttttcatc tcatcacttc     240
ataaacgata taaaccagaa aaagaactat tttcaaacac gcttctcaaa agcggtatgt     300
ccttccacgt ctccttagaa tctggcaagt ccgcgagggg gatccagatc tgatagcttt     360
caatcaatga atcgaaaatg tcattaaaat agtatataaa ttgaaactaa gtcataaagc     420
tataaaaaga aaatttattt aaatgcaaga ctttaaagta aattcactta agccttggca     480
acgtgttcaa ccaagtcgag atcgttaatt aactattagt gatggtggtg atggtgtctg     540
ccctcgatca cctgccactc tgttgtagac agcagcagcg agctaagctc tgatctatcc     600
ctgtcctcca agtcacaacg ctctcctcga gtccaattgc atgcggcttc gaacctgtgc     660
tccacgcccc ccacgtacat cctaaccttg aagatggtga agttgacagt gcagggtag     720 tgccagagcc tatatgggta atgaaccata cacctaggtg tcagccaggg cccagaaccg     780
catctggcgt aagtggcctc ggggtgcttc cgaaaacagt cagtggggca ggtcaaggtg     840
ttgttgccgg ccccccgat gttgcacggg gggcccccac acgtcttggt gaacccagtg     900
ccattcatcc atgtacagcc gaaccagttg cctcgcggcg gccgcgtgtt gttgagaatc     960
agcacatccg agtcgttcgc ccccagtta tacgtgggga caccaaaccg atcggtcgtc    1020
cccaccacaa cagggctcgg ggtgaagcaa tacactggac cgcacacctg agacgcgggt    1080
acaataccac acgcgtcgag gcgcgtagtg cagcagtagg gcctctggtc cgagctgtta    1140
ggctcagtgt aagtgagggg accccacccc tgagcgaact tgtcgatgga gcgacagctg    1200
gccaagcgct ctgggcatcc agacgagttg aatttgtgtt tgtagaatag tgcggcaaag    1260
aaccctgttt ggagggagtc gttgcagttc agggcagtcc tgttgatgtg ccaactgccg    1320
ttggtgttta cgagctggat tttctgagcc gacccgggc taagagggga cacaaggccc    1380
ctggtatcgg aggctgctgc ccctcctgac acgcgggtat gccttttatc tagagatacc    1440
```

```
ccttcttctt tagcagcaat gctggcaata gtagtattta taaacaataa cccgttattt    1500
gtgctgttgg aaaatggcaa aacagcaaca tcgaaatccc cttctaaatc tgagtaaccg    1560
atgacagctt cagccggaat ttgtgccgtt tcatcttctg ttgtagtgtt gactggagca    1620
gctaatgcgg aggatgctgc gaataaaact gcagtaaaaa ttgaaggaaa tctcatgaat    1680
tcccgatgaa gcagagagcg caggaggcgg tatttatagt gccattcccc tctctgagag    1740
acccggatgg tagtcgagtg tatcggagac agcttgatgt agactccgtg cctgccggct    1800
cctcttattg gcggacacca gtgagacacc ccggaacttg ctgtttttct gcaaaatccg    1860
gggtgaccag tgggagccta tttgcacaca cgagcgggac accccactct ggtgaagagt    1920
gccaaagtca ttcttttttcc cgttgcgggg cagccgattg catgttttag gaaaatatta    1980
cctttgctac accctgtcag atttaccctc cacacatata tattccgtca cctcagggga    2040
ctattattcg tcgttgcgcc gccagcggaa gatatccaga agctgttttc cgagagactc    2100
ggttggcgcc tggtatattt gatggatgtc gcgctgcctc acgtcccggt acccaggaac    2160
gcggtgggat ctcgggccca tcgaagactg tgctccagac tgctcgccca gcaggtgttt    2220
cttgatcgcc gcctctaaat tgtccgcgca tcgccggtaa catttttcca gctcggagtt    2280
tgcgtttaga tacagtttct gcgatgccaa aggagcctgc agattataac ctcggatgct    2340
gtcattcagc gcttttaatt tgacctccag atagttgctg tatttctgtt cccattggct    2400
gctgcgcagc ttcgtataac tcgagttatt gttgcgctct gcctcggcgt actggctcat    2460
gatctggatc ttgtccgtgt cgcttttctt cgagtgtttc tcgcaaacga tgtgcacggc    2520
ctgcagtgtc caatcggagt cgagctggcg ccgaaactgg cggatctgag cctccacact    2580
gccctgtttc tctatccacg gcggaaccgc ctcctgccgt ttcagaatgt tgttcaagtg    2640
gtactctgtg cggtcaatga aggcgttatt gccggtgaaa tctttgggaa gcggttttcc    2700
tcggggaaga ttacgaaatt ccccgcgtcg ttgcgcttcc tggatctcga ggagatcgtt    2760
ctccgcgtcg aggagatcgt tctccgcgtc gacaccattc cttgcggcgg cggtgctcaa    2820
cggcctcaac ctactactgg gctgcttcct aatgcaggag tcgcataagg gagagcgtcg    2880
acaaacccgc gtttgagaac ttgctcaagc ttctggtaaa cgttgtagta ctctgaaaca    2940
aggccctagc actctgatct gtttctcttg ggtagcggtg agtggtttat tggagttcac    3000
tggtttcagc acatctgtca tctagacaat attgttacta aattttttg aactacaatt    3060 gttcgtaatt catctattat tatacatcct cgtcagcaat ttctggcaga cggagtttac    3120
taacgtcttg agtatgaggc cgagaatcca gctctgtggc catactcagt cttgacagcc    3180
tgctgatgtg gctgcgttca acgcaataag cgtgtcctcc gactccgagt tgtgctcgtt    3240
atcgtcgttc tcatcctcgg aaaaatcaca cgaaagaaca tactcaccag taggctttct    3300
ggtccctggg gcacggctgt ttctgacgta ttccggcgtt gataatagct cgaaagtgaa    3360
cgccgagtcg cgggagtcga ccgatgccct tgagagcctt caacccagtc agctccttcc    3420
ggtgggcgcg gggcatgact atcgtcgccg cacttatgac tgtcttcttt atcatgcaac    3480
tcgtaggaca ggtgccggca gcgctctggg tcatttttcgg cgaggaccgc tttcgctgga    3540
gcgcgacgat gatcggcctg tcgcttgcgg tattcggaat cttgcacgcc ctcgctcaag    3600
ccttcgtcac tggtcccgcc accaaacgtt tcggcgagaa gcaggccatt atcgccggca    3660
tggcggccga cgcgctgggc tacgtcttgc tggcgttcgc gacgcgaggc tggatggcct    3720
tccccattat gattcttctc gcttccgcg catcgggat gccgcgttg caggccatgc    3780 tgtccaggca ggtagatgac gaccatcagg gacagcttca aggatcgctc gcggctctta    3840
```

-continued

| | |
|---|---|
| ccagcctaac ttcgatcact ggaccgctga tcgtcacggc gatttatgcc gcctcggcga | 3900 |
| gcacatggaa cgggttggca tggattgtag gcgccgccct ataccttgtc tgcctccccg | 3960 |
| cgttgcgtcg cggtgcatgg agccgggcca cctcgacctg aatggaagcc ggcggcacct | 4020 |
| cgctaacgga ttcaccactc caagaattgg agccaatcaa ttcttgcgga gaactgtgaa | 4080 |
| tgcgcaaacc aacccttggc agaacatatc catcgcgtcc gccatctcca gcagccgcac | 4140 |
| gcggcgcatc ggggggggggg ggggggggggg gggcaaaca attcatcatt ttttttttat | 4200 |
| tctttttttt gatttcggtt tctttgaaat ttttttgatt cggtaatctc cgaacagaag | 4260 |
| gaagaacgaa ggaaggagca cagacttaga ttggtatata tacgcatatg tagtgttgaa | 4320 |
| gaaacatgaa attgcccagt attcttaacc caactgcaca gaacaaaaac ctgcaggaaa | 4380 |
| cgaagataaa tcatgtcgaa agctacatat aaggaacgtg ctgctactca tcctagtcct | 4440 |
| gttgctgcca agctatttaa tatcatgcac gaaaagcaaa caaacttgtg tgcttcattg | 4500 |
| gatgttcgta ccaccaagga attactggag ttagttgaag cattaggtcc caaaatttgt | 4560 |
| ttactaaaaa cacatgtgga tatcttgact gattttttcca tggagggcac agttaagccg | 4620 |
| ctaaaggcat tatccgccaa gtacaatttt ttactcttcg aagacagaaa atttgctgac | 4680 |
| attggtaata cagtcaaatt gcagtactct gcgggtgtat acagaatagc agaatgggca | 4740 |
| gacattacga atgcacacgg tgtggtgggc ccaggtattg ttagcggttt gaagcaggcg | 4800 |
| gcagaagaag taacaaagga acctagaggc cttttgatgt tagcagaatt gtcatgcaag | 4860 |
| ggctccctat ctactggaga atatactaag ggtactgttg acattgcgaa gagcgacaaa | 4920 |
| gattttgtta tcggctttat tgctcaaaga gacatgggtg gaagagatga aggttacgat | 4980 |
| tggttgatta tgacacccgg tgtgggttta gatgacaagg gagacgcatt gggtcaacag | 5040 |
| tatagaaccg tggatgatgt ggtctctaca ggatctgaca ttattattgt tggaagagga | 5100 |
| ctatttgcaa agggaaggga tgctaaggta gagggtgaac gttacagaaa agcaggctgg | 5160 |
| gaagcatatt tgagaagatg cggccagcaa aactaaaaaa ctgtattata agtaaatgca | 5220 |
| tgtatactaa actcacaaat tagagcttca atttaattat atcagttatt acccgggaat | 5280 |
| ctcggtcgta atgatttttta taatgacgaa aaaaaaaaa ttggaaagaa aagccccccc | 5340 |
| ccccccccc cccccccccc cccccccgca gcgttgggtc ctggccacgg gtgcgcatga | 5400 |
| tcgtgctcct gtcgttgagg acccggctag gctggcgggg ttgccttact ggttagcaga | 5460 |
| atgaatcacc gatacgcgag cgaacgtgaa gcgactgctg ctgcaaaacg tctgcgacct | 5520 |
| gagcaacaac atgaatggtc ttcggttttcc gtgtttcgta aagtctggaa acgcggaagt | 5580 |
| cagcgccctg caccattatg ttccggatct gcatcgcagg atgctgctgg ctaccctgtg | 5640 |
| gaacacctac atctgtatta acgaagcgct ggcattgacc ctgagtgatt tttctctggt | 5700 |
| cccgccgcat ccataccgcc agttgtttac cctcacaacg ttccagtaac cgggcatgtt | 5760 |
| catcatcagt aacccgtatc gtgagcatcc tctctcgttt catcggtatc attaccccca | 5820 |
| tgaacagaaa ttcccccctta cacggaggca tcaagtgacc aaacaggaaa aaaccgccct | 5880 |
| taacatggcc cgctttatca gaagccagac attaacgctt ctggagaaac tcaacgagct | 5940 |
| ggacgcggat gaacaggcag acatctgtga atcgcttcac gaccacgctg atgagcttta | 6000 |
| ccgcagctgc ctcgcgcgtt tcggtgatga cggtgaaaac ctctgacaca tgcagctccc | 6060 |
| ggagacggtc acagcttgtc tgtaagcgga tgccgggagc agacaagccc gtcagggcgc | 6120 |
| gtcagcgggt gttggcgggt gtcggggcgc agccatgacc cagtcacgta gcgatagcgg | 6180 |

```
agtgtatact ggcttaacta tgcggcatca gagcagattg tactgagagt gcaccatatg    6240
cggtgtgaaa taccgcacag atgcgtaagg agaaaatacc gcatcaggcg ctcttccgct    6300
tcctcgctca ctgactcgct gcgctcggtc gttcggctgc ggcgagcggt atcagctcac    6360
tcaaaggcgg taatacggtt atccacagaa tcagggata cgcaggaaa gaacatgtga    6420 gcaaaaggcc agcaaaaggc caggaaccgt aaaaaggccg cgttgctggc gtttttccat    6480
aggctccgcc cccctgacga gcatcacaaa aatcgacgct caagtcagag gtggcgaaac    6540
ccgacaggac tataaagata ccaggcgttt ccccctggaa gctccctcgt gcgctctcct    6600
gttccgaccc tgccgcttac cggatacctg tccgcctttc tcccttcggg aagcgtggcg    6660
ctttctcata gctcacgctg taggtatctc agttcggtgt aggtcgttcg ctccaagctg    6720
ggctgtgtgc acgaaccccc cgttcagccc gaccgctgcg ccttatccgg taactatcgt    6780
cttgagtcca acccggtaag acacgactta tcgccactgg cagcagccac tggtaacagg    6840
attagcagag cgaggtatgt aggcggtgct acagagttct tgaagtggtg cctaactac    6900 ggctacacta gaaggacagt atttggtatc tgcgctctgc tgaagccagt taccttcgga    6960
aaaagagttg gtagctcttg atccggcaaa caaaccaccg ctggtagcgg tggtttttt    7020 gtttgcaagc agcagattac gcgcagaaaa aaaggatctc aagaagatcc tttgatcttt    7080
tctacggggt ctgacgctca gtggaacgaa aactcacgtt aagggatttt ggtcatgaga    7140
ttatcaaaaa ggatcttcac ctagatcctt ttaaattaaa aatgaagttt taaatcaatc    7200
taaagtatat atgagtaaac ttggtctgac agttaccaat gcttaatcag tgaggcacct    7260
atctcagcga tctgtctatt tcgttcatcc atagttgcct gactccccgt cgtgtagata    7320
actacgatac gggagggctt accatctggc cccagtgctg caatgatacc gcgagaccca    7380
cgctcaccgg ctccagattt atcagcaata aaccagccag ccggaagggc cgagcgcaga    7440
agtggtcctg caactttatc cgcctccatc cagtctatta attgttgccg ggaagctaga    7500
gtaagtagtt cgccagttaa tagtttgcgc aacgttgttg ccattgctgc aggcatcgtg    7560
gtgtcacgct cgtcgtttgg tatggcttca ttcagctccg gttcccaacg atcaaggcga    7620
gttacatgat cccccatgtt gtgcaaaaaa gcggttagct ccttcggtcc tccgatcgtt    7680
gtcagaagta agttggccgc agtgttatca ctcatggtta tggcagcact gcataattct    7740
cttactgtca tgccatccgt aagatgcttt tctgtgactg gtgagtactc aaccaagtca    7800
ttctgagaat agtgtatgcg gcgaccgagt tgctcttgcc cggcgtcaac acgggataat    7860
accgcgccac atagcagaac tttaaaagtg ctcatcattg gaaaacgttc ttcggggcga    7920
aaactctcaa ggatcttacc gctgttgaga tccagttcga tgtaacccac tcgtgcaccc    7980
aactgatctt cagcatcttt tactttcacc agcgtttctg ggtgagcaaa aacaggaagg    8040
caaaatgccg caaaaaaggg aataagggcg acacggaaat gttgaatact catactcttc    8100
ctttttcaat attattgaag catttatcag ggttattgtc tcatgagcgg atacatattt    8160
gaatgtattt agaaaaataa acaataggg gttccgcgca catttccccg aaaagtgcca    8220
cctgacgtct aagaaaccat tattatcatg acattaacct ataaaaatag gcgtatcacg    8280 aggcccttc gtcttcaa                                                  8298
```

<210> SEQ ID NO 25
<211> LENGTH: 8695
<212> TYPE: DNA
<213> ORGANISM: vector pMPT-Mfalfa-E2-H6
<220> FEATURE:
<221> NAME/KEY: misc_feature
<222> LOCATION: (2103)..(2103)
<223> OTHER INFORMATION: N is any nucleotide

<400> SEQUENCE: 25

| | | | | | |
|---|---|---|---|---|---|
| ggtaccctgc | tcaatctccg | gaatggtgat | ctgatcgttc | ctgaaaacct | cgacattggc | 60 |
| tccctcctga | cacaggtact | cgtacaggtt | ccaggtaaac | gagtcgtagt | tgtcgatcat | 120 |
| gacaacgttc | ttagaagcgg | ccggcatttt | gaaggtgact | aatagcctaa | gaaaatattt | 180 |
| aatttaattt | tcattaaatt | ttcctatact | cgctatttca | gcttttcatc | tcatcacttc | 240 |
| ataaacgata | taaccagaa | aaagaactat | tttcaaacac | gcttctcaaa | agcggtatgt | 300 |
| ccttccacgt | ctccttagaa | tctggcaagt | ccgcgagggg | gatccagatc | tgatagcttt | 360 |
| caatcaatga | atcgaaaatg | tcattaaaat | agtatataaa | ttgaaactaa | gtcataaagc | 420 |
| tataaaaga | aaatttattt | aaatgcaaga | ctttaaagta | aattcactta | agccttggca | 480 |
| acgtgttcaa | ccaagtcgag | atcgttaatt | aactattagt | gatggtggtg | atggtgtctg | 540 |
| ccctcgatca | cctgccactc | tgttgtagac | agcagcagcg | agctaagctc | tgatctatcc | 600 |
| ctgtcctcca | agtcacaacg | ctctcctcga | gtccaattgc | atgcggcttc | gaacctgtgc | 660 |
| tccacgcccc | ccacgtacat | cctaaccttg | aagatggtga | agttgacagt | gcaggggtag | 720 |
| tgccagagcc | tatatgggta | atgaaccata | cacctaggtg | tcagccaggg | cccagaaccg | 780 |
| catctggcgt | aagtggcctc | ggggtgcttc | cgaaaacagt | cagtggggca | ggtcaaggtg | 840 |
| ttgttgccgg | ccccccgat | gttgcacggg | gggcccccac | acgtcttggt | gaacccagtg | 900 |
| ccattcatcc | atgtacagcc | gaaccagttg | cctcgcggcg | gccgcgtgtt | gttgagaatc | 960 |
| agcacatccg | agtcgttcgc | ccccagtta | tacgtgggga | caccaaaccg | atcggtcgtc | 1020 |
| cccaccacaa | cagggctcgg | ggtgaagcaa | tacactggac | cgcacacctg | agacgcgggt | 1080 |
| acaataccac | acggtcgagg | cgcgtagtgc | cagcagtagg | gcctctggtc | cgagctgtta | 1140 |
| ggctcagtgt | aagtgagggg | accccacccc | tgagcgaact | tgtcgatgga | gcgacagctg | 1200 |
| gccaagcgct | ctgggcatcc | agacgagttg | aatttgtgtt | tgtagaatag | tgcggcaaag | 1260 |
| aaccctgttt | ggagggagtc | gttgcagttc | agggcagtcc | tgttgatgtg | ccaactgccg | 1320 |
| ttggtgttta | cgagctggat | tttctgagcc | gacccggggc | taaagaggga | cacaaggccc | 1380 |
| ctggtatcgg | aggctgctgc | ccctcctgac | acgcgggtat | gccttttatc | tagagatacc | 1440 |
| ccttcttctt | tagcagcaat | gctggcaata | gtagtattta | taaacaataa | cccgttattt | 1500 |
| gtgctgttgg | aaaatggcaa | aacagcaaca | tcgaaatccc | cttctaaatc | tgagtaaccg | 1560 |
| atgacagctt | cagccggaat | tgtgccgtt | tcatcttctg | ttgtagtgtt | gactggagca | 1620 |
| gctaatgcgg | aggatgctgc | gaataaaact | gcagtaaaaa | ttgaaggaaa | tctcatgaat | 1680 |
| tcgttttgt | actttagatt | gatgtcacca | ccgtgcactg | gcagcagtat | ttatagatgg | 1740 |
| accgtgtggg | gacggttggg | tacacttagc | ggcagcgctg | accccatctg | tgatcaagta | 1800 |
| gggcaaaaac | tggggatgtc | ggagtcgctg | cacggtagca | taagaattta | ctttctggcc | 1860 |
| ggttcacccg | catttgcact | gtggagaaac | agcctgtccg | acaccccacc | agttgccaca | 1920 |
| tcggccctct | gctgctctgg | tgattttctg | gtagcaggca | cagacagcag | tgggtagcgc | 1980 |
| cgtccggtta | ggcaaggtca | cgttgtaggc | tacccagca | aacagagcct | cacatgacac | 2040 |
| catccagctg | cgtcctcgaa | gcgaaaagtt | cggttgcggc | tgcagaaccc | cctcagttgc | 2100 |
| canattcaca | agttttacgc | gacggctaaa | gcgagtgggt | tttaaaaact | tgcggtgcaa | 2160 |
| ggatgcatgc | ggcaacaatt | aattggtgca | tccagcacag | caagcccagt | ctcgagatgt | 2220 |

```
ccagtcgcta cagagtggag tacgcactca aggaacaccg tcgagatggc ctcatagaat   2280
ggatcaaggg cctgctggcc acgccgttcg tcctgtacgc ggtgaagagc aacggcatct   2340
ctgcagtgga cgacctcatg gtaaactctg aggcaaaacg ccgctacgcg gaaatcttcc   2400
acgacctcga actcctcatc gacgacaaca ttgaaatgac caaagccggc accccgaat    2460
tgtctcggct cgtgcagctg gttccgagcg ttggcagctt cttcacgaga ctgcctctgg   2520
aaaaggcctt ctacatcgag gacgagcgcc gcgccatcca caaacgccgg cttgtggccc   2580
cctcgttcaa cgacgtccgg ctcattctca acacggccca gctgttggag atgtcgcggt   2640
tcttccattc caaaaccatc cgagatcgca agctgcagct cattacattc gatggtgaca   2700
tcacactgta cgacgacggc aaaaatttcg atgccgagtc gcccatcctg ccccacctca   2760
tcaaactaat ggccaaggac ctctatgtgg gtatcgtcac cgcggccggc tacagcgacg   2820
gaacaagtac tacgagcgcc tcaagggcct catcgacgcc gtccagacgt ccccgctgct   2880
cacaggccac cagaaagaga acctgttcat tatgggcggc gaggcaaact acctcttccg   2940
gtacagtaac gaggagcaga gattacgctt ctactccaaa gacagatggc tgctcgagaa   3000
catgctgaat tggtccgagg aggacattca tctgacactg gactttgcgc aggacgttct   3060
aaacgacctc gttcacaaac tgggctcgcc agccaccgtg gtccgcaagg agcgtcgcgt   3120
cggcctggtt ccattaccgg gccacaagct gatccgcgag cagctcgagg agatcgttct   3180
ccgcgtcgac accattcctt gcggcggcgg tgctcaacgg cctcaaccta ctactgggct   3240
gcttcctaat gcaggagtcg cataaggag  agcgtcgact cccgcgactc ggcgttcact   3300
ttcgagctat tatcaacgcc ggaatacgtc agaaacagcc gtgccccagg gaccagaaag   3360
cctactggtg agtatgttct ttcgtgtgat ttttccgagg atgagaacga cgataacgag   3420
cacaactcgg agtcggagga cacgcttatt gcgttgaacg cagccacatc agcaggctgt   3480
caagactgag tatggccaca gagctggatt ctcggcctca tactcaagac gttagtaaac   3540
tccgtctgcc agaaattgct gacgaggatg tataataata gatgaattac gaacaattgt   3600
agttcaaaaa aatttagtaa caatattgtc tagatgacag atgtgctgaa accagtgaac   3660
tccaataaac cactcaccgc tacccaagag aaacagatca gagtgctagg gccttgtttc   3720
agagtactac aacgtttacc agaagcttga gcaagttctc aaacgcgggt ttgtcgaccg   3780
atgcccttga gagccttcaa cccagtcagc tccttccggt gggcgcgggg catgactatc   3840
gtcgccgcac ttatgactgt cttctttatc atgcaactcg taggacaggt gccggcagcg   3900
ctctgggtca ttttcggcga ggaccgcttt cgctggagcg cgacgatgat cggcctgtcg   3960
cttgcggtat tcggaatctt gcacgccctc gctcaagcct tcgtcactgg tcccgccacc   4020
aaacgtttcg gcgagaagca ggccattatc gccggcatgg cggccgacgc gctgggctac   4080
gtcttgctgg cgttcgcgac gcgaggctgg atggccttcc ccattatgat tcttctcgct   4140
tccggcggca tcgggatgcc cgcgttgcag gccatgctgt ccaggcaggt agatgacgac   4200
catcagggac agcttcaagg atcgctcgcg gctcttacca gcctaacttc gatcactgga   4260
ccgctgatcg tcacggcgat ttatgccgcc tcggcgagca catggaacgg ttggcatgg    4320
attgtaggcg ccgccctata ccttgtctgc ctccccgcgt tgcgtcgcgg tgcatggagc   4380
cgggccacct cgacctgaat ggaagccggc ggcacctcgc taacggattc accactccaa   4440
gaattggagc caatcaattc ttgcggagaa ctgtgaatgc gcaaaccaac ccttggcaga   4500
acatatccat cgcgtccgcc atctccagca gccgcacgcg gcgcatcggg ggggggggg    4560
ggggggggg gcaaacaatt catcattttt tttttattct ttttttgat ttcggtttct     4620
```

-continued

```
ttgaaatttt tttgattcgg taatctccga acagaaggaa gaacgaagga aggagcacag    4680
acttagattg gtatatatac gcatatgtag tgttgaagaa acatgaaatt gcccagtatt    4740
cttaacccaa ctgcacagaa caaaaacctg caggaaacga agataaatca tgtcgaaagc    4800
tacatataag gaacgtgctg ctactcatcc tagtcctgtt gctgccaagc tatttaatat    4860
catgcacgaa aagcaaacaa acttgtgtgc ttcattggat gttcgtacca ccaaggaatt    4920
actggagtta gttgaagcat taggtcccaa aatttgttta ctaaaaacac atgtggatat    4980
cttgactgat ttttccatgg agggcacagt taagccgcta aaggcattat ccgccaagta    5040
caatttttta ctcttcgaag acagaaaatt tgctgacatt ggtaatacag tcaaattgca    5100
gtactctgcg ggtgtataca gaatagcaga atgggcagac attacgaatg cacacggtgt    5160
ggtgggccca ggtattgtta gcggtttgaa gcaggcggca gaagaagtaa caaaggaacc    5220
tagaggcctt ttgatgttag cagaattgtc atgcaagggc tccctatcta ctggagaata    5280
tactaagggt actgttgaca ttgcgaagag cgacaaagat tttgttatcg gctttattgc    5340
tcaaagagac atgggtggaa gagatgaagg ttacgattgg ttgattatga cacccggtgt    5400
gggtttagat gacaagggag acgcattggg tcaacagtat agaaccgtgg atgatgtggt    5460
ctctacagga tctgacatta ttattgttgg aagaggacta tttgcaaagg aagggatgc     5520
taaggtagag ggtgaacgtt acagaaaagc aggctgggaa gcatatttga aagatgcgg     5580
ccagcaaaac taaaaaactg tattataagt aaatgcatgt atactaaact cacaaattag    5640
agcttcaatt taattatatc agttattacc cgggaatctc ggtcgtaatg attttttataa   5700
tgacgaaaaa aaaaaaattg gaaagaaaag ccccccccccc cccccccccc ccccccccc    5760
ccccgcagcg ttgggtcctg gccacgggtg cgcatgatcg tgctcctgtc gttgaggacc    5820
cggctaggct ggcggggttg ccttactggt tagcagaatg aatcaccgat acgcgagcga    5880
acgtgaagcg actgctgctg caaaacgtct gcgacctgag caacaacatg aatggtcttc    5940
ggtttccgtg tttcgtaaag tctggaaacg cggaagtcag cgccctgcac cattatgttc    6000
cggatctgca tcgcaggatg ctgctggcta ccctgtggaa cacctacatc tgtattaacg    6060
aagcgctggc attgaccctg agtgattttt ctctggtccc gccgcatcca taccgccagt    6120
tgtttaccct cacaacgttc cagtaaccgg gcatgttcat catcagtaac ccgtatcgtg    6180
agcatcctct ctcgtttcat cggtatcatt accccatga acagaaattc cccttacac     6240
ggaggcatca agtgaccaaa caggaaaaaa ccgcccttaa catggcccgc tttatcagaa    6300
gccagacatt aacgcttctg gagaaactca acgagctgga cgcggatgaa caggcagaca    6360
tctgtgaatc gcttcacgac cacgctgatg agctttaccg cagctgcctc gcgcgtttcg    6420
gtgatgacgg tgaaaacctc tgacacatgc agctcccgga cggtcaca gcttgtctgt      6480
aagcggatgc cgggagcaga caagcccgtc agggcgcgtc agcgggtgtt ggcgggtgtc    6540
ggggcgcagc catgacccag tcacgtagcg atagcggagt gtatactggc ttaactatgc    6600
ggcatcagag cagattgtac tgagagtgca ccatatgcgg tgtgaaatac cgcacagatg    6660
cgtaaggaga aaataccgca tcaggcgctc ttccgcttcc tcgctcactg actcgctgcg    6720
ctcggtcgtt cggctgcggc gagcggtatc agctcactca aaggcggtaa tacggttatc    6780
cacagaatca ggggataacg caggaaagaa catgtgagca aaaggccagc aaaaggccag    6840
gaaccgtaaa aaggccgcgt tgctggcgtt tttccatagg ctccgccccc ctgacgagca    6900
tcacaaaaat cgacgctcaa gtcagaggtg gcgaaacccg acaggactat aaagatacca    6960
```

-continued

```
ggcgtttccc cctggaagct ccctcgtgcg ctctcctgtt ccgaccctgc cgcttaccgg      7020
atacctgtcc gcctttctcc cttcgggaag cgtggcgctt tctcatagct cacgctgtag      7080
gtatctcagt tcggtgtagg tcgttcgctc caagctgggc tgtgtgcacg aaccccccgt      7140
tcagcccgac cgctgcgcct tatccggtaa ctatcgtctt gagtccaacc cggtaagaca      7200
cgacttatcg ccactggcag cagccactgg taacaggatt agcagagcga ggtatgtagg      7260
cggtgctaca gagttcttga agtggtggcc taactacggc tacactagaa ggacagtatt      7320
tggtatctgc gctctgctga agccagttac cttcggaaaa agagttggta gctcttgatc      7380
cggcaaacaa accaccgctg gtagcggtgg ttttttttgtt gcaagcagc agattacgcg      7440 cagaaaaaaa ggatctcaag aagatccttt gatcttttct acggggtctg acgctcagtg      7500
gaacgaaaac tcacgttaag ggattttggt catgagatta tcaaaaagga tcttcaccta      7560 gatccttta aattaaaaat gaagttttaa atcaatctaa agtatatatg agtaaacttg      7620
gtctgacagt taccaatgct taatcagtga ggcacctatc tcagcgatct gtctatttcg      7680
ttcatccata gttgcctgac tccccgtcgt gtagataact acgatacggg agggcttacc      7740
atctggcccc agtgctgcaa tgataccgcg agacccacgc tcaccggctc cagatttatc      7800
agcaataaac cagccagccg gaagggccga gcgcagaagt ggtcctgcaa ctttatccgc      7860
ctccatccag tctattaatt gttgccggga agctagagta agtagttcgc cagttaatag      7920
tttgcgcaac gttgttgcca ttgctgcagg catcgtggtg tcacgctcgt cgtttggtat      7980
ggcttcattc agctccggtt cccaacgatc aaggcgagtt acatgatccc ccatgttgtg      8040
caaaaaagcg gttagctcct tcggtcctcc gatcgttgtc agaagtaagt tggccgcagt      8100
gttatcactc atggttatgg cagcactgca taattctctt actgtcatgc catccgtaag      8160
atgcttttct gtgactggtg agtactcaac caagtcattc tgagaatagt gtatgcggcg      8220
accgagttgc tcttgcccgg cgtcaacacg ggataatacc gcgccacata gcagaacttt      8280
aaaagtgctc atcattggaa aacgttcttc ggggcgaaaa ctctcaagga tcttaccgct      8340
gttgagatcc agttcgatgt aacccactcg tgcacccaac tgatcttcag catcttttac      8400
tttcaccagc gtttctgggt gagcaaaaac aggaaggcaa aatgccgcaa aaaagggaat      8460
aagggcgaca cggaaatgtt gaatactcat actcttcctt tttcaatatt attgaagcat      8520
ttatcagggt tattgtctca tgagcggata catatttgaa tgtatttaga aaaataaaca      8580
aataggggtt ccgcgcacat ttccccgaaa agtgccacct gacgtctaag aaaccattat      8640
tatcatgaca ttaacctata aaaataggcg tatcacgagg ccctttcgtc ttcaa           8695
```

<210> SEQ ID NO 26
<211> LENGTH: 36
<212> TYPE: DNA
<213> ORGANISM: synthetic probe or primer

<400> SEQUENCE: 26

```
agtcactctt caaggcatac ccgcgtgtca ggaggg                                 36
```

<210> SEQ ID NO 27
<211> LENGTH: 39
<212> TYPE: DNA
<213> ORGANISM: synthetic probe or primer

<400> SEQUENCE: 27

```
agtcactctt cacagggatc cttagtgatg gtggtgatg                              39
```

<210> SEQ ID NO 28
<211> LENGTH: 4190
<212> TYPE: DNA
<213> ORGANISM: vector pMF30

<400> SEQUENCE: 28

```
gcgcccaata cgcaaaccgc ctctcccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagcttgc     240
atgcctgcag ttgattgcag atgccagatc ccgaaagaac agaggacgga gcgtaaactt     300
gtggcattcc accagaaatt gatacagata agcttccgga gtcaccagct aaaacggaat     360
tgcaagaaat aatatcgata actttatcac cactagaata gccggtgttg ctgacagtaa     420
tatcctgtga cccgtttgaa cctaaattat taaaaatgga aatcaattga ttagcatcgc     480
taccettcct agtggctata tagtggtctg aagaagaaac aactgaggat ttgtaagttg     540
aataggcaga atccttctta atagcttgat ttcttatttg atttagttta ctgattagct     600
cgtagtattc tgaatcggta ttatatccac ttaaccataa agcttctcta ttggcaggat     660
cggaaccacc attgagacct tgttcttggc cataataaat aattgggata ccatcaccca     720
aaattataaa agccatgtca ttcttaatca aggatgtgtc tgaggtaact gatggaaatc     780
taacttggtc atggttttca ataaagtttc ccaacaaaga gacgtccgaa caagatgact     840
gtaacgtgga gatcattgaa gttaactcac tggaagtcgc cgaagtatca ctgaagaatc     900
tatatactgg atagtataat ggatagttgg taactccttt catataattc tgatatggac     960
aagtataagt tggatctcct tgataaactt cacctaagtt ataaacacca gaagcgtcct    1020
caaacttcgt taatgaagcg gtatctacgt gctttgcact atcaattctt aaaccatcga    1080
ttgaatagtt ttgaacaaaa tctgacaccc aagtttgaaa tactcctata acttcattat    1140
cctcggtact taaatctgga agggagactt cagtatcacc ttcccaacaa tcttcaacat    1200
tggtttgatc attataattt gtaatcaaac aataatcgtg gaagtaagat tgttgattga    1260
atggagtgaa actagaataa tctacgcttg aaccatctcc gttccaagca taatggttgt    1320
aaacaacgtc gaccatcaat aacatgcttc tggaatgcaa ttcgctagct aattgtttca    1380
attcatcagc ggtaccaaaa ttagtgttca attcatcaat attttcatc caataaccat    1440
ggtaagcata accataagca gtattgtcag gaatttgctc aacaactggg gagatccaga    1500
tcgcagtgaa acccatacct tgaatataat ccaacttgtc gataatccct ttataagatc    1560
caccacagta cttgcgatca ctcactaaac agtcagctgt ggtcgagcca tcagatctgg    1620
caaacctatc agtaacgatt tgataaatcg attggtcttt ccatttatca gctgacgagc    1680
taacatccct cttgtcaaaa ataatcggtt gagcagatac caatcttgag aatgctaaaa    1740
ttgctgcaac aactttactt gtaaatcctt cagttgaaaa tctcattgaa ttcactggcc    1800
gtcgttttac aacgtcgtga ctgggaaaac cctggcgtta cccaacttaa tcgccttgca    1860
gcacatcccc ctttcgccag ctggcgtaat agcgaagagg cccgcaccga tcgcccttcc    1920
caacagttgc gcagcctgaa tggcgaatgg cgcctgatgc ggtattttct ccttacgcat    1980
ctgtgcggta tttcacaccg catatggtgc actctcagta caatctgctc tgatgccgca    2040
tagttaagcc agccccgaca cccgccaaca cccgctgacg cgccctgacg ggcttgtctg    2100
ctcccggcat ccgcttacag acaagctgtg accgtctccg ggagctgcat gtgtcagagg    2160
```

```
ttttcaccgt catcaccgaa acgcgcgaga cgaaagggcc tcgtgatacg cctattttta    2220
taggttaatg tcatgataat aatggtttct tagacgtcag gtggcacttt tcggggaaat    2280
gtgcgcggaa cccctatttg tttattttc taaatacatt caaatatgta tccgctcatg    2340
agacaataac cctgataaat gcttcaataa tattgaaaaa ggaagagtat gagtattcaa    2400
catttccgtg tcgcccttat tcccttttt gcggcatttt gccttcctgt ttttgctcac    2460
ccagaaacgc tggtgaaagt aaaagatgct gaagatcagt tgggtgcacg agtgggttac    2520
atcgaactgg atctcaacag cggtaagatc cttgagagtt ttcgccccga agaacgtttt    2580
ccaatgatga gcacttttaa agttctgcta tgtggcgcgg tattatcccg tattgacgcc    2640
gggcaagagc aactcggtcg ccgcatacac tattctcaga atgacttggt tgagtactca    2700
ccagtcacag aaaagcatct tacgatggc atgacagtaa gagaattatg cagtgctgcc    2760
ataaccatga gtgataacac tgcggccaac ttacttctga caacgatcgg aggaccgaag    2820
gagctaaccg ctttttttgca caacatgggg gatcatgtaa ctcgccttga tcgttgggaa    2880
ccggagctga atgaagccat accaaacgac gagcgtgaca ccacgatgcc tgtagcaatg    2940
gcaacaacgt tgcgcaaact attaactggc gaactactta ctctagcttc ccggcaacaa    3000
ttaatagact ggatggaggc ggataaagtt gcaggaccac ttctgcgctc ggcccttccg    3060
gctggctggt ttattgctga taaatctgga gccggtgagc gtgggtctcg cggtatcatt    3120
gcagcactgg ggccagatgg taagccctcc cgtatcgtag ttatctacac gacggggagt    3180
caggcaacta tggatgaacg aaatagacag atcgctgaga taggtgcctc actgattaag    3240
cattggtaac tgtcagacca gtttactca tatatacttt agattgattt aaaacttcat    3300
ttttaattta aaaggatcta ggtgaagatc ctttttgata atctcatgac caaaatccct    3360
taacgtgagt tttcgttcca ctgagcgtca gaccccgtag aaaagatcaa aggatcttct    3420
tgagatcctt ttttttctgcg cgtaatctgc tgcttgcaaa caaaaaaacc accgctacca    3480
gcggtggttt gtttgccgga tcaagagcta ccaactcttt ttccgaaggt aactggcttc    3540
agcagagcgc agataccaaa tactgtcctt ctagtgtagc cgtagttagg ccaccacttc    3600
aagaactctg tagcaccgcc tacataccct gctctgctaa tcctgttacc agtggctgct    3660
gccagtggcg ataagtcgtg tcttaccggg ttggactcaa gacgatagtt accggataag    3720
gcgcagcggt cgggctgaac ggggggttcg tgcacacagc ccagcttgga gcgaacgacc    3780
tacaccgaac tgagatacct acagcgtgag ctatgagaaa gcgccacgct tcccgaaggg    3840
agaaaggcgg acaggtatcc ggtaagcggc agggtcggaa caggagagcg cacgagggag    3900
cttccagggg gaaacgcctg gtatctttat agtcctgtcg ggtttcgcca cctctgactt    3960
gagcgtcgat ttttgtgatg ctcgtcaggg ggcggagcc tatggaaaaa cgccagcaac    4020
gcggcctttt tacggttcct ggccttttgc tggccttttg ctcacatgtt ctttcctgcg    4080
ttatcccctg attctgtgga taaccgtatt accgcctttg agtgagctga taccgctcgc    4140
cgcagccgaa cgaccgagcg cagcgagtca gtgagcgagg aagcggaaga               4190

<210> SEQ ID NO 29
<211> LENGTH: 38
<212> TYPE: DNA
<213> ORGANISM: synthetic probe or primer

<400> SEQUENCE: 29
agtcactctt cacctcttgt caaaaataat cggttgag                              38
```

-continued

```
<210> SEQ ID NO 30
<211> LENGTH: 52
<212> TYPE: DNA
<213> ORGANISM: synthetic probe or primer

<400> SEQUENCE: 30
tgcttcctac cactagcagc actaggacat acccgcgtgt caggaggggc ag            52

<210> SEQ ID NO 31
<211> LENGTH: 57
<212> TYPE: DNA
<213> ORGANISM: synthetic probe or primer

<400> SEQUENCE: 31
tagtactagt attagtaggc ttcgcatgga attcactggc cgtcgtttta caacgtc       57

<210> SEQ ID NO 32
<211> LENGTH: 7927
<212> TYPE: DNA
<213> ORGANISM: vector pFMPT-CL-E2-H6

<400> SEQUENCE: 32
ggtaccctgc tcaatctccg gaatggtgat ctgatcgttc ctgaaaacct cgacattggc      60
tccctcctga cacaggtact cgtacaggtt ccaggtaaac gagtcgtagt tgtcgatcat     120
gacaacgttc ttagaagcgg ccggcatttt gaaggtgact aatagcctaa gaaaatattt     180
aatttaattt tcattaaatt ttcctatact cgctatttca gcttttcatc tcatcacttc     240
ataaacgata taaaccagaa aaagaactat tttcaaacac gcttctcaaa agcggtatgt     300
ccttccacgt ctccttagaa tctggcaagt ccgcgagggg gatccttagt gatggtggtg     360
atggtgtctg ccctcgatca cctgccactc tgttgtagac agcagcagcg agctaagctc     420
tgatctatcc ctgtcctcca agtcacaacg ctctcctcga gtccaattgc atgcggcttc     480
gaacctgtgc tccacgcccc ccacgtacat cctaaccttg aagatggtga agttgacagt     540 gcagggtag tgccagagcc tatatgggta atgaaccata cacctaggtg tcagccaggg      600
cccagaaccg catctggcgt aagtggcctc ggggtgcttc cgaaaacagt cagtgggca      660 ggtcaaggtg ttgttgccgg cccccccgat gttgcacggg gggccccac acgtcttggt      720 gaacccagtg ccattcatcc atgtacagcc gaaccagttg cctcgcggcg gccgcgtgtt     780
gttgagaatc agcacatccg agtcgttcgc ccccagtta tacgtgggga caccaaaccg      840
atcggtcgtc cccaccacaa cagggctcgg ggtgaagcaa tacactggac cgcacacctg     900
agacgcgggt acaataccac acggtcgagg cgcgtagtgc cagcagtagg gcctctggtc     960
cgagctgtta ggctcagtgt aagtgagggg acccccaccc tgagcgaact tgtcgatgga    1020
gcgacagctg gccaagcgct ctgggcatcc agacgagttg aatttgtgtt tgtagaatag    1080
tgcggcaaag aaccctgttt ggagggagtc gttgcagttc agggcagtcc tgttgatgtg    1140
ccaactgccg ttggtgttta cgagctggat tttctgagcc gacccggggc taagagggca   1200
cacaaggccc ctggtatcgg aggctgctgc ccctcctgac acgcgggtat gtcctagtgc    1260
tgctagtggt aggaagcata gtactagtat tagtaggctg cgcatgaatt cccgatgaag    1320
cagagagcgc aggaggcggt atttatagtg ccattcccct ctctgagaga cccgatggt     1380 agtcgagtgt atcggagaca gcttgatgta gactccgtgc ctgccggctc ctcttattgg    1440
cggacaccag tgagcaccc cggaacttgc tgtttttctg caaatccgg ggtgaccagt      1500 gggagcctat ttgcacacac gagcgggaca ccccactctg tgaagagtg ccaaagtcat     1560
```

-continued

```
tcttttttccc gttgcggggc agccgattgc atgttttagg aaaatattac ctttgctaca    1620
ccctgtcaga tttaccctcc acacatatat attccgtcac ctccagggac tattattcgt    1680
cgttgcgccg ccagcggaag atatccagaa gctgttttcc gagagactcg gttggcgcct    1740
ggtatatttg atggatgtcg cgctgcctca cgtcccggta cccaggaacg cggtgggatc    1800
tcgggcccat cgaagactgt gctccagact gctcgcccag caggtgtttc ttgatcgccg    1860
cctctaaatt gtccgcgcat cgccggtaac atttttccag ctcggagttt gcgtttagat    1920
acagtttctg cgatgccaaa ggagcctgca gattataacc tcggatgctg tcattcagcg    1980
cttttaattt gacctccaga tagttgctgt atttctgttc ccattggctg ctgcgcagct    2040
tcgtataact cgagttattg ttgcgctctg cctcggcgta ctggctcatg atctggatct    2100
tgtccgtgtc gcttttcttc gagtgtttct cgcaaacgat gtgcacggcc tgcagtgtcc    2160
aatcggagtc gagctggcgc cgaaactggc ggatctgagc ctccacactg ccctgtttct    2220
ctatccacgg cggaaccgcc tcctgccgtt tcagaatgtt gttcaagtgg tactctgtgc    2280
ggtcaatgaa ggcgttattg ccggtgaaat ctttgggaag cggttttcct cggggaagat    2340
tacgaaattc cccgcgtcgt tgcgcttcct ggatctcgag gagatcgttc tccgcgtcga    2400
ggagatcgtt ctccgcgtcg acaccattcc ttgcggcggc ggtgctcaac ggcctcaacc    2460
tactactggg ctgcttccta atgcaggagt cgcataaggg agagcgtcga caaacccgcg    2520
tttgagaact tgctcaagct tctggtaaac gttgtagtac tctgaaacaa ggccctagca    2580
ctctgatctg tttctcttgg gtagcggtga gtggtttatt ggagttcact ggtttcagca    2640
catctgtcat ctagacaata ttgttactaa attttttga actacaattg ttcgtaattc    2700
atctattatt atacatcctc gtcagcaatt tctggcagac ggagtttact aacgtcttga    2760
gtatgaggcc gagaatccag ctctgtggcc atactcagtc ttgacagcct gctgatgtgg    2820
ctgcgttcaa cgcaataagc gtgtcctccg actccgagtt gtgctcgtta tcgtcgttct    2880
catcctcgga aaaatcacac gaaagaacat actccaccagt aggctttctg gtccctgggg    2940
cacggctgtt tctgacgtat tccggcgttg ataatagctc gaaagtgaac gccgagtcgc    3000
gggagtcgac cgatgcccct gagagccttc aacccagtca gctccttccg gtgggcgcgg    3060
ggcatgacta tcgtcgccgc acttatgact gtcttcttta tcatgcaact cgtaggacag    3120
gtgccggcag cgctctgggt cattttcggc gaggaccgct ttcgctggag cgcgacgatg    3180
atcggcctgt cgcttgcggt attcggaatc ttgcacgccc tcgctcaagc cttcgtcact    3240
ggtccccgcca ccaaacgttt cggcgagaag caggccatta tcgccggcat ggcggccgac    3300
gcgctgggct acgtcttgct ggcgttcgcg acgcgaggct ggatggcctt ccccattatg    3360
attcttctcg cttccggcgg catcgggatg cccgcgttgc aggccatgct gtccaggcag    3420
gtagatgacg accatcaggg acagcttcaa ggatcgctcg cggctcttac cagcctaact    3480
tcgatcactg gaccgctgat cgtcacgcg atttatgccg cctcggcgag cacatggaac    3540
gggttggcat ggattgtagg cgccgcccta taccttgtct gcctccccgc gttgcgtcgc    3600
ggtgcatgga gccgggccac ctcgacctga atggaagccg gcggcacctc gctaacggat    3660
tcaccactcc aagaattgga gccaatcaat tcttgcggag aactgtgaat gcgcaaacca    3720
acccttggca gaacatatcc atcgcgtccg ccatctccag cagccgcacg cggcgcatcg    3780
ggggggggg ggggggggg gggcaaacaa ttcatcattt ttttttattt cttttttttg    3840
atttcggttt ctttgaaatt ttttgattc ggtaatctcc gaacagaagg aagaacgaag    3900
gaaggagcac agacttagat tggtatatat acgcatatgt agtgttgaag aaacatgaaa    3960
```

-continued

```
ttgcccagta ttcttaaccc aactgcacag aacaaaaacc tgcaggaaac gaagataaat    4020
catgtcgaaa gctacatata aggaacgtgc tgctactcat cctagtcctg ttgctgccaa    4080
gctatttaat atcatgcacg aaaagcaaac aaacttgtgt gcttcattgg atgttcgtac    4140
caccaaggaa ttactggagt tagttgaagc attaggtccc aaaatttgtt tactaaaaac    4200
acatgtggat atcttgactg attttttccat ggagggcaca gttaagccgc taaaggcatt    4260
atccgccaag tacaattttt tactcttcga agacagaaaa tttgctgaca ttggtaatac    4320
agtcaaattg cagtactctg cgggtgtata cagaatagca gaatgggcag acattacgaa    4380
tgcacacggt gtggtgggcc caggtattgt tagcggtttg aagcaggcgg cagaagaagt    4440
aacaaaggaa cctagaggcc ttttgatgtt agcagaattg tcatgcaagg ctccctatc     4500
tactggagaa tatactaagg gtactgttga cattgcgaag agcgacaaag attttgttat    4560
cggctttatt gctcaaagag acatgggtgg aagagatgaa ggttacgatt ggttgattat    4620
gacacccggt gtgggtttag atgacaaggg agacgcattg ggtcaacagt atagaaccgt    4680
ggatgatgtg gtctctacag gatctgacat tattattgtt ggaagaggac tatttgcaaa    4740
gggaagggat gctaaggtag agggtgaacg ttacagaaaa gcaggctggg aagcatattt    4800
gagaagatgc ggccagcaaa actaaaaaac tgtattataa gtaaatgcat gtatactaaa    4860
ctcacaaatt agagcttcaa tttaattata tcagttatta cccgggaatc tcggtcgtaa    4920
tgattttttat aatgacgaaa aaaaaaaaat tggaaagaaa agcccccccc cccccccccc    4980
cccccccccc ccccccgcag cgttgggtcc tggccacggg tgcgcatgat cgtgctcctg    5040
tcgttgagga cccggctagg ctggcggggt tgccttactg gttagcagaa tgaatcaccg    5100
atacgcgagc gaacgtgaag cgactgctgc tgcaaaacgt ctgcgacctg agcaacaaca    5160
tgaatggtct tcggtttccg tgtttcgtaa agtctggaaa cgcggaagtc agcgccctgc    5220
accattatgt tccggatctg catcgcagga tgctgctggc taccctgtgg aacacctaca    5280
tctgtattaa cgaagcgctg gcattgaccc tgagtgattt ttctctggtc ccgccgcatc    5340
cataccgcca gttgtttacc ctcacaacgt tccagtaacc gggcatgttc atcatcagta    5400
acccgtatcg tgagcatcct ctctcgtttc atcggtatca ttaccccat gaacagaaat     5460
tccccttac acgaggcat caagtgacca aacaggaaaa aaccgccctt aacatggccc       5520
gctttatcag aagccagaca ttaacgcttc tggagaaact caacgagctg gacgcggatg    5580
aacaggcaga catctgtgaa tcgcttcacg accacgctga tgagctttac cgcagctgcc    5640
tcgcgcgttt cggtgatgac ggtgaaaacc tctgacacat gcagctcccg gagacggtca    5700
cagcttgtct gtaagcggat gccgggagca gacaagcccg tcaggcgcg tcagcgggtg     5760
ttggcgggtg tcgggcgca gccatgaccc agtcacgtag cgatagcgga gtgtatactg    5820
gcttaactat gcggcatcag agcagattgt actgagagtg caccatatgc ggtgtgaaat    5880
accgcacaga tgcgtaagga gaaataccg catcaggcgc tcttccgctt cctcgctcac     5940
tgactcgctg cgctcggtcg ttcggctgcg gcgagcggta tcagctcact caaaggcggt    6000
aatacggtta tccacagaat cagggataa cgcaggaaag aacatgtgag caaaaggcca     6060
gcaaaaggcc aggaaccgta aaaaggccgc gttgctggcg tttttccata ggctccgccc    6120
ccctgacgag catcacaaaa atcgacgctc aagtcagagg tggcgaaacc cgacaggact    6180
ataaagatac caggcgtttc ccctggaag ctccctcgtg cgctctcctg ttccgaccct     6240
gccgcttacc ggatacctgt ccgcctttct cccttcggga agcgtggcgc tttctcatag    6300
```

```
ctcacgctgt aggtatctca gttcggtgta ggtcgttcgc tccaagctgg gctgtgtgca      6360
cgaacccccc gttcagcccg accgctgcgc cttatccggt aactatcgtc ttgagtccaa      6420
cccggtaaga cacgacttat cgccactggc agcagccact ggtaacagga ttagcagagc      6480
gaggtatgta ggcggtgcta cagagttctt gaagtggtgg cctaactacg gctacactag      6540
aaggacagta tttggtatct gcgctctgct gaagccagtt accttcggaa aaagagttgg      6600
tagctcttga tccggcaaac aaaccaccgc tggtagcggt ggtttttttg tttgcaagca      6660
gcagattacg cgcagaaaaa aaggatctca agaagatcct ttgatctttt ctacggggtc      6720
tgacgctcag tggaacgaaa actcacgtta agggattttg gtcatgagat tatcaaaaag      6780
gatcttcacc tagatccttt taaattaaaa atgaagtttt aaatcaatct aaagtatata      6840
tgagtaaact tggtctgaca gttaccaatg cttaatcagt gaggcaccta tctcagcgat      6900
ctgtctattt cgttcatcca tagttgcctg actccccgtc gtgtagataa ctacgatacg      6960
ggagggctta ccatctggcc ccagtgctgc aatgataccg cgagacccac gctcaccggc      7020
tccagattta tcagcaataa accagccagc cggaagggcc gagcgcagaa gtggtcctgc      7080
aactttatcc gcctccatcc agtctattaa ttgttgccgg gaagctagag taagtagttc      7140
gccagttaat agtttgcgca acgttgttgc cattgctgca ggcatcgtgg tgtcacgctc      7200
gtcgtttggt atggcttcat tcagctccgg ttcccaacga tcaaggcgag ttacatgatc      7260
ccccatgttg tgcaaaaaag cggttagctc cttcggtcct ccgatcgttg tcagaagtaa      7320
gttggccgca gtgttatcac tcatggttat ggcagcactg cataattctc ttactgtcat      7380
gccatccgta agatgctttt ctgtgactgg tgagtactca accaagtcat tctgagaata      7440
gtgtatgcgg cgaccgagtt gctcttgccc ggcgtcaaca cgggataata ccgcgccaca      7500
tagcagaact ttaaaagtgc tcatcattgg aaaacgttct cggggcgaaa actctcaag      7560
gatcttaccg ctgttgagat ccagttcgat gtaacccact cgtgcaccca actgatcttc      7620
agcatctttt actttcacca gcgtttctgg gtgagcaaaa acaggaaggc aaaatgccgc      7680
aaaaaaggga ataagggcga cacggaaatg ttgaatactc atactcttcc tttttcaata      7740
ttattgaagc atttatcagg gttattgtct catgagcgga tacatatttg aatgtattta      7800
gaaaaataaa caaataggg ttccgcgcac atttccccga aaagtgccac ctgacgtcta      7860
agaaaccatt attatcatga cattaaccta taaaaatagg cgtatcacga ggccctttcg      7920
tcttcaa                                                              7927

<210> SEQ ID NO 33
<211> LENGTH: 24
<212> TYPE: DNA
<213> ORGANISM: synthetic probe or primer

<400> SEQUENCE: 33
taaggatccc cgggtaccga gctc                                             24

<210> SEQ ID NO 34
<211> LENGTH: 25
<212> TYPE: DNA
<213> ORGANISM: synthetic probe or primer

<400> SEQUENCE: 34
ccagttcatc atcatatccc aagcc                                            25

<210> SEQ ID NO 35
<211> LENGTH: 4234
```

-continued

<212> TYPE: DNA
<213> ORGANISM: vector pUC18-FMD-CL-E1
<220> FEATURE:
<221> NAME/KEY: misc_feature
<222> LOCATION: (988)..(989)
<223> OTHER INFORMATION: N is any nucleotide
<220> FEATURE:
<221> NAME/KEY: misc_feature
<222> LOCATION: (1167)..(1168)
<223> OTHER INFORMATION: N is any nucleotide

<400> SEQUENCE: 35

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg aattcgagct    240
cggtacccgg ggatccttac cagttcatca tcatatccca agccatacgg tgacctgtta    300
tgtggccggg atagattgag caattgcagt cctgcaccgt ctcatgccgg cgaggcgaga    360
tggtgaacag ctgggagacg aggaagacag atccgcagag atcccccacg tacatagcgg    420
aacagaaagc agccgcccca acgagcaaat cgacgtggcg tcgtattgtc gtagtgggga    480
cgctggcgtt cctagctgcg agcgtggggg tgagcgctac ccagcagcgg gaagagttgt    540
tctcccgaac gcagggcacg cacccggggg tgtgcatgat catgtccgct gcctcataca    600
caatgcttga gttggagcag tcgttcgtga catggtacat cccggacacg ttgcgcacct    660
catatcctag tgctgctagt ggtaggaagc atagtactag tattagtagg cttcgcatga    720
attcccgatg aaggcagaga gcgcaaggag gcggtattta tagtgccatt cccctctctg    780
agagacccgg atggtagtcg agtgttatcg gagacagctt gatgtagact ccgtgcctgc    840
cggtcctctt attggcggac accagtgaga caccccggaa cttgctgttt ttctgcaaaa    900
tccggggtga ccagtgggag cctatttgca cacacgagcg ggacacccca ctctggtgaa    960
gagtgccaaa gtcattcttt ttcccgtnnc ggggcagccg attgcatgtt ttaggaaaat   1020
attacctttg ctacaccctg tcagatttac cctccacaca tatatattcc gtcacctcca   1080
gggactattc ttggctcgtt gcgccgccgc ggaagatatc cagaagctgt gttttccgag   1140
agactcggtt ggcgcctggt atatttnnag gatgtcgcgc tgcctcacgt cccggtaccc   1200
aggaacgcgg tgggatctcg ggcccatcga agactgtgct ccagactgct cgcccagcag   1260
gtgtttcttg attgccgcct ctaaatagtc cgcgcatcgc cggtaacatt tttccagctc   1320
ggagtttgcg tttagataca tttctgcgat gccaaaggag cctgcagatt ataacctcgg   1380
atgctgtcat tcagcgcttt taatttgacc tccagatagt tgctgtattt ctgttccatt   1440
ggctgctgga cgttcgtata actcgagtta ttgttgcgct ctgcctcggc gtactggctc   1500
atgactgact gcggtcgctt ctcgagtgtt ctcgcaacag gacgcctgca ggtcatcgag   1560
tcgagctggc gccgaaactg gcggatctga cctccacact gccctgtatc tctatccacc   1620
gggaaccgcc tcctgccgtt ccagaatgtt gttcaagtgg tagctctgtg cggtcaatga   1680
aggcgttatt gccggtgaaa tctttgggaa gcggtttatc ctcggggaag attacgaaat   1740
tcccgcgcgt cgttgcgctt cctggatctc gaggaagatc gttctccgcg tcgaggagat   1800
cgttctccgc gtcgacctgc aggcatgcaa gcttggcact ggccgtcgtt ttacaacgtc   1860
gtgactggga aaaccctggc gttacccaac ttaatcgcct tgcagcacat cccccttccg   1920
ccagctggcg taatagcgaa gaggcccgca ccgatcgccc ttcccaacag ttgcgcagcc   1980
```

-continued

```
tgaatggcga atggcgcctg atgcggtatt ttctccttac gcatctgtgc ggtatttcac      2040
accgcatatg gtgcactctc agtacaatct gctctgatgc cgcatagtta agccagcccc      2100
gacacccgcc aacacccgct gacgcgccct gacgggcttg tctgctcccg gcatccgctt      2160
acagacaagc tgtgaccgtc tccgggagct gcatgtgtca gaggttttca ccgtcatcac      2220
cgaaacgcgc gagacgaaag ggcctcgtga tacgcctatt tttataggtt aatgtcatga      2280
taataatggt ttcttagacg tcaggtggca cttttcgggg aaatgtgcgc ggaaccccta      2340
tttgtttatt tttctaaata cattcaaata tgtatccgct catgagacaa taaccctgat      2400
aaatgcttca ataatattga aaaggaaga gtatgagtat tcaacatttc cgtgtcgccc       2460
ttattccctt ttttgcggca ttttgccttc ctgtttttgc tcacccagaa acgctggtga      2520
aagtaaaaga tgctgaagat cagttgggtg cacgagtggg ttacatcgaa ctggatctca      2580
acagcggtaa gatccttgag agttttcgcc ccgaagaacg ttttccaatg atgagcactt      2640
ttaaagttct gctatgtggc gcggtattat cccgtattga cgccgggcaa gagcaactcg      2700
gtcgccgcat acactattct cagaatgact tggttgagta ctcaccagtc acagaaaagc      2760
atcttacgga tggcatgaca gtaagagaat tatgcagtgc tgccataacc atgagtgata      2820
acactgcggc caacttactt ctgacaacga tcggaggacc gaaggagcta accgcttttt      2880
tgcacaacat gggggatcat gtaactcgcc ttgatcgttg ggaaccggag ctgaatgaag      2940
ccataccaaa cgacgagcgt gacaccacga tgcctgtagc aatggcaaca acgttgcgca      3000
aactattaac tggcgaacta cttactctag cttcccggca acaattaata gactggatgg      3060
aggcggataa agttgcagga ccacttctgc gctcggccct tccggctggc tggtttattg      3120
ctgataaatc tggagccggt gagcgtgggt ctcgcggtat cattgcagca ctggggccag      3180
atggtaagcc ctcccgtatc gtagttatct acacgacggg gagtcaggca actatggatg      3240
aacgaaatag acagatcgct gagataggtg cctcactgat taagcattgg taactgtcag      3300
accaagttta ctcatatata ctttagattg atttaaaact tcattttaa tttaaaagga      3360 tctaggtgaa gatcctttt gataatctca tgaccaaaat cccttaacgt gagttttcgt       3420
tccactgagc gtcagacccc gtagaaaaga tcaaggatc ttcttgagat cctttttttc       3480
tgcgcgtaat ctgctgcttg caaacaaaaa aaccaccgct accagcggtg gtttgtttgc      3540
cggatcaaga gctaccaact ctttttccga aggtaactgg cttcagcaga gcgcagatac      3600
caaatactgt ccttctagtg tagccgtagt taggccacca cttcaagaac tctgtagcac      3660
cgcctacata cctcgctctg ctaatcctgt taccagtggc tgctgccagt ggcgataagt      3720
cgtgtcttac cgggttggac tcaagacgat agttaccgga taaggcgcag cggtcgggct      3780 gaacggggggg ttcgtgcaca cagcccagct tggagcgaac gacctacacc gaactgagat      3840
acctacagcg tgagctatga gaaagcgcca cgcttcccga agggagaaag gcggacaggt      3900
atccggtaag cggcagggtc ggaacaggag agcgcacgag ggagcttcca gggggaaacg      3960
cctggtatct ttatagtcct gtcgggtttc gccacctctg acttgagcgt cgatttttgt      4020
gatgctcgtc aggggggcgg agcctatgga aaaacgccag caacgcggcc ttttttacggt     4080 tcctggcctt ttgctggcct tttgctcaca tgttctttcc tgcgttatcc cctgattctg      4140
tggataaccg tattaccgcc tttgagtgag ctgataccgc tcgccgcagc cgaacgaccg      4200
agcgcagcga gtcagtgagc gaggaagcgg aaga                                  4234
```

<210> SEQ ID NO 36
<211> LENGTH: 7429

<212> TYPE: DNA
<213> ORGANISM: vector pFPMT-CL-E1

<400> SEQUENCE: 36

| | | | | | |
|---|---|---|---|---|---:|
| ggtaccctgc | tcaatctccg | gaatggtgat | ctgatcgttc | ctgaaaacct | cgacattggc | 60 |
| tccctcctga | cacaggtact | cgtacaggtt | ccaggtaaac | gagtcgtagt | tgtcgatcat | 120 |
| gacaacgttc | ttagaagcgg | ccggcatttt | gaaggtgact | aatagcctaa | gaaaatattt | 180 |
| aatttaattt | tcattaaatt | ttcctatact | cgctatttca | gcttttcatc | tcatcacttc | 240 |
| ataaacgata | taaaccagaa | aaagaactat | tttcaaacac | gcttctcaaa | agcggtatgt | 300 |
| ccttccacgt | ctccttagaa | tctggcaagt | ccgcgagggg | gatccttacc | agttcatcat | 360 |
| catatcccaa | gccatacggt | gacctgttat | gtggccggga | tagattgagc | aattgcagtc | 420 |
| ctgcaccgtc | tcatgccggc | gaggcgagat | ggtgaacagc | tgggagacga | ggaagacaga | 480 |
| tccgcagaga | tcccccacgt | acatagcgga | acagaaagca | gccgcccaa | cgagcaaatc | 540 |
| gacgtggcgt | cgtattgtcg | tagtggggac | gctggcgttc | ctagctgcga | gcgtggggt | 600 |
| gagcgctacc | cagcagcggg | aagagttgtt | ctcccgaacg | cagggcacgc | acccggggt | 660 |
| gtgcatgatc | atgtccgctg | cctcatacac | aatgcttgag | ttggagcagt | cgttcgtgac | 720 |
| atggtacatc | ccggacacgt | tgcgcacctc | atatcctagt | gctgctagtg | gtaggaagca | 780 |
| tagtactagt | attagtaggc | ttcgcatgaa | ttcccgatga | agcagagagc | gcaggaggcg | 840 |
| gtatttatag | tgccattccc | ctctctgaga | gacccggatg | gtagtcgagt | gtatcggaga | 900 |
| cagcttgatg | tagactccgt | gcctgccggc | tcctcttatt | ggcggacacc | agtgagacac | 960 |
| cccggaactt | gctgtttttc | tgcaaaatcc | ggggtgacca | gtgggagcct | atttgcacac | 1020 |
| acgagcggga | caccccactc | tggtgaagag | tgccaaagtc | attctttttc | ccgttgcggg | 1080 |
| gcagccgatt | gcatgtttta | ggaaaatatt | acctttgcta | caccctgtca | gatttaccct | 1140 |
| ccacacatat | atattccgtc | acctccaggg | actattattc | gtcgttgcgc | cgccagcgga | 1200 |
| agatatccag | aagctgtttt | ccgagagact | cggttggcgc | ctggtatatt | tgatggatgt | 1260 |
| cgcgctgcct | cacgtcccgg | tacccaggaa | cgcggtggga | tctcgggccc | atcgaagact | 1320 |
| gtgctccaga | ctgctcgccc | agcaggtgtt | tcttgatcgc | cgcctctaaa | ttgtccgcgc | 1380 |
| atcgccggta | acattttcc | agctcggagt | ttgcgtttag | atacagtttc | tgcgatgcca | 1440 |
| aaggagcctg | cagattataa | cctcggatgc | tgtcattcag | cgcttttaat | ttgacctcca | 1500 |
| gatagttgct | gtatttctgt | tcccattggc | tgctgcgcag | cttcgtataa | ctcgagttat | 1560 |
| tgttgcgctc | tgcctcggcg | tactggctca | tgatctggat | cttgtccgtg | tcgcttttct | 1620 |
| tcgagtgttt | ctcgcaaacg | atgtgcacgg | cctgcagtgt | ccaatcggag | tcgagctggc | 1680 |
| gccgaaactg | gcggatctga | gcctccacac | tgccctgttt | ctctatccac | ggcggaaccg | 1740 |
| cctcctgccg | tttcagaatg | ttgttcaagt | ggtactctgt | gcggtcaatg | aaggcgttat | 1800 |
| tgccggtgaa | atctttggga | agcggttttc | ctcggggaag | attacgaaat | tccccgcgtc | 1860 |
| gttgcgcttc | ctggatctcg | aggagatcgt | tctccgcgtc | gaggagatcg | ttctccgcgt | 1920 |
| cgacaccatt | ccttgcggcg | gcggtgctca | acggcctcaa | cctactactg | ggctgcttcc | 1980 |
| taatgcagga | gtcgcataag | ggagagcgtc | gacaaacccg | cgtttgagaa | cttgctcaag | 2040 |
| cttctggtaa | acgttgtagt | actctgaaac | aaggccctag | cactctgatc | tgtttctctt | 2100 |
| gggtagcggt | gagtggttta | ttggagttca | ctggtttcag | cacatctgtc | atctagacaa | 2160 |
| tattgttact | aaattttttt | gaactacaat | tgttcgtaat | tcatctatta | ttatacatcc | 2220 |

```
tcgtcagcaa tttctggcag acggagttta ctaacgtctt gagtatgagg ccgagaatcc    2280
agctctgtgg ccatactcag tcttgacagc ctgctgatgt ggctgcgttc aacgcaataa    2340
gcgtgtcctc cgactccgag ttgtgctcgt tatcgtcgtt ctcatcctcg gaaaaatcac    2400
acgaaagaac atactcacca gtaggctttc tggtccctgg ggcacggctg tttctgacgt    2460
attccggcgt tgataatagc tcgaaagtga acgccgagtc gcgggagtcg accgatgccc    2520
ttgagagcct tcaacccagt cagctccttc cggtgggcgc ggggcatgac tatcgtcgcc    2580
gcacttatga ctgtcttctt tatcatgcaa ctcgtaggac aggtgccggc agcgctctgg    2640
gtcattttcg gcgaggaccg ctttcgctgg agcgcgacga tgatcggcct gtcgcttgcg    2700
gtattcggaa tcttgcacgc cctcgctcaa gccttcgtca ctggtcccgc caccaaacgt    2760
ttcggcgaga agcaggccat tatcgccggc atggcggccg acgcgctggg ctacgtcttg    2820
ctggcgttcg cgacgcgagg ctggatggcc ttccccatta tgattcttct cgcttccggc    2880
ggcatcggga tgcccgcgtt gcaggccatg ctgtccaggc aggtagatga cgaccatcag    2940
ggacagcttc aaggatcgct cgcggctctt accagcctaa cttcgatcac tggaccgctg    3000
atcgtcacgg cgatttatgc cgcctcggcg agcacatgga acgggttggc atggattgta    3060
ggcgccgccc tataccttgt ctgcctcccc gcgttgcgtc gcggtgcatg gagccgggcc    3120
acctcgacct gaatggaagc cggcggcacc tcgctaacgg attcaccact ccaagaattg    3180
gagccaatca attcttgcgg agaactgtga atgcgcaaac caaccctggg cagaacatat    3240
ccatcgcgtc cgccatctcc agcagccgca cgcggcgcat cggggggggg ggggggggg     3300 ggggcaaac aattcatcat ttttttttta ttcttttttt tgatttcggt ttctttgaaa     3360 ttttttgat tcggtaatct ccgaacagaa ggaagaacga aggaaggagc acagacttag     3420
attggtatat atacgcatat gtagtgttga agaaacatga aattgcccag tattcttaac    3480
ccaactgcac agaacaaaaa cctgcaggaa acgaagataa atcatgtcga agctacata     3540 taaggaacgt gctgctactc atcctagtcc tgttgctgcc aagctattta atatcatgca    3600
cgaaaagcaa acaaacttgt gtgcttcatt ggatgttcgt accaccaagg aattactgga    3660
gttagttgaa gcattaggtc ccaaaatttg tttactaaaa acacatgtgg atatcttgac    3720 tgattttcc atggagggca cagttaagcc gctaaaggca ttatccgcca agtacaattt     3780
tttactcttc gaagacagaa aatttgctga cattggtaat acagtcaaat tgcagtactc    3840
tgcgggtgta tacagaatag cagaatgggc agacattacg aatgcacacg gtgtggtggg    3900
cccaggtatt gttagcggtt tgaagcaggc ggcagaagaa gtaacaaagg aacctagagg    3960
ccttttgatg ttagcagaat tgtcatgcaa gggctcccta tctactggag aatatactaa    4020
gggtactgtt gacattgcga agagcgacaa agattttgtt atcggcttta ttgctcaaag    4080 agacatggt ggaagagatg aaggttacga ttggttgatt atgacacccg gtgtgggttt    4140
agatgacaag ggagacgcat tggtcaaca gtatagaacc gtggatgatg tggtctctac    4200
aggatctgac attattattg ttggaagagg actatttgca aagggaaggg atgctaaggt    4260
agagggtgaa cgttacagaa aagcaggctg ggaagcatat ttgagaagat gcggccagca    4320
aaactaaaaa actgtattat aagtaaatgc atgtatacta aactcacaaa ttagagcttc    4380
aatttaatta tatcagttat tacccgggaa tctcggtcgt aatgattttt ataatgacga    4440
aaaaaaaaaa attggaaaga aaagcccccc cccccccccc cccccccccc cccccccgc     4500 agcgttgggt cctggccacg ggtgcgcatg atcgtgctcc tgtcgttgag gacccggcta    4560
ggctggcggg gttgccttac tggttagcag aatgaatcac cgatacgcga gcgaacgtga    4620
```

-continued

```
agcgactgct gctgcaaaac gtctgcgacc tgagcaacaa catgaatggt cttcggtttc    4680
cgtgtttcgt aaagtctgga aacgcggaag tcagcgccct gcaccattat gttccggatc    4740
tgcatcgcag gatgctgctg gctaccctgt ggaacaccta catctgtatt aacgaagcgc    4800
tggcattgac cctgagtgat ttttctctgg tcccgccgca tccataccgc cagttgttta    4860
ccctcacaac gttccagtaa ccgggcatgt tcatcatcag taacccgtat cgtgagcatc    4920
ctctctcgtt tcatcggtat cattaccccc atgaacagaa attcccccctt acacggaggc    4980 atcaagtgac caaacaggaa aaaccgccc ttaacatggc ccgctttatc agaagccaga    5040
cattaacgct tctggagaaa ctcaacgagc tggacgcgga tgaacaggca gacatctgtg    5100
aatcgcttca cgaccacgct gatgagcttt accgcagctg cctcgcgcgt ttcggtgatg    5160
acggtgaaaa cctctgacac atgcagctcc cggagacggt cacagcttgt ctgtaagcgg    5220
atgccgggag cagacaagcc cgtcaggcg cgtcagcggg tgttggcggg tgtcggggcg    5280
cagccatgac ccagtcacgt agcgatagcg gagtgtatac tggcttaact atgcggcatc    5340
agagcagatt gtactgagag tgcaccatat gcggtgtgaa ataccgcaca gatgcgtaag    5400
gagaaaatac cgcatcaggc gctcttccgc ttcctcgctc actgactcgc tgcgctcggt    5460
cgttcggctg cggcgagcgg tatcagctca ctcaaaggcg gtaatacggt tatccacaga    5520
atcaggggat aacgcaggaa agaacatgtg agcaaaaggc cagcaaaagg ccaggaaccg    5580
taaaaaggcc gcgttgctgg cgttttttcca taggctccgc cccctgacg agcatcacaa    5640 aaatcgacgc tcaagtcaga ggtggcgaaa cccgacagga ctataaagat accaggcgtt    5700
tccccctgga agctccctcg tgcgctctcc tgttccgacc ctgccgctta ccggatacct    5760
gtccgccttt ctcccttcgg gaagcgtggc gctttctcat agctcacgct gtaggtatct    5820
cagttcggtg taggtcgttc gctccaagct gggctgtgtg cacgaaccc ccgttcagcc    5880 cgaccgctgc gccttatccg gtaactatcg tcttgagtcc aacccggtaa gacacgactt    5940
atcgccactg gcagcagcca ctggtaacag gattagcaga gcgaggtatg taggcggtgc    6000
tacagagttc ttgaagtggt ggcctaacta cggctacact agaaggacag tatttggtat    6060
ctgcgctctg ctgaagccag ttaccttcgg aaaaagagtt ggtagctctt gatccggcaa    6120
acaaaccacc gctggtagcg gtggtttttt tgtttgcaag cagcagatta cgcgcagaaa    6180
aaaaggatct caagaagatc ctttgatctt ttctacgggg tctgacgctc agtggaacga    6240
aaactcacgt taagggattt tggtcatgag attatcaaaa aggatcttca cctagatcct    6300
tttaaattaa aaatgaagtt ttaaatcaat ctaaagtata tatgagtaaa cttggtctga    6360
cagttaccaa tgcttaatca gtgaggcacc tatctcagcg atctgtctat ttcgttcatc    6420
catagttgcc tgactccccg tcgtgtagat aactacgata cgggagggct taccatctgg    6480
ccccagtgct gcaatgatac cgcgagaccc acgctcaccg gctccagatt tatcagcaat    6540
aaaccagcca gccggaaggg ccgagcgcag aagtggtcct gcaactttat ccgcctccat    6600
ccagtctatt aattgttgcc gggaagctag agtaagtagt tcgccagtta atagtttgcg    6660
caacgttgtt gccattgctg caggcatcgt ggtgtcacgc tcgtcgtttg gtatggcttc    6720
attcagctcc ggttcccaac gatcaaggcg agttacatga tcccccatgt tgtgcaaaaa    6780
agcggttagc tccttcggtc ctccgatcgt tgtcagaagt aagttggccg cagtgttatc    6840
actcatggtt atggcagcac tgcataattc tcttactgtc atgccatccg taagatgctt    6900
ttctgtgact ggtgagtact caaccaagtc attctgagaa tagtgtatgc ggcgaccgag    6960
```

| | |
|---|---:|
| ttgctcttgc ccggcgtcaa cacgggataa taccgcgcca catagcagaa ctttaaaagt | 7020 |
| gctcatcatt ggaaaacgtt cttcggggcg aaaactctca aggatcttac cgctgttgag | 7080 |
| atccagttcg atgtaaccca ctcgtgcacc caactgatct tcagcatctt ttactttcac | 7140 |
| cagcgtttct gggtgagcaa aaacaggaag gcaaaatgcc gcaaaaaagg gaataagggc | 7200 |
| gacacggaaa tgttgaatac tcatactctt ccttttcaa tattattgaa gcatttatca | 7260 |
| gggttattgt ctcatgagcg gatacatatt tgaatgtatt tagaaaaata aacaaatagg | 7320 |
| ggttccgcgc acatttcccc gaaaagtgcc acctgacgtc taagaaacca ttattatcat | 7380 |
| gacattaacc tataaaaata ggcgtatcac gaggcccttt cgtcttcaa | 7429 |

<210> SEQ ID NO 37
<211> LENGTH: 39
<212> TYPE: DNA
<213> ORGANISM: synthetic probe or primer

<400> SEQUENCE: 37

| | |
|---|---:|
| catcacaaat atgaggtgcg caacgtgtcc gggatgtac | 39 |

<210> SEQ ID NO 38
<211> LENGTH: 42
<212> TYPE: DNA
<213> ORGANISM: synthetic probe or primer

<400> SEQUENCE: 38

| | |
|---|---:|
| gtgatggtgg tgtcctagtg ctgctagtgg taggaagcat ag | 42 |

<210> SEQ ID NO 39
<211> LENGTH: 4273
<212> TYPE: DNA
<213> ORGANISM: vector pUC18-FMD-CL-E1-H-K6
<220> FEATURE:
<221> NAME/KEY: misc_feature
<222> LOCATION: (1027)..(1028)
<223> OTHER INFORMATION: N is any nucleotide
<220> FEATURE:
<221> NAME/KEY: misc_feature
<222> LOCATION: (1206)..(1207)
<223> OTHER INFORMATION: N is any nucleotide

<400> SEQUENCE: 39

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg aattcgagct    240
cggtacccgg ggatccttaa tggtgatggt ggtggtgcca gttcatcatc atatcccaag    300
ccatacggtg acctgttatg tggccgggat agattgagca attgcagtcc tgcaccgtct    360
catgccggcg aggcgagatg gtgaacagct gggagacgag gaagacagat ccgcagagat    420
cccccacgta catagcggaa cagaaagcag ccgccccaac gagcaaatcg acgtggcgtc    480
gtattgtcgt agtggggacg ctggcgttcc tagctgcgag cgtgggggtg agcgctaccc    540
agcagcggga agagttgttc tcccgaacgc agggcacgca cccgggggtg tgcatgatca    600
tgtccgctgc ctcatacaca atgcttgagt tggagcagtc gttcgtgaca tggtacatcc    660
cggacacgtt gcgcacctca tatttgtgat ggtgatggtg gtgtcctagt gctgctagtg    720
gtaggaagca tagtactagt attagtaggc ttcgcatgaa ttcccgatga aggcagagag    780
cgcaaggagg cggtatttat agtgccattc ccctctctga gagacccgga tggtagtcga    840
```

-continued

```
gtgttatcgg agacagcttg atgtagactc cgtgcctgcc ggtcctctta ttggcggaca    900
ccagtgagac accccggaac ttgctgtttt tctgcaaaat ccggggtgac cagtgggagc    960
ctatttgcac acacgagcgg gacaccccac tctggtgaag agtgccaaag tcattctttt   1020
tcccgtnncg gggcagccga ttgcatgttt taggaaaata ttacctttgc tacaccctgt   1080
cagatttacc ctccacacat atatattccg tcacctccag ggactattct ggctcgttg    1140
cgccgccgcg gaagatatcc agaagctgtg ttttccgaga gactcggttg gcgcctggta   1200
tatttnnagg atgtcgcgct gcctcacgtc ccggtaccca ggaacgcggt gggatctcgg   1260
gcccatcgaa gactgtgctc cagactgctc gcccagcagg tgtttcttga ttgccgcctc   1320
taaatagtcc gcgcatcgcc ggtaacattt tccagctcg gagtttgcgt ttagatacat    1380
ttctgcgatg ccaaaggagc ctgcagatta aacctcgga tgctgtcatt cagcgctttt    1440
aatttgacct ccagatagtt gctgtatttc tgttccattg gctgctggac gttcgtataa   1500
ctcgagttat tgttgcgctc tgcctcggcg tactggctca tgactgactg cggtcgcttc   1560
tcgagtgttc tcgcaacagg acgcctgcag gtcatcgagt cgagctggcg ccgaaactgg   1620
cggatctgac ctccacactg ccctgtatct ctatccaccg ggaaccgcct cctgccgttc   1680
cagaatgttg ttcaagtggt agctctgtgc ggtcaatgaa ggcgttattg ccggtgaaat   1740
cttttgggaag cggtttatcc tcggggaaga ttacgaaatt cccgcgcgtc gttgcgcttc  1800
ctggatctcg aggaagatcg ttctccgcgt cgaggagatc gttctccgcg tcgacctgca   1860
ggcatgcaag cttggcactg ccgtcgtttt tacaacgtcg tgactgggaa acccctggcg   1920
ttacccaact taatcgcctt gcagcacatc cccctttcgc cagctggcgt aatagcgaag   1980
aggcccgcac cgatcgccct tcccaacagt tgcgcagcct gaatggcgaa tggcgcctga   2040
tgcggtattt tctccttacg catctgtgcg gtatttcaca ccgcatatgg tgcactctca   2100
gtacaatctg ctctgatgcc gcatagttaa gccagccccg acacccgcca cacccgctg    2160
acgcgccctg acgggcttgt ctgctcccgg catccgctta cagacaagct gtgaccgtct   2220
ccgggagctg catgtgtcag aggttttcac cgtcatcacc gaaacgcgcg agacgaaagg   2280
gcctcgtgat acgcctattt ttataggtta atgtcatgat aataatggtt cttagacgt    2340
caggtggcac ttttcgggga atgtgcgcg gaacccctat ttgtttattt ttctaaatac    2400
attcaaatat gtatccgctc atgagacaat aaccctgata aatgcttcaa taatattgaa   2460
aaaggaagag tatgagtatt caacatttcc gtgtcgccct tattcccttt tttgcggcat   2520
tttgccttcc tgtttttgct cacccagaaa cgctggtgaa agtaaaagat gctgaagatc   2580
agttgggtgc acgagtgggt tacatcgaac tggatctcaa cagcggtaag atccttgaga   2640
gttttcgccc cgaagaacgt tttccaatga tgagcacttt taaagttctg ctatgtggcg   2700
cggtattatc ccgtattgac gccgggcaag agcaactcgg tcgccgcata cactattctc   2760
agaatgactt ggttgagtac tcaccagtca cagaaaagca tcttacggat ggcatgacag   2820
taagagaatt atgcagtgct gccataacca tgagtgataa cactgcggcc aacttacttc   2880
tgacaacgat cggaggaccg aaggagctaa ccgcttttt gcacaacatg ggggatcatg    2940
taactcgcct tgatcgttgg gaaccggagc tgaatgaagc cataccaaac gacgagcgtg   3000
acaccacgat gcctgtagca atggcaacaa cgttgcgcaa actattaact ggcgaactac   3060
ttactctagc ttcccggcaa caattaatag actggatgga ggcggataaa gttgcaggac   3120
cacttctgcg ctcggccctt ccggctggct ggtttattgc tgataaatct ggagccggtg   3180
```

-continued

| | |
|---|---|
| agcgtgggtc tcgcggtatc attgcagcac tgggcccaga tggtaagccc tcccgtatcg | 3240 |
| tagttatcta cacgacgggg agtcaggcaa ctatggatga cgaaataga cagatcgctg | 3300 |
| agataggtgc ctcactgatt aagcattggt aactgtcaga ccaagtttac tcatatatac | 3360 |
| tttagattga tttaaaactt catttttaat ttaaaaggat ctaggtgaag atccttttg | 3420 |
| ataatctcat gaccaaaatc ccttaacgtg agttttcgtt ccactgagcg tcagaccccg | 3480 |
| tagaaaagat caaaggatct tcttgagatc cttttttct gcgcgtaatc tgctgcttgc | 3540 |
| aaacaaaaaa accaccgcta ccagcggtgg tttgtttgcc ggatcaagag ctaccaactc | 3600 |
| tttttccgaa ggtaactggc ttcagcagag cgcagatacc aaatactgtc cttctagtgt | 3660 |
| agccgtagtt aggccaccac ttcaagaact ctgtagcacc gcctacatac ctcgctctgc | 3720 |
| taatcctgtt accagtggct gctgccagtg gcgataagtc gtgtcttacc gggttggact | 3780 |
| caagacgata gttaccggat aaggcgcagc ggtcgggctg aacggggggt cgtgcacac | 3840 |
| agcccagctt ggagcgaacg acctacaccg aactgagata cctacagcgt gagctatgag | 3900 |
| aaagcgccac gcttcccgaa gggagaaagg cggacaggta tccggtaagc ggcagggtcg | 3960 |
| gaacaggaga gcgcacgagg gagcttccag ggggaaacgc ctggtatctt tatagtcctg | 4020 |
| tcgggtttcg ccacctctga cttgagcgtc gatttttgtg atgctcgtca gggggggcgga | 4080 |
| gcctatggaa aaacgccagc aacgcggcct ttttacggtt cctggccttt tgctggcctt | 4140 |
| ttgctcacat gttctttcct gcgttatccc ctgattctgt ggataaccgt attaccgcct | 4200 |
| ttgagtgagc tgataccgct cgccgcagcc gaacgaccga gcgcagcgag tcagtgagcg | 4260 |
| aggaagcgga aga | 4273 |

<210> SEQ ID NO 40
<211> LENGTH: 7330
<212> TYPE: DNA
<213> ORGANISM: vector pFPMT-CL-H6-K-E1
<220> FEATURE:
<221> NAME/KEY: misc_feature
<222> LOCATION: (1098)..(1099)
<223> OTHER INFORMATION: N is any nucleotide
<220> FEATURE:
<221> NAME/KEY: misc_feature
<222> LOCATION: (1277)..(1278)
<223> OTHER INFORMATION: N is any nucleotide

<400> SEQUENCE: 40

| | |
|---|---|
| ggtaccctgc tcaatctccg gaatggtgat ctgatcgttc ctgaaaacct cgacattggc | 60 |
| tccctcctga cacaggtact cgtacaggtt ccaggtaaac gagtcgtagt tgtcgatcat | 120 |
| gacaacgttc ttagaagcgg ccggcatttt gaaggtgact aatagcctaa gaaaatattt | 180 |
| aatttaattt tcattaaatt ttcctatact cgctatttca gcttttcatc tcatcacttc | 240 |
| ataaacgata taaccagaa aaagaactat tttcaaacac gcttctcaaa agcggtatgt | 300 |
| ccttccacgt ctccttagaa tctggcaagt ccgcagggg gatccttacc agttcatcat | 360 |
| catatcccaa gccatacggt gacctgttat gtggccggga tagattgagc aattgcagtc | 420 |
| ctgcaccgtc tcatgccggc gaggcagat ggtgaacagc tggagacga ggaagacaga | 480 |
| tccgcagaga tcccccacgt acatagcgga acagaaagca gccgcccaa cgagcaaatc | 540 |
| gacgtggcgt cgtattgtcg tagtggggac gctggcgttc ctagctgcga gcgtgggggt | 600 |
| gagcgctacc cagcagcggg aagagttgtt ctcccgaacg cagggcacgc acccggggt | 660 |
| gtgcatgatc atgtccgctg cctcatacac aatgcttgag ttggagcagt cgttcgtgac | 720 |
| atggtacatc ccggacacgt tgcgcacctc atatttgtga tggtgatggt ggtgtcctag | 780 |

```
tgctgctagt ggtaggaagc atagtactag tattagtagg cttcgcatga attcccgatg    840
aaggcagaga gcgcaaggag gcggtattta tagtgccatt cccctctctg agagacccgg    900
atggtagtcg agtgttatcg agacagctt gatgtagact ccgtgcctgc cggtcctctt    960
attggcggac accagtgaga cacccggaa cttgctgttt ttctgcaaaa tccggggtga   1020
ccagtgggag cctatttgca cacgagcg ggacacccca ctctggtgaa gagtgccaaa    1080
gtcattcttt ttcccgtnnc ggggcagccg attgcatgtt ttaggaaaat attacctttg   1140
ctacaccctg tcagatttac cctccacaca tatatattcc gtcacctcca gggactattc   1200
ttggctcgtt gcgccgccgc ggaagatatc cagaagctgt gttttccgag agactcggtt   1260
ggcgcctggt atatttnnag gatgtcgcgc tgcctcacgt cccggtaccc aggaacgcgg   1320
tgggatctcg ggcccatcga agactgtgct ccagactgct cgcccagcag gtgtttcttg   1380
attgccgcct ctaaatagtc cgcgcatcgc cggtaacatt tttccagctc ggagtttgcg   1440
tttagataca tttctgcgat gccaaggag cctgcagatt ataacctcgg atgctgtcat    1500
tcagcgcttt taatttgacc tccagatagt tgctgtattt ctgttccatt ggctgctgga   1560
cgttcgtata actcgagtta ttgttgcgct ctgcctcggc gtactggctc atgactgact   1620
gcggtcgctt ctcgagtgtt ctcgcaacag gacgcctgca ggtcatcgag tcgagctggc   1680
gccgaaactg gcggatctga cctccacact gccctgtatc tctatccacc gggaaccgcc   1740
tcctgccgtt ccagaatgtt gttcaagtgg tagctctgtg cggtcaatga aggcgttatt   1800
gccggtgaaa tctttgggaa gcggtttatc ctcggggaag attacgaaat tcccgcgcgt   1860
cgttgcgctt cctggatctc gaggaagatc gttctccgcg tcgaggagat cgttctccgc   1920
gtcgacctgc aggcatgcaa gcttctggta acgttgtag tactctgaaa caaggcccta   1980
gcactctgat ctgtttctct tgggtagcgg tgagtggttt attggagttc actggtttca   2040
gcacatctgt catctagaca atattgttac taaattttt tgaactacaa ttgttcgtaa   2100
ttcatctatt attatacatc ctcgtcagca atttctggca gacggagttt actaacgtct   2160
tgagtatgag gccgagaatc cagctctgtg gccatactca gtcttgacag cctgctgatg   2220
tggctgcgtt caacgcaata agcgtgtcct ccgactccga gttgtgctcg ttatcgtcgt   2280
tctcatcctc ggaaaaatca cacgaaagaa catactcacc agtaggcttt ctggtccctg   2340
gggcacggct gtttctgacg tattccggcg ttgataatag ctcgaaagtg aacgccgagt   2400
cgcgggagtc gaccgatgcc cttgagagcc ttcaacccag tcagctcctt ccggtgggcg   2460
cggggcatga ctatcgtcgc cgcacttatg actgtcttct ttatcatgca actcgtagga   2520
caggtgccgg cagcgctctg ggtcattttc ggcgaggacc gctttcgctg gagcgcgacg   2580
atgatcggcc tgtcgcttgc ggtattcgga atcttgcacg ccctcgctca gccttcgtc   2640
actggtcccg ccaccaaacg tttcggcgag aagcaggcca ttatcgccgg catggcggcc   2700
gacgcgctgg gctacgtctt gctggcgttc gcgacgcgag gctggatggc cttccccatt   2760
atgattcttc tcgcttccgg cggcatcggg atgcccgcgt tgcaggccat gctgtccagg   2820
caggtagatg acgaccatca gggacagctt caaggatcgc tcgcggctct taccagccta   2880
acttcgatca ctggaccgct gatcgtcacg gcgatttatg ccgcctcggc gagcacatgg   2940
aacgggttgg catggattgt aggcgccgcc ctataccttg tctgcctccc cgcgttgcgt   3000
cgcggtgcat ggagccgggc cacctcgacc tgaatggaag ccggcggcac ctcgctaacg   3060
gattcaccac tccaagaatt ggagccaatc aattcttgcg gagaactgtg aatgcgcaaa   3120
```

| | | | | |
|---|---|---|---|---|
| ccaacccttg | gcagaacata | tccatcgcgt | ccgccatctc | cagcagccgc acgcggcgca | 3180 |
| tcggggggggg | ggggggggggg | gggggggcaaa | caattcatca | tttttttttt attcttttttt | 3240 |
| ttgatttcgg | tttctttgaa | attttttttga | ttcggtaatc | tccgaacaga aggaagaacg | 3300 |
| aaggaaggag | cacagactta | gattggtata | tatacgcata | tgtagtgttg aagaaacatg | 3360 |
| aaattgccca | gtattcttaa | cccaactgca | cagaacaaaa | acctgcagga acgaagata | 3420 |
| aatcatgtcg | aaagctacat | ataaggaacg | tgctgctact | catcctagtc ctgttgctgc | 3480 |
| caagctattt | aatatcatgc | acgaaaagca | aacaaacttg | tgtgcttcat tggatgttcg | 3540 |
| taccaccaag | gaattactgg | agttagttga | agcattaggt | cccaaaattt gtttactaaa | 3600 |
| aacacatgtg | gatatcttga | ctgattttttc | catggagggc | acagttaagc cgctaaaggc | 3660 |
| attatccgcc | aagtacaatt | ttttactctt | cgaagacaga | aaatttgctg acattggtaa | 3720 |
| tacagtcaaa | ttgcagtact | ctgcgggtgt | atacagaata | gcagaatggg cagacattac | 3780 |
| gaatgcacac | ggtgtggtgg | gcccaggtat | tgttagcggt | ttgaagcagg cggcagaaga | 3840 |
| agtaacaaag | gaacctagag | gccttttgat | gttagcagaa | ttgtcatgca agggctccct | 3900 |
| atctactgga | gaatatacta | agggtactgt | tgacattgcg | aagagcgaca aagattttgt | 3960 |
| tatcggcttt | attgctcaaa | gagacatggg | tggaagagat | gaaggttacg attggttgat | 4020 |
| tatgacaccc | ggtgtgggtt | tagatgacaa | gggagacgaa | ttgggtcaac agtatagaac | 4080 |
| cgtggatgat | gtggtctcta | caggatctga | cattattatt | gttggaagag gactatttgc | 4140 |
| aaagggaagg | gatgctaagg | tagagggtga | acgttacaga | aaagcaggct gggaagcata | 4200 |
| tttgagaaga | tgcggccagc | aaaactaaaa | aactgtatta | aagtaaatg catgtatact | 4260 |
| aaactcacaa | attagagctt | caatttaatt | atatcagtta | ttacccggga atctcggtcg | 4320 |
| taatgatttt | tataatgacg | aaaaaaaaaa | aattggaaag | aaaagccccc cccccccccc | 4380 |
| cccccccccc | cccccccccg | cagcgttggg | tcctggccac | gggtgcgcat gatcgtgctc | 4440 |
| ctgtcgttga | ggacccggct | aggctggcgg | ggttgcctta | ctggttagca gaatgaatca | 4500 |
| ccgatacgcg | agcgaacgtg | aagcgactgc | tgctgcaaaa | cgtctgcgac ctgagcaaca | 4560 |
| acatgaatgg | tcttcggttt | ccgtgtttcg | taaagtctgg | aaacgcggaa gtcagcgccc | 4620 |
| tgcaccatta | tgttccggat | ctgcatcgca | ggatgctgct | ggctaccctg tggaacacct | 4680 |
| acatctgtat | taacgaagcg | ctggcattga | ccctgagtga | ttttttctctg gtcccgccgc | 4740 |
| atccataccg | ccagttgttt | accctcacaa | cgttccagta | accggcatg ttcatcatca | 4800 |
| gtaacccgta | tcgtgagcat | cctctctcgt | ttcatcggta | tcattacccc catgaacaga | 4860 |
| aattcccct | tacacggagg | catcaagtga | ccaaacagga | aaaaccgcc cttaacatgg | 4920 |
| cccgctttat | cagaagccag | acattaacgc | ttctggagaa | actcaacgag ctggacgcgg | 4980 |
| atgaacaggc | agacatctgt | gaatcgcttc | acgaccacgc | tgatgagctt taccgcagct | 5040 |
| gcctcgcgcg | tttcggtgat | gacggtgaaa | acctctgaca | catgcagctc ccggagacgg | 5100 |
| tcacagcttg | tctgtaagcg | gatgccggga | gcagacaagc | ccgtcagggc gcgtcagcgg | 5160 |
| gtgttggcgg | gtgtcgggc | gcagccatga | cccagtcacg | tagcgatagc ggagtgtata | 5220 |
| ctggcttaac | tatgcggcat | cagagcagat | tgtactgaga | gtgcaccata tgcggtgtga | 5280 |
| aataccgcac | agatgcgtaa | ggagaaaata | ccgcatcagg | cgctcttccg cttcctcgct | 5340 |
| cactgactcg | ctgcgctcgg | tcgttcggct | gcggcgagcg | gtatcagctc actcaaaggc | 5400 |
| ggtaatacgg | ttatccacag | aatcagggga | taacgcagga | agaacatgt gagcaaaagg | 5460 |
| ccagcaaaag | gccaggaacc | gtaaaaaggc | cgcgttgctg | gcgtttttcc ataggctccg | 5520 |

-continued

```
cccccctgac gagcatcaca aaaatcgacg ctcaagtcag aggtggcgaa acccgacagg    5580
actataaaga taccaggcgt tccccctgg aagctccctc gtgcgctctc ctgttccgac    5640
cctgccgctt accggatacc tgtccgcctt tctcccttcg ggaagcgtgg cgctttctca    5700
tagctcacgc tgtaggtatc tcagttcggt gtaggtcgtt cgctccaagc tgggctgtgt    5760
gcacgaaccc cccgttcagc ccgaccgctg cgccttatcc ggtaactatc gtcttgagtc    5820
caacccggta agacacgact tatcgccact ggcagcagcc actggtaaca ggattagcag    5880
agcgaggtat gtaggcggtg ctacagagtt cttgaagtgg tggcctaact acggctacac    5940
tagaaggaca gtatttggta tctgcgctct gctgaagcca gttaccttcg aaaaagagt    6000 tggtagctct tgatccggca acaaaccac cgctggtagc ggtggttttt ttgtttgcaa    6060
gcagcagatt acgcgcagaa aaaaggatc tcaagaagat cctttgatct tttctacggg    6120
gtctgacgct cagtggaacg aaaactcacg ttaagggatt ttggtcatga gattatcaaa    6180
aaggatcttc acctagatcc ttttaaatta aaatgaagt tttaaatcaa tctaaagtat    6240
atatgagtaa acttggtctg acagttacca atgcttaatc agtgaggcac ctatctcagc    6300
gatctgtcta tttcgttcat ccatagttgc ctgactcccc gtcgtgtaga taactacgat    6360
acgggagggc ttaccatctg gccccagtgc tgcaatgata ccgcgagacc cacgctcacc    6420
ggctccagat ttatcagcaa taaaccagcc agccggaagg gccgagcgca gaagtggtcc    6480
tgcaacttta tccgcctcca tccagtctat taattgttgc cgggaagcta gagtaagtag    6540
ttcgccagtt aatagtttgc gcaacgttgt tgccattgct gcaggcatcg tggtgtcacg    6600
ctcgtcgttt ggtatggctt cattcagctc cggttcccaa cgatcaaggc gagttacatg    6660
atcccccatg ttgtgcaaaa aagcggttag ctccttcggt cctccgatcg ttgtcagaag    6720
taagttggcc gcagtgttat cactcatggt tatggcagca ctgcataatt ctcttactgt    6780
catgccatcc gtaagatgct tttctgtgac tggtgagtac tcaaccaagt cattctgaga    6840
atagtgtatg cggcgaccga gttgctcttg cccggcgtca acacgggata ataccgcgcc    6900
acatagcaga actttaaaag tgctcatcat tggaaaacgt tcttcgggc gaaaactctc    6960 aaggatctta ccgctgttga tccagttc gatgtaaccc actcgtgcac ccaactgatc    7020
ttcagcatct tttactttca ccagcgtttc tgggtgagca aaaacaggaa ggcaaaatgc    7080
cgcaaaaaag ggaataaggg cgacacggaa atgttgaata ctcatactct ccttttttca    7140
atattattga agcatttatc agggttattg tctcatgagc ggatacatat ttgaatgtat    7200
ttagaaaaat aaacaaatag gggttccgcg cacatttccc cgaaaagtgc cacctgacgt    7260
ctaagaaacc attattatca tgacattaac ctataaaaat aggcgtatca cgaggccctt    7320
tcgtcttcaa                                                          7330
```

<210> SEQ ID NO 41
<211> LENGTH: 5202
<212> TYPE: DNA
<213> ORGANISM: vector pYIG5

<400> SEQUENCE: 41

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gaatttaata     240
```

```
cgactcacta tagggaattc gaggatcctt caatatgcgc acatacgctg ttatgttcaa    300
ggtcccttcg tttaagaacg aaagcggtct tccttttgag ggatgtttca agttgttcaa    360
atctatcaaa tttgcaaatc cccagtctgt atctagagcg ttgaatcggt gatgcgattt    420
gttaattaaa ttgatggtgt caccattacc aggtctagat ataccaatgg caaactgagc    480
acaacaatac cagtccggat caactggcac catctctccc gtagtctcat ctaattttc     540
ttccggatga ggttccagat ataccgcaac acctttatta tggtttccct gagggaataa    600
tagaatgtcc cattcgaaat caccaattct aaacctgggc gaattgtatt tcgggtttgt    660
taactcgttc cagtcaggaa tgttccacgt gaagctatct tccagcaaag tctccacttc    720
ttcatcaaat tgtggagaat actcccaatg ctcttatcta tgggacttcc gggaaacaca    780
gtaccgatac ttcccaattc gtcttcagag ctcattgttt gtttgaagag actaatcaaa    840
gaatcgtttt ctcaaaaaaa ttaatatctt aactgatagt ttgatcaaag gggcaaaacg    900
tagggcaaa caaacggaaa aatcgtttct caaattttct gatgccaaga actctaacca     960
gtcttatcta aaaattgcct tatgatccgt ctctccggtt acagcctgtg taactgatta   1020
atcctgcctt tctaatcacc attcaatgt tttaattaag ggattttgtc ttcattaacg    1080
gctttcgctc ataaaaatgt tatgacgttt tgcccgcagg cgggaaacca tccacttcac   1140
gagactgatc tcctctgccg gaacaccggg catctccaac ttataagttg agaaataag    1200
agaatttcag attgagagaa tgaaaaaaaa aaaccctgaa aaaaaaggtt gaaaccagtt   1260
ccctgaaatt attcccctac ttgactaata agtatataaa gacggtaggt attgattgta   1320
attctgtaaa tctatttctt aaacttctta aattctactt ttatagttag tcttttttt    1380
agttttaaaa caccaagaac ttagtttcga ataaacacac ataaacaaac accatgagat   1440
ttccttcaat ttttactgca gttttattcg cagcatcctc cgcattagct gctccagtca   1500
acactacaac agaagatgaa acggcacaaa ttccggctga agctgtcatc ggttactcag   1560
atttagaagg ggatttcgat gttgctgttt tgccattttc caacagcaca ataacgggt    1620
tattgtttat aaatactact attgccagca ttgctgctaa agaagaaggg gtatctctag   1680
ataaaaggcc tgtcgacggt accagatctc gacttggttg aacacgttgc caaggcttaa   1740
gtgaatttac tttaaagtct tgcatttaaa taaattttct ttttatagct ttatgactta   1800
gtttcaattt atatactatt ttaatgacat tttcgattca ttgattgaaa gctttgtgtt   1860
ttttcttgat gcgctattgc attgttcttg tcttttcgc cacatgtaat atctgtagta    1920
gatacctgat acattgtgga tgctgagtga aattttagtt aataatggag gcgctcttaa   1980
taattttggg gatattggct ttttttttta agtttacaa atgaattttt tccgccagga    2040
taacgattct gaagttactc ttagcgttcc tatcggtaca gccatcaaat catgcctata   2100
aatcatgcct atatttgcgt gcagtcagta tcatctacat gaaaaaaact cccgcaattt   2160
cttatagaat acgttgaaaa ttaaatgtac gcgccaagat aagataacat atatctagct   2220
agatgcagta atatacacag attcccgcgg acgtgggaag gaaaaaatta gataacaaaa   2280
tctgagtgat atggaaattc cgctgtatag ctcatatctt tcccttcaac accagaaatg   2340
taaaaatctt gttacgaagg atctttttgc taatgtttct cgctcaatcc tcatttcttc   2400
cctacgaaga gtcaaatcta cttgtttct gccggtatca agatccatat cttctagttt    2460
caccatcaaa gtccaatttc tagtatacag tttatgtccc aacgtaacag acaatcaaaa   2520
ttggaaagga taagtatcct tcaagaatg attctgcgct ggctcctgaa ccgcctaatg    2580
ggaacagaga agtccaaaac gatgctataa gaaccagaaa taaaacgata aaaccatacc   2640
```

```
aggatccaag cttggcactg gccgtcgttt tacaacgtcg tgactgggaa aaccctggcg    2700
ttacccaact taatcgcctt gcagcacatc ccccttccgc cagctggcgt aatagcgaag    2760
aggcccgcac cgatcgccct tcccaacagt tgcgcagcct gaatggcgaa tgggaaattg    2820
taaacgttaa tattttgtta aaattcgcgt taaattttg ttaaatcagc tcattttta    2880 accaataggc cgaaatcggc aaaatccctt ataaatcaaa agaatagacc gagatagggt    2940
tgagtgttgt tccagtttgg aacaagagtc cactattaaa gaacgtggac tccaacgtca    3000
aagggcgaaa aaccgtctat cagggcgatg gcccactacg tgaaccatca ccctaatcaa    3060
gttttttggg gtcgaggtgc cgtaaagcac taaatcggaa ccctaaaggg agccccgat    3120 ttagagcttg acggggaaag ccggcgaacg tggcgagaaa ggaagggaag aaagcgaaag    3180
gagcgggcgc tagggcgctg gcaagtgtag cggtcacgct gcgcgtaacc accacacccg    3240
ccgcgcttaa tgcgccgcta cagggcgcgt caggtggcac ttttcgggga atgtgcgcg    3300 gaacccctat ttgtttattt ttctaaatac attcaaatat gtatccgctc atgagacaat    3360
aaccctgata aatgcttcaa taatattgaa aaaggaagag tatgagtatt caacatttcc    3420
gtgtcgccct tattccctt tttgcggcat tttgccttcc tgttttgct cacccagaaa    3480 cgctggtgaa agtaaaagat gctgaagatc agttgggtgc acgagtgggt tacatcgaac    3540
tggatctcaa cagcggtaag atccttgaga gttttcgccc cgaagaacgt tttccaatga    3600
tgagcacttt taaagttctg ctatgtggcg cggtattatc ccgtattgac gccgggcaag    3660
agcaactcgg tcgccgcata cactattctc agaatgactt ggttgagtac tcaccagtca    3720
cagaaaagca tcttacggat ggcatgacag taagagaatt atgcagtgct gccataacca    3780
tgagtgataa cactgcggcc aacttacttc tgacaacgat cggaggaccg aaggagctaa    3840 ccgcttttt gcacaacatg gggatcatg taactcgcct tgatcgttgg aaccggagc    3900 tgaatgaagc cataccaaac gacgagcgtg acaccacgat gcctgtagca atggcaacaa    3960
cgttgcgcaa actattaact ggcgaactac ttactctagc ttcccggcaa caattaatag    4020
actggatgga ggcggataaa gttgcaggac cacttctgcg ctcggccctt ccggctggct    4080
ggtttattgc tgataaatct ggagccggtg agcgtgggtc tcgcggtatc attgcagcac    4140
tggggccaga tggtaagccc tcccgtatcg tagttatcta cacgacgggg agtcaggcaa    4200
ctatggatga acgaaataga cagatcgctg agataggtgc ctcactgatt aagcattggt    4260
aactgtcaga ccaagtttac tcatatatac tttagattga tttaaaactt cattttaat    4320 ttaaaaggat ctaggtgaag atcctttttg ataatctcat gaccaaaatc ccttaacgtg    4380
agttttcgtt ccactgagcg tcagaccccg tagaaaagat caaaggatct tcttgagatc    4440
ctttttttct gcgcgtaatc tgctgcttgc aaacaaaaaa accaccgcta ccagcggtgg    4500
tttgtttgcc ggatcaagag ctaccaactc tttttccgaa ggtaactggc ttcagcagag    4560
cgcagatacc aaatactgtc cttctagtgt agccgtagtt aggccaccac ttcaagaact    4620
ctgtagcacc gcctacatac ctcgctctgc taatcctgtt accagtggct gctgccagtg    4680
gcgataagtc gtgtcttacc gggttggact caagacgata gttaccggat aaggcgcagc    4740
ggtcgggctg aacggggggt tcgtgcacac agcccagctt ggagcgaacg acctacaccg    4800
aactgagata cctacagcgt gagcattgag aaagcgccac gcttcccgaa gggagaaagg    4860
cggacaggta tccggtaagc ggcagggtcg gaacaggaga gcgcacgagg gagcttccag    4920
ggggaaacgc ctggtatctt tatagtcctg tcgggtttcg ccacctctga cttgagcgtc    4980
```

```
gattttttgtg atgctcgtca gggggggcgga gcctatggaa aaacgccagc aacgcggcct     5040
ttttacggtt cctggccttt tgctggcctt ttgctcacat gttctttcct gcgttatccc     5100
ctgattctgt ggataaccgt attaccgcct ttgagtgagc tgataccgct cgccgcagcc     5160
gaacgaccga gcgcagcgag tcagtgagcg aggaagcgga ag                         5202

<210> SEQ ID NO 42
<211> LENGTH: 5613
<212> TYPE: DNA
<213> ORGANISM: vector pYIG5E1H6

<400> SEQUENCE: 42
ggatccttca atatgcgcac atacgctgtt atgttcaagg tcccttcgtt taagaacgaa       60
agcggtcttc cttttgaggg atgtttcaag ttgttcaaat ctatcaaatt tgcaaatccc      120
cagtctgtat ctagagcgtt gaatcggtga tgcgatttgt taattaaatt gatggtgtca      180
ccattaccag gtctagatat accaatggca aactgagcac aacaatacca gtccggatca      240
actggcacca tctctcccgt agtctcatct aattttttctt ccggatgagg ttccagatat      300
accgcaacac ctttattatg gtttccctga gggaataata gaatgtccca ttcgaaatca      360
ccaattctaa acctgggcga attgtatttc gggtttgtta actcgttcca gtcaggaatg      420
ttccacgtga agctatcttc cagcaaagtc tccacttctt catcaaattg tggagaatac      480
tcccaatgct cttatctatg ggacttccgg gaaacacagt accgatactt cccaattcgt      540
cttcagagct cattgtttgt ttgaagagac taatcaaaga atcgttttct caaaaaaatt      600
aatatcttaa ctgatagttt gatcaaaggg gcaaaacgta ggggcaaaca aacggaaaaa      660
tcgtttctca aattttctga tgccaagaac tctaaccagt cttatctaaa aattgcctta      720
tgatccgtct ctccggttac agcctgtgta actgattaat cctgcctttc taatcaccat      780
tctaatgttt taattaaggg attttgtctt cattaacggc tttcgctcat aaaaatgtta      840
tgacgttttg cccgcaggcg ggaaaccatc cacttcacga gactgatctc ctctgccgga      900
acaccgggca tctccaactt ataagttgga gaaataagag aatttcagat tgagagaatg      960
aaaaaaaaaa accctgaaaa aaaaggttga aaccagttcc ctgaaattat tcccctactt     1020
gactaataag tatataaaga cggtaggtat tgattgtaat tctgtaaatc tatttcttaa     1080
acttcttaaa ttctactttt atagttagtc ttttttttag tttaaaaca ccaagaactt     1140 agtttcgaat aaacacacat aaacaaacac catgagattt ccttcaattt ttactgcagt     1200
tttattcgca gcatcctccg cattagctgc tccagtcaac actacaacag aagatgaaac     1260
ggcacaaatt ccggctgaag ctgtcatcgg ttacttagat ttagaagggg atttcgatgt     1320
tgctgttttg ccatttttcca acagcacaaa taacggggtta ttgttttataa atactactat     1380 tgccagcatt gctgctaaag aagaaggggt atctctagat aaaaggtatg aggtgcgcaa     1440
cgtgtccggg atgtaccatg tcacgaacga ctgctccaac tcaagcattg tgtatgaggc     1500
agcggacatg atcatgcaca ccccccgggtg cgtgccctgc gttcgggaga caactcttc     1560 ccgctgctgg gtagcgctca cccccacgct cgcagctagg aacgccagcg tccccactac     1620
gacaatacga cgccacgtcg atttgctcgt tggggcggct gctttctgtt ccgctatgta     1680
cgtgggggat ctctgcggat ctgtcttcct cgtctcccag ctgttcacca tctcgcctcg     1740
ccggcatgag acggtgcagg actgcaattg ctcaatctat cccggccaca taacaggtca     1800
ccgtatggct tgggatatga tgatgaactg gcaccaccac catcaccatt aaagatctcg     1860
acttggttga acacgttgcc aaggcttaag tgaatttact ttaaagtctt gcatttaaat     1920
```

```
aaattttctt tttatagctt tatgacttag tttcaattta tatactatttt taatgacatt    1980
ttcgattcat tgattgaaag ctttgtgttt tttcttgatg cgctattgca ttgttcttgt    2040
cttttttcgcc acatgtaata tctgtagtag atacctgata cattgtggat gctgagtgaa   2100
attttagtta ataatggagg cgctcttaat aattttgggg atattggctt ttttttttaa    2160
agtttacaaa tgaattttt ccgccaggat aacgattctg aagttactct tagcgttcct     2220
atcggtacag ccatcaaatc atgcctataa atcatgccta tatttgcgtg cagtcagtat    2280
catctacatg aaaaaaactc ccgcaatttc ttatagaata cgttgaaaat taaatgtacg    2340
cgccaagata agataacata tatctagcta gatgcagtaa tatacacaga ttcccgcgga    2400
cgtgggaagg aaaaaattag ataacaaaat ctgagtgata tggaaattcc gctgtatagc    2460
tcatatcttt cccttcaaca ccagaaatgt aaaaatcttg ttacgaagga tcttttgct    2520
aatgttctc gctcaatcct catttcttcc ctacgaagag tcaaatctac ttgttttctg     2580
ccggtatcaa gatccatatc ttctagtttc accatcaaag tccaatttct agtatacagt    2640
ttatgtccca acgtaacaga caatcaaaat tggaaaggat aagtatcctt caaagaatga    2700
ttctgcgctg gctcctgaac cgcctaatgg gaacagagaa gtccaaaacg atgctataag    2760
aaccagaaat aaaacgataa aaccatacca ggatccaagc ttggcactgg ccgtcgtttt    2820
acaacgtcgt gactgggaaa accctggcgt tacccaactt aatcgccttg cagcacatcc    2880
cccttcgcc agctggcgta atagcgaaga ggcccgcacc gatcgccctt cccaacagtt     2940
gcgcagcctg aatggcgaat gggaaattgt aaacgttaat attttgttaa aattcgcgtt    3000
aaattttgt taaatcagct cattttttaa ccaataggcc gaaatcggca aaatccctta    3060
taaatcaaaa gaatagaccg agataggggtt gagtgttgtt ccagtttgga acaagagtcc   3120
actattaaag aacgtggact ccaacgtcaa agggcgaaaa accgtctatc agggcgatgg    3180
cccactacgt gaaccatcac cctaatcaag ttttttgggg tcgaggtgcc gtaaagcact    3240
aaatcggaac cctaaaggga gcccccgatt tagagcttga cggggaaagc cggcgaacgt    3300
ggcgagaaag gaagggaaga aagcgaaagg agcgggcgct agggcgctgg caagtgtagc    3360
ggtcacgctg cgcgtaacca ccacacccgc cgcgcttaat gcgccgctac agggcgcgtc    3420
aggtggcact tttcggggaa atgtgcgcgg aaccccctatt tgtttatttt tctaaataca   3480
ttcaaatatg tatccgctca tgagacaata accctgataa atgcttcaat aatattgaaa    3540
aaggaagagt atgagtattc aacatttccg tgtcgccctt attcccttt ttgcggcatt     3600
ttgccttcct gtttttgctc acccagaaac gctggtgaaa gtaaaagatg ctgaagatca    3660
gttgggtgca cgagtgggtt acatcgaact ggatctcaac agcggtaaga tccttgagag    3720
ttttcgcccc gaagaacgtt ttccaatgat gagcactttt aaagttctgc tatgtggcgc    3780
ggtattatcc cgtattgacg ccgggcaaga gcaactcggt cgccgcatac actattctca    3840
gaatgacttg gttgagtact caccagtcac agaaaagcat cttacggatg gcatgacagt    3900
aagagaatta tgcagtgctg ccataaccat gagtgataac actgcggcca acttacttct    3960
gacaacgatc ggaggaccga aggagctaac cgcttttttg cacaacatgg gggatcatgt    4020
aactcgcctt gatcgttggg aaccggagct gaatgaagcc ataccaaacg acgagcgtga    4080
caccacgatg cctgtagcaa tggcaacaac gttgcgcaaa ctattaactg gcgaactact    4140
tactctagct tcccggcaac aattaataga ctggatggag gcggataaag ttgcaggacc    4200
acttctgcgc tcggcccttc cggctggctg gtttattgct gataaatctg gagccggtga    4260
```

```
gcgtgggtct cgcggtatca ttgcagcact ggggccagat ggtaagccct cccgtatcgt    4320
agttatctac acgacgggga gtcaggcaac tatggatgaa cgaaatagac agatcgctga    4380
gataggtgcc tcactgatta agcattggta actgtcagac caagtttact catatatact    4440
ttagattgat ttaaaacttc attttttaatt taaaaggatc taggtgaaga tccttttttga  4500 taatctcatg accaaaatcc cttaacgtga gttttcgttc cactgagcgt cagacccccgt  4560 agaaaagatc aaaggatctt cttgagatcc ttttttttctg cgcgtaatct gctgcttgca   4620
aacaaaaaaa ccaccgctac cagcggtggt ttgtttgccg gatcaagagc taccaactct    4680 tttttccgaag gtaactggct tcagcagagc gcagatacca aatactgtcc ttctagtgta   4740
gccgtagtta ggccaccact tcaagaactc tgtagcaccg cctacatacc tcgctctgct    4800
aatcctgtta ccagtggctg ctgccagtgg cgataagtcg tgtcttaccg ggttggactc    4860
aagacgatag ttaccggata aggcgcagcg gtcgggctga acggggggtt cgtgcacaca    4920
gcccagcttg gagcgaacga cctacaccga actgagatac ctacagcgtg agcattgaga   4980
aagcgccacg cttcccgaag ggagaaaggc ggacaggtat ccggtaagcg gcagggtcgg    5040
aacaggagag cgcacgaggg agcttccagg gggaaacgcc tggtatcttt atagtcctgt    5100
cgggtttcgc cacctctgac ttgagcgtcg atttttgtga tgctcgtcag gggggcggag    5160
cctatggaaa aacgccagca acgcggcctt tttacggttc ctggccttt tgctgccttt    5220 tgctcacatg ttctttcctg cgttatcccc tgattctgtg gataaccgta ttaccgcctt    5280
tgagtgagct gataccgctc gccgcagccg aacgaccgag cgcagcgagt cagtgagcga    5340
ggaagcggaa gagcgcccaa tacgcaaacc gcctctcccc gcgcgttggc cgattcatta   5400
atgcagctgg cacgacaggt ttcccgactg gaaagcgggc agtgagcgca acgcaattaa   5460
tgtgagttag ctcactcatt aggcacccca ggctttacac tttatgcttc cggctcgtat    5520
gttgtgtgga attgtgagcg gataacaatt tcacacagga aacagctatg accatgatta    5580
cgaatttaat acgactcact atagggaatt cga                                 5613
```

<210> SEQ ID NO 43
<211> LENGTH: 13020
<212> TYPE: DNA
<213> ORGANISM: vector pSY1

<400> SEQUENCE: 43

```
atcgataagc ttttcaattc aattcatcat ttttttttta ttcttttttt tgatttcgt     60 ttctttgaaa ttttttttgat tcggtaatct ccgaacagaa ggaagaacga aggaaggagc   120
acagacttag attggtatat atacgcatat gtagtgttga agaaacatga aattgcccag   180
tattcttaac ccaactgcac agaacaaaaa cctgcaggaa acgaagataa atcatgtcga   240
aagctacata taaggaacgt gctgctactc atcctagtcc tgttgctgcc aagctattta   300
atatcatgca cgaaaagcaa acaaacttgt gtgcttcatt ggatgttcgt accaccaagg   360
aattactgga gttagttgaa gcattaggtc ccaaaatttg tttactaaaa acacatgtgg   420
atatcttgac tgattttttcc atggagggca cagttaagcc gctaaaggca ttatccgcca   480
agtacaattt tttactcttc gaagacagaa aatttgctga cattggtaat acagtcaaat    540
tgcagtactc tgcgggtgta tacagaatag cagaatgggc agacattacg aatgcacacg    600
gtgtggtggg cccaggtatt gttagcggtt tgaagcaggc ggcagaagaa gtaacaaagg    660
aacctagagg cctttttgatg ttagcagaat tgtcatgcaa gggctcccta tctactggag   720
aatatactaa gggtactgtt gacattgcga agagcgacaa agattttgtt atcggctttta  780
```

```
ttgctcaaag agacatgggt ggaagagatg aaggttacga ttggttgatt atgacacccg      840
gtgtgggttt agatgacaag ggagacgcat tgggtcaaca gtatagaacc gtggatgatg      900
tggtctctac aggatctgac attattattg ttggaagagg actatttgca agggaaggg       960
atgctaaggt agagggtgaa cgttacagaa aagcaggctg ggaagcatat tgagaagat      1020
gcggccagca aaactaaaaa actgtattat aagtaaatgc atgtatacta aactcacaaa     1080
ttagagcttc aatttaatta tatcagttat tacccgggaa tctcggtcgt aatgattttt     1140
ataatgacga aaaaaaaaaa attggaaaga aaaagcttta atgcggtagt ttatcacagt     1200
taaattgcta acgcagtcag gcaccgtgta tgaaatctaa caatgcgctc atcgtcatcc     1260
tcggcaccgt caccctggat gctgtaggca taggcttggt tatgccggta ctgccgggcc     1320
tcttgcggga tatcgtccat tccgacagca tcgccagtca ctatggcgtg ctgctagcgc     1380
tatatgcgtt gatgcaattt ctatgcgcac ccgttctcgg agcactgtcc gaccgctttg     1440
gccgccgccc agtcctgctc gcttcgctac ttggagccac tatcgactac gcgatcatgg     1500
cgaccacacc cgtcctgtgg atcctctacg ccggacgcat cgtggccggc atcaccggcg     1560
ccacaggtgc ggttgctggc ccctatatcg ccgacatcac cgatggggaa gatcgggctc     1620
gccacttcgg gctcatgagc gcttgttttcg gcgtgggtat ggtggcaggc cccgtggccg     1680
ggggactgtt gggcgccatc tccttgcatg caccattcct tgcggcggcg gtgctcaacg     1740
gcctcaacct actactgggc tgcttcctaa tgcaggagtc gcataaggga gagcgtcgac     1800
cgatgccctt gagagccttc aacccagtca gctccttccg gtgggcgcgg ggcatgacta     1860
tcgtcgccgc acttatgact gtcttcttta tcatgcaact cgtaggacag gtgccggcag     1920
cgctctgggt cattttcggc gaggaccgct ttcgctggag cgcgacgatg atcggcctgt     1980
cgcttgcggt attcggaatc ttgcacgccc tcgctcaagc cttcgtcact ggtcccgcca     2040
ccaaacgttt cggcgagaag caggccatta tcgccggcat ggcggccgac gcgctgggct     2100
acgtcttgct ggcgttcgcg acgcgaggct ggatggcctt ccccattatg attcttctcg     2160
cttccggcgg catcgggatg cccgcgttgc aggccatgct gtccaggcag gtagatgacg     2220
accatcaggg acagcttcaa ggatcgctcg cggctcttac cagcctaact tcgatcactg     2280
gaccgctgat cgtcacggcg atttatgccg cctcggcgag cacatggaac gggttggcat     2340
ggattgtagg cgccgcccta taccttgtct gcctccccgc gttgcgtcgc ggtgcatgga     2400
gccgggccac ctcgacctga atggaagccg cggcacctc gctaacggat tcaccactcc     2460
aagaattgga gccaatcaat tcttgcggag aactgtgaat gcgcaaacca acccttggca     2520
gaacatatcc atcgcgtccg ccatctccag cagccgcacg cggcgcatct cgggcagcgt     2580
tgggtcctgg ccacgggtgc gcatgatcgt gctcctgtcg ttgaggaccc ggctaggctg     2640
gcggggttgc cttactggtt agcagaatga atcaccgata cgcgagcgaa cgtgaagcga     2700
ctgctgctgc aaaacgtctg cgacctgagc aacaacatga atggtcttcg gtttccgtgt     2760
ttcgtaaagt ctgaaacgc ggaagtcagc gccctgcacc attatgttcc ggatctgcat     2820
cgcaggatgc tgctggctac cctgtggaac acctacatct gtattaacga agcgctggca     2880
ttgaccctga gtgatttttc tctggtcccg ccgcatccat accgccagtt gtttaccctc     2940
acaacgttcc agtaaccggg catgttcatc atcagtaacc cgtatcgtga gcatcctctc     3000
tcgtttcatc ggtatcatta cccccatgaa cagaaattcc cccttacacg gaggcatcaa     3060
gtgaccaaac aggaaaaaac cgcccttaac atggcccgct ttatcagaag ccagacatta     3120
```

-continued

```
acgcttctgg agaaactcaa cgagctggac gcggatgaac aggcagacat ctgtgaatcg    3180
cttcacgacc acgctgatga gctttaccgc agctgcctcg cgcgtttcgg tgatgacggt    3240
gaaaacctct gacacatgca gctcccggag acggtcacag cttgtctgta agcggtgccg    3300
ggagcagaca agcccgtcag ggcgcgtcag cgggtgttgg cgggtgtcgg ggcgcagcca    3360
tgacccagtc acgtagcgat agcggagtgt atactggctt aactatgcgg catcagagca    3420
gattgtactg agagtgcacc atatgcggtg tgaaataccg cacagatgcg taaggagaaa    3480
ataccgcatc aggcgctctt ccgcttcctc gctcactgac tcgctgcgct cggtcgttcg    3540
gctgcggcga gcggtatcag ctcactcaaa ggcggtaata cggttatcca cagaatcagg    3600
ggataacgca ggaaagaaca tgtgagcaaa aggccagcaa aaggccagga accgtaaaaa    3660
ggccgcgttg ctggcgtttt tccataggct ccgcccccct gacgagcatc acaaaaatcg    3720
acgctcaagt cagaggtggc gaaacccgac aggactataa agataccagg cgtttccccc    3780
tggaagctcc ctcgtgcgct ctcctgttcc gaccctgccg cttaccggat acctgtccgc    3840
ctttctccct tcgggaagcg tggcgctttc tcatagctca cgctgtaggt atctcagttc    3900
ggtgtaggtc gttcgctcca agctgggctg tgtgcacgaa ccccccgttc agcccgaccg    3960
ctgcgcctta tccggtaact atcgtcttga gtccaacccg gtaagacacg acttatcgcc    4020
actggcagca gccactggta acaggattag cagagcgagg tatgtaggcg gtgctacaga    4080
gttcttgaag tggtggccta actacggcta cactagaagg acagtatttg gtatctgcgc    4140
tctgctgaag ccagttacct tcggaaaaag agttggtagc tcttgatccg gcaaacaaac    4200
caccgctggt agcggtggtt tttttgtttg caagcagcag attacgcgca gaaaaaaagg    4260
atctcaagaa gatcctttga tcttttctac ggggtctgac gctcagtgga acgaaaactc    4320
acgttaaggg attttggtca tgagattatc aaaaaggatc ttcacctaga tccttttaaa    4380
ttaaaaatga agttttaaat caatctaaag tatatatgag taaacttggt ctgacagtta    4440
ccaatgctta atcagtgagg cacctatctc agcgatctgt ctatttcgtt catccatagt    4500
tgcctgactc cccgtcgtgt agataactac gatacgggag ggcttaccat ctggccccag    4560
tgctgcaatg ataccgcgag acccacgctc accggctcca gatttatcag caataaacca    4620
gccagccgga agggccgagc gcagaagtgg tcctgcaact ttatccgcct ccatccagtc    4680
tattaattgt tgccgggaag ctagagtaag tagttcgcca gttaatagtt tgcgcaacgt    4740
tgttgccatt gctgcaggca tcgtggtgtc acgctcgtcg tttggtatgg cttcattcag    4800
ctccggttcc caacgatcaa ggcgagttac atgatccccc atgttgtgca aaaaagcggt    4860
tagctccttc ggtcctccga tcgttgtcag aagtaagttg gccgcagtgt tatcactcat    4920
ggttatggca gcactgcata attctcttac tgtcatgcca tccgtaagat gcttttctgt    4980
gactggtgag tactcaacca agtcattctg agaatagtgt atgcggcgac cgagttgctc    5040
ttgcccggcg tcaacacggg ataataccgc gccacatagc agaactttaa aagtgctcat    5100
cattggaaaa cgttcttcgg ggcgaaaact ctcaaggatc ttaccgctgt tgagatccag    5160
ttcgatgtaa cccactcgtg cacccaactg atcttcagca tcttttactt tcaccagcgt    5220
ttctgggtga gcaaaaacag gaaggcaaaa tgccgcaaaa aagggaataa gggcgacacg    5280
gaaatgttga atactcatac tcttcctttt tcaatattat tgaagcattt atcagggtta    5340
ttgtctcatg agcggataca tatttgaatg tatttagaaa aataaacaaa tagggggttcc    5400 gcgcacattt ccccgaaaag tgccacctga cgtctaagaa accattatta tcatgacatt    5460
aacctataaa aataggcgt atcacgaggc cctttcgtct tcaagaattc tcatgtttga    5520
```

-continued

```
cagcttatca tcgatccact tgtatatttg gatgaattt tgaggaattc tgaaccagtc    5580
ctaaaacgag taaataggac cggcaattct tcaagcaata acaggaata ccaattatta    5640
aaagataact tagtcagatc gtacaataaa gctttgaaga aaaatgcgcc ttattcaatc    5700
tttgcataaa aaatggccc aaaatctcac attggaagac atttgatgac ctcatttctt    5760
tcaatgaagg gcctaacgga gttgactaat gttgtgggaa attggaccga taagcgtgct    5820
tctgccgtgg ccaggacaac gtatactcat cagataacag caatacctga tcactacttc    5880
gcactagttt ctcggtacta tgcatatgat ccaatatcaa aggaaatgat agcattgaag    5940
gatgagacta atccaattga ggagtggcag catatagaac agctaaaggg tagtgctgaa    6000
ggaagcatac gatacccgc atggaatggg ataatatcac aggaggtact agactacctt    6060
tcatcctaca taaatagacg catataagta cgcatttaag cataaacacg cactatgccg    6120
ttcttctcat gtatatatat atacaggcaa cacgcagata taggtgcgac gtgaacagtg    6180
agctgtatgt gcgcagctcg cgttgcattt tcggaagcgc tcgttttcgg aaacgctttg    6240
aagttcctat tccgaagttc ctattctcta gaaagtatag gaacttcaga gcgcttttga    6300
aaaccaaaag cgctctgaag acgcactttc aaaaaaccaa aaacgcaccg gactgtaacg    6360
agctactaaa atattgcgaa taccgcttcc acaaacattg ctcaaaagta tctctttgct    6420
atatatctct gtgctatatc cctatataac catcccatcc acctttcgct ccttgaactt    6480
gcatctaaac tcgacctcta cattttttat gtttatctct agtattacct cttagacaaa    6540
aaaattgtag taagaactat tcatagagtt aatcgaaaac aatacgaaaa tgtaaacatt    6600
tcctatacgt agtatataga gacaaaatag aagaaccgt tcataatttt ctgaccaatg    6660
aagaatcatc aacgctatca ctttctgttc acaaagtatg cgcaatccac atcggtatag    6720
aatataatcg gggatgcctt tatcttgaaa aaatgcaccc gcagcttcgc tagtaatcag    6780
taaacgcggg aagtggagtc aggcttttt tatggaagag aaaatagaca ccaaagtagc    6840
cttcttctaa ccttaacgga cctacagtgc aaaaagttat caagagactg cattatagag    6900
cgcacaaagg agaaaaaaag taatctaaga tgctttgtta gaaaaatagc gctctcggga    6960
tgcattttg tagaacaaaa agaagtata gattcttgtt ggtaaaatag cgctctcgcg    7020
ttgcatttct gttctgtaaa aatgcagctc agattctttg tttgaaaaat tagcgctctc    7080
gcgttgcatt tttgttttac aaaaatgaag cacagattct tcgttggtaa aatagcgctt    7140
tcgcgttgca tttctgttct gtaaaaatgc agctcagatt ctttgtttga aaaattagcg    7200
ctctcgcgtt gcattttgt tctacaaaat gaagcacaga tgcttcgtta caaagatat    7260
gctattgaag tgcaagatgg aaacgcagaa aatgaaccgg ggatgcgacg tgcaagatta    7320
cctatgcaat agatgcaata gtttctccag gaaccgaaat acatacattg tcttccgtaa    7380
agcgctagac tatatattat tatacaggtt caaatatact atctgtttca gggaaaactc    7440
ccaggttcgg atgttcaaaa ttcaatgatg ggtaacaagt acgatcgtaa atctgtaaaa    7500
cagtttgtcg gatattaggc tgtatctcct caaagcgtat tcgaatatca ttgagaagct    7560
gcatttttt tttttttttt ttttttttt ttttatata tatttcaagg ataaccatt    7620
gtaatgtctg cccctaagaa gatcgtcgtt ttgccaggtg accacgttgg tcaagaaatc    7680
acagccgaag ccattaaggt tcttaaagct atttctgatg ttcgttccaa tgtcaagttc    7740
gatttcgaaa atcatttaat tggtggtgct gctatcgatg ctacaggtgt cccacttcca    7800
gatgaggcgc tggaagcctc caagaaggtt gatgccgttt tgttaggtgc tgtgggtggt    7860
```

```
cctaaatggg gtaccggtag tgttagacct gaacaaggtt tactaaaaat ccgtaaagaa    7920
cttcaattgt acgccaactt aagaccatgt aactttgcat ccgactctct tttagactta    7980
tctccaatca agccacaatt tgctaaaggt actgacttcg ttgttgtcag agaattagtg    8040
ggaggtattt actttggtaa gagaaaggaa gacgatggtg atggtgtcgc ttgggatagt    8100
gaacaataca ccgttccaga agtgcaaaga atcacaagaa tggccgcttt catggcccta    8160
caacatgagc caccattgcc tatttggtcc ttggataaag ctaatgtttt ggcctcttca    8220
agattatgga gaaaaactgt ggaggaaacc atcaagaacg aattccctac attgaaggtt    8280
caacatcaat tgattgattc tgccgccatg atcctagtta agaacccaac ccacctaaat    8340
ggtattataa tcaccagcaa catgtttggt gatatcatct ccgatgaagc ctccgttatc    8400
ccaggttcct tgggtttgtt gccatctgcg tccttggcct ctttgccaga caagaacacc    8460
gcatttggtt tgtacgaacc atgccacggt tctgctccag atttgccaaa gaataaggtt    8520
gaccctatcg ccactatctt gtctgctgca atgatgttga aattgtcatt gaacttgcct    8580
gaagaaggta aggccattga agatgcagtt aaaaaggttt tggatgcagg tatcagaact    8640
ggtgatttag gtggttccaa cagtaccacc gaagtcggtg atgctgtcgc cgaagaagtt    8700
aagaaaatcc ttgcttaaaa agattctctt ttttttatgat atttgtacaa aaaaaaaaa    8760
aaaaaaaaa aaaaaaaaa aaaaaaaaa aaatgcagc gtcacatcgg ataataatga    8820
tggcagccat tgtagaagtg cctttttgcat ttctagtctc tttctcggtc tagctagttt    8880
tactacatcg cgaagataga atcttagatc acactgcctt tgctgagctg atcatatga    8940
gtaacaaaag agtggtaagg cctcgttaaa ggacaaggac ctgagcggaa gtgtatcgta    9000
aagtagacgg agtatactag tatagtctat agtccgtgga attctaagtg ccagctttat    9060
aatgtcattc tccttactac agacccgcct gaaagtagac acatcatcat cagtaagctt    9120
tgacaaaaag cattgagtag ctaactcttc tatgcaatct atagctgttt tataaggcat    9180
tcaatggaca gattgaggtt tttgaaacat actagtgaaa ttagccttaa tcccttctcg    9240
aagttaatca tgcattatgg tgtaaaaaat gcaactcgcg ttgctctact ttttcccgaa    9300
tttccaaata cgcagctggg gtgattgctc gatttcgtaa cgaaagtttt gtttataaaa    9360
accgcgaaaa ccttctgtaa cagatagatt tttacagcgc tgatatacaa tgacatcagc    9420
tgtaatggaa aataactgaa atatgaatgg cgagagactg cttgcttgta ttaagcaatg    9480
tattatgcag cacttccaac ctatggtgta cgatgaaagt aggtgtgtaa tcgagacgac    9540
aagggggact tttccagttc ctgatcatta taagaaatac aaaacgttag catttgcatt    9600
tgttggacat gtactgaata cagacgacac accggtaatt gaaaagaac tggattggcc    9660
tgatcctgca ctagtgtaca atacaattgt cgatcgaatc ataaatcacc cagaattatc    9720
acagtttata tcggttgcat ttattagtca gttaaaggcc accatcggag agggtttaga    9780
tattaatgta aaaggcacgc taaaccgcag gggaaagggt atcagaaggc ctaaaggcgt    9840
attttttaga tacatggaat ctccatttgt caatacaaag gtcactgcat tcttctctta    9900
tcttcgagat tataataaaa ttgcctcaga atatcacaat aatactaaat tcattctcac    9960
gttttcatgt caagcatatt gggcatctgg cccaaacttc tccgccttga agaatgttat   10020
ttggtgctcc ataattcatg aatacatttc taagtttgtg gaaagagaac aggataaagg   10080
tcatatagga gatcaggagc taccgcctga agaggaccct tctcgtgaac taaacaatgt   10140
acaacatgaa gtcaatagtt taacggaaca agatgcggag gcggatgaag gattgtgggg   10200
tgaaatagat tcattatgtg aaaaatggca gtctgaagcg gagagtcaaa ctgaggcgga   10260
```

```
gataatagcc gacaggataa ttggaaatag ccagaggatg gcgaacctca aaattcgtcg    10320
tacaaagttc aaaagtgtct tgtatcatat actaaaggaa ctaattcaat ctcagggaac    10380
cgtaaaggtt tatcgcggta gtagttttc acacgattcg ataaagataa gcttacatta    10440
tgaagagcag catattacag ccgtatgggt ctacttgata gtaaaatttg aagagcattg    10500
gaagcctgtt gatgtagagg tcgagtttag atgcaagttc aaggagcgaa aggtggatgg    10560
gtaggttata tagggatata gcacagagat atatagcaaa gagatacttt tgaggcaatg    10620
tttgtggaag cggtattcgc aatattttag tagctcgtta cagtccggtg cgttttggt    10680
ttttgaaag tgcgtcttca gagcgctttt ggttttcaaa agcgctctga agttcctata    10740
ctttctagag aataggaact tcggaatagg aacttcaaag cgtttccgaa aacgagcgct    10800
tccgaaaatg caacgcgagc tgcgcacata cagctcactg ttcacgtcgc acctatatct    10860
gcgtgttgcc tgtatatata tatacatgag aagaacggca tagtgcgtgt ttatgcttaa    10920
atgcgtactt atatgcgtct atttatgtag gatgaaaggt agtctagtac ctcctgtgat    10980
attatcccat tccatgcggg gtatcgtatg cttccttcag cactaccctt tagctgttct    11040
atatgctgcc actcctcaat tggattagtc tcatccttca atgcattcat ttcctttgat    11100
attggatcat accctagaag tattacgtga ttttctgccc cttaccctcg ttgctactct    11160
ccttttttc gtgggaaccg ctttagggcc ctcagtgatg gtgttttgta atttatatgc    11220
tcctcttgca tttgtgtctc tacttcttgt tcgcctggag ggaacttctt catttgtatt    11280
agcatggttc acttcagtcc ttccttccaa ctcactcttt ttttgctgta aacgattctc    11340
tgccgccagt tcattgaaac tattgaatat atcctttaga gattccggga tgaataaatc    11400
acctattaaa gcagcttgac gatctggtgg aactaaagta agcaattggg taacgacgct    11460
tacgagcttc ataacatctt cttccgttgg agctggtggg actaataact gtgtacaatc    11520
cattttctc atgagcattt cggtagctct cttcttgtct ttctcgggca atcttcctat    11580
tattatagca atagatttgt atagttgctt tctattgtct aacagcttgt tattctgtag    11640
catcaaatct atggcagcct gacttgcttc ttgtgaagag agcataccat ttccaatcga    11700
agatacgctg gaatcttctg cgctagaatc aagaccatac ggcctaccgg ttgtgagaga    11760
ttccatgggc cttatgacat atcctggaaa gagtagctca tcagacttac gtttactctc    11820
tatatcaata tctacatcag gagcaatcat ttcaataaac agccgacata catcccagac    11880
gctataagct gtacgtgctt ttaccgtcag attcttggct gtttcaatgt cgtccatttt    11940
ggttttcttt taccagtatt gttcgtttga taatgtattc ttgcttatta cattataaaa    12000
tctgtgcaga tcacatgtca aaacaacttt ttatcacaag atagtaccgc aaaacgaacc    12060
tgcgggccgt ctaaaaatta aggaaaagca gcaaaggtgc atttttaaaa tatgaaatga    12120
agataccgca gtaccaatta ttttcgcagt acaaataatg cgcggccggt gcattttcg    12180
aaagaacgcg agacaaacag gacaattaaa gttagttttt cgagttagcg tgtttgaata    12240
ctgcaagata caagataaat agagtagttg aaactagata tcaattgcac acaagatcgg    12300
cgctaagcat gccacaattt ggtatattat gtaaaacacc acctaaggtg cttgttcgtc    12360
agtttgtgga aaggtttgaa agaccttcag gtgagaaaat agcattatgt gctgctgaac    12420
taacctattt atgttggatg attacacata acggaacagc aatcaagaga gccacattca    12480
tgagctataa tactatcata agcaattcgc tgagtttcga tattgtcaat aaatcactcc    12540
agtttaaata caagacgcaa aaagcaacaa ttctggaagc ctcattaaag aaattgattc    12600
```

-continued

| | |
|---|---|
| ctgcttggga atttacaatt attccttact atggacaaaa acatcaatct gatatcactg | 12660 |
| atattgtaag tagtttgcaa ttacagttcg aatcatcgga agaagcagat aagggaaata | 12720 |
| gccacagtaa aaaatgcta aagcacttct aagtgagggt gaaagcatct gggagatcac | 12780 |
| tgagaaaata ctaaattcgt ttgagtatac ttcgagattt acaaaaacaa aaactttata | 12840 |
| ccaattcctc ttcctagcta ctttcatcaa ttgtggaaga ttcagcgata ttaagaacgt | 12900 |
| tgatccgaaa tcatttaaat tagtccaaaa taagtatctg ggagtaataa tccagtgttt | 12960 |
| agtgacagag acaaagacaa gcgttagtag gcacatatac ttctttagcg caaggggtag | 13020 |

<210> SEQ ID NO 44
<211> LENGTH: 15810
<212> TYPE: DNA
<213> ORGANISM: vector pSY1aMFE1sH6a

<400> SEQUENCE: 44

| | |
|---|---|
| atcgataagc ttttcaattc aattcatcat ttttttttta ttctttttttt tgatttcggt | 60 |
| ttctttgaaa ttttttttgat tcggtaatct ccgaacagaa ggaagaacga aggaaggagc | 120 |
| acagacttag attggtatat atacgcatat gtagtgttga agaaacatga aattgcccag | 180 |
| tattcttaac ccaactgcac agaacaaaaa cctgcaggaa acgaagataa atcatgtcga | 240 |
| aagctacata taaggaacgt gctgctactc atcctagtcc tgttgctgcc aagctattta | 300 |
| atatcatgca cgaaaagcaa acaaacttgt gtgcttcatt ggatgttcgt accaccaagg | 360 |
| aattactgga gttagttgaa gcattaggtc ccaaaatttg tttactaaaa acacatgtgg | 420 |
| atatcttgac tgattttttcc atggagggca cagttaagcc gctaaaggca ttatccgcca | 480 |
| agtacaattt tttactcttc gaagacagaa aatttgctga cattggtaat acagtcaaat | 540 |
| tgcagtactc tgcgggtgta tacagaatag cagaatgggc agacattacg aatgcacacg | 600 |
| gtgtggtggg cccaggtatt gttagcggtt tgaagcaggc ggcagaagaa gtaacaaagg | 660 |
| aacctagagg ccttttgatg ttagcagaat tgtcatgcaa gggctcccta tctactggag | 720 |
| aatatactaa gggtactgtt gacattgcga agagcgacaa agattttgtt atcggcttta | 780 |
| ttgctcaaag agacatgggt ggaagagatg aaggttacga ttggttgatt atgacacccg | 840 |
| gtgtgggttt agatgacaag ggagacgcat gggtcaaca gtatagaacc gtggatgatg | 900 |
| tggtctctac aggatctgac attattattg ttggaagagg actatttgca agggaagggg | 960 |
| atgctaaggt agagggtgaa cgttacagaa aagcaggctg ggaagcatat ttgagaagat | 1020 |
| gcggccagca aaactaaaaa actgtattat aagtaaatgc atgtatacta aactcacaaa | 1080 |
| ttagagcttc aatttaatta tatcagttat tacccgggaa tctcggtcgt aatgatttt | 1140 |
| ataatgacga aaaaaaaaa attggaaaga aaaagcttta atgcggtagt ttatcacagt | 1200 |
| taaattgcta acgcagtcag gcaccgtgta tgaaatctaa caatgcgctc atcgtcatcc | 1260 |
| tcggcaccgt caccctggat gctgtaggca taggcttggt tatgccggta ctgccgggcc | 1320 |
| tcttgcggga tatcgtccat tccgacagca tcgccagtca ctatggcgtg ctgctagcgc | 1380 |
| tatatgcgtt gatgcaattt ctatgcgcac ccgttctcgg agcactgtcc gaccgctttg | 1440 |
| gccgccgccc agtcctgctc gcttcgctac ttggagccac tatcgactac gcgatcatgg | 1500 |
| cgaccacacc cgtcctgtgg atccttcaat atgcgcacat acgctgttat gttcaaggtc | 1560 |
| ccttcgttta agaacgaaag cggtcttcct tttgagggat gtttcaagtt gttcaaatct | 1620 |
| atcaaatttg caaatcccca gtctgtatct agagcgttga atcggtgatg cgatttgtta | 1680 |
| attaaattga tggtgtcacc attaccaggt ctagatatac caatggcaaa ctgagcacaa | 1740 |

```
caataccagt ccggatcaac tggcaccatc tctcccgtag tctcatctaa ttttcttcc    1800 ggatgaggtt ccagatatac cgcaacacct ttattatggt ttccctgagg gaataataga    1860
atgtcccatt cgaaatcacc aattctaaac ctgggcgaat tgtatttcgg gtttgttaac    1920
tcgttccagt caggaatgtt ccacgtgaag ctatcttcca gcaaagtctc cacttcttca    1980
tcaaattgtg gagaatactc ccaatgctct tatctatggg acttccggga aacacagtac    2040
cgatacttcc caattcgtct tcagagctca ttgtttgttt gaagagacta atcaaagaat    2100
cgttttctca aaaaaattaa tatcttaact gatagtttga tcaaagggc aaaacgtagg      2160 ggcaaacaaa cggaaaaatc gtttctcaaa ttttctgatg ccaagaactc taaccagtct    2220
tatctaaaaa ttgccttatg atccgtctct ccggttacag cctgtgtaac tgattaatcc    2280
tgcctttcta atcaccattc taatgttta attaagggat tttgtcttca ttaacggctt     2340
tcgctcataa aaatgttatg acgttttgcc cgcaggcggg aaaccatcca cttcacgaga    2400
ctgatctcct ctgccggaac accgggcatc tccaacttat aagttggaga ataagagaa     2460 tttcagattg agagaatgaa aaaaaaaaac cctgaaaaaa aaggttgaaa ccagttccct    2520
gaaattattc ccctacttga ctaataagta tataaagacg gtaggtattg attgtaattc    2580
tgtaaatcta tttcttaaac ttcttaaatt ctacttttat agttagtctt ttttttagtt    2640
ttaaaacacc aagaacttag tttcgaataa acacacataa acaaacacca tgagatttcc    2700
ttcaattttt actgcagttt tattcgcagc atcctccgca ttagctgctc cagtcaacac    2760
tacaacagaa gatgaaacgg cacaaattcc ggctgaagct gtcatcggtt actcagattt    2820
agaaggggat ttcgatgttg ctgttttgcc attttccaac agcacaaata acgggttatt    2880 gttttataaat actactattg ccagcattgc tgctaaagaa gaaggggtat ctctagataa    2940
aaggtatgag gtgcgcaacg tgtccgggat gtaccatgtc acgaacgact gctccaactc    3000
aagcattgtg tatgaggcag cggacatgat catgcacacc cccgggtgcg tgccctgcgt    3060
tcgggagaac aactcttccc gctgctgggt agcgctcacc cccacgctcg cagctaggaa    3120
cgccagcgtc cccactacga caatacgacg ccacgtcgat ttgctcgttg gggcggctgc    3180
tttctgttcc gctatgtacg tgggggatct ctgcggatct gtcttcctcg tctcccagct    3240
gttcaccatc tcgcctcgcc ggcatgagac ggtgcaggac tgcaattgct caatctatcc    3300
cggccacata acgggtcacc gtatggcttg ggatatgatg atgaactggc accaccacca    3360
tcaccattaa agatctcgac ttggttgaac acgttgccaa ggcttaagtg aatttacttt    3420
aaagtcttgc atttaaataa attttctttt tatagcttta tgacttagtt tcaatttata    3480
tactatttta atgacatttt cgattcattg attgaaagct ttgtgttttt tcttgatgcg    3540
ctattgcatt gttcttgtct ttttcgccac atgtaatatc tgtagtagat acctgataca    3600
ttgtggatgc tgagtgaaat tttagttaat aatggaggcg ctcttaataa ttttggggat    3660
attggctttt ttttttaaag tttacaaatg aattttttcc gccaggataa cgattctgaa    3720
gttactctta gcgttcctat cggtacagcc atcaaatcat gcctataaat catgcctata    3780
tttgcgtgca gtcagtatca tctacatgaa aaaaactccc gcaatttctt atagaatacg    3840
ttgaaaatta aatgtacgcg ccaagataag ataacatata tctagctaga tgcagtaata    3900
tacacagatt cccgcggacg tgggaaggaa aaaattagat aacaaaatct gagtgatatg    3960
gaaattccgc tgtatagctc atatcttccc cttcaacacc agaaatgtaa aaatcttgtt    4020
acgaaggatc ttttttgctaa tgtttctcgc tcaatcctca tttcttccct acgaagagtc    4080
```

-continued

| | |
|---|---|
| aaatctactt gttttctgcc ggtatcaaga tccatatctt ctagtttcac catcaaagtc | 4140 |
| caatttctag tatacagttt atgtcccaac gtaacagaca atcaaaattg gaaaggataa | 4200 |
| gtatccttca aagaatgatt ctgcgctggc tcctgaaccg cctaatggga acagagaagt | 4260 |
| ccaaaacgat gctataagaa ccagaaataa acgataaaa ccataccagg atcctctacg | 4320 |
| ccggacgcat cgtggccggc atcaccggcg ccacaggtgc ggttgctggc ccctatatcg | 4380 |
| ccgacatcac cgatggggaa gatcgggctc gccacttcgg gctcatgagc gcttgtttcg | 4440 |
| gcgtgggtat ggtggcaggc cccgtggccg ggggactgtt gggcgccatc tccttgcatg | 4500 |
| caccattcct tgcggcggcg gtgctcaacg gcctcaacct actactgggc tgcttcctaa | 4560 |
| tgcaggagtc gcataaggga gagcgtcgac cgatgccctt gagagccttc aacccagtca | 4620 |
| gctccttccg gtgggcgcgg ggcatgacta tcgtcgccgc acttatgact gtcttcttta | 4680 |
| tcatgcaact cgtaggacag gtgccggcag cgctctgggt cattttcggc gaggaccgct | 4740 |
| ttcgctggag cgcgacgatg atcggcctgt cgcttgcggt attcggaatc ttgcacgccc | 4800 |
| tcgctcaagc cttcgtcact ggtcccgcca ccaaacgttt cggcgagaag caggccatta | 4860 |
| tcgccggcat ggcggccgac gcgctgggct acgtcttgct ggcgttcgcg acgcgaggct | 4920 |
| ggatggcctt ccccattatg attcttctcg cttccggcgg catcgggatg cccgcgttgc | 4980 |
| aggccatgct gtccaggcag gtagatgacg accatcaggg acagcttcaa ggatcgctcg | 5040 |
| cggctcttac cagcctaact tcgatcactg gaccgctgat cgtcacggcg atttatgccg | 5100 |
| cctcggcgag cacatggaac gggttggcat ggattgtagg cgccgcccta taccttgtct | 5160 |
| gcctccccgc gttgcgtcgc ggtgcatgga gccgggccac ctcgacctga atggaagccg | 5220 |
| gcggcacctc gctaacggat tcaccactcc aagaattgga gccaatcaat tcttgcggag | 5280 |
| aactgtgaat gcgcaaacca accctttggca gaacatatcc atcgcgtccg ccatctccag | 5340 |
| cagccgcacg cggcgcatct cgggcagcgt tgggtcctgg ccacgggtgc gcatgatcgt | 5400 |
| gctcctgtcg ttgaggaccc ggctaggctg gcggggttgc cttactggtt agcagaatga | 5460 |
| atcaccgata cgcgagcgaa cgtgaagcga ctgctgctgc aaaacgtctg cgacctgagc | 5520 |
| aacaacatga atggtcttcg gtttccgtgt ttcgtaaagt ctggaaacgc ggaagtcagc | 5580 |
| gccctgcacc attatgttcc ggatctgcat cgcaggatgc tgctggctac cctgtggaac | 5640 |
| acctacatct gtattaacga agcgctggca ttgaccctga gtgattttc tctggtcccg | 5700 |
| ccgcatccat accgccagtt gtttacccctc acaacgttcc agtaaccggg catgttcatc | 5760 |
| atcagtaacc cgtatcgtga gcatcctctc tcgtttcatc ggtatcatta ccccatgaa | 5820 |
| cagaaattcc cccttacacg gaggcatcaa gtgaccaaac aggaaaaaac cgcccttaac | 5880 |
| atggcccgct ttatcagaag ccagacatta acgcttctgg agaaactcaa cgagctggac | 5940 |
| gcggatgaac aggcagacat ctgtgaatcg cttcacgacc acgctgatga gctttaccgc | 6000 |
| agctgcctcg cgcgtttcgg tgatgacggt gaaaacctct gacacatgca gctcccggag | 6060 |
| acggtcacag cttgtctgta agcggtgccg ggagcagaca agcccgtcag gcgcgtcag | 6120 |
| cgggtgttgg cgggtgtcgg ggcgcagcca tgacccagtc acgtagcgat agcggagtgt | 6180 |
| atactggctt aactatgcgg catcagagca gattgtactg agagtgcacc atatgcggtg | 6240 |
| tgaaataccg cacagatgcg taaggagaaa ataccgcatc aggcgctctt ccgcttcctc | 6300 |
| gctcactgac tcgctgcgct cggtcgttcg gctgcggcga gcggtatcag ctcactcaaa | 6360 |
| ggcggtaata cggttatcca cagaatcagg ggataacgca ggaaagaaca tgtgagcaaa | 6420 |
| aggccagcaa aaggccagga accgtaaaaa ggccgcgttg ctggcgtttt tccataggct | 6480 |

```
ccgcccccct gacgagcatc acaaaaatcg acgctcaagt cagaggtggc gaaacccgac   6540
aggactataa agataccagg cgtttccccc tggaagctcc ctcgtgcgct ctcctgttcc   6600
gaccctgccg cttaccggat acctgtccgc ctttctccct tcgggaagcg tggcgctttc   6660
tcatagctca cgctgtaggt atctcagttc ggtgtaggtc gttcgctcca agctgggctg   6720
tgtgcacgaa ccccccgttc agcccgaccg ctgcgcctta tccggtaact atcgtcttga   6780
gtccaacccg gtaagacacg acttatcgcc actggcagca gccactggta acaggattag   6840
cagagcgagg tatgtaggcg gtgctacaga gttcttgaag tggtggccta actacggcta   6900
cactagaagg acagtatttg gtatctgcgc tctgctgaag ccagttacct tcggaaaaag   6960
agttggtagc tcttgatccg gcaaacaaac caccgctggt agcggtggtt ttttgtttg    7020 caagcagcag attacgcgca gaaaaaaagg atctcaagaa gatcctttga tcttttctac   7080
ggggtctgac gctcagtgga acgaaaactc acgttaaggg attttggtca tgagattatc   7140 aaaaggatc ttcacctaga tccttttaaa ttaaaaatga agttttaaat caatctaaag    7200
tatatatgag taaacttggt ctgacagtta ccaatgctta atcagtgagg cacctatctc   7260
agcgatctgt ctatttcgtt catccatagt tgcctgactc cccgtcgtgt agataactac   7320
gatacgggag ggcttaccat ctggccccag tgctgcaatg ataccgcgag acccacgctc   7380
accggctcca gatttatcag caataaacca gccagccgga agggccgagc gcagaagtgg   7440
tcctgcaact ttatccgcct ccatccagtc tattaattgt tgccgggaag ctagagtaag   7500
tagttcgcca gttaatagtt tgcgcaacgt tgttgccatt gctgcaggca tcgtggtgtc   7560
acgctcgtcg tttggtatgg cttcattcag ctccggttcc caacgatcaa ggcgagttac   7620
atgatccccc atgttgtgca aaaaagcggt tagctccttc ggtcctccga tcgttgtcag   7680
aagtaagttg gccgcagtgt tatcactcat ggttatggca gcactgcata attctcttac   7740
tgtcatgcca tccgtaagat gcttttctgt gactggtgag tactcaacca agtcattctg   7800
agaatagtgt atgcggcgac cgagttgctc ttgcccggcg tcaacacggg ataataccgc   7860
gccacatagc agaactttaa aagtgctcat cattggaaaa cgttcttcgg ggcgaaaact   7920
ctcaaggatc ttaccgctgt tgagatccag ttcgatgtaa cccactcgtg cacccaactg   7980
atcttcagca tcttttactt tcaccagcgt ttctgggtga gcaaaacag gaaggcaaaa    8040 tgccgcaaaa aagggaataa gggcgacacg gaaatgttga atactcatac tcttcctttt   8100
tcaatattat tgaagcattt atcagggtta ttgtctcatg agcggataca tatttgaatg   8160
tatttagaaa aataaacaaa tagggggttcc gcgcacattt ccccgaaaag tgccacctga   8220
cgtctaagaa accattatta tcatgacatt aacctataaa aataggcgt atcacgaggc    8280 cctttcgtct tcaagaattc tcatgtttga cagcttatca tcgatccact tgtatatttg    8340
gatgaatttt tgaggaattc tgaaccagtc taaaacgag taaataggac cggcaattct    8400
tcaagcaata acaggaata ccaattatta aaagataact tagtcagatc gtacaataaa    8460
gctttgaaga aaaatgcgcc ttattcaatc tttgcataaa aaaatggccc aaaatctcac   8520
attggaagac atttgatgac ctcatttctt tcaatgaagg gcctaacgga gttgactaat   8580
gttgtgggaa attggaccga taagcgtgct tctgccgtgg ccaggacaac gtatactcat   8640
cagataacag caataacctga tcactacttc gcactagttt ctcggtacta tgcatatgat   8700
ccaatatcaa aggaaatgat agcattgaag gatgagacta atccaattga ggagtggcag   8760
catatagaac agctaaaggg tagtgctgaa ggaagcatac gataccccgc atggaatggg   8820
```

```
ataatatcac aggaggtact agactacctt tcatcctaca taaatagacg catataagta    8880
cgcatttaag cataaacacg cactatgccg ttcttctcat gtatatatat atacaggcaa    8940
cacgcagata taggtgcgac gtgaacagtg agctgtatgt gcgcagctcg cgttgcattt    9000
tcggaagcgc tcgttttcgg aaacgctttg aagttcctat tccgaagttc ctattctcta    9060
gaaagtatag gaacttcaga gcgcttttga aaaccaaaag cgctctgaag acgcactttc    9120
aaaaaaccaa aaacgcaccg gactgtaacg agctactaaa atattgcgaa taccgcttcc    9180
acaaacattg ctcaaaagta tctctttgct atatatctct gtgctatatc cctatataac    9240
catcccatcc acctttcgct ccttgaactt gcatctaaac tcgacctcta cattttttat    9300
gtttatctct agtattacct cttagacaaa aaaattgtag taagaactat tcatagagtt    9360
aatcgaaaac aatacgaaaa tgtaaacatt tcctatacgt agtatataga gacaaaaatag   9420
aagaaaccgt tcataatttt ctgaccaatg aagaatcatc aacgctatca ctttctgttc    9480
acaaagtatg cgcaatccac atcggtatag aatataatcg gggatgcctt tatcttgaaa    9540
aaatgcaccc gcagcttcgc tagtaatcag taaacgcggg aagtggagtc aggctttttt    9600
tatggaagag aaaatagaca ccaaagtagc cttcttctaa ccttaacgga cctacagtgc    9660
aaaaagttat caagagactg cattatagag cgcacaaagg agaaaaaaag taatctaaga    9720
tgctttgtta gaaaaatagc gctctcggga tgcattttg tagaacaaaa aagaagtata    9780
gattcttgtt ggtaaaatag cgctctcgcg ttgcatttct gttctgtaaa aatgcagctc    9840
agattctttg tttgaaaaat tagcgctctc gcgttgcatt tttgttttac aaaaatgaag    9900
cacagattct tcgttggtaa aatagcgctt tcgcgttgca tttctgttct gtaaaaatgc    9960
agctcagatt ctttgtttga aaaattagcg ctctcgcgtt gcattttgt tctacaaaat    10020
gaagcacaga tgcttcgtta acaaagatat gctattgaag tgcaagatgg aaacgcagaa    10080
aatgaaccgg ggatgcgacg tgcaagatta ccctatgcaat agatgcaata gtttctccag   10140
gaaccgaaat acatacattg tcttccgtaa agcgctagac tatatattat tatacaggtt    10200
caaatatact atctgtttca gggaaaaactc ccaggttcgg atgttcaaaa ttcaatgatg    10260
ggtaacaagt acgatcgtaa atctgtaaaa cagtttgtcg gatattaggc tgtatctcct    10320
caaagcgtat tcgaatatca ttgagaagct gcatttttt tttttttttt tttttttttt    10380
tttttatata tatttcaagg ataaccatt gtaatgtctg cccctaagaa gatcgtcgtt    10440
ttgccaggtg accacgttgg tcaagaaatc acagccgaag ccattaaggt tcttaaagct    10500
atttctgatg ttcgttccaa tgtcaagttc gatttcgaaa atcatttaat tggtggtgct    10560
gctatcgatg ctacaggtgt cccacttcca gatgaggcgc tggaagcctc caagaaggtt    10620
gatgccgttt tgttaggtgc tgtgggtggt cctaaatggg gtaccggtag tgttagacct    10680
gaacaaggtt tactaaaaat ccgtaaagaa cttcaattgt acgccaactt aagaccatgt    10740
aactttgcat ccgactctct tttagactta tctccaatca agccacaatt tgctaaaggt    10800
actgacttcg ttgttgtcag agaattagtg ggaggtattt actttggtaa gagaaaggaa    10860
gacgatggta atggtgtcgc ttgggatagt gaacaataca ccgttccaga agtgcaaaga    10920
atcacaagaa tggccgcttt catggcccta aacatgagc caccattgcc tatttggtcc    10980
ttggataaag ctaatgtttt ggcctcttca agattatgga gaaaaactgt ggaggaaacc    11040
atcaagaacg aattccctac attgaaggtt caacatcaat tgattgattc tgccgccatg    11100
atcctagtta agaacccaac ccacctaaat ggtattataa tcaccagcaa catgtttggt    11160
gatatcatct ccgatgaagc ctccgttatc ccaggttcct tgggtttgtt gccatctgcg    11220
```

```
tccttggcct ctttgccaga caagaacacc gcatttggtt tgtacgaacc atgccacggt   11280
tctgctccag atttgccaaa gaataaggtt gaccctatcg ccactatctt gtctgctgca   11340
atgatgttga aattgtcatt gaacttgcct gaagaaggta aggccattga agatgcagtt   11400
aaaaaggttt tggatgcagg tatcagaact ggtgatttag gtggttccaa cagtaccacc   11460
gaagtcggtg atgctgtcgc cgaagaagtt aagaaaatcc ttgcttaaaa agattctctt   11520
tttttatgat atttgtacaa aaaaaaaaaa aaaaaaaaa aaaaaaaaa aaaaaaaaa      11580 aaaatgcagc gtcacatcgg ataataatga tggcagccat tgtagaagtg cctttttgcat  11640 ttctagtctc tttctcggtc tagctagttt tactacatcg cgaagataga atcttagatc   11700
acactgcctt tgctgagctg gatcatatga gtaacaaaag agtggtaagg cctcgttaaa   11760
ggacaaggac ctgagcggaa gtgtatcgta aagtagacgg agtatactag tatagtctat   11820
agtccgtgga attctaagtg ccagctttat aatgtcattc tccttactac agacccgcct   11880
gaaagtagac acatcatcat cagtaagctt tgacaaaaag cattgagtag ctaactcttc   11940
tatgcaatct atagctgttt tataaggcat tcaatggaca gattgaggtt tttgaaacat   12000
actagtgaaa ttagccttaa tcccttctcg aagttaatca tgcattatgg tgtaaaaaat   12060
gcaactcgcg ttgctctact ttttcccgaa tttccaaata cgcagctggg gtgattgctc   12120
gatttcgtaa cgaaagtttt gtttataaaa accgcgaaaa ccttctgtaa cagatagatt   12180
tttacagcgc tgatatacaa tgacatcagc tgtaatggaa ataactgaa atatgaatgg    12240 cgagagactg cttgcttgta ttaagcaatg tattatgcag cacttccaac ctatggtgta   12300
cgatgaaagt aggtgtgtaa tcgagacgac aagggggact tttccagttc ctgatcatta   12360
taagaaatac aaaacgttag catttgcatt tgttggacat gtactgaata cagacgacac   12420
accggtaatt gaaaagaac tggattggcc tgatcctgca ctagtgtaca atacaattgt    12480
cgatcgaatc ataaatcacc cagaattatc acagtttata tcggttgcat ttattagtca   12540
gttaaaggcc accatcggag agggtttaga tattaatgta aaaggcacgc taaaccgcag   12600
gggaaagggt atcagaaggc ctaaaggcgt attttttaga tacatggaat ctccatttgt   12660
caatacaaag gtcactgcat tcttctctta tcttcgagat tataataaaa ttgcctcaga   12720
atatcacaat aatactaaat tcattctcac gttttcatgt caagcatatt gggcatctgg   12780
cccaaacttc tccgccttga agaatgttat ttggtgctcc ataattcatg aatacatttc   12840
taagtttgtg gaaagagaac aggataaagg tcatatagga gatcaggagc taccgcctga   12900
agaggaccct tctcgtgaac taaacaatgt acaacatgaa gtcaatagtt taacggaaca   12960
agatgcggag gcggatgaag gattgtgggg tgaaatagat tcattatgtg aaaaatggca   13020
gtctgaagcg gagagtcaaa ctgaggcgga gataatagcc gacaggataa ttggaaatag   13080
ccagaggatg gcgaacctca aaattcgtcg tacaaagttc aaaagtgtct tgtatcatat   13140
actaaaggaa ctaattcaat ctcagggaac cgtaaaggtt tatcgcggta gtagttttc    13200 acacgattcg ataagataa gcttacatta tgaagagcag catattacag ccgtatgggt   13260
ctacttgata gtaaaatttg aagagcattg gaagcctgtt gatgtagagg tcgagtttag   13320
atgcaagttc aaggagcgaa aggtggatgg gtaggttata tagggatata gcacagagat   13380
atatagcaaa gagatacttt tgaggcaatg tttgtggaag cggtattcgc aatatttag    13440 tagctcgtta cagtccggtg cgttttttggt tttttgaaag tgcgtcttca gagcgctttt   13500
ggttttcaaa agcgctctga agttcctata ctttctagag aataggaact tcggaatagg   13560
```

```
aacttcaaag cgtttccgaa aacgagcgct tccgaaaatg caacgcgagc tgcgcacata    13620
cagctcactg ttcacgtcgc acctatatct gcgtgttgcc tgtatatata tatacatgag    13680
aagaacggca tagtgcgtgt ttatgcttaa atgcgtactt atatgcgtct atttatgtag    13740
gatgaaaggt agtctagtac ctcctgtgat attatcccat tccatgcggg gtatcgtatg    13800
cttccttcag cactacccctt tagctgttct atatgctgcc actcctcaat tggattagtc    13860
tcatccttca atgcattcat ttcctttgat attggatcat accctagaag tattacgtga    13920
ttttctgccc cttaccctcg ttgctactct ccttttttttc gtgggaaccg ctttagggcc    13980
ctcagtgatg gtgttttgta atttatatgc tcctcttgca tttgtgtctc tacttcttgt    14040
tcgcctggag ggaacttctt catttgtatt agcatggttc acttcagtcc ttccttccaa    14100
ctcactcttt ttttgctgta aacgattctc tgccgccagt tcattgaaac tattgaatat    14160
atcctttaga gattccggga tgaataaatc acctattaaa gcagcttgac gatctggtgg    14220
aactaaagta agcaattggg taacgacgct tacgagcttc ataacatctt cttccgttgg    14280
agctggtggg actaataact gtgtacaatc cattttttctc atgagcattt cggtagctct    14340
cttcttgtct ttctcgggca atcttcctat tattatagca atagatttgt atagttgctt    14400
tctattgtct aacagcttgt tattctgtag catcaaatct atggcagcct gacttgcttc    14460
ttgtgaagag agcataccat ttccaatcga agatacgctg gaatcttctg cgctagaatc    14520
aagaccatac ggcctaccgg ttgtgagaga ttccatgggc cttatgacat atcctggaaa    14580
gagtagctca tcagacttac gtttactctc tatatcaata tctacatcag gagcaatcat    14640
ttcaataaac agccgacata catcccagac gctataagct gtacgtgctt ttaccgtcag    14700
attcttggct gtttcaatgt cgtccatttt ggttttcttt taccagtatt gttcgtttga    14760
taatgtattc ttgcttatta cattataaaa tctgtgcaga tcacatgtca aaacaacttt    14820
ttatcacaag atagtaccgc aaaacgaacc tgcgggccgt ctaaaaatta aggaaaagca    14880
gcaaaggtgc atttttaaaa tatgaaatga agataccgca gtaccaatta ttttcgcagt    14940
acaaataatg cgcggccggt gcattttttcg aaagaacgcg agacaaacag gacaattaaa    15000
gttagttttt cgagttagcg tgtttgaata ctgcaagata caagataaat agagtagttg    15060
aaactagata tcaattgcac acaagatcgg cgctaagcat gccacaattt ggtatattat    15120
gtaaaacacc acctaaggtg cttgttcgtc agtttgtgga aaggtttgaa agaccttcag    15180
gtgagaaaat agcattatgt gctgctgaac taacctattt atgttggatg attacacata    15240
acggaacagc aatcaagaga gccacattca tgagctataa tactatcata agcaattcgc    15300
tgagtttcga tattgtcaat aaatcactcc agtttaaata caagacgcaa aaagcaacaa    15360
ttctggaagc ctcattaaag aaattgattc ctgcttggga atttacaatt attccttact    15420
atggacaaaa acatcaatct gatatcactg atattgtaag tagtttgcaa ttacagttcg    15480
aatcatcgga agaagcagat aagggaaata gccacagtaa aaaaatgcta aagcacttct    15540
aagtgagggt gaaagcatct gggagatcac tgagaaaata ctaaattcgt ttgagtatac    15600
ttcgagattt acaaaaacaa aaactttata ccaattcctc ttcctagcta ctttcatcaa    15660
ttgtggaaga ttcagcgata ttaagaacgt tgatccgaaa tcatttaaat tagtccaaaa    15720
taagtatctg ggagtaataa tccagtgttt agtgacagag acaaagacaa gcgttagtag    15780
gcacatatac ttctttagcg caagggtag                                       15810
```

<210> SEQ ID NO 45
<211> LENGTH: 3928

<212> TYPE: DNA
<213> ORGANISM: vector pBKS-E2sH6

<400> SEQUENCE: 45

```
cacctaaatt gtaagcgtta atattttgtt aaaattcgcg ttaaattttt gttaaatcag      60
ctcattttt aaccaatagg ccgaaatcgg caaaatccct tataaatcaa agaatagac      120
cgagataggg ttgagtgttg ttccagtttg gaacaagagt ccactattaa agaacgtgga     180
ctccaacgtc aaagggcgaa aaaccgtcta tcagggcgat ggcccactac gtgaaccatc     240
accctaatca gtttttgg ggtcgaggtg ccgtaaagca ctaaatcgga accctaaagg      300
gagcccccga tttagagctt gacggggaaa gccggcgaac gtggcgagaa aggaagggaa     360
gaaagcgaaa ggagcgggcg ctagggcgct ggcaagtgta gcggtcacgc tgcgcgtaac     420
caccacaccc gccgcgctta atgcgccgct acagggcgcg tcccattcgc cattcaggct     480
gcgcaactgt tgggaaggc gatcggtgcg ggcctcttcg ctattacgcc agctggcgaa     540
agggggatgt gctgcaaggc gattaagttg ggtaacgcca gggttttccc agtcacgacg     600
ttgtaaaacg acggccagtg aattgtaata cgactcacta tagggcgaat tgggtaccgg     660
gccccccctc gaggtcgacg gtatcgataa gcttgcatgc ctgcagttaa ttaactatta     720
gtgatggtgg tgatggtgtc tgccctcgat cacctgccac tctgttgtag acagcagcag     780
cgggctaagc tctgatctat ccctgtcctc caagtcacaa cgctctcctc gagtccaatt     840
gcatgcggct tcgaacctgt gctccacgcc ccccacgtac atcctaacct tgaagatggt     900
gaagttgaca gtgcagggt agtgccgagg cctatatggg taatgaacca tacacctagg     960
tgtcagccag ggcccagaac cgcatctggc gtaggtggcc tcggggtgct tccgaaaaca    1020
gtcagtgggg caggtcaagg tgttgttgcc ggccccccg atgttgcacg gggggccccc    1080
acacgtcttg gtgaacccag tgccattcat ccatgtacag ccgaaccagt tgcctcgcgg    1140
cggccgcgtg ttgttgagaa tcagcacatc cgagtcgttc gccccccagt tatacgtggg    1200
gacaccaaac cgatcggtcg tccccaccac aacagggctc ggggtgaagc aatacactgg    1260
accgcacacc tgagacgcgg gtacaatacc acacggtcga ggcgcgtagt gccagcagta    1320
gggcctctgg tccgagctgt taggctcagt gtaagtgagg ggaccccacc cctgagcgaa    1380
cttgtcgatg gagcgacagc tggccaagcg ctctgggcat ccagacgagt tgaatttgtg    1440
tttgtagaat agtgcggcaa agaaccctgt ttggagggag tcgttgcagt tcagggcagt    1500
cctgttgatg tgccaactgc cgttggtgtt tacgagctgg atttctgag ccgacccggg    1560
gctaaagagg gacacaaggc ccctggtatc ggaggctgct gcccctcctg acacgcgggt    1620
atggtaccgg gccccccctc gaggtcgacg gtatcgataa gcttgatatc gaattcctgc    1680
agcccggggg atccactagt tctagagcgg ccgccaccgc ggtggagctc cagcttttgt    1740
tcccttagt gagggttaat ttcgagcttg gcgtaatcat ggtcatagct gtttcctgtg    1800
tgaaattgtt atccgctcac aattccacac aacatacgag ccggaagcat aaagtgtaaa    1860
gcctggggtg cctaatgagt gagctaactc acattaattg cgttgcgctc actgcccgct    1920
ttccagtcgg gaaacctgtc gtgccagctg cattaatgaa tcggccaacg cgcggggaga    1980
ggcggtttgc gtattgggcg ctcttccgct tcctcgctca ctgactcgct gcgctcggtc    2040
gttcggctgc ggcgagcggt atcagctcac tcaaaggcgg taatacggtt atccacagaa    2100
tcaggggata acgcaggaaa gaacatgtga gcaaaaggcc agcaaaaggc caggaaccgt    2160
aaaaaggccg cgttgctggc gttttccat aggctccgcc cccctgacga gcatcacaaa    2220
```

-continued

| | |
|---|---|
| aatcgacgct caagtcagag gtggcgaaac ccgacaggac tataaagata ccaggcgttt | 2280 |
| ccccctggaa gctccctcgt gcgctctcct gttccgaccc tgccgcttac cggatacctg | 2340 |
| tccgcctttc tcccttcggg aagcgtggcg cttttctcata gctcacgctg taggtatctc | 2400 |
| agttcggtgt aggtcgttcg ctccaagctg ggctgtgtgc acgaaccccc cgttcagccc | 2460 |
| gaccgctgcg ccttatccgg taactatcgt cttgagtcca acccgtaag acacgactta | 2520 |
| tcgccactgg cagcagccac tggtaacagg attagcagag cgaggtatgt aggcggtgct | 2580 |
| acagagttct tgaagtggtg gcctaactac ggctacacta aaggacagt atttggtatc | 2640 |
| tgcgctctgc tgaagccagt taccttcgga aaaagagttg gtagctcttg atccggcaaa | 2700 |
| caaaccaccg ctggtagcgg tggttttttt gtttgcaagc agcagattac gcgcagaaaa | 2760 |
| aaaggatctc aagaagatcc tttgatcttt tctacgggt ctgacgctca gtggaacgaa | 2820 |
| aactcacgtt aagggatttt ggtcatgaga ttatcaaaaa ggatcttcac ctagatcctt | 2880 |
| ttaaattaaa aatgaagttt taaatcaatc taaagtatat atgagtaaac ttggtctgac | 2940 |
| agttaccaat gcttaatcag tgaggcacct atctcagcga tctgtctatt tcgttcatcc | 3000 |
| atagttgcct gactccccgt cgtgtagata actacgatac gggagggctt accatctggc | 3060 |
| cccagtgctg caatgatacc gcgagaccca cgctcaccgg ctccagattt atcagcaata | 3120 |
| aaccagccag ccggaagggc cgagcgcaga agtggtcctg caactttatc cgcctccatc | 3180 |
| cagtctatta attgttgccg ggaagctaga gtaagtagtt cgccagttaa tagtttgcgc | 3240 |
| aacgttgttg ccattgctac aggcatcgtg gtgtcacgct cgtcgtttgg tatggcttca | 3300 |
| ttcagctccg gttcccaacg atcaaggcga gttacatgat cccccatgtt gtgcaaaaaa | 3360 |
| gcggttagct ccttcggtcc tccgatcgtt gtcagaagta agttggccgc agtgttatca | 3420 |
| ctcatggtta tggcagcact gcataattct cttactgtca tgccatccgt aagatgcttt | 3480 |
| tctgtgactg gtgagtactc aaccaagtca ttctgagaat agtgtatgcg gcgaccgagt | 3540 |
| tgctcttgcc cggcgtcaat acgggataat accgcgccac atagcagaac tttaaaagtg | 3600 |
| ctcatcattg gaaaacgttc ttcggggcga aaactctcaa ggatcttacc gctgttgaga | 3660 |
| tccagttcga tgtaacccac tcgtgcaccc aactgatctt cagcatcttt tactttcacc | 3720 |
| agcgtttctg ggtgagcaaa aacaggaagg caaaatgccg caaaaaaggg aataagggcg | 3780 |
| acacggaaat gttgaatact catactcttc cttttcaat attattgaag catttatcag | 3840 |
| ggttattgtc tcatgagcgg atacatattt gaatgtattt agaaaaataa acaaataggg | 3900 |
| gttccgcgca catttccccg aaaagtgc | 3928 |

<210> SEQ ID NO 46
<211> LENGTH: 6104
<212> TYPE: DNA
<213> ORGANISM: vector pYIG5HCCL-22aH6

<400> SEQUENCE: 46

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gaatttaata | 240 |
| cgactcacta tagggaattc gaggatcctt caatatgcgc acatacgctg ttatgttcaa | 300 |
| ggtcccttcg tttaagaacg aaagcggtct tcctttgag gatgtttca agttgttcaa | 360 |
| atctatcaaa tttgcaaatc cccagtctgt atctagagcg ttgaatcggt gatgcgattt | 420 |

```
gttaattaaa ttgatggtgt caccattacc aggtctagat ataccaatgg caaactgagc      480
acaacaatac cagtccggat caactggcac catctctccc gtagtctcat ctaattttc       540 ttccggatga ggttccagat ataccgcaac acctttatta tggtttccct gagggaataa      600
tagaatgtcc cattcgaaat caccaattct aaacctgggc gaattgtatt tcgggtttgt      660
taactcgttc cagtcaggaa tgttccacgt gaagctatct tccagcaaag tctccacttc      720
ttcatcaaat tgtggagaat actcccaatg ctcttatcta tgggacttcc gggaaacaca      780
gtaccgatac ttcccaattc gtcttcagag ctcattgttt gtttgaagag actaatcaaa      840
gaatcgtttt ctcaaaaaaa ttaatatctt aactgatagt ttgatcaaag gggcaaaacg      900 tagggcaaa caaacggaaa aatcgtttct caaattttct gatgccaaga actctaacca      960
gtcttatcta aaaattgcct tatgatccgt ctctccggtt acagcctgtg taactgatta     1020
atcctgcctt tctaatcacc attctaatgt tttaattaag ggattttgtc ttcattaacg     1080
gctttcgctc ataaaaatgt tatgacgttt tgcccgcagg cgggaaacca tccacttcac     1140
gagactgatc tcctctgccg gaacaccggg catctccaac ttataagttg gagaaataag     1200
agaatttcag attgagagaa tgaaaaaaaa aaaccctgaa aaaaaaggtt gaaaccagtt     1260
ccctgaaatt attcccctac ttgactaata agtatataaa gacggtaggt attgattgta     1320
attctgtaaa tctatttctt aaacttctta aattctactt ttatagttag tcttttttt     1380 agttttaaaa caccaagaac ttagtttcga ataaacacac ataaacaaac accatgagat     1440
ttccttcaat ttttactgca gttttattcg cagcatcctc cgcattagct gctccagtca     1500
acactacaac agaagatgaa acggcacaaa ttccggctga agctgtcatc ggttactcag     1560
atttagaagg ggatttcgat gttgctgttt tgccattttc caacagcaca aataacgggt     1620
tattgtttat aaatactact attgccagca ttgctgctaa agaagaaggg gtatctctag     1680
ataaaaggca tacccgcgtg tcaggagggg cagcagcctc cgataccagg ggccttgtgt     1740
ccctctttag ccccgggtcg gctcagaaaa tccagctcgt aaacaccaac ggcagttggc     1800
acatcaacag gactgccctg aactgcaacg actccctcca aacagggttc tttgccgcac     1860
tattctacaa acacaaattc aactcgtctg gatgcccaga gcgcttggcc agctgtcgct     1920
ccatcgacaa gttcgctcag gggtggggtc cctcactta cactgagcct aacagctcgg     1980
accagaggcc ctactgctgg cactacgcgc ctcgaccgtg tggtattgta cccgcgtctc     2040
aggtgtgcgg tccagtgtat tgcttcaccc cgagccctgt tgtggtgggg acgaccgatc     2100
ggtttggtgt ccccacgtat aactgggggg cgaacgactc ggatgtgctg attctcaaca     2160
acacgcggcc gccgcgaggc aactggttcg gctgtacatg gatgaatggc actgggttca     2220
ccaagacgtg tggggccccc cgtgcaaca tcggggggc cggcaacaac accttgacct     2280
gccccactga ctgttttcgg aagcaccccg aggccactta cgccagatgc ggttctgggc     2340
cctggctgac acctaggtgt atggttcatt acccatatag gctctggcac taccctgca      2400 ctgtcaactt caccatcttc aaggttagga tgtacgtggg gggcgtggag cacaggttcg     2460
aagccgcatg caattggact cgaggagagc gttgtgactt ggaggacagg gatagatcag     2520
agcttagctc gctgctgctg tctacaacag agtggcaggt gatcgaggc agacaccatc      2580 accaccatca ctaatagtta attaacgatc tcgacttggt tgaacacgtt gccaaggctt     2640
aagtgaattt actttaaagt cttgcattta aataaatttt cttttttatag ctttatgact     2700 tagtttcaat ttatatacta ttttaatgac attttcgatt cattgattga aagctttgtg     2760
```

```
tttttcttg atgcgctatt gcattgttct tgtcttttc gccacatgta atatctgtag    2820
tagatacctg atacattgtg gatgctgagt gaaattttag ttaataatgg aggcgctctt    2880
aataattttg gggatattgg cttttttttt taaagtttac aaatgaattt tttccgccag    2940
gataacgatt ctgaagttac tcttagcgtt cctatcggta cagccatcaa atcatgccta    3000
taaatcatgc ctatatttgc gtgcagtcag tatcatctac atgaaaaaaa ctcccgcaat    3060
ttcttataga atacgttgaa aattaaatgt acgcgccaag ataagataac atatatctag    3120
ctagatgcag taatatacac agattcccgc ggacgtggga aggaaaaaat tagataacaa    3180
aatctgagtg atatggaaat tccgctgtat agctcatatc tttcccttca acaccagaaa    3240
tgtaaaaatc ttgttacgaa ggatcttttt gctaatgttt ctcgctcaat cctcatttct    3300
tccctacgaa gagtcaaatc tacttgtttt ctgccggtat caagatccat atcttctagt    3360
ttcaccatca aagtccaatt tctagtatac agtttatgtc caacgtaac agacaatcaa    3420
aattggaaag gataagtatc cttcaaagaa tgattctgcg ctggctcctg aaccgcctaa    3480
tgggaacaga gaagtccaaa cgatgctat aagaaccaga ataaaacga taaaaccata    3540
ccaggatcca agcttggcac tggccgtcgt tttacaacgt cgtgactggg aaaaccctgg    3600
cgttacccaa cttaatcgcc ttgcagcaca tccccctttc gccagctggc gtaatagcga    3660
agaggcccgc accgatcgcc cttcccaaca gttgcgcagc ctgaatggcg aatgggaaat    3720
tgtaaacgtt aatattttgt taaaattcgc gttaaatttt tgttaaatca gctcattttt    3780
taaccaatag gccgaaatcg gcaaaatccc ttataaatca aaagaataga ccgagatagg    3840
gttgagtgtt gttccagttt ggaacaagag tccactatta agaacgtgg actccaacgt    3900
caaagggcga aaaaccgtct atcagggcga tggcccacta cgtgaaccat cccctaatc    3960
aagttttttg gggtcgaggt gccgtaaagc actaaatcgg aaccctaaag ggagcccccg    4020
atttagagct tgacggggaa agccggcgaa cgtggcgaga aggaaggga agaaagcgaa    4080
aggagcgggc gctagggcgc tggcaagtgt agcggtcacg ctgcgcgtaa ccaccacacc    4140
cgccgcgctt aatgcgccgc tacagggcgc gtcaggtggc acttttcggg gaaatgtgcg    4200
cggaacccct atttgtttat ttttctaaat acattcaaat atgtatccgc tcatgagaca    4260
ataaccctga taaatgcttc aataatattg aaaaggaag agtatgagta ttcaacattt    4320
ccgtgtcgcc cttattccct tttttgcggc attttgcctt cctgttttg ctcacccaga    4380
aacgctggtg aaagtaaaag atgctgaaga tcagttgggt gcacgagtgg gttacatcga    4440
actggatctc aacagcggta agatccttga gagttttcgc cccgaagaac gttttccaat    4500
gatgagcact tttaaagttc tgctatgtgg cgcggtatta tcccgtattg acgccgggca    4560
agagcaactc ggtcgccgca tacactattc tcagaatgac ttggttgagt actcaccagt    4620
cacagaaaag catcttacgg atggcatgac agtaagagaa ttatgcagtg ctgccataac    4680
catgagtgat aacactgcgg ccaacttact tctgacaacg atcggaggac cgaaggagct    4740
aaccgctttt ttgcacaaca tgggggatca tgtaactcgc cttgatcgtt gggaaccgga    4800
gctgaatgaa gccataccaa acgacgagcg tgacaccacg atgcctgtag caatggcaac    4860
aacgttgcgc aaactattaa ctggcgaact acttactcta gcttcccggc aacaattaat    4920
agactggatg gaggcggata agttgcagg accacttctg cgctcggccc ttccggctgg    4980
ctggtttatt gctgataaat ctggagccgg tgagcgtggg tctcgcggta tcattgcagc    5040
actgggccca gatggtaagc cctcccgtat cgtagttatc tacacgacgg ggagtcaggc    5100
aactatggat gaacgaaata gacagatcgc tgagataggt gcctcactga ttaagcattg    5160
```

-continued

| | |
|---|---|
| gtaactgtca gaccaagttt actcatatat actttagatt gatttaaaac ttcattttta | 5220 |
| atttaaaagg atctaggtga agatcctttt tgataatctc atgaccaaaa tcccttaacg | 5280 |
| tgagttttcg ttccactgag cgtcagaccc cgtagaaaag atcaaaggat cttcttgaga | 5340 |
| tccttttttt ctgcgcgtaa tctgctgctt gcaaacaaaa aaaccaccgc taccagcggt | 5400 |
| ggtttgtttg ccggatcaag agctaccaac tcttttccg aaggtaactg gcttcagcag | 5460 |
| agcgcagata ccaaatactg tccttctagt gtagccgtag ttaggccacc acttcaagaa | 5520 |
| ctctgtagca ccgcctacat acctcgctct gctaatcctg ttaccagtgg ctgctgccag | 5580 |
| tggcgataag tcgtgtctta ccgggttgga ctcaagacga tagttaccgg ataaggcgca | 5640 |
| gcggtcgggc tgaacggggg gttcgtgcac acagcccagc ttggagcgaa cgacctacac | 5700 |
| cgaactgaga tacctacagc gtgagcattg agaaagcgcc acgcttcccg aagggagaaa | 5760 |
| ggcggacagg tatccggtaa gcggcagggt cggaacagga gagcgcacga gggagcttcc | 5820 |
| aggggggaaac gcctggtatc tttatagtcc tgtcgggttt cgccacctct gacttgagcg | 5880 |
| tcgatttttg tgatgctcgt caggggggcg gagcctatgg aaaaacgcca gcaacgcggc | 5940 |
| cttttttacgg ttcctggcct tttgctggcc ttttgctcac atgttctttc ctgcgttatc | 6000 |
| ccctgattct gtggataacc gtattaccgc ctttgagtga gctgataccg ctcgccgcag | 6060 |
| ccgaacgacc gagcgcagcg agtcagtgag cgaggaagcg gaag | 6104 |

<210> SEQ ID NO 47
<211> LENGTH: 16301
<212> TYPE: DNA
<213> ORGANISM: vector pYYIGSE2H6

<400> SEQUENCE: 47

| | |
|---|---|
| atcgataagc ttttcaattc aattcatcat ttttttttta ttcttttttt tgatttcggt | 60 |
| ttctttgaaa ttttttttgat tcggtaatct ccgaacagaa ggaagaacga aggaaggagc | 120 |
| acagacttag attggtatat atacgcatat gtagtgttga agaaacatga aattgcccag | 180 |
| tattcttaac ccaactgcac agaacaaaaa cctgcaggaa acgaagataa atcatgtcga | 240 |
| aagctacata taaggaacgt gctgctactc atcctagtcc tgttgctgcc aagctattta | 300 |
| atatcatgca cgaaaagcaa acaaacttgt gtgcttcatt ggatgttcgt accaccaagg | 360 |
| aattactgga gttagttgaa gcattaggtc ccaaaatttg tttactaaaa acacatgtgg | 420 |
| atatcttgac tgatttttcc atggagggca cagttaagcc gctaaaggca ttatccgcca | 480 |
| agtacaattt tttactcttc gaagacagaa aatttgctga cattggtaat acagtcaaat | 540 |
| tgcagtactc tgcgggtgta tacagaatag cagaatgggc agacattacg aatgcacacg | 600 |
| gtgtggtggg cccaggtatt gttagcggtt tgaagcaggc ggcagaagaa gtaacaaagg | 660 |
| aacctagagg ccttttgatg ttagcagaat tgtcatgcaa gggctcccta tctactggag | 720 |
| aatatactaa gggtactgtt gacattgcga agagcgacaa agattttgtt atcggcttta | 780 |
| ttgctcaaag agacatgggt ggaagagatg aaggttacga ttggttgatt atgacacccg | 840 |
| gtgtgggttt agatgacaag ggagacgcat tgggtcaaca gtatagaacc gtggatgatg | 900 |
| tggtctctac aggatctgac attattattg ttggaagagg actatttgca agggaaggg | 960 |
| atgctaaggt agagggtgaa cgttacagaa agcaggctg ggaagcatat ttgagaagat | 1020 |
| gcggccagca aaactaaaaa actgtattat aagtaaatgc atgtatacta aactcacaaa | 1080 |
| ttagagcttc aatttaatta tatcagttat tacccgggaa tctcggtcgt aatgattttt | 1140 |

```
ataatgacga aaaaaaaaaa attggaaaga aaaagcttta atgcggtagt ttatcacagt    1200
taaattgcta acgcagtcag gcaccgtgta tgaaatctaa caatgcgctc atcgtcatcc    1260
tcggcaccgt caccctggat gctgtaggca taggcttggt tatgccggta ctgccgggcc    1320
tcttgcggga tatcgtccat tccgacagca tcgccagtca ctatggcgtg ctgctagcgc    1380
tatatgcgtt gatgcaattt ctatgcgcac ccgttctcgg agcactgtcc gaccgctttg    1440
gccgccgccc agtcctgctc gcttcgctac ttggagccac tatcgactac gcgatcatgg    1500
cgaccacacc cgtcctgtgg atccttcaat atgcgcacat acgctgttat gttcaaggtc    1560
ccttcgttta agaacgaaag cggtcttcct tttgagggat gtttcaagtt gttcaaatct    1620
atcaaatttg caaatcccca gtctgtatct agagcgttga atcggtgatg cgatttgtta    1680
attaaattga tggtgtcacc attaccaggt ctagatatac caatggcaaa ctgagcacaa    1740
caataccagt ccggatcaac tggcaccatc tctcccgtag tctcatctaa ttttcttcc     1800 ggatgaggtt ccagatatac cgcaacacct ttattatggt ttccctgagg gaataataga    1860
atgtcccatt cgaaatcacc aattctaaac ctgggcgaat tgtatttcgg gtttgttaac    1920
tcgttccagt caggaatgtt ccacgtgaag ctatcttcca gcaaagtctc cacttcttca    1980
tcaaattgtg gagaatactc ccaatgctct tatctatggg acttccggga aacacagtac    2040
cgatacttcc caattcgtct tcagagctca ttgtttgttt gaagagacta atcaaagaat    2100
cgttttctca aaaaaattaa tatcttaact gatagtttga tcaaagggggc aaaacgtagg    2160 ggcaaacaaa cggaaaaatc gtttctcaaa ttttctgatg ccaagaactc taaccagtct    2220
tatctaaaaa ttgccttatg atccgtctct ccggttacag cctgtgtaac tgattaatcc    2280
tgcctttcta atcaccattc taatgttta attaagggat tttgtcttca ttaacggctt     2340
tcgctcataa aaatgttatg acgttttgcc cgcaggcggg aaaccatcca cttcacgaga    2400
ctgatctcct ctgccggaac accgggcatc tccaacttat aagttggaga ataagagaa    2460 tttcagattg agagaatgaa aaaaaaac cctgaaaaaa aaggttgaaa ccagttccct      2520
gaaattattc ccctacttga ctaataagta tataaagacg gtaggtattg attgtaattc    2580
tgtaaatcta tttcttaaac ttcttaaatt ctacttttat agttagtctt tttttagt      2640 ttaaaacacc aagaacttag tttcgaataa acacacataa acaaaccaca tgagatttcc    2700 ttcaatttt actgcagttt tattcgcagc atcctccgca ttagctgctc cagtcaacac     2760
tacaacagaa gatgaaacgg cacaaattcc ggctgaagct gtcatcggtt actcagattt    2820 agaagggggat ttcgatgttg ctgttttgcc attttccaac agcacaaata acgggttatt   2880
gtttataaat actactattg ccagcattgc tgctaaagaa gaaggggtat ctctagataa    2940
aaggcatacc cgcgtgtcag gagggcagc agcctccgat accaggggcc ttgtgtccct    3000 cttttagcccc gggtcggctc agaaaatcca gctcgtaaac accaacgca gttggcacat    3060 caacaggact gccctgaact gcaacgactc cctccaaaca gggttctttg ccgcactatt    3120
ctacaaacac aaattcaact cgtctggatg cccagagcgc ttggccagct gtcgctccat    3180
cgacaagttc gctcagggggt gggtcccct cacttacact gagcctaaca gctcggacca   3240
gaggccctac tgctggcact acgcgcctcg accgtgtggt attgtacccg cgtctcaggt    3300
gtgcggtcca gtgtattgct tcaccccgag ccctgttgtg gtgggacga ccgatcggtt    3360 tggtgtcccc acgtataact ggggggcgaa cgactcggat gtgctgattc tcaacaacac    3420
gcggccgccg cgaggcaact ggttcggctg tacatggatg aatggcactg ggttcaccaa    3480
gacgtgtggg ggccccccgt gcaacatcgg gggggccggc aacaacacct tgacctgccc    3540
```

-continued

```
cactgactgt tttcggaagc accccgaggc cacttacgcc agatgcggtt ctgggccctg    3600
gctgacacct aggtgtatgg ttcattaccc ataggctc tggcactacc cctgcactgt      3660
caacttcacc atcttcaagg ttaggatgta cgtgggggc gtggagcaca ggttcgaagc     3720
cgcatgcaat tggactcgag gagagcgttg tgacttggag gacagggata gatcagagct   3780
tagctcgctg ctgctgtcta caacagagtg gcaggtgatc gagggcagac accatcacca   3840
ccatcactaa tagttaatta cgatctcga cttggttgaa cacgttgcca aggcttaagt    3900
gaatttactt taaagtcttg catttaaata aattttcttt ttatagcttt atgacttagt    3960
ttcaatttat atactatttt aatgacattt tcgattcatt gattgaaagc tttgtgtttt    4020
ttcttgatgc gctattgcat tgttcttgtc tttttcgcca catgtaatat ctgtagtaga    4080
tacctgatac attgtggatg ctgagtgaaa ttttagttaa taatgaggc gctcttaata     4140
attttgggga tattggcttt ttttttttaaa gtttacaaat gaattttttc cgccaggata    4200
acgattctga agttactctt agcgttccta tcggtacagc catcaaatca tgcctataaa    4260
tcatgcctat atttgcgtgc agtcagtatc atctacatga aaaaaactcc cgcaatttct    4320
tatagaatac gttgaaaatt aaatgtacgc gccaagataa gataacatat atctagctag    4380
atgcagtaat atacacagat tcccgcggac gtgggaagga aaaattaga taacaaaatc     4440
tgagtgatat ggaaattccg ctgtatagct catatcttc ccttcaacac cagaaatgta     4500
aaaatcttgt tacgaaggat ctttttgcta atgtttctcg ctcaatcctc atttcttccc    4560
tacgaagagt caaatctact tgtttttctgc cggtatcaag atccatatct tctagtttca    4620
ccatcaaagt ccaattccta gtatacagtt tatgtcccaa cgtaacagac aatcaaaatt    4680
ggaaaggata agtatccttc aaagaatgat tctgcgctgg ctcctgaacc gcctaatggg   4740
aacagagaag tccaaaacga tgctataaga accagaaata aaacgataaa accataccag    4800
gatcctctac gccggacgca tcgtggccgg catcaccggc gccacaggtg cggttgctgg   4860
cccctatatc gccgacatca ccgatgggga agatcgggct cgccacttcg ggctcatgag   4920
cgcttgttc ggcgtgggta tggtggcagg ccccgtggcc gggggactgt tgggcgccat    4980
ctccttgcat gcaccattcc ttgcggcggc ggtgctcaac ggcctcaacc tactactggg   5040
ctgcttccta atgcaggagt cgcataaggg agagcgtcga ccgatgccct tgagagcctt   5100
caacccagtc agctccttcc ggtgggcgcg gggcatgact atcgtcgccg cacttatgac   5160
tgtcttcttt atcatgcaac tcgtaggaca ggtgccggca gcgctctggg tcattttcgg   5220
cgaggaccgc tttcgctgga gcgcgacgat gatcggcctg tcgcttgcgg tattcggaat   5280
cttgcacgcc ctcgctcaag ccttcgtcac tggtcccgcc accaaacgtt tcggcgagaa   5340
gcaggccatt atcgccggca tggcggccga cgcgctgggc tacgtcttgc tggcgttcgc   5400
gacgcgaggc tggatggcct tccccattat gattcttctc gcttccggcg gcatcgggat   5460
gcccgcgttg caggccatgc tgtccaggca ggtagatgac gaccatcagg gacagcttca   5520
aggatcgctc gcggctctta ccagcctaac ttcgatcact ggaccgctga tcgtcacggc   5580
gatttatgcc gcctcggcga gcacatggaa cgggttggca tggattgtag gcgccgccct   5640
ataccttgtc tgcctccccg cgttgcgtcg cggtgcatgg agccgggcca cctcgacctg   5700
aatggaagcc ggcggcacct cgctaacgga ttcaccactc caagaattgg agccaatcaa   5760
ttcttgcgga gaactgtgaa tgcgcaaacc aaccccttggc agaacatatc catcgcgtcc   5820
gccatctcca gcagccgcac gcggcgcatc tcgggcagcg ttgggtcctg gccacgggtg   5880
```

```
cgcatgatcg tgctcctgtc gttgaggacc cggctaggct ggcggggttg ccttactggt    5940
tagcagaatg aatcaccgat acgcgagcga acgtgaagcg actgctgctg caaaacgtct    6000
gcgacctgag caacaacatg aatggtcttc ggtttccgtg tttcgtaaag tctggaaacg    6060
cggaagtcag cgccctgcac cattatgttc cggatctgca tcgcaggatg ctgctggcta    6120
ccctgtggaa cacctacatc tgtattaacg aagcgctggc attgaccctg agtgattttt    6180
ctctggtccc gccgcatcca taccgccagt tgtttaccct cacaacgttc cagtaaccgg    6240
gcatgttcat catcagtaac ccgtatcgtg agcatcctct ctcgtttcat cggtatcatt    6300 accccatga acagaaattc ccccttacac ggaggcatca agtgaccaaa caggaaaaaa    6360
ccgcccttaa catggcccgc tttatcagaa gccagacatt aacgcttctg gagaaactca    6420
acgagctgga cgcggatgaa caggcagaca tctgtgaatc gcttcacgac cacgctgatg    6480
agctttaccg cagctgcctc gcgcgtttcg gtgatgacgg tgaaaacctc tgacacatgc    6540
agctcccgga cacggtcaca gcttgtctgt aagcggtgcc gggagcagac aagcccgtca    6600
gggcgcgtca gcgggtgttg gcgggtgtcg gggcgcagcc atgacccagt cacgtagcga    6660
tagcggagtg tatactggct taactatgcg gcatcagagc agattgtact gagagtgcac    6720
catatgcggt gtgaaatacc gcacagatgc gtaaggagaa ataccgcat caggcgctct    6780 tccgcttcct cgctcactga ctcgctgcgc tcggtcgttc ggctgcggcg agcggtatca    6840
gctcactcaa aggcggtaat acggttatcc acagaatcag gggataacgc aggaaagaac    6900
atgtgagcaa aaggccagca aaaggccagg aaccgtaaaa aggccgcgtt gctggcgttt    6960
ttccataggc tccgcccccc tgacgagcat cacaaaaatc gacgctcaag tcagaggtgg    7020
cgaaacccga caggactata aagataccag gcgtttcccc ctggaagctc cctcgtgcgc    7080
tctcctgttc cgaccctgcc gcttaccgga tacctgtccg cctttctccc ttcgggaagc    7140
gtggcgcttt ctcatagctc acgctgtagg tatctcagtt cggtgtaggt cgttcgctcc    7200
aagctgggct gtgtgcacga accccccgtt cagcccgacc gctgcgcctt atccggtaac    7260
tatcgtcttg agtccaaccc ggtaagacac gacttatcgc cactggcagc agccactggt    7320
aacaggatta gcagagcgag gtatgtaggc ggtgctacag agttcttgaa gtggtggcct    7380
aactacggct acactagaag gacagtattt ggtatctgcg ctctgctgaa gccagttacc    7440
ttcggaaaaa gagttggtag ctcttgatcc ggcaaacaaa ccaccgctgg tagcggtggt    7500
ttttttgttt gcaagcagca gattacgcgc agaaaaaaag gatctcaaga agatcctttg    7560
atcttttcta cggggtctga cgctcagtgg aacgaaaact cacgttaagg gattttggtc    7620
atgagattat caaaaaggat cttcacctag atccttttaa attaaaaatg aagttttaaa    7680
tcaatctaaa gtatatatga gtaaacttgg tctgacagtt accaatgctt aatcagtgag    7740
gcacctatct cagcgatctg tctatttcgt tcatccatag ttgcctgact ccccgtcgtg    7800
tagataacta cgatacggga gggcttacca tctggcccca gtgctgcaat gataccgcga    7860
gacccacgct caccggctcc agatttatca gcaataaacc agccagccgg aagggccgag    7920
cgcagaagtg gtcctgcaac tttatccgcc tccatccagt ctattaattg ttgccgggaa    7980
gctagagtaa gtagttcgcc agttaatagt ttgcgcaacg ttgttgccat tgctgcaggc    8040
atcgtggtgt cacgctcgtc gtttggtatg gcttcattca gctccggttc ccaacgatca    8100
aggcgagtta catgatcccc catgttgtgc aaaaaagcgg ttagctcctt cggtcctccg    8160
atcgttgtca gaagtaagtt ggccgcagtg ttatcactca tggttatggc agcactgcat    8220
aattctctta ctgtcatgcc atccgtaaga tgcttttctg tgactggtga gtactcaacc    8280
```

-continued

| | |
|---|---|
| aagtcattct gagaatagtg tatgcggcga ccgagttgct cttgcccggc gtcaacacgg | 8340 |
| gataataccg cgccacatag cagaacttta aaagtgctca tcattggaaa acgttcttcg | 8400 |
| gggcgaaaac tctcaaggat cttaccgctg ttgagatcca gttcgatgta acccactcgt | 8460 |
| gcacccaact gatcttcagc atcttttact ttcaccagcg tttctgggtg agcaaaaaca | 8520 |
| ggaaggcaaa atgccgcaaa aaagggaata agggcgacac ggaaatgttg aatactcata | 8580 |
| ctcttccttt ttcaatatta ttgaagcatt tatcagggtt attgtctcat gagcggatac | 8640 |
| atatttgaat gtatttagaa aaataaacaa ataggggttc cgcgcacatt tccccgaaaa | 8700 |
| gtgccacctg acgtctaaga aaccattatt atcatgacat aacctataa aaaataggcg | 8760 |
| tatcacgagg ccctttcgtc ttcaagaatt ctcatgtttg acagcttatc atcgatccac | 8820 |
| ttgtatattt ggatgaattt tgaggaatt ctgaaccagt cctaaaacga gtaaatagga | 8880 |
| ccggcaattc ttcaagcaat aaacaggaat accaattatt aaaagataac ttagtcagat | 8940 |
| cgtacaataa agctttgaag aaaaatgcgc cttattcaat ctttgcataa aaaaatggcc | 9000 |
| caaaatctca cattggaaga catttgatga cctcatttct ttcaatgaag ggcctaacgg | 9060 |
| agttgactaa tgttgtggga aattggaccg ataagcgtgc ttctgccgtg gccaggacaa | 9120 |
| cgtatactca tcagataaca gcaatacctg atcactactt cgcactagtt tctcggtact | 9180 |
| atgcatatga tccaatatca aaggaaatga tagcattgaa ggatgagact aatccaattg | 9240 |
| aggagtggca gcatatagaa cagctaaagg gtagtgctga aggaagcata cgatacccccg | 9300 |
| catggaatgg gataatatca caggaggtac tagactacct ttcatcctac ataaatagac | 9360 |
| gcatataagt acgcatttaa gcataaacac gcactatgcc gttcttctca tgtatatata | 9420 |
| tatacaggca acacgcagat ataggtgcga cgtgaacagt gagctgtatg tgcgcagctc | 9480 |
| gcgttgcatt ttcggaagcg ctcgtttttcg gaaacgcttt gaagttccta ttccgaagtt | 9540 |
| cctattctct agaaagtata ggaacttcag agcgcttttg aaaaccaaaa gcgctctgaa | 9600 |
| gacgcacttt caaaaaacca aaaacgcacc ggactgtaac gagctactaa atattgcga | 9660 |
| ataccgcttc cacaaacatt gctcaaaagt atctctttgc tatatatctc tgtgctatat | 9720 |
| ccctatataa ccatcccatc cacctttcgc tccttgaact tgcatctaaa ctcgacctct | 9780 |
| acattttta tgtttatctc tagtattacc tcttagacaa aaaaattgta gtaagaacta | 9840 |
| ttcatagagt taatcgaaaa caatacgaaa atgtaaacat ttcctatacg tagtatatag | 9900 |
| agacaaaata gaagaaaccg ttcataattt tctgaccaat gaagaatcat caacgctatc | 9960 |
| actttctgtt cacaaagtat gcgcaatcca catcggtata gaatataatc ggggatgcct | 10020 |
| ttatcttgaa aaaatgcacc cgcagcttcg ctagtaatca gtaaacgcgg gaagtggagt | 10080 |
| caggcttttt ttatggaaga gaaatagac accaaagtag ccttcttcta accttaacgg | 10140 |
| acctacagtg caaaaagtta tcaagagact gcattataga gcgcacaaag gagaaaaaaa | 10200 |
| gtaatctaag atgctttgtt agaaaaatag cgctctcggg atgcatttt gtagaacaaa | 10260 |
| aaagaagtat agattcttgt tggtaaaata gcgctctcgc gttgcatttc tgttctgtaa | 10320 |
| aaatgcagct cagattcttt gtttgaaaaa ttagcgctct cgcgttgcat tttgttttta | 10380 |
| caaaaatgaa gcacagattc ttcgttggta aatagcgct ttcgcgttgc atttctgttc | 10440 |
| tgtaaaaatg cagctcagat tctttgtttg aaaaattagc gctctcgcgt tgcattttg | 10500 |
| ttctacaaaa tgaagcacag atgcttcgtt aacaaagata tgctattgaa gtgcaagatg | 10560 |
| gaaacgcaga aaatgaaccg gggatgcgac gtgcaagatt acctatgcaa tagatgcaat | 10620 |

```
agtttctcca ggaaccgaaa tacatacatt gtcttccgta aagcgctaga ctatatatta    10680
ttatacaggt tcaaatatac tatctgtttc agggaaaact cccaggttcg gatgttcaaa    10740
attcaatgat gggtaacaag tacgatcgta aatctgtaaa acagtttgtc ggatattagg    10800
ctgtatctcc tcaaagcgta ttcgaatatc attgagaagc tgcatttttt ttttttttt    10860 tttttttttt ttttttatat atatttcaag gatataccat tgtaatgtct gccctaaga    10920 agatcgtcgt tttgccaggt gaccacgttg gtcaagaaat cacagccgaa gccattaagg    10980
ttcttaaagc tatttctgat gttcgttcca atgtcaagtt cgatttcgaa aatcatttaa    11040
ttggtggtgc tgctatcgat gctacaggtg tcccacttcc agatgaggcg ctggaagcct    11100
ccaagaaggt tgatgccgtt ttgttaggtg ctgtgggtgg tcctaaatgg ggtaccggta    11160
gtgttagacc tgaacaaggt ttactaaaaa tccgtaaaga acttcaattg tacgccaact    11220
taagaccatg taactttgca tccgactctc ttttagactt atctccaatc aagccacaat    11280
ttgctaaagg tactgacttc gttgttgtca gagaattagt gggaggtatt tactttggta    11340
agagaaagga agacgatggt gatggtgtcg cttgggatag tgaacaatac accgttccag    11400
aagtgcaaag aatcacaaga atggccgctt tcatggccct acaacatgag ccaccattgc    11460
ctatttggtc cttggataaa gctaatgttt tggcctcttc aagattatgg agaaaaactg    11520
tggaggaaac catcaagaac gaattcccta cattgaaggt tcaacatcaa ttgattgatt    11580
ctgccgccat gatcctagtt aagaacccaa cccacctaaa tggtattata atcaccagca    11640
acatgtttgg tgatatcatc tccgatgaag cctccgttat cccaggttcc ttgggtttgt    11700
tgccatctgc gtccttggcc tctttgccag acaagaacac cgcatttggt ttgtacgaac    11760
catgccacgg ttctgctcca gatttgccaa agaataaggt tgaccctatc gccactatct    11820
tgtctgctgc aatgatgttg aaattgtcat tgaacttgcc tgaagaaggt aaggccattg    11880
aagatgcagt taaaaaggtt ttggatgcag gtatcagaac tggtgattta ggtggttcca    11940
acagtaccac cgaagtcggt gatgctgtcg ccgaagaagt taagaaaatc cttgcttaaa    12000
aagattctct tttttttatga tatttgtaca aaaaaaaaaa aaaaaaaaaa aaaaaaaaa    12060 aaaaaaaaaa aaaaatgcag cgtcacatcg gataataatg atggcagcca ttgtagaagt    12120 gcctttttgca tttctagtct ctttctcggt ctagctagtt ttactacatc gcgaagatag    12180
aatcttagat cacactgcct ttgctgagct ggatcatatg agtaacaaaa gagtggtaag    12240
gcctcgttaa aggacaagga cctgagcgga agtgtatcgt aaagtagacg gagtatacta    12300
gtatagtcta tagtccgtgg aattctaagt gccagcttta taatgtcatt ctccttacta    12360
cagacccgcc tgaaagtaga cacatcatca tcagtaagct ttgacaaaaa gcattgagta    12420
gctaactctt ctatgcaatc tatagctgtt ttataaggca ttcaatggac agattgaggt    12480
ttttgaaaca tactagtgaa attagcctta atcccttctc gaagttaatc atgcattatg    12540
gtgtaaaaaa tgcaactcgc gttgctctac ttttcccga atttcaaat acgcagctgg    12600 ggtgattgct cgatttcgta acgaaagttt tgtttataaa aaccgcgaaa accttctgta    12660
acagatagat tttacagcg ctgatataca atgacatcag ctgtaatgga aaataactga    12720
aatatgaatg gcgagagact gcttgcttgt attaagcaat gtattatgca gcacttccaa    12780
cctatggtgt acgatgaaag taggtgtgta atcgagacga caaggggac ttttccagtt    12840 cctgatcatt ataagaaata caaaacgtta gcatttgcat ttgttggaca tgtactgaat    12900
acagacgaca caccggtaat tgaaaaagaa ctggattggc ctgatcctgc actagtgtac    12960
aatacaattg tcgatcgaat cataaatcac ccagaattat cacagtttat atcggttgca    13020
```

```
tttattagtc agttaaaggc caccatcgga gagggtttag atattaatgt aaaaggcacg    13080
ctaaaccgca ggggaaaggg tatcagaagg cctaaaggcg tattttttag atacatggaa    13140
tctccatttg tcaatacaaa ggtcactgca ttcttctctt atcttcgaga ttataataaa    13200
attgcctcag aatatcacaa taatactaaa ttcattctca cgttttcatg tcaagcatat    13260
tgggcatctg gcccaaactt ctccgccttg aagaatgtta tttggtgctc cataattcat    13320
gaatacattt ctaagtttgt ggaaagagaa caggataaag gtcatatagg agatcaggag    13380
ctaccgcctg aagaggaccc ttctcgtgaa ctaaacaatg tacaacatga agtcaatagt    13440
ttaacggaac aagatgcgga ggcggatgaa ggattgtggg gtgaaataga ttcattatgt    13500
gaaaaatggc agtctgaagc ggagagtcaa actgaggcgg agataatagc cgacaggata    13560
attggaaata gccagaggat ggcgaacctc aaaattcgtc gtacaaagtt caaaagtgtc    13620
ttgtatcata tactaaagga actaattcaa tctcagggaa ccgtaaaggt ttatcgcggt    13680
agtagttttt cacacgattc gataaagata agcttacatt atgaagagca gcatattaca    13740
gccgtatggg tctacttgat agtaaaattt gaagagcatt ggaagcctgt tgatgtagag    13800
gtcgagttta gatgcaagtt caaggagcga aaggtggatg ggtaggttat atagggatat    13860
agcacagaga tatatagcaa agagatactt ttgaggcaat gtttgtggaa gcggtattcg    13920
caatatttta gtagctcgtt acagtccggt gcgttttttgg ttttttgaaa gtgcgtcttc    13980
agagcgcttt tggttttcaa aagcgctctg aagttcctat actttctaga gaataggaac    14040
ttcggaatag gaacttcaaa gcgtttccga aaacgagcgc ttccgaaaat gcaacgcgag    14100
ctgcgcacat acagctcact gttcacgtcg cacctatatc tgcgtgttgc ctgtatatat    14160
atatacatga gaagaacggc atagtgcgtg tttatgctta aatgcgtact tatatgcgtc    14220
tatttatgta ggatgaaagg tagtctagta cctcctgtga tattatccca ttccatgcgg    14280
ggtatcgtat gcttccttca gcactaccct ttagctgttc tatatgctgc cactcctcaa    14340
ttggattagt ctcatccttc aatgcattca tttcctttga tattggatca taccctagaa    14400
gtattacgtg attttctgcc ccttaccctc gttgctactc tccttttttt cgtgggaacc    14460
gctttagggc cctcagtgat ggtgttttgt aatttatatg ctcctcttgc atttgtgtct    14520
ctacttcttg ttcgcctgga gggaacttct tcatttgtat tagcatggtt cacttcagtc    14580
cttccttcca actcactctt tttttgctgt aaacgattct ctgccgccag ttcattgaaa    14640
ctattgaata tatcctttag agattccggg atgaataaat cacctattaa agcagcttga    14700
cgatctggtg gaactaaagt aagcaattgg gtaacgacgc ttacgagctt cataacatct    14760
tcttccgttg gagctggtgg gactaataac tgtgtacaat ccattttttct catgagcatt    14820 tcggtagctc tcttcttgtc tttctcgggc aatcttccta ttattatagc aatagatttg    14880
tatagttgct ttctattgtc taacagcttg ttattctgta gcatcaaatc tatggcagcc    14940
tgacttgctt cttgtgaaga gagcatacca tttccaatcg aagatacgct ggaatcttct    15000
gcgctagaat caagaccata cggcctaccg gttgtgagag attccatggg ccttatgaca    15060
tatcctggaa agagtagctc atcagactta cgtttactct ctatatcaat atctacatca    15120
ggagcaatca tttcaataaa cagccgacat acatcccaga cgctataagc tgtacgtgct    15180
tttaccgtca gattcttggc tgtttcaatg tcgtccattt tggttttctt ttaccagtat    15240
tgttcgtttg ataatgtatt cttgcttatt acattataaa atctgtgcag atcacatgtc    15300
aaaacaactt tttatcacaa gatagtaccg caaaacgaac ctgcgggccg tctaaaaatt    15360
```

-continued

```
aaggaaaagc agcaaaggtg cattttaaa atatgaaatg aagataccgc agtaccaatt      15420 atttcgcag tacaaataat gcgcggccgg tgcattttc gaaagaacgc gagacaaaca       15480
ggacaattaa agttagtttt tcgagttagc gtgtttgaat actgcaagat acaagataaa     15540
tagagtagtt gaaactagat atcaattgca cacaagatcg cgctaagca tgccacaatt      15600 tggtatatta tgtaaaacac cacctaaggt gcttgttcgt cagtttgtgg aaaggtttga     15660
aagaccttca ggtgagaaaa tagcattatg tgctgctgaa ctaacctatt tatgttggat    15720
gattacacat aacggaacag caatcaagag agccacattc atgagctata atactatcat     15780
aagcaattcg ctgagtttcg atattgtcaa taaatcactc cagtttaaat acaagacgca     15840
aaaagcaaca attctggaag cctcattaaa gaaattgatt cctgcttggg aatttacaat     15900
tattccttac tatggacaaa aacatcaatc tgatatcact gatattgtaa gtagtttgca     15960
attacagttc gaatcatcgg aagaagcaga taagggaaat agccacagta aaaaaatgct     16020
aaagcacttc taagtgaggg tgaaagcatc tgggagatca ctgagaaaat actaaattcg     16080
tttgagtata cttcgagatt tacaaaaaca aaaactttat accaattcct cttcctagct     16140
actttcatca attgtggaag attcagcgat attaagaacg ttgatccgaa atcatttaaa    16200
ttagtccaaa ataagtatct gggagtaata atccagtgtt tagtgacaga gacaaagaca     16260
agcgttagta ggcacatata cttctttagc gcaaggggta g                         16301
```

<210> SEQ ID NO 48
<211> LENGTH: 4989
<212> TYPE: DNA
<213> ORGANISM: vector pYIG7

<400> SEQUENCE: 48

```
agcgcccaat acgcaaaccg cctctccccg cgcgttggcc gattcattaa tgcagctggc       60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gaatttaata     240
cgactcacta tagggaattc ggatccttca atatgcgcac atacgctgtt atgttcaagg     300
tcccttcgtt taagaacgaa agcggtcttc cttttgaggg atgtttcaag ttgttcaaat     360
ctatcaaatt tgcaaatccc cagtctgtat ctagagcgtt gaatcggtga tgcgatttgt     420
taattaaatt gatggtgtca ccattaccag gtctagatat accaatggca aactgagcac     480
aacaatacca gtccggatca actggcacca tctctcccgt agtctcatct aatttttctt     540
ccggatgagg ttccagatat accgcaacac ctttattatg gtttccctga gggaataata     600
gaatgtccca ttcgaaatca ccaattctaa acctgggcga attgtatttc gggtttgtta     660
actcgttcca gtcaggaatg ttccacgtga agctatcttc cagcaaagtc tccacttctt     720
catcaaattg tggagaatac tcccaatgct cttatctatg ggacttccgg gaaacacagt     780
accgatactt cccaattcgt cttcagagct cattgtttgt ttgaagagac taatcaaaga     840 atcgtttttct caaaaaaatt aatatcttaa ctgatagttt gatcaagggg caaaacgta    900 ggggcaaaca aacggaaaaa tcgtttctca aattttctga tgccaagaac tctaaccagt    960
cttatctaaa aattgcctta tgatccgtct ctccggttac agcctgtgta actgattaat    1020
cctgcctttc taatcaccat tctaatgttt taattaaggg attttgtctt cattaacggc   1080
tttcgctcat aaaaatgtta tgacgttttg cccgcaggcg ggaaaccatc cacttcacga   1140
gactgatctc ctctgccgga acaccgggca tctccaactt ataagttgga gaaataagag   1200
```

-continued

```
aatttcagat tgagagaatg aaaaaaaaaa accctgaaaa aaaaggttga aaccagttcc    1260
ctgaaattat tccectactt gactaataag tatataaaga cggtaggtat tgattgtaat    1320
tctgtaaatc tatttcttaa acttcttaaa ttctactttt atagttagtc ttttttttag    1380
ttttaaaaca ccaagaactt agtttcgaat aaacacacat aaacaaacac catgaggtct    1440
ttgctaatac tagtgctttg cttcctgccc ctggctgctc tggggtacc  agatctcgac    1500 ttggttgaac acgttgccaa ggcttaagtg aatttacttt aaagtcttgc atttaaataa    1560
attttctttt tatagcttta tgacttagtt tcaatttata tactatttta atgacatttt    1620
cgattcattg attgaaagct ttgtgttttt tcttgatgcg ctattgcatt gttcttgtct    1680
ttttcgccac atgtaatatc tgtagtagat acctgataca ttgtggatgc tgagtgaaat    1740
tttagttaat aatggaggcg ctcttaataa ttttggggat attggctttt ttttttaaag    1800
tttacaaatg aattttttcc gccaggataa cgattctgaa gttactctta gcgttcctat    1860
cggtacagcc atcaaatcat gcctataaat catgcctata tttgcgtgca gtcagtatca    1920
tctacatgaa aaaactccc  gcaatttctt atagaatacg ttgaaaatta aatgtacgcg    1980
ccaagataag ataacatata tctagctaga tgcagtaata tacacagatt cccgcggacg    2040
tgggaaggaa aaattagat  aacaaaatct gagtgtatg  gaattccgc  tgtatagctc    2100 atatctttcc cttcaacacc agaaatgtaa aaatcttgtt acgaaggatc tttttgctaa    2160
tgtttctcgc tcaatcctca tttcttccct acgaagagtc aaatctactt gttttctgcc    2220
ggtatcaaga tccatatctt ctagtttcac catcaaagtc caatttctag tatacagttt    2280
atgtcccaac gtaacagaca atcaaaattg gaaggataa  gtatccttca aagaatgatt    2340
ctgcgctggc tcctgaaccg cctaatggga acagagaagt ccaaaacgat gctataagaa    2400
ccagaaataa aacgataaaa ccataccagg atccaagctt ggcactggcc gtcgttttac    2460
aacgtcgtga ctgggaaaac cctggcgtta cccaacttaa tcgccttgca gcacatcccc    2520
ctttcgccag ctggcgtaat agcgaagagg cccgcaccga tcgcccttcc caacagttgc    2580
gcagcctgaa tggcgaatgg gaaattgtaa acgttaatat tttgttaaaa ttcgcgttaa    2640 attttttgtta aatcagctca ttttttaacc aataggccga atcggcaaa  atccettata    2700 aatcaaaaga atagaccgag ataggggttga gtgttgttcc agtttggaac aagagtccac    2760
tattaaagaa cgtggactcc aacgtcaaag ggcgaaaaac cgtctatcag ggcgatggcc    2820
cactacgtga accatcaccc taatcaagtt ttttggggtc gaggtgccgt aaagcactaa    2880
atcggaaccc taagggagc  ccccgattta gagcttgacg gggaaagccg gcgaacgtgg    2940
cgagaaagga agggaagaaa gcgaaaggag cgggcgctag gcgctggca  agtgtagcgg    3000 tcacgctgcg cgtaaccacc acacccgccg cgcttaatgc gccgctacag ggcgcgtcag    3060
gtggcacttt tcggggaaat gtgcgcggaa cccctatttg tttatttttc taaatacatt    3120
caaatatgta tccgctcatg agacaataac cctgataaat gcttcaataa tattgaaaaa    3180
ggaagagtat gagtattcaa catttccgtg tcgcccttat tcccttttt  gcggcatttt    3240 gccttcctgt ttttgctcac ccagaaacgc tggtgaaagt aaaagatgct gaagatcagt    3300
tgggtgcacg agtgggttac atcgaactgg atctcaacag cggtaagatc cttgagagtt    3360
ttcgccccga agaacgtttt ccaatgatga gcacttttaa agttctgcta tgtggcgcgg    3420
tattatcccg tattgacgcc gggcaagagc aactcggtcg ccgcatacac tattctcaga    3480
atgacttggt tgagtactca ccagtcacag aaaagcatct tacggatggc atgacagtaa    3540
```

```
gagaattatg cagtgctgcc ataaccatga gtgataacac tgcggccaac ttacttctga    3600
caacgatcgg aggaccgaag gagctaaccg ctttttttgca caacatgggg gatcatgtaa   3660
ctcgccttga tcgttgggaa ccggagctga atgaagccat accaaacgac gagcgtgaca    3720
ccacgatgcc tgtagcaatg gcaacaacgt tgcgcaaact attaactggc gaactactta    3780
ctctagcttc ccggcaacaa ttaatagact ggatggaggc ggataaagtt gcaggaccac    3840
ttctgcgctc ggcccttccg gctggctggt ttattgctga taaatctgga gccggtgagc    3900
gtgggtctcg cggtatcatt gcagcactgg ggccagatgg taagccctcc cgtatcgtag    3960
ttatctacac gacggggagt caggcaacta tggatgaacg aaatagacag atcgctgaga    4020
taggtgcctc actgattaag cattggtaac tgtcagacca agtttactca tatatacttt    4080
agattgattt aaaacttcat ttttaattta aaaggatcta ggtgaagatc ctttttgata    4140
atctcatgac caaaatccct taacgtgagt tttcgttcca ctgagcgtca gaccccgtag    4200
aaaagatcaa aggatcttct tgagatcctt ttttttctgcg cgtaatctgc tgcttgcaaa    4260
caaaaaaacc accgctacca gcggtggttt gtttgccgga tcaagagcta ccaactcttt    4320
ttccgaaggt aactggcttc agcagagcgc agataccaaa tactgtcctt ctagtgtagc    4380
cgtagttagg ccaccacttc aagaactctg tagcaccgcc tacatacctc gctctgctaa    4440
tcctgttacc agtggctgct gccagtggcg ataagtcgtg tcttaccggg ttggactcaa    4500
gacgatagtt accggataag gcgcagcggt cgggctgaac ggggggttcg tgcacacagc    4560
ccagcttgga gcgaacgacc tacaccgaac tgagatacct acagcgtgag cattgagaaa    4620
gcgccacgct tcccgaaggg agaaaggcgg acaggtatcc ggtaagcggc agggtcggaa    4680
caggagagcg cacgagggag cttccagggg gaaacgcctg gtatctttat agtcctgtcg    4740
ggtttcgcca cctctgactt gagcgtcgat ttttgtgatg ctcgtcaggg gggcggagcc    4800
tatgaaaaaa cgccagcaac gcggcctttt tacggttcct ggccttttgc tggccttttg    4860
ctcacatgtt ctttcctgcg ttatcccctg attctgtgga taaccgtatt accgcctttg    4920
agtgagctga taccgctcgc cgcagccgaa cgaccgagcg cagcgagtca gtgagcgagg    4980
aagcggaag                                                            4989
```

<210> SEQ ID NO 49
<211> LENGTH: 5422
<212> TYPE: DNA
<213> ORGANISM: vector pYIG7E1

<400> SEQUENCE: 49

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gaatttaata    240
cgactcacta tagggaattc ggatccttca atatgcgcac atacgctgtt atgttcaagg    300
tcccttcgtt taagaacgaa agcggtcttc cttttgaggg atgtttcaag ttgttcaaat    360
ctatcaaatt tgcaaatccc cagtctgtat ctagagcgtt gaatcggtga tgcgatttgt    420
taattaaatt gatggtgtca ccattaccag gtctagatat accaatggca aactgagcac    480
aacaatacca gtccggatca actggcacca tctctcccgt agtctcatct aattttttctt    540 ccggatgagg ttccagatat accgcaacac ctttattatg gtttccctga gggaataata    600
gaatgtccca ttcgaaatca ccaattctaa acctgggcga attgtatttc gggtttgtta    660
```

-continued

```
actcgttcca gtcaggaatg ttccacgtga agctatcttc cagcaaagtc tccacttctt    720
catcaaattg tggagaatac tcccaatgct cttatctatg ggacttccgg gaaacacagt    780
accgatactt cccaattcgt cttcagagct cattgtttgt ttgaagagac taatcaaaga    840
atcgttttct caaaaaaatt aatatcttaa ctgatagttt gatcaaaggg gcaaaacgta    900
ggggcaaaca aacggaaaaa tcgtttctca aattttctga tgccaagaac tctaaccagt    960
cttatctaaa aattgcctta tgatccgtct ctccggttac agcctgtgta actgattaat   1020
cctgcctttc taatcaccat tctaatgttt taattaaggg attttgtctt cattaacggc   1080
tttcgctcat aaaaatgtta tgacgttttg cccgcaggcg ggaaaccatc cacttcacga   1140
gactgatctc ctctgccgga acaccgggca tctccaactt ataagttgga gaataagag    1200
aatttcagat tgagagaatg aaaaaaaaaa accctgaaaa aaaggttga aaccagttcc     1260
ctgaaattat tcccctactt gactaataag tatataaaga cggtaggtat tgattgtaat   1320
tctgtaaatc tatttcttaa acttcttaaa ttctactttt atagttagtc ttttttttag   1380
ttttaaaaca ccaagaactt agtttcgaat aaacacacat aaacaaacac catgaggtct   1440
ttgctaatac tagtgctttg cttcctgccc ctggctgctc tggggtatga ggtgcgcaac   1500
gtgtccggga tgtaccatgt cacgaacgac tgctccaact caagcattgt gtatgaggca   1560
gcggacatga tcatgcacac ccccgggtgc gtgccctgcg ttcgggagaa caactcttcc   1620
cgctgctggg tagcgctcac ccccacgctc gcagctagga acgccagcgt ccccaccacg   1680
acaatacgac gccacgtcga tttgctcgtt ggggcggctg ctttctgttc cgctatgtac   1740
gtgggggacc tctgcggatc tgtcttcctc gtctcccagc tgttcaccat ctcgcctcgc   1800
cggcatgaga cggtgcagga ctgcaattgc tcaatctatc ccggccacat aacgggtcac   1860
cgtatggctt gggatatgat gatgaactgg taatagaccc ttctcacctc ggccgataag   1920
ctcagatctc gacttggttg aacacgttgc caaggcttaa gtgaatttac tttaaagtct   1980
tgcatttaaa taaattttct ttttatagct ttatgactta gtttcaattt atatactatt   2040
ttaatgacat tttcgattca ttgattgaaa gctttgtgtt ttttcttgat gcgctattgc   2100
attgttcttg tctttttcgc cacatgtaat atctgtagta gatacctgat acattgtgga   2160
tgctgagtga aattttagtt aataatggag gcgctcttaa taattttggg gatattggct   2220
tttttttta aagtttacaa atgaattttt tccgccagga taacgattct gaagttactc   2280
ttagcgttcc tatcggtaca gccatcaaat catgcctata atcatgcct atatttgcgt    2340
gcagtcagta tcatctacat gaaaaaaact cccgcaattt cttatagaat acgttgaaaa   2400
ttaaatgtac gcgccaagat aagataacat atatctagct agatgcagta atatacacag   2460
attcccgcgg acgtgggaag gaaaaaatta gataacaaaa tctgagtgat atggaaattc   2520
cgctgtatag ctcatatctt tcccttcaac accagaaatg taaaaatctt gttacgaagg   2580
atctttttgc taatgtttct cgctcaatcc tcatttcttc cctacgaaga gtcaaatcta   2640
cttgttttct gccggtatca agatccatat cttctagttt caccatcaaa gtccaatttc   2700
tagtatacag tttatgtccc aacgtaacag acaatcaaaa ttggaaagga taagtatcct   2760
tcaaagaatg attctgcgct ggctcctgaa ccgcctaatg ggaacagaga agtccaaaac   2820
gatgctataa gaaccagaaa taaaacgata aaccataccc aggatccaag cttggcactg   2880
gccgtcgttt tacaacgtcg tgactgggaa accctggcg ttacccaact taatcgcctt    2940
gcagcacatc cccctttcgc cagctggcgt aatagcgaag aggcccgcac cgatcgccct   3000
```

```
tcccaacagt tgcgcagcct gaatggcgaa tgggaaattg taaacgttaa tattttgtta    3060
aaattcgcgt taaatttttg ttaaatcagc tcatttttta accaataggc cgaaatcggc    3120 aaaatcccctt ataaatcaaa agaatagacc gagatagggt tgagtgttgt tccagtttgg    3180
aacaagagtc cactattaaa gaacgtggac tccaacgtca aagggcgaaa aaccgtctat    3240
cagggcgatg gcccactacg tgaaccatca ccctaatcaa gttttttggg gtcgaggtgc    3300
cgtaaagcac taaatcggaa ccctaaaggg agccccgat ttagagcttg acggggaaag    3360
ccggcgaacg tggcgagaaa ggaagggaag aaagcgaaag gagcgggcgc tagggcgctg    3420
gcaagtgtag cggtcacgct gcgcgtaacc accacacccg ccgcgcttaa tgcgccgcta    3480
cagggcgcgt caggtggcac ttttcgggga atgtgcgcg gaaccccctat ttgtttattt    3540 ttctaaatac attcaaatat gtatccgctc atgagacaat aaccctgata aatgcttcaa    3600
taatattgaa aaggaagag tatgagtatt caacatttcc gtgtcgccct tattcccttt    3660
tttgcggcat tttgccttcc tgttttttgct cacccagaaa cgctggtgaa agtaaaagat    3720
gctgaagatc agttgggtgc acgagtgggt tacatcgaac tggatctcaa cagcggtaag    3780
atccttgaga gttttcgccc cgaagaacgt tttccaatga tgagcacttt taaagttctg    3840
ctatgtggcg cggtattatc ccgtattgac gccgggcaag agcaactcgg tcgccgcata    3900
cactattctc agaatgactt ggttgagtac tcaccagtca cagaaaagca tcttacggat    3960
ggcatgacag taagagaatt atgcagtgct gccataacca tgagtgataa cactgcggcc    4020
aacttacttc tgacaacgat cggaggaccg aaggagctaa ccgcttttttt gcacaacatg    4080 ggggatcatg taactcgcct tgatcgttgg gaaccggagc tgaatgaagc cataccaaac    4140
gacgagcgtg acaccacgat gcctgtagca atggcaacaa cgttgcgcaa actattaact    4200
ggcgaactac ttactctagc ttcccggcaa caattaatag actggatgga ggcggataaa    4260
gttgcaggac cacttctgcg ctcggccctt ccggctggct ggtttattgc tgataaatct    4320
ggagccggtg agcgtgggtc tcgcggtatc attgcagcac tggggccaga tggtaagccc    4380
tcccgtatcg tagttatcta cacgacgggg agtcaggcaa ctatggatga acgaaataga    4440
cagatcgctg agataggtgc ctcactgatt aagcattggt aactgtcaga ccaagtttac    4500
tcatatatac tttagattga tttaaaactt cattttttaat ttaaaaggat ctaggtgaag    4560
atcctttttg ataatctcat gaccaaaatc ccttaacgtg agttttcgtt ccactgagcg    4620
tcagaccccg tagaaaagat caaaggatct tcttgagatc ctttttttct gcgcgtaatc    4680
tgctgcttgc aaacaaaaaa accaccgcta ccagcggtgg tttgtttgcc ggatcaagag    4740
ctaccaactc tttttccgaa ggtaactggc ttcagcagag cgcagatacc aaatactgtc    4800
cttctagtgt agccgtagtt aggccaccac ttcaagaact ctgtagcacc gcctacatac    4860
ctcgctctgc taatcctgtt accagtggct gctgccagtg gcgataagtc gtgtcttacc    4920
gggttggact caagacgata gttaccggat aaggcgcagc ggtcgggctg aacggggggt    4980
tcgtgcacac agcccagctt ggagcgaacg acctacaccg aactgagata cctacagcgt    5040
gagcattgag aaagcgccac gcttcccgaa gggagaaagg cggacaggta tccggtaagc    5100
ggcagggtcg gaacaggaga gcgcacgagg gagcttccag ggggaaacgc ctggtatctt    5160
tatagtcctg tcgggtttcg ccacctctga cttgagcgtc gatttttgtg atgctcgtca    5220
ggggggcgga gcctatggaa aaacgccagc aacgcggcct ttttacggtt cctggccttt    5280
tgctggcctt tgctcacat gttctttcct gcgttatccc ctgattctgt ggataaccgt    5340
attaccgcct ttgagtgagc tgataccgct cgccgcagcc gaacgaccga gcgcagcgag    5400
```

-continued

```
tcagtgagcg aggaagcgga ag                                           5422

<210> SEQ ID NO 50
<211> LENGTH: 15621
<212> TYPE: DNA
<213> ORGANISM: vector pSY1YIG7E1s

<400> SEQUENCE: 50
atcgataagc ttttcaattc aattcatcat ttttttttta ttcttttttt tgatttcggt     60
ttctttgaaa ttttttttgat tcggtaatct ccgaacagaa ggaagaacga aggaaggagc   120
acagacttag attggtatat atacgcatat gtagtgttga agaaacatga aattgcccag   180
tattcttaac ccaactgcac agaacaaaaa cctgcaggaa acgaagataa atcatgtcga   240
aagctacata taaggaacgt gctgctactc atcctagtcc tgttgctgcc aagctattta   300
atatcatgca cgaaaagcaa acaaacttgt gtgcttcatt ggatgttcgt accaccaagg   360
aattactgga gttagttgaa gcattaggtc ccaaaatttg tttactaaaa acacatgtgg   420
atatcttgac tgattttttcc atggagggca cagttaagcc gctaaaggca ttatccgcca   480
agtacaattt tttactcttc aagacagaa aatttgctga cattggtaat acagtcaaat   540
tgcagtactc tgcgggtgta tacagaatag cagaatgggc agacattacg aatgcacacg   600
gtgtggtggg cccaggtatt gttagcggtt tgaagcaggc ggcagaagaa gtaacaaagg   660
aacctagagg cctttttgatg ttagcagaat tgtcatgcaa gggctcccta tctactggag   720
aatatactaa gggtactgtt gacattgcga agagcgacaa agattttgtt atcggcttta   780
ttgctcaaag agacatgggt ggaagagatg aaggttacga ttggttgatt atgacacccg   840
gtgtgggttt agatgacaag ggagacgcat gggtcaaca gtatagaacc gtggatgatg   900
tggtctctac aggatctgac attattattg ttggaagagg actatttgca aagggaaggg   960
atgctaaggt agagggtgaa cgttacagaa agcaggctg ggaagcatat ttgagaagat  1020
gcggccagca aaactaaaaa actgtattat aagtaaatgc atgtatacta aactcacaaa  1080
ttagagcttc aatttaatta tatcagttat tacccgggaa tctcggtcgt aatgattttt  1140
ataatgacga aaaaaaaaaa attggaaaga aaaagcttta atgcggtagt ttatcacagt  1200
taaattgcta acgcagtcag gcaccgtgta tgaaatctaa caatgcgctc atcgtcatcc  1260
tcggcaccgt caccctggat gctgtaggca taggcttggt tatgccggta ctgccgggcc  1320
tcttgcggga tatcgtccat tccgacagca tcgccagtca ctatgcgtg ctgctagcgc  1380 tatatgcgtt gatgcaattt ctatgcgcac ccgttctcgg agcactgtcc gaccgctttg  1440
gccgccgccc agtcctgctc gcttcgctac ttggagccac tatcgactac gcgatcatgg  1500
cgaccacacc cgtcctgtgg atcctggtat ggttttatcg ttttatttct ggttcttata  1560
gcatcgtttt ggacttctct gttcccatta ggcggttcag gagccagcgc agaatcattc  1620
tttgaaggat acttatcctt tccaattttg attgtctgtt acgttgggac ataaactgta  1680
tactagaaat tggactttga tggtgaaact agaagatatg gatcttgata ccggcagaaa  1740
acaagtagat ttgactcttc gtagggaaga aatgaggatt gagcgagaaa cattagcaaa  1800
aagatccttc gtaacaagat ttttacattt ctggtgttga agggaaagat atgagctata  1860
cagcggaatt ccatatcac tcagattttg ttatctaatt ttttccttcc cacgtccgcg  1920
ggaatctgtg tatattactg catctagcta gatatatgtt atcttatctt ggcgcgtaca  1980
tttaattttc aacgtattct ataagaaatt gcgggagttt ttttcatgta gatgatactg  2040
```

```
actgcacgca aatataggca tgatttatag gcatgatttg atggctgtac cgataggaac    2100
gctaagagta acttcagaat cgttatcctg gcggaaaaaa ttcatttgta aactttaaaa    2160
aaaaaagcca atatcccaa aattattaag agcgcctcca ttattaacta aaatttcact     2220
cagcatccac aatgtatcag gtatctacta cagatattac atgtggcgaa aaagacaaga    2280
acaatgcaat agcgcatcaa gaaaaaacac aaagctttca atcaatgaat cgaaaatgtc    2340
attaaaatag tatataaatt gaaactaagt cataaagcta taaaaagaaa atttatttaa    2400
atgcaagact ttaaagtaaa ttcacttaag ccttggcaac gtgttcaacc aagtcgagat    2460
ctgagcttat cggccgaggt gagaagggtc tattaccagt tcatcatcat atcccaagcc    2520
atacggtgac ccgttatgtg gccgggatag attgagcaat gcagtcctg caccgtctca     2580 tgccggcgag gcgagatggt gaacagctgg gagacgagga agacagatcc gcagaggtcc    2640
cccacgtaca tagcggaaca gaaagcagcc gccccaacga gcaaatcgac gtggcgtcgt    2700
attgtcgtgg tggggacgct ggcgttccta gctgcgagcg tggggtgag cgctacccag      2760 cagcgggaag agttgttctc ccgaacgcag ggcacgcacc cggggggtgtg catgatcatg    2820 tccgctgcct catacacaat gcttgagttg gagcagtcgt tcgtgacatg gtacatcccg    2880
gacacgttgc gcacctcata ccccagagca gccaggggca ggaagcaaag cactagtatt    2940
agcaaagacc tcatggtgtt tgtttatgtg tgtttattcg aaactaagtt cttggtgttt    3000
taaaactaaa aaaagacta actataaaag tagaatttaa gaagtttaag aaatagattt      3060
acagaattac aatcaatacc taccgtcttt atatacttat tagtcaagta ggggaataat    3120
ttcagggaac tggtttcaac cttttttttc agggtttttt tttttcattc tctcaatctg    3180
aaattctctt atttctccaa cttataagtt ggagatgccc ggtgttccgg cagaggagat    3240
cagtctcgtg aagtggatgg tttcccgcct gcgggcaaaa cgtcataaca ttttttatgag   3300 cgaaagccgt taatgaagac aaaatcccctt aattaaaaca ttagaatggt gattagaaag   3360
gcaggattaa tcagttacac aggctgtaac cggagagacg gatcataagg caattttttag   3420 ataagactgg ttagagttct tggcatcaga aaatttgaga acgattttt ccgtttgttt      3480 gccctacgt tttgcccctt tgatcaaact atcagttaag atattaattt ttttgagaaa     3540
acgattcttt gattagtctc ttcaaacaaa caatgagctc tgaagacgaa ttgggaagta    3600
tcggtactgt gtttcccgga agtcccatag ataagagcat gggagtatt ctccacaatt      3660 tgatgaagaa gtgagactt tgctggaaga tagcttcacg tggaacattc ctgactggaa      3720
cgagttaaca aacccgaaat acaattcgcc caggtttaga attggtgatt tcgaatggga    3780
cattctatta ttccctcagg gaaaccataa taaaggtgtt gcggtatatc tggaacctca    3840 tccgaagaa aaattagatg agactacggg agagatggtg ccagttgatc cggactggta     3900
ttgttgtgct cagttgcca ttggtatatc tagacctggt aatggtgaca ccatcaattt      3960
aattaacaaa tcgcatcacc gattcaacgc tctagataca gactgggat ttgcaaattt      4020 gatagatttg aacaacttga acatccctc aaaggaaga ccgctttcgt tcttaaacga       4080
agggaccttg aacataacag cgtatgtgcg catattgaag gatcctctac gccggacgca    4140
tcgtggccgg catcaccggc gccacaggtg cggttgctgg ccctatatc gccgacatca     4200 ccgatgggga gatcgggct cgccacttcg ggctcatgag gcttgtttc ggcgtgggta      4260 tggtggcagg ccccgtggcc gggggactgt tgggcgccat ctccttgcat gcaccattcc    4320
ttgcggcggc ggtgctcaac ggcctcaacc tactactggg ctgcttccta atgcaggagt    4380
cgcataaggg agagcgtcga ccgatgccct tgagagcctt caacccagtc agctccttcc    4440
```

-continued

```
ggtgggcgcg gggcatgact atcgtcgccg cacttatgac tgtcttcttt atcatgcaac    4500
tcgtaggaca ggtgccggca gcgctctggg tcattttcgg cgaggaccgc tttcgctgga    4560
gcgcgacgat gatcggcctg tcgcttgcgg tattcggaat cttgcacgcc ctcgctcaag    4620
ccttcgtcac tggtcccgcc accaaacgtt tcggcgagaa gcaggccatt atcgccggca    4680
tggcggccga cgcgctgggc tacgtcttgc tggcgttcgc gacgcgaggc tggatggcct    4740
tccccattat gattcttctc gcttccggcg gcatcgggat gcccgcgttg caggccatgc    4800
tgtccaggca ggtagatgac gaccatcagg gacagcttca aggatcgctc gcggctctta    4860
ccagcctaac ttcgatcact ggaccgctga tcgtcacggc gatttatgcc gcctcggcga    4920
gcacatggaa cggggttggca tggattgtag gcgccgccct ataccttgtc tgcctccccg    4980
cgttgcgtcg cggtgcatgg agccgggcca cctcgacctg aatggaagcc ggcggcacct    5040
cgctaacgga ttcaccactc caagaattgg agccaatcaa ttcttgcgga gaactgtgaa    5100
tgcgcaaacc aacccttggc agaacatatc catcgcgtcc gccatctcca gcagccgcac    5160
gcggcgcatc tcgggcagcg ttgggtcctg gccacgggtg cgcatgatcg tgctcctgtc    5220
gttgaggacc cggctaggct ggcggggttg ccttactggt tagcagaatg aatcaccgat    5280
acgcgagcga acgtgaagcg actgctgctg caaaacgtct gcgacctgag caacaacatg    5340
aatggtcttc ggtttccgtg tttcgtaaag tctggaaacg cggaagtcag cgccctgcac    5400
cattatgttc cggatctgca tcgcaggatg ctgctggcta ccctgtggaa cacctacatc    5460
tgtattaacg aagcgctggc attgaccctg agtgatttt ctctggtccc gccgcatcca    5520
taccgccagt tgtttaccct cacaacgttc cagtaaccgg gcatgttcat catcagtaac    5580
ccgtatcgtg agcatcctct ctcgtttcat cggtatcatt accccatga acagaaattc    5640 ccccttacac ggaggcatca agtgaccaaa caggaaaaaa ccgcccttaa catggcccgc    5700
tttatcagaa gccagacatt aacgcttctg gagaaactca acgagctgga cgcggatgaa    5760
caggcagaca tctgtgaatc gcttcacgac cacgctgatg agctttaccg cagctgcctc    5820
gcgcgtttcg gtgatgacgg tgaaaacctc tgacacatgc agctcccgga gacggtcaca    5880
gcttgtctgt aagcggtgcc gggagcagac aagcccgtca gggcgcgtca gcgggtgttg    5940
gcgggtgtcg gggcgcagcc atgacccagt cacgtagcga tagcgagtg tatactggct    6000 taactatgcg gcatcagagc agattgtact gagagtgcac catatgcggt gtgaaatacc    6060
gcacagatgc gtaaggagaa aataccgcat caggcgctct ccgcttcct cgctcactga    6120 ctcgctgcgc tcggtcgttc ggctgcggcg agcggtatca gctcactcaa aggcggtaat    6180
acggttatcc acagaatcag gggataacgc aggaaagaac atgtgagcaa aaggccagca    6240
aaaggccagg aaccgtaaaa aggccgcgtt gctggcgttt ttccataggc tccgcccccc    6300
tgacgagcat cacaaaaatc gacgctcaag tcagaggtgg cgaaacccga caggactata    6360
aagataccag gcgtttcccc ctggaagctc cctcgtgcgc tctcctgttc cgaccctgcc    6420
gcttaccgga tacctgtccg cctttctccc ttcgggaagc gtggcgcttt ctcatagctc    6480
acgctgtagg tatctcagtt cggtgtaggt cgttcgctcc aagctgggct gtgtgcacga    6540
accccccgtt cagcccgacc gctgcgcctt atccggtaac tatcgtcttg agtccaaccc    6600
ggtaagacac gacttatcgc cactggcagc agccactggt aacaggatta gcagagcgag    6660
gtatgtaggc ggtgctacag agttcttgaa gtggtggcct aactacggct acactagaag    6720
gacagtattt ggtatctgcg ctctgctgaa gccagttacc ttcggaaaaa gagttggtag    6780
```

```
ctcttgatcc ggcaaacaaa ccaccgctgg tagcggtggt ttttttgttt gcaagcagca   6840
gattacgcgc agaaaaaaag gatctcaaga agatcctttg atcttttcta cggggtctga   6900
cgctcagtgg aacgaaaact cacgttaagg gattttggtc atgagattat caaaaaggat   6960
cttcacctag atccttttaa attaaaaatg aagttttaaa tcaatctaaa gtatatatga   7020
gtaaacttgg tctgacagtt accaatgctt aatcagtgag gcacctatct cagcgatctg   7080
tctatttcgt tcatccatag ttgcctgact ccccgtcgtg tagataacta cgatacggga   7140
gggcttacca tctggcccca gtgctgcaat gataccgcga gacccacgct caccggctcc   7200
agatttatca gcaataaacc agccagccgg aagggccgag cgcagaagtg gtcctgcaac   7260
tttatccgcc tccatccagt ctattaattg ttgccgggaa gctagagtaa gtagttcgcc   7320
agttaatagt ttgcgcaacg ttgttgccat tgctgcaggc atcgtggtgt cacgctcgtc   7380
gtttggtatg gcttcattca gctccggttc ccaacgatca aggcgagtta catgatcccc   7440
catgttgtgc aaaaaagcgg ttagctcctt cggtcctccg atcgttgtca gaagtaagtt   7500
ggccgcagtg ttatcactca tggttatggc agcactgcat aattctctta ctgtcatgcc   7560
atccgtaaga tgcttttctg tgactggtga gtactcaacc aagtcattct gagaatagtg   7620
tatgcggcga ccgagttgct cttgcccggc gtcaacacgg gataataccg cgccacatag   7680
cagaacttta aaagtgctca tcattggaaa acgttcttcg gggcgaaaac tctcaaggat   7740
cttaccgctg ttgagatcca gttcgatgta acccactcgt gcacccaact gatcttcagc   7800
atcttttact ttcaccagcg tttctgggtg agcaaaaaca ggaaggcaaa atgccgcaaa   7860
aaagggaata agggcgacac ggaaatgttg aatactcata ctcttccttt ttcaatatta   7920
ttgaagcatt tatcagggtt attgtctcat gagcggatac atatttgaat gtatttagaa   7980
aaataaacaa ataggggttc cgcgcacatt tccccgaaaa gtgccacctg acgtctaaga   8040
aaccattatt atcatgacat taacctataa aaataggcg tatcacgagg cccttttcgtc   8100
ttcaagaatt ctcatgtttg acagcttatc atcgatccac ttgtatattt ggatgaattt   8160
ttgaggaatt ctgaaccagt cctaaaacga gtaaatagga ccggcaattc ttcaagcaat   8220
aaacaggaat accaattatt aaaagataac ttagtcagat cgtacaataa agctttgaag   8280
aaaaatgcgc cttattcaat cttttgcataa aaaaatggcc caaaatctca cattggaaga   8340
catttgatga cctcatttct ttcaatgaag ggcctaacgg agttgactaa tgttgtggga   8400
aattggaccg ataagcgtgc ttctgccgtg gccaggacaa cgtatactca tcagataaca   8460
gcaatacctg atcactactt cgcactagtt tctcggtact atgcatatga tccaatatca   8520
aaggaaatga tagcattgaa ggatgagact aatccaattg aggagtggca gcatatagaa   8580
cagctaaagg gtagtgctga aggaagcata cgatacccg catggaatgg gataatatca   8640
caggaggtac tagactacct ttcatcctac ataaatagac gcatataagt acgcatttaa   8700
gcataaacac gcactatgcc gttcttctca tgtatatata tatacaggca acacgcagat   8760
ataggtgcga cgtgaacagt gagctgtatg tgcgcagctc gcgttgcatt tcggaagcg   8820
ctcgttttcg gaaacgcttt gaagttccta ttccgaagtt cctattctct agaaagtata   8880
ggaacttcag agcgcttttg aaaccaaaa gcgctctgaa gacgcacttt caaaaaacca   8940
aaaacgcacc ggactgtaac gagctactaa aatattgcga ataccgcttc cacaaacatt   9000
gctcaaaagt atctctttgc tatatatctc tgtgctatat ccctatataa ccatcccatc   9060
cacctttcgc tccttgaact tgcatctaaa ctcgacctct acatttttta tgtttatctc   9120
tagtattacc tcttagacaa aaaaattgta gtaagaacta ttcatagagt taatcgaaaa   9180
```

```
caatacgaaa atgtaaacat ttcctatacg tagtatatag agacaaaata gaagaaaccg   9240
ttcataattt tctgaccaat gaagaatcat caacgctatc actttctgtt cacaaagtat   9300
gcgcaatcca catcggtata gaatataatc ggggatgcct ttatcttgaa aaaatgcacc   9360
cgcagcttcg ctagtaatca gtaaacgcgg gaagtggagt caggcttttt ttatggaaga   9420
gaaaatagac accaaagtag ccttcttcta accttaacgg acctacagtg caaaaagtta   9480
tcaagagact gcattataga gcgcacaaag gagaaaaaaa gtaatctaag atgctttgtt   9540
agaaaaatag cgctctcggg atgcattttt gtagaacaaa aaagaagtat agattcttgt   9600
tggtaaaata gcgctctcgc gttgcatttc tgttctgtaa aaatgcagct cagattcttt   9660
gtttgaaaaa ttagcgctct cgcgttgcat ttttgtttta caaaaatgaa gcacagattc   9720
ttcgttggta aaatagcgct ttcgcgttgc atttctgttc tgtaaaaatg cagctcagat   9780
tctttgtttg aaaaattagc gctctcgcgt tgcattttg ttctacaaaa tgaagcacag   9840
atgcttcgtt aacaaagata tgctattgaa gtgcaagatg gaaacgcaga aaatgaaccg   9900
gggatgcgac gtgcaagatt acctatgcaa tagatgcaat agtttctcca ggaaccgaaa   9960
tacatacatt gtcttccgta aagcgctaga ctatatatta ttatacaggt tcaaatatac  10020
tatctgtttc agggaaaact cccaggttcg gatgttcaaa attcaatgat gggtaacaag  10080
tacgatcgta aatctgtaaa acagtttgtc ggatattagg ctgtatctcc tcaaagcgta  10140
ttcgaatatc attgagaagc tgcattttt tttttttttt tttttttttt tttttttatat  10200
atatttcaag gatataccat tgtaatgtct gcccctaaga agatcgtcgt tttgccaggt  10260
gaccacgttg gtcaagaaat cacagccgaa gccattaagg ttcttaaagc tatttctgat  10320
gttcgttcca atgtcaagtt cgatttcgaa aatcatttaa ttggtggtgc tgctatcgat  10380
gctacaggtg tcccacttcc agatgaggcg ctggaagcct ccaagaaggt tgatgccgtt  10440
ttgttaggtg ctgtgggtgg tcctaaatgg ggtaccggta gtgttagacc tgaacaaggt  10500
ttactaaaaa tccgtaaaga acttcaattg tacgccaact taagaccatg taactttgca  10560
tccgactctc ttttagactt atctccaatc aagcccacaat ttgctaaagg tactgacttc  10620
gttgttgtca gagaattagt gggaggtatt tactttggta agagaaagga agacgatggt  10680
gatggtgtcg cttgggatag tgaacaatac accgttccag aagtgcaaag aatcacaaga  10740
atggccgctt tcatggccct acaacatgag ccaccattgc ctatttggtc cttggataaa  10800
gctaatgttt tggcctcttc aagattatgg agaaaaactg tggaggaaac catcaagaac  10860
gaattcccta cattgaaggt tcaacatcaa ttgattgatt ctgccgccat gatcctagtt  10920
aagaacccaa cccacctaaa tggtattata atcaccagca acatgtttgg tgatatcatc  10980
tccgatgaag cctccgttat cccaggttcc ttgggtttgt tgccatctgc gtccttggcc  11040
tctttgccag acaagaacac cgcatttggt ttgtacgaac catgccacgg ttctgctcca  11100
gatttgccaa agaataaggt tgaccctatc gccactatct tgtctgctgc aatgatgttg  11160
aaattgtcat tgaacttgcc tgaagaaggt aaggccattg aagatgcagt taaaaaggtt  11220
ttggatgcag gtatcagaac tggtgattta ggtggttcca acagtaccac cgaagtcggt  11280
gatgctgtcg ccgaagaagt taagaaaatc cttgcttaaa aagattctct tttttatga  11340
tatttgtaca aaaaaaaaa aaaaaaaaa aaaaaaaaaa aaaaaaaaa aaaaatgcag  11400
cgtcacatcg gataataatg atggcagcca ttgtagaagt gccttttgca tttctagtct  11460
cttttctcggt ctagctagtt ttactacatc gcgaagatag aatcttagat cacactgcct  11520
```

```
ttgctgagct ggatcatatg agtaacaaaa gagtggtaag gcctcgttaa aggacaagga    11580
cctgagcgga agtgtatcgt aaagtagacg gagtatacta gtatagtcta tagtccgtgg    11640
aattctaagt gccagcttta taatgtcatt ctccttacta cagacccgcc tgaaagtaga    11700
cacatcatca tcagtaagct tgacaaaaa gcattgagta gctaactctt ctatgcaatc     11760
tatagctgtt ttataaggca ttcaatggac agattgaggt ttttgaaaca tactagtgaa    11820
attagcctta atcccttctc gaagttaatc atgcattatg gtgtaaaaaa tgcaactcgc    11880
gttgctctac ttttttcccga atttccaaat acgcagctgg ggtgattgct cgatttcgta   11940
acgaaagttt tgtttataaa aaccgcgaaa accttctgta acagatagat ttttacagcg    12000
ctgatataca atgacatcag ctgtaatgga aaataactga aatatgaatg gcgagagact    12060
gcttgcttgt attaagcaat gtattatgca gcacttccaa cctatggtgt acgatgaaag    12120
taggtgtgta atcgagacga caaggggac ttttccagtt cctgatcatt ataagaaata     12180
caaaacgtta gcatttgcat tgttggaca tgtactgaat acagacgaca caccggtaat     12240 tgaaaagaa ctggattggc ctgatcctgc actagtgtac aatacaattg tcgatcgaat     12300
cataaatcac ccagaattat cacagtttat atcggttgca tttattagtc agttaaaggc    12360
caccatcgga gagggtttag atattaatgt aaaaggcacg ctaaaccgca ggggaaaggg    12420
tatcagaagg cctaaaggcg tatttttag atacatggaa tctccatttg tcaatacaaa     12480
ggtcactgca ttcttctctt atcttcgaga ttataataaa attgcctcag aatatcacaa    12540
taatactaaa ttcattctca cgttttcatg tcaagcatat tgggcatctg gcccaaactt    12600
ctccgccttg aagaatgtta tttggtgctc cataattcat gaatacattt ctaagtttgt    12660
ggaaagagaa caggataaag gtcatatagg agatcaggag ctaccgcctg aagaggaccc    12720
ttctcgtgaa ctaaacaatg tacaacatga agtcaatagt ttaacggaac aagatgcgga    12780
ggcggatgaa ggattgtggg gtgaaataga ttcattatgt gaaaaatggc agtctgaagc    12840
ggagagtcaa actgaggcgg agataatagc cgacaggata attggaaata gccagaggat    12900
ggcgaacctc aaaattcgtc gtacaaagtt caaaagtgtc ttgtatcata tactaaagga    12960
actaattcaa tctcagggaa ccgtaaaggt ttatcgcggt agtagttttt cacacgattc    13020
gataaagata agcttacatt atgaagagca gcatattaca gccgtatggg tctacttgat    13080
agtaaaattt gaagagcatt ggaagcctgt tgatgtagag gtcgagttta gatgcaagtt    13140
caaggagcga aaggtggatg ggtaggttat atagggatat agcacagaga tatatagcaa    13200
agagatactt ttgaggcaat gtttgtggaa gcggtattcg caatatttta gtagctcgtt    13260
acagtccggt gcgttttgg ttttttgaaa gtgcgtcttc agagcgcttt tggttttcaa     13320
aagcgctctg aagttcctat actttctaga aataggaac ttcggaatag gaacttcaaa     13380
gcgtttccga aaacgagcgc ttccgaaaat gcaacgcgag ctgcgcacat acagctcact    13440
gttcacgtcg cacctatatc tgcgtgttgc ctgtatatat atatacatga gaagaacggc    13500
atagtgcgtg tttatgctta aatgcgtact tatatgcgtc tatttatgta ggatgaaagg    13560
tagtctagta cctcctgtga tattatccca ttccatgcgg ggtatcgtat gcttccttca    13620
gcactaccct ttagctgttc tatatgctgc cactcctcaa ttggattagt ctcatccttc    13680
aatgcattca tttcctttga tattggatca tacctagaa gtattacgtg attttctgcc     13740
ccttaccctc gttgctactc tccttttttt cgtgggaacc gctttagggc cctcagtgat    13800
ggtgttttgt aatttatatg ctcctcttgc atttgtgtct ctacttcttg ttcgcctgga    13860
gggaacttct tcatttgtat tagcatggtt cacttcagtc cttccttcca actcactctt    13920
```

-continued ttttgctgt aaacgattct ctgccgccag ttcattgaaa ctattgaata tatcctttag 13980
agattccggg atgaataaat cacctattaa agcagcttga cgatctggtg gaactaaagt 14040
aagcaattgg gtaacgacgc ttacgagctt cataacatct tcttccgttg gagctggtgg 14100
gactaataac tgtgtacaat ccattttct catgagcatt tcggtagctc tcttcttgtc 14160
tttctcgggc aatcttccta ttattatagc aatagatttg tatagttgct ttctattgtc 14220
taacagcttg ttattctgta gcatcaaatc tatggcagcc tgacttgctt cttgtgaaga 14280
gagcatacca tttccaatcg aagatacgct ggaatcttct cgctagaat caagaccata 14340
cggcctaccg gttgtgagag attccatggg ccttatgaca tatcctggaa agagtagctc 14400
atcagactta cgtttactct ctatatcaat atctacatca ggagcaatca tttcaataaa 14460
cagccgacat acatcccaga cgctataagc tgtacgtgct tttaccgtca gattcttggc 14520
tgtttcaatg tcgtccattt tggttttctt ttaccagtat tgttcgtttg ataatgtatt 14580
cttgcttatt acattataaa atctgtgcag atcacatgtc aaaacaactt tttatcacaa 14640
gatagtaccg caaaacgaac ctgcgggccg tctaaaaatt aaggaaaagc agcaaaggtg 14700
cattttaaa atatgaaatg aagataccgc agtaccaatt attttcgcag tacaaataat 14760
gcgcggccgg tgcattttc gaaagaacgc gagacaaaca ggacaattaa agttagtttt 14820
tcgagttagc gtgtttgaat actgcaagat acaagataaa tagagtagtt gaaactagat 14880
atcaattgca cacaagatcg gcgctaagca tgccacaatt tggtatatta tgtaaaacac 14940
cacctaaggt gcttgttcgt cagtttgtgg aaaggtttga agaccttca ggtgagaaaa 15000
tagcattatg tgctgctgaa ctaacctatt tatgttggat gattacacat aacggaacag 15060
caatcaagag agccacattc atgagctata atactatcat aagcaattcg ctgagtttcg 15120
atattgtcaa taaatcactc cagtttaaat acaagacgca aaaagcaaca attctggaag 15180
cctcattaaa gaaattgatt cctgcttggg aatttacaat tattccttac tatggacaaa 15240
aacatcaatc tgatatcact gatattgtaa gtagtttgca attacagttc gaatcatcgg 15300
aagaagcaga taagggaaat agccacagta aaaaaatgct aaagcacttc taagtgaggg 15360
tgaaagcatc tgggagatca ctgagaaaat actaaattcg tttgagtata cttcgagatt 15420
tacaaaaaca aaaactttat accaattcct cttcctagct actttcatca attgtggaag 15480
attcagcgat attaagaacg ttgatccgaa atcatttaaa ttagtccaaa ataagtatct 15540
gggagtaata atccagtgtt tagtgacaga gacaaagaca agcgttagta ggcacatata 15600
cttctttagc gcaagggta g 15621

<210> SEQ ID NO 51
<211> LENGTH: 3593
<212> TYPE: DNA
<213> ORGANISM: vector pPICZalphaA

<400> SEQUENCE: 51
agatctaaca tccaaagacg aaaggttgaa tgaaacctt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggccccctg gcgaggttca tgtttgttta 300
tttccgaatg caacaagctc cgcattacac ccgaacatca ctccagatga gggctttctg 360

```
agtgtggggt caaatagttt catgttcccc aaatggccca aaactgacag tttaaacgct     420
gtcttggaac ctaatatgac aaaagcgtga tctcatccaa gatgaactaa gtttggttcg     480
ttgaaatgct aacggccagt tggtcaaaaa gaaacttcca aaagtcggca taccgtttgt     540
cttgtttggt attgattgac gaatgctcaa aaataatctc attaatgctt agcgcagtct     600
ctctatcgct tctgaacccc ggtgcacctg tgccgaaacg caaatgggga acacccgct     660 ttttggatga ttatgcattg tctccacatt gtatgcttcc aagattctgg tgggaatact     720
gctgatagcc taacgttcat gatcaaaatt taactgttct aaccoctact tgacagcaat     780 atataaacag aaggaagctg ccctgtctta aaccttttt tttatcatca ttattagctt     840
actttcataa ttgcgactgg ttccaattga caagcttttg attttaacga cttttaacga     900
caacttgaga agatcaaaaa acaactaatt attcgaaacg atgagatttc cttcaatttt     960
tactgctgtt ttattcgcag catcctccgc attagctgct ccagtcaaca ctacaacaga    1020
agatgaaacg gcacaaattc cggctgaagc tgtcatcggt tactcagatt tagaagggga    1080
tttcgatgtt gctgttttgc cattttccaa cagcacaaat aacgggttat tgtttataaa    1140
tactactatt gccagcattg ctgctaaaga agaaggggta tctctcgaga aaagagaggc    1200
tgaagctgaa ttcacgtggc ccagccggcc gtctcggatc ggtacctcga gccgcggcgg    1260
ccgccagctt tctagaacaa aaactcatct cagaagagga tctgaatagc gccgtcgacc    1320
atcatcatca tcatcattga gtttgtagcc ttagacatga ctgttcctca gttcaagttg    1380
ggcacttacg agaagaccgg tcttgctaga ttctaatcaa gaggatgtca gaatgccatt    1440
tgcctgagag atgcaggctt cattttgat acttttttat ttgtaaccta tatagtatag    1500 gattttttt gtcattttgt ttcttctcgt acgagcttgc tcctgatcag cctatctcgc    1560
agctgatgaa tatcttgtgg tagggggtttg ggaaaatcat tcgagtttga tgttttcttt    1620
ggtatttccc actcctcttc agagtacaga agattaagtg agaccttcgt ttgtgcggat    1680
cccccacaca ccatagcttc aaaatgtttc tactccttt ttactcttcc agatttctct    1740
ggactccgcg catcgccgta ccacttcaaa acacccaagc acagcatact aaattttcccc    1800 tctttcttcc tctagggtgt cgttaattac ccgtactaaa ggtttggaaa agaaaaaaga    1860
gaccgcctcg tttcttttc ttcgtcgaaa aaggcaataa aaattttat cacgtttctt    1920 tttcttgaaa ttttttttt tagtttttt ctctttcagt gacctccatt gatatttaag    1980
ttaataaacg gtcttcaatt tctcaagttt cagtttcatt tttcttgttc tattacaact    2040 tttttactt cttgttcatt agaaagaaag catagcaatc taatctaagg ggcggtgttg    2100
acaattaatc atcggcatag tatatcggca tagtataata cgacaaggtg aggaactaaa    2160
ccatggccaa gttgaccagt gccgttccgg tgctcaccgc gcgcgacgtc gccggagcgg    2220
tcgagttctg gaccgaccgg ctcgggttct cccgggactt cgtggaggac gacttcgccg    2280
gtgtggtccg ggacgacgtg accctgttca tcagcgcggt ccaggaccag gtggtgccgg    2340
acaacaccct ggcctgggtg tgggtgcgcg gcctggacga gctgtacgcc gagtggtcgg    2400
aggtcgtgtc cacgaacttc cgggacgcct ccggccggc catgaccgag atcgcgagc    2460 agccgtgggg gcgggagttc gccctgcgcg acccggccgg caactgcgtg cacttcgtgg    2520
ccgaggagca ggactgacac gtccgacggc ggccacggg tcccaggcct cggagatccg    2580
tccccctttt cctttgtcga tatcatgtaa ttagttatgt cacgcttaca ttcacgccct    2640 cccccacat ccgctctaac cgaaaaggaa ggagttagac aacctgaagt ctaggtccct    2700
atttattttt ttatagttat gttagtatta agaacgttat ttatatttca aatttttctt    2760
```

-continued

| | |
|---|---|
| ttttttctgt acagacgcgt gtacgcatgt aacattatac tgaaaacctt gcttgagaag | 2820 |
| gttttgggac gctcgaaggc tttaatttgc aagctggaga ccaacatgtg agcaaaaggc | 2880 |
| cagcaaaagg ccaggaaccg taaaaaggcc gcgttgctgg cgttttttcca taggctccgc | 2940 |
| cccctgacg agcatcacaa aaatcgacgc tcaagtcaga ggtggcgaaa cccgacagga | 3000 |
| ctataaagat accaggcgtt ccccctgga agctccctcg tgcgctctcc tgttccgacc | 3060 |
| ctgccgctta ccggatacct gtccgccttt ctcccttcgg gaagcgtggc gctttctcaa | 3120 |
| tgctcacgct gtaggtatct cagttcggtg taggtcgttc gctccaagct gggctgtgtg | 3180 |
| cacgaacccc ccgttcagcc cgaccgctgc gccttatccg gtaactatcg tcttgagtcc | 3240 |
| aacccggtaa gacacgactt atcgccactg gcagcagcca ctggtaacag gattagcaga | 3300 |
| gcgaggtatg taggcggtgc tacagagttc ttgaagtggt ggcctaacta cggctacact | 3360 |
| agaaggacag tatttggtat ctgcgctctg ctgaagccag ttaccttcgg aaaaagagtt | 3420 |
| ggtagctctt gatccggcaa acaaaccacc gctggtagcg gtggtttttt tgtttgcaag | 3480 |
| cagcagatta cgcgcagaaa aaaggatct caagaagatc ctttgatctt ttctacgggg | 3540 |
| tctgacgctc agtggaacga aaactcacgt taagggattt tggtcatgag atc | 3593 |

<210> SEQ ID NO 52
<211> LENGTH: 3547
<212> TYPE: DNA
<213> ORGANISM: vector pPICZalphaD'

<400> SEQUENCE: 52

| | |
|---|---|
| agatctaaca tccaaagacg aaaggttgaa tgaaacctttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggcccccctg gcgaggttca tgtttgttta | 300 |
| tttccgaatg caacaagctc cgcattacac ccgaacatca ctccagatga gggctttctg | 360 |
| agtgtgggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcggca taccgtttgt | 540 |
| cttgtttggt attgattgac gaatgctcaa aaataatctc attaatgctt agcgcagtct | 600 |
| ctctatcgct tctgaacccc ggtgcacctg tgccgaaacg caaatgggga acacccgct | 660 |
| ttttggatga ttatgcattg tctccacatt gtatgcttcc aagattctgg tgggaatact | 720 |
| gctgatagcc taacgttcat gatcaaaatt taactgttct aacccctact tgacagcaat | 780 |
| atataaacag aaggaagctg ccctgtctta aaccttttt tttatcatca ttattagctt | 840 |
| actttcataa ttgcgactgg ttccaattga caagcttttg attttaacga cttttaacga | 900 |
| caacttgaga agatcaaaaa acaactaatt attcgaaacg atgagatttc cttcaatttt | 960 |
| tactgctgtt ttattcgcag catcctccgc attagctgct ccagtcaaca ctacaacaga | 1020 |
| agatgaaacg gcacaaattc cggctgaagc tgtcatcggt tactcagatt tagaagggga | 1080 |
| tttcgatgtt gctgttttgc catttttccaa cagcacaaat aacgggttat tgtttataaa | 1140 |
| tactactatt gccagcattg ctgctaaaga agaaggggta tctctcgaga aaagggggccc | 1200 |
| gaattcgcat gcggccgcca gctttctaga acaaaaactc atctcagaag aggatctgaa | 1260 |

-continued

```
tagcgccgtc gaccatcatc atcatcatca ttgagtttgt agccttagac atgactgttc    1320
ctcagttcaa gttgggcact tacgagaaga ccggtcttgc tagattctaa tcaagaggat    1380
gtcagaatgc catttgcctg agagatgcag gcttcatttt tgatactttt ttatttgtaa    1440
cctatatagt ataggatttt ttttgtcatt ttgtttcttc tcgtacgagc ttgctcctga    1500
tcagcctatc tcgcagctga tgaatatctt gtggtagggg tttgggaaaa tcattcgagt    1560
ttgatgtttt tcttggtatt tcccactcct cttcagagta cagaagatta agtgagacct    1620
tcgtttgtgc ggatccccca cacaccatag cttcaaaatg tttctactcc ttttttactc    1680
ttccagattt tctcggactc cgcgcatcgc cgtaccactt caaaacaccc aagcacagca    1740
tactaaattt tccctctttc ttcctctagg gtgtcgttaa ttacccgtac taaaggtttg    1800
gaaaagaaaa aagagaccgc ctcgtttctt tttcttcgtc gaaaaaggca ataaaaattt    1860
ttatcacgtt tctttttctt gaaattttt ttttagttt ttttctcttt cagtgacctc      1920
cattgatatt taagttaata aacggtcttc aatttctcaa gtttcagttt cattttctt     1980 gttctattac aacttttttt acttcttgtt cattagaaag aaagcatagc aatctaatct    2040 aagggggcggt gttgacaatt aatcatcggc atagtatatc ggcatagtat aatacgacaa   2100
ggtgaggaac taaaccatgg ccaagttgac cagtgccgtt ccggtgctca ccgcgcgcga    2160
cgtcgccgga gcggtcgagt tctggaccga ccggctcggg ttctcccggg acttcgtgga    2220
ggacgacttc gccggtgtgg tccgggacga cgtgaccctg ttcatcagcg cggtccagga    2280
ccaggtggtg ccggacaaca ccctggcctg gtgtgggtg cgcggcctgg acgagctgta     2340
cgccgagtgg tcggaggtcg tgtccacgaa cttccgggac gcctccgggc cggccatgac    2400
cgagatcggc gagcagccgt gggggcggga gttcgccctg cgcgacccgg ccggcaactg    2460
cgtgcacttc gtggccgagg agcaggactg acacgtccga cggcggccca cgggtcccag    2520
gcctcggaga tccgtccccc ttttcctttg tcgatatcat gtaattagtt atgtcacgct    2580
tacattcacg ccctccccccc acatccgctc taaccgaaaa ggaaggagtt agacaacctg   2640
aagtctaggt ccctatttat tttttttatag ttatgttagt attaagaacg ttatttatat   2700
ttcaaatttt tctttttttt ctgtacagac gcgtgtacgc atgtaacatt atactgaaaa    2760
ccttgcttga aaggttttg ggacgctcga aggctttaat ttgcaagctg agaccaaca      2820 tgtgagcaaa aggccagcaa aaggccagga accgtaaaaa ggccgcgttg ctggcgtttt    2880
tccataggct ccgcccccct gacgagcatc acaaaaatcg acgctcaagt cagaggtggc    2940
gaaacccgac aggactataa agataccagg cgtttccccc tggaagctcc ctcgtgcgct    3000
ctcctgttcc gaccctgccg cttaccggat acctgtccgc ctttctccct tcggaagcg     3060 tggcgctttc tcaatgctca cgctgtaggt atctcagttc ggtgtaggtc gttcgctcca    3120
agctgggctg tgtgcacgaa ccccccgttc agcccgaccg ctgcgcctta tccggtaact    3180
atcgtcttga gtccaacccg gtaagacacg acttatcgcc actggcagca gccactggta    3240
acaggattag cagagcgagg tatgtaggcg gtgctacaga gttcttgaag tggtggccta    3300
actacggcta cactagaagg acagtatttg gtatctgcgc tctgctgaag ccagttacct    3360
tcggaaaaag agttggtagc tcttgatccg gcaaacaaac caccgctggt agcggtggtt    3420 ttttgtttg caagcagcag attacgcgca gaaaaaagg atctcaagaa gatcctttga      3480
tcttttctac ggggtctgac gctcagtgga acgaaaactc acgttaaggg attttggtca    3540
tgagatc                                                              3547
```

-continued

<210> SEQ ID NO 53
<211> LENGTH: 3558
<212> TYPE: DNA
<213> ORGANISM: vector pPICZalphaE'

<400> SEQUENCE: 53

| | | | | | | |
|---|---|---|---|---|---|---|
| agatctaaca | tccaaagacg | aaaggttgaa | tgaaaccttt | ttgccatccg | acatccacag | 60 |
| gtccattctc | acacataagt | gccaaacgca | acaggagggg | atacactagc | agcagaccgt | 120 |
| tgcaaacgca | ggacctccac | tcctcttctc | ctcaacaccc | acttttgcca | tcgaaaaacc | 180 |
| agcccagtta | ttgggcttga | ttggagctcg | ctcattccaa | ttccttctat | taggctacta | 240 |
| acaccatgac | tttattagcc | tgtctatcct | ggcccccctg | gcgaggttca | tgtttgttta | 300 |
| tttccgaatg | caacaagctc | cgcattacac | ccgaacatca | ctccagatga | gggctttctg | 360 |
| agtgtggggt | caaatagttt | catgttcccc | aaatggccca | aaactgacag | tttaaacgct | 420 |
| gtcttggaac | ctaatatgac | aaaagcgtga | tctcatccaa | gatgaactaa | gtttggttcg | 480 |
| ttgaaatgct | aacggccagt | tggtcaaaaa | gaaacttcca | aaagtcggca | taccgtttgt | 540 |
| cttgtttggt | attgattgac | gaatgctcaa | aaataatctc | attaatgctt | agcgcagtct | 600 |
| ctctatcgct | tctgaacccc | ggtgcacctg | tgccgaaacg | caaatgggga | aacacccgct | 660 |
| ttttggatga | ttatgcattg | tctccacatt | gtatgcttcc | aagattctgg | tgggaatact | 720 |
| gctgatagcc | taacgttcat | gatcaaaatt | taactgttct | aaccccctact | tgacagcaat | 780 |
| atataaacag | aaggaagctg | ccctgtctta | aaccttttt | tttatcatca | ttattagctt | 840 |
| actttcataa | ttgcgactgg | ttccaattga | caagcttttg | attttaacga | cttttaacga | 900 |
| caacttgaga | agatcaaaaa | acaactaatt | attcgaaacg | atgagatttc | cttcaatttt | 960 |
| tactgctgtt | ttattcgcag | catcctccgc | attagctgct | ccagtcaaca | ctacaacaga | 1020 |
| agatgaaacg | gcacaaattc | cggctgaagc | tgtcatcggt | tactcagatt | tagaagggga | 1080 |
| tttcgatgtt | gctgttttgc | cattttccaa | cagcacaaat | aacgggttat | tgtttataaa | 1140 |
| tactactatt | gccagcattg | ctgctaaaga | agaagggta | tctctcgaga | aaagagaggc | 1200 |
| tgaagcctgc | agcatatgct | cgaggccgcc | agctttctag | aacaaaaact | catctcagaa | 1260 |
| gaggatctga | atagcgccgt | cgaccatcat | catcatcatc | attgagtttg | tagccttaga | 1320 |
| catgactgtt | cctcagttca | agttgggcac | ttacgagaag | accggtcttg | ctagattcta | 1380 |
| atcaagagga | tgtcagaatg | ccatttgcct | gagagatgca | ggcttcattt | ttgatacttt | 1440 |
| tttatttgta | acctatatag | tataggattt | ttttttgtcat | tttgtttctt | ctcgtacgag | 1500 |
| cttgctcctg | atcagcctat | ctcgcagctg | atgaatatct | tgtggtaggg | gtttgggaaa | 1560 |
| atcattcgag | tttgatgttt | tcttggtat | tcccactcc | tcttcagagt | acagaagatt | 1620 |
| aagtgagacc | ttcgtttgtg | cggatccccc | acacaccata | gcttcaaaat | gtttctactc | 1680 |
| ctttttact | cttccagatt | ttctcggact | ccgcgcatcg | ccgtaccact | tcaaaacacc | 1740 |
| caagcacagc | atactaaatt | ttccctcttt | cttcctctag | ggtgtcgtta | attacccgta | 1800 |
| ctaaaggttt | ggaaagaaa | aaagagaccg | cctcgtttct | ttttcttcgt | cgaaaaaggc | 1860 |
| aataaaaatt | tttatcacgt | ttcttttttct | tgaatttttt | tttttagtt | tttttctctt | 1920 |
| tcagtgacct | ccattgatat | ttaagttaat | aaacggtctt | caatttctca | gtttcagtt | 1980 |
| tcatttttct | tgttctatta | caacttttt | tacttcttgt | tcattagaaa | gaaagcatag | 2040 |
| caatctaatc | taaggggcgg | tgttgacaat | taatcatcgg | catagtatat | cggcatagta | 2100 |
| taatacgaca | aggtgaggaa | ctaaaccatg | gccaagttga | ccagtgccgt | tccggtgctc | 2160 |

```
accgcgcgcg acgtcgccgg agcggtcgag ttctggaccg accggctcgg gttctcccgg    2220
gacttcgtgg aggacgactt cgccggtgtg gtccgggacg acgtgaccct gttcatcagc    2280
gcggtccagg accaggtggt gccggacaac accctggcct gggtgtgggt gcgcggcctg    2340
gacgagctgt acgccgagtg gtcggaggtc gtgtccacga acttccggga cgcctccggg    2400
ccggccatga ccgagatcgg cgagcagccg tggggcgggg agttcgccct gcgcgacccg    2460
gccggcaact gcgtgcactt cgtggccgag gagcaggact gacacgtccg acggcggccc    2520
acgggtccca ggcctcggag atccgtcccc cttttccttt gtcgatatca tgtaattagt    2580
tatgtcacgc ttacattcac gccctccccc cacatccgct ctaaccgaaa aggaaggagt    2640
tagacaacct gaagtctagg tccctattta ttttttata gttatgttag tattaagaac    2700
gttatttata tttcaaattt ttcttttttt tctgtacaga cgcgtgtacg catgtaacat    2760
tatactgaaa accttgcttg agaaggtttt gggacgctcg aaggctttaa tttgcaagct    2820
ggagaccaac atgtgagcaa aaggccagca aaaggccagg aaccgtaaaa aggccgcgtt    2880
gctggcgttt ttccataggc tccgcccccc tgacgagcat cacaaaaatc gacgctcaag    2940
tcagaggtgg cgaaacccga caggactata aagataccag gcgtttcccc ctggaagctc    3000
cctcgtgcgc tctcctgttc cgaccctgcc gcttaccgga tacctgtccg cctttctccc    3060
ttcgggaagc gtggcgcttt ctcaatgctc acgctgtagg tatctcagtt cggtgtaggt    3120
cgttcgctcc aagctgggct gtgtgcacga accccccgtt cagcccgacc gctgcgcctt    3180
atccggtaac tatcgtcttg agtccaaccc ggtaagacac gacttatcgc cactggcagc    3240
agccactggt aacaggatta gcagagcgag gtatgtaggc ggtgctacag agttcttgaa    3300
gtggtggcct aactacggct acactagaag gacagtattt ggtatctgcg ctctgctgaa    3360
gccagttacc ttcggaaaaa gagttggtag ctcttgatcc ggcaaacaaa ccaccgctgg    3420
tagcggtggt ttttttgttt gcaagcagca gattacgcgc agaaaaaaag gatctcaaga    3480
agatcctttg atcttttcta cggggtctga cgctcagtgg aacgaaaact cacgttaagg    3540
gattttggtc atgagatc                                                 3558
```

```
<210> SEQ ID NO 54
<211> LENGTH: 28
<212> TYPE: DNA
<213> ORGANISM: synthetic probe or primer

<400> SEQUENCE: 54
tcgagaaaag gggcccgaat tcgcatgc                                        28

<210> SEQ ID NO 55
<211> LENGTH: 28
<212> TYPE: DNA
<213> ORGANISM: synthetic probe or primer

<400> SEQUENCE: 55
ggccgcatgc gaattcgggc ccctttc                                         28

<210> SEQ ID NO 56
<211> LENGTH: 35
<212> TYPE: DNA
<213> ORGANISM: synthetic probe or primer

<400> SEQUENCE: 56
tcgagaaaag agaggctgaa gcctgcagca tatgc                                35
```

<210> SEQ ID NO 57
<211> LENGTH: 35
<212> TYPE: DNA
<213> ORGANISM: synthetic probe or primer

<400> SEQUENCE: 57
ggccgcatat gctgcaggct tcagcctctc ttttc          35

<210> SEQ ID NO 58
<211> LENGTH: 3997
<212> TYPE: DNA
<213> ORGANISM: vector pPICZalphaD'E1sH6

<400> SEQUENCE: 58

| | | |
|---|---|---|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggcccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcggca taccgtttgt | 540 |
| cttgtttggt attgattgac gaatgctcaa aaataatctc attaatgctt agcgcagtct | 600 |
| ctctatcgct tctgaacccc ggtgcacctg tgccgaaacg caaatgggga acacccgct | 660 |
| ttttggatga ttatgcattg tctccacatt gtatgcttcc aagattctgg tgggaatact | 720 |
| gctgatagcc taacgttcat gatcaaaatt taactgttct aaccccctact tgacagcaat | 780 |
| atataaacag aaggaagctg ccctgtctta accttttttt tttatcatca ttattagctt | 840 |
| actttcataa ttgcgactgg ttccaattga caagcttttg attttaacga cttttaacga | 900 |
| caacttgaga agatcaaaaa acaactaatt attcgaaacg atgagatttc cttcaatttt | 960 |
| tactgctgtt ttattcgcag catcctccgc attagctgct ccagtcaaca ctacaacaga | 1020 |
| agatgaaacg gcacaaattc cggctgaagc tgtcatcggt tactcagatt tagaagggga | 1080 |
| tttcgatgtt gctgttttgc cattttccaa cagcacaaat aacgggttat tgtttataaa | 1140 |
| tactactatt gccagcattg ctgctaaaga agaaggggta tctctcgaga aaaggtatga | 1200 |
| ggtgcgcaac gtgtccggga tgtaccatgt cacgaacgac tgctccaact caagcattgt | 1260 |
| gtatgaggca gcggacatga tcatgcacac ccccgggtgc gtgccctgcg ttcgggagaa | 1320 |
| caactcttcc cgctgctggg tagcgctcac ccccacgctc gcagctagga acgccagcgt | 1380 |
| ccccactacg acaatacgac gccacgtcga tttgctcgtt ggggcggctg ctttctgttc | 1440 |
| cgctatgtac gtgggggatc tctgcggatc tgtcttcctc gtctcccagc tgttcaccat | 1500 |
| ctcgcctcgc cggcatgaga cggtgcagga ctgcaattgc tcaatctatc ccggccacat | 1560 |
| aacaggtcac cgtatggctt gggatatgat gatgaactgg caccaccacc atcaccatta | 1620 |
| aagatctaag cttgaatccc gcggccatgc gaattcgcat gcggccgcca gctttctaga | 1680 |
| acaaaaactc atctcagaag aggatctgaa tagcgccgtc gaccatcatc atcatcatca | 1740 |
| ttgagtttgt agccttagac atgactgttc ctcagttcaa gttgggcact tacgagaaga | 1800 |
| ccggtcttgc tagattctaa tcaagaggat gtcagaatgc catttgcctg agagatgcag | 1860 |

-continued

```
gcttcatttt tgatactttt ttatttgtaa cctatatagt ataggatttt ttttgtcatt      1920
ttgtttcttc tcgtacgagc ttgctcctga tcagcctatc tcgcagctga tgaatatctt      1980
gtggtagggg tttgggaaaa tcattcgagt ttgatgtttt tcttggtatt tcccactcct      2040
cttcagagta cagaagatta agtgagacct tcgtttgtgc ggatccccca cacaccatag      2100
cttcaaaatg tttctactcc tttttttactc ttccagattt tctcggactc cgcgcatcgc     2160
cgtaccactt caaaacaccc aagcacagca tactaaattt tccctctttc ttcctctagg      2220
gtgtcgttaa ttacccgtac taaaggtttg gaaagaaaaa agagaccgc ctcgtttctt       2280 tttcttcgtc gaaaaaggca ataaaaattt ttatcacgtt tctttttctt gaaattttt      2340 tttttagttt ttttctcttt cagtgacctc cattgatatt taagttaata aacggtcttc      2400
aatttctcaa gtttcagttt cattttcttt gttctattac actttttttt acttcttgtt     2460
cattagaaag aaagcatagc aatctaatct aaggggcggt gttgacaatt aatcatcggc     2520
atagtatatc ggcatagtat aatacgacaa ggtgaggaac taaaccatgg ccaagttgac     2580
cagtgccgtt ccggtgctca ccgcgcgcga cgtcgccgga gcggtcgagt tctggaccga     2640
ccggctcggg ttctcccggg acttcgtgga ggacgacttc gccggtgtgg tccgggacga     2700
cgtgaccctg ttcatcagcg cggtccagga ccaggtggtg ccggacaaca ccctggcctg     2760
ggtgtgggtg cgcggcctgg acgagctgta cgccgagtgg tcgaggtcg tgtccacgaa      2820 cttccgggac gcctccgggc cggccatgac cgagatcggc gagcagccgt ggggcggga     2880 gttcgccctg cgcgacccgg ccggcaactg cgtgcacttc gtggccgagg agcaggactg     2940
acacgtccga cggcggccca cgggtcccag gcctcggaga tccgtccccc ttttcctttg     3000
tcgatatcat gtaattagtt atgtcacgct tacattcacg ccctccccc acatccgctc      3060 taaccgaaaa ggaaggagtt agacaacctg aagtctaggt ccctatttat tttttatag     3120 ttatgttagt attaagaacg ttatttatat ttcaaatttt tctttttttt ctgtacagac     3180
gcgtgtacgc atgtaacatt atactgaaaa ccttgcttga aaggttttg ggacgctcga      3240 aggctttaat ttgcaagctg gagaccaaca tgtgagcaaa aggccagcaa aaggccagga     3300
accgtaaaaa ggccgcgttg ctggcgtttt tccataggct ccgcccccct gacgagcatc     3360
acaaaaatcg acgctcaagt cagaggtggc gaaacccgac aggactataa agataccagg     3420
cgtttccccc tggaagctcc ctcgtgcgct ctcctgttcc gaccctgccg cttaccggat     3480
acctgtccgc ctttctccct tcgggaagcg tggcgctttc tcaatgctca cgctgtaggt     3540
atctcagttc ggtgtaggtc gttcgctcca agctgggctg tgtgcacgaa ccccccgttc     3600
agcccgaccg ctgcgcctta tccggtaact atcgtcttga gtccaacccg gtaagacacg     3660
acttatcgcc actggcagca gccactggta acaggattag cagagcgagg tatgtaggcg     3720
gtgctacaga gttcttgaag tggtggccta actacggcta cactagaagg acagtatttg     3780
gtatctgcgc tctgctgaag ccagttacct tcggaaaaag agttggtagc tcttgatccg     3840
gcaaacaaac caccgctggt agcggtggtt ttttgtttg caagcagcag attacgcgca     3900
gaaaaaaagg atctcaagaa gatcctttga tcttttctac ggggtctgac gctcagtgga     3960
acgaaaactc acgttaaggg attttggtca tgagatc                              3997
```

<210> SEQ ID NO 59
<211> LENGTH: 4004
<212> TYPE: DNA
<213> ORGANISM: vector pPICZalphaE'E1sH6

<400> SEQUENCE: 59

-continued

```
agatctaaca tccaaagacg aaaggttgaa tgaaaccttt ttgccatccg acatccacag      60
gtccattctc acacataagt gccaaacgca acaggagggg atacactagc agcagaccgt     120
tgcaaacgca ggacctccac tcctcttctc ctcaacaccc acttttgcca tcgaaaaacc     180
agcccagtta ttgggcttga ttggagctcg ctcattccaa ttccttctat taggctacta     240
acaccatgac tttattagcc tgtctatcct ggcccccctg gcgaggttca tgtttgttta     300
tttccgaatg caacaagctc cgcattacac ccgaacatca ctccagatga gggctttctg     360
agtgtggggt caaatagttt catgttcccc aaatggccca aaactgacag tttaaacgct     420
gtcttggaac ctaatatgac aaaagcgtga tctcatccaa gatgaactaa gtttggttcg     480
ttgaaatgct aacggccagt tggtcaaaaa gaaacttcca aaagtcggca taccgtttgt     540
cttgtttggt attgattgac gaatgctcaa aaataatctc attaatgctt agcgcagtct     600
ctctatcgct tctgaacccc ggtgcacctg tgccgaaacg caaatggggga aacacccgct     660 ttttggatga ttatgcattg tctccacatt gtatgcttcc aagattctgg tgggaatact     720
gctgatagcc taacgttcat gatcaaaatt taactgttct aacccctact tgacagcaat     780
atataaacag aaggaagctg ccctgtctta aaccttttt tttatcatca ttattagctt     840
actttcataa ttgcgactgg ttccaattga caagcttttg attttaacga cttttaacga     900
caacttgaga agatcaaaaa acaactaatt attcgaaacg atgagatttc cttcaattt     960 tactgctgtt ttattcgcag catcctccgc attagctgct ccagtcaaca ctacaacaga    1020
agatgaaacg gcacaaattc cggctgaagc tgtcatcggt tactcagatt tagaagggga    1080
tttcgatgtt gctgttttgc cattttccaa cagcacaaat aacgggttat tgtttataaa    1140
tactactatt gccagcattg ctgctaaaga agaaggggta tctctcgaga aaagagaggc    1200
tgaagcctat gaggtgcgca acgtgtccgg gatgtaccat gtcacgaacg actgctccaa    1260
ctcaagcatt gtgtatgagg cagcggacat gatcatgcac ccccccgggt gcgtgccctg    1320
cgttcgggag aacaactctt cccgctgctg ggtagcgctc acccccacgc tcgcagctag    1380
gaacgccagc gtccccacta cgacaatacg acgccacgtc gatttgctcg ttggggcggc    1440
tgctttctgt tccgctatgt acgtggggga tctctgcgga tctgtcttcc tcgtctccca    1500
gctgttcacc atctcgcctc gccggcatga gacggtgcag gactgcaatt gctcaatcta    1560
tcccggccac ataacgggtc accgtatggc ttgggatatg atgatgaact ggcaccacca    1620
ccatcaccat taaagatcta agcttgaatc ccgcggccat ggcatatgcg gccgccagct    1680
ttctagaaca aaaactcatc tcagaagagg atctgaatag cgccgtcgac catcatcatc    1740
atcatcattg agtttgtagc cttagacatg actgttcctc agttcaagtt gggcacttac    1800
gagaagaccg gtcttgctag attctaatca agaggatgtc agaatgccat tgcctgaga    1860 gatgcaggct tcatttttga tactttttta tttgtaacct atatagtata ggatttttt    1920 tgtcattttg tttcttctcg tacgagcttg ctcctgatca gcctatctcg cagctgatga    1980
atatcttgtg gtagggtttt gggaaaatca ttcgagtttg atgttttttct tggtatttcc    2040 cactcctctt cagagtacag aagattaagt gagaccttcg tttgtgcgga tccccacac    2100 accatagctt caaaatgttt ctactccttt tttactcttc cagatttttct cggactccgc    2160 gcatcgccgt accacttcaa aacacccaag cacagcatac taaatttttcc ctctttcttc    2220 ctctagggtg tcgttaatta cccgtactaa aggtttggaa agaaaaaag agaccgcctc    2280 gtttcttttt cttcgtcgaa aaaggcaata aaaatttta tcacgtttct ttttcttgaa    2340
```

-continued

```
atttttttttt ttagtttttt tctctttcag tgacctccat tgatatttaa gttaataaac    2400
ggtcttcaat ttctcaagtt tcagtttcat ttttcttgtt ctattacaac ttttttttact   2460 tcttgttcat tagaaagaaa gcatagcaat ctaatctaag gggcggtgtt gacaattaat    2520
catcggcata gtatatcggc atagtataat acgacaaggt gaggaactaa accatggcca    2580
agttgaccag tgccgttccg gtgctcaccg cgcgcgacgt cgccgagcg gtcgagttct     2640 ggaccgaccg gctcgggttc tcccgggact tcgtggagga cgacttcgcc ggtgtggtcc    2700
gggacgacgt gaccctgttc atcagcgcgg tccaggacca ggtggtgccg gacaacaccc    2760
tggcctgggt gtgggtgcgc ggcctggacg agctgtacgc cgagtggtcg gaggtcgtgt    2820
ccacgaactt ccgggacgcc tccgggccgg ccatgaccga gatcggcgag cagccgtggg    2880
ggcgggagtt cgccctgcgc gacccggccg gcaactgcgt gcacttcgtg gccgaggagc    2940
aggactgaca cgtccgacgg cggcccacgg gtcccaggcc tcggagatcc gtccccttt     3000 tcctttgtcg atatcatgta attagttatg tcacgcttac attcacgccc tccccccaca    3060
tccgctctaa ccgaaaagga aggagttaga caacctgaag tctaggtccc tatttatttt    3120
tttatagtta tgttagtatt aagaacgtta tttatattc aaattttct tttttttctg      3180 tacagacgcg tgtacgcatg taacattata ctgaaaacct tgcttgagaa ggttttggga    3240
cgctcgaagg ctttaatttg caagctggag accaacatgt gagcaaaagg ccagcaaaag    3300
gccaggaacc gtaaaaaggc cgcgttgctg gcgtttttcc ataggctccg ccccctgac    3360 gagcatcaca aaaatcgacg ctcaagtcag aggtggcgaa acccgacagg actataaaga    3420
taccaggcgt ttccccctgg aagctccctc gtgcgctctc ctgttccgac cctgccgctt    3480
accggatacc tgtccgcctt tctcccttcg ggaagcgtgg cgctttctca atgctcacgc    3540
tgtaggtatc tcagttcggt gtaggtcgtt cgctccaagc tgggctgtgt gcacgaaccc    3600
cccgttcagc ccgaccgctg cgccttatcc ggtaactatc gtcttgagtc aacccggta    3660 agacacgact tatcgccact ggcagcagcc actggtaaca ggattagcag agcgaggtat    3720
gtaggcggtg ctacagagtt cttgaagtgg tggcctaact acggctacac tagaaggaca    3780
gtatttggta tctgcgctct gctgaagcca gttaccttcg aaaaagagt tggtagctct    3840 tgatccggca acaaaccac cgctggtagc ggtggttttt tgtttgcaa gcagcagatt     3900 acgcgcagaa aaaaggatc tcaagaagat cctttgatct tttctacggg gtctgacgct    3960
cagtggaacg aaaactcacg ttaagggatt ttggtcatga gatc                    4004
```

<210> SEQ ID NO 60
<211> LENGTH: 4492
<212> TYPE: DNA
<213> ORGANISM: vector pPICZalphaD'E2sH6

<400> SEQUENCE: 60

```
agatctaaca tccaaagacg aaaggttgaa tgaaaccttt ttgccatccg acatccacag      60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggccccctg gcgaggttca tgtttgttta     300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
```

```
ttgaaatgct aacggccagt tggtcaaaaa gaaacttcca aaagtcggca taccgtttgt    540
cttgtttggt attgattgac gaatgctcaa aataatctc attaatgctt agcgcagtct     600
ctctatcgct tctgaacccc ggtgcacctg tgccgaaacg caaatgggga acacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta accttttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc ttcaattttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaaggcatac   1200
ccgcgtgtca ggaggggcag cagcctccga taccaggggc cttgtgtccc tctttagccc   1260
cgggtcggct cagaaaatcc agctcgtaaa caccaacggc agttggcaca tcaacaggac   1320
tgccctgaac tgcaacgact ccctccaaac agggttcttt gccgcactat tctacaaaca   1380
caaattcaac tcgtctggat gcccagagcg cttggccagc tgtcgctcca tcgacaagtt   1440
cgctcagggg tggggtcccc tcacttacac tgagcctaac agctcggacc agaggcccta   1500
ctgctggcac tacgcgcctc gaccgtgtgg tattgtaccc gcgtctcagg tgtgcggtcc   1560
agtgtattgc ttcaccccga gccctgttgt ggtggggacg accgatcggt ttggtgtccc   1620
cacgtataac tgggggcga acgactcgga tgtgctgatt ctcaacaaca cgcggccgcc   1680
gcgaggcaac tggttcggct gtacatggat gaatggcact gggttcacca agacgtgtgg   1740
gggccccccg tgcaacatcg gggggccgg caacaacacc ttgacctgcc ccactgactg   1800
ttttcggaag caccccgagg ccacctacgc cagatgcggt tctgggccct ggctgacacc   1860
taggtgtatg gttcattacc catataggct ctggcactac ccctgcactg tcaacttcac   1920
catcttcaag gttaggatgt acgtgggggg cgtggagcac aggttcgaag ccgcatgcaa   1980
ttggactcga ggagagcgtt gtgacttgga ggacagggga agatcagagc ttagcccgct   2040
gctgctgtct acaacagagt ggcaggtgat cgagggcaga caccatcacc accatcacta   2100
atagttaatt aactgcaggc atgcaagctt atcgataccg tcgacgaatt cgcatgcggc   2160
cgccagcttt ctagaacaaa aactcatctc agaagaggat ctgaatagcg ccgtcgacca   2220
tcatcatcat catcattgag tttgtagcct tagacatgac tgttcctcag ttcaagttgg   2280
gcacttacga gaagaccggt cttgctagat tctaatcaag aggatgtcag aatgccattt   2340
gcctgagaga tgcaggcttc attttttgata ctttttttatt tgtaacctat atagtatagg   2400
attttttttg tcattttgtt tcttctcgta cgagcttgct cctgatcagc ctatctcgca   2460
gctgatgaat atcttgtggt aggggtttgg gaaaatcatt cgagtttgat gttttttcttg   2520
gtatttccca ctcctcttca gagtacagaa gattaagtga gaccttcgtt tgtgcggatc   2580
ccccacacac catagcttca aaatgttcct actccttttt tactcttcca gattttctcg   2640
gactccgcgc atcgccgtac cacttcaaaa cacccaagca cagcatacta aattttccct   2700
cttcttcct ctagggtgtc gttaattacc cgtactaaag gtttggaaaa gaaaaaagag   2760
accgcctcgt ttcttttttct tcgtcgaaaa aggcaataaa aatttttatc acgtttcttt   2820
```

| | |
|---|---:|
| ttcttgaaat tttttttttt agttttttc tctttcagtg acctccattg atatttaagt | 2880 |
| taataaacgg tcttcaattt ctcaagtttc agtttcattt tcttgttct attacaactt | 2940 |
| tttttacttc ttgttcatta gaaagaaagc atagcaatct aatctaaggg gcggtgttga | 3000 |
| caattaatca tcggcatagt atatcggcat agtataatac gacaaggtga ggaactaaac | 3060 |
| catggccaag ttgaccagtg ccgttccggt gctcaccgcg cgcgacgtcg ccggagcggt | 3120 |
| cgagttctgg accgaccggc tcgggttctc ccgggacttc gtggaggacg acttcgccgg | 3180 |
| tgtggtccgg gacgacgtga ccctgttcat cagcgcggtc caggaccagg tggtgccgga | 3240 |
| caacaccctg gcctgggtgt gggtgcgcgg cctggacgag ctgtacgccg agtggtcgga | 3300 |
| ggtcgtgtcc acgaacttcc gggacgcctc cgggccggcc atgaccgaga tcggcgagca | 3360 |
| gccgtggggg cgggagttcg ccctgcgcga cccggccggc aactgcgtgc acttcgtggc | 3420 |
| cgaggagcag gactgacacg tccgacggcg gcccacgggt cccaggcctc ggagatccgt | 3480 |
| cccccttttc ctttgtcgat atcatgtaat tagttatgtc acgcttacat tcacgccctc | 3540 |
| cccccacatc cgctctaacc gaaaaggaag gagttagaca acctgaagtc taggtcccta | 3600 |
| tttatttttt tatagttatg ttagtattaa gaacgttatt tatatttcaa attttctttt | 3660 |
| ttttctgta cagacgcgtg tacgcatgta acattatact gaaaaccttg cttgagaagg | 3720 |
| ttttgggacg ctcgaaggct ttaatttgca agctggagac caacatgtga gcaaaaggcc | 3780 |
| agcaaaaggc caggaaccgt aaaaaggccg cgttgctggc gtttttccat aggctccgcc | 3840 |
| cccctgacga gcatcacaaa aatcgacgct caagtcagag gtggcgaaac ccgacaggac | 3900 |
| tataaagata ccaggcgttt ccccctggaa gctccctcgt gcgctctcct gttccgaccc | 3960 |
| tgccgcttac cggatacctg tccgcctttc tcccttcggg aagcgtggcg ctttctcaat | 4020 |
| gctcacgctg taggtatctc agttcggtgt aggtcgttcg ctccaagctg ggctgtgtgc | 4080 |
| acgaaccccc cgttcagccc gaccgctgcg ccttatccgg taactatcgt cttgagtcca | 4140 |
| acccggtaag acacgactta tcgccactgg cagcagccac tggtaacagg attagcagag | 4200 |
| cgaggtatgt aggcggtgct acagagttct tgaagtggtg gcctaactac ggctacacta | 4260 |
| gaaggacagt atttggtatc tgcgctctgc tgaagccagt taccttcgga aaaagagttg | 4320 |
| gtagctcttg atccggcaaa caaaccaccg ctggtagcgg tggttttttt gtttgcaagc | 4380 |
| agcagattac gcgcagaaaa aaggatctc aagaagatcc tttgatcttt tctacggggt | 4440 |
| ctgacgctca gtggaacgaa aactcacgtt aagggatttt ggtcatgaga tc | 4492 |

<210> SEQ ID NO 61
<211> LENGTH: 4431
<212> TYPE: DNA
<213> ORGANISM: vector pPICZalphaE'E2sH6

<400> SEQUENCE: 61

| | |
|---|---:|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggcccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |

-continued

```
ttgaaatgct aacggccagt tggtcaaaaa gaaacttcca aaagtcggca taccgtttgt      540
cttgtttggt attgattgac gaatgctcaa aataatctc attaatgctt agcgcagtct      600
ctctatcgct tctgaacccc ggtgcacctg tgccgaaacg caaatgggga aacacccgct      660
ttttggatga ttatgcattg tctccacatt gtatgcttcc aagattctgg tgggaatact      720
gctgatagcc taacgttcat gatcaaaatt taactgttct aacccctact tgacagcaat      780
atataaacag aaggaagctg ccctgtctta aaccttttt tttatcatca ttattagctt      840
actttcataa ttgcgactgg ttccaattga caagcttttg atttttaacga cttttaacga      900 caacttgaga agatcaaaaa acaactaatt attcgaaacg atgagatttc cttcaatttt      960
tactgctgtt ttattcgcag catcctccgc attagctgct ccagtcaaca ctacaacaga     1020
agatgaaacg gcacaaattc cggctgaagc tgtcatcggt tactcagatt tagaagggga     1080
tttcgatgtt gctgtttgc cattttccaa cagcacaaat aacgggttat tgtttataaa     1140
tactactatt gccagcattg ctgctaaaga agaagggta tctctcgaga aaagagaggc     1200
tgaagcccat acccgcgtgt caggagggc agcagcctcc gataccaggg gccttgtgtc     1260
cctctttagc cccgggtcgg ctcagaaaat ccagctcgta acaccaacg gcagttggca     1320 catcaacagg actgccctga actgcaacga ctccctccaa acagggttct ttgccgcact     1380
attctacaaa cacaaattca actcgtctgg atgcccagag cgcttggcca gctgtcgctc     1440
catcgacaag ttcgctcagg ggtgggtc cctcacttac actgagccta acagctcgga     1500
ccagaggccc tactgctggc actacgcgcc tcgaccgtgt ggtattgtac ccgcgtctca     1560
ggtgtgcggt ccagtgtatt gcttcacccc gagccctgtt gtggtgggga cgaccgatcg     1620
gtttggtgtc cccacgtata actgggggc gaacgactcg gatgtgctga ttctcaacaa     1680
cacgcggccg ccgcgaggca actggttcgg ctgtacatgg atgaatggca ctgggttcac     1740
caagacgtgt gggggccccc cgtgcaacat cgggggggcc ggcaacaaca ccttgacctg     1800
ccccactgac tgttttcgga agcaccccga ggccacctac gccagatgcg gttctgggcc     1860
ctggctgaca cctaggtgta tggttcatta cccatatagg ctctggcact accccctgcac     1920 tgtcaacttc accatcttca aggttaggat gtacgtgggg ggcgtggagc acaggttcga     1980
agccgcatgc aattggactc gaggagagcg ttgtgacttg gaggacaggg atagatcaga     2040
gcttagcccg ctgctgctgt ctacaacaga gtggcaggtg atcgagggca gacaccatca     2100
ccaccatcac taatagttaa ttaactgcag gcatgcaagc ttatcgatac cgtcgaccat     2160
catcatcatc atcattgagt ttgtagcctt agacatgact gttcctcagt tcaagttggg     2220
cacttacgag aagaccggtc ttgctagatt ctaatcaaga ggatgtcaga atgccatttg     2280
cctgagagat gcaggcttca ttttgatac ttttttattt gtaacctata tagtatagga     2340
ttttttttgt cattttgttt cttctcgtac gagcttgctc ctgatcagcc tatctcgcag     2400
ctgatgaata tcttgtggta ggggtttggg aaaatcattc gagtttgatg ttttttcttgg     2460 tatttcccac tcctcttcag agtacagaag attaagtgag accttcgttt gtgcggatcc     2520
cccacacacc atagcttcaa aatgtttcta ctccttttt actcttccag attttctcgg     2580
actccgcgca tcgccgtacc acttcaaaac acccaagcac agcatactaa attttccctc     2640
tttcttcctc tagggtgtcg ttaattaccc gtactaaagg tttggaaaag aaaaagaga     2700 ccgcctcgtt tctttttctt cgtcgaaaaa ggcaataaaa attttatca cgtttctttt     2760 tcttgaaatt ttttttttta gttttttct ctttcagtga cctccattga tatttaagtt     2820
```

-continued

| | |
|---|---|
| aataaacggt cttcaatttc tcaagtttca gtttcatttt tcttgttcta ttacaacttt | 2880 |
| ttttacttct tgttcattag aaagaaagca tagcaatcta atctaagggg cggtgttgac | 2940 |
| aattaatcat cggcatagta tatcggcata gtataatacg acaaggtgag gaactaaacc | 3000 |
| atggccaagt tgaccagtgc cgttccggtg ctcaccgcgc gcgacgtcgc cggagcggtc | 3060 |
| gagttctgga ccgaccggct cgggttctcc cgggacttcg tggaggacga cttcgccggt | 3120 |
| gtggtccggg acgacgtgac cctgttcatc agcgcggtcc aggaccaggt ggtgccggac | 3180 |
| aacaccctgg cctgggtgtg ggtgcgcggc ctggacgagc tgtacgccga gtggtcggag | 3240 |
| gtcgtgtcca cgaacttccg ggacgcctcc gggccggcca tgaccgagat cggcgagcag | 3300 |
| ccgtgggggc gggagttcgc cctgcgcgac ccggccggca actgcgtgca cttcgtggcc | 3360 |
| gaggagcagg actgacacgt ccgacggcgg cccacgggtc ccaggcctcg agatccgtc | 3420 |
| ccccttttcc tttgtcgata tcatgtaatt agttatgtca cgcttacatt cacgccctcc | 3480 |
| ccccacatcc gctctaaccg aaaggaagg agttagacaa cctgaagtct aggtccctat | 3540 |
| ttatttttt atagttatgt tagtattaag aacgttattt atatttcaaa ttttctttt | 3600 |
| ttttctgtac agacgcgtgt acgcatgtaa cattatactg aaaaccttgc ttgagaaggt | 3660 |
| tttgggacgc tcgaaggctt taatttgcaa gctggagacc aacatgtgag caaaaggcca | 3720 |
| gcaaaaggcc aggaaccgta aaaaggccgc gttgctggcg ttttccata ggctccgccc | 3780 |
| ccctgacgag catcacaaaa atcgacgctc aagtcagagg tggcgaaacc cgacaggact | 3840 |
| ataaagatac caggcgtttc ccctggaag ctccctcgtg cgctctcctg ttccgaccct | 3900 |
| gccgcttacc ggatacctgt ccgcctttct cccttcggga agcgtggcgc tttctcaatg | 3960 |
| ctcacgctgt aggtatctca gttcggtgta ggtcgttcgc tccaagctgg gctgtgtgca | 4020 |
| cgaaccccc gttcagcccg accgctgcgc cttatccggt aactatcgtc ttgagtccaa | 4080 |
| cccggtaaga cacgacttat cgccactggc agcagccact ggtaacagga ttagcagagc | 4140 |
| gaggtatgta ggcggtgcta cagagttctt gaagtggtgg cctaactacg gctacactag | 4200 |
| aaggacagta tttggtatct gcgctctgct gaagccagtt accttcggaa aaagagttgg | 4260 |
| tagctcttga tccggcaaac aaaccaccgc tggtagcggt ggtttttttg tttgcaagca | 4320 |
| gcagattacg cgcagaaaaa aaggatctca agaagatcct ttgatctttt ctacggggtc | 4380 |
| tgacgctcag tggaacgaaa actcacgtta agggattttg gtcatgagat c | 4431 |

<210> SEQ ID NO 62
<211> LENGTH: 2880
<212> TYPE: DNA
<213> ORGANISM: vector pUC18MFa

<400> SEQUENCE: 62

| | |
|---|---|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg ccaagcttac | 240 |
| cccttcttct ttagcagcaa tgctggcaat agtagtattt ataaacaata cccgttatt | 300 |
| tgtgctgttg gaaatggca aaacagcaac atcgaaatcc ccttctaaat ctgagtaacc | 360 |
| gatgacagct tcagccggaa tttgtgccgt tcatcttct gttgtagtgt tgactggagc | 420 |
| agctaatgcg gaggatgctg cgaataaaac tgcagtaaaa attgaaggaa atctcatgaa | 480 |
| ttcactggcc gtcgttttac aacgtcgtga ctgggaaaac cctggcgtta cccaacttaa | 540 |

-continued

```
tcgccttgca gcacatcccc ctttcgccag ctggcgtaat agcgaagagg cccgcaccga      600
tcgcccttcc caacagttgc gcagcctgaa tggcgaatgg cgcctgatgc ggtattttct      660
ccttacgcat ctgtgcggta tttcacaccg catatggtgc actctcagta caatctgctc      720
tgatgccgca tagttaagcc agccccgaca cccgccaaca cccgctgacg cgccctgacg      780
ggcttgtctg ctcccggcat ccgcttacag acaagctgtg accgtctccg ggagctgcat      840
gtgtcagagg ttttcaccgt catcaccgaa acgcgcgaga cgaaagggcc tcgtgatacg      900
cctattttta taggttaatg tcatgataat aatggtttct tagacgtcag gtggcacttt      960
tcggggaaat gtgcgcggaa cccctatttg tttatttttc taaatacatt caaatatgta     1020
tccgctcatg agacaataac cctgataaat gcttcaataa tattgaaaaa ggaagagtat     1080
gagtattcaa catttccgtg tcgcccttat cccttttttt gcggcatttt gccttcctgt     1140
ttttgctcac ccagaaacgc tggtgaaagt aaaagatgct gaagatcagt tgggtgcacg     1200
agtgggttac atcgaactgg atctcaacag cggtaagatc cttgagagtt ttcgccccga     1260
agaacgtttt ccaatgatga gcacttttaa agttctgcta tgtggcgcgg tattatcccg     1320
tattgacgcc gggcaagagc aactcggtcg ccgcatacac tattctcaga atgacttggt     1380
tgagtactca ccagtcacag aaaagcatct tacggatggc atgacagtaa gagaattatg     1440
cagtgctgcc ataaccatga gtgataacac tgcggccaac ttacttctga caacgatcgg     1500
aggaccgaag gagctaaccg cttttttgca acatggggg gatcatgtaa ctcgccttga     1560
tcgttgggaa ccggagctga atgaagccat accaaacgac gagcgtgaca ccacgatgcc     1620
tgtagcaatg gcaacaacgt tgcgcaaact attaactggc gaactactta ctctagcttc     1680
ccggcaacaa ttaatagact ggatggaggc ggataaagtt gcaggaccac ttctgcgctc     1740
ggcccttccg gctggctggt ttattgctga taaatctgga gccggtgagc gtgggtctcg     1800
cggtatcatt gcagcactgg ggccagatgg taagccctcc cgtatcgtag ttatctacac     1860 gacgggagt caggcaacta tggatgaacg aaatagacag atcgctgaga taggtgcctc     1920
actgattaag cattggtaac tgtcagacca agtttactca tatatacttt agattgattt     1980
aaaacttcat ttttaattta aaaggatcta ggtgaagatc ctttttgata atctcatgac     2040
caaaatccct taacgtgagt tttcgttcca ctgagcgtca ccccgtag aaaagatcaa     2100 aggatcttct tgagatcctt ttttttctgcg cgtaatctgc tgcttgcaaa caaaaaaacc     2160
accgctacca gcggtggttt gtttgccgga tcaagagcta ccaactcttt ttccgaaggt     2220
aactggcttc agcagagcgc agataccaaa tactgtcctt ctagtgtagc cgtagttagg     2280
ccaccacttc aagaactctg tagcaccgcc tacatacctc gctctgctaa tcctgttacc     2340
agtggctgct gccagtggcg ataagtcgtg tcttaccggg ttggactcaa gacgatagtt     2400
accggataag cgcagcggt cgggctgaac ggggggttcg tgcacacagc ccagcttgga     2460
gcgaacgacc tacaccgaac tgagatacct acagcgtgag ctatgagaaa gcgccacgct     2520
tcccgaaggg agaaaggcgg acaggtatcc ggtaagcggc agggtcggaa caggagagcg     2580
cacgagggag cttccagggg gaaacgcctg gtatctttat agtcctgtcg gtttcgcca     2640 cctctgactt gagcgtcgat ttttgtgatg ctcgtcaggg gggcggagcc tatggaaaaa     2700
cgccagcaac gcggcctttt tacggttcct ggccttttgc tggccttttg ctcacatgtt     2760
ctttcctgcg ttatcccctg attctgtgga taaccgtatt accgcctttg agtgagctga     2820
taccgctcgc cgcagccgaa cgaccgagcg cagcgagtca gtgagcgagg aagcggaaga     2880
```

```
<210> SEQ ID NO 63
<211> LENGTH: 6
<212> TYPE: PRT
<213> ORGANISM: adaptor peptide

<400> SEQUENCE: 63

His His His His His His
1               5

<210> SEQ ID NO 64
<211> LENGTH: 6
<212> TYPE: PRT
<213> ORGANISM: adaptor peptide

<400> SEQUENCE: 64

Glu Glu Gly Glu Pro Lys
1               5

<210> SEQ ID NO 65
<211> LENGTH: 6
<212> TYPE: PRT
<213> ORGANISM: adaptor peptide

<400> SEQUENCE: 65

Glu Glu Ala Glu Pro Lys
1               5

<210> SEQ ID NO 66
<211> LENGTH: 5
<212> TYPE: PRT
<213> ORGANISM: processing site
<220> FEATURE:
<221> NAME/KEY: MISC_FEATURE
<222> LOCATION: (5)..(5)
<223> OTHER INFORMATION: X is any amino acid

<400> SEQUENCE: 66

Ile Glu Gly Arg Xaa
1               5

<210> SEQ ID NO 67
<211> LENGTH: 5
<212> TYPE: PRT
<213> ORGANISM: processing site
<220> FEATURE:
<221> NAME/KEY: MISC_FEATURE
<222> LOCATION: (5)..(5)
<223> OTHER INFORMATION: X is any amino acid

<400> SEQUENCE: 67

Ile Asp Gly Arg Xaa
1               5

<210> SEQ ID NO 68
<211> LENGTH: 5
<212> TYPE: PRT
<213> ORGANISM: processing site
<220> FEATURE:
<221> NAME/KEY: MISC_FEATURE
<222> LOCATION: (5)..(5)
<223> OTHER INFORMATION: X is any amino acid

<400> SEQUENCE: 68

Ala Glu Gly Arg Xaa
1               5
```

```
<210> SEQ ID NO 69
<211> LENGTH: 5
<212> TYPE: PRT
<213> ORGANISM: adaptor peptide

<400> SEQUENCE: 69

Val Ile Glu Gly Arg
1               5

<210> SEQ ID NO 70
<211> LENGTH: 4
<212> TYPE: PRT
<213> ORGANISM: adaptor peptide

<400> SEQUENCE: 70

Ile Glu Gly Arg
1

<210> SEQ ID NO 71
<211> LENGTH: 4
<212> TYPE: PRT
<213> ORGANISM: adaptor peptide

<400> SEQUENCE: 71

Ile Asp Gly Arg
1

<210> SEQ ID NO 72
<211> LENGTH: 4
<212> TYPE: PRT
<213> ORGANISM: adaptor peptide

<400> SEQUENCE: 72

Ala Glu Gly Arg
1

<210> SEQ ID NO 73
<211> LENGTH: 4
<212> TYPE: PRT
<213> ORGANISM: HCV E1

<400> SEQUENCE: 73

Asn Asn Ser Ser
1

<210> SEQ ID NO 74
<211> LENGTH: 8
<212> TYPE: PRT
<213> ORGANISM: FLAG epitope

<400> SEQUENCE: 74

Asp Tyr Lys Asp Asp Asp Asp Lys
1               5

<210> SEQ ID NO 75
<211> LENGTH: 12
<212> TYPE: PRT
<213> ORGANISM: Protein C epitope

<400> SEQUENCE: 75

Glu Asp Gln Val Asp Pro Arg Leu Ile Asp Gly Lys
1               5                   10

<210> SEQ ID NO 76
<211> LENGTH: 11
```

```
<212> TYPE: PRT
<213> ORGANISM: VSV epitope

<400> SEQUENCE: 76

Tyr Thr Asp Ile Glu Met Asn Arg Leu Gly Lys
1               5                   10

<210> SEQ ID NO 77
<211> LENGTH: 9
<212> TYPE: PRT
<213> ORGANISM: streptag

<400> SEQUENCE: 77

Ala Trp Arg His Pro Gln Phe Gly Gly
1               5

<210> SEQ ID NO 78
<211> LENGTH: 12
<212> TYPE: PRT
<213> ORGANISM: Tag100 epitope

<400> SEQUENCE: 78

Glu Glu Thr Ala Arg Phe Gln Pro Gly Tyr Arg Ser
1               5                   10

<210> SEQ ID NO 79
<211> LENGTH: 10
<212> TYPE: PRT
<213> ORGANISM: c-myc epitope

<400> SEQUENCE: 79

Glu Gln Lys Leu Ile Ser Glu Glu Asp Leu
1               5                   10

<210> SEQ ID NO 80
<211> LENGTH: 11
<212> TYPE: PRT
<213> ORGANISM: HA epitope

<400> SEQUENCE: 80

Tyr Pro Tyr Asp Val Pro Asp Tyr Ala Ser Leu
1               5                   10

<210> SEQ ID NO 81
<211> LENGTH: 9
<212> TYPE: PRT
<213> ORGANISM: HA epitope

<400> SEQUENCE: 81

Tyr Pro Tyr Asp Val Pro Asp Tyr Ala
1               5

<210> SEQ ID NO 82
<211> LENGTH: 12
<212> TYPE: PRT
<213> ORGANISM: HA epitope

<400> SEQUENCE: 82

Cys Tyr Pro Tyr Asp Val Pro Asp Tyr Ala Ser Leu
1               5                   10

<210> SEQ ID NO 83
<211> LENGTH: 6
<212> TYPE: PRT
<213> ORGANISM: thrombin cleavage site
```

```
<400> SEQUENCE: 83

Leu Val Pro Arg Gly Ser
1               5

<210> SEQ ID NO 84
<211> LENGTH: 4
<212> TYPE: PRT
<213> ORGANISM: collagenase recognition site
<220> FEATURE:
<221> NAME/KEY: MISC_FEATURE
<222> LOCATION: (2)..(2)
<223> OTHER INFORMATION: Xaa is any amino acid but most frequently a
      neutral amino acid

<400> SEQUENCE: 84

Pro Xaa Gly Pro
1

<210> SEQ ID NO 85
<211> LENGTH: 192
<212> TYPE: PRT
<213> ORGANISM: hepatitis C virus

<400> SEQUENCE: 85

Tyr Gln Val Arg Asn Ser Ser Gly Leu Tyr His Val Thr Asn Asp Cys
1               5                   10                  15

Pro Asn Ser Ser Val Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Val Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg His His Trp Thr Thr Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Val Ala
    130                 135                 140

Gln Leu Leu Arg Ile Pro Gln Ala Ile Met Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Glu Val Leu Val Val Leu Leu Leu Phe Ala Gly Val Asp Ala
            180                 185                 190

<210> SEQ ID NO 86
<211> LENGTH: 209
<212> TYPE: PRT
<213> ORGANISM: hepatitis C virus

<400> SEQUENCE: 86

Met Leu Gly Lys Leu Ile Asp Thr Leu Thr Cys Gly Phe Ala Asp Leu
1               5                   10                  15

Met Gly Tyr Ile Pro Leu Val Gly Ala Pro Leu Gly Gly Ala Ala Arg
            20                  25                  30
```

```
Ala Leu Ala His Gly Ala Arg Val Leu Glu Asp Gly Val Ile Tyr Ala
            35                  40                  45

Thr Gly Asn Leu Pro Gly Cys Ser Phe Ser Ile Phe Leu Leu Ala Leu
 50                  55                  60

Leu Ser Cys Leu Thr Val Pro Ala Ser Ala Tyr Gln Val Arg Asn Ser
 65                  70                  75                  80

Ser Gly Leu Tyr His Val Thr Asn Asp Cys Pro Asn Ser Ser Val Val
                 85                  90                  95

Tyr Glu Ala Ala Asp Ala Ile Leu His Thr Pro Gly Cys Val Pro Cys
            100                 105                 110

Val Arg Glu Gly Asn Ala Ser Arg Cys Trp Val Ala Val Thr Pro Thr
        115                 120                 125

Val Ala Thr Arg Asp Gly Lys Leu Pro Thr Thr Gln Leu Arg Arg His
    130                 135                 140

Ile Asp Leu Leu Val Gly Ser Ala Thr Leu Cys Ser Ala Leu Tyr Val
145                 150                 155                 160

Gly Asp Leu Cys Gly Ser Val Phe Leu Val Gly Gln Leu Phe Thr Phe
                165                 170                 175

Ser Pro Arg His His Trp Thr Thr Gln Asp Cys Asn Cys Ser Ile Tyr
            180                 185                 190

Pro Gly His Ile Thr Gly His Arg Met Ala Trp Asp Met Met Met Asn
        195                 200                 205

Trp

<210> SEQ ID NO 87
<211> LENGTH: 192
<212> TYPE: PRT
<213> ORGANISM: hepatitis C virus

<400> SEQUENCE: 87

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Val Ser
    130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Val Val Met Leu Leu Phe Ala Gly Val Asp Gly
            180                 185                 190
```

<210> SEQ ID NO 88
<211> LENGTH: 209
<212> TYPE: PRT
<213> ORGANISM: hepatitis C virus

<400> SEQUENCE: 88

Met Leu Gly Lys Val Ile Asp Thr Leu Thr Cys Gly Phe Ala Asp Leu
1               5                   10                  15

Met Gly Tyr Ile Pro Leu Val Gly Ala Pro Leu Gly Gly Ala Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Ile Pro Ala Ser Ala Tyr Glu Val Arg Asn Val
65                  70                  75                  80

Ser Gly Met Tyr His Val Thr Asn Asp Cys Ser Asn Ser Ser Ile Val
                85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125

Leu Ala Ala Arg Asn Ala Ser Val Pro Thr Thr Thr Ile Arg Arg His
    130                 135                 140

Val Asp Leu Leu Val Gly Ala Ala Ala Phe Cys Ser Ala Met Tyr Val
145                 150                 155                 160

Gly Asp Leu Cys Gly Ser Val Phe Leu Val Ser Gln Leu Phe Thr Ile
                165                 170                 175

Ser Pro Arg Arg His Glu Thr Val Gln Asp Cys Asn Cys Ser Ile Tyr
            180                 185                 190

Pro Gly His Ile Thr Gly His Arg Met Ala Trp Asp Met Met Met Asn
        195                 200                 205

Trp

<210> SEQ ID NO 89
<211> LENGTH: 209
<212> TYPE: PRT
<213> ORGANISM: hepatitis C virus

<400> SEQUENCE: 89

Met Leu Gly Lys Val Ile Asp Thr Leu Thr Cys Gly Phe Ala Asp Leu
1               5                   10                  15

Met Gly Tyr Ile Pro Val Val Gly Ala Pro Val Gly Gly Val Ala Arg
            20                  25                  30

Ala Leu Ala His Gly Val Arg Val Leu Glu Asp Gly Ile Asn Tyr Ala
        35                  40                  45

Thr Gly Asn Leu Pro Gly Cys Ser Phe Ser Ile Phe Leu Leu Ala Leu
    50                  55                  60

Leu Ser Cys Ile Thr Thr Pro Val Ser Ala Val Glu Val Lys Asn Asn
65                  70                  75                  80

Ser Asn Ser Tyr Met Ala Thr Asn Asp Cys Ser Asn Ser Ser Ile Ile
                85                  90                  95

Trp Gln Leu Glu Gly Ala Val Leu His Thr Pro Gly Cys Val Pro Cys
            100                 105                 110

-continued

Glu Leu Ala Asp Asn Thr Ser Arg Cys Trp Val Pro Val Thr Pro Asn
            115                 120                 125

Met Ala Ile Arg Gln Pro Gly Glu Leu Thr Lys Gly Leu Arg Ala His
    130                 135                 140

Val Asp Val Ile Val Met Ser Ala Thr Leu Cys Ser Ala Leu Tyr Val
145                 150                 155                 160

Gly Asp Val Cys Gly Ala Leu Met Ile Ala Ala Gln Val Val Val Val
                165                 170                 175

Ser Pro Gln His His His Phe Val Gln Glu Cys Asn Cys Ser Ile Tyr
            180                 185                 190

Pro Gly His Ile Thr Gly His Arg Met Ala Trp Asp Met Met Met Asn
            195                 200                 205

Trp

<210> SEQ ID NO 90
<211> LENGTH: 209
<212> TYPE: PRT
<213> ORGANISM: hepatitis C virus

<400> SEQUENCE: 90

Met Leu Gly Lys Val Ile Asp Thr Leu Thr Cys Gly Phe Ala Asp Leu
1               5                   10                  15

Met Gly Tyr Ile Pro Val Val Gly Ala Pro Val Gly Val Ala Arg
            20                  25                  30

Ala Leu Ala His Gly Val Arg Val Leu Glu Asp Gly Ile Asn Tyr Ala
            35                  40                  45

Thr Gly Asn Leu Pro Gly Cys Ser Phe Ser Ile Phe Leu Leu Ala Leu
    50                  55                  60

Leu Ser Cys Val Thr Ala Pro Val Ser Ala Val Glu Val Lys Asn Thr
65                  70                  75                  80

Ser Gln Ala Tyr Met Ala Thr Asn Asp Cys Ser Asn Asn Ser Ile Val
                85                  90                  95

Trp Gln Leu Glu Asp Ala Val Leu His Val Pro Gly Cys Val Pro Cys
            100                 105                 110

Glu Asn Ser Ser Gly Arg Phe His Cys Trp Ile Pro Ile Ser Pro Asn
            115                 120                 125

Ile Ala Val Ser Lys Pro Gly Ala Leu Thr Lys Gly Leu Arg Ala Arg
            130                 135                 140

Ile Asp Ala Val Val Met Ser Ala Thr Leu Cys Ser Ala Leu Tyr Val
145                 150                 155                 160

Gly Asp Val Cys Gly Ala Val Met Ile Ala Ala Gln Ala Phe Ile Val
                165                 170                 175

Ala Pro Lys Arg His Tyr Phe Val Gln Glu Cys Asn Cys Ser Ile Tyr
            180                 185                 190

Pro Gly His Ile Thr Gly His Arg Met Ala Trp Asp Met Met Met Asn
            195                 200                 205

Trp

<210> SEQ ID NO 91
<211> LENGTH: 209
<212> TYPE: PRT
<213> ORGANISM: hepatitis C virus

<400> SEQUENCE: 91

Met Leu Gly Lys Val Ile Asp Thr Leu Thr Cys Gly Phe Ala Asp Leu
1               5                   10                  15

```
Met Gly Tyr Ile Pro Leu Val Gly Ala Pro Val Gly Gly Val Ala Arg
            20                  25                  30

Ala Leu Ala His Gly Val Arg Ala Leu Glu Asp Gly Ile Asn Phe Ala
            35                  40                  45

Thr Gly Asn Leu Pro Gly Cys Ser Phe Ser Ile Phe Leu Leu Ala Leu
    50                  55                  60

Phe Ser Cys Leu Ile His Pro Ala Ala Ser Leu Glu Trp Arg Asn Thr
65                  70                  75                  80

Ser Gly Leu Tyr Val Leu Thr Asn Asp Cys Ser Asn Ser Ser Ile Val
                85                  90                  95

Tyr Glu Ala Asp Asp Val Ile Leu His Thr Pro Gly Cys Ile Pro Cys
            100                 105                 110

Val Gln Asp Gly Asn Thr Ser Thr Cys Trp Thr Pro Val Thr Pro Thr
            115                 120                 125

Val Ala Val Lys Tyr Val Gly Ala Thr Thr Ala Ser Ile Arg Ser His
            130                 135                 140

Val Asp Leu Leu Val Gly Ala Ala Thr Met Cys Ser Ala Leu Tyr Val
145                 150                 155                 160

Gly Asp Met Cys Gly Ala Val Phe Leu Val Gly Gln Ala Phe Thr Phe
                165                 170                 175

Arg Pro Arg Arg His Gln Thr Val Gln Thr Cys Asn Cys Ser Leu Tyr
            180                 185                 190

Pro Gly His Leu Ser Gly His Arg Met Ala Trp Asp Met Met Met Asn
                195                 200                 205

Trp

<210> SEQ ID NO 92
<211> LENGTH: 209
<212> TYPE: PRT
<213> ORGANISM: hepatitis C virus

<400> SEQUENCE: 92

Met Ser Gly Lys Val Ile Asp Thr Leu Thr Cys Gly Phe Ala Asp Leu
1               5                   10                  15

Met Gly Tyr Ile Pro Leu Val Gly Ala Pro Val Gly Gly Val Ala Arg
            20                  25                  30

Ala Leu Ala His Gly Val Arg Ala Val Glu Asp Gly Ile Asn Tyr Ala
            35                  40                  45

Thr Gly Asn Leu Pro Gly Cys Ser Phe Ser Ile Phe Leu Leu Ala Leu
    50                  55                  60

Leu Ser Cys Leu Thr Val Pro Thr Ser Ala Val Asn Tyr Arg Asn Ala
65                  70                  75                  80

Ser Gly Val Tyr His Ile Thr Asn Asp Cys Pro Asn Ser Ser Ile Val
                85                  90                  95

Tyr Glu Thr Glu His His Ile Leu His Leu Pro Gly Cys Leu Pro Cys
            100                 105                 110

Val Arg Val Gly Asn Gln Ser Arg Cys Trp Val Ala Leu Thr Pro Thr
            115                 120                 125

Val Ala Ala Pro Tyr Ile Gly Ala Pro Leu Glu Ser Leu Arg Ser His
            130                 135                 140

Val Asp Leu Met Val Gly Ala Ala Thr Ala Cys Ser Ala Leu Tyr Ile
145                 150                 155                 160

Gly Asp Leu Cys Gly Gly Val Phe Leu Val Gly Gln Met Phe Ser Phe
                165                 170                 175
```

-continued

```
Gln Pro Arg Arg His Trp Thr Thr Gln Asp Cys Asn Cys Ser Ile Tyr
            180                 185                 190

Ala Gly His Val Thr Gly His Arg Met Ala Trp Asp Met Met Met Asn
        195                 200                 205

Trp

<210> SEQ ID NO 93
<211> LENGTH: 209
<212> TYPE: PRT
<213> ORGANISM: hepatitis C virus

<400> SEQUENCE: 93

Met Leu Gly Lys Val Ile Asp Thr Leu Thr Cys Gly Phe Ala Asp Leu
1               5                   10                  15

Met Gly Tyr Ile Pro Leu Val Gly Gly Pro Ile Gly Val Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Ile Leu Ala Leu
    50                  55                  60

Leu Ser Cys Leu Thr Val Pro Ala Ser Ala Val Pro Tyr Arg Asn Ala
65                  70                  75                  80

Ser Gly Ile Tyr His Val Thr Asn Asp Cys Pro Asn Ser Ser Ile Val
                85                  90                  95

Tyr Glu Ala Asp Asn Leu Ile Leu His Ala Pro Gly Cys Val Pro Cys
            100                 105                 110

Val Met Thr Gly Asn Val Ser Arg Cys Trp Val Gln Ile Thr Pro Thr
        115                 120                 125

Leu Ser Ala Pro Ser Leu Gly Ala Val Thr Ala Pro Leu Arg Arg Ala
    130                 135                 140

Val Asp Tyr Leu Ala Gly Gly Ala Ala Leu Cys Ser Ala Leu Tyr Val
145                 150                 155                 160

Gly Asp Ala Cys Gly Ala Leu Phe Leu Val Gly Gln Met Phe Thr Tyr
                165                 170                 175

Arg Pro Arg Gln His Ala Thr Val Gln Asn Cys Asn Cys Ser Ile Tyr
            180                 185                 190

Ser Gly His Val Thr Gly His Arg Met Ala Trp Asp Met Met Met Asn
        195                 200                 205

Trp

<210> SEQ ID NO 94
<211> LENGTH: 209
<212> TYPE: PRT
<213> ORGANISM: hepatitis C virus

<400> SEQUENCE: 94

Met Leu Gly Lys Val Ile Asp Thr Leu Thr Cys Gly Phe Ala Asp Leu
1               5                   10                  15

Met Gly Tyr Ile Pro Val Val Gly Ala Pro Leu Gly Gly Val Ala Ala
            20                  25                  30

Ala Phe Ala His Gly Val Arg Ala Leu Glu Asp Gly Ile Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Thr Pro Ala Ser Ala Leu Thr Tyr Gly Asn Ser
```

```
                 65                  70                  75                  80
Ser Gly Leu Tyr His Leu Thr Asn Asp Cys Pro Asn Ser Ser Ile Val
                     85                  90                  95

Leu Glu Ala Asp Ala Met Ile Leu His Leu Pro Gly Cys Leu Pro Cys
            100                 105                 110

Val Arg Val Asn Asn Gln Ser Thr Cys Trp His Ala Val Ser Pro Thr
        115                 120                 125

Leu Ala Ile Pro Asn Ala Ser Thr Pro Ala Thr Gly Phe Arg Arg His
        130                 135                 140

Val Asp Leu Leu Ala Gly Ala Val Val Cys Ser Ser Leu Tyr Ile
145                 150                 155                 160

Gly Asp Leu Cys Gly Ser Leu Phe Leu Ala Gly Gln Leu Phe Thr Phe
                165                 170                 175

Gln Pro Arg Arg His Trp Thr Val Gln Asp Cys Asn Cys Ser Ile Tyr
            180                 185                 190

Thr Gly His Val Thr Gly His Arg Met Ala Trp Asp Met Met Met Asn
        195                 200                 205

Trp

<210> SEQ ID NO 95
<211> LENGTH: 209
<212> TYPE: PRT
<213> ORGANISM: hepatitis C virus

<400> SEQUENCE: 95

Met Leu Gly Lys Val Ile Asp Thr Leu Thr Cys Gly Phe Ala Asp Leu
1               5                   10                  15

Met Gly Tyr Ile Pro Val Val Gly Ala Pro Leu Gly Gly Ile Ala Ala
            20                  25                  30

Ala Leu Ala His Gly Val Arg Ala Val Glu Asp Gly Ile Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Thr Pro Ala Ser Ala Val His Tyr Ala Asn Lys
65                  70                  75                  80

Ser Gly Leu Tyr His Leu Thr Asn Asp Cys Pro Asn Ser Ser Ile Val
                85                  90                  95

Tyr Glu Ala Pro Ala Val Ile Met His Leu Pro Gly Cys Val Pro Cys
            100                 105                 110

Val Lys Val Gly Asn Gln Ser Thr Cys Trp Leu Pro Ala Ser Pro Thr
        115                 120                 125

Leu Ala Val Pro Asn Ala Ser Thr Pro Leu Thr Arg Phe Arg Lys His
        130                 135                 140

Val Asp Leu Met Val Gly Ala Ala Ala Phe Cys Ser Ala Met Tyr Val
145                 150                 155                 160

Gly Asp Ile Cys Gly Gly Leu Phe Leu Leu Gly Gln Val Val Thr Ile
                165                 170                 175

Arg Pro Arg Leu His Gln Thr Val Gln Glu Cys Asn Cys Ser Ile Tyr
            180                 185                 190

Thr Gly Lys Ile Thr Gly His Arg Met Ala Trp Asp Ile Met Met Asn
        195                 200                 205

Trp

<210> SEQ ID NO 96
```

```
<211> LENGTH: 209
<212> TYPE: PRT
<213> ORGANISM: hepatitis C virus

<400> SEQUENCE: 96

Met Leu Gly Lys Val Ile Asp Thr Leu Thr Cys Gly Leu Ala Asp Leu
1               5                   10                  15

Met Gly Tyr Ile Pro Val Leu Gly Gly Pro Leu Gly Val Ala Ala
            20                  25                  30

Ala Leu Ala His Gly Val Arg Ala Ile Glu Asp Gly Val Asn Tyr Ala
            35                  40                  45

Thr Gly Asn Leu Pro Gly Cys Ser Phe Ser Ile Leu Leu Leu Ala Leu
        50                  55                  60

Leu Ser Cys Leu Thr Ile Pro Ala Ser Ala Ile Gln Val Lys Asn Ala
65                  70                  75                  80

Ser Gly Ile Tyr His Leu Thr Asn Asp Cys Ser Asn Asn Ser Ile Val
                85                  90                  95

Phe Glu Ala Glu Thr Met Ile Leu His Leu Pro Gly Cys Val Pro Cys
            100                 105                 110

Ile Lys Ala Gly Asn Glu Ser Arg Cys Trp Leu Pro Val Ser Pro Thr
        115                 120                 125

Leu Ala Val Pro Asn Ser Ser Val Pro Ile His Gly Phe Arg Arg His
130                 135                 140

Val Asp Leu Leu Val Gly Ala Ala Ala Phe Cys Ser Ala Met Tyr Ile
145                 150                 155                 160

Gly Asp Leu Cys Gly Ser Ile Phe Leu Val Gly Gln Leu Phe Thr Phe
                165                 170                 175

Arg Pro Lys Tyr His Gln Val Thr Gln Asp Cys Asn Cys Ser Ile Tyr
            180                 185                 190

Ala Gly His Ile Thr Gly His Arg Met Ala Trp Asp Met Met Met Asn
        195                 200                 205

Trp

<210> SEQ ID NO 97
<211> LENGTH: 363
<212> TYPE: PRT
<213> ORGANISM: hepatitis C virus

<400> SEQUENCE: 97

Glu Thr His Val Thr Gly Gly Asn Ala Gly Arg Thr Thr Ala Gly Pro
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Arg Pro Cys Gly
            100                 105                 110

Ile Val Pro Ala Lys Ser Val Cys Gly Pro Val Tyr Cys Phe Thr Pro
        115                 120                 125
```

Ser Pro Val Val Gly Thr Asp Arg Ser Gly Ala Pro Thr Tyr
130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Glu Phe
            340                 345                 350

Trp Met Met Leu Leu Ile Ser Gln Ala Glu Ala
        355                 360

<210> SEQ ID NO 98
<211> LENGTH: 363
<212> TYPE: PRT
<213> ORGANISM: hepatitis C virus

<400> SEQUENCE: 98

His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Val Gly Thr Asp Arg Phe Gly Val Pro Thr Tyr
130                 135                 140

```
Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205

Ala Thr Tyr Ala Arg Cys Gly Ser Gly Pro Trp Leu Thr Pro Arg Cys
        210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Glu Ala Ala Cys Asn Trp Thr Arg Gly Glu Arg Cys Asp Leu Glu
                260                 265                 270

Asp Arg Asp Arg Ser Glu Leu Ser Pro Leu Leu Leu Ser Thr Thr Glu
            275                 280                 285

Trp Gln Ile Leu Pro Cys Ser Phe Thr Thr Leu Pro Ala Leu Ser Thr
        290                 295                 300

Gly Leu Ile His Leu His Gln Asn Ile Val Asp Val Gln Tyr Leu Tyr
305                 310                 315                 320

Gly Val Gly Ser Ala Val Val Ser Leu Val Ile Lys Trp Glu Tyr Val
                325                 330                 335

Leu Leu Leu Phe Leu Leu Leu Ala Asp Ala Arg Ile Cys Ala Cys Leu
            340                 345                 350

Trp Met Met Leu Leu Ile Ala Gln Ala Glu Ala
        355                 360
```